(12) United States Patent
Sugiura et al.

(10) Patent No.: US 7,071,359 B1
(45) Date of Patent: Jul. 4, 2006

(54) NEUROPATHY IMPROVERS CONTAINING NITROGENOUS COMPOUNDS AS THE ACTIVE INGREDIENT

(75) Inventors: Satoshi Sugiura, Tokyo (JP); Takaharu Tsutsumi, Tokyo (JP); Yorimasa Suwa, Tokyo (JP); Takami Arai, Tokyo (JP); Katsutoshi Sakurai, Tokyo (JP); Noboru Yoshioka, Tokyo (JP); Akira Tanokura, Tokyo (JP); Jun Suzuki, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/048,952

(22) PCT Filed: Aug. 7, 2000

(86) PCT No.: PCT/JP00/05287

§ 371 (c)(1),
(2), (4) Date: Feb. 5, 2002

(87) PCT Pub. No.: WO01/93328

PCT Pub. Date: Dec. 6, 2001

(30) Foreign Application Priority Data

Aug. 5, 1999 (JP) .................................. 11/222259
Aug. 5, 1999 (JP) .................................. 11/222260

(51) Int. Cl.
*C07C 233/00* (2006.01)
(52) U.S. Cl. ...................... 564/189; 560/119; 548/570; 546/194; 544/170; 549/359; 549/416
(58) Field of Classification Search ................ 560/119; 564/460, 189; 544/170; 546/194; 548/570; 549/359, 416
See application file for complete search history.

(56) References Cited

U.S. PATENT DOCUMENTS

| | | |
|---|---|---|
| 4,110,532 A | 8/1978 | Johnson et al. |
| 4,124,601 A | 11/1978 | Smith |
| 4,128,713 A | 12/1978 | Schneider |
| 4,161,585 A | 7/1979 | Johnson et al. |
| 4,161,586 A | 7/1979 | Johnson et al. |
| 4,161,587 A | 7/1979 | Johnson et al. |
| 4,163,842 A | 8/1979 | Johnson et al. |
| 4,166,903 A | 9/1979 | Johnson et al. |
| 4,167,624 A | 9/1979 | Johnson et al. |
| 4,170,703 A | 10/1979 | Johnson et al. |
| 4,171,447 A | 10/1979 | Smith |
| 4,174,441 A | 11/1979 | Johnson et al. |
| 4,191,822 A | 3/1980 | Johnson et al. |
| 4,205,178 A | 5/1980 | Axen |
| 4,226,984 A | 10/1980 | Ayer |
| 4,301,164 A | 11/1981 | Ohno et al. |
| 4,423,067 A | 12/1983 | Skuballa et al. |
| 4,464,388 A | 8/1984 | Sakai et al. |
| 4,499,085 A | 2/1985 | Masuda |

(Continued)

FOREIGN PATENT DOCUMENTS

CA 1320447 A 7/1993

(Continued)

OTHER PUBLICATIONS

Skuballa et al., 1983, CAS:98:179076.*

(Continued)

*Primary Examiner*—Taofiq Solola
*Assistant Examiner*—Robert Shiao
(74) *Attorney, Agent, or Firm*—Sughrue Mion, PLLC

(57) ABSTRACT

A compound represented by the Formula below, and an agent for the remedy of neural damage having the said compound as the active ingredient.

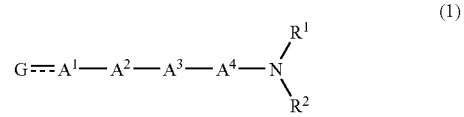

[Here, G represents G1 shown below

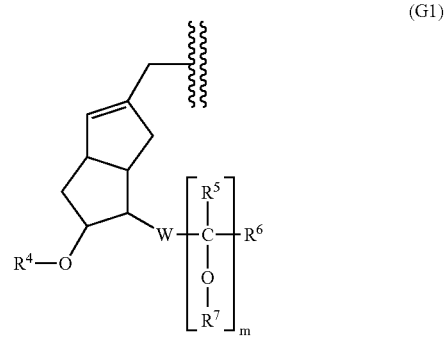

$R^4$ represents, hydrogen atoms and acyl groups, W represents single bonds and alkylenes, m represents 0 or 1, $R^5$ and $R^6$ represent hydrogen atoms, aliphatic hydrocarbon groups, alicyclic hydrocarbon groups, aromatic hydrocarbon groups and heterocyclic groups, and $R^7$ represents hydrogen atoms, acyl groups and alkoxycarbonyl groups. $A^2$ represents, single bonds, —O—, —$NR^3$—, and —$S(=O)_n$—, $A^1$ and $A^3$ represent single bonds, aliphatic hydrocarbon groups, alicyclic hydrocarbon groups, heterocyclic groups and phenylene groups, and $A^4$ represents single bonds, carbonyl groups and aliphatic hydrocarbon groups. $R^1$ and $R^2$ represent hydrogen atoms, alkyl groups, cycloalkyl groups, phenyl groups and heterocyclic groups. The previously mentioned functional groups may be substituted.]

6 Claims, No Drawings

U.S. PATENT DOCUMENTS

| | | | |
|---|---|---|---|
| 4,552,875 | A | 11/1985 | Skuballa et al. |
| 4,564,620 | A | 1/1986 | Ohno et al. |
| 4,680,307 | A | 7/1987 | Muraoka et al. |
| 4,705,806 | A | 11/1987 | Morton, Jr. et al. |
| 5,124,343 | A | 6/1992 | Vorbrueggen et al. |
| 6,340,693 | B1 | 1/2002 | Kurumatani et al. |

FOREIGN PATENT DOCUMENTS

| | | | | |
|---|---|---|---|---|
| DE | 2724555 | A | | 12/1977 |
| DE | 2753986 | A | | 7/1978 |
| DE | 2830100 | A | | 2/1979 |
| DE | 2850304 | A | | 6/1979 |
| DE | 3209702 | A1 | | 9/1983 |
| DE | 3226550 | A1 | | 1/1984 |
| DE | 266102 | A | | 3/1989 |
| DE | 197 39 693 | A1 | | 3/1999 |
| DE | 19739693 | A1 | | 3/1999 |
| EP | 0 024 943 | A1 | | 3/1981 |
| EP | 0 057 660 | A2 | | 8/1982 |
| EP | 0330025 | A2 | | 8/1989 |
| EP | 911 314 | A1 | | 4/1999 |
| FR | 2353543 | A | | 12/1977 |
| FR | 2422653 | A | | 9/1978 |
| FR | 2397410 | A | | 2/1979 |
| FR | 2422654 | A | | 9/1979 |
| GB | 2001064 | A | | 1/1979 |
| GB | 2010247 | A | | 6/1979 |
| GB | 1 554 048 | | | 10/1979 |
| GB | 1554048 | A | | 10/1979 |
| JP | 52-156854 | A | | 12/1977 |
| JP | 53-84942 | A | | 7/1978 |
| JP | 54 19961 | | | 2/1979 |
| JP | 54-19961 | A | | 2/1979 |
| JP | 54-92953 | A | | 7/1979 |
| JP | 54 117450 | | | 9/1979 |
| JP | 53 84942 | | | 7/1980 |
| JP | 58 192821 | | | 11/1983 |
| JP | 59 141536 | | | 8/1984 |
| JP | 59 210044 | | | 11/1984 |
| JP | 60 899443 | | | 5/1985 |
| JP | 61 129146 | | | 5/1986 |
| JP | 61 197518 | | | 9/1986 |
| JP | 62 67046 | | | 3/1987 |
| JP | 62-67046 | A | | 3/1987 |
| JP | 63 141927 | | | 6/1988 |
| JP | 2 167227 | | | 6/1990 |
| JP | 2 262519 | | | 10/1990 |
| JP | 4 26654 | | | 1/1992 |
| JP | 04 026654 | A | | 1/1992 |
| JP | 6-80028 | B2 | | 10/1994 |
| JP | 06080028 | B | * 10/1994 | .................. 560/500 |
| JP | 8 245498 | | | 9/1996 |
| JP | 9 67285 | | | 3/1997 |
| JP | 9-67285 | A | | 3/1997 |
| JP | 9 67285 | | | 11/1997 |
| JP | 10 101610 | | | 4/1998 |
| JP | 11 005764 | | | 1/1999 |
| WO | WO 83/03248 | A1 | | 9/1983 |
| WO | WO 89 03387 | A | | 4/1989 |
| WO | WO 98 41209 | A1 | | 9/1998 |
| WO | WO 00 24727 | A1 | | 5/2000 |
| WO | WO 00/24727 | A1 | | 5/2000 |

OTHER PUBLICATIONS

Patent Abstracts of Japan, Sakai Yoshinori, et al., Publication No. 58-164512, Sep. 29, 1983, "Remedy for Cell Disorder Containing Prostaglandin Analog Compound as an Active Ingredient."

Atsumi Nitta, et al., Neuroscience Letters, β-Amylod protein-induced Alzheimer's disease animal model, vol. 170, 1994, pp. 63-66.

Robert F. Newton, et al., Strategies Employed in the Synthesis of Prostacyclins and Thromboxanes, pp. 449-478, in Clinical Pharmacology Of Prostacyclin, Ed. Peter J. Lewis and John O'Grady.

Fourth Edition of the Experimental Chemistry Course, Chemical Society of Japan, vol. 22, pp. 137-173, Maruzen Co., Ltd. © 1992.

Fourth Edition of the Experimental Chemistry Course, Chemical Society of Japan, vol. 20, pp. 279-317, Maruzen Co., Ltd. © 1992.

Miki, et al., Drugs and treatments, The Neurite Outgrowth Action of Prostaglandins in Neuronal Cells, vol. 21, p 37. (1993).

Synthesis and Anti-platelet Aggregating Activity of 3-Hetero Analogues of (+)-9(O)-Methano-Delta. 6(9. Alpha.)-prostaglandin 1, Koichi Kojima, et al., Chemical Pharmaceutical Bulletin, 1987, vol. 35, pp. 4000-4015.

European Patent Office Communication dated May 22, 2003, submitting supplemental European Search report for Patent Application No. 00 99 0027.

T. Tomiyama, et al., "Synthesis and Biological Activity of Novel Carbacyclins Having Bicyclic Substituents on the ω-Chain", *J. Med. Chem* (1989), vol. 32, pp. 1988-1996.

A. Tsai, et al., "Characterization of the Interaction Between Prostacyclin and Human Serum Albumin Using a Fluorescent Analogue, 2,6-dichloro-4-aminophenol iloprost", *Biochimica et Biophysica Acta* (1989), vol. 993, No. 1, pp. 74-82.

Patent Abstracts of Japan for JP No. 57-032277-A, Publication Date: Feb. 20, 1982, Applicant: Toray Ind Inc.

Patent Abstracts of Japan for JP No. 04-026654-A, Publication Date: Jan. 29, 1992, Applicant: Teijin Ltd.

Kojima, K., et al. Synthesis and Anti-platelet Aggregating Activity of 3-Hetero Analogues of (+)-9(O)-Methano-Delta. 6(9. Alpha.)-prostaglandin II, Chemical Pharmaceutical Bulletin, 1987, vol. 35, No. 10, pp. 4000-4015.

Casals-Stenzel, et al. Abstract of Canadian patent No. 1248525, published Feb. 1, 1984 Australian Search Report, dated Mar. 5, 2004.

* cited by examiner

NEUROPATHY IMPROVERS CONTAINING NITROGENOUS COMPOUNDS AS THE ACTIVE INGREDIENT

TECHNICAL FIELD

The present invention relates to an agent for the remedy of neural damage wherein the active ingredient is a nitrogen-containing compound having a prostacyclin analog structure and an amido group or an amino group at the extremity of the α-chain, as well as pharmaceutical compositions thereof. In addition, the invention relates to a nitrogen-containing compound having a prostacyclin analog structure and an amino group at the extremity of the α-chain, as well as salts thereof.

TECHNICAL BACKGROUND

In the nervous system, neurons perform their function once they have formed a network through synapses between neurons by extending neurites (either axon or dendrite). In addition, such intercellular communication allows the cells to maintain their own existence through a mutual exchange of transmitters and nutritional factors. Therefore, even if the neurons themselves do not suffer fatal damage, if the neural network is damaged, neural functions decrease and, further, may lead to the death of the neurons themselves. Such neural network damage is thought to be what takes place first, not only in cases such as in external injuries where axons are disrupted, but also in many disorders causing neural damage, or in the surroundings of the damaged site. Therefore, a drug agent having a capability such as restoring neural network damage is thought to be both a drug agent capable of controlling the cellular death of neurons and an extremely active drug agent for the remedy of many disorders due to neural damage as well as lesion of nerves due to external injuries.

The following may be cited as disorders caused by neural damage: 1) Neuro-degenerative disorders such as Alzheimer's disease, Pick's disease, Lewy body disease, Parkinson's disease, Huntington's chorea, spinocerebellar degeneration and amyotrophic lateral sclerosis, 2) demyelinating disorders such as acute disseminated encephalomyelitis and multiple sclerosis, 3) metabolic disorders such as brain lipidosis and Wilson's Disease, 4) infectious disorders such as meningitis and Creutzfeld-Jacob disease, 5) peripheral neural disorders such as polyneuritis and Guillain-Barre Syndrome, 6) cerebrovascular disorder such as cerebral infarction and transient ischemia, 7) nervous disorders (neuropathies) associated with diabetes and renal diseases and 8) brain tumors.

Among the previously mentioned disorders which cause neural damage, Alzheimer's disease is the most representative, and constitutes a serious social issue together with the increase in the population of the elderly. In the past, the drug agents used for treating Alzheimer's disease could be roughly divided into those classified as activators of brain circulation and metabolism, and those classified as cholinergic nervous system activators. However, the activities of these drug agents are not sufficient.

In other words, activators of brain circulation and metabolism are drugs that are used to treat cerebrovascular damage and their after-effects, do not aid recovery directly from neural damage and therefore have a low efficacy against dementia which is the core disorder in Alzheimer's disease. In addition, activators of the cholinergic nervous system were developed based on the pathological findings that Alzheimer's disease patients had notable damage in the cholinergic nervous system. However, in Alzheimer's disease, cholinergic nervous systems are actually not the only ones that are damaged, therefore, the effects of such drugs are thought to be limited.

Given the situation, development of drugs based on novel drug effects for the treatment of Alzheimer's disease are strongly in demand. Among others, drug agents having an activity such as restoring neural network damage, as mentioned above, are anticipated to display extremely high efficacy for the treatment of Alzheimer's disease, if put into practical application.

In the past, for the development of drugs for the treatment of Alzheimer's disease, the models used for evaluating the drug's efficacy at the animal level were mainly models where the cholinergic nervous system was specifically damaged by methods such as administration of scoporamine or electric destruction, or models where damage was produced by cerebral ischemia or hypoxic stress due to carbon dioxide. Although many of these evaluation systems are reasonable as evaluation systems for the activators of the cholinergic nervous system or activators of brain circulation and metabolism, they are pathogenetically and pathologically distant from actual Alzheimer's disease, and are therefore not suited to the evaluation of novel drugs for the treatment of Alzheimer disease.

One important characteristic of Alzheimer's disease is the formation of senile plaques in the brain. β-amyloid proteins, which are the main constituents of these senile plaques, agglutinate in the brain to form amyloids and while being deposited in the brain tissue, exhibit their neurotoxicity, which is thought to be the main cause for Alzheimer's disease. Based on this, an animal model of Alzheimer's disease was made, wherein a mini-osmotic pump is implanted under the dorsal skin of a rat, for a continuous intracerebroventricular administration of β-amyloid proteins to lower the ability of learning and memory (Neuroscience Letters, vol. 170, pp. 63–66, 1994). In this model, deposition of the β-amyloid proteins could be recognized in the periphery of the cerebral ventricle. However, no clear neural cell death could be observed, therefore, there is a high possibility that the disorder of learning and memory observed in this model are due to damage in the neural network. Therefore, this model is an extremely rational system for screening and evaluating novel drugs for the treatment of Alzheimer's disease, and at the same time, is an adequate system for screening and evaluating novel drugs for the treatment of neural lesion due to a whole range of diseases causing neural damage, or due to injuries.

On the other hand, prostaglandin (PG) compounds are known to have multiple physiological activities such as strong platelet aggregation inhibition activity, vasodilatation and the associated hypotension activities, gastric acid secretion inhibition activity, smooth muscle contraction activity, cell protection activity, and diuretic activity. Based on such physiological activities, a number of attempts have been made to develop medicine from natural PG present in vivo, or from PG derivatives synthesized to serve as its agonists, and some of these attempts actually reached the market.

Prostacyclin, which is a PG, has the structure represented by the formula below (PGI2),

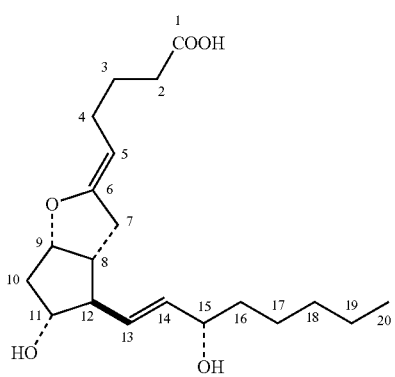

(PGI2)

(in the formula, the numbers are identification numbers for the carbon atoms in prostacyclin) which is a substance containing a structure called α-chain comprising the carbon chain from 1 to 7, and a structure called ω-chain from carbon 13 to 20. In vivo it is known as a local hormone, mainly made in the vascular endothelium, and attempts were made to use its strong physiological activities, for example, platelet aggregation inhibition, smooth muscle contraction, hypotension, gastric acid secretion inhibition, peripheral vasodilatation and bronchodilatation, to provide it directly as a medicine (P. J. Lewis, J. O. Grady, Clinical Pharmacology of Prostaglandin).

However, because a prostacyclin molecule has a highly hydrolizable enol-ether bond, it is easily inactivated under neutral or acidic conditions, which makes it problematic in compounds to be used as medicines. Therefore, synthetic research was carried out on a compound having a prostacyclin analog structure, displaying the same activity as prostacyclin and being chemically stable (Synthesis, 1984, p. 449). In other words, this objective was achieved mainly by modifying the bicyclo[3.3.0]octane ring structure of from carbon 5 to 12 in prostacyclin. For example, the oxygen atoms bridging position 6 to 9 may be substituted with a methene group (—CH=) to synthesize the compound 9(O)-methano-$\Delta^{6(9\alpha)}$-prostaglandin $I_1$ (Isocarbacyclin) indicated by the formula below (Isocarbacyclin),

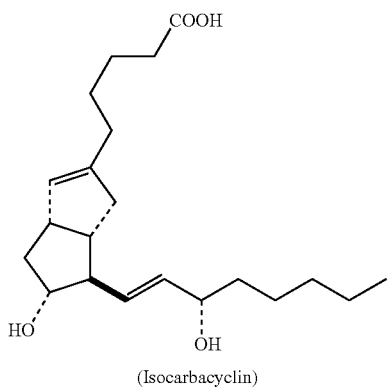

(Isocarbacyclin)

which is a compound having a prostacyclin analog structure fully satisfying the chemical stability (Japanese patent publication Sho. 59-210044). This compound displayed biological activities comparable to those of prostacyclin such as strong platelet aggregation inhibitory activity and vasodilatory-hypotensive activities (Japanese patent publication Sho. 59-210044 and Japanese patent publication Sho. 61-197518).

In the past, development of PG compounds to be used as medicine was mainly carried out in the field of obstetrics and gynecology, circulation or digestion. In the nerve field, there are no examples of these compounds commercialized as medicine, although there have been reports on the possibility of using PG compounds in nervous systems.

The following are known examples describing in particular the effect of compounds having a prostacyclin analog structure and which remedy neural damage: 1) in Japanese patent publication Sho. 61-129146, a compound having an isocarbacyclin analog structure was used for the prevention of or the treatment of the brain for disorders such as cerebral oxygen deficiency, 2) in Japanese patent publication Hei. 2-167227, a compound having an isocarbacyclin analog structure was used for the treatment of diabetic neuropathy, 3) in Japanese patent publication Hei. 8-245498, Japanese patent publication Hei. 10-101610, Japanese patent publication Hei. 11-5764 and patent No. EP-911314, a compound having an isocarbacyclin analog structure was used as a drug for the treatment of central nervous system disease, via the prostacyclin receptor of the central nervous system 4) in patent No. WO89/03387, 2,5,6,7-tetranor-4,8-inter-m-phenylene $PGI_2$ derivative was used as a drug for the treatment of cerebral ischemia 5) in Japanese patent publication Hei. 2-262519, beraprost was used for the treatment of diabetic neuropathy, 6) in Japanese patent publication Sho. 63-141927, treatment and prevention of cerebral thrombosis and cerebral infarction.

In the previously mentioned examples, however, the efficacy is described for compounds with a carboxyl group at position 1 of the prostacyclin or an ester thereof. Only in the compounds having a prostacyclin analog structure described in the above mentioned 6), a compound having a prostacyclin analog structure wherein the carboxyl group at position 1 is substituted by an amide group is described. However, there is no concrete description related to its pharmacological activity. Therefore, the usability of a compound having a prostacyclin analog structure wherein the carboxyl group at position 1 is substituted with an amide group, as a drug for the remedy of neural damage, was not known.

On the other hand, most of the compounds of the past known to have a prostaglandin analog activity, are compounds having a prostacyclin analog structure with, at position 1, a carboxyl group which is thought to be important for expressing the activity, or a chemical structure that can be easily substituted with a carboxyl group in vivo. Therefore, there are only few publicly known substances having a prostacyclin analog structure with an amino group at the extremity of the α-chain. For example, the compound below, described in the (East) German patent No. DD266102,

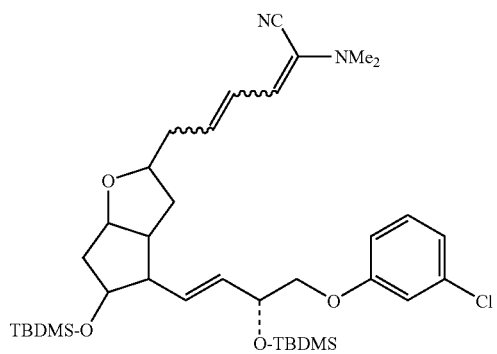

(in the formula, the symbol ～ indicates the E or the Z configuration with respect to the attached double-bond and TBDMS represents a t-butyl-dimethylsilyl group). However, it is positioned as a synthetic intermediate, and a description of its activity is not available.

In addition, in the U.S. patent publication No. U.S. Pat. No. 4,226,984, the compounds having the structure indicated below

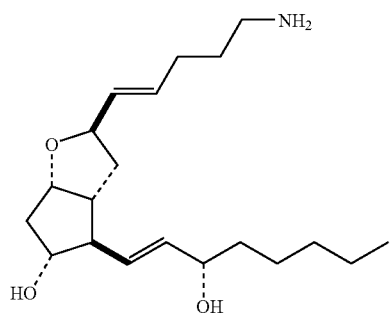

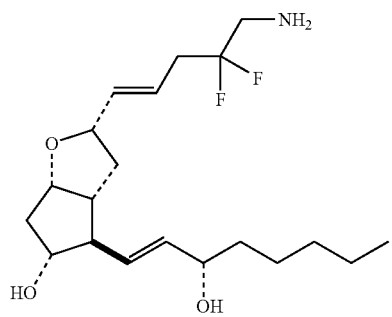

and their substituted versions on the (o-chain are described as having a stimulatory effect on smooth muscles. However, no concrete example is given.

In addition, in the Japanese patent publication Sho. 54-117450, a synthesis of the compound having the structure below

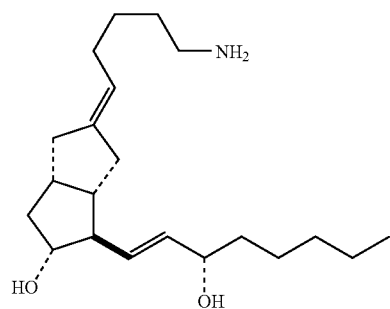

is described. However, no description on its activity is given.

In addition, in the Japanese patent publication Sho. 62-67046, the compounds of the scheme below

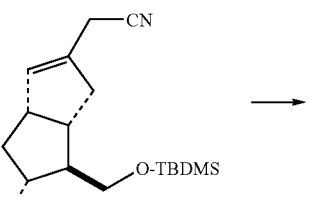

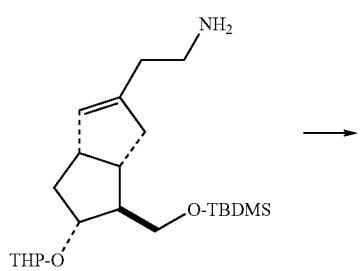

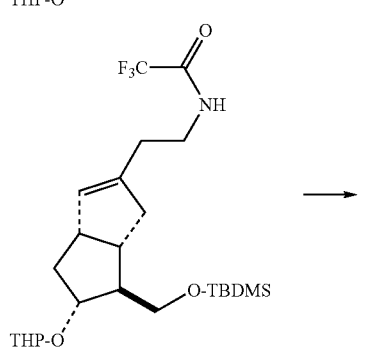

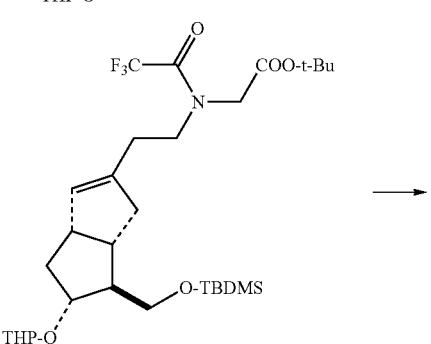

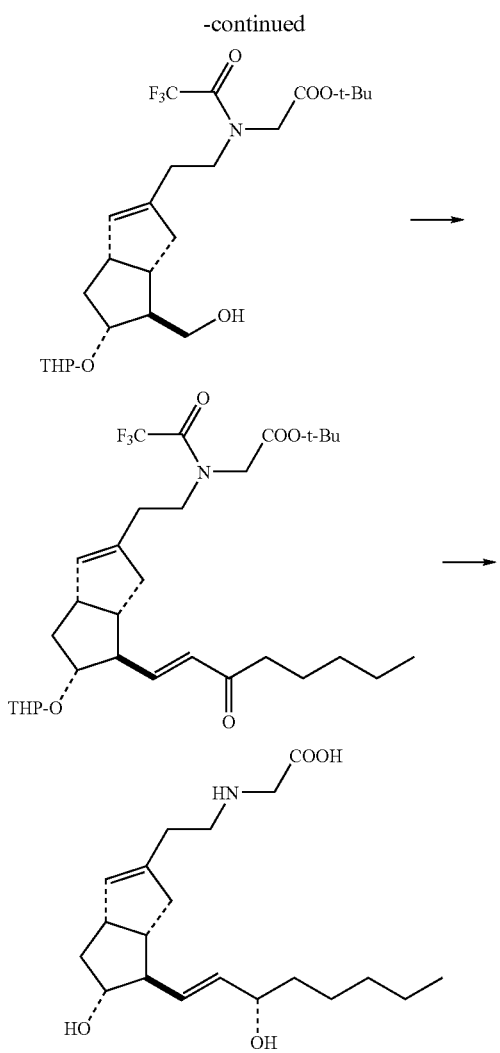
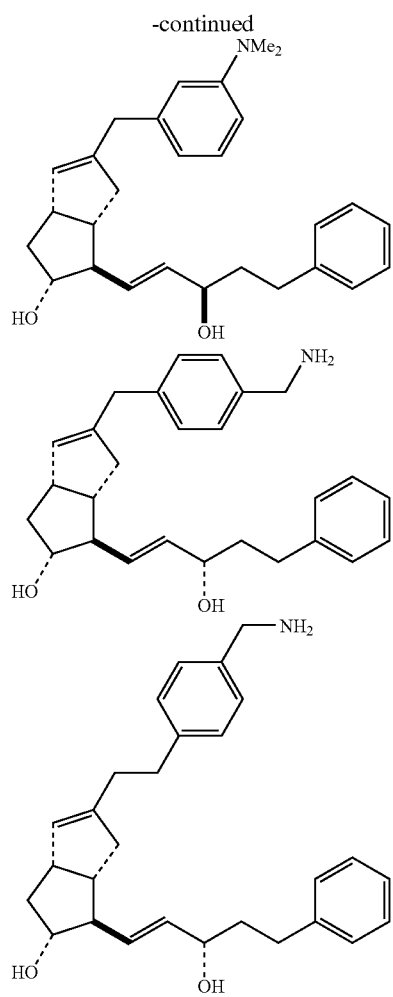

(in the scheme, THP represents tetrahydropyrane-2-yl group and TBDMS represents a t-butyl-dimethylsilyl group.) and their substituted versions on the ω-chain are described. However, no description of their activity is given.

In addition, in the Japanese patent publication Hei. 9-67285, the 4 compounds below are described. However, no description of their activity is given.

In addition, in the detailed description of WO00/24727, only a description of the anti-helicobacter activity is given, of a derivative of the compound having an amino group at the extremity of the α-chain, comprising the compound indicated by the formula below,

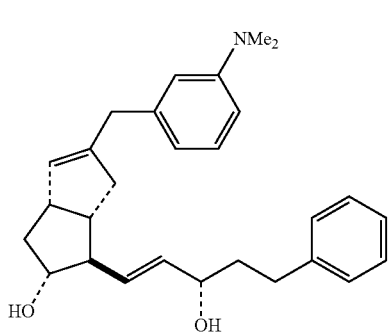
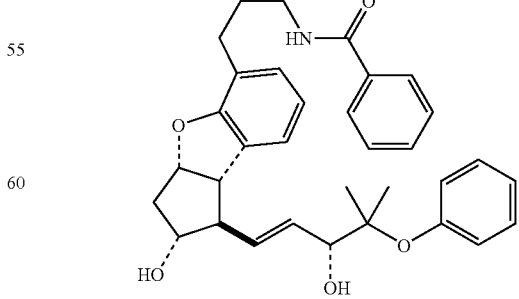

and being a compound with a prostacyclin analog structure.

Therefore, most of the compounds having a prostacyclin analog structure with an amino group at the extremity of the α-chain were novel substances with no known usability.

DISCLOSURE OF THE INVENTION

The problem to be solved by the present invention is to provide a novel agent for the remedy of neural damage which can act against disorders due to neural damage, or against neural lesions due to external injuries. Here, disorders caused by neural damage, or disorders caused by neural lesions due to external injuries may be cited as disorders in which the agent for the remedy of neural damage of the present invention can be used. Concretely, the following may be cited as disorders caused by neural damage: 1) Neuro-degenerative disorders such as Alzheimer's disease, Pick's disease, Lewy body disease, Parkinson's disease, Huntington's chorea, spinocerebellar degeneration and amyotrophic lateral sclerosis, 2) demyelinating disorders such as acute disseminated encephalomyelitis and multiple sclerosis, 3) metabolic disorders such as brain lipidosis and Wilson's Disease, 4) infectious disorders such as meningitis and Creutzfeld-Jacob disease, 5) peripheral neuropathies such as polyneuritis and Guillain-Barre Syndrome, 6) cerebrovascular disorder such as cerebral infarction and transient ischemia, 7) nervous disorders (neuropathies) associated with diabetes and renal diseases and 8) brain tumors.

In addition, when attempting to develop PG compounds to serve as a medicine in the cerebral nerve field, two problems have to be considered. The first problem is that the diversity of activities that PG compound has may cause adverse events. In order to solve this problem, it is necessary to use compounds that are active as specifically on the cerebral nervous system as possible, with low influences on other parts such as circulatory organs. The second problem is that, in contrast to the vascular system in peripheral organs, in the vascular system of the brain, the vascular endothelial cells are associated by tight junctions, which results in a limitation of the delivery of substances from the circulating blood to the parenchymal tissue of the brain, that is, a so-called blood brain barrier exists. Therefore, in order to develop drug agents for the cerebral nervous system, it is necessary to obtain drugs with a high permeability across the blood brain barrier.

After performing extensive research on the above-mentioned problems employing neuroid cells to evaluate the promotion activity on the neurite outgrowth, an evaluation system using an animal model for Alzheimer type dementia wherein β-amyloid protein is continuously injected, and a system to evaluate the decrease of blood pressure, the inventors of the present application found that the nitrogen-containing compound in the formula (1) shown below, having a prostacyclin analog structure and an amido group or an amino group at the extremity of the α-chain, had the activity of promoting the neurite outgrowth, as well as the activity of remedying disorders of learning and memory provoked by the β-amyloid protein. In addition, the above-mentioned compounds showed that they have only a low influence on the peripheral circulatory system, that their activity displays a high specificity for the brain, and that the above mentioned compound has a high permeability across blood brain barriers, allowing the present invention to be completed.

In other words, the present invention is an agent for the remedy of nerve disorders having as the active ingredient the compound represented by the formula (1) shown below.

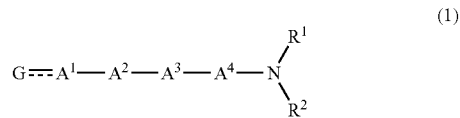

[In Formula (1), the symbol ═ represents a single bond or a double bond.

G represents one functional group chosen from the group consisting of the Formulae (G1), (G2), (G3), (G4), (G5), (G6), (G7), (G8), (G9), (G10), (G11) and (G12) shown below.

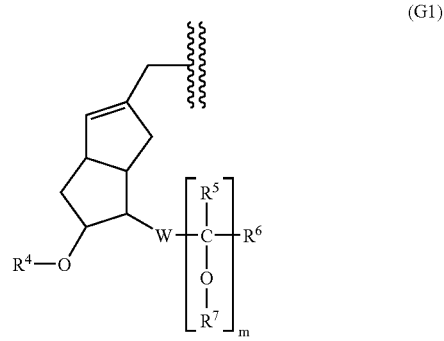

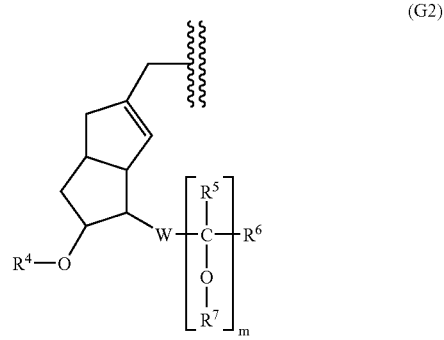

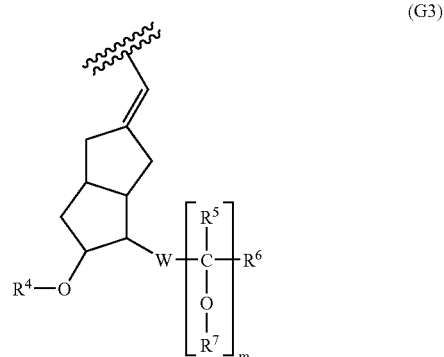

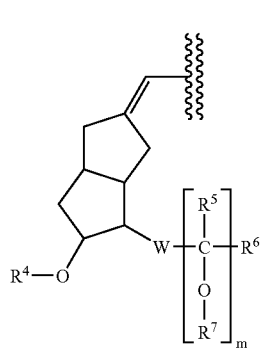
(G4)
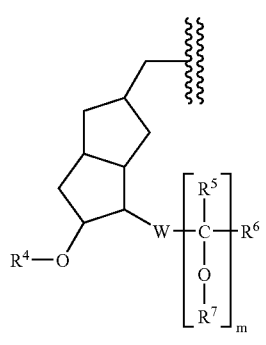
(G5)
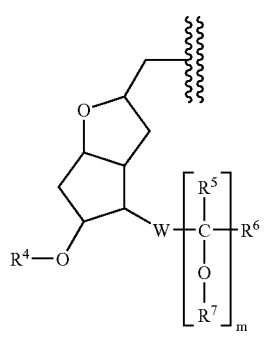
(G6)
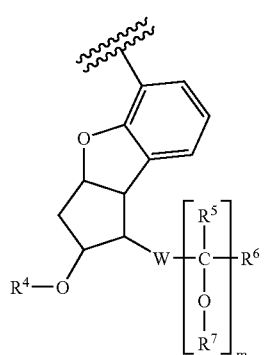
(G7)
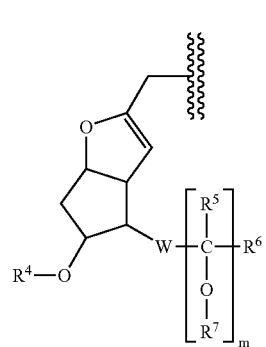
(G8)
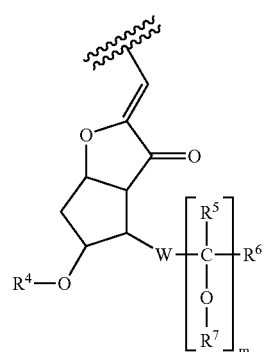
(G9)
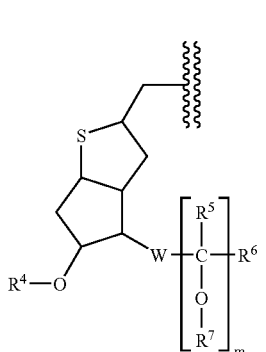
(G10)
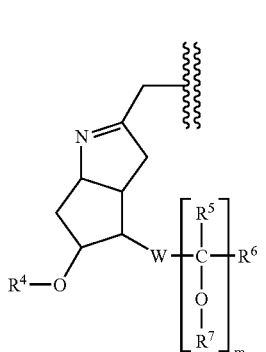
(G11)

-continued

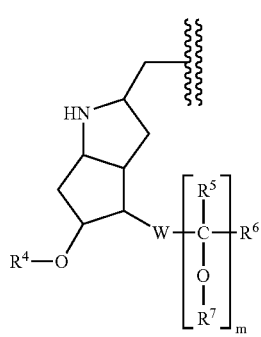

(G12)

(In Formula G1), Formula (G2), Formula (G3), Formula (G4), Formula (G5), Formula (G6), Formula (G7), Formula (G8), Formula (G9), Formula (G10), Formula (G11) and Formula (G12), the symbol § represents the site of linkage with $A^1$.

$R^4$ represents a hydrogen atom, an acyl group having 2 to 10 carbon atoms, a tri(hydrocarbon group having 1 to 7 carbon atoms) silyl group or a functional group forming the acetal bond together with the oxygen atom bonded to $R^4$.

W represents a single bond, —$CH_2$—, —$(CH_2)_2$—, —$(CH_2)_3$—, —CH=CH—, —CH=$CHCH_2$—, —C≡C— or —C≡$CCH_2$—.

m may be either 0 or 1. However, when W is a single bond, m is equal to 1.

$R^5$ and $R^6$ are either identical or different and, either represents one functional group chosen from the following items 1) to 5), i.e., 1) a hydrogen atom,
2) a substituted or an unsubstituted aliphatic hydrocarbon group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), or, when $R^5$ and $R^6$ are bonded to each other, they represent a substituted or an unsubstituted alicyclic hydrocarbon chain having 4 to 7 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, an acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

$R^7$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, a functional group forming the acetal bond together with the oxygen atom bound to $R^7$, or, when $R^7$ and $R^5$ are bonded to each other, it represents one portion of the bond forming the carbonyl group together with the carbon atom bonded to $R^5$ and the oxygen atom bonded to $R^7$.

$A^2$ represents a single bond, a Formula (A2A) shown below, a Formula (A2B) shown below or a Formula (A2C) shown below.

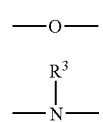

(In the formula, $R^3$ represents a hydrogen atom, an alkyl group having 1 to 4 carbon atoms, or an acyl group having 1 to 10 carbon atoms.)

(In the formula, n represents 0, 1, or 2.)

$A^1$ represents the items 1) or 2) below
1) a single bond
2) a functional group which bridges G and $A^2$ through an identical atom or through different atoms, and chosen from: an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^3$ represents the items 1) or 2) below
1) a single bond
2) a functional group which bridges $A^2$ and $A^4$ through an identical atom or through different atoms, and chosen from: an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^4$ represents either of the items 1) to 4) below
1) a single bond
2) a carbonyl group
3) an aliphatic hydrocarbon group having 1 to 3 carbon atoms, which bridges the nitrogen atom, bonded to $R^1$ and $R^2$, and $A^3$ through an identical atom or through different atoms.
4) when $A^4$ and $R^1$ are bonded to each other, a functional group forming a 5 to 8 membered ring together with the nitrogen atom they are bonded to (when $A^4$ or $R^1$ and the nitrogen atom they are bonded to are bonded through a double bond, $R^2$ represents the bond between $A^4$ or $R^1$ and the nitrogen atom.)

However, in the combination of $A^1, A^2, A^3$ and $A^4, A^1, A^2, A^3$ and $A^4$ may not simultaneously represent bonds. In addition, when $A^2$ represents one of the Formula (A2A), Formula (A2B) or Formula (A2C), $A^2$ and the nitrogen atom bonded to $R^1$ and $R^2$ must be bonded with more than two carbon atoms in between.

$R^1$ and $R^2$ are either identical or different, and either represent one functional group chosen from the following items 1) to 7), i.e.,
1) a hydrogen atom,
2) a substituted or an unsubstituted alkyl group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, phenyl group, and, heterocyclic group (containing 1 to 4 oxygen atoms, nitrogen atoms, or sulfur atoms) may be cited as substituents),
3) a substituted or an unsubstituted cycloalkyl group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
4) a substituted or an unsubstituted phenyl group (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
5) a substituted or an unsubstituted heterocyclic group (containing 1 to 4 oxygen atoms, nitrogen atoms, or sulfur atoms, and, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
6) an acyl group having 1 to 10 carbon atoms when $A^4$ is not a carbonyl group,
7) a sulfonyl group having 1 to 8 carbon atoms when $A^4$ is not a carbonyl group (however, when either $R^1$ or $R^2$ represents a sulfonyl group having 1 to 8 carbon atoms, the other may be neither an acyl group having 1 to 10 carbon atoms nor a sulfonyl group having 1 to 8 carbon atoms), or, when $R^1$ and $R^2$ are bonded together, they represent a functional group forming a cyclic amino group having 4 to 8 carbon atoms together with the nitrogen atom they are bonded to (for said cyclic amino group having 4 to 8 carbon atoms, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents)].

In addition, the present invention is a nitrogen-containing compound represented by Formula (2) below or a salt thereof.

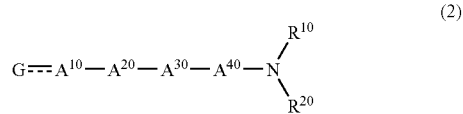

(2)

[In Formula (2), the symbol ═ represents a single bond or a double bond. G represents one functional group chosen from the group consisting of the Formulae (G1), (G2), (G3), (G4), (G5), (G6), (G7), (G8), (G9), (G10), (G11) and (G12) shown above. (In Formula (G1), Formula (G2), Formula (G3), Formula (G4), Formula (G5), Formula (G6), Formula (G7), Formula (G8), Formula (G9), Formula (G10), Formula (G11) and Formula (G12), the symbol ⁂ represents the site of linkage with $A^{10}$.

$R^4$, W, m, $R^5$, $R^6$ and $R^7$ have the same definitions as above.

$A^{20}$ represents a single bond, a Formula (A2A) shown below, a Formula (A2B) shown below or a Formula (A2C) shown below.

(A2A)

(A2B)

(In the formula, $R^3$ represents a hydrogen atom, an alkyl group having 1 to 4 carbon atoms, or an acyl group having 1 to 10 carbon atoms.)

(A2C)

(In the formula, n represents 0, 1, or 2.)

$A^{10}$ represents the items 1) or 2) below
1) a single bond
2) a functional group which bridges G and $A^{20}$ through an identical atom or through different atoms, and chosen from: an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^{30}$ represents the items 1) or 2) below
1) a single bond
2) a functional group which bridges $A^{20}$ and $A^{40}$ through an identical atom or through different atoms, and chosen from: an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^{40}$ represents any of the items 1) to 3) below
1) a single bond
2) an aliphatic hydrocarbon group having 1 to 3 carbon atoms, which bridges the nitrogen atom, bonded to $R^{10}$ and $R^{20}$, and $A^{30}$ through an identical atom or through different atoms.
3) when $A^{40}$ and $R^{10}$ are bonded to each other, a functional group forming a 5 to 8 membered ring together with the nitrogen atom they are bonded to (when $A^{40}$ or $R^{10}$ and the nitrogen atom they are bonded to are bonded through a double bond, $R^{20}$ represents the bond between $A^{40}$ or $R^{10}$ and the nitrogen atom.)

However, in the combination of G, $A^{10}$, $A^{20}$, $A^{30}$, and $A^{40}$, when G represents the Formula (G1), and either of $A^{10}$ or $A^{30}$ is a phenylene group, $A^{20}$ may not be a single bond and when $A^{20}$ represents a single bond, then G and the nitrogen atom bonded to $R^{10}$ and $R^{20}$ must be bonded with more than two carbon atoms in between. In addition, when $A^{20}$ represents one of the Formula (A2A), Formula (A2B) or Formula (A2C), $A^{20}$ and the nitrogen atom bonded to $R^{10}$ and $R^{20}$ must be bonded with more than two carbon atoms in between.

$R^{10}$ and $R^{20}$ are either identical or different, and either represent one functional group chosen from the following items 1) to 7), i.e.,
1) a hydrogen atom (however, when $R^{10}$ and $R^{20}$ both represent a hydrogen atom, only in the case where G is equal to Formula (G1)),
2) when G is not equal to Formula (G7), a substituted or an unsubstituted alkyl group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, phenyl group, and, heterocyclic group (containing 1 to 4 oxygen atoms, nitrogen atoms, or sulfur atoms) may be cited as substituents),
3) when G is not equal to Formula (G7), a substituted or an unsubstituted cycloalkyl group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
4) when G is not equal to Formula (G7), a substituted or an unsubstituted phenyl group (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
5) a substituted or an unsubstituted heterocyclic group (containing 1 to 4 oxygen atoms, nitrogen atoms, or sulfur atoms, and, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
6) when G is not equal to Formula (G7), an acyl group having 1 to 10 carbon atoms
7) when G is not equal to Formula (G7), a sulfonyl group having 1 to 8 carbon atoms (however, when either $R^{10}$ or $R^{20}$ represents a sulfonyl group having 1 to 8 carbon atoms, the other may neither be an acyl group having 1 to 10 carbon atoms nor a sulfonyl group having 1 to 8 carbon atoms), or, when $R^{10}$ and $R^{20}$ are bonded together, they represent a functional group forming a cyclic amino group having 4 to 8 carbon atoms together with the nitrogen atom they are bonded to (for said cyclic amino group having 4 to 8 carbon atoms, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents)]

PREFERRED EMBODIMENTS

In the following, the present invention will be explained in detail.

In Formula (1) above, the symbol ═ represents a single bond or a double bond. G1, G2, G5, G6, G8, G10, G11 and G12 may be cited as acceptable G for forming a double bond with such a bonding site.

In other words, Formula (1) above, in combination with G, forms one of the Formulae (1-G1), (1-G2), (1-G3), (1-G4), (1-G5), (1-G6), (1-G7), (1-G8), (1-G9), (1-G10), (1-G11) or (1-G12), below.

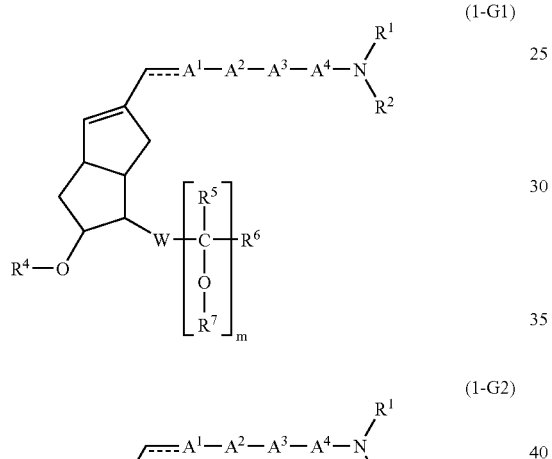
(1-G1)

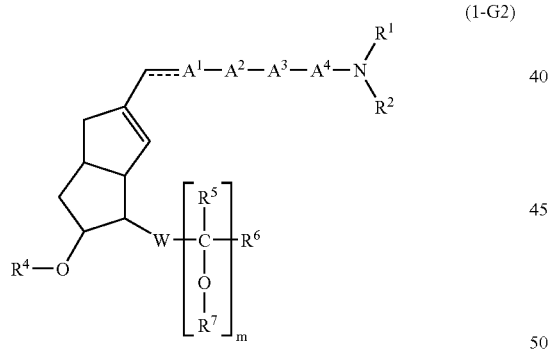
(1-G2)

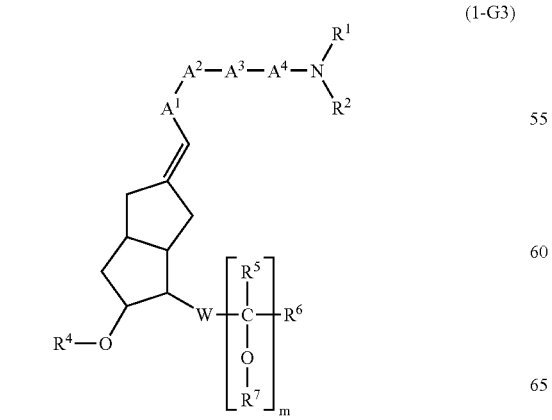
(1-G3)

-continued

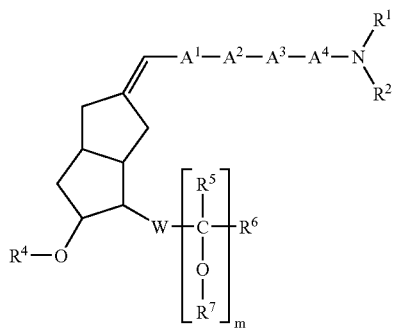
(1-G4)

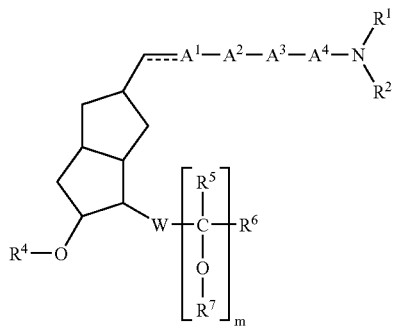
(1-G5)

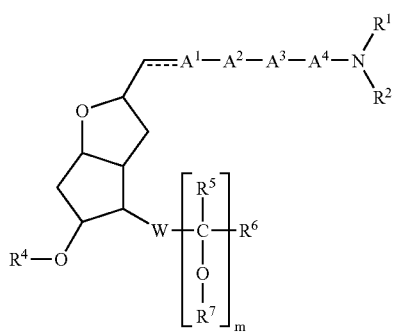
(1-G6)

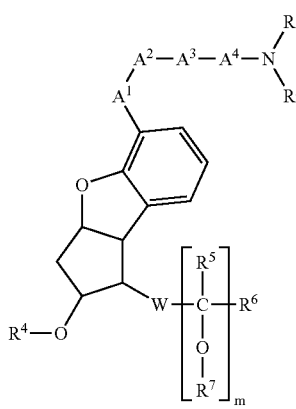
(1-G7)

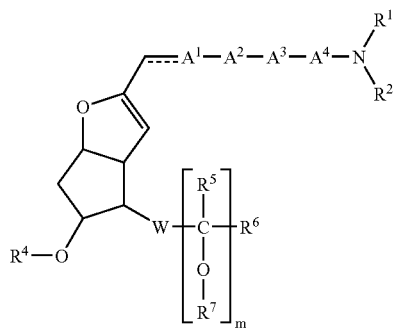
(1-G8)

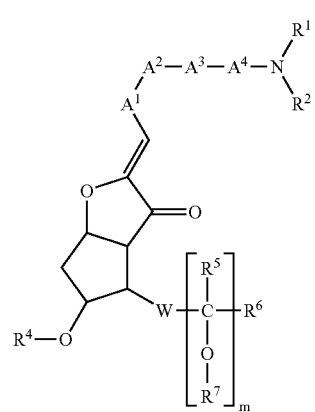
(1-G9)

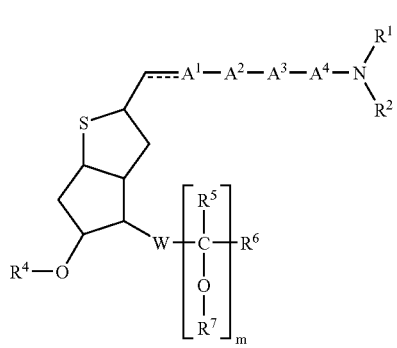
(1-G10)

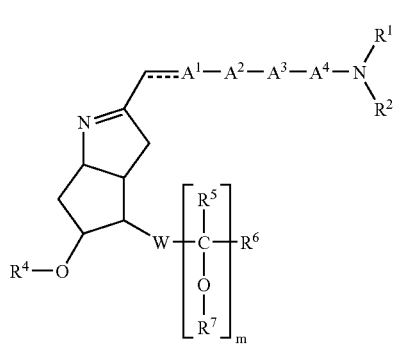
(1-G11)

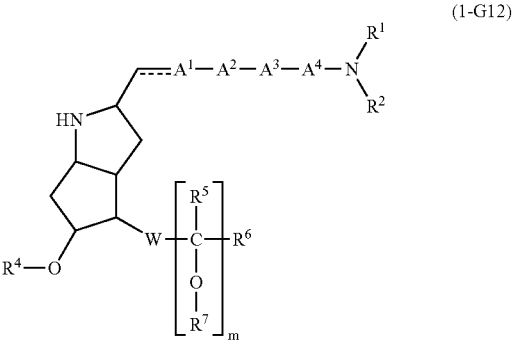
(1-G12)

[In Formula (1-G1), Formula (1-G2), Formula (1-G3), Formula (1-G4), Formula (1-G5), Formula (1-G6), Formula (1-G7), Formula (1-G8), Formula (1-G9), Formula (1-G10), Formula (1-G11) and Formula (1-G12), the symbol ═══, $A^1$, $A^2$, $A^3$, $A^4$, $R^1$, $R^2$, $R^4$, $R^5$, $R^6$, $R^7$, m and W, have the same definitions as above.]

G1, G2, G3, G4, G5, G6 and G7 may be cited as such a preferred functional group for G. Among them G1, G3 and G7 are more preferred and G1 is especially preferred.

Each of the above Formulae (1-G1), (1-G2), (1-G3), (1-G4), (1-G5), (1-G6), (1-G7), (1-G8), (1-G9), (1-G10), (1-G11) and (1-G12) have a preferred spatial configuration and the ones represented by the Formulae (1-G1E), (1-G2E), (1-G3E), (1-G4E), (1-G5E), (1-G6E), (1-G7E), (1-G8E), (1-G9E), (1-G10E), (1-G11E) and (1-G12E) below may be cited.

(1-G1E)

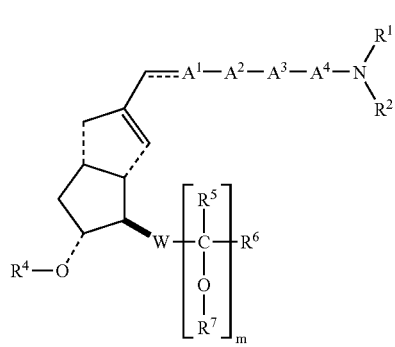
(1-G2E)

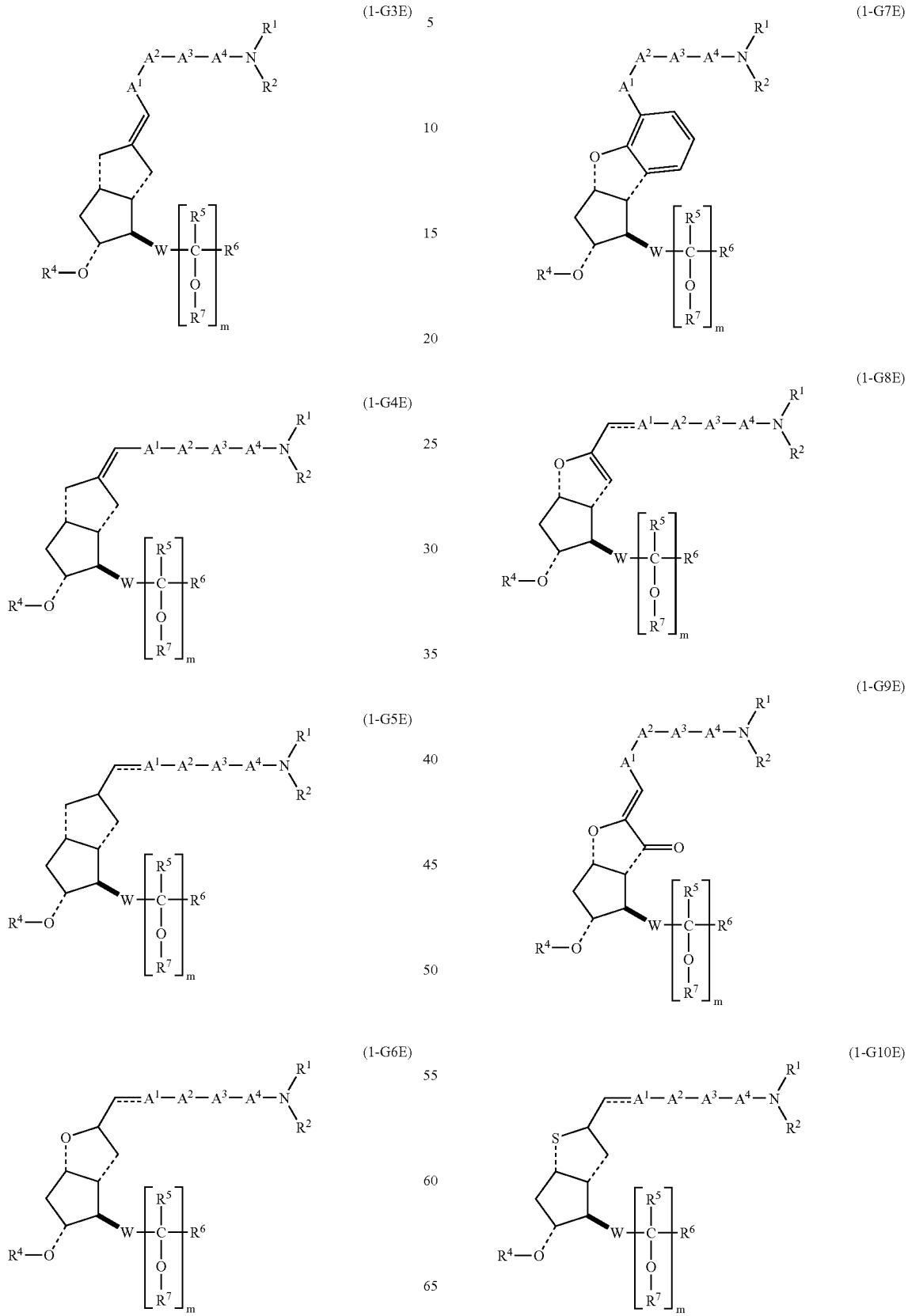

-continued

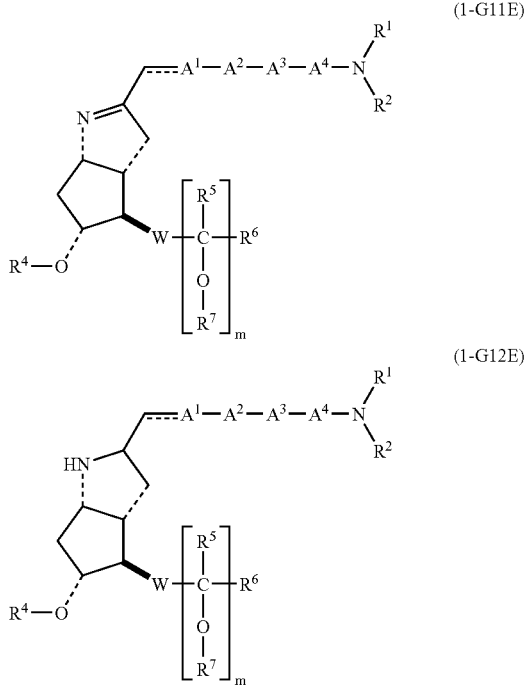

(1-G11E)

(1-G12E)

[In Formula (1-G1E), Formula (1-G2E), Formula (1-G3E), Formula (1-G4E), Formula (1-G5E), Formula (1-G6E), Formula (1-G7E), Formula (1-G8E), Formula (1-G9E), Formula (1-G10E), Formula (1-G11E) and Formula (1-G12E), the symbol ===, $A^1$, $A^2$, $A^3$, $A^4$, $R^1$, $R^2$, $R^4$, $R^5$, $R^6$, $R^7$, m, and W have the same definitions as above. The symbol ▬ indicates that the bond is in the β position with respect to the carbon atom forming the cyclic structure it is bonded to. The symbol ---- indicates that the bonds are in the α position with respect to the carbon atoms forming the cyclic structure they are bonded to.]

In the above Formula (1), $R^4$ represents a hydrogen atom, an acyl group having 2 to 10 carbon atoms, a tri(hydrocarbon group having 1 to 7 carbon atoms) silyl group or a functional group forming the acetal bond together with the oxygen atom bonded to $R^4$.

As examples of such $R^4$ which are acyl groups having 2 to 10 carbon atoms, an acetyl group, a trifluoroacetyl group, a propionyl group, a butyryl group, an isobutyryl group, a valeryl group, an hexanoyl group, a benzoyl group, a phenylacetyl group, a phenylpropionyl group, and a cinnamoyl group may be cited. However, an acetyl group and a benzoyl group may be cited as preferred examples.

In addition, as examples of a tri(hydrocarbon group having 1 to 7 carbon atoms) silyl group, a trimethylsilyl group, a triethylsilyl group, a dimethylisopropylsilyl group, a dimethylhexylsilyl group, a t-butyldimethylsilyl group, a triisopropylsilyl group, a t-butyldiphenylsilyl group, and a tribenzylsilyl group may be cited. However, a trimethylsilyl group, a triethylsilyl group, and a t-butyldimethylsilyl group may be cited as preferred examples.

In addition, as examples of functional groups forming the acetal bond together with the oxygen atom bonded to $R^4$, a methoxymethyl group, a 1-ethoxyethyl group, a 1-methoxy-1-methylethyl group, a 2-ethoxy-1-methylethyl group, a 2-methoxyethoxymethyl group, a tetrahydropyrane-2-yl group and a 6,6-dimethyl-3-oxa-2-oxo-bicyclo[3.1.0]hexane-4-yl group may be cited. However, a methoxymethyl group, a 2-methoxyethoxymethyl group, and a tetrahydropyran-2-yl group may be cited as preferred examples.

As particularly preferred examples of such $R^4$, a hydrogen atom; an acetyl group, a t-butyldimethylsilyl group and a tetrahydropyran-2-yl group may be cited.

In the above formula (1), W represents one of: a single bond, —CH$_2$—, —(CH$_2$)$_2$—, —(CH$_2$)$_3$—, —CH═CH—, —CH═CHCH$_2$—, —C≡C— or —C≡CCH$_2$—. For said W, —CH═CH— or —CH═CHCH$_2$— may be cited as preferred examples.

$R^5$ and $R^6$ are either identical or different and, either represents one functional group chosen from the following items 1) to 5), i.e., 1) a hydrogen atom,
2) a substituted or an unsubstituted aliphatic hydrocarbon group having 1 to 10 carbon atoms fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), or, when $R^5$ and $R^6$ are bonded to each other, they represent a substituted or an unsubstituted alicyclic hydrocarbon chain having 4 to 7 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

$R^7$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, a functional group forming the acetal bond together with the oxygen atom bound to $R^7$, or, when $R^7$ and $R^5$ are bonded to each other, $R^7$ represents one portion of the bond forming the carbonyl group together with the carbon atom bonded to $R^5$ and the oxygen atom bonded to $R^7$.

In the partial structure represented by the Formula (W1) below, of the above Formula (1),

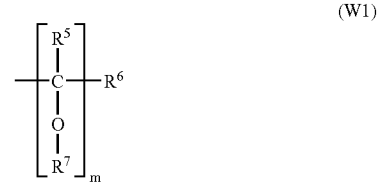

(W1)

m may be either 0 or 1. However, when W is a single bond, m is equal to 1. When m equals 1, the above Formula (1) represents Formula (W1A) below,

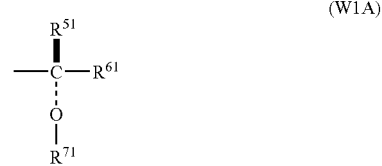

(W1A)

[In the formula, the symbol ▌ indicates that $R^{51}$ is in the β position with respect to the carbon atom it is bonded to. The symbol ⁞ indicates that the oxygen atom is in the α position with respect to the carbon atom it is bonded to.

$R^{51}$ and $R^{61}$ are either identical or different and, either represents one functional group chosen from the following items 1) to 5), i.e., 1) a hydrogen atom,
2) a substituted or an unsubstituted aliphatic hydrocarbon group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), or, when $R^{51}$ and $R^{61}$ are bonded to each other, they represent a substituted or an unsubstituted alicyclic hydrocarbon chain having 4 to 7 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

$R^{71}$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, and a functional group forming the acetal bond together with the oxygen atom bound to $R^{71}$.]

Formula (W1B) below,

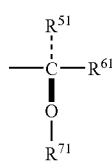

(W1B)

[In the formula, $R^{51}$, $R^{61}$ and $R^{71}$ have the same definitions as above. The symbol ▮ indicates that the oxygen is in the β position with respect to the carbon atom it is bonded to. The symbol ⋮ indicates that $R^{51}$ is in the α position with respect to the carbon atom it is bonded to.] or Formula (W1C) below,

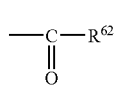

(W1C)

[In the formula, $R^{62}$ represents a functional group chosen from the following items 1] to 5], i.e., 1) a hydrogen atom,
2) a substituted or an unsubstituted aliphatic hydrocarbon group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents)].

If m equals to 0 the above Formula (W1) represents the Formula (W1D) below $$—R^{62} \quad (W1D)$$

[In the formula, $R^{62}$ has the same definition as above.]

When the above Formula (W1) represents the above Formula (W1A) or (W1B), these may be combined in any proportion.

In the above formulae(W1A), (W1B), (W1C) or (W1D), $R^{51}$, $R^{61}$ and $R^{62}$ represent one of the items 1) to 5):

1) a hydrogen atom,
2) a substituted or an unsubstituted aliphatic hydrocarbon group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 0.1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

As examples of such $R^{51}$, $R^{61}$ or $R^{62}$ which are unsubstituted aliphatic hydrocarbon groups having 1 to 10 carbon atoms, alkyl groups such as a methyl group, an ethyl group, a propyl group, an isopropyl group, a butyl group, an isobutyl group, an s-butyl group, a t-butyl group, a pentyl group, an isopentyl group, a neopentyl group, a 4-methylpentyl group, a hexyl group, a heptyl group, a 2-methylhexyl group, a 1,1-dimethylpentyl group, an octyl group, a 3,7-dimethyloctyl group, a nonyl group, and a decyl group, alkenyl groups such as a vinyl group, a 1-methylvinyl group, a 1-ethylvinyl group, a 1-propenyl group, a 2-propenyl group, a 2-methyl-1-propenyl group, a 1-butenyl group, a 2-butenyl group, a 2-methyl-1-butenyl group, a 1,3-butadienyl group, a 1-pentenyl group, a 2-pentenyl group, a 4-methyl-1-pentenyl group, a 1-hexenyl group, a 2-hexenyl group, a 3-hexenyl group, a 4-hexenyl group, a 5-hexenyl group, a 1,5-hexadienyl group, a 2-heptenyl group, a 2-octenyl group, a 2-nonenyl group, and a 2-decenyl group, and alkynyl groups such as an ethynyl group, a 1-propynyl group, a 2-propynyl group, a 1-butynyl group, a 2-methyl-1-butynyl group, a 3,3-dimethyl-1-butynyl group, a 1-pentynyl group, a 2-pentynyl group, a 3-pentynyl group, a 1-hexynyl group, a 2-hexynyl group, a 3-hexynyl group, a 4-hexynyl group, a 1-methyl-3-pentynyl group, a 1-methyl-3-hexynyl group, a 2-heptynyl group, a 2-octynyl group, a 2-nonynyl group and a 2-decynyl group may be cited. As preferred examples, a methyl group, an ethyl group, a propyl group, a butyl group, a pentyl group, a hexyl group, a heptyl group, a 2-methylhexyl group, a 1,1-dimethylpentyl group, a 1-propenyl group, a 1-butenyl group, a 2-pentenyl group, a 1-octenyl group and a 1-methyl-3-pentynyl group may be cited.

As examples of such $R^{51}$, $R^{61}$ or $R^{62}$ which are unsubstituted alicyclic hydrocarbon groups having 3 to 8 carbon atoms, a cyclopropyl group, a cyclobutyl group, a cyclopentyl group, a 1-cyclopentenyl group, a cyclohexyl group, a 1-cyclohexenyl group, a 3-cyclohexenyl group, a 4-cyclohexenyl group, a cycloheptyl group, a 1-cycloheptenyl group, and a cyclooctyl group may be cited. As preferred examples, the cyclopentyl group and the cyclohexyl group may be cited.

As examples of such $R^{51}$, $R^{61}$ or $R^{62}$ which are unsubstituted aromatic hydrocarbon groups having 6 to 10 carbon atoms, a phenyl group, a 1-naphthyl group and a 2-naphthyl group may be cited. As a preferred example, a phenyl group may be cited.

As examples of such $R^{51}$, $R^{61}$ or $R^{62}$ which are unsubstituted heterocyclic groups having 1 to 4 oxygen atoms, nitrogen atoms, or sulfur atoms in the cycle, monocyclic or bicyclic groups such as a furyl group, a thiophenyl group, a pyrrolyl group, an oxazolyl group, an isooxazolyl group, a thiazolyl group, an isothiazolyl group, an imidazolyl group, a pyrazolyl group, a triazolyl group, a tetrazolyl group, a pyranyl group, a pyridyl group, a pyrazinyl group, a pyrimidinyl group, a pyridazinyl group, a benzofuranyl group, an indolyl group, a benzimidazolyl group, a benzothiazolyl group, a benzoxazolyl group, a quinolyl group, an isoquinolyl group, a quinazolyl group, a purinyl group, a pteridinyl group, an azetidinyl group, a pyrrolidinyl group, a morpholino group, a piperidino group and a piperazinyl group may be cited. As a preferred example, a pyridyl group may be cited.

As examples of substitution groups when $R^{51}$, $R^{61}$ or $R^{62}$ is a substituted aliphatic hydrocarbon group having 1 to 10 carbon atoms, a fluorine atom, a chlorine atom, a bromine atom, an iodine atom, a hydroxyl group, alkoxy groups having 1 to 4 carbon atoms which are a methoxy group, an ethoxy group, a propoxy group, an isopropoxy group, a butoxy group, an s-butoxy group and a t-butoxy group, aryloxy groups having 6 to 10 carbon atoms which are a phenoxy group, a 1-naphthoxy group and a 2-naphthoxy group, aralkoxy groups having 7 to 9 carbon atoms such as a benzyloxy group, an α-phenethyloxy group, a β-phenethyloxy group, a phenylpropyloxy group and a cinnamyloxy group, acyloxy groups having 2 to 10 carbon atoms such as an acetoxy group, a trifluoroacetoxy group, a propionyloxy group, an isopropionyloxy group, a butyryloxy group, an isobutyryloxy group, an s-butyryloxy group, a valeryloxy group, an isovaleryloxy group, a hexanoyloxy group, a heptanoyloxy group, an octanoyloxy group, a nonanoyloxy group, a decanoyloxy group, a benzoyloxy group, a phenylacetyloxy group, a cinnamoyloxy group, a cyclopentylcarboxy group, a cyclohexylcarboxy group and a cycloheptylcarboxy group, sulfonyloxy groups having 1 to 8 carbon atoms such as a methanesulfonyloxy group, a trifluoromethanesulfonyloxy group, an ethanesulfonyloxy group, a butanesulfonyloxy group, a t-butanesulfonyloxy group, a nonafluorobutanesulfonyloxy group, a benzenesulfonyloxy group, a p-bromobenzenesulfonyloxy group, a p-toluenesulfonyloxy group, a benzylsulfonyloxy group, an α-phenethylsulfonyloxy group and a β-phenethylsulfonyloxy group, an oxo group, a carboxyl group, alkoxycarbonyl groups having 2 to 10 carbon atoms such as a methoxycarbonyl group, an ethoxycarbonyl group, a propoxycarbonyl group, an isopropoxycarbonyl group, a butoxycarbonyl group, an isobutoxycarbonyl group, an s-butoxycarbonyl group, a t-butoxycarbonyl group, a phenoxycarbonyl group, a 1-naphthoxycarbonyl group, a 2-naphthoxycarbonyl group, a benzyloxycarbonyl group, an α-phenethyloxycarbonyl group, a β-phenethyloxycarbonyl group, carbamoyl groups having 1 to 15 carbon atoms such as a carbamoyl group, an N-methylcarbamoyl group, an N-ethylcarbamoyl group, an N-propylcarbamoyl group, an N-isopropylcarbamoyl group, an N-butylcarbamoyl group, an N-isobutylcarbamoyl group, an N–s-butylcarbamoyl group, an N-t- butylcarbamoyl group, an N-pentylcarbamoyl group, an N-hexylcarbamoyl group, an N-phenylcarbamoyl group, an N-benzylcarbamoyl group, an N-phenethylcarbamoyl group, an N-cyclopropylcarbamoyl group, an N-cyclobutylcarbamoyl group, an N-cyclopentylcarbamoyl group, an N-cyclohexylcarbamoyl group, an N-cycloheptylcarbamoyl group, an N-cyclopropanemethylcarbamoyl group, an N,N-dimethylcarbamoyl group, an N,N-ethylmethylcarbamoyl group, an N,N-diethylcarbamoyl group, an N,N-dipropylcarbamoyl group, an N,N-dibutylcarbamoyl group, an N,N-dicyclohexylcarbamoyl group, an N,N-diphenylcarbamoyl group, and an N,N-dibenzylcarbamoyl group, amino groups having 0 to 14 carbon atoms such as an amino group, a methylamino group, an ethylamino group, a propylamino group, an isopropylamino group, a butylamino group, an isobutylamino group, an s-butylamino group, a t-butylamino group, a pentylamino group, an hexylamino group, an heptylamino group, an octylamino group, a nonylamino group, a decylamino group, a phenylamino group, a benzylamino group, a phenethylamino group, a cyclopropylamino group, a cyclobutylamino group, a cyclopentylamino group, a cyclohexylamino group, a cycloheptylamino group, a cyclooctylamino group, a cyclopropanemethylamino group, a dimethylamino group, an N-methylamino group, a diethylamino group, an N-methylpropylamino group, an N-methylisopropylamino group, an N-methylbutylamino group, an N-methyl-t-butylamino group, an N-ethylisopropylamino group, a dipropylamino group, a diisopropylamino group, an ethylbutylamino group, an N-methylhexylamino group, a dibutylamino group, a dipentylamino group, a dicyclohexylamino group, a diphenylamino group, a dibenzylamino group a piperidino group and a morpholino group, acylamino groups having 1 to 10 carbon atoms such as a formylamino group, an acetylamino group, a trifluoroacetylamino group, a propionylamino group, a butyrylamino group, an isobutyrylamino group, a valerylamino group, an hexanoylamino group, a benzoylamino group, a phenylacetylamino group, a phenylpropionylamino group, and a cinnamoylamino group, sulfonylamino groups having 1 to 8 carbon atoms such as a methanesulfonylamino group, a trifluoromethanesulfonylamino group, an ethanesulfonylamino group, a butanesulfonylamino group, a t-butanesulfonylamino group, a nonafluorobutanesulfonylamino group, a benzenesulfonylamino group, a p-bromobenzenesulfonylamino group, a p-toluenesulfonylamino group, a benzylsulfonylamino group, an α-phenethylsulfonylamino group and a β-phenethylsulfonylamino group, imino groups having 1 to 10 carbon atoms such as a methylimino group, an ethylimino group, a propylimino group, an isopropylimino group, a butylimino group, an isobutylimino group, a pentylimino group, an hexylimino group, an heptylimino group, an octylimino group, a nonylimino group, a decylimino group, a phenylimino group, a benzylimino group, a phenethylimino group, a cyclopropylimino group, a cyclobutylimino group, a cyclopentylimino group, a cyclohexylimino group, and a cycloheptylimino group, a cyano group, a nitro group, sulfide groups having 1 to 6 carbon atoms such as a methylthio group, an ethylthio group, a propylthio group, an isopropylthio group, a butylthio group, an isobutylthio group, an s-butylthio group, a t-butylthio group, a pentylthio group, an hexylthio group, a phenylthio group, a cyclopentylthio group and a cyclohexylthio group, sulfinyl groups having 1 to 6 carbon atoms such as a methylsulfinyl group, an ethylsulfinyl group, a propylsulfinyl group, an isopropylsulfinyl group, a butylsulfinyl group, an isobutylsulfinyl group, an s-butylsulfinyl group, a t-butylsulfinyl group, a pentylsulfinyl group, a hexylsulfinyl group, a phenylsulfinyl group, a cyclopentylsulfinyl group, and a cyclohexylsulfinyl group, sulfonyl groups having 1 to 6 carbon atoms such as a methylsulfonyl group, an ethylsulfonyl group, a propylsulfonyl group, an isopropylsulfonyl group, a butylsulfonyl group, an isobutylsulfonyl group, an s-butylsulfonyl group, a t-butylsulfonyl group, a pentylsulfonyl group, a hexylsulfonyl group, a phenylsulfonyl group, a cyclopentylsulfonyl group and a cyclohexylsulfonyl group, a substituted or unsubstituted alicyclic hydrocarbon group having 3 to 8 carbon atoms (in addition to the same examples as the examples chosen among the examples indicated as examples of substitution group in the case of the previously-mentioned aliphatic hydrocarbon group having 1 to 10 carbon atoms, aliphatic hydrocarbon groups having 1 to 6 carbon atoms which are a methyl group, an ethyl group, a propyl group, an isopropyl group, a butyl group, an isobutyl group, an s-butyl group, an t-butyl group, a pentyl group, a hexyl group, a 2-propenyl group, a 1-butenyl group, a 2-butenyl group, a 2-pentenyl group, a 3-pentenyl group, a 2-hexenyl group, a 3-hexenyl group, a 4-hexenyl group, a 2-butynyl group, a 2-pentynyl group, a 3-pentynyl group, a 2-hexynyl group and a 3-hexynyl group, acyl groups having 1 to 10 carbon atoms such as a formyl group, an acetyl group, a trifluoroacetyl group, a propionyl group, a butyryl group, an isobutyryl group, a valeryl group, an hexanoyl group, a benzoyl group, a phenylacetyl group, a phenylpropionyl group and a cinnamoyl group may be cited as examples of substitution groups for such an alicyclic hydrocarbon group having 3 to 8 carbon atoms), a substituted or unsubstituted aromatic hydrocarbon group having 6 to 10 carbon atoms (in addition to the same examples as the examples chosen among the examples indicated as examples of substitution groups in the case of the previously-mentioned aliphatic hydrocarbon group having 1 to 10 carbon atoms, and in the case of the previously-mentioned alicyclic hydrocarbon group having 3 to 8 carbon atoms, alkyl groups having 1 to 4 carbon atoms which are a methyl group, an ethyl group, a propyl group, an isopropyl group, a butyl group, an isobutyl group, an s-butyl group and a t-butyl group may be cited as substitution examples for such aromatic hydrocarbon groups having 6 to 10 carbon atoms), a substituted or unsubstituted heterocyclic group having 1 to 4 oxygen atoms, nitrogen atoms, or sulfur atoms in the cycle (the same examples as the examples chosen among the examples indicated as examples of substitution groups in the case of the previously-mentioned aliphatic hydrocarbon group having 1 to 10 carbon atoms, and in the case of the previously-mentioned alicyclic hydrocarbon group having 3 to 8 carbon atoms may be cited as substitution examples of such a heteocyclic group) may be cited. As preferred examples of such substitution groups for aliphatic hydrocarbon groups having 1 to 10 carbon atoms, a fluorine atom, a hydroxyl group, a phenyl group, a tolyl group, a 4-methoxyphenyl group, a 4-dimethylaminophenyl group, a phenoxy group, a 3,5-dichlorophenoxy group, a cyclopentyl group, a cyclohexyl group, a 3-ethylcyclopentyl group and a phenylsulfonyl group may be cited.

As examples of substitution groups when $R^{51}$, $R^{61}$ or $R^{62}$ are substituted alicyclic hydrocarbon groups having 3 to 8 carbon atoms, the same example as the examples chosen among the examples given for the above-mentioned substituted aliphatic hydrocarbon group having 1 to 10 carbon atoms may be cited. As preferred examples of substitution groups for such alicyclic hydrocarbon groups having 3 to 8 carbon atoms, a methyl group, an ethyl group, a propyl group, a hydroxyl group, a methoxy group and an ethoxy group may be cited.

As examples of substitution groups when $R^{51}$, $R^{61}$ or $R^{62}$ are substituted aromatic hydrocarbon groups having 6 to 10 carbon atoms, the same example as the examples chosen among the examples given for the above-mentioned substituted aliphatic hydrocarbon group having 1 to 10 carbon atoms may be cited. As preferred examples of substitution groups for aromatic hydrocarbon groups having 6 to 10 carbon atoms, a methyl group, an ethyl group, a propyl group, a hydroxyl group, a methoxy group, an ethoxy group, a fluorine atom, a chlorine atom, a bromine atom and an iodine atom may be cited.

As examples of substitution groups when $R^{51}$, $R^{61}$ or $R^{62}$ are substituted heterocyclic groups having 1 to 4 oxygen atoms, nitrogen atoms, or sulfur atoms in the cycle, the same examples as the examples chosen among the examples given for the above-mentioned substituted aliphatic hydrocarbon group having 1 to 10 carbon atoms may be cited. As preferred examples of substitution groups for such heterocyclic groups having 1 to 4 oxygen atoms, nitrogen atoms, or sulfur atoms in the cycle, a methyl group, an ethyl group, a propyl group, a hydroxyl group, a methoxy group and an ethoxy group may be cited.

In addition, in the above Formula (W1A) or Formula (W1B), $R^{51}$ and $R^{61}$ are bonded to each other, and represent a substituted or an unsubstituted alicyclic hydrocarbon chain having 4 to 7 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

As examples of such unsubstituted alicyclic hydrocarbon chains having 4 to 7 carbon atoms, tetramethylene group, pentamethylene group, hexamethylene group and heptamethylene group may be cited. As preferred examples the tetramethylene group and the pentamethylene group may be cited.

As examples of substitution groups wherein $R^{51}$ and $R^{61}$ are bonded to each other and form a substituted alicyclic hydrocarbon chain having 4 to 7 carbon atoms, the same examples as the examples chosen among the examples given for the above-mentioned substituted aliphatic hydrocarbon group having 1 to 10 carbon atoms may be cited. As preferred examples of substitution groups for such groups forming an alicyclic hydrocarbon chain having 4 to 7 carbon atoms, a methyl group, an ethyl group, a propyl group, a hydroxyl group, a methoxy group and an ethoxy may be cited.

In the above Formula (W1A) or Formula (W1B), $R^{71}$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, a functional group forming the acetal bond together with the oxygen atom bound to $R^{71}$.

As examples of such acyl groups having 2 to 10 carbon atoms, an acetyl group, a trifluoroacetyl group, a propionyl group, a butyryl group, an isobutyryl group, a valeryl group, an hexanoyl group, a benzoyl group, a phenylacetyl group, a phenylpropionyl group and a cinnamoly group may be cited. As preferred examples an acetyl group and a benzoyl group may be cited. As examples of tri(hydrocarbon group having 1 to 7 carbon atoms) silyl group, a trimethylsilyl group, a triethylsilyl group, a dimethylisopropyls group, a dimethylhexylsilyl group, a t-butyldimethylsilyl group, a triisopropylsilyl group, a t-butyldiphenylsilyl group and a tribenzylsilyl group may be cited. As preferred examples, a trimethylsilyl group, a triethylsilyl group and a t-butyldimethylsilyl group may be cited.

As examples of alkoxycarbonyl groups having 2 to 5 carbon atoms, a methoxycarbonyl group, an ethoxycarbonyl group, a propoxycarbonyl group, an isopropoxycarbonyl group, a butoxycarbonyl group, a s-butoxycarbonyl group and a t-butoxycarbonyl group may be cited. As preferred examples, a methoxycarbonyl group and an ethoxycarbonyl group may be cited.

As examples of sulfonyl groups having 1 to 8 carbon atoms, a methanesulfonyl group, a trifluoromethanesulfonyl group, an ethanesulfonyl group, a butanesulfonyl group, a t-butanesulfonyl group, a nonafluorobutanesulfonyl group, a benzenesulfonyl group, a p-bromobenzenesulfonyl group, a p-toluenesulfonyl group, a benzylsulfonyl group, an α-phenethylsulfonylamino group, and a β-phenethylsulfonylamino group may be cited. As preferred examples a methanesulfonyl group and a trifluoromethanesulfonyl group may be cited.

As examples of functional groups forming the acetal bond together with the oxygen atom bound to $R^{71}$ a methoxymethyl group, a 1-ethoxyethyl group, a 1-methoxy-1-methylethyl group, a 2-ethoxy-1-methylethyl group, a 2-methoxyethoxymethyl group, a tetrahydropyrane-2-yl group, a 6,6-dimethyl-3-oxa-2-oxo-bicyclo[3.1.0]hexane-4-yl group may be cited. As preferred examples, a methoxymethyl group, a 2-methoxyethoxymethyl group and a tetrahydropyran-2-yl group may be cited. As particularly preferred such functional groups for $R^{71}$, a hydrogen atom, an acetyl group, a trimethylsilyl group, a t-butyldimethylsilyl group and a tetrahydropyran-2-yl may be cited.

As such preferred examples of the above Formula (W1), the items 1) to 6) shown below may be cited.

1) a hydrogen atom,
2) a hydroxymethy group, a formyl group, a methanesulfonyloxymehyl group, a methoxycarbonyloxymethyl group, a methyl group, an ethyl group, a propyl group, a butyl group, a pentyl group, a hexyl group, a heptyl group, an octyl group, a cyclopentyl group, a cyclohexyl group, a cycloheptyl group, a phenyl group, an o-tolyl group, an m-tolyl group, a p-tolyl group, a 4-methoxyphenyl group, an 4-N,N-dimethylaminophenyl group, a 3-chlorophenyl group, a 4-chlorophenyl group, a 4-fluorophenyl group, a 4-bromophenyl group, 3,5-dichlorophenyl group, a benzyl group, an α-phenethyl group, a β-phenethyl group, an o-tolylmethyl group, an m-tolylmethyl group, a p-tolylmethyl group, a 3-ethylphenyl group, a 4-ethylphenyl group, a 3-propylphenyl group, a 2-(o-tolyl)ethyl group, a 2-(m-tolyl)ethyl group, a 2-(p-tolyl)ethyl group, a 3-(o-tolyl)propyl group, a 3-(m-tolyl)propyl group, a 3-(p-tolyl)propyl group, a 1,1-bis(phenylsulfonyl)-2-(o-tolyl)ethyl group, a 1,1-bis(phenylsulfonyl)-2-(m-tolyl)ethyl group, a 1,1-bis(phenylsulfonyl)-2-(p-tolyl)ethyl group, a 1,1-bis(phenylsulfonyl)-2-(o-tolyl)propyl group, a 1,1-bis(phenylsulfonyl)-2-(m-tolyl)propyl group, a 1,1-bis(phenylsulfonyl)-2-(p-tolyl)propyl group,
3) a 1-hydroxypentyl group, a 1-hydroxyhexyl group, a 1-hydroxyheptyl group, a 1-hydroxyoctyl group, a 1-hydroxy-1-methylpentyl group, a 1-hydroxy-1-ethylpentyl group, a 1-hydroxy-1-vinylpentyl group, a 1-hydroxy-1-methylhexyl group, a 1-hydroxy-1-ethylhexyl group, a 1-hydroxy-3-methylhexyl group, 1-hydroxy-2-butyl-2-propene group, a 1-hydroxy-2-methylhexyl group, a 1-hydroxy-2-fluorohexyl group, a 1-hydroxy-2,2-dimethylhexyl group, a 1 hydroxy-3-ethoxy-2,2-dimethylpropane group, a 1-hydroxy-2,2-difluorohexyl group, a 1-hydroxy-2,2,6-trimethylheptyl group, a 1-hydroxy-2-fluoro-1-methyloctyl group, a 1-hydroxyhexa-3-enyl group, a 1-hydroxy-5-methylhexa-4-enyl group, a 1-hydroxy-2,5-dimethylhexa-4-enyl group, a 1-hydroxy-3,7-dimethylhexa-4-enyl group, a 1-hydroxy-2,2,5-trimethylhexa-4-enyl group, 1-hydroxy-2,2-dimethylpenta-3-ynyl group, a 1-hydroxy-2,2-dimethylpenta-3-ynyl group, a 1-hydroxy-hexa-4-ynyl group, a 1-hydroxy-2-methylhexa-4-ynyl group, a 1-hydroxy-2,2-dimethylhexa-4-ynyl group, a 1-hydroxy-2-methylhepta-4-ynyl group, a 1-hydroxy-4-cyclopropyl-2-methylbutyl group, a 1-hydroxy-2-cyclopentylethyl group, a 1-hydroxy-2-cyclohexylethyl group, a 1-hydroxy-2-phenylethyl group, a 1-hydroxy-2-phenylpropy group, a 1-hydroxy-1-(o-tolyl)methyl group, a 1-hydroxy-1-(m-tolyl)methyl group, a 1-hydroxy-1-(p-tolyl)methyl group, a 1-hydroxy-1-(3-ethylphenyl)methyl group, a 1-hydroxy-1-(4-ethylphenyl)methyl group, a 1-hydroxy-1-(3-propylphenyl)methyl group, a 1-hydroxy-2(o-tolyl)ethyl group, a 1-hydroxy-2-(m-tolyl)ethyl group, a 1-hydroxy-2-(p-tolyl)ethyl group, a 1-hydroxy-3-(o-tolyl)propyl group, a 1-hydroxy-3-(m-tolyl)propyl group, a 1-hydroxy-3-(p-tolyl)propyl group, a 1-hydroxy-4-(o-tolyl)butyl group, a 1-hydroxy-4-(m-tolyl)butyl group, a 1-hydroxy-4-(p-tolyl)butyl group, a 1-hydroxy-2-(3-chlorophenyl)ethyl group, a 1-hydroxy-2-phenoxyethyl group, a 1-hydroxy-2-(4-fluorophenoxy)ethyl group, a 1-hydroxy-2-(3-chloropheoxyl)ethyl group, a 1-hydroxy-1-cyclopentylmethyl group, a 1-hydroxy-1-cyclohexylmethyl group, a 1-hydroxy-1-cyclopentylethyl group, a 1-hydroxy-[(4-cyclohexenyl)methyl group, a 1-hydroxy-1-(3-ethylcyclopentyl)methyl group, a 1-hydroxy-1-(2-methylcyclopentyl)methyl group, a 1-hydroxy-1-(2-methylcyclohexyl)methyl group, a 1-hydroxy-1-(3-methylcyclohexyl)methyl group, a 1-hydroxy-1-(4-methylcyclohexyl)methyl group, a 1-hydroxy-1-(2,2,4-trimethylcyclohexyl)methyl group, a 1-hydroxy-1-(1-(2-butynyl) cyclobutyl)methyl group, a 1-hydroxy-1-(1-(2-pentynyl)cyclobutyl)methyl group, a 1-hydroxy-1-phenylmethyl group, a 1-hydroxy-1-(4-chlorophenyl)methyl group, a 1-hydroxy-1-(4-bromophenyl)methyl group, a 1-hydroxy-1-(3-chlorophenyl)methyl group, a 1-hydroxy-1-(4-methoxyphenyl)methyl group, a 1-hydroxy-1-(4-N,N-dimetylaminophenyl)methyl group, a 1-hydroxy-1-(1-naphthyl)methyl group, a 1-hydroxy-1-(2-naphthyl)methyl group, 4) a functional group described in 3) above, wherein the hydroxy group has been substituted for an acetyloxy group, a benzoyloxy group, a trimethylsilyloxy group, a t-butyldimethylsilyloxy group, a tetrahydropyrane-2-yloxy group or a methanesulfonyloxy group, 5) a pentanoyl group, a hexanoyl group, a heptanoyl group, an octanoyl group, a 3-methylhexanoyl group, a 2-methylhexanoyl group, a 2,2-dimethylhexanoyl group, a 2,2,6-trimethylheptanoyl group, a 3-hexenoyl group, a 5-methyl-4-hexenoyl group, a 2,5-dimethyl-4-hexenoyl group, a 3,7-dimethyl-6-octenoyl group, a 2,2,5-trimethyl-4-hexenoyl group, a 3-pentynoyl group, a 2,2-dimethyl-3-pentynoyl group, a 4-hexynoyl group, a 2-methyl-4-hexynoyl group, a 2,2-dimethyl-4-hexynoyl group, a 2-methyl-4-heptynoyl group, a 4-cyclopropyl-2-methylbutanoyl group, a cyclopentylacetyl group, a cyclohexylacetyl group, a 2-phenylacetyl group, a 3-phenylpropanoyl group, a 2-methylbenzoyl group, a 3-methylbenzoyl group, a 4-methylbenzoyl group, a 3-ethylbenzoyl group, a 4-ethylbenzoyl group, a 3-propylbenzoyl group, an (o-tolyl)acetyl group, an (m-tolyl)acetyl group, a (p-tolyl)acetyl group, 3-(o-tolyl)propanoyl group, a 3-(m-tolyl)propanoyl group, a 3-(p-tolyl)propanoyl group, a 4-(o-tolyl)butanoyl group, a 4-(m-tolyl)butanoyl group, a 4-(p-tolyl)butanoyl group, a (3-chlorophenyl)acetyl group, a cyclopentylcarbonyl group, a cyclohexylcarbonyl group, a 3-ethylcyclopentylcarbonyl group, a 2-methylcyclopentylcarbonyl group, a 2-methylcyclohexylcarbonyl group, a 3-methylcyclohexylcarbonyl group, a 4-methylcyclohexylcarbonyl group, a benzoyl group, a 4-chlorobenzoyl group, a 4-bromobenzoyl group, a 3-chlorobenzoyl group, a 4-methoxybenzoyl group, a 4-N,N-dimethylaminobenzoyl group, a 1-naphthylcarbonyl group, a 2-naphthylcarbonyl group, 6) a 1-pentenyl group, a 1-hexenyl group, a 1-heptenyl group, a 1-octenyl group, a 2-methylhexene-1-yl group, a 2-ethylhexene-1-yl group, a 2-methylheptene-1-yl group, a 2-ethylheptene-1-yl group, a 1-methylhexene-1-yl group, a 1-ethylhexene-1-yl group, a 3-methylhexene-1-yl group, a 1,3-hexadiene-1-yl group, a 5-methyl-1,4-hexadiene-1-yl group, a 2,5-dimethyl-1,4-hexadiene-1-yl group, a 3,7-dimethyl-1,6-octadiene-1-yl group, a penta-3-yn-1-en-1-yl group, a hexa-4-yn-1-en-1-yl group, a 2-methylhexa-4-yn-1-en-1-yl group, a 2-methylhepta-4-yn-1-en-1-yl group, a 4-cyclopropyl-2-methyl-1-butene-1-yl group, a 2-cyclopentylvinyl group, a 2-cyclohexylvinyl group, a 2-phenylvinyl, a 3-phenyl-1-propene-1-yl group, a 2-(o-tolyl)vinyl group, a 2-(m-tolyl)vinyl group, a 2-(p-tolyl)vinyl group, a 3-(o-tolyl)-1-propene-1-yl group, a 3-(m-tolyl)-1-propene-1-yl group, a 3-(p-tolyl)-1-propene-1-yl group, a 4-(o-tolyl)-1-butene-1-yl group, a 4-(m-tolyl)-1-butene-1-yl group, a 4-(p-tolyl)-1-butene-1-yl group, a 2-(3-ethylphenyl)vinyl group, a 2-(4-ethylphenyl)vinyl group, a 2-(3-propylphenyl)vinyl group, a 2-(3-chlorophenyl)vinyl group, a 2-(4-chlorophenyl)vinyl group, a 2-(4-methoxyphenyl)vinyl group, a 2-(4-N,N-dimethylaminophenyl)vinyl group.

In the above Formula (1) $A^2$ represents a single bond, a Formula (A2A) shown below, a Formula (A2B) shown below or a Formula (A2C) shown below.

(A2A)

(A2B)

[In the formula, $R^3$ represents a hydrogen atom, an alkyl group having 1 to 4 carbon atoms, or an acyl group having 1 to 10 carbon atoms.]

(A2C)

[In the formula, n represents 0, 1, or 2.]

In the above Formula (A2B), $R^3$ represents a hydrogen atom, an alkyl group having 1 to 4 carbon atoms, or an acyl group having 1 to 10 carbon atoms.

As examples of $R^3$ which are alkyl groups having 1 to 4 carbon atoms, a methyl group, an ethyl group, a propyl group, an isopropyl group, a butyl group, an isobutyl group, an s-butyl group and a t-butyl group may be cited. As examples of $R^3$ which are acyl groups having 1 to 10 carbon atoms, a formyl group, an acetyl group, a trifluoroacetyl group, a propionyl group, a butyryl group, an isobutyryl group, a valeryl group, an hexanoyl group, a benzoyl group, a phenylacetyl group, a phenylpropionyl group and a cinnamoly group may be cited. As preferred examples of such an $R^3$, a hydrogen atom, a methyl group, a formyl group and an acetyl group may be cited.

In the above Formula (A2C), n represents 0, 1, or 2. However, 0 may be cited as the preferred value for n.

A single bond, —O—, —NH—, —N(CH$_3$)— and —S— may be cited as such preferred functional groups for $A^2$.

In the above Formula (1), $A^1$ represents the items 1) or 2) below
1) a single bond
2) a functional group which bridges G and $A^2$ through an identical atom or through different atoms, and chosen from a group consisting of an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

Examples of such $A^1$ which are aliphatic hydrocarbon groups having 1 to 3 carbon atoms, are functional groups derived by removing hydrogen atoms from the same carbon atom or two different carbon atoms of a methane, an ethene, a propane, an ethene, a propene, an acetylene or a propyne: when G and $A^1$ are bonded through a single bond, $A^1$ is a bivalent functional group derived by removing one hydrogen atom for each bond; when G and $A^1$ are bonded through a double bond, $A^1$ is a trivalent functional group derived by removing one hydrogen atom for one bond and two hydrogens for the other bond. As preferred examples of such bivalent functional groups, —CH$_2$—, —(CH$_2$)$_2$—, —CH(CH$_3$)—, —(CH$_2$)$_3$—, —C(CH$_3$)$_2$—, —CH=CH—, —CH=CHCH$_2$—, —CH=C(CH$_3$)—, —C≡C— and —C≡CCH$_2$— may be cited, and as preferred examples of such trivalent functional groups, =CH—, =CHCH$_2$—, =C(CH$_3$)—, =CH(CH$_2$)$_2$—, =CHCH=CH— and =CH—CH(CH$_3$)— may be cited.

As examples of $A^1$ which are alicyclic hydrocarbon groups having 3 to 8 carbon atoms, are functional groups derived from a cyclopropane, a cyclobutane, a cyclopentane, a cyclopentene, a cyclohexane, a cyclohexene, a cycloheptane and a cyclooctane by removing hydrogen atoms on the same carbon atom or two different carbon atoms: when G and $A^1$ are bonded through a single bond, $A^1$ is a bivalent functional group derived by removing one hydrogen atom for each bond; when G and $A^1$ are bonded through a double bond, $A^1$ is a trivalent functional group derived by removing one hydrogen atom for one bond and two hydrogens for the other bond. As preferred examples of such bivalent functional groups, a 1,2-cyclopropylene group, a cyclopropylydene group, a 1,2-cyclopentylene group, a 1,3-cyclopentylene group, a 1,2-cyclohexylene group, a 1,3-cyclohexylene group, a 1,4-cyclohexylene may be cited, and as a preferred example of such a trivalent functional group, a 1-cyclohexyl-4-ylidedene group may be cited.

As examples of $A^1$ which are heterocyclic groups having between 1 and 2 oxygen atoms, nitrogen atoms, or sulfur atoms, bivalent functional groups derived by removing one hydrogen atom from each of two different carbon atoms such as a furan cycle, a thiofuran cycle, a pyrrole cycle, an oxazole cycle, an isooxazole cycle, a thiazole cycle, an isothioazole cycle, an imidazole cycle, a pyrazole cycle, a pyran group, a pyridine cycle, a pyrazine cycle, a pyrimidine cycle, a pyridazine cycle, an azetidine cycle, a pyrrolidine cycle, a piperidine cycle, a piperazine cycle and a morpholine cycle may be cited. As preferred functional group for such an $A^1$, the bond representing a single bond, —CH$_2$—, —(CH$_2$)$_2$—, =CH— and =CHCH$_2$— may be cited.

In the above Formula (1), $A^3$ represents the items 1) or 2) below
1) a single bond
2) a functional group which bridges $A^2$ and $A^4$ through an identical atom or through different atoms, and chosen from a group consisting of an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

As examples of such $A^3$ which are aliphatic hydrocarbon groups having 1 to 3 carbon atoms, alicyclic hydrocarbon groups having 3 to 8 carbon atoms, or heterocycles and which have heterocyclic groups having between 1 and 2 oxygen atoms, nitrogen atoms, or sulfur atoms, among the examples given in the above-mentioned $A^1$, the examples given as bivalent functional groups may be may be cited. As particularly preferred functional groups for such $A^3$, the bond representing a single bond; —CH$_2$—, —(CH$_2$)$_2$—, —CH=CH— and a phenylene group may be cited.

In the above Formula (1), $A^4$ represents either of the items 1) to 4) below
1) a single bond
2) a carbonyl group
3) an aliphatic hydrocarbon group having 1 to 3 carbon atoms, which bridges the nitrogen atom, bonded to $R^1$ and $R^2$, and $A^3$ through an identical atom or through different atoms.
4) when $A^4$ and $R^1$ are bonded to each other, a functional group forming a 5 to 8 membered ring together with the nitrogen atom they are bonded to (when $A^4$ or $R^1$ and the nitrogen atom they are bonded to are bonded through a double bond, $R^2$ represents the bond between $A^4$ or $R^1$ and the nitrogen atom.)

When $A^4$ represents an aliphatic hydrocarbon group having 1 to 3 carbon atoms, which bridges the nitrogen atom, bonded to $R^1$ and $R^2$, and $A^3$ through an identical atom or through different atoms, such as an aliphatic hydrocarbon group having 1 to 3 carbon atoms is a bivalent functional group derived by removing one hydrogen atom for each bond, from the same carbon atom or two different carbon atoms of a methane, a methene, a propane or a propene. As preferred examples of such $A^4$ which are aliphatic hydrocarbon groups having 1 to 3 carbon atoms, —CH$_2$—, —(CH$_2$)$_2$—, —CH(CH$_3$)—, —(CH$_2$)$_3$—, —C(CH$_3$)$_2$— and —CH=CHCH$_2$— may be cited.

When $A^4$ represents a functional group wherein $A^4$ and $R^1$ are bonded to each other forming a 5 to 8 membered ring together with the nitrogen atom they are bonded to, as examples of such functional groups forming 5 to 8 membered rings, monovalent functional groups derived by removing one hydrogen atom from one carbone atom of a pyrrole cycle, an oxazole cycle, an isooxazole cycle, a thiazole cycle, an isothioazole cycle, a pyrazole cycle, a pyridine cycle, a pyrazine cycle, a pyrimidine cycle, a pyridazine cycle, an azetidine cycle, a pyrrolidine cycle, a piperidine cycle, a piperazine cycle and a morpholine cycle may be cited. When $A^4$ or $R^1$ and the nitrogen atom they are bonded to are bonded through a double bond, in other words, when forming a cycle, for example, such as an oxazole cycle, an isooxazole cycle, a thiazole cycle, an isothioazole cycle, an imidazole cycle, a pyrazole cycle, a pyridine cycle, a pyrazine cycle, a pyrimidine cycle and a pyridazine cycle with $A^4$, $R^1$ and the nitrogen atom they are bonded to, $R^2$ represents a bond between $A^4$ or $R^1$, and the nitrogen atom. As preferred examples of such functional groups forming 5 to 8 membered rings, a 2-pyrrolidinyl group, a 2-piperidinyl group, a 3-piperidinyl group, a 4-piperidinyl group, a 2-piperazinyl group, a 2-morpholinyl group, a 2-pyridyl group, a 3-pyridyl group and a 4-pyridyl group may be cited.

As particularly preferred examples of such a functional group for $A^4$, the bond representing a single bond, a carbonyl group, —CH$_2$— and —(CH$_2$)$_2$— may be cited. In addition, when representing a functional group wherein $A^4$ and $R^1$ are bonded to each other forming a 5 to 8 membered ring together with the nitrogen atom they are bonded to, as particularly preferred examples, a 2-pyridyl group, a 4-pyridyl group and a 4-piperidinyl group may be cited.

In the above Formula (1), the combination of functional groups $A^1$, $A^2$, $A^3$ and $A^4$, represented by Formula (A) below,

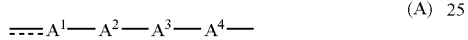
(A)

[In Formula (A), $A^1$, $A^2$, $A^3$, $A^4$, and the symbol ═══ have the same definition as above.] $A^1$, $A^2$, $A^3$ and $A^4$ may not simultaneously represent bonds. In addition, when $A^2$ represents one of the Formula (A2A), Formula (A2B) or Formula (A2C), $A^2$ and the nitrogen atom bonded to $R^1$ and $R^2$ must be bonded with more than two carbon atoms in between. As preferred examples of such functional groups, —(CH$_2$)$_3$—, —(CH$_2$)$_4$—, —(CH$_2$)$_5$—, ═CH(CH$_2$)$_2$—, ═CH(CH$_2$)$_3$—, ═CH(CH$_2$)$_4$—, —CH$_2$CH═CHCH$_2$—, —NH(CH$_2$)$_2$—, —NH(CH$_2$)$_3$—, —NH(CH$_2$)$_4$—, —N(CH$_3$)(CH$_2$)$_3$—, —CH$_2$NH(CH$_2$)$_2$—, —O(CH$_2$)$_3$—, —CH$_2$O(CH$_2$)$_2$—, —S(CH$_2$)$_3$—, —CH$_2$S(CH$_2$)$_2$—, -(o-phenylene)-, -(m-phenylene)-, -(p-phenylene)-, —CH$_2$—(o-phenylene)-, —CH$_2$—(m-phenylene)-, —CH$_2$—(p-phenylene)-, —(CH$_2$)$_2$-(o-phenylene)-, —(CH$_2$)$_2$-(m-phenylene)-, —(CH$_2$)$_2$-(p-phenylene)-, -(o-phenylene)-CH$_2$—, -(m-phenylene)-CH$_2$—, -(p-phenylene)-CH$_2$—, -(o-phenylene)-(CH$_2$)$_2$—, -(m-phenylene)-(CH$_2$)$_2$—, -(p-phenylene)-(CH$_2$)$_2$—, —CH$_2$— (o-phenylene)-CH$_2$—, —CH$_2$— (m-phenylene)-CH$_2$—, —CH$_2$—(p-phenylene)-CH$_2$—, —(CH$_2$)$_2$CO—, —(CH$_2$)$_3$CO—, —(CH$_2$)$_4$CO—, ═CHCH$_2$CO—, ═CH(CH$_2$)$_2$CO—, ═CH(CH$_2$)$_3$CO—, —CH$_2$CH═CHCO—, —NHCH$_2$CO—, —NH(CH$_2$)$_2$CO—, —NH(CH$_2$)$_3$CO—, —N(CH$_3$)(CH$_2$)$_2$CO—, —CH$_2$NHCH$_2$CO—, —O(CH$_2$)$_2$CO—, —CH$_2$OCH$_2$CO—, —S(CH$_2$)$_2$CO—, —CH$_2$SCH$_2$CO—, -(o-phenylene)-CO—, -(m-phenylene)-CO—, -(p-phenylene)-CO—, —CH$_2$— (o-phenylene)-CO—, -(o-phenylene)-CH$_2$CO—, -(m-phenylene)-CH$_2$CO—, -(p-phenylene)-CH$_2$CO—, —CH$_2$— (m-phenylene)-CO— and —CH$_2$— (p-phenylene)-CO— may be cited.

In the above Formula (1), $R^1$ and $R^2$ may be identical or different and represent one of the items 1) to 7) shown below.

1) a hydrogen atom,
2) a substituted or an unsubstituted alkyl group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, phenyl group, and, heterocyclic group (containing 1 to 4 oxygen atoms, nitrogen atoms, or sulfur atoms) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents)

6) an acyl group having 1 to 10 carbon atoms when $A^4$ is not a carbonyl group, 7) a sulfonyl group having 1 to 8 carbon atoms when $A^4$ is not a carbonyl group (however, when either $R^1$ or $R^2$ represents a sulfonyl group having 1 to 8 carbon atoms, the other may neither be an acyl group having 1 to 10 carbon atoms nor a sulfonyl group having 1 to 8 carbon atoms), or, when $R^1$ and $R^2$ are bonded together, they represent a functional group forming a cyclic amino group having 4 to 8 carbon atoms together with the nitrogen atom they are bonded to (for said cyclic amino group having 4 to 8 carbon atoms, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

As examples of such $R^1$ and $R^2$ which are unsubstituted alkyl groups having 1 to 10 carbon atoms, a methyl group, an ethyl group, a propyl group, an isopropyl group, a butyl group, an isobutyl group, an s-butyl group, an t-butyl group, a pentyl group, an isopentyl group, a neopentyl group, a hexyl group, a heptyl group, an octyl group, a nonyl group and a decyl group may be cited.

As examples of unsubstituted cycloalkyl groups having 3 to 8 carbon atoms, a cyclopropyl group, a cyclobutyl group, a cyclopentyl group, a cyclohexyl group, a cycloheptyl group and a cyclooctyl group may be cited.

As examples of unsubstituted heterocycles, monocyclic or bicyclic functional groups such as a furyl group, a thiophenyl group, a pyrrolyl group, an oxazolyl group, an isooxazolyl group, a thiazolyl group, an isothiazolyl group, an imidazolyl group, a pyrazolyl group, a triazolyl group, a tetrazolyl group, a pyranyl group, a pyridyl group, a pyrazinyl group, a pyrimidinyl group, a pyridazinyl group, a benzofuranyl group, an indolyl group, a benzimidazolyl group, a benzothiazolyl group, a benzoxazolyl group, a quinolyl group, an isoquinolyl group, a quinazolyl group, a purinyl group, a pteridinyl group, an azetidinyl group, a pyrrolidinyl group, a morpholino group, a piperidino group and pyperazinyl may be cited.

As examples of substitution groups when $R^{51}$, $R^{61}$ or $R^{62}$ is a substituted aliphatic hydrocarbon group having 1 to 10 carbon atoms, a fluorine atom, a chlorine atom, a bromine atom, an iodine atom, a hydroxyl group, alkoxy groups having 1 to 4 carbon atoms which are a methoxy group, an ethoxy group, a propoxy group, an isopropoxy group, a butoxy group, an s-butoxy group and a t-butoxy group, aryloxy groups having 6 to 10 carbon atoms which are a phenoxy group, a 1-naphthoxy group and a 2-naphthoxy group, aralkoxy groups having 7 to 9 carbon atoms such as a benzyloxy group, an α-phenethyloxy group, a β-phenethyloxy group, a phenylpropyloxy group and a cinnamyloxy group, acyloxy groups having 2 to 10 carbon atoms such as an acetoxy group, a trifluoroacetoxy group, a propionyloxy group, an isopropionyloxy group, a butyryloxy group, an isobutyryloxy group, an s-butyryloxy group, a valeryloxy group, an isovaleryloxy group, a hexanoyloxy group, a heptanoyloxy group, an octanoyloxy group, a nonanoyloxy group, a decanoyloxy group, a benzoyloxy group, a phenylacetyloxy group, a cinnamoyloxy group, a cyclopentylcarboxy group, a cyclohexylcarboxy group and a cycloheptylcarboxy group, sulfonyloxy groups having 1 to 8 carbon atoms such as a methanesulfonyloxy group, a trifluoromethanesulfonyloxy group, an ethanesulfonyloxy group, a butanesulfonyloxy group, a t-butanesulfonyloxy group, a nonafluorobutanesulfonyloxy group, a benzenesulfonyloxy group, a p-bromobenzenesulfonyloxy group, a p-toluenesulfonyloxy group, a benzylsulfonyloxy group, an α-phenethylsulfonyloxy group and a β-phenethylsulfonyloxy group, an oxo group, a carboxyl group, alkoxycaobonyl groups having 2 to 10 carbon atoms such as a methoxycarbonyl group, an ethoxycarbonyl group, a propoxycarbonyl group, an isopropoxycarbonyl group, a butoxycarbonyl group, an isobutoxycarbonyl group, an s-butoxycarbonyl group, a t-butoxycarbonyl group, a phenoxycarbonyl group, a 1-naphthoxycarbonyl group, a 2-naphthoxycarbonyl group, a benzyloxycarbonyl group, an α-phenethyloxycarbonyl group and a β-phenethyloxycarbonyl group, carbamoyl groups having 1 to 15 carbon atoms such as a carbamoyl group, an N-methylcarbamoyl group, an N-ethylcarbamoyl group, an N-propylcarbamoyl group, an N-isopropylcarbamoyl group, an N-butylcarbamoyl group, an N-isobutylcarbamoyl group, an N-s-butylcarbamoyl group, an N-t-butylcarbamoyl group, an N-pentylcarbamoyl group, an N-hexylcarbamoyl group, an N-phenylcarbamoyl group, an N-benzylcarbamoyl group, an N-phenethylcarbamoyl group, an N-cyclopropylcarbamoyl group, an N-cyclobutylcarbamoyl group, an N-cyclopentylcarbamoyl group, an N-cyclohexylcarbamoyl group, an N-cycloheptylcarbamoyl group, an N-cyclopropanemethylcarbamoyl group, an N,N-dimethylcarbamoyl group, an N,N-ethylmethylcarbamoyl group, an N,N-diethylcarbamoyl group, an N,N-dipropylcarbamoyl group, an N,N-dibutylcarbamoyl group, an N,N-dicyclohexylcarbamoyl group, an N,N-diphenylcarbamoyl group, an N,N-dibenzylcarbamoyl group, a piperidinocarbonyl group, and a morpholinocarbonyl group, amino groups having 0 to 14 carbon atoms such as an amino group, a methylamino group, an ethylamino group, a propylamino group, an isopropylamino group, a butylamino group, an isobutylamino group, an s-butylamino group, a t-butylamino group, a pentylamino group, an hexylamino group, an heptylamino group, an octylamino group, a nonylamino group, a decylamino group, a phenylamino group, a benzylamino group, a phenethylamino group, a cyclopropylamino group, a cyclobutylamino group, a cyclopentylamino group, a cyclohexylamino group, a cycloheptylamino group, a cyclooctylamino group, a cyclopropanemethylamino group, a dimethylamino group, an N-ethylmethylamino group, a diethylamino group, an N— methylpropylamino group, an L N-methylisopropylamino group, an N-meth ylbutylamino group, an N-methyl-t-butylamino group, an N-ethylisopropylamino group, a dipropylamino group, a diisopropylamino group, an ethylbutylamino group, an N-methylhexylamino group, a dibutylamino group, a dipentylamino group, a dicyclohexylamino group, a diphenylamino group, a dibenzylamino group, a piperidino group and a morpholino group, acylamino groups having 1 to 10 carbon atoms such as a formylamino group, an acetylamino group, a trifluoroacetylamino group, a propionylamino group, a butyrylamino group, an isobutyrylamino group, a valerylamino group, an hexanoylamino group, a benzoylamino group, a phenylacetylamino group, a phenylpropionylamino group, and a cinnamoylamino group, sulfonylamino groups having 1 to 8 carbon atoms such as a methanesulfonylamino group, a trifluoromethanesulfonylamino group, an ethanesulfonylamino group, a butanesulfonylamino group, a t-butanesulfonylamino group, a nonafluorobutanesulfonylamino group, a benzenesulfonylamino group, a p-bromobenzenesulfonylamino group, a p-toluenesulfonylamino group, a benzylsulfonylamino group, an c-phenethylsulfonylamino group and a β-phenethylsulfonylamino group, imino groups having 1 to 10 carbon atoms such as a methylimino group, an ethylimino group, a propylimino group, an isopropylimino group, a butylimino group, an isobutylimino group, a pentylimino group, an hexylimino group, an heptylimino group, an octylimino group, a nonylimino group, a decylimino group, a phenylimino group, a benzylimino group, a phenethylimino group, a cyclopropylimino group, a cyclobutylimino group, a cyclopentylimino group, a cyclohexylimino group, and a cycloheptylimino group, a cyano group, a nitro group, sulfide groups having 1 to 6 carbon atoms such as a methylthio group, an ethylthio group, a propylthio group, an isopropylthio group, a butylthio group, an isobutylthio group, an s-butylthio group, a t-butylthio group, a pentylthio group, an hexylthio group, a phenylthio group, a cyclopentylthio group and a cyclohexylthio group, sulfinyl groups having 1 to 6 carbon atoms such as a methylsulfinyl group, an ethylsulfinyl group, a propylsulfinyl group, an isopropylsulfinyl group, a butylsulfinyl group, an isobutylsulfinyl group, an s-butylsulfinyl group, a t-butylsulfinyl group, a pentylsulfinyl group, a hexylsulfinyl group, a phenylsulfinyl group, a cyclopentylsulfinyl group, and a cyclohexylsulfinyl group, sulfonyl groups having 1 to 6 carbon atoms such as a methylsulfonyl group, an ethylsulfonyl group, a propylsulfonyl group, an isopropylsulfonyl group, a butylsulfonyl group, an isobutylsulfonyl group, an s-butylsulfonyl group, a t-butylsulfonyl group, a pentylsulfonyl group, a hexylsulfonyl group, a phenylsulfonyl group, a cyclopentylsulfonyl group and a cyclohexylsulfonyl group, a substituted or unsubstituted cycloalkyl group having 3 to 8 carbon atoms (in addition to the same examples as the examples chosen among the examples indicated as examples of substitution groups in the case of the previously mentioned alkyl group having 1 to 10 carbon atoms, alkyl groups having 1 to 4 carbon atoms which are a methyl group, an ethyl group, a propyl group, an isopropyl group, a butyl group, an isobutyl group, an s-butyl and a t-butyl group, acyl groups having 1 to 10 carbon atoms such as a formyl group, an acetyl group, a trifluoroacetyl group, a propionyl group, a butyryl group, an isobutyryl group, a valeryl group, an hexanoyl group, a benzoyl group, a phenylacetyl group, a phenylpropionyl group and a cinnamoyl group may be cited as examples of such cycloalkyl groups having 3 to 8 carbon atoms), a substituted or unsubstituted phenyl group (as examples of substitution groups for such a pheyl group, the substitution groups given in the case of the previously-mentioned alkyl group having 1 to 10 carbon atoms and the same examples as the examples chosen among the examples indicated as examples of substitution groups in the case of the previously-mentioned cycloalkyl groups having 3 to 8 carbon atoms may be cited), a substituted or unsubstituted heterocyclic group (include 1 to 4 oxygen atoms, nitrogen atoms or sulfur atoms. As examples of substitution groups for such a heterocyclic group, the same examples as the examples chosen among the examples indicated as examples of substitution groups in the case of the previously-mentioned alkyl group having 1 to 10 carbon atoms and in the case of the previously-mentioned cycloalkyl groups having 3 to 8 carbon atoms may be cited) may be cited.

When $R^1$ or $R^2$ represents an acyl group having 1 to 10 carbon atoms, as examples of such an acyl group having 1 to 10 carbon atoms, a formyl group, an acetyl group, a trifluoroacetyl group, a propionyl group, a butyryl group, an isobutyryl group, a valeryl group, an hexanoyl group, a benzoyl group, a phenylacetyl group, a phenylpropionyl group and a cinnamoyl group may be cited.

When $R^1$ or $^2$ represents a solfonyl group having 1 to 8 carbon atoms, as examples of such a solfonyl group having 1 to 8 carbon atoms, a methanesulfonyl group, a trifluoromethanesulfonyl group, an ethanesulfonyl group, a butanesulfonyl group, a t-butanesulfonyl group, a nonafluorobutanesulfonyl group, a benzenesulfonyl group, a p-bromobenzenesulfonyl group, a p-toluenesulfonyl group, a benzylsulfonyl group, an α-phenethylsulfonyl group, β-phenethylsulfonyl group may be cited. As preferred examples of such $R^1$ and $R^2$, a hydrogen atom, a methyl group, an ethyl group, a propyl group, an isopropyl group, a butyl group, a t-butyl group, a 2-hydroxyethyl group, a carboxymethyl group, a carboxyethyl group, a methoxycarbonylethyl group, a cyclopropyl group, a cyclobutyl group, a cyclopentyl group, a cyclohexyl group, a cyclopropylmethyl group, a phenyl group, a tolyl group, a benzyl group, a phenethyl group, a pyridyl group, a 4-pyridyl group, a formyl group, an acetyl group, a propanoyl group, a benzoyl group, a methanesulfonyl group, a benzenesulfonyl group and a p-toluenesulphonyl may be cited.

When representing a functional group wherein $R^1$ and $R^2$ are bonded to each other and form an amino group having 4 to 8 carbon atoms together with the nitrogen atom they are bonded to, as examples of functional groups forming such an amino group having 4 to 8 carbon atoms, an azetidinyl group, a pyrrolidinyl group, a piperidino group, a morpholino group, a piperazinyl group and a perhydroazepinyl group may be cited.

As preferred examples of such amino groups formed by $R^1$, $R^2$ and the nitrogen atom they are bonded to, an amino group, a methylamino group, an ethylamino group, a propylamino group, a butylamino group, a dimethylamino group, an N-methylamino group, a diethylamino group, a dipropylamino group, a diisopropylamino group, a dibutylamino group, an N-methylamino group, a cyclohexylamino group, a phenylamino group, a benzylamino group, a tolylamino group, a (4-pyridylmethyl)amino group, a 2-pyridylamino group, a 1-pyrrolidinyl group, a piperidino group, a morpholino group, a 4-N-methylpiperadin-1-yl group, a carboxymethylamino group, a 1-carboxyethylamino group, a 2-hydroxyethylamino group, a 3-hydroxyethylamino group and a 2-methoxycarbonylethyl group may be cited.

In the above Formula (1), the compound represented by the Formula (2) below is a novel substance.

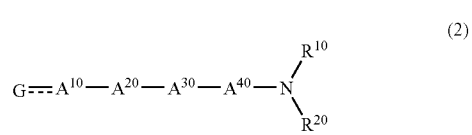

[In Formula (2), the symbol ══ represents a single bond or a double bond.
G represents one functional group chosen from the group consisting of the Formulae (G1), (G2), (G3), (G4), (G5), (G6), (G7), (G8), (G9), (G10), (G11) and (G12) shown below.
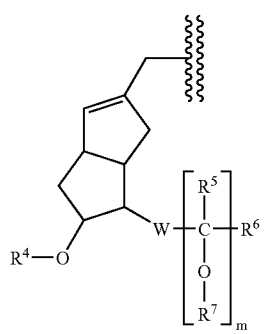
(G1)
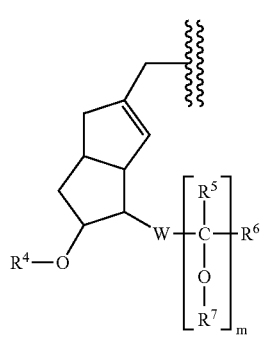
(G2)
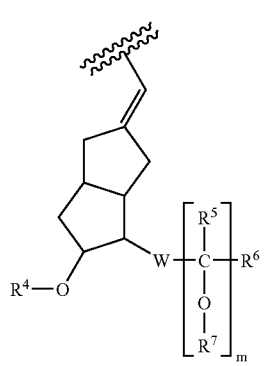
(G3)
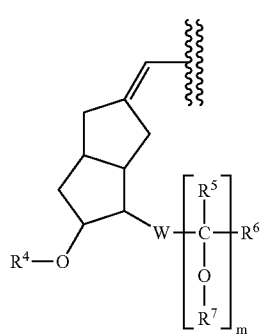
(G4)
-continued
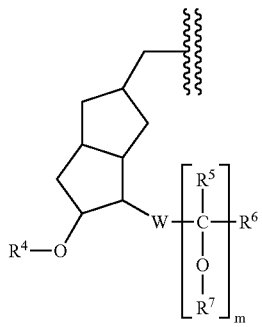
(G5)
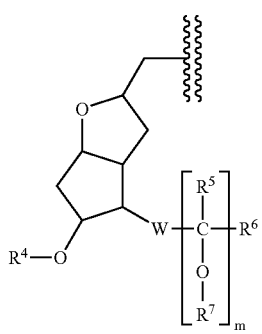
(G6)
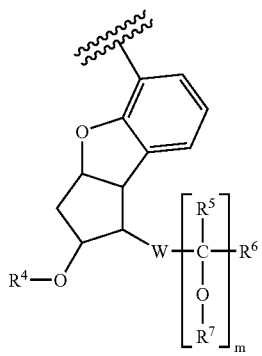
(G7)
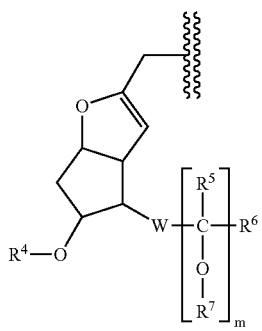
(G8)

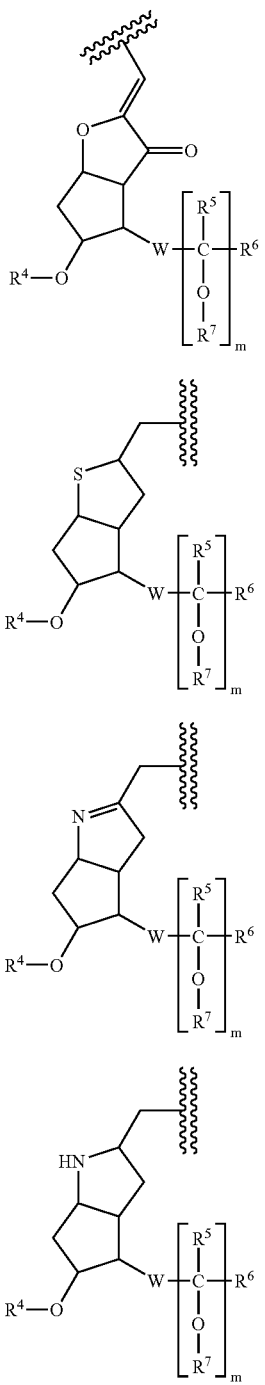

(In Formula G1), Formula (G2), Formula (G3), Formula (G4), Formula (G5), Formula (G6), Formula (G7), Formula (G8), Formula (G9), Formula (G10), Formula (G11) and Formula (G12), the symbol ⸽ represents the site of linkage with $A^{10}$.

$R^4$ represents a hydrogen atom, an acyl group having 2 to 10 carbon atoms, a tri(hydrocarbon group having 1 to 7 carbon atoms) silyl group or a functional group forming the acetal bond together with the oxygen atom bonded to $R^4$.

W represents a single bond, —$CH_2$—, —$(CH_2)_2$—, —$(CH_2)_3$—, —CH=CH—, —CH=$CHCH_2$—, —C≡C— or —C≡$CCH_2$—.

m may be either 0 or 1. However, when W is a single bond, m is equal to 1.

$R^5$ and $R^6$ are either identical or different and, either represent one functional group chosen from the following items 1) to 5), i.e., 1) a hydrogen atom,
2) a substituted or an unsubstituted aliphatic hydrocarbon group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents, substituted or unsubstituted alicyclic hydrocarbon group having 3 to 8 carbon atoms (aliphatic hydrocarbon group having 1 to 6 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), substituted or unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), and, substituted or unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents) may be cited as substituents), 3) a substituted or an unsubstituted alicyclic hydrocarbon group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) a substituted or an unsubstituted aromatic hydrocarbon group having 6 to 10 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group having 1 to 4 oxygen atoms, nitrogen atoms, or sulfur atoms in the cycle (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), or, when $R^5$ and $R^6$ are bonded to each other, they represent a substituted or an unsubstituted alicyclic hydrocarbon chain having 4 to 7 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

$R^7$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, a functional group forming the acetal bond together with the oxygen atom bound to $R^7$, or, when $R^7$ and $R^5$ are bonded to each other, it represents one portion of the bond forming the carbonyl group together with the carbon atom bonded to $R^5$ and the oxygen atom bonded to $R^7$.

$A^{20}$ represents a single bond, a Formula (A2A) shown below, a Formula (A2B) shown below or a Formula (A2C) shown below.

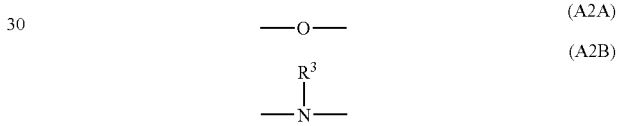

(In the formula, $R^3$ represents a hydrogen atom, an alkyl group having 1 to 4 carbon atoms, or an acyl group having 1 to 10 carbon atoms.)

(In the formula, n represents 0, 1, or 2.)

$A^{10}$ represents the items 1) or 2) below 1) a single bond 2) a functional group which bridges G and $A^{20}$ through an identical atom or through different a toms, and chosen from a group consisting of an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^{30}$ represents the items 1) or 2) below 1) a single bond 2) a functional group which bridges $A^{20}$ and $A^{40}$ through an identical atom or through different atoms, and chosen from a group consisting of an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

$A^{40}$ represents any of the items 1) to 3) below
1) a single bond
2) an aliphatic hydrocarbon group having 1 to 3 carbon atoms, which bridges the nitrogen atom, bonded to $R^{10}$ and $R^{20}$, and $A^{30}$ through an identical atom or through different atoms.
3) when $A^{40}$ and $R^{10}$ are bonded to each other, a functional group forming a 5 to 8 membered ring together with the nitrogen atom they are bonded to (when $A^{40}$ or $R^{10}$ and the nitrogen atom they are bonded to are bonded through a double bond, $R^{20}$ represents the bond between $A^{40}$ or $R^{10}$ and the nitrogen atom.)

However, in the combination of G, $A^{10}$, $A^{20}$, $A^{30}$, and $A^{40}$ of the above Formula (2), when G represents the Formula (G1), and either of $A^{10}$ or $A^{30}$ is a phenylene group, $A^{20}$ may not be a single bond. In addition, when $A^{20}$ represents one of the Formula (A2A), Formula (A2B) or Formula (A2C), $A^{20}$ and the nitrogen atom bonded to $R^{10}$ and $R^{20}$ must be bonded with more than two carbon atoms in between.

$R^{10}$ and $R^{20}$ are either identical or different, and either represent one functional group chosen from the following items 1) to 7), i.e.,
1) a hydrogen atom (however, when $R^{10}$ and $R^{20}$ both represent a hydrogen atom, only in the case where G is equal to Formula (G1)),
2) when G is not equal to Formula (G7), a substituted or an unsubstituted alkyl group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, phenyl group, and, heterocyclic group (containing 1 to 4 oxygen atoms, nitrogen atoms, or sulfur atoms) may be cited as substituents),
3) when G is not equal to Formula (G7), a substituted or an unsubstituted cycloalkyl group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
4) when G is not equal to Formula (G7), a substituted or an unsubstituted phenyl group (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
5) a substituted or an unsubstituted heterocyclic group (containing 1 to 4 oxygen atoms, nitrogen atoms, or sulfur atoms, and, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents),
6) when G is not equal to Formula (G7), an acyl group having 1 to 10 carbon atoms
7) when G is not equal to Formula (G7), a sulfonyl group having 1 to 8 carbon atoms (however, when either $R^{10}$ or $R^{20}$ represents a sulfonyl group having 1 to 8 carbon atoms, the other may be neither an acyl group having 1 to 10 carbon atoms nor a sulfonyl group having 1 to 8 carbon atoms),
or, when $R^{10}$ and $R^{20}$ are bonded together, they represent a functional group forming a cyclic amino group having 4 to 8 carbon atoms together with the nitrogen atom they are bonded to (for said cyclic amino group having 4 to 8 carbon atoms, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents)].

The same examples given for G in the above Formula (1) may be cited as preferred examples for G in the above Formula (2).

In the above Formula (2), $A^{20}$ represents a single bond, a Formula (A2A) shown below, a Formula (A2B) shown below or a Formula (A2C) shown below.

(A2A)

(A2B)

[In the formula, $R^3$ represents a hydrogen atom, an alkyl group having 1 to 4 carbon atoms, or an acyl group having 1 to 10 carbon atoms.]

(A2C)

[In the formula, n represents 0, 1, or 2.]

The same examples given as concrete examples for $R^3$ in the above Formula (1) may be cited as concrete examples for $R^3$ in the above Formula (A2B).

In the above Formula (A2C), n represents 0, 1, or 2. However, 0 may be cited as the preferred value for n.

A single bond, —O—, —NH—, —N(CH$_3$)— and —S— may be cited as such preferred functional groups for $A^{20}$.

$A^{10}$ represents the items 1) or 2) below
1) a single bond
2) a functional group which bridges G and $A^{20}$ through an identical atom or through different atoms, and chosen from a group consisting of an aliphatic hydrocarbon group having 1 to 3 carbon atoms, an alicyclic hydrocarbon group having 3 to 8 carbon atoms, a heterocyclic group having 1 or 2 oxygen atoms, nitrogen atoms, or sulfur atoms, and a phenylene group.

The same examples given as concrete examples for $A^1$ in the above Formula (1) may be cited as such concrete examples for $A^{10}$. A bond representing a single bond, —CH$_2$—, —(CH$_2$)$_2$—, =CH— and =CHCH$_2$— may be cited as particularly preferred functional groups.

In the above Formula (2), $A^{30}$ represents the items 1) or 2) below
1) a single bond
2) a functional group which bridges $A^{20}$ and $A^{40}$ through an identical atom or through different atoms, and chosen from a group consisting of an aliphatic hydrocarbon group having 1 to 3 carbon atoms, an alicyclic hydrocarbon group having 3 to 8 carbon atoms, a heterocyclic group f having 1 or 2 oxygen atoms, nitrogen atoms, or sulfur atoms, and a phenylene group.

The same examples given as concrete examples for $A^3$ in the above Formula (1) may be cited as concrete examples for $A^{30}$. A bond representing a single bond, —CH$_2$—, —(CH$_2$)$_2$— and —CH=CH— may be cited as particularly preferred functional groups.

In the above Formula (2), $A^{40}$ represents any of the items 1) to 3) below
1) a single bond
2) an aliphatic hydrocarbon group having 1 to 3 carbon atoms, which bridges the nitrogen atom, bonded to $R^{10}$ and $R^{20}$, and $A^{30}$ through an identical atom or through different atoms.

3) when $A^{40}$ and $R^{10}$ are bonded to each other, a functional group forming a 5 to 8 membered ring together with the nitrogen atom they are bonded to (when $A^{40}$ or $R^{10}$ and the nitrogen atom they are bonded to are bonded through a double bond, $R^{20}$ represents the bond between $A^{40}$ or $R^{10}$ and the nitrogen atom.). The same examples given as concrete examples for $A^4$ in the above Formula (1) may be cited as such concrete examples for $A^{40}$. A bond representing a single bond, —CH$_2$— and —(CH$_2$)$_2$— may be cited as particularly preferred functional groups. In addition, when $A^{40}$ and $R^{10}$ are bonded to each other, to represent a functional group forming a 5 to 8 membered ring together with the nitrogen atom they are bonded to, 2-pyridyl, 4-pyridyl and 4-piperidinyl may be cited as particularly preferred examples.

However, in the combination of G, $A^{10}$, $A^{20}$, $A^{30}$, and $A^{40}$, when G represents the Formula (G1), and either of $A^{10}$ or $A^{30}$ is a phenylene group, $A^{20}$ may not be a single bond. In addition, when $A^{20}$ represents one of the Formula (A2A), Formula (A2B) or Formula (A2C), $A^{20}$ and the nitrogen atom bonded to $R^{10}$ and $R^{20}$ must be bonded with more than two carbon atoms in between.

In the above Formula (2), as preferred examples of functional groups represented by the Formula (A0) below,

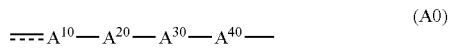

(A0)

[In Formula (A0), $A^{10}$, $A^{20}$, $A^{30}$, $A^{40}$, and the symbol === have the same definition as above.]

—(CH$_2$)$_3$—, —(CH$_2$)$_4$—, —(CH$_2$)$_5$—, =CH(CH$_2$)$_2$—, =CH(CH$_2$)$_3$—, =CH(CH$_2$)$_4$—, —CH$_2$CH=CHCH$_2$—, —NH(CH$_2$)$_2$—, —NH(CH$_2$)$_3$—, —NH(CH$_2$)$_4$—, —N(CH$_3$)(CH$_2$)$_3$—, —CH$_2$NH(CH$_2$)$_2$—, —O(CH$_2$)$_3$—, —CH$_2$O(CH$_2$)$_2$—, —S(CH$_2$)$_3$— and —CH$_2$S(CH$_2$)$_2$— may be cited.

In the above Formula (2), $R^{10}$ and $R^{20}$ are either identical or different, and either represent one functional group chosen from the following items 1) to 7), i.e.,
1) a hydrogen atom (however, when $R^{10}$ and $R^{20}$ both represent a hydrogen atom, only in the case where G is equal to Formula (G1)),
2) when G is not equal to Formula (G7), a substituted or an unsubstituted alkyl group having 1 to 10 carbon atoms (fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, phenyl group, and, heterocyclic group (containing 1 to 4 oxygen atoms, nitrogen atoms, or sulfur atoms) may be cited as substituents),
3) when G is not equal to Formula (G7), a substituted or an unsubstituted cycloalkyl group having 3 to 8 carbon atoms (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 4) when G is not equal to Formula (G7), a substituted or an unsubstituted phenyl group (alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 5) a substituted or an unsubstituted heterocyclic group (containing 1 to 4 oxygen atoms, nitrogen atoms, or sulfur atoms, and, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents), 6) when G is not equal to Formula (G7), an acyl group having 1 to 10 carbon atoms 7) when G is not equal to Formula (G7), a sulfonyl group having 1 to 8 carbon atoms (however, when either $R^{10}$ or $R^{20}$ represents a sulfonyl group having 1 to 8 carbon atoms, the other may neither be an acyl group having 1 to 10 carbon atoms nor a sulfonyl group having 1 to 8 carbon atoms), or, when $R^{10}$ and $R^{20}$ are bonded together, they represent a functional group forming a cyclic amino group having 4 to 8 carbon atoms together with the nitrogen atom they are bonded to (for said cyclic amino group having 4 to 8 carbon atoms, alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms may be cited as substituents).

As concrete examples of $R^{10}$ and $R^{20}$, the same examples as the examples given in the above Formula (1) as concrete examples may be cited, and, as particularly preferred examples, a hydrogen atom, a methyl group, an ethyl group, a propyl group, an isopropyl group, a butyl group, a t-butyl group, a 2-hydroxyethyl group, a 3-hydroxyethyl group, a carboxymethyl group, a carboxyethyl group, a methoxycarbonylethyl group, a cyclopropyl group, a cyclobutyl group, a cyclopentyl group, a cyclohexyl group, a cyclopropylmethyl group, a phenyl group, a tolyl group, a benzyl group, a phenethyl group, a pyridyl group, a 4-pyridyl group, a formyl group, an acetyl group, a propanoyl group, a benzoyl group, a methanesulfonyl group, a benzenesulfonyl group and a p-toluenesulfonyl may be cited.

When representing a functional group wherein $R^1$ and $R^2$ are bonded to each other and form an amino group having 4 to 8 carbon atoms together with the nitrogen atom they are bonded to, as examples of functional groups forming such an amino group having 4 to 8 carbon atoms, the same examples as the examples given in the above Formula (1) as concrete examples of $R^1$ and $R^2$ may be cited.

As preferred examples of such amino groups formed by $R^{10}$, $R^{20}$ and the nitrogen atom they are bonded to, an amino group, a methylamino group, an ethylamino group, a propylamino group, a butylamino group, a dimethylamino group, an N-methylamino group, a diethylamino group, a dipropylamino group, a diisopropylamino group, a dibutylamino group, an N-methylamino group, a cyclohexylamino group, a phenylamino group, a benzylamino group, a tolylamino group, a (4-pyridylmethyl)amino group, a 2-pyridylamino group, a 1-pyrrolidinyl group, a piperidino group, a morpholino group, a 4-N-methylpiperidin-1-yl group, a carboxymethylamino group, a 1-carboxyethylamino group, a 2-hydroxyethylamino group, and a 3-hydroxyethylamino group may be cited.

There are instances where the nitrogen-containing compound represented by the above Formula (1) may form salts. No particular restriction exists for such salts provided they are pharmacologically accepted. Concretely, mineral acid salts such as hydrochlorides, hydrobromates, hydroiodates, phosphates, nitrates, and sulfates, organic sulfonates such as methane sulfonates, 1-hydroxyethane sulfonates, and p-toluenesulfonates, and, organic carboxylates such as acetates, trifluoroacetates, propionates, oxalates, malonates, succinates, glutarates, adipinates, tartrates, maleates, malates and mendelates may be included as added acidic salts, and, salts formed with inorganic bases such as sodium salts, potassium salts, magnesium salts, calcium salts, inorganic salt groups such as aluminium salts, and, salts formed with organic bases such as methylamine salts, ethylamine salts, lysine salts, and ornithin salts may be cited as salts made with bases.

Concrete examples of the nitrogen-containing compounds represented by the above Formula (1) provided by the present invention will be given in the following. However, the invention is not limited to these examples.

1) (1S,5S,6R,7R)-3-(4-carbamoylbutyl)-6-[(3S,1E)-3-hydroxy-1-octenyl]-7-hydroxybicyclo [3.3.0]-2-octene
2) (1S,5S,6R,7R)-3-(4-N,N-dimethylcarbamoylbutyl)-6-[(3S, 1E)-3-hydroxy-1-octenyl]-7-hydroxybicyclo[3.3.0]-2-octene
3) (1S,5S,6R,7R)-3-(4-N,N-diethylcarbamoylbutyl)-6-[(3S, 1E)-3-hydroxy-1-octenyl]-7-hydroxybicyclo[3.3.0]-2-octene
4) (1S,5S,6R,7R)-3-[4-N-(2-methoxycarbonylethyl)carbamoylbutyl]-6-[(3S,1E)-3-hydroxy-1-octenyl]-7-hydroxybicyclo[3.3.0]-2-octene
5) (1S,5S,6R,7R)-3-[4-N-(4-pyridylmethyl)carbamoylbutyl]-6-[(3S,1E)-3-hydroxy-1-octenyl]-7-hydroxybicyclo[3.3.0]-2-octene
6) (1S,5S,6R,7R)-3-(4-N,N-diisopropylcarbamoylbutyl)-6-[(3S, 1E)-3-hydroxy-1-octenyl]-7-hydroxybicyclo[3.3.0]-2-octene
7) (1S,5S,6R,7R)-3-[4-(1-pyrrolidinyl)carbonylbutyl]-6-[(3S,1E)-3-hydroxy-1-octenyl]-7-hydroxybicyclo[3.3.0]-2-octene
8) (1S,5S,6R,7R)-3-(4-piperidinocarbonylbutyl)-6-[(3S, 1E)-3-hydroxy-1-octenyl]-7-hydroxybicyclo[3.3.0]-2-octene
9) (1S,5S,6R,7R)-3-(4-morpholinocarbonylbutyl)-6-[(3S, 1E)-3-hydroxy-1-octenyl]-7-hydroxybicyclo[3.3.0]-2-octene
10) (1S,5S,6R,7R)-3-(4-N-methylcarbamoylbutyl)-6-[(3S, 1E)-3-hydroxy-1-octenyl]-7-hydroxybicyclo[3.3.0]-2-octene
11) (1S,5S,6R,7R)-3-(4-N-ethylcarbamoylbutyl)-6-[(3S, 1E)-3-hydroxy-1-octenyl]-7-hydroxybicyclo[3.3.0]-2-octene
12) (1S,5S,6R,7R)-3-(4-N-propylcarbamoylbutyl)-6-[(3S, 1E)-3-hydroxy-1-octenyl]-7-hydroxybicyclo[3.3.0]-2-octene
13) (1S,5S,6R,7R)-3-(4-N-isopropylcarbamoylbutyl)-6-[(3S, 1E)-3-hydroxy-1-octenyl]-7-hydroxybicyclo[3.3.0]-2-octene
14) (1S,5S,6R,7R)-3-(4-N-butylcarbamoylbutyl)-6-[(3S, 1E)-3-hydroxy-1-octenyl]-7-hydroxybicyclo[3.3.0]-2-octene
15) (1S,5S,6R,7R)-3-(4-N-t-butylcarbamoylbutyl)-6-[(3S, 1E)-3-hydroxy-1-octenyl]-7-hydroxybicyclo[3.3.0]-2-octene
16) (1S,5S,6R,7R)-3-(4-N-phenylcarbamoylbutyl)-6-[(3S, 1E)-3-hydroxy-1-octenyl]-7-hydroxybicyclo[3.3.0]-2-octene
17) (1S,5S,6R,7R)-3-(4-N-benzylcarbamoylbutyl)-6-[(3S, 1E)-3-hydroxy-1-octenyl]-7-hydroxybicyclo[3.3.0]-2-octene
18) (1S,5S,6R,7R)-3-[4-N-(4-pyridylmethyl)carbamoylbutyl]-6-[(3S,1E)-3-hydroxy-1-octenyl]-7-hydroxybicyclo[3.3.0]-2-octene
19) (1S,5S,6R,7R)-3-[4-(4-N-methyl-1-piperazinyl)carbonylbutyl]-6-[(3S, 1E)-3-hydroxy-1-octenyl]-7-hydroxybicyclo[3.3.0]-2-octene
20) (1S,5S,6R,7R)-3-[4-N-(2-pyridyl)carbamoylbutyl]-6-[(3S,1E)-3-hydroxy-1-octenyl]-7-hydroxybicyclo[3.3.0]-2-octene
21) (1S,5S,6R,7R)-3-(4-N,N-dipropylcarbamoylbutyl)-6-[(3S, 1E)-3-hydroxy-1-octenyl]-7-hydroxybicyclo[3.3.0]-2-octene
22) (1S,5S,6R,7R)-3-(47N,N-dibutylcarbamoylbutyl)-6-[(3S, 1E)-3-hydroxy-1-octenyl]-7-hydroxybicyclo[3.3.0]-2-octene
23) (1S,5S,6R,7R)-3-(4-N-t-butyl-N-methylcarbamoylbutyl)-6-[(3S,1E)-3-hydroxy-1-octenyl]-7-hydroxybicyclo[3.3.0]-2-octene
24) (1S,5S,6R,7R)-3-[4-N-(2-hydroxyethyl)carbamoylbutyl]-6-[(3S, 1E)-3-hydroxy-1-octenyl]-7-hydroxybicyclo[3.3.0]-2-octene
25) (1S,5S,6R,7R)-3-[4-N-(3-hydroxypropyl)carbamoylbutyl]-6-[(3S,1E)-3-hydroxy-1-octenyl]-7-hydroxybicyclo[3.3.0]-2-octene
26) (1S,5S,6R,7R)-3-(3-carbamoylpropyl)-6-[(3S, 1E)-3-hydroxy-1-octenyl]-7-hydroxybicyclo[3.3.0]-2-octene
27) (1S,5S,6R,7R)-3-(3-N,N-dimethylcarbamoylpropyl)-6-[(3S,1E)-3-hydroxy-1-octenyl]-7-hydroxybicyclo[3.3.0]-2-octene
28) (1S,5S,6R,7R)-3-(3-N,N-diisopropylcarbamoylpropyl)-6-[(3S,1E)-3-hydroxy-1-octenyl]-7-hydroxybicyclo[3.3.0]-2-octene
29) (1S,5S,6R,7R)-3-(3-N-t-butyl-N-methylcarbamoylpropyl)-6-[(3S,1E)-3-hydroxy-1-octenyl]-7-hydroxybicyclo[3.3.0]-2-octene
30) (1S,5S,6R,7R)-3-[3-(1-pyrrolidinyl)carbonylpropyl]-6-[(3S,1E)-3-hydroxy-1-octenyl]-7-hydroxybicyclo[3.3.0]-2-octene
31) (1S,5S,6R,7R)-3-(3-piperidinocarbonylpropyl)-6-[(3S, 1E)-3-hydroxy-1-octenyl]-7-hydroxybicyclo[3.3.0]-2-octene
32) (1S,5S,6R,7R)-3-(3-morpholinocarbonylpropyl)-6-[(3S, 1E)-3-hydroxy-1-octenyl]-7-hydroxybicyclo[3.3.0]-2-octene
33) (1S,5S,6R,7R)-3-(5-carbamoylpentyl)-6-[(3S,1E)-3-hydroxy-1-octenyl]-7-hydroxybicyclo[3.3.0]-2-octene
34) (1S,5S,6R,7R)-3-(5-N,N-dimethylcarbamoylpentyl)-6-[(3S,1E)-3-hydroxy-1-octenyl]-7-hydroxybicyclo[3.3.0]-2-octene
35) (1S,5S,6R,7R)-3-(5-N,N-diisopropylcarbamoylpentyl)-6-[(3S,1E)-3-hydroxy-1-octenyl]-7-hydroxybicyclo[3.3.0]-2-octene
36) (1S,5S,6R,7R)-3-(5-N-t-butyl-N-methylcarbamoylpentyl)-6-[(3S,1E)-3-hydroxy-1-octenyl]-7-hydroxybicyclo[3.3.0]-2-octene
37) (1S,5S,6R,7R)-3-[5-(1-pyrrolidinyl)carbonylpentyl]-6-[(3S,1E)-3-hydroxy-1-octenyl]-7-hydroxybicyclo[3.3.0]-2-octene
38) (1S,5S,6R,7R)-3-(5-piperidinocarbonylpentyl)-6-[(3S, 1E)-3-hydroxy-1-octenyl]-7-hydroxybicyclo[3.3.0]-2-octene
39) (1S,5S,6R,7R)-3-(5-morpholinocarbonylpentyl)-6-[(3S, 1E)-3-hydroxy-1-octenyl]-7-hydroxybicyclo[3.3.0]-2-octene
40) (1S,5S,6R,7R)-3-[(1Z)-3-N,N-dimethylcarbamoyl-1-propenyl]-6-[(3S,1E)-3-hydroxy-1-octenyl]-7-hydroxybicyclo[3.3.0]-2-octene
41) (1S,5S,6R,7R)-3-[(1Z)-4-N,N-dimethylcarbamoyl-1-butenyl]-6-[(3S,1E)-3-hydroxy-1-octenyl]-7-hydroxybicyclo[3.3.0]-2-octene
42) (1S,5S,6R,7R)-3-[(1E)-4-N,N-dimethylcarbamoyl-1-butenyl]-6-[(3S,1E)-3-hydroxy-1-octenyl]-7-hydroxybicyclo[3.3.0]-2-octene
43) (1S,5S,6R,7R)-3-[(1Z)-5-N,N-dimethylcarbamoyl-1-pentenyl-]-6-[(3S,1E)-3-hydroxy-1-octenyl]-7-hydroxybicyclo[3.3.0]-2-octene
44) (1S,5S,6R,7R)-3-[N—(N,N-dimethylcarbamoylmethyl)aminomethyl]-6-[(3S,1E)-3-hydroxy-1-octenyl]-7-hydroxybicyclo[3.3.0]-2-octene
45) (1S,5S,6R,7R)-3-[N-(2-N,N-dimethylcarbamoylethyl)aminomethyl]-6-[(3S,1E)-3-hydroxy-1-octenyl]-7-hydroxy-1-bicyclo[3.3.0]-2-octene 46) (1S,5S,6R,7R)-3-[N-(2-N,N-diisopropylcarbamoylethyl)aminomethyl]-6-[(3S,1E)-3-hydroxy-1-octenyl]-7-hydroxybicyclo[3.3.0]-2-octene
47) (1S,5S,6R,7R)-3-[N-(2-N-t-butyl-N-methylcarbamoylethyl)aminomethyl]-6-[(3S,1E)-3-hydroxy-1-octenyl]-7-hydroxybicyclo[3.3.0]-2-octene
48) (1S,5S,6R,7R)-3-[N-[2-(1-pyrrolidinyl)carbonylethyl]aminomethyl]-6-[(3S,1E)-3-hydroxy-1-octenyl]-7-hydroxybicyclo[3.3.0]-2-octene
49) (1S,5S,6R,7R)-3-[N-(2-piperidinocarbonylethyl)aminomethyl]-6-[(3S,1E)-3-hydroxy-1-octenyl]-7-hydroxybicyclo[3.3.0]-2-octene
50) (1S,5S,6R,7R)-3-[N-(2-morpholinocarbonylethyl)aminomethyl]-6-[(3S,1E)-3-hydroxy-1-octenyl]-7-hydroxybicyclo[3.3.0]-2-octene
51) (1S,5S,6R,7R)-3-[N-(3-N,N-dimethylcarbamoylpropyl)aminomethyl]-6-[(3S,1E)-3-hydroxy-1-octenyl]-7-hydroxybicyclo[3.3.0]-2-octene
52) (1S,5S,6R,7R)-3-[N-(2-N,N-dimethylcarbamoylethyl)-N-methylaminomethyl]-6-[(3S,1E)-3-hydroxy-1-octenyl]-7-hydroxybicyclo[3.3.0]-2-octene
53) (1S,5S,6R,7R)-3-[N—(N,N-dimethylcarbamoylmethyl)aminoethyl]-6-[(3S,1E)-3-hydroxy-1-octenyl]-7-hydroxybicyclo[3.3.0]-2-octene
54) (1S,5S,6R,7R)-3-[N-(N,N-diisopropylcarbamoylmethyl)aminoethyl]-6-[(3S,1E)-3-hydroxy-1-octenyl]-7-hydroxybicyclo[3.3.0]-2-octene
55) (1S,5S,6R,7R)-3-[N-(N-t-butyl-N-methylcarbamoylmethyl)aminoethyl]-6-[(3S,1E)-3-hydroxy-1-octenyl]-7-hydroxybicyclo[3.3.0]-2-octene
56) (1S,5S,6 R,7R)-3-[2-N-[(1-pyrrolidinyl)carbonylmethyl]haminoethyl]-6-[(3S,1E)-3-hydroxy-1-octenyl]-7-hydroxybicyclo[3.3.0]-2-octene
57) (1S,5S,6R,7R)-3-[2-N-(piperidinocarbonylmethyl)aminoethyl]-6-[(3S,1E)-3-hydroxy-1-octenyl]-7-hydroxybicyclo[3.3.0]-2-octene
58) (1S,5S,6R,7R)-3-[2-N-(morpholinocarbonylmethyl)aminoethyl]-6-[(3S,1E)-3-hydroxy-1-octenyl]-7-hydroxybicyclo[3.3.0]-2-octene
59) (1S,5S,6R,7R)-3-[2-N-(2-N,N-dimethylcarbamoylethyl)aminoethyl]-6-[(3S,1E)-3-hydroxy-1-octenyl]-7-hydroxybicyclo[3.3.0]-2-octene
60) (1S,5S,6R,7R)-3-[(2-N,N-dimethylcarbamoylethyl)oxymethyl]-6-[(3S,1E)-3-hydroxy-1-octenyl]-7-hydroxybicyclo[3.3.0]-2-octene
61) (1S,5S,6R,7R)-3-[(2-N,N-diisopropylcarbamoylethyl)oxymethyl]-6-[(3S,1E)-3-hydroxy-1-octenyl]-7-hydroxybicyclo[3.3.0]-2-octene
62) (1S,5S,6R,7R)-3-[(2-N-t-butyl-N-methylcarbamoylethyl)oxymethyl]-6-[(3S,1E)-3-hydroxy-1-octenyl]-7-hydroxybicyclo[3.3.0]-2-octene
63) (1S,5S,6R,7R)-3-[[2-(1-pyrrolidinyl)carbonylethyl]oxymethyl]-6-[(3S,1E)-3-hydroxy-1-octenyl]-7-hydroxybicyclo[3.3.0]-2-octene
64) (1S,5S,6R,7R)-3-[(2-piperidinocarbonylethyl)oxymethyl]-6-[(3S,1E)-3-hydroxy-1-octenyl]-7-hydroxybicyclo[3.3.0]-2-octene
65) (1S,5S,6R,7R)-3-[(2-morpholinocarbonylethyl)oxymethyl]-6-[(3S,1E)-3-hydroxy-1-octenyl]-7-hydroxybicyclo[3.3.0]-2-octene
66) (1S,5S,6R,7R)-3-[2-(N,N-dimethylcarbamoylmethyl)oxyethyl]-6-[(3S,1E)-3-hydroxy-1-octenyl]-7-hydroxybicyclo[3.3.0]-2-octene
67) (1S,5S,6R,7R)-3-[2-(N,N-diisopropylcarbamoylmethyl)oxyethyl]-6-[(3S,1E)-3-hydroxy-1-octenyl]-7-hydroxybicyclo[3.3.0]-2-octene
68) (1S,5S,6R,7R)-3-[2-(N-t-butyl-N-methylcarbamoylmethyl)oxyethyl]-6-[(3S,1E)-3-hydroxy-1-octenyl]-7-hydroxybicyclo[3.3.0]-2-octene
69) (1S,5S,6R,7R)-3-[2-[(1-pyrrolidinyl)carbonylmethyl]oxyethyl]-6-[(3S,1E)-3-hydroxy-1-octenyl]-7-hydroxybicyclo[3.3.0]-2-octene
70) (1S,5S,6R,7R)-3-[2-(piperidinocarbonylmethyl)oxyethyl]-6-[(3S,1E)-3-hydroxy-1-octenyl]-7-hydroxybicyclo[3.3.0]-2-octene
71) (1S,5S,6R,7R)-3-[2-(morpholinocarbonylmethyl)oxyethyl]-6-[(3S,1E)-3-hydroxy-1-octenyl]-7-hydroxybicyclo[3.3.0]-2-octene
72) (1S,5S,6R,7R)-3-[(2-N,N-dimethylcarbamoylethyl)thiomethyl]-6-[(3S,1E)-3-hydroxy-1-octenyl]-7-hydroxybicyclo[3.3.0]-2-octene
73) (1S,5S,6R,7R)-3-[(2-N,N-diisopropylcarbamoylethyl)thiomethyl]-6-[(3S,1E)-3-hydroxy-1-octenyl]-7-hydroxybicyclo[3.3.0]-2-octene
74) (1S,5S,6R,7R)-3-[(2-N-t-butyl-N-methylcarbamoylethyl)thiomethyl]-6-[(3S,1E)-3-hydroxy-1-octenyl]-7-hydroxybicyclo[3.3.0]-2-octene
75) (1S,5S,6R,7R)-3-[[2-(1-pyrrolidinylcarbonyl)ethyl]thiomethyl]-6-[(3S,1E)-3-hydroxy-1-octenyl]-7-hydroxybicyclo[3.3.0]-2-octene
76) (1S,5S,6R,7R)-3-[(2-piperidinocarbonylethyl)thiomethyl]-6-[(3S,1E)-3-hydroxy-1-octenyl]-7-hydroxybicyclo[3.3.0]-2-octene
77) (1S,5S,6R,7R)-3-[(2-morpholinocarbonylethyl)thiomethyl]-6-[(3S,1E)-3-hydroxy-1-octenyl]-7-hydroxybicyclo[3.3.0]-2-octene
78) (1S,5S,6R,7R)-3-[2-(N,N-dimethylcarbamoylmethyl)thioethyl]-6-[(3S,1E)-3-hydroxy-1-octenyl]-7-hydroxybicyclo[3.3.0]-2-octene
79) (1S,5S,6R,7R)-3-[2-(N,N-diisopropylcarbamoylmethyl)thioethyl]-6-[(3S,1E)-3-hydroxy-1-octenyl]-7-hydroxybicyclo[3.3.0]-2-octene
80) (1S,5S,6R,7R)-3-[2-(N-t-butyl-N-methylcarbamoylmethyl)thioethyl]-6-[(3S,1E)-3-hydroxy-1-octenyl]-7-hydroxybicyclo[3.3.0]-2-octene
81) (1S,5S,6R,7R)-3-[2-[(1-pyrrolidinyl)carbonylmethyl]thioethyl]-6-[(3S,1E)-3-hydroxy-1-octenyl]-7-hydroxybicyclo[3.3.0]-2-octene
82) (1S,5S,6R,7R)-3-[2-(piperidinocarbonylmethyl)thioethyl]-6-[(3S,1E)-3-hydroxy-1-octenyl]-7-hydroxybicyclo[3.3.0]-2-octene
83) (1S,5S,6R,7R)-3-[2-(morpholinocarbonylmethyl)thioethyl]-6-[(3S,1E)-3-hydroxy-1-octenyl]-7-hydroxybicyclo[3.3.0]-2-octene
84) (1S,5S,6R,7R)-3-[(2-carbamoylphenyl)methyl]-6-[(3S,1E)-3-hydroxy-1-octenyl]-7-hydroxybicyclo[3.3.0]-2-octene
85) (1S,5S,6R,7R)-3-[(4-carbamoylphenyl)methyl]-6-[(3S,1E)-3-hydroxy-1-octenyl]-7-hydroxybicyclo[3.3.0]-2-octene
86) (1S,5S,6R,7R)-3-[2-(3-carbamoylphenyl)ethyl]-6-[(3S,1E)-3-hydroxy-1-octenyl]-7-hydroxybicyclo[3.3.0]-2-octene
87) (1S,5S,6R,7R)-3-[2-[3-(piperidinocarbonyl)phenyl]ethyl]-6-[(3S,1E)-3-hydroxy-1-octenyl]-7-hydroxybicyclo[3.3.0]-2-octene
88) (1S,5S,6R,7R)-3-(4-carbamoylbutyl)-6-[(3S,5S,1E)-3-hydroxy-5-methyl-1-nonenyl]-7-hydroxybicyclo[3.3.0]-2-octene
89) (1S,5S,6R,7R)-3-(4-N,N-dimethylcarbamoylbutyl)-6-[(3S,5S, 1E)-3-hydroxy-5-methyl-1-nonenyl]-7-hydroxybicyclo[3.3.0]-2-octene 90) (1S,5S,6R,7R)-3-(4-N,N-diethylcarbamoylbutyl)-6-[(3S,5S,1E)-3-hydroxy-5-methyl-1-nonenyl]-7-hydroxybicyclo[3.3.0]-2-octene
91) (1S,5S,6R,7R)-3-[4-N-(2-methoxycarbonylethyl)carbamoylbutyl]-6-[(3S,5S,1E)-3-hydroxy-5-methyl-1-nonenyl]-7-hydroxybicyclo[3.3.0]-2-octene
92) (1S,5S,6R,7R)-3-[4-N-(4-pyridylmethyl)carbamoylbutyl]-6-[(3S,5S,1E)-3-hydroxy-5-methyl-1-nonenyl]-7-hydroxybicyclo[3.3.0]-2-octene
93) (1S,5S,6R,7R)-3-(4-N,N-diisopropylcarbamoylbutyl)-6-[(3S,5 S,1E)-3-hydroxy-5-methyl-1-nonenyl]-7-hydroxybicyclo[3.3.0]-2-octene
94) (1S,5S,6R,7R)-3-[4-(1-pyrrolidinyl)carbonylbutyl]-6-[(3S,5S,1E)-3-hydroxy-5-methyl-1-nonenyl]-7-hydroxybicyclo[3.3.0]-2-octene
95) (1S,5S,6R,7R)-3-(4-piperidinocarbonylbutyl)-6-[(3S,5S,1E)-3-hydroxy-5-methyl-1-nonenyl]-7-hydroxybicyclo[3.3.0]-2-octene
96) (1S,5S,6R,7R)-3-(4-morpholinocarbonylbutyl)-6-[(3S,5S,1E)-3-hydroxy-5-methyl-1-nonenyl]-7-hydroxybicyclo[3.3.0]-2-octene
97) (1S,5S,6R,7R)-3-(4-N-methylcarbamoylbutyl)-6-[(3S,5S,1E)-3-hydroxy-5-methyl-1-nonenyl]-7-hydroxybicyclo[3.3.0]-2-octene
98) (1S,5S,6R,7R)-3-(4-N-ethylcarbamoylbutyl)-6-[(3S,5S,1E)-3-hydroxy-5-methyl-1-nonenyl]-7-hydroxybicyclo[3.3.0]-2-octene
99) (1S,5S,6R,7R)-3-(4-N-propylcarbamoylbutyl)-6-[(3S,5S,1E)-3-hydroxy-5-methyl-1-nonenyl]-7-hydroxybicyclo[3.3.0]-2-octene
100) (1S,5S,6R,7R)-3-(4-N-isopropylcarbamoylbutyl)-6-[(3S,5S,1E)-3-hydroxy-5-methyl-1-nonenyl]-7-hydroxybicyclo[3.3.0]-2-octene
101) (1S,5S,6R,7R)-3-(4-N-butylcarbamoylbutyl)-6-[(3S,5S,1E)-3-hydroxy-5-methyl-1-nonenyl]-7-hydroxybicyclo[3.3.0]-2-octene
102) (1S,5S,6R,7R)-3-(4-N-t-butylcarbamoylbutyl)-6-[(3S,5S,1E)-3-hydroxy-5-methyl-1-nonenyl]-7-hydroxybicyclo[3.3.0]-2-octene
103) (1S,5S,6R,7R)-3-(4-N-phenylcarbamoylbutyl)-6-[(3S,5S,1E)-3-hydroxy-5-methyl-1-nonenyl]-7-hydroxybicyclo[3.3.0]-2-octene
104) (1S,5S,6R,7R)-3-(4-N-benzylcarbamoylbutyl)-6-[(3S,5S,1E)-3-hydroxy-5-methyl-1-nonenyl]-7-hydroxybicyclo[3.3.0]-2-octene
105) (1S,5S,6R,7R)-3-[4-N-(4-pyridylmethyl)carbamoylbutyl]-6-[(3S,5S,1E)-3-hydroxy-5-methyl-1-nonenyl]-7-hydroxybicyclo[3.3.0]-2-octene
106) (1S,5S,6R,7R)-3-[4-(4-N-methyl-1-piperazinyl)carbonylbutyl]-6-[(3S,5S,1E)-3-hydroxy-5-methyl-1-nonenyl]-7-hydroxybicyclo[3.3.0]-2-octene
107) (1S,5S,6R,7R)-3-[4-N-(2-pyridyl)carbamoylbutyl]-6-[(3S,5S,1E)-3-hydroxy-5-methyl-1-nonenyl]-7-hydroxybicyclo[3.3.0]-2-octene
108) (1S,5S,6R,7R)-3-(4-N,N-dipropylcarbamoylbutyl)-6-[(3S,5S,1E)-3-hydroxy-5-methyl-1-nonenyl]-7-hydroxybicyclo[3.3.0]-2-octene
109) (1S,5S,6R,7R)-3-(4-N,N-dibutylcarbamoylbutyl)-6-[(3S,5S,1E)-3-hydroxy-5-methyl-1-nonenyl]-7-hydroxybicyclo[3.3.0]-2-octene
110) (1S,5S,6R,7R)-3-(4-N-t-butyl-N-methylcarbamoylbutyl)-6-[(3S,5S,1E)-3-hydroxy-5-methyl-1-nonenyl]-7-hydroxybicyclo[3.3.0]-2-octene
111) (1S,5S,6R,7R)-3-[4-N-(2-hydroxyethyl)carbamoylbutyl]-6-[(3S,5S,1E)-3-hydroxy-5-methyl-1-nonenyl]-7-hydroxybicyclo[3.3.0]-2-octene
112) (1S,5S,6R,7R)-3-[4-N-(3-hydroxypropyl)carbamoylbutyl]-6-[(3S,5S,1E)-3-hydroxy-5-methyl-1-nonenyl]-7-hydroxybicyclo[3.3.0]-2-octene
113) (1S,5S,6R,7R)-3-(3-carbamoylpropyl)-6-[(3S,5S,1E)-3-hydroxy-5-methyl-1-nonenyl]-7-hydroxybicyclo[3.3.0]-2-octene
114) (1S,5S,6R,7R)-3-(3-N,N-dimethylcarbamoylpropyl)-6-[(3S,5S,1E)-3-hydroxy-5-methyl-1-nonenyl]-7-hydroxybicyclo[3.3.0]-2-octene
115) (1S,5S,6R,7R)-3-(3-N,N-diisopropylcarbamoylpropyl)-6-[(3S,5S,1E)-3-hydroxy-5-methyl-1-nonenyl]-7-hydroxybicyclo[3.3.0]-2-octene
116) (1S,5S,6R,7R)-3-(3-N-t-butyl-N-methylcarbamoylpropyl)-6-[(3S,5S,1E)-3-hydroxy-5-methyl-1-nonenyl]-7-hydroxybicyclo[3.3.0]-2-octene
117) (1S,5S,6R,7R)-3-[3-(1-pyrrolidinyl)carbonylpropyl]-6-[(3S,5S, 1E)-3-hydroxy-5-methyl-1-nonenyl]-7-hydroxybicyclo[3.3.0]-2-octene
118) (1S,5S,6R,7R)-3-(3-piperidinocarbonylpropyl)-6-[(3S,5S,1E)-3-hydroxy-5-methyl-1-nonenyl]-7-hydroxybicyclo[3.3.0]-2-octene
119) (1S,5S,6R,7R)-3-(3-morpholinocarbonylpropyl)-6-[(3S,5S,1E)-3-hydroxy-5-methyl-1-nonenyl]-7-hydroxybicyclo[3.3.0]-2-octene
120) (1S,5S,6R,7R)-3-(5-carbamoylpentyl)-6-[(3S,5S,1E)-3-hydroxy-5-methyl-1-nonenyl]-7-hydroxybicyclo[3.3.0]-2-octene
121) (1S,5S,6R,7R)-3-(5-N,N-dimethylcarbamoylpentyl)-6-[(3S,5S,1E)-3-hydroxy-5-methyl-1-nonenyl]-7-hydroxybicyclo[3.3.0]-2-octene
122) (1S,5S,6R,7R)-3-(5-N,N-diisopropylcarbamoylpentyl)-6-[(3S,5S,1E)-3-hydroxy-5-methyl-1-nonenyl]-7-hydroxybicyclo[3.3.0]-2-octene
123) (1S,5S,6R,7R)-3-(5-N-t-butyl-N-methylcarbamoylpentyl)-6-[(3S,5S,1E)-3-hydroxy-5-methyl-1-nonenyl]-7-hydroxybicyclo[3.3.0]-2-octene
124) (1S,5S,6R,7R)-3-[5-(1-pyrrolidinyl)carbonylpentyl]-6-[(3S,5S,1E)-3-hydroxy-5-methyl-1-nonenyl]-7-hydroxybicyclo[3.3.0]-2-octene
125) (1S,5S,6R,7R)-3-(5-piperidinocarbonylpentyl)-6-[(3S,5S,1E)-3-hydroxy-5-methyl-1-nonenyl]-7-hydroxybicyclo[3.3.0]-2-octene
126) (1S,5S,6R,7R)-3-(5-morpholinocarbonylpentyl)-6-[(3S,5S,1E)-3-hydroxy-5-methyl-1-nonenyl]-7-hydroxybicyclo[3.3.0]-2-octene
127) (1S,5S,6R,7R)-3-[(1Z)-3-N,N-dimethylcarbamoyl-1-propenyl]-6-[(3S,5S,1E)-3-hydroxy-5-methyl-1-nonenyl]-7-hydroxybicyclo[3.3.0]-2-octene
128) (1S,5S,6R,7R)-3-[(1Z)-4-N,N-dimethylcarbamoyl-1-butenyl]-6-[(3S,5S, 1E)-3-hydroxy-5-methyl-1-nonenyl]-7-hydroxybicyclo[3.3.0]-2-octene
129) (1S,5S,6R,7R)-3-[(1E)-4-N,N-dimethylcarbamoyl-1-butenyl]-6-[(3S,5S,1E)-3-hydroxy-5-methyl-1-nonenyl]-7-hydroxybicyclo[3.3.0]-2-octene
130) (1S,5S,6R,7R)-3-[(1Z)-5-N,N-dimethylcarbamoyl-1-pentenyl]-6-[(3S,5S,1E)-3-hydroxy-5-methyl-1-nonenyl]-7-hydroxybicyclo[3.3.0]-2-octene
131) (1S,5S,6R,7R)-3-[N—(N,N-dimethylcarbamoylmethyl)aminomethyl]-6-[(3S,5S,1E)-3-hydroxy-5-methyl-1-nonenyl]-7-hydroxybicyclo[3.3.0]-2-octene
132) (1S,5S,6R,7R)-3-[N-(2-N,N-dimethylcarbamoylethyl)aminomethyl]-6-[(3S,5S,1E)-3-hydroxy-5-methyl-1-nonenyl]-7-hydroxybicyclo[3.3.0]-2-octene
133) (1S,5S,6R,7R)-3-[N-(2-N,N-diisopropylcarbamoylethyl)aminomethyl]-6-[(3S,5S,1E)-3-hydroxy-5-methyl-1-nonenyl]-7-hydroxybicyclo[3.3.0]-2-octene 134) (1S,5S,6R,7R)-3-[N-(2-N-t-butyl-N-methylcarbamoylethyl)aminomethyl]-6-[(3S,5S,1E)-3-hydroxy-5-methyl-1-nonenyl]-7-hydroxybicyclo[3.3.0]-2-octene 135) (1S,5S,6R,7R)-3-[N-[2-(1-pyrrolidinyl)carbonylethyl]aminomethyl]-6-[(3S,5S,1E)-3-hydroxy-5-methyl-1-nonenyl]-7-hydroxybicyclo[3.3.0]-2-octene 136) (1S,5S,6 R,7R)-3-[N-(2-piperidinocarbonylethyl)aminomethyl]-6-[(3S,5S,1E)-3-hydroxy-5-methyl-1-nonenyl]-7-hydroxybicyclo[3.3.0]-2-octene 137) (1S,5S,6R,7R)-3-[N-(2-morpholinocarbonylethyl)aminomethyl]-6-[(3S,5S,1E)-3-hydroxy-5-methyl-1-nonenyl]-7-hydroxybicyclo[3.3.0]-2-octene 138) (1S,5S,6R,7R)-3-[N-(3-N,N-dimethylcarbamoylpropyl)aminomethyl]-6-[(3S,5S,8E)-3-hydroxy-5-methyl-1-nonenyl]-7-hydroxybicyclo[3.3.0]-2-octene 139) (1S,5S,6R,7R)-3-[N-(2-N,N-dimethylcarbamoylethyl)-N-methylaminomethyl]-6-[(3S,5S, 1E)-3-hydroxy-5-methyl-1-nonenyl]-7-hydroxybicyclo[3.3.0]-2-octene 140) (1S,5S,6R,7R)-3-[N—(N,N-dimethylcarbamoylmethyl)aminoethyl]-6-[(3S,5S,1E)-3-hydroxy-5-methyl-1-nonenyl]-7-hydroxybicyclo[3.3.0]-2-octene 141) (1S,3S,6R,7R)₃-[N—(N,N-diisopropylcarbamoylmethyl)aminoethyl]-6-[(3S,5S,1E)-3-hydroxy-5-methyl-1-nonenyl]-7-hydroxybicyclo[3.3.0]-2-octene 142) (1S,5S,6R,7R)-3-[N-(N-t-butyl-N-methylcarbamoylmethyl)aminoethyl]-6-[(3S,5S,1E)-3-hydroxy-5-methyl-1-nonenyl]-7-hydroxybicyclo[3.3.0]-2-octene 143) (1S,5S,6R,7R)-3-[2-N-[(1-pyrrolidinyl)carbonylmethyl]aminoethyl]-6-[(3S,5S,1E)-3-hydroxy-5-methyl-1-nonenyl]-7-hydroxybicyclo[3.3.0]-2-octene 144) (1S,5S,6R,7R)-3-[2-N-(piperidinocarbonylmethyl)aminoethyl]-6-[(3S,5S,1E)-3-hydroxy-5-methyl-1-nonenyl]-7-hydroxybicyclo[3.3.0]-2-octene 145) (1S,5S,6R,7R)-3-[2-N-(morpholinocarbonylmethyl)aminoethyl]-6-[(3S,5S,1E)-3-hydroxy-5-methyl-1-nonenyl]-7-hydroxybicyclo[3.3.0]-2-octene 146) (1S,3S,6R,7R)-3-[2-N-(2-N,N-dimethylcarbamoylethyl)aminoethyl]-6-[(3S,5S,1E)-3-hydroxy-5-methyl-1-nonenyl]-7-hydroxybicyclo [3.3.0]-2-octene 147) (1S,5S,6R,7R)-3-[(2-N,N-dimethylcarbamoylethyl)oxymethyl]-6-[(3S,5S,1E)-3-hydroxy-5-methyl-1-nonenyl]-7-hydroxybicyclo[3.3.0]-2-octene 148) (1S,5S,6R,7R)-3-[(2-N,N-diisopropylcarbamoylethyl)oxymethyl]-6-[(3S,5S,1E)-3-hydroxy-5-methyl-1-nonenyl]-7-hydroxybicyclo[3.3.0]-2-octene 149) (1S,5S,6R,7R)-3-[(2-N-t-butyl-N-methylcarbamoylethyl)oxymethyl]-6-[(3S,5S,1E)-3-hydroxy-5-methyl-1-nonenyl]-7-hydroxybicyclo[3.3.0]-2-octene 150) (1S,5S,6R,7R)-3-[[2-(1-pyrrolidinyl)carbonylethyl]oxymethyl]-6-[(3S,5S,1E)-3-hydroxy-5-methyl-1-nonenyl]-7-hydroxybicyclo[3.3.0]-2-octene 151) (1S,5S,6R,7R)-3-[(2-piperidinocarbonylethyl)oxymethyl]-6-[(3S,5S,1E)-3-hydroxy-5-methyl-1-nonenyl]-7-hydroxybicyclo[3.3.0]-2-octene 152) (1S,5S,6R,7R)-3-[(2-morpholinocarbonylethyl)oxymethyl]-6-[(3S,5S,1E)-3-hydroxy-5-methyl-1-nonenyl]-7-hydroxybicyclo[3.3.0]-2-octene 153) (1S,5S,6R,7R)-3-[2-(N,N-dimethylcarbamoylmethyl)oxyethyl]-6-[(3S,5S,1E)-3-hydroxy-5-methyl-1-nonenyl]-7-hydroxybicyclo[3.3.0]-2-octene 154) (1S,5S,6R,7R)-3-[2-(N,N-diisopropylcarbamoylmethyl)oxyethyl]-6-[(3S,5S,1E)-3-hydroxy-5-methyl-1-nonenyl]-7-hydroxybicyclo[3.3.0]-2-octene 155) (1S,5S,6R,7R)-3-[2-(N-t-butyl-N-methylcarbamoylmethyl)oxyethyl]-6-[(3S,5S,1E)-3-hydroxy-5-methyl-1-nonenyl]-7-hydroxybicyclo[3.3.0]-2-octene 156) (1S,5S,6R,7R)-3-[2-[(1-pyrrolidinyl)carbonylmethyl]oxyethyl]-6-[(3S,5S,1E)-3-hydroxy-5-methyl-1-nonenyl]-7-hydroxybicyclo[3.3.0]-2-octene 157) (1S,5S,6R,7R)-3-[2-(piperidinocarbonylmethyl)oxyethyl]-6-[(3S,5S,1E)-3-hydroxy-5-methyl-1-nonenyl]-7-hydroxybicyclo[3.3.0]-2-octene 158) (1S,5S,6R,7R)-3-[2-(morpholinocarbonylmethyl)oxyethyl]-6-[(3S,5S,1E)-3-hydroxy-5-methyl-1-nonenyl]-7-hydroxybicyclo[3.3.0]-2-octene 159) (1S,5S,6R,7R)-3-[(2-N,N-dimethylcarbamoylethyl)thiomethyl]-6-[(3S,5S,1E)-3-hydroxy-5-methyl-1-nonenyl]-7-hydroxybicyclo[3.3.0]-2-octene 160) (1S,5S,6R,7R)-3-[(2-N,N-diisopropylcarbamoylethyl)thiomethyl]-6-[(3S,5S,1E)-3-hydroxy-5-methyl-1-nonenyl]-7-hydroxybicyclo[3.3.0]-2-octene 161) (1S,5S,6R,7R)-3-[(2-N-t-butyl-N-methylcarbamoylethyl)thiomethyl]-6-[(3S,5S,1E)-3-hydroxy-5-methyl-1-nonenyl]-7-hydroxybicyclo[3.3.0]-2-octene 162) (1S,5S,6R,7R)-3-[[2-(1-pyrrolidinylcarbonyl)ethyl]thiomethyl]-6-[(3S,5S,1E)-3-hydroxy-5-methyl-1-nonenyl]-7-hydroxybicyclo[3.3.0]-2-octene 163) (1S,5S,6R,7R)-3-[(2-piperidinocarbonylethyl)thiomethyl]-6-[(3S,5S, 1E)-3-hydroxy-5-methyl-1-nonenyl]-7-hydroxybicyclo[3.3.0]-2-octene 164) (1S,5S,6R,7R)-3-[(2-morpholinocarbonylethyl)thiomethyl]-6-[(3S,5S,1E)-3-hydroxy-5-methyl-1-nonenyl]-7-hydroxybicyclo[3.3.0]-2-octene 165) (1S,5S,6R,7R)-3-[2-(N,N-dimethylcarbamoylmethyl)thioethyl]-6-[(3S,5S,1E)-3-hydroxy-5-methyl-1-nonenyl]-7-hydroxybicyclo[3.3.0]-2-octene 166) (1S,5S,6R,7R)-3-[2-(N,N-diisopropylcarbamoylmethyl)thioethyl]-6-[(3S,5S,1E)-3-hydroxy-5-methyl-1-nonenyl]-7-hydroxybicyclo[3.3.0]-2-octene 167) (1S,5S,6R,7R)-3-[2-(N-t-butyl-N-methylcarbamoylmethyl)thioethyl]-6-[(3S,5S,1E)-3-hydroxy-5-methyl-1-nonenyl]-7-hydroxybicyclo[3.3.0]-2-octene 168) (1S,5S,6R,7R)-3-[2-[(1-pyrrolidinyl)carbonylmethyl]thioethyl]-6-[(3S,5S, 1E)-3-hydroxy-5-methyl-1-nonenyl]-7-hydroxybicyclo[3.3.0]-2-octene 169) (1S,5S,6R,7R)-3-[2-(piperidinocarbonylmethyl)thioethyl]-6-[(3S,5S,1E)-3-hydroxy-5-methyl-1-nonenyl]-7-hydroxybicyclo[3.3.0]-2-octene 170) (1S,5S,6R,7R)-3-[2-(morpholinocarbonylmethyl)thioethyl]-6-[(3S,5S,1E)-3-hydroxy-5-methyl-1-nonenyl]-7-hydroxybicyclo[3.3.0]-2-octene 171) (1S,5S,6R,7R)-3-[(2-carbamoylphenyl)methyl]-6-[(3S,5S,1E)-3-hydroxy-5-methyl-1-nonenyl]-7-hydroxybicyclo[3.3.0]-2-octene 172) (1S,5S,6R,7R)-3-[(4-carbamoylphenyl)methyl]-6-[(3S,5S,1E)-3-hydroxy-5-methyl-1-nonenyl]-7-hydroxybicyclo[3.3.0]-2-octene 173) (1S,5S,6R,7R)-3-[2-(3-carbamoylphenyl)ethyl]-6-[(3S,5S,1E)-3-hydroxy-5-methyl-1-nonenyl]-7-hydroxybicyclo[3.3.0]-2-octene 174) (1S,5S,6R,7R)-3-[2-[3-(piperidinocarbonyl)phenyl]ethyl]-6-[(3S,5S,1E)-3-hydroxy-5-methyl-1-nonenyl]-7-hydroxybicyclo[3.3.0]-2-octene 175) (1S,5S,6R,7R)-3-(4-carbamoylbutyl)-6-[(4S,1E)-4-hydroxy-4-methyl-1-octenyl]-7-hydroxybicyclo[3.3.0]-2-octene 176) (1S,5S,6R,7R)-3-(4-N,N-dimethylcarbamoylbutyl)-6-[(4S,1E)-4-hydroxy-4-1-octenyl-1-octenyl]-7-hydroxybicyclo[3.3.0]-2-octene 177) (1S,5S,6R,7R)-3-(4-N,N-diethylcarbamoylbutyl)-6-[(4S, 1E)-4-hydroxy-4-methyl-1-octenyl]-7-hydroxybicyclo[3.3.0]-2-octene 178) (1S,5S,6R,7R)-3-[4-N-(2-methoxycarbonylethyl)carbamoylbutyl]-6-[(4S,1E)-4-hydroxy-4-methyl-1-octenyl]-7-hydroxybicyclo[3.3.0]-2-octene
179) (1S,5S,6R,7R)-3-[4-N-(4-pyridylmethyl)carbamoylbutyl]-6-[(4S,1E)-4-hydroxy-4-methyl-1-octenyl]-7-hydroxybicyclo[3.3.0]-2-octene
180) (1S,5S,6R,7R)-3-(4-N,N-diisopropylcarbamoylbutyl)-6-[(4S,1E)-4-hydroxy-4-methyl-1-octenyl]-7-hydroxybicyclo[3.3.0]-2-octene
181) (1S,5S,6R,7R)-3-[4-(1-pyrrolidinyl)carbonylbutyl]-6-[(4S, 1E)-4-hydroxy-4-methyl-1-octenyl]-7-hydroxybicyclo[3.3.0]-2-octene
182) (1S,5S,6R,7R)-3-(4-piperidinocarbonylbutyl)-6-[(4S, 1E)-4-hydroxy-4-methyl-1-octenyl]-7-hydroxybicyclo[3.3.0]-2-octene
183) (1S,5S,6R,7R)-3-(4-morpholinocarbonylbutyl)-6-[(4S, 1E)-4-hydroxy-4-methyl-1-octenyl]-7-hydroxybicyclo[3.3.0]-2-octene
184) (1S,5S,6R,7R)-3-(4-N-methylcarbamoylbutyl)-6-[(4S, 1E)-4-hydroxy-4-methyl-1-octenyl]-7-hydroxybicyclo[3.3.0]-2-octene
185) (1S,5S,6R,7R)-3-(4-N-ethylcarbamoylbutyl)-6-[(4S, E)-4-hydroxy-4-methyl-1-octenyl]-7-hydroxybicyclo[3.3.0]-2-octene
186) (1S,5S,6R,7R)-3-(4-N-propylcarbamoylbutyl)-6-[(4S, 1E)-4-hydroxy-4-methyl-1-octenyl]-7-hydroxybicyclo[3.3.0]-2-octene
187) (1S,5S,6R,7R)-3-(4-N-isopropylcarbamoylbutyl)-6-[(4S, 1E)-4-hydroxy-4-methyl-1-octenyl]-7-hydroxybicyclo[3.3.0]-2-octene
188) (1S,5S,6R,7R)-3-(4-N-butylcarbamoylbutyl)-6-[(4S, 1E)-4-hydroxy-4-methyl-1-octenyl]-7-hydroxybicyclo[3.3.0]-2-octene
189) (1S,5S,6R,7R)-3-(4-N-t-butylcarbamoylbutyl)-6-[(4S, 1E)-4-hydroxy-4-methyl-1-octenyl]-7-hydroxybicyclo[3.3.0]-2-octene
190) (1S,5S,6R,7R)-3-(4-N-phenylcarbamoylbutyl)-6-[(4S, 1E)-4-hydroxy-4-methyl-1-octenyl]7-hydroxybicyclo[3.3.0]-2-octene
191) (1S,5S,6R,7R)-3-(4-N-benzylcarbamoylbutyl)-6-[(4S, 1E)-4-hydroxy-4-methyl-1-octenyl]-7-hydroxybicyclo[3.3.0]-2-octene
192) (1S,5S,6R,7R)-3-[4-N-(4-pyridylmethyl)carbamoylbutyl]-6-[(4S, 1E)-4-hydroxy-4-methyl-1-octenyl]-7-hydroxybicyclo[3.3.0]-2-octene
193) (1S,5S,6R,7R)-3-[4-(4-N-methyl-1-piperazinyl)carbonylbutyl]-6-[(4S,1E)-4-hydroxy-4-methyl-1-octenyl]-7-hydroxybicyclo[3.3.0]-2-octene
194) (1S,5S,6R,7R)-3-[4-N-(2-pyridyl)carbamoylbutyl]-6-[(4S,1E)-4-hydroxy-4-methyl-1-octenyl]-7-hydroxybicyclo[3.3.0]-2-octene
195) (1S,5S,6R,7R)-3-(4-N,N-dipropylcarbamoylbutyl)-6-[(4S,1E)-4-hydroxy-4-methyl-1-octenyl]-7-hydroxybicyclo[3.3.0]-2-octene
196) (1S,5S,6R,7R)-3-(4-N,N-dibutylcarbamoylbutyl)-6-[(4S,1E)-4-hydroxy-4-methyl-1-octenyl]-7-hydroxybicyclo[3.3.0]-2-octene
197) (1S,5S,6R,7R)-3-(4-N-t-butyl-N-methylcarbamoylbutyl)-6-[(4S,1E)-4-hydroxy-4-methyl-1-octenyl]-7-hydroxybicyclo[3.3.0]-2-octene
198) (1S,5S,6R,7R)-3-[4-N-(2-hydroxyethyl)carbamoylbutyl]-6-[(4S,1E)-4-hydroxy-4-methyl-1-octenyl]-7-hydroxybicyclo[3.3.0]-2-octene
199) (1S,5S,6R,7R)-3-[4-N-(3-hydroxypropyl)carbamoylbutyl]-6-[(4S,1E)-4-hydroxy-4-methyl-1-octenyl]-7-hydroxybicyclo[3.3.0]-2-octene
200) (1S,5S,6R,7R)-3-(3-carbamoylpropyl)-6-[(4S,1E)-4-hydroxy-4-methyl-1-octenyl]-7-hydroxybicyclo[3.3.0]-2-octene
201) (1S,5S,6R,7R)-3-(3-N,N-dimethylcarbamoylpropyl)-6-[(4S,1E)-4-hydroxy-4-methyl-1-octenyl]-7-hydroxybicyclo[3.3.0]-2-octene
202) (1S,5S,6R,7R)-3-(3-N,N-diisopropylcarbamoylpropyl)-6-[(4S,1E)-4-hydroxy-4-methyl-1-octenyl]-7-hydroxybicyclo[3.3.0]-2-octene
203) (1S,5S,6R,7R)-3-(3-N-t-butyl-N-methylcarbamoylpropyl)-6-[(4S,1E)-4-hydroxy-4-methyl-1-octenyl]-7-hydroxybicyclo[3.3.0]-2-octene
204) (1S,5S,6R,7R)-3-[3-(1-pyrrolidinyl)carbonylpropyl]-6-[(4S,1E)-4-hydroxy-4-methyl-1-octenyl]-7-hydroxybicyclo[3.3.0]-2-octene
205) (1S,5S,6R,7R)-3-(3-piperidinocarbonylpropyl)-6-[(4S, 1E)-4-hydroxy-4-methyl-1-octenyl]-7-hydroxybicyclo[3.3.0]-2-octene
206) (1S,5S,6R,7R)-3-(3-morpholinocarbonylpropyl)-6-[(4S,1E)-4-hydroxy-4-methyl-1-octenyl]-7-hydroxybicyclo[3.3.0]-2-octene
207) (1S,5S,6R,7R)-3-(5-carbamoylpentyl)-6-[(4S,1E)-4-hydroxy-4-methyl-1-octenyl]-7-hydroxybicyclo[3.3.0]-2-octene
208) (1S,5S,6R,7R)-3-(5-N,N-dimethylcarbamoylpentyl)-6-[(4S,1E)-4-hydroxy-4-methyl-1-octenyl]-7-hydroxybicyclo[3.3.0]-2-octene
209) (1S,5S,6R,7R)-3-(5-N,N-diisopropylcarbamoylpentyl)-6-[(4S,1E)-4-hydroxy-4-methyl-1-octenyl]-7-hydroxybicyclo[3.3.0]-2-octene
210) (1S,5S,6R,7R)-3-(5-N-t-butyl-N-methylcarbamoylpentyl)-6-[(4S,1E)-4-hydroxy-4-methyl-1-octenyl]-7-hydroxybicyclo (3.3.0]-2-octene
211) (1S,5S,6R,7R)-3-[5-(1-pyrrolidinyl)carbonylpentyl]-6-[(4S,1E)-4-hydroxy-4-methyl-1-octenyl]-7-hydroxybicyclo[3.3.0]-2-octene
212) (1S,5S,6R,7R)-3-(5-piperidinocarbonylpentyl)-6-[(4S, 1E)-4-hydroxy-4-methyl-1-octenyl]-7-hydroxybicyclo[3.3.0]-2-octene
213) (1S,5S,6R,7R)-3-(5-morpholinocarbonylpentyl)-6-[(4S, E)-4-hydroxy-4-methyl-1-octenyl]-7-hydroxybicyclo[3.3.0]-2-octene
214) (1S,5S,6R,7R)-3-[(1Z)-3-N,N-dimethylcarbamoyl-1-propenyl]-6-[(4S,1E)-4-hydroxy-4-methyl-1-octenyl]-7-hydroxybicyclo[3.3.0]-2-octene
215) (1S,5S,6R,7R)-3-[(1Z)-4-N,N-dimethylcarbamoyl-1-butenyl]-6-[(4S,1E)-4-hydroxy-4-methyl-1-octenyl]-7-hydroxybicyclo[3.3.0]-2-octene
216) (1S,5S,6R,7R)-3-[(1E)-4-N,N-dimethylcarbamoyl-1-butenyl]-6-[(4S, 1E)-4-hydroxy-4-methyl-1-octenyl]-7-hydroxybicyclo[3.3.0]-2-octene
217) (1S,5S,6R,7R)-3-[(1Z)-5-N,N-dimethylcarbamoyl-1-pentenyl]-6-[(4S,1E)-4-hydroxy-4-methyl-1-octenyl]-7-hydroxybicyclo[3.3.0]-2-octene
218) (1S,5S,6R,7R)-3-[N—(N,N-dimethylcarbamoylmethyl)aminomethyl]-6-[(4S,1E)-4-hydroxy-4-methyl-1-octenyl]-7-hydroxybicyclo[3.3.0]-2-octene
219) (1S,5S,6R,7R)-3-[N-(2-N,N-dimethylcarbamoylethyl)aminomethyl]-6-[(4S,1E)-4-hydroxy-4-methyl-1-octenyl]-7-hydroxybicyclo[3.3.0]-2-octene
220) (1S,5S,6R,7R)-3-[N-(2-N,N-diisopropylcarbamoylethyl)aminomethyl]-6-[(4S,1E)-4-hydroxy-4-methyl-1-octenyl]-7-hydroxybicyclo[3.3.0]-2-octene
221) (1S,5S,6R,7R)-3-[N-(2-N-t-butyl-N-methylcarbamoylethyl)aminomethyl]-6-[(4S,1E)-4-hydroxy-4-methyl-1-octenyl]-7-hydroxybicyclo[3.3.0]-2-octene 222) (1S,5S,6R,7R)-3-[N-[2-(1-pyrrolidinyl)carbonylethyl]aminomethyl]-6-[(4S,1E)-4-hydroxy-4-methyl-1-octenyl]-7-hydroxybicyclo[3.3.0]-2-octene 223) (1S,5S,6R,7R)-3-[N-(2-piperidinocarbonylethyl)aminomethyl]-6-[(4S,1E)-4-hydroxy-4-methyl-1-octenyl]-7-hydroxybicyclo[3.3.0]-2-octene 224) (1S,5S,6R,7R)-3-[N-(2-morpholinocarbonylethyl)aminomethyl]-6-[(4S,1E)-4-hydroxy-4-methyl-1-octenyl]-7-hydroxybicyclo[3.3.0]-2-octene 225) (1S,5S,6R,7R)-3-[N-(3-N,N-dimethylcarbamoylpropyl)aminomethyl]-6-[(4S,1E)-4-hydroxy-4-methyl-1-octenyl]-7-hydroxybicyclo [3.3.0]-2-octene 226) (1S,5S,6R,7R)-3-[N-(2-N,N-dimethylcarbamoyethyl)-N-methylaminomethyl]-6-[(4S,1E)-4-hydroxy-4-methyl-1-octenyl]-7-hydroxybicyclo[3.3.0]-2-octene 227) (1S,5S,6R,7R)-3-[N—(N,N-dimethylcarbamoylmethyl)aminoethyl]-6-[(4S,1E)-4-hydroxy-4-methyl-1-octenyl]-7-hydroxybicyclo[3.3.0]-2-octene 228) (1S,5S,6R,7R)-3-[N—(N,N-diisopropylcarbamoylmethyl)aminoethyl]-6-[(4S,1E)-4-hydroxy-4-methyl-1-octenyl]-7-hydroxybicyclo[3.3.0]-2-octene 229) (1S,5S,6R,7R)-3-[N-(N-t-butyl-N-methylcarbamoylmethyl)aminoethyl]-6-[(4S,1E)-4-hydroxy-4-methyl-1-octenyl]-7-hydroxybicyclo[3.3.0]-2-octene 230) (1S,5S,6R,7R)-3-[2-N-[(1-pyrrolidinyl)carbonylmethyl]aminoethyl]-6-[(4S,1E)-4-hydroxy-4-methyl-1-octenyl]-7-hydroxybicyclo[3.3.0]-2-octene 231) (1S,5S,6R,7R)-3-[2-N-(piperidinocarbonylmethyl)aminoethyl]-6-[(4S,1E)-4-hydroxy-4-methyl-1-octenyl]-7-hydroxybicyclo[3.3.0]-2-octene 232) (1S,5S,6R,7R)-3-[2-N-(morpholinocarbonylmethyl)aminoethyl]-6-[(4S,1E)-4-hydroxy-4-methyl-1-octenyl]-7-hydroxybicyclo[3.3.0]-2-octene 233) (1S,5S,6R,7R)-3-[2-N-(2-N,N-dimethylcarbamoylethyl)aminoethyl]-6-[(4S,1E)-4-hydroxy-4-methyl-1-octenyl]-7-hydroxybicyclo[3.3.0]-2-octene 234) (1S,5S,6R,7R)-3-[(2-N,N-dimethylcarbamoylethyl)oxymethyl]-6-[(4S,1E)-4-hydroxy-4-methyl-1-octenyl]-7-hydroxybicyclo[3.3.0]-2-octene 235) (1S,5S,6R,7R)-3-[(2-N,N-diisopropylcarbamoylethyl)oxymethyl]-6-[(4S,1E)-4-hydroxy-4-methyl-1-octenyl]-7-hydroxybicyclo[3.3.0]-2-octene 236) (1S,5S,6R,7R)-3-[(2-N-t-butyl-N-methylcarbamoylethyl)oxymethyl]-6-[(4S,1E)-4-hydroxy-4-methyl-1-octenyl]-7-hydroxybicyclo[3.3.0]-2-octene 237) (1S,5S,6R,7R)-3-[[2-(1-pyrrolidinyl)carbonylethyl]oxymethyl]-6-[(4S,1E)-4-hydroxy-4-methyl-1-octenyl]-7-hydroxybicyclo[3.3.0]-2-octene 238) (1S,5S,6R,7R)-3-[(2-piperidinocarbonylethyl)oxyethyl]-6-[(4S,1E)-4-hydroxy-4-methyl-1-octenyl]-7-hydroxybicyclo[3.3.0]-2-octene 239) (1S,5S,6R,7R)-3-[(2-morpholinocarbonylethyl)oxyethyl]-6-[(4S, 1E)-4-hydroxy-4-methyl-1-octenyl]-7-hydroxybicyclo[3.3.0]-2-octene 240) (1S,5S,6R,7R)-3-[2-(N,N-dimethylcarbamoylmethyl)oxyethyl]-6-[(4S,1E)-4-hydroxy-4-methyl-1-octenyl]-7-hydroxybicyclo[3.3.0]-2-octene 241) (1S,5S,6R,7R)-3-[2-(N,N-diisopropylcarbamoylmethyl)oxyethyl]-6-[(4S,1E)-4-hydroxy-4-methyl-1-octenyl]-7-hydroxybicyclo[3.3.0]-2-octene 242) (1S,5S,6R,7R)-3-[2-(N-t-butyl-N-methylcarbamoylmethyl)oxyethyl]-6-[(4S,4E)-4-hydroxy-4-methyl-1-octenyl]-7-hydroxybicyclo[3.3.0]-2-octene 243) (1S,5S,6R,7R)-3-[2-[(1-pyrrolidinyl)carbonylmethyl]oxyethyl]-6-[(4S,1E)-4-hydroxy-4-methyl-1-octenyl]-7-hydroxybicyclo[3.3.0]-2-octene 244) (1S,5S,6R,7R)-3-[2-(piperidinocarbonylmethyl)oxyethyl]-6-[(4S,1E)-4-hydroxy-4-methyl-1-octenyl]-7-hydroxybicyclo[3.3.0]-2-octene 245) (1S,5S,6R,7R)-3-[2-(morpholinocarbonylmethyl)oxyethyl]-6-[(4S,1E)-4-hydroxy-4-methyl-1-octenyl]-7-hydroxybicyclo[3.3.0]-2-octene 246) (1S,5S,6R,7R)-3-[(2-N,N-dimethylcarbamoylethyl)thiomethyl]-6-[(4S,1E)-4-hydroxy-4-methyl-1-octenyl]-7-hydroxybicyclo[3.3.0]-2-octene 247) (1S,5S,6R,7R)-3-[(2-N,N-diisopropylcarbamoylethyl)thiomethyl]-6-[(4S,1E)-4-hydroxy-4-methyl-1-octenyl]-7-hydroxybicyclo[3.3.0]-2-octene 248) (1S,5S,6R,7R)-3-[(2-N-t-butyl-N-methylcarbamoylethyl)thiomethyl]-6-[(4S,1E)-4-hydroxy-4-methyl-1-octenyl]-7-hydroxybicyclo[3.3.0]-2-octene 249) (1S,5S,6R,7R)-3-[[2-(1-pyrrolidinylcarbonyl)ethyl]thiomethyl]-6-[(4S,1E)-4-hydroxy-4-methyl-1-octenyl]-7-hydroxybicyclo[3.3.0]-2-octene 250) (1S,5S,6R,7R)-3-[(2-piperidinocarbonylethyl)thiomethyl]-6-[(4S,1E)-4-hydroxy-4-methyl-1-octenyl]-7-hydroxybicyclo[3.3.0]-2-octene 251) (1S,5S,6R,7R)-3-[(2-morpholinocarbonylethyl)thiomethyl]-6-[(4S,1E)-4-hydroxy-4-methyl-1-octenyl]-7-hydroxybicyclo[3.3.0]-2-octene 252) (1S,5S,6R,7R)-3-[2-(N,N-dimethylcarbamoylmethyl)thioethyl]-6-[(4S,1E)-4-hydroxy-4-methyl-1-octenyl]-7-hydroxybicyclo[3.3.0]-2-octene 253) (1S,5S,6R,7R)-3-[2-(N,N-diisopropylcarbamoylmethyl)thioethyl]-6-[(4S,1E)-4-hydroxy-4-methyl-1-octenyl]-7-hydroxybicyclo[3.3.0]-2-octene 254) (1S,5S,6R,7R)-3-[2-(N-t-butyl-N-methylcarbamoylmethyl)thioethyl]-6-[(4S,1E)-4-hydroxy-4-methyl-1-octenyl]-7-hydroxybicyclo[3.3.0]-2-octene 255) (1S,5S,6R,7R)-3-[2-[(1-pyrrolidinyl)carbonylmethyl]thioethyl]-6-[(4S,1E)-4-hydroxy-4-methyl-1-octenyl]-7-hydroxybicyclo[3.3.0]-2-octene 256) (1S,5S,6R,7R)-3-[2-(piperidinocarbonylmethyl)thioethyl]-6-[(4S,1E)-4-hydroxy-4-methyl-1-octenyl]-7-hydroxybicyclo[3.3.0]-2-octene 257) (1S,5S,6R,7R)-3-[2-(morpholinocarbonylmethyl)thioethyl]-6-[(4S,1E)-4-hydroxy-4-methyl-1-octenyl]-7-hydroxybicyclo[3.3.0]-2-octene 258) (1S,5S,6R,7R)-3-[(2-carbamoylphenyl)methyl]-6-[(4S,1E)-4-hydroxy-4-methyl-1-octenyl]-7-hydroxybicyclo[3.3.0]-2-octene 259) (1S,5S,6R,7R)-3-[(4-carbamoylphenyl)methyl]-6-[(4S,1E)-4-hydroxy-4-methyl-1-octenyl]-7-hydroxybicyclo[3.3.0]-2-octene 260) (1S,5S,6R,7R)-3-[2-(3-carbamoylphenyl)ethyl]-6-[(4S,1E)-4-hydroxy-4-methyl-1-octenyl]-7-hydroxybicyclo[3.3.0]-2-octene 261) (1S,5S,6R,7R)-3-[2-[3-(piperidinocarbonyl)phenyl]ethyl]-6-[(4S,1E)-4-hydroxy-4-methyl-1-octenyl]-7-hydroxybicyclo[3.3.0]-2-octene 262) (1S,5S,6R,7R)-3-(4-carbamoylbutyl)-6-[(3S,1E)-3-hydroxy-4-(m-tolyl)-1-butenyl]-7-hydroxybicyclo[33.0]-2-octene 263) (1S,5S,6R,7R)-3-(4-N,N-dimethylcarbamoylbutyl)-6-[(3S,1E)-3-hydroxy-4-(m-tolyl)-1-butenyl]-7-hydroxybicyclo[3.3.0]-2-octene 264) (1S,5S,6R,7R)-3-(4-N,N-diethylcarbamoylbutyl)-6-[(3S,1E)-3-hydroxy-4-(m-tolyl)-1-butenyl]-7-hydroxybicyclo[3.3.0]-2-octene 265) (1S,5S,6R,7R)-3-[4-N-(2-methoxycarbonylethyl)carbamoylbutyl]-6-[(3S,1E)-3-hydroxy-4-(m-tolyl)-1-butenyl]-7-hydroxybicyclo[3.3.0]-2-octene 266) (1S,5S,6R,7R)-3-[4-N-(4-pyridylmethyl)carbamoylbutyl]-6-[(3S,1E)-3-hydroxy-4-tolyl)-1-butenyl]-7-hydroxybicyclo[3.3.0]-2-octene 267) (1S,5S,6R,7R)-3-(4-N,N-diisopropylcarbamoylbutyl)-6-[(3S,1E)-3-hydroxy-4-(m-tolyl)-1-butenyl]-7-hydroxybicyclo[3.3.0]-2-octene 268) (1S,5S,6R,7R)-3-[4-(1-pyrrolidinyl)carbonylbutyl]-6-[(3S,1E)-3-hydroxy-4-(m-tolyl)-1-butenyl]-7-hydroxybicyclo[3.3.0]-2-octene 269) (1S,5S,6R,7R)-3-(4-piperidinocarbonylbutyl)-6-[(3S,1E)-3-hydroxy-4-(m-tolyl)-1-butenyl]-7-hydroxybicyclo[3.3.0]-2-octene 270) (1S,5S,6R,7R)-3-(4-morpholinocarbonylbutyl)-6-[(3S,1E)-3-hydroxy-4-(m-tolyl)-1-butenyl]-7-hydroxybicyclo[3.3.0]-2-octene 271) (1S,5S,6R,7R)-3-(4-N-methylcarbamoylbutyl)-6-[(3S,1E)-3-hydroxy-4-(m-tolyl)-1-butenyl]-7-hydroxybicyclo[3.3.0]-2-octene 272) (1S,5S,6R,7R)-3-(4-N-ethylcarbamoylbutyl)-6-[(3S,1E)-3-hydroxy-4-(m-tolyl)-1-butenyl]-7-hydroxybicyclo[3.3.0]-2-octene 273) (1S,5S,6R,7R)-3-(4-N-propylcarbamoylbutyl)-6-[(3S,1E)-3-hydroxy-4-(m-tolyl)-1-butenyl]-7-hydroxybicyclo[3.3.0]-2-octene 274) (1S,5S,6R,7R)-3-(4-N-isopropylcarbamoylbutyl)-6-[(3S,1E)-3-hydroxy-4-(m-tolyl)-1-butenyl]-7-hydroxybicyclo[3.3.0]-2-octene 275) (1S,5S,6R,7R)-3-(4-N-butylcarbamoylbutyl)-6-[(3S,1E)-3-hydroxy-4-(m-tolyl)-1-butenyl]-7-hydroxybicyclo[3.3.0]-2-octene 276) (1S,5S,6R,7R)-3-(4-N-t-butylcarbamoylbutyl)-6-[(3S,1E)-3-hydroxy-4-(m-tolyl)-1-butenyl]-7-hydroxybicyclo[3.3.0]-2-octene 277) (1S,5S,6R,7R)-3-(4-N-phenylcarbamoylbutyl)-6-[(3S,1E)-3-hydroxy-4-(m-tolyl)-1-butenyl]-7-hydroxybicyclo[3.3.0]-2-octene 278) (1S,5S,6R,7R)-3-(4-N-benzylcarbamoylbutyl)-6-[(3S,1E)-3-hydroxy-4-(m-tolyl)-1-butenyl]-7-hydroxybicyclo[3.3.0]-2-octene 279) (1S,5S,6R,7R)-3-[4-N-(4-pyridylmethyl)carbamoylbutyl]-6-[(3S,1E)-3-hydroxy-4-(m-tolyl)-1-butenyl]-7-hydroxybicyclo[3.3.0]-2-octene 280) (1S,5S,6R,7R)-3-[4-(4-N-methyl-1-piperazinyl)carbonylbutyl]-6-[(3S,1E)-3-hydroxy-4-(m-tolyl)-1-butenyl]-7-hydroxybicyclo[3.3.0]-2-octene 281) (1S,5S,6R,7R)-3-[4-N-(2-pyridyl)carbamoylbutyl]-6-[(3S, 1E)-3-hydroxy-4-(m-tolyl)-1-butenyl]-7-hydroxybicyclo[3.3.0]-2-octene 282) (1S,5S,6R,7R)-3-(4-N,N-dipropylcarbamoylbutyl)-6-[(3S,1E)-3-hydroxy-4-(m-tolyl)-1-butenyl]-7-hydroxybicyclo [3.3.0]-2-octene 283) (1S,5S,6R,7R)-3-(4-N,N-dibutylcarbamoylbutyl)-6-[(3S,1E)-3-hydroxy-4-(m-tolyl)-1-butenyl]-7-hydroxybicyclo[3.3.0]-2-octene 284) (1S,5S,6R,7R)-3-(4-N-t-butyl-N-methylcarbamoylbutyl)-6-[(3S,1E)-3-hydroxy-4-(m-tolyl)-1-butenyl]-7-hydroxybicyclo[3.3.0]-2-octene 285) (1S,5S,6R,7R)-3-[4-N-(2-hydroxyethyl)carbamoylbutyl]-6-[(3S,1E)-3-hydroxy-4-(m-tolyl)-1-butenyl]-7-hydroxybicyclo[3.3.0]-2-octene 286) (1S,5S,6R,7R)-3-[4-N-(3-hydroxypropyl)carbamoylbutyl]-6-[(3S,1E)-3-hydroxy-4-(m-tolyl)-1-butenyl]-7-hydroxybicyclo[3.3.0]-2-octene 287) (1S,5S,6R,7R)-3-(3-carbamoylpropyl)-6-[(3S,1E)-3-hydroxy-4-(m-tolyl)-1-butenyl]-7-hydroxybicyclo[3.3.0]-2-octene 288) (1S,5S,6R,7R)-3-(3-N,N-dimethylcarbamoylpropyl)-6-[(3S,1E)-3-hydroxy-4-(m-tolyl)-1-butenyl]-7-hydroxybicyclo[3.3.0]-2-octene 289) (1S,5S,6R,7R)-3-(3-N,N-diisopropylcarbamoylpropyl)-6-[(3S,1E)-3-hydroxy-4-(m-tolyl)-1-butenyl]-7-hydroxybicyclo[3.3.0]-2-octene 290) (1S,5S,6R,7R)-3-(3-N-t-butyl-N-methylcarbamoylpropyl)-6-[(3S,1E)-3-hydroxy-4-(m-tolyl)-1-butenyl]-7-hydroxybicyclo [3.3.0]-2-octene 291) (1S,5S,6R,7R)-3-[3-(1-pyrrolidinyl)carbonylpropyl]-6-[(3S,1E)-3-hydroxy-4-(m-tolyl)-1 butenyl]-7-hydroxybicyclo[3.3.0]-2-octene 292) (1S,5S,6R,7R)-3-(3-piperidinocarbonylpropyl)-6-[(3S,1E)-3-hydroxy-4-(m-tolyl)-1 butenyl]-7-hydroxybicyclo [3.3.0]-2-octene 293) (1S,5S,6R,7R)-3-(3-morpholinocarbonylpropyl)-6-[(3S,1E)-3-hydroxy-4-(m-tolyl)-1-butenyl]-7-hydroxybicyclo[3.3.0]-2-octene 294) (1S,5S,6R,7R)-3-(5-carbamoylpentyl)-6-[(3S,1E)-3-hydroxy-4-(m-tolyl)-1-butenyl]-7-hydroxybicyclo [3.3.0]-2-octene 295) (1S,5S,6R,7R)-3-(5-N,N-dimethylcarbamoylpentyl)-6-[(3S,1E)-3-hydroxy-4-(m-tolyl)-1 butenyl]-7-hydroxybicyclo[3.3.0]-2-octene 296) (1S,5S,6R,7R)-3-(5-N,N-diisopropylcarbamoylpentyl)-6-[(3S,1E)-3-hydroxy-4-(m-tolyl)-1-butenyl]-7-hydroxybicyclo[3.3.0]-2-octene 297) (1S,5S,6R,7R)-3-(5-N-t-butyl-N-methylcarbamoylpentyl)-6-[(3S,1E)-3-hydroxy-4-(m-tolyl)-1-butenyl]-7-hydroxybicyclo[3.3.0]-2-octene 298) (1S,5S,6R,7R)-3-[5-(1-pyrrolidinyl)carbonylpentyl]-6-[(3S,1E)-3-hydroxy-4-(m-tolyl)-1-butenyl]-7-hydroxybicyclo[3.3.0]-2-octene 299) (1S,5S,6R,7R)-3-(5-piperidinocarbonylpentyl)-6-[(3S,1E)-3-hydroxy-4-(m-tolyl)-1-butenyl]-7-hydroxybicyclo [3.3.0]-2-octene 300) (1S,5S,6R,7R)-3-(5-morpholinocarbonylpentyl)-6-[(3S,1E)-3-hydroxy-4-(m-tolyl)-1-butenyl]-7-hydroxybicyclo[3.3.0]-2-octene 301) (1S,5S,6R,7R)-3-[(1Z)-3-N,N-dimethylcarbamoyl-1-propenyl]-6-[(3S,1E)-3-hydroxy-4-(m-tolyl)-1-butenyl]-7-hydroxybicyclo[3.3.0]-2-octene 302) (1S,5S,6R,7R)-3-[(1Z)-4-N,N-dimethylcarbamoyl-1-butenyl]-6-[(3S,1E)-3-hydroxy-4-(m-tolyl)-1-butenyl]-7-hydroxybicyclo[3.3.0]-2-octene 303) (1S,5S,6R,7R)-3-[(1E)-4-N,N-dimethylcarbamoyl-1-butenyl]-6-[(3S, 1E)-3-hydroxy-4-(m-tolyl)-1-butenyl]-7-hydroxybicyclo[3.3.0]-2-octene 304) (1S,5S,6R,7R)-3-[(1Z)-5-N,N-dimethylcarbamoyl-1-pentenyl]-6-[(3S,1E)-3-hydroxy-4-(m-tolyl)-1-butenyl]-7-hydroxybicyclo[3.3.0]-2-octene 305) (1S,5S,6R,7R)-3-[N—(N,N-dimethylcarbamoylmethyl)aminomethyl]-6-[(3S,1E)-3-hydroxy-4-(m-tolyl)-1-butenyl]-7-hydroxybicyclo[3.3.0]-2-octene 306) (1S,5S,6R,7R)-3-[N-(2-N,N-dimethylcarbamoylethyl)aminomethyl]-6-[(3S,1E)-3-hydroxy-4-(m-tolyl)-1-butenyl]-7-hydroxybicyclo[3.3.0]-2-octene 307) (1S,5S,6R,7R)-3-[N-(2-N,N-diisopropylcarbamoylethyl)aminomethyl]-6-[(3S,1E)-3-hydroxy-4-(m-tolyl)-1-butenyl]-7-hydroxybicyclo[3.3.0]-2-octene 308) (1S,5S,6R,7R)-3-[N-(2-N-t-butyl-N-methylcarbamoylethyl)aminomethyl]-6-[(3S,1E)-3-hydroxy-4-(m-tolyl)-1-butenyl]-7-hydroxybicyclo [3.3.0]-2-octene 309) (1S,5S,6R,7R)-3-[N-[2-(1-pyrrolidinyl)carbonylethyl]aminomethyl]-6-[(3S,1E)-3-hydroxy-4-(m-tolyl)-1-butenyl]-7-hydroxybicyclo[3.3.0]-2-octene 310) (1S,5S,6R,7R)-3-[N-(2-piperidinocarbonylethyl)aminomethyl]-6-[(3S,1E)-3-hydroxy-4-(m-tolyl)-1-butenyl]-7-hydroxybicyclo[3.3.0]-2-octene
311) (1S,5S,6R,7R)-3-[N-(2-morpholinocarbonylethyl)aminomethyl]-6-[(3S,1E)-3-hydroxy-4-(m-tolyl)-1-butenyl]-7-hydroxybicyclo[3.3.0]-2-octene
312) (1S,5S,6R,7R)-3-[N-(3-N,N-dimethylcarbamoylpropyl)aminomethyl]-6-[(3S,1E)-3-hydroxy-4-(m-tolyl)-1-butenyl]-7-hydroxybicyclo[3.3.0]-2-octene
313) (1S,5S,6R,7R)-3-[N-(2-N,N-dimethylcarbamoylethyl)-N-methylaminomethyl]-6-[(3S,1E)-3-hydroxy-4-(m-tolyl)-1-butenyl]-7-hydroxybicyclo[3.3.0]-2-octene
314) (1S,5S,6R,7R)-3-[N—(N,N-dimethylcarbamoylmethyl)aminoethyl-6-[(3S,1E)-3-hydroxy-4-(m-tolyl)-1-butenyl]-7-hydroxybicyclo[3.3.0]-2-octene
315) (1S,5S,6R,7R)-3-[N—(N,N-diisopropylcarbamoylmethyl)aminoethyl]-6-[(3S,1E)-3-hydroxy-4-(m-tolyl)-1-butenyl]-7-hydroxybicyclo[3.3.0]-2-octene
316) (1S,3S,6R,7R)-3-[N-(N-t-butyl-N-methylcarbamoylmethyl)aminoethyl-6-[(3S,1E)-3-hydroxy-4-(m-tolyl)-1-butenyl]-7-hydroxybicyclo[3.3.0]-2-octene
317) (1S,5S,6R,7R)-3-[2-N-[(1-pyrrolidinyl)carbonylmethyl]aminoethyl]-6-[(3S,1E)-3-hydroxy-4-(m-tolyl)-1-butenyl]-7-hydroxybicyclo[3.3.0]-2-octene
318) (1S,5S,6R,7R)-3-[2-N-(piperidinocarbonylmethyl)aminoethyl]-6-[(3S,1E)-3-hydroxy-4-(m-tolyl)-1-butenyl]-7-hydroxybicyclo[3.3.0]-2-octene
319) (1S,5S,6R,7R)-3-[2-N-(morpholinocarbonylmethyl)aminoethyl]-6-[(3S,1E)-3-hydroxy-4-(m-tolyl)-1-butenyl]-7-hydroxybicyclo[3.3.0]-2-octene
320) (1S,5S,6R,7R)-3-[2-N-(2-N,N-dimethylcarbamoylethyl)aminoethyl]-6-[(3S,1E)-3-hydroxy-4-(m-tolyl)-1-butenyl]-7-hydroxybicyclo[3.3.0]-2-octene
321) (1S,5S,6R,7R)-3-[(2-N,N-dimethylcarbamoylethyl)oxymethyl]-6-[(3S,1E)-3-hydroxy-4-(m-tolyl)-1-butenyl]-7-hydroxybicyclo[3.3.0]-2-octene
322) (1S,5S,6R,7R)-3-[(2-N,N-diisopropylcarbamoylethyl)oxymethyl]-6-[(3S,1E)-3-hydroxy-4-(m-tolyl)-1-butenyl]-7-hydroxybicyclo[3.3.0]-2-octene
323) (1S,5S,6R,7R)-3-[(2-N-t-butyl-N-methylcarbamoylethyl)oxymethyl]-6-[(3S,1E)-3-hydroxy-4-(m-tolyl)-1-butenyl]-7-hydroxybicyclo[3.3.0]-2-octene
324) (1S,5S,6R,7R)-3-[[2-(1-pyrrolidinyl)carbonylethyl]oxymethyl]-6-[(3S,1E)-3-hydroxy-4-(m-tolyl)-1-butenyl]-7-hydroxybicyclo[3.3.0]-2-octene
325) (1S,5S,6R,7R)-3-[(2-piperidinocarbonylethyl)oxymethyl]-6-[(3S,1E)-3-hydroxy-4-(m-tolyl)-1-butenyl]-7-hydroxybicyclo[3.3.0]-2-octene
326) (1S,5S,6R,7R)-3-[(2-morpholinocarbonylethyl)oxymethyl]-6-[(3S,1E)-3-hydroxy-4-(m-tolyl)-1-butenyl]-7-hydroxybicyclo[3.3.0]-2-octene
327) (1S,5S,6R,7R)-3-[2-(N,N-dimethylcarbamoylmethyl)oxyethyl]-6-[(3S,1E)-3-hydroxy-4-(m-tolyl)-1-butenyl]-7-hydroxybicyclo[3.3.0]-2-octene
328) (1S,5S,6R,7R)-3-[2-(N,N-diisopropylcarbamoylmethyl)oxyethyl]-6-[(3S,1E)-3-hydroxy-4-(m-tolyl)-1-butenyl]-7-hydroxybicyclo[3.3.0]-2-octene
329) (1S,5S,6R,7R)-3-[2-(N-t-butyl-N-methylcarbamoylmethyl)oxyethyl]-6-[(3S,1E)-3-hydroxy-4-(m-tolyl)-1-butenyl]-7-hydroxybicyclo[3.3.0]-2-octene
330) (1S,5S,6R,7R)-3-[2-[(1-pyrrolidinyl)carbonylmethyl]oxyethyl]-6-[(3S,1E)-3-hydroxy-4-(m-tolyl)-1-butenyl]-7-hydroxybicyclo[3.3.0]-2-octene
331) (1S,5S,6R,7R)-3-[2-(piperidinocarbonylmethyl)oxyethyl]-6-[(3S,1E)-3-hydroxy-4-(m-tolyl)-1-butenyl]-7-hydroxybicyclo[3.3.0]-2-octene
332) (1S,5S,6R,7R)-3-[2-(morpholinocarbonylmethyl)oxyethyl]-6-[(3S,1E)-3-hydroxy-4-(m-tolyl)-1-butenyl]-7-hydroxybicyclo[3.3.0]-2-octene
333) (1S,5S,6R,7R)-3-[(2-N,N-dimethylcarbamoylethyl)thiomethyl]-6-[(3S,1E)-3-hydroxy-4-(m-tolyl)-1-butenyl]-7-hydroxybicyclo[3.3.0]-2-octene
334) (1S,5S,6R,7R)-3-[(2-N,N-diisopropylcarbamoylethyl)thiomethyl]-6-[(3S,1E)-3-hydroxy-4-(m-tolyl)-1-butenyl]-7-hydroxybicyclo[3.3.0]-2-octene
335) (1S,5S,6R,7R)-3-[(2-N-t-butyl-N-methylcarbamoylethyl)thiomethyl]-6-[(3S,1E)-3-hydroxy-4-(m-tolyl)-1-butenyl]-7-hydroxybicyclo[3.3.0]-2-octene
336) (1S,5S,6R,7R)-3-[[2-(1-pyrrolidinylcarbonyl)ethyl]thiomethyl]-6-[(3S,1E)-3-hydroxy-4-(m-tolyl)-1-butenyl]-7-hydroxybicyclo[3.3.0]-2-octene
337) (1S,5S,6R,7R)-3-[(2-piperidinocarbonylethyl)thiomethyl]-6-[(3S,1E)-3-hydroxy-4-(m-tolyl)-1-butenyl]-7-hydroxybicyclo[3.3.0]-2-octene
338) (1S,5S,6R,7R)-3-[(2-morpholinocarbonylethyl)thiomethyl]-6-[(3S,1E)-3-hydroxy-4-(m-tolyl)-1-butenyl]-7-hydroxybicyclo[3.3.0]-2-octene
339) (1S,5S,6R,7R)-3-[2-(N,N-dimethylcarbamoylmethyl)thioethyl]-6-[(3S,1E)-3-hydroxy-4-(m-tolyl)-1-butenyl]-7-hydroxybicyclo[3.3.0]-2-octene
340) (1S,5S,6R,7R)-3-[2-(N,N-diisopropylcarbamoylmethyl)thioethyl]-6-[(3S,1E)-3-hydroxy-4-(m-tolyl)-1-butenyl]-7-hydroxybicyclo[3.3.0]-2-octene
341) (1S,5S,6R,7R)-3-[2-(N-t-butyl-N-methylcarbamoylmethyl)thioethyl]-6-[(3S,1E)-3-hydroxy-4-(m-tolyl)-1-butenyl]-7-hydroxybicyclo[3.3.0]-2-octene
342) (1S,5S,6R,7R)-3-[2-[(1-pyrrolidinyl)carbonylmethyl]thioethyl]-6-[(3S,1E)-3-hydroxy-4-(m-tolyl)-1-butenyl]-7-hydroxybicyclo[3.3.0]-2-octene
343) (1S,5S,6R,7R)-3-[2-(piperidinocarbonylmethyl)thioethyl]-6-[(3S,1E)-3-hydroxy-4-(m-tolyl)-1-butenyl]-7-hydroxybicyclo[3.3.0]-2-octene
344) (1S,5S,6R,7R)-3-[2-(morpholinocarbonylmethyl)thioethyl]-6-[(3S,1E)-3-hydroxy-4-(m-tolyl)-1-butenyl]-7-hydroxybicyclo[3.3.0]-2-octene
345) (1S,5S,6R,7R)-3-[(2-carbamoylphenyl)methyl]-6-[(3S,1E)-3-hydroxy-4-(m-tolyl)-1-butenyl]-7-hydroxybicyclo[3.3.0]-2-octene
346) (1S,5S,6R,7R)-3-[(4-carbamoylphenyl)methyl]-6-[(3S,1E)-3-hydroxy-4-(m-tolyl)-1-butenyl]-7-hydroxybicyclo[3.3.0]-2-octene
347) (1S,5S,6R,7R)-3-[2-(3-carbamoylphenyl)ethyl]-6-[(3S,1E)-3-hydroxy-4-(m-tolyl)-1-butenyl]-7-hydroxybicyclo[3.3.0]-2-octene
348) (1S,5S,6R,7R)-3-[2-[3-(piperidinocarbonyl)phenyl]ethyl]-6-[(3S,1E)-3-hydroxy-4-(m-tolyl)-1-butenyl]-7-hydroxybicyclo[3.3.0]-2-octene
349) (1S,5S,6R,7R)-3-(4-carbamoylbutyl)-6-[(3R,1E)-3-hydroxy-4-(m-tolyl)-1-butenyl]-7-hydroxybicyclo[3.3.0]-2-octene
350) (1S,5S,6R,7R)-3-(4-N,N-dimethylcarbamoylbutyl)-6-[(3R,1E)-3-hydroxy-4-(m-tolyl)-1-butenyl]-7-hydroxybicyclo[3.3.0]-2-octene
351) (1S,5S,6R,7R)-3-(4-N,N-diethylcarbamoylbutyl)-6-[(3R,1E)-3-hydroxy-4-(m-tolyl)-1-butenyl]-7-hydroxybicyclo[3.3.0]-2-octene
352) (1S,5S,6R,7R)-3-[4-N-(2-methoxycarbonylethyl)carbamoylbutyl]-6-[(3R,1E)-3-hydroxy-4-(m-tolyl)-1-butenyl]-7-hydroxybicyclo[3.3.0]-2-octene
353) (1S,5S,6R,7R)-3-[4-N-(4-pyridylmethyl)carbamoylbutyl]-6-[(3R,1E)-3-hydroxy-4-(m-tolyl)-1-butenyl]-7-hydroxybicyclo[3.3.0]-2-octene 354) (1S,5S,6R,7R)-3-(4-N,N-diisopropylcarbamoylbutyl)-6-[(3R,1E)-3-hydroxy-4-(m-tolyl)-1-butenyl]-7-hydroxybicyclo[3.3.0]-2-octene 355) (1S,5S,6R,7R)-3-[4-(1-pyrrolidinyl)carbonylbutyl]-6-[(3R,1E)-3-hydroxy-4-(m-tolyl)-1-butenyl]-7-hydroxybicyclo[3.3.0]-2-octene 356) (1S,5S,6R,7R)-3-(4-piperidinocarbonylbutyl)-6-[(3R,1E)-3-hydroxy-4-(m-tolyl)-1-butenyl]-7-hydroxybicyclo[3.3.0]-2-octene 357) (1S,5S,6R,7R)-3-(4-morpholinocarbonylbutyl)-6-[(3R,1E)-3-hydroxy-4-(m-tolyl)-1-butenyl]-7-hydroxybicyclo[3.3.0]-2-octene 358) (1S,5S,6R,7R)-3-(4-N-methylcarbamoylbutyl)-6-[(3R,1E)-3-hydroxy-4-(m-tolyl)-1-butenyl]-7-hydroxybicyclo[3.3.0]-2-octene 359) (1S,5S,6R,7R)-3-(4-N-ethylcarbamoylbutyl)-6-[(3R,1E)-3-hydroxy-4-(m-tolyl)-1-butenyl]-7-hydroxybicyclo[3.3.0]-2-octene 360) (1S,5S,6R,7R)-3-(4-N-propylcarbamoylbutyl)-6-[(3R,1E)-3-hydroxy-4-(m-tolyl)-1-butenyl]-7-hydroxybicyclo[3.3.0]-2-octene 361) (1S,5S,6R,7R)-3-(4-N-isopropylcarbamoylbutyl)-6-[(3R,1E)-3-hydroxy-4-(m-tolyl)-1-butenyl]-7-hydroxybicyclo[3.3.0]-2-octene 362) (1S,5S,6R,7R)-3-(4-N-butylcarbamoylbutyl)-6-[(3R,1E)-3-hydroxy-4-(m-tolyl)-1-butenyl]-7-hydroxybicyclo[3.3.0]-2-octene 363) (1S,5S,6R,7R)-3-(4-N-t-butylcarbamoylbutyl)-6-[(3R,1E)-3-hydroxy-4-(m-tolyl)-1-butenyl]-7-hydroxybicyclo[3.3.0]-2-octene 364) (1S,5S,6R,7R)-3-(4-N-phenylcarbamoylbutyl)-6-[(3R,1E)-3-hydroxy-4-(m-tolyl)-1-butenyl]-7-hydroxybicyclo[3.3.0]-2-octene 365) (1S,5S,6R,7R)-3-(4-N-benzylcarbamoylbutyl)-6-[(3R,1E)-3-hydroxy-4-(m-tolyl)-1-butenyl]-7-hydroxybicyclo[3.3.0]-2-octene 366) (1S,5S,6R,7R)-3-[4-N-(4-pyridylmethyl)carbamoylbutyl]-6-[(3R, E)-3-hydroxy-4-(m-tolyl)-1-butenyl]-7-hydroxybicyclo[3.3.0]-2-octene 367) (1S,5S,6R,7R)-3-[4-(4-N-methyl-1-piperazinyl)carbonylbutyl]-6-[(3R,1E)-3-hydroxy-4-(m-tolyl)-1-butenyl]-7-hydroxybicyclo[3.3.0]-2-octene 368) (1S,5S,6R,7R)-3-[4-N-(2-pyridyl)carbamoylbutyl]-6-[(3R,1E)-3-hydroxy-4-(m-tolyl)-1-butenyl]-7-hydroxybicyclo[3.3.0]-2-octene 369) (1S,5S,6R,7R)-3-(4-N,N-dipropylcarbamoylbutyl)-6-[(3R,1E)-3-hydroxy-4-(m-tolyl)-1-butenyl]-7-hydroxybicyclo[3.3.0]-2-octene 370) (1S,5S,6R,7R)-3-(4-N,N-dibutylcarbamoylbutyl)-6-[(3R,1E)-3-hydroxy-4-(m-tolyl)-1-butenyl]-7-hydroxybicyclo[3.3.0]-2-octene 371) (1S,5S,6R,7R)-3-(4-N-t-butyl-N-methylcarbamoylbutyl)-6-[(3R, 1E)-3-hydroxy-4-(m-tolyl)-1-butenyl]-7-hydroxybicyclo[3.3.0]-2-octene 372) (1S,5S,6R,7R)-3-[4-N-(2-hydroxyethyl)carbamoylbutyl]-6-[(3R,1E)-3-hydroxy-4-(m-tolyl)-1-butenyl]-7-hydroxybicyclo[3.3.0]-2-octene 373) (1S,5S,6R,7R)-3-[4-N-(3-hydroxypropyl)carbamoylbutyl]-6-[(3R,1E)-3-hydroxy-4-(m-tolyl)-1-butenyl]-7-hydroxybicyclo[3.3.0]-2-octene 374) (1S,5S,6R,7R)-3-(3-carbamoylpropyl)-6-[(3R,1E)-3-hydroxy-4-(m-tolyl)-1-butenyl]-7-hydroxybicyclo[3.3.0]-2-octene 375) (1S,5S,6R,7R)-3-(3-N,N-dimethylcarbamoylpropyl)-6-[(3R,1E)-3-hydroxy-4-(m-tolyl)-1-butenyl]-7-hydroxybicyclo[3.3.0]-2-octene 376) (1S,5S,6R,7R)-3-(3-N,N-diisopropylcarbamoylpropyl)-6-[(3R,1E)-3-hydroxy-4-(m-tolyl)-1-butenyl]-7-hydroxybicyclo[3.3.0]-2-octene 377) (1S,5S,6R,7R)-3-(3-N-t-butyl-N-methylcarbamoylpropyl)-6-[(3R,1E)-3-hydroxy-4-(m-tolyl)-1-butenyl]-7-hydroxybicyclo [3.3.0]-2-octene 378) (1S,5S,6R,7R)-3-[3-(1-pyrrolidinyl)carbonylpropyl]-6-[(3R,1E)-3-hydroxy-4-(m-tolyl)-1-butenyl]-7-hydroxybicyclo[3.3.0]-2-octene 379) (1S,5S,6R,7R)-3-(3-piperidinocarbonylpropyl)-6-[(3R,1E)-3-hydroxy-4-(m-tolyl)-1-butenyl]-7-hydroxybicyclo[3.3.0]-2-octene 380) (1S,5S,6R,7R)-3-(3-morpholinocarbonylpropyl)-6-[(3R,1E)-3-hydroxy-4-(m-tolyl)-1-butenyl]-7-hydroxybicyclo[3.3.0]-2-octene 381) (1S,5S,6R,7R)-3-(5-carbamoylpentyl)-6-[(3R,1E)-3-hydroxy-4-(m-tolyl)-1-butenyl]-7-hydroxybicyclo [3.3.0]-2-octene 382) (1S,5S,6R,7R)-3-(5-N,N-dimethylcarbamoylpentyl)-6-[(3R,1E)-3-hydroxy-4-(m-tolyl)-1-butenyl]-7-hydroxybicyclo[3.3.0]-2-octene 383) (1S,5S,6R,7R)-3-(5-N,N-diisopropylcarbamoylpentyl)-6-[(3R,1E)-3-hydroxy-4-(m-tolyl)-1-butenyl]-7-hydroxybicyclo[3.3.0]-2-octene 384) (1S,5S,6R,7R)-3-(5-N-t-butyl-N-methylcarbamoy8-pentyl)-6-[(3R, E)-3-hydroxy-4-(m-tolyl)-1-butenyl]-7-hydroxybicyclo[3.3.0]-2-octene 385) (1S,5S,6R,7R)-3-[5-(1-pyrrolidinyl)carbonylpentyl]-6-[(3R,1E)-3-hydroxy-4-(m-tolyl)-1-butenyl]-7-hydroxybicyclo[3.3.0]-2-octene 386) (1S,5S,6R,7R)-3-(5-piperidinocarbonylpentyl)-6-[(3R,1E)-3-hydroxy-4-(m-tolyl)-1-butenyl]-7-hydroxybicyclo[3.3.0]-2-octene 387) (1S,5S,6R,7R)-3-(5-morpholinocarbonylpentyl)-6-[(3R,1E)-3-hydroxy-4-(m-tolyl)-1-butenyl]-7-hydroxybicyclo[3.3.0]-2-octene 388) (1S,5S,6R,7R)-3-[(1Z)-3-N,N-dimethylcarbamoyl-1-propenyl]-6-[(3R,1E)-3-hydroxy-4-(m-tolyl)-1-butenyl]-7-hydroxybicyclo[3.3.0]-2-octene 389) (1S,5S,6R,7R)-3-[(1Z)-4-N,N-dimethylcarbamoyl-1-butenyl]-6-[(3R,1E)-3-hydroxy-4-(m-tolyl)-1-butenyl]-7-hydroxybicyclo[3.3.0]-2-octene 390) (1S,5S,6R,7R)-3-[(1E)-4-N,N-dimethylcarbamoyl-1-butenyl]-6-[(3R,1E)-3-hydroxy-4-(m-tolyl)-1-butenyl]-7-hydroxybicyclo[3.3.0]-2-octene 391) (1S,5S,6R,7R)-3-[(1Z)-5-N,N-dimethylcarbamoyl-pentenyl]-6-[(3R,1E)-3-hydroxy-4-(m-tolyl)-1-butenyl]-7-hydroxybicyclo[3.3.0]-2-octene 392) (1S,5S,6R,7R)-3-[N—(N,N-dimethylcarbamoylmethyl)aminomethyl]-6-[(3R,1E)-3-hydroxy-4-(m-tolyl)-1-butenyl]-7-hydroxybicyclo[3.3.0]-2-octene 393) (1S,5S,6R,7R)-3-[N-(2-N,N-dimethylcarbamoylethyl)aminomethyl]-6-[(3R,1E)-3-hydroxy-4-(m-tolyl)-1-butenyl]-7-hydroxybicyclo[3.3.0]-2-octene 394) (1S,5S,6R,7R)-3-[N-(2-N,N-diisopropylcarbamoylethyl)aminomethyl]-6-[(3R,9E)-3-hydroxy-4-(m-tolyl)-1-butenyl]-7-hydroxybicyclo[3.3.0]-2-octene 395) (1S,5S,6R,7R)-3-[N-(2-N-t-butyl-N-methylcarbamoylethyl)aminomethyl]-6-[(3R,1E)-3-hydroxy-4-(m-tolyl)-1-butenyl]-7-hydroxybicyclo[3.3.0]-2-octene 396) (1S,5S,6R,7R)-3-[N-[2-(1-pyrrolidinyl)carbonylethyl]aminomethyl]-6-[(3R,1E)-3-hydroxy-4-(m-tolyl)-1-butenyl]-7-hydroxybicyclo[3.3.0]-2-octene 397) (1S,5S,6R,7R)-3-[N-(2-piperidinocarbonylethyl)aminomethyl]-6-[(3R,1E)-3-hydroxy-4-(m-tolyl)-1-butenyl]-7-hydroxybicyclo[3.3.0]-2-octene 398) (1S,5S,6R,7R)-3-[N-(2-morpholinocarbonylethyl)aminomethyl]-6-[(3R,1E)-3-hydroxy-4-(m-tolyl)-1-butenyl]-7-hydroxybicyclo[3.3.0]-2-octene 399) (1S,5S,6R,7R)-3-[N-(3-N,N-dimethylcarbamoylpropyl)aminomethyl]-6-[(3R,1E)-3-hydroxy-4-(m-tolyl)-1-butenyl]-7-hydroxybicyclo [3.3.0]-2-octene 400) (1S,5S,6R,7R)-3-[N-(2-N,N-dimethylcarbamoylethyl)-N-methylaminomethyl]-6-[(3R,1E)-3-hydroxy-4-(m-tolyl)-1-butenyl]-7-hydroxybicyclo[3.3.0]-2-octene 401) (1S,5S,6R,7R)-3-[N—(N,N-dimethylcarbamoylmethyl)aminoethyl]-6-[(3R,1E)-3-hydroxy-4-(m-tolyl)-1-butenyl]-7-hydroxybicyclo[3.3.0]-2-octene 402) (1S,5S,6R,7R)-3-[N—(N,N-diisopropylcarbamoylmethyl)aminoethyl]-6-[(3R,1E)-3-hydroxy-4-(m-tolyl)-1-butenyl]-7-hydroxybicyclo[3.3.0]-2-octene 403) (1S,5S,6R,7R)-3-[N-(N-t-butyl-N-methylcarbamoylmethyl)aminoethyl]-6-[(3R,1E)-3-hydroxy-4-(m-tolyl)-1-butenyl]-7-hydroxybicyclo[3.3.0]-2-octene 404) (1S,5S,6R,7R)-3-[2-N-[(1-pyrrolidinyl)carbonylmethyl]aminoethyl]-6-[(3R,1E)-3-hydroxy-4-(m-tolyl)-1-butenyl]-7-hydroxybicyclo[3.3.0]-2-octene 405) (1S,5S,6R,7R)-3-[2-N-(piperidinocarbonylmethyl)aminoethyl]-6-[(3R,1E)-3-hydroxy-4-(m-tolyl)-1-butenyl]-7-hydroxybicyclo[3.3.0]-2-octene 406) (1S,5S,6R,7R)-3-[2-N-(morpholinocarbonylmethyl)aminoethyl]-6-[(3R,1E)-3-hydroxy-4-(m-tolyl)-1-butenyl]-7-hydroxybicyclo[3.3.0]-2-octene 407) (1S,5S,6R,7R)-3-[2-N-(2-N,N-dimethylcarbamoylethyl)aminoethyl]-6-[(3R,1E)-3-hydroxy-4-(m-tolyl)-1-butenyl]-7-hydroxybicyclo[3.3.0]-2-octene 408) (1S,5S,6R,7R)-3-[(2-N,N-dimethylcarbamoylethyl)oxymethyl]-6-[(3R,1E)-3-hydroxy-4-(m-tolyl)-1-butenyl]-7-hydroxybicyclo[3.3.0]-2-octene 409) (1S,5S,6R,7R)-3-[(2-N,N-diisopropylcarbamoylethyl)oxymethyl]-6-[(3R,1E)-3-hydroxy-4-(m-tolyl)-1-butenyl]-7-hydroxybicyclo[3.3.0]-2-octene 410) (1S,5S,6R,7R)-3-[(2-N-t-butyl-N-methylcarbamoylethyl)oxymethyl]-6-[(3R,1E)-3-hydroxy-4-(m-tolyl)-1-butenyl]-7-hydroxybicyclo[3.3.0]-2-octene 411) (1S,5S,6R,7R)-3-[[2-(1-pyrrolidinyl)carbonylethyl]oxymethyl]-6-[(3R,1E)-3-hydroxy-4-(m-tolyl)-1-butenyl]-7-hydroxybicyclo[3.3.0]-2-octene 412) (1S,5S,6R,7R)-3-[(2-piperidinocarbonylethyl)oxymethyl]-6-[(3R,1E)-3-hydroxy-4-(m-tolyl)-1-butenyl]-7-hydroxybicyclo[3.3.0]-2-octene 413) (1S,5S,6R,7R)-3-[(2-morpholinocarbonylethyl)oxymethyl]-6-[(3R,1E)-3-hydroxy-4-(m-tolyl)-1-butenyl]-7-hydroxybicyclo[3.3.0]-2-octene 414) (1S,5S,6R,7R)-3-[2-(N,N-dimethylcarbamoylmethyl)oxyethyl]-6-[(3R,1E)-3-hydroxy-4-(m-tolyl)-1-butenyl]-7-hydroxybicyclo[3.3.0]-2-octene 415) (1S,5S,6R,7R)-3-[2-(N,N-diisopropylcarbamoylmethyl)oxyethyl]-6-[(3R,1E)-3-hydroxy-4-(m-tolyl)-1-butenyl]-7-hydroxybicyclo[3.3.0]-2-octene 416) (1S,5S,6R,7R)-3-[2-(N-t-butyl-N-methylcarbamoylmethyl)oxyethyl]-6-[(3R,1E)-3-hydroxy-4-(m-tolyl)-1-butenyl]-7-hydroxybicyclo[3.3.0]-2-octene 417) (1S,5S,6R,7R)-3-[2-[(1-pyrrolidinyl)carbonylmethyl]oxyethyl]-6-[(3R,1E)-3-hydroxy-4-(m-tolyl)-1-butenyl]-7-hydroxybicyclo[3.3.0]-2-octene 418) (1S,5S,6R,7R)-3-[2-(piperidinocarbonylmethyl)oxyethyl]-6-[(3R,1E)-3-hydroxy-4-(m-tolyl)-1-butenyl]-7-hydroxybicyclo[3.3.0]-2-octene 419) (1S,5S,6R,7R)-3-[2-(morpholinocarbonylmethyl)oxyethyl]-6-[(3R,1E)-3-hydroxy-4-(m-tolyl)-1-butenyl]-7-hydroxybicyclo[3.3.0]-2-octene 420) (1S,5S,6R,7R)-3-[(2-N,N-dimethylcarbamoylethyl)thiomethyl]-6-[(3R, 1E)-3-hydroxy-4-(m-tolyl)-1-butenyl]-7-hydroxybicyclo[3.3.0]-2-octene 421) (1S,5S,6R,7R)-3-[(2-N,N-diisopropylcarbamoylethyl)thiomethyl]-6-[(3R,1E)-3-hydroxy-4-(m-tolyl)-1-butenyl]-7-hydroxybicyclo[3.3.0]-2-octene 422) (1S,5S,6R,7R)-3-[(2-N-t-butyl-N-methylcarbamoylethyl)thiomethyl]-6-[(3R,1E)-3-hydroxy-4-(m-tolyl)-1-butenyl]-7-hydroxybicyclo[3.3.0]-2-octene 423) (1S,5S,6R,7R)-3-[[2-(1-pyrrolidinylcarbonyl)ethyl]thiomethyl]-6-[(3R,1E)-3-hydroxy-4-(m-tolyl)-1-butenyl]-7-hydroxybicyclo[3.3.0]-2-octene 424) (1S,5S,6R,7R)-3-[(2-piperidinocarbonylethyl)thiomethyl]-6-[(3R,1E)-3-hydroxy-4-(m-tolyl)-1-butenyl]-7-hydroxybicyclo[3.3.0]-2-octene 425) (1S,5S,6R,7R)-3-[(2-morpholinocarbonylethyl)thiomethyl]-6-[(3R,1E)-3-hydroxy-4-(m-tolyl)-1-butenyl]-7-hydroxybicyclo[3.3.0]-2-octene 426) (1S,5S,6R,7R)-3-[2-(N,N-dimethylcarbamoylmethyl)thioethyl]-6-[(3R,1E)-3-hydroxy-4-(m-tolyl)-1-butenyl]-7-hydroxybicyclo[3.3.0]-2-octene 427) (1S,5S,6R,7R)-3-[2-(N,N-diisopropylcarbamoylmethyl)thioethyl]-6-[(3R,1E)-3-hydroxy-4-(m-tolyl)-1-butenyl]-7-hydroxybicyclo[3.3.0]-2-octene 428) (1S,5S,6R,7R)-3-[2-(N-t-butyl-N-methylcarbamoylmethyl)thioethyl]-6-[(3R,1E)-3-hydroxy-4-(m-tolyl)-1-butenyl]-7-hydroxybicyclo[3.3.0]-2-octene 429) (1S,5S,6R,7R)-3-[2-[(1-pyrrolidinyl)carbonylmethyl]thioethyl]-6-[(3R,1E)-3-hydroxy-4-(m-tolyl)-1-butenyl]-7-hydroxybicyclo[3.3.0]-2-octene 430) (1S,5S,6R,7R)-3-[2-(piperidinocarbonylmethyl)thioethyl]-6-[(3R,1E)-3-hydroxy-4-(m-tolyl)-1-butenyl]-7-hydroxybicyclo[3.3.0]-2-octene 431) (1S,5S,6R,7R)-3-[2-(morpholinocarbonylmethyl)thioethyl]-6-[(3R,1E)-3-hydroxy-4-(m-tolyl)-1-butenyl]-7-hydroxybicyclo[3.3.0]-2-octene 432) (1S,5S,6R,7R)-3-[(2-carbamoylphenyl)methyl]-6-[(3R,1E)-3-hydroxy-4-(m-tolyl)-1-butenyl]-7-hydroxybicyclo[3.3.0]-2-octene 433) (1S,5S,6R,7R)-3-[(4-carbamoylphenyl)methyl]-6-[(3R,1E)-3-hydroxy-4-(m-tolyl)-1-butenyl]-7-hydroxybicyclo[3.3.0]-2-octene 434) (1S,5S,6R,7R)-3-[2-(3-carbamoylphenyl)ethyl]-6-[(3R,1E)-3-hydroxy-4-(m-tolyl)-1-butenyl]-7-hydroxybicyclo[3.3.0]-2-octene 435) (1S,5S,6R,7R)-3-[2-[3-(piperidinocarbonyl)phenyl]ethyl]-6-[(3R,1E)-3-hydroxy-4-(m-tolyl)-1-butenyl]-7-hydroxybicyclo[3.3.0]-2-octene 436) (1S,5S,6R,7R)-3-(4-carbamoylbutyl)-6-[(E)-4-(m-tolyl)-1-butenyl]-7-hydroxybicyclo[3.3.0]-2-octene 437) (1S,5S,6R,7R)-3-(4-N,N-dimethylcarbamoylbutyl)-6-[(E)-4-(m-tolyl)-1-butenyl]-7-hydroxybicyclo[3.3.0]-2-octene 438) (1S,5S,6R,7R)-3-(4-N,N-diethylcarbamoylbutyl)-6-[(E)-4-(m-tolyl)-1-butenyl]-7-hydroxybicyclo[3.3.0]-2-octene 439) (1S,5S,6R,7R)-3-[4-N-(2-methoxycarbonylethyl)carbamoylbutyl]-6-[(E)-4-(m-tolyl)-1-butenyl]-7-hydroxybicyclo [3.3.0]-2-octene 440) (1S,5S,6R,7R)-3-[4-N-(4-pyridylmethyl)carbamoylbutyl]-6-[(E)-4-(m-tolyl)-1-butenyl]-7-hydroxybicyclo [3.3.0]-2-octene 441) (1S,5S,6R,7R)-3-(4-N,N-diisopropylcarbamoylbutyl)-6-[(E)-4-(m-tolyl)-1-butenyl]-7-hydroxybicyclo[3.3.0]-2-octene 442) (1S,5S,6R,7R)-3-[4-(1-pyrrolidinyl)carbonylbutyl]-6-[(E)-4-(m-tolyl)-1-butenyl]-7-hydroxybicyclo[3.3.0]-2-octene 443) (1S,5S,6R,7R)-3-(4-piperidinocarbonylbutyl)-6-[(E)-4-(m-tolyl)—butenyl]-7-hydroxybicyclo[3.3.0]-2-octene 444) (1S,5S,6R,7R)-3-(4-morpholinocarbonylbutyl)-6-[(E)-4-(m-tolyl)-1-butenyl]-7-hydroxybicyclo[3.3.0]-2-octene 445) (1S,5S,6R,7R)-3-(4-N-methylcarbamoylbutyl)-6-[(E)-4-(m-tolyl)-1-butenyl]-7-hydroxybicyclo[3.3.0]-2-octene 446) (1S,5S,6R,7R)-3-(4-N-ethylcarbamoylbutyl)-6-[(E)-4-(m-tolyl)-1-butenyl]-7-hydroxybicyclo[3.3.0]-2-octene 447) (1S,5S,6R,7R)-3-(4-N-propylcarbamoylbutyl)-6-[(E)-4-(m-tolyl)-1-butenyl]-7-hydroxybicyclo[3.3.0]-2-octene 448) (1S,5S,6R,7R)-3-(4-N-isopropylcarbamoylbutyl)-6-[(E)-4-(m-tolyl)-1-butenyl]-7-hydroxybicyclo[3.3.0]-2-octene 449) (1S,5S,6R,7R)-3-(4-N-butylcarbamoylbutyl)-6-[(E)-4-(m-tolyl)-1-butenyl]-7-hydroxybicyclo[3.3.0]-2-octene 450) (1S,5S,6R,7R)-3-(4-N-t-butylcarbamoylbutyl)-6-[(E)-4-(m-tolyl)-1-butenyl]-7-hydroxybicyclo[3.3.0]-2-octene 451) (1S,5S,6R,7R)-3-(4-N-phenylcarbamoylbutyl)-6-[(E)-4-(m-tolyl)-1-butenyl]-7-hydroxybicyclo[3.3.0]-2-octene 452) (1S,5S,6R,7R)-3-(4-N-benzylcarbamoylbutyl)-6-[(E)-4-(m-tolyl)-1-butenyl]-7-hydroxybicyclo[3.3.0]-2-octene 453) (1S,5S 6R,7R)-3-[4-N-(4-pyridylmethyl)carbamoylbutyl]-6-[(E)-4-(m-tolyl)-1-butenyl]-7-hydroxybicyclo[3.3.0]-2-octene 454) (1S,5S,6R,7R)-3-[4-(4-N-methyl-1-piperazinyl)carbonylbutyl]-6-[(E)-4-(m-tolyl)-1-butenyl]-7-hydroxybicyclo[3.3.0]-2-octene 455) (1S,5S,6R,7R)-3-(4-N-(2-pyridyl)carbamoylbutyl]-6-[(E)-4-(m-tolyl)-1-butenyl]-7-hydroxybicyclo[3.3.0]-2-octene 456) (1S,5S,6R,7R)-3-(4-N,N-dipropylcarbamoylbutyl)-6-[(E)-4-(m-tolyl)-1-butenyl]-7-hydroxybicyclo[3.3.0]-2-octene 457) (1S,5S,6R,7R)-3-(4-N,N-dibutylcarbamoylbutyl)-6-[(E)-4-(m-tolyl)-1-butenyl]-7-hydroxybicyclo[3.3.0]-2-octene 458) (1S,5S,6R,7R)-3-(4-N-t-butyl-N-methylcarbamoylbutyl)-6-[(E)-4-(m-tolyl)-1-butenyl]-7-hydroxybicyclo[3.3.0]-2-octene 459) (1S,5S,6R,7R)-3-[4-N-(2-hydroxyethyl)carbamoylbutyl]-6-[(E)-4-(m-tolyl)-1-butenyl]-7-hydroxybicyclo[3.3.0]-2-octene 460) (1S,5S,5S,6R,7R)-3-[4-N-(3-hydroxypropyl)carbamoylbutyl]-6-[(E)-4-(m-tolyl)—butenyl]-7-hydroxybicyclo[3.3.0]-2-octene 461) (1S,5S,6R,7R)-3-(3-carbamoylpropyl)-6-[(E)-4-(m-tolyl)-1-butenyl]-7-hydroxybicyclo[3.3.0]-2-octene 462) (1S,5S,6R,7%)-3-(3-N,N-dimethylcarbamoylpropyl)-6-[(E)-4-(m-tolyl)-1-butenyl]-7-hydroxybicyclo[3.3.0]-2-octene 463) (1S,5S,6R,7R)-3-(3-N,N-diisopropylcarbamoylpropyl)-6-[(E)-4-(m-tolyl)-1-butenyl]-7-hydroxybicyclo[3.3.0]-2-octene 464) (1S,5S,6R,7R)-3-(3-N-t-butyl-N-methylcarbamoylpropyl)-6-[(E)-4-(m-tolyl)-1-butenyl]-7-hydroxybicyclo[3.3.0]-2-octene 465) (1S,5S,6R,7R)-3-[3-(1-pyrrolidinyl)carbonylpropyl]-6-[(E)-4-(m-tolyl)-1-butenyl]-7-hydroxybicyclo[3.3.0]-2-octene 466) (1S,5S,6R,7R)-3-(3-piperidinocarbonylpropyl)-6-[(E)-4-(m-tolyl)-1-butenyl]-7-hydroxybicyclo[3.3.0]-2-octene 467) (1S,5S,6R,7R)-3-(3-morpholinocarbonylpropyl)-6-[(E)-4-(m-tolyl)-1-butenyl]-7-hydroxybicyclo[3.3.0]-2-octene 468) (1S,5S,6R,7R)-3-(5-carbamoylpentyl)-6-[(E)-4-(m-tolyl)-1-butenyl]-7-hydroxybicyclo[3.3.0]-2-octene 469) (1S,5S,6R,7R)-3-(5-N,N-dimethylcarbamoylpentyl)-6-[(E)-4-(m-tolyl)-1-butenyl]-7-hydroxybicyclo[3.3.0]-2-octene 470) (1S,5S,6R,7R)-3-(5-N,N-diisopropylcarbamoylpentyl)-6-[(E)-4-(m-tolyl)-1-butenyl]-7-hydroxybicyclo[3.3.0]-2-octene 471) (1S,5S,6R,7R)-3-(5-N-t-butyl-N-methylcarbamoylpentyl)-6-[(E)-4-(m-tolyl)-1-butenyl]-7-hydroxybicyclo[3.3.0]-2-octene 472) (1S,5S,6R,7R)-3-[5-(1-pyrrolidinyl)carbonylpentyl]-6-[(E)-4-(m-tolyl)-1-butenyl]-7-hydroxybicyclo[3.3.0]-2-octene 473) (1S,5S,6R,7R)-3-(5-piperidinocarbonylpentyl)-6-[(E)-4-(m-tolyl)-1-butenyl]-7-hydroxybicyclo[3.3.0]-2-octene 474) (1S,5S,6R,7R)-3-(5-morpholinocarbonylpentyl)-6-[(E)-4-(m-tolyl)-1-butenyl]-7-hydroxybicyclo[3.3.0]-2-octene 475) (1S,5S,6R,7R)-3-[(1Z)-3-N,N-dimethylcarbamoyl-1-propenyl]-6-[(E)-4-(m-tolyl)-1-butenyl]-7-hydroxybicyclo[3.3.0]-2-octene 476) (1S,5S,6R,7R)-3-[(1Z)-4-N,N-dimethylcarbamoyl-1-butenyl]-6-[(E)-4-(m-tolyl)-1-butenyl]-7-hydroxybicyclo[3.3.0]-2-octene 477) (1S,1S,6R,7R)-3-[(1E)-4-N,N-dimethylcarbamoyl-1-butenyl]-6-[(E)-4-(m-tolyl)-1-butenyl]-7-hydroxybicyclo[3.3.0]-2-octene 478) (1S,5S,6R,7R)-3-[(1Z)-5-N,N-dimethylcarbamoyl-1-pentenyl]-6-[(E)-4-(m-tolyl)-1-butenyl]-7-hydroxybicyclo[3.3.0]-2-octene 479) (1S,5S,6R,7R)-3-[N—(N,N-dimethylcarbamoylmethyl)aminomethyl]-6-[(E)-4-(m-tolyl)-1 butenyl]-7-hydroxybicyclo[3.3.0]-2-octene 480) (1S,5S,6R,7R)-3-[N-(2-N,N-dimethylcarbamoylethyl)aminomethyl]-6-[(E)-4-(m-tolyl)-1-butenyl]-7-hydroxybicyclo[3.3.0]-2-octene 481) (1S,5S,6R,7R)-3-[N-(2-N,N-diisopropylcarbamoylethyl)aminomethyl]-6-[(E)-4-(m-tolyl)-1-butenyl]-7-hydroxybicyclo[3.3.0]-2-octene 482) (1S,5S,6R,7R)-3-[N-(2-N-t-butyl-N-methylcarbamoylethyl)aminomethyl]-6-[(E)-4-(m-tolyl)-1-butenyl]-7-hydroxybicyclo[3.3.0]-2-octene 483) (1S,5S,6R,7R)-3-[N-[2-(1-pyrrolidinyl)carbonylethyl]aminomethyl]-6-[(E)-4-(m-tolyl)-1-butenyl]-7-hydroxybicyclo[3.3.0]-2-octene 484) (1S,5S,6R,7R)-3-[N-(2-piperidinocarbonylethyl)aminomethyl]-6-[(E)-4-(m-tolyl)-1-butenyl]-7-hydroxybicyclo[3.3.0]-2-octene 485) (1S,5S,6R,7R)-3-[N-(2-morpholinocarbonylethyl)aminomethyl]-6-[(E)-4-(m-tolyl)-1-butenyl]-7-hydroxybicyclo[3.3.0]-2-octene 486) (1S,5S,6R,7R)-3-[N-(3-N,N-dimethylcarbamoylpropyl)aminomethyl]-6-[(E)-4-(m-tolyl)-1-butenyl]-7-hydroxybicyclo[3.3.0]-2-octene 487) (1S,5S,6R,7R)-3-[N-(2-N,N-dimethylcarbamoylethyl)-N-methylaminomethyl]-6-[(E)-4-(m-tolyl)-1-butenyl]-7-hydroxybicyclo[3.3.0]-2-octene 488) (1S,5S,6R,7R)-3-[N—(N,N-dimethylcarbamoylmethyl)aminoethyl]-6-[(E)-4-(m-tolyl)-1-butenyl]-7-hydroxybicyclo[3.3.0]-2-octene 489) (1S,5S,6R,7R)-3-[N—(N,N-diisopropylcarbamoylmethyl)aminoethyl]-6-[(E)-4-(m-tolyl)-1-butenyl]-7-hydroxybicyclo[3.3.0]-2-octene 490) (1S,5S,6R,7R)-3-[N-(N-t-butyl-N-methylcarbamoylmethyl)aminoethyl]-6-[(E)-4-(m-tolyl)-1-butenyl]-7-hydroxybicyclo[3.3.0]-2-octene 491) (1S,5S,6R,7R)-3-[2-N-[(1-pyrrolidinyl)carbonylmethyl]aminoethyl]-6-[(E)-4-(m-tolyl)-1-butenyl]-7-hydroxybicyclo[3.3.0]-2-octene
492) (1S,5S,6R,7R)-3-[2-N-(piperidinocarbonylmethyl)aminoethyl]-6-[(E)-4-(m-tolyl)-1-butenyl]-7-hydroxybicyclo[3.3.0]-2-octene
493) (1S,5S,6R,7R)-3-[2-N-(morpholinocarbonylmethyl)aminoethyl]-6-[(E)-4-(m-tolyl)-1-butenyl]-7-hydroxybicyclo[3.3.0]-2-octene
494) (1S,5S,6R,7R)-3-[2-N-(2-N,N-dimethylcarbamoylethyl)aminoethyl]-6-[(E)-4-(m-tolyl)-1-butenyl]-7-hydroxybicyclo[3.3.0]-2-octene
495) (1S,5S,6R,7R)-3-[(2-N,N-dimethylcarbamoylethyl)oxymethyl]-6-[(E)-4-(m-tolyl)-1-butenyl]-7-hydroxybicyclo[3.3.0]-2-octene
496) (1S,5S,6R,7R)-3-[(2-N,N-diisopropylcarbamoylethyl)oxymethyl]-6-[(E)-4-(m-tolyl)-1-butenyl]-7-hydroxybicyclo[3.3.0]-2-octene
497) (1S,5S,6R,7R)-3-[(2-N-t-butyl-N-methylcarbamoylethyl)oxymethyl]-6-[(E)-4-(m-tolyl)-1-butenyl]-7-hydroxybicyclo[3.3.0]-2-octene
498) (1S,5S,6R,7R)-3-[[2-(1-pyrrolidinyl)carbonylethyl]oxymethyl]-6-[(E)-4-(m-tolyl) 1-butenyl]-7-hydroxybicyclo [3.3.0]-2-octene
499) (1S,5S,6R,7R)-3-[(2-piperidinocarbonylethyl)oxymethyl]-6-[(E)-4-(m-tolyl)-1-butenyl]-7-hydroxybicyclo[3.3.0]-2-octene
500) (1S,5S,6R,7R)-3-[(2-morpholinocarbonylethyl)oxymethyl]-6-[(E)-4-(m-tolyl)-1-butenyl]-7-hydroxybicyclo[3.3.0]-2-octene
501) (1S,5S,6R,7R)-3-[2-(N,N-dimethylcarbamoylmethyl)oxyethyl]-6-[(E)-4-(m-tolyl)-1-butenyl]-7-hydroxybicyclo[3.3.0]-2-octene
502) (1S,5S,6R,7R)-3-[2-(N,N-diisopropylcarbamoylmethyl)oxyethyl]-6-[(E)-4-(m-tolyl)-1-butenyl]-7-hydroxybicyclo[3.3.0]-2-octene
503) (1S,5S,6R,7R)-3-[2-(N-t-butyl-N-methylcarbamoylmethyl)oxyethyl]-6-[(E)-4-(m-tolyl)-1-butenyl]-7-hydroxybicyclo[3.3.0]-2-octene
504) (1S,5S,6R,7R)-3-[2-[(1-pyrrolidinyl)carbonylmethyl]oxyethyl]-6-[(E)-4-(m-tolyl)-1-butenyl]-7-hydroxybicyclo[3.3.0]-2-octene
505) (1S,5S,6R,7R)-3-[2-(piperidinocarbonylmethyl)oxyethyl]-6-[(E)-4-(m-tolyl)-1-butenyl]-7-hydroxybicyclo[3.3.0]-2-octene
506) (1S,5S,6R,7R)-3-[2-(morpholinocarbonylmethyl)oxyethyl]-6-[(E)-4-(m-tolyl)-1-butenyl]-7-hydroxybicyclo[3.3.0]-2-octene
507) (1S,5S,6R,7R)-3-[(2-N,N-dimethylcarbamoylethyl)thiomethyl]-6-[(E)-4-(m-tolyl)-1-butenyl]-7-hydroxybicyclo[3.3.0]-2-octene
508) (1S,5S,6R,7R)-3-[(2-N,N-diisopropylcarbamoylethyl)thiomethyl]-6-[(E)-4-(m-tolyl)-1-butenyl]-7-hydroxybicyclo[3.3.0]-2-octene
509) (1S,5S,6R,7R)-3-[(2-N-t-butyl-N-methylcarbamoylethyl)thiomethyl]-6-[(E)-4-(m-tolyl)-1-butenyl]-7-hydroxybicyclo[3.3.0]-2-octene
510) (1S,5S,6R,7R)-3-[[2-(1-pyrrolidinylcarbonyl)ethyl]thiomethyl]-6-[(E)-4-(m-tolyl)-1-butenyl]-7-hydroxybicyclo[3.3.0]-2-octene
511) (1S,5S,6R,7R)-3-[(2-piperidinocarbonylethyl)thiomethyl]-6-[(E)-4-(m-tolyl)-1-butenyl]-7-hydroxybicyclo[3.3.0]-2-octene
512) (1S,5S,6R,7R)-3-[(2-morpholinocarbonylethyl)thiomethyl]-6-[(E)-4-(m-tolyl)-1-butenyl]-7-hydroxybicyclo[3.3.0]-2-octene
513) (1S,5S,6R,7R)-3-[2-(N,N-dimethylcarbamoylmethyl)thioethyl]-6-[(E)-4-(m-tolyl)-1-butenyl]-7-hydroxybicyclo[3.3.0]-2-octene
514) (1S,5S,6R,7R)-3-[2-(N,N-diisopropylcarbamoylmethyl)thioethyl]-6-[(E)-4-(m-tolyl)-1-butenyl]-7-hydroxybicyclo[3.3.0]-2-octene
515) (1S,5S,6R,7R)-3-[2-(N-t-butyl-N-methylcarbamoylmethyl)thioethyl]-6-[(E)-4-(m-tolyl)-1-butenyl]-7-hydroxybicyclo[3.3.0]-2-octene
516) (1S,5S,6R,7R)-3-[2-[(1-pyrrolidinyl)carbonylmethyl]thioethyl]-6-[(E)-4-(m-tolyl)-1-butenyl]-7-hydroxybicyclo[3.3.0]-2-octene
517) (1S,5S,6R,7R)-3-[2-(piperidinocarbonylmethyl)thioethyl]-6-[(E)-4-(m-tolyl)-1-butenyl]-7-hydroxybicyclo[3.3.0]-2-octene
518) (1S,5S,6R,7R)-3-[2-(morpholinocarbonylmethyl)thioethyl]-6-[(E)-4-(m-tolyl)-1-butenyl]-7-hydroxybicyclo[3.3.0]-2-octene
519) (1S,5S,6R,7R)-3-[(2-carbamoylphenyl)methyl]-6-[(E)-4-(m-tolyl)-1-butenyl]-7-hydroxybicyclo[3.3.0]-2-octene
520) (1S,5S,6R,7R)-3-[(4-carbamoylphenyl)methyl]-6-[(E)-4-(m-tolyl)-1-butenyl]-7-hydroxybicyclo[3.3.0]-2-octene
521) (1S,5S,6R,7R)-3-[2-(3-carbamoylphenyl)ethyl]-6-[(E)-4-(m-tolyl)-2-butenyl-7-hydroxybicyclo[3.3.0]-2-octene
522) (1S,5S,6R,7R)-3-[2-[3-(piperidinocarbonyl)phenyl]ethyl]-6-[(E)-4-(m-tolyl)-1-butenyl]-7-hydroxybicyclo[3.3.0]-2-octene
523) (1S,5S,6R,7R)-3-(4-carbamoylbutyl)-6-[(3S,5R,1E)-3-hydroxy-5-methyl-1-nonenyl]-7-hydroxybicyclo[3.3.0]-2-octene
524) (1S,5S,6R,7R)-3-(4-N,N-dimethylcarbamoylbutyl)-6-[(3S,5R,1E)-3-hydroxy-5-methyl-1-nonenyl]-7-hydroxybicyclo[3.3.0]-2-octene
525) (1S,5S,6R,7R)-3-(4-N,N-diethylcarbamoylbutyl)-6-[(3S,5R,1E)-3-hydroxy-5-methyl-1-nonenyl]-7-hydroxybicyclo[3.3.0]-2-octene
526) (1S,5S,6R,7R)-3-[4-N-(2-methoxycarbonylethyl)carbamoylbutyl]-6-[(3S,5R,1E)-3-hydroxy-5-methyl-1-nonenyl]-7-hydroxybicyclo[3.3.0]-2-octene
527) (1S,5S,6R,7R)-3-[4-N-(4-pyridylmethyl)carbamoylbutyl]-6-[(3S,5R,1E)-3-hydroxy-5-methyl-1-nonenyl]-7-hydroxybicyclo[3.3.0]-2-octene
528) (1S,5S,6R,7R)-3-(4-N,N-diisopropylcarbamoylbutyl)-6-[(3S,5R,1E)-3-hydroxy-5-methyl-1-nonenyl]-7-hydroxybicyclo[3.3.0]-2-octene
529) (1S,5S,6R,7R)-3-[4-(1-pyrrolidinyl)carbonylbutyl]-6-[(3S,5R,1E)-3-hydroxy-5-methyl-1-nonenyl]-7-hydroxybicyclo[3.3.0]-2-octene
530) (1S,5S,6R,7R)-3-(4-piperidinocarbonylbutyl)-6-[(3S,5R,1E)-3-hydroxy-5-methyl-1-nonenyl]-7-hydroxybicyclo[3.3.0]-2-octene
531) (1S,5S,6R,7R)-3-(4-morpholinocarbonylbutyl)-6-[(3S,5R,1E)-3-hydroxy-5-methyl-1-nonenyl]-7-hydroxybicyclo[3.3.0]-2-octene
532) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,5R,1E)-3-hydroxy-5-methyl]-nonenyl group
533) (1S,5S,6R,7R)-3-(4-carbamoylbutyl)-6-[(4R,1E)-4-hydroxy-4-methyl-1-octenyl]-7-hydroxybicyclo[3.3.0]-2-octene 534) (1S,5S,6R,7R)-3-(4-N,N-dimethylcarbamoylbutyl)-6-[(4R,1E)-4-hydroxy-4-methyl-1-octenyl]-7-hydroxybicyclo[3.3.0]-2-octene
535) (1S,5S,6R,7R)-3-(4-N,N-diethylcarbamoylbutyl)-6-[(4R,1E)-4-hydroxy-4-methyl-1-octenyl]-7-hydroxybicyclo[3.3.0]-2-octene
536) (1S,5S,6R,7R)-3-[4-N-(2-methoxycarbonylethyl)carbamoylbutyl]-6-[(4R,1E)-4-hydroxy-4-methyl-1-octenyl]-7-hydroxybicyclo[3.3.0]-2-octene
537) (1S,5S,6R,7R)-3-[4-N-(4-pyridylmethyl)carbamoylbutyl]-6-[(4R,1E)-4-hydroxy-4-methyl]-octenyl]-7-hydroxybicyclo [3.3.0]-2-octene
538) (1S,5S,6R,7R)-3-(4-N,N-diisopropylcarbamoylbutyl)-6-[(4R,1E)-4-hydroxy-4-methyl-1-octenyl]-7-hydroxybicyclo [3.3.0]-2-octene
539) (1S,5S,6R,7R)-3-[4-(1-pyrrolidinyl)carbonylbutyl]-6-[(4R,1E)-4-hydroxy-4-methyl-1-octenyl]-7-hydroxybicyclo[3.3.0]-2-octene
540) (1S,5S,6R,7R)-3-(4-piperidinocarbonylbutyl)-6-[(4R,1E)-4-hydroxy-4-methyl-1-octenyl]-7-hydroxybicyclo [3.3.0]-2-octene
541) (1S,5S,6R,7R)-3-(4-morpholinocarbonylbutyl)-6-[(4R,1E)-4-hydroxy-4-methyl-1-octenyl]-7-hydroxybicyclo[3.3.0]-2-octene
542) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (4R,1E)-4-hydroxy-4-methyl-1-octenyl group
543) (1S,5S,6R,7R)-3-(4-carbamoylbutyl)-6-[(3S,4S, 1E)-3-hydroxy-4-methyl-6-octyn-1-enyl]7-hydroxybicyclo [3.3.0]-2-octene
544) (1S,5S,6R,7R)-3-(4-N,N-dimethylcarbamoylbutyl)-6-[(3S,4S,1E)-3-hydroxy-4-methyl-6-octyn-1-enyl]-7-hydroxybicyclo[3.3.0]-2-octene
545) (1S,5S,6R,7R)-3-(4-N,N-diethylcarbamoylbutyl)-6-[(3S,4S,1E)-3-hydroxy-4-methyl-6-octyn-1-enyl]-7-hydroxybicyclo[3.3.0]-2-octene
546) (1S,5S,6R,7R)-3-[4-N-(2-methoxycarbonylethyl)carbamoylbutyl]-6-[(3S,4S,1E)-3-hydroxy-4-methyl-6-octyn-1-enyl]-7-hydroxybicyclo [3.3.0]-2-octene
547) (1S,5S,6R,7R)-3-[4-N-(4-pyridylmethyl)carbamoylbutyl]-6-[(3S,4S,1E)-3-hydroxy-4-methyl-6-octyn-1-enyl]-7-hydroxybicyclo[3.3.0]-2-octene
548) (1S,5S,6R,7R)-3-(4-N,N-diisopropylcarbamoylbutyl)-6-[(3S,4S,1E)-3-hydroxy-4-methyl-6-octyn-1-enyl]-7-hydroxybicyclo[3.3.0]-2-octene
549) (1S,5S,6R,7R)-3-[4-(1-pyrrolidinyl)carbonylbutyl]-6-[(3S,4S,1E)-3-hydroxy-4-methyl-6-octyn-1-enyl]-7-hydroxybicyclo[3.3.0]-2-octene
550) (1S,5S,6R,7R)-3-(4-piperidinocarbonylbutyl)-6-[(3S,4S,1E)-3-hydroxy-4-methyl-6-octyn-1-enyl]-7-hydroxybicyclo[3.3.0]-2-octene
551) (1S,5S,6R,7R)-3-(4-morpholinocarbonylbutyl)-6-[(3S,4S,1E)-3-hydroxy-4-methyl-6-octyn-1-enyl]-7-hydroxybicyclo[3.3.0]-2-octene
552) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,4S,1E)-3-hydroxy-4-methyl-6-octyn-1-enyl group
553) (1S,5S,6R,7R)-3-(4-carbamoylbutyl)-6-[(3S,4R,1E)-3-hydroxy-4-methyl-6-octyn-1-enyl]-7-hydroxybicyclo [3.3.0]-2-octene
554) (1S,5S,6R,7R)-3-(4-N,N-dimethylcarbamoylbutyl)-6-[(3S,4R,1E)-3-hydroxy-4-methyl-6-octyn-1-enyl]-7-hydroxybicyclo[3.3.0]-2-octene
555) (1S,5S,6R,7R)-3-(4-N,N-diethylcarbamoylbutyl)-6-[(3S,4R,1E)-3-hydroxy-4-methyl-6-octyn-1-enyl]-7-hydroxybicyclo[3.3.0]-2-octene
556) (1S,5S,6R,7R)-3-[4-N-(2-methoxycarbonylethyl)carbamoylbutyl]-6-[(3S,4R,1E)-3-hydroxy-4-methyl-6-octyn-1-enyl]-7-hydroxybicyclo[3.3.0]-2-octene
557) (1S,5S,6R,7R)-3-[4-N-(4-pyridylmethyl)carbamoylbutyl]-6-[(3S,4R,1E)-3-hydroxy-4-methyl-6-octyn-1-enyl]-7-hydroxybicyclo[3.3.0]-2-octene
558) (1S,5S,6R,7R)-3-(4-N,N-diisopropylcarbamoylbutyl)-6-[(3S,4R,1E)-3-hydroxy-4-methyl-6-octyn-1-enyl]-7-hydroxybicyclo[3.3.0]-2-octene
559) (1S,5S,6R,7R)-3-[4-(1-pyrrolidinyl)carbonylbutyl]-6-[(3S,4R,1E)-3-hydroxy-4-methyl-6-octyn-1-enyl]-7-hydroxybicyclo[3.3.0]-2-octene
560) (1S,5S,6R,7R)-3-(4-piperidinocarbonylbutyl)-6-[(3S,4R,1E)-3-hydroxy-4-methyl-6-octyn-1-enyl]-7-hydroxybicyclo[3.3.0]-2-octene
561) (1S,5S,6R,7R)-3-(4-morpholinocarbonylbutyl)-6-[(3S,4R,1E)-3-hydroxy-4-methyl-6-octyn-1-enyl]-7-hydroxybicyclo[3.3.0]-2-octene
562) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,4R,1E)-3-hydroxy-4-methyl-6-octyn-1-enyl group
563) (1S,5S,6R,7R)-3-(4-carbamoylbutyl)-6-[(3S,1E)-3-hydroxy-3-cyclopentyl-1-propenyl]- 7-hydroxybicyclo [3.3.0]-2-octene
564) (1S,5S,6R,7R)-3-(4-N,N-dimethylcarbamoylbutyl)-6-[(3S,1E)-3-hydroxy-3-cyclopentyl-1 propenyl]-7-hydroxybicyclo [3.3.0]-2-octene
565) (1S,5S,6R,7R)-3-(4-N,N-diethylcarbamoylbutyl)-6-[(3S,1E)-3-hydroxy-3-cyclopentyl-1 propenyl]-7-hydroxybicyclo[3.3.0]-2-octene
566) (1S,5S,6R,7R)-3-[4-N-(2-methoxycarbonylethyl)carbamoylbutyl]-6-[(3S,1E)-3-hydroxy-3-cyclopentyl-1-propenyl]-7-hydroxybicyclo[3.3.0]-2-octene
567) (1S,5S,6R,7R)-3-[4-N-(4-pyridylmethyl)carbamoylbutyl]-6-[(3S,1E)-3-hydroxy-3-cyclopentyl-1-propenyl]-7-hydroxybicyclo[3.3.0]-2-octene
568) (1S,5S,6R,7R)-3-(4-N,N-diisopropylcarbamoylbutyl)-6-[(3S,1E)-3-hydroxy-3-cyclopentyl-1-propenyl]-7-hydroxybicyclo [3.3.0]-2-octene
569) (1S,5S,6R,7R)-3-[4-(1-pyrrolidinyl)carbonylbutyl]-6-[(3S,1E)-3-hydroxy-3-cyclopentyl-1-propenyl]-7-hydroxybicyclo [3.3.0]-2-octene
570) (1S,5S,6R,7R)-3-(4-piperidinocarbonylbutyl)-6-[(3S, 1E)-3-hydroxy-3-cyclopentyl-1-propenyl]-7-hydroxybicyclo[3.3.0]-2-octene
571) (1S,5S,6R,7R)-3-(4-morpholinocarbonylbutyl)-6-[(3S, 1E)-3-hydroxy-3-cyclopentyl-1-propenyl]-7-hydroxybicyclo [3.3.0]-2-octene
572) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-3-cyclopentyl-1-propenyl group
573) (1S,5S,6R,7R)-3-(4-carbamoylbutyl)-6-[(3S,1E)-3-hydroxy-3-cyclohexyl-1-propenyl]-7-hydroxybicyclo [3.3.0]-2-octene 574) (1S,5S,6R,7R)-3-(4-N,N-dimethylcarbamoylbutyl)-6-[(3S,1E)-3-hydroxy-3-cyclohexyl-1-propenyl]-7-hydroxybicyclo[3.3.0]-2-octene 575) (1S,5S,6R,7R)-3-(4-N,N-diethylcarbamoylbutyl)-6-[(3S,1E)-3-hydroxy-3-cyclohexyl-1-propenyl]-7-hydroxybicyclo[3.3.0]-2-octene 576) (1S,5S,6R,7R)-3-[4-N-(2-methoxycarbonylethyl)carbamoylbutyl]-6-[(3S,1E)-3-hydroxy-3-cyclohexyl-1-propenyl]-7-hydroxybicyclo[3.3.0]-2-octene 577) (1S,5S,6R,7R)-3-[4-N-(4-pyridylmethyl)carbamoylbutyl]-6-[(3S,1E)-3-hydroxy-3-cyclohexyl-1-propenyl]-7-hydroxybicyclo[3.3.0]-2-octene 578) (1S,5S,6R,7R)-3-(4-N,N-diisopropylcarbamoylbutyl)-6-[(3S,1E)-3-hydroxy-3-cyclohexyl-1-propenyl]-7-hydroxybicyclo[3.3.0]-2-octene 579) (1S,5S,6R,7R)-3-[4-(1-pyrrolidinyl)carbonylbutyl]-6-[(3S,1E)-3-hydroxy-3-cyclohexyl-1-propenyl]-7-hydroxybicyclo[3.3.0]-2-octene 580) (1S,5S,6R,7R)-3-(4-piperidinocarbonylbutyl)-6-[(3S,1E)-3-hydroxy-3-cyclohexyl-1-propenyl]-7-hydroxybicyclo[3.3.0]-2-octene 581) (1S,5S,6R,7R)-3-(4-morpholinocarbonylbutyl)-6-[(3S,1E)-3-hydroxy-3-cyclohexyl-1-propenyl]-7-hydroxybicyclo[3.3.0]-2-octene 582) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-3-cyclohexyl-1-propenyl group 583) (1S,5S,6R,7R)-3-(4-carbamoylbutyl)-6-[(3S,1E)-3-hydroxy-4-cyclopentyl-1-butenyl]-7-hydroxybicyclo[3.3.0]-2-octene 584) (1S,5S,6R,7R)-3-(4-N,N-dimethylcarbamoylbutyl)-6-[(3S,1E)-3-hydroxy-4-cyclopentyl-1-butenyl]-7-hydroxybicyclo[3.3.0]-2-octene 585) (1S,5S,6R,7R)-3-(4-N,N-diethylcarbamoylbutyl)-6-[(3S,1E)-3-hydroxy-4-cyclopentyl-1-butenyl]-7-hydroxybicyclo[3.3.0]-2-octene 586) (1S,5S,6R,7R)-3-[4-N-(2-methoxycarbonylethyl)carbamoylbutyl]-6-[(3S,1E)-3-hydroxy-4-cyclopentyl-1-butenyl]-7-hydroxybicyclo[3.3.0]-2-octene 587) (1S,5S,6R,7R)-3-[4-N-(4-pyridylmethyl)carbamoylbutyl]-6-[(3S,1E)-3-hydroxy-4-cyclopentyl-1-butenyl]-7-hydroxybicyclo[3.3.0]-2-octene 588) (S,5S,6R,7R)-3-(4-N,N-diisopropylcarbamoylbutyl)-6-[(3S,1E)-3-hydroxy-4-cyclopentyl-1-butenyl]-7-hydroxybicyclo[3.3.0]-2-octene 589) (1S,5S,6R,7R)-3-[4-(1-pyrrolidinyl)carbonylbutyl]-6-[(3S,1E)-3-hydroxy-4-cyclopentyl-1-butenyl]-7-hydroxybicyclo[3.3.0]-2-octene 590) (1S,5S,6R,7R)-3-(4-piperidinocarbonylbutyl)-6-[(3S,1E)-3-hydroxy-4-cyclopentyl-1-butenyl]-7-hydroxybicyclo[3.3.0]-2-octene 591) (1S,5S,6R,7R)-3-(4-morpholinocarbonylbutyl)-6-[(3S,1E)-3-hydroxy-4-cyclopentyl-1-butenyl]-7-hydroxybicyclo[3.3.0]-2-octene 592) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-4-cyclopentyl-1-butenyl group 593) (1S,5S,6R,7R)-3-(4-carbamoylbutyl)-6-[(3R,1E)-3-hydroxy-3-phenyl-1-propenyl]-7-hydroxybicyclo[3.3.0]-2-octene 594) (1S,5S,6R,7R)-3-(4-N,N-dimethylcarbamoylbutyl)-6-[(3R, 1E)-3-hydroxy-3-phenyl-1 propenyl]-7-hydroxybicyclo[3.3.0]-2-octene 595) (1S,5S,6R,7R)-3-(4-N,N-diethylcarbamoylbutyl)-6-[(3R,1E)—hydroxy-3-phenyl-1-propenyl]-7-hydroxybicyclo [3.3.0]-2-octene 596) (1S,5S,6R,7R)-3-[4-N-(2-methoxycarbonylethyl)carbamoylbutyl]-6-[(3R,1E)-3-hydroxy-3-phenyl-1-propenyl]-7-hydroxybicyclo [3.3.0]-2-octene 597) (1S,5S,6R,7R)-3-[4-N-(4-pyridylmethyl)carbamoylbutyl]-6-[(3R,1E)-3-hydroxy-3-phenyl-1-propenyl]-7-hydroxybicyclo[3.3.0]-2-octene 598) (1S,5S,6R,7R)-3-(4-N,N-diisopropylcarbamoylbutyl)-6-[(3R,1E)-3-hydroxy-3-phenyl-1-propenyl]-7-hydroxybicyclo[3.3.0]-2-octene 599) (1S,5S,6R,7R)-3-[4-(1-pyrrolidinyl)carbonylbutyl]-6-[(3R,1E)-3-hydroxy-3-phenyl-1-propenyl]-7-hydroxybicyclo [3.3.0]-2-octene 600) (1S,5S,6R,7R)-3-(4-piperidinocarbonylbutyl)-6-[(3R, 1E)-3-hydroxy-3-phenyl-1-propenyl]-7-hydroxybicyclo [3.3.0]-2-octene 601) (1S,5S,6 R,7R)-3-(4-morpholinocarbonylbutyl)-6-[(3R,1E)-3-hydroxy-3-phenyl-1-propenyl]-7-hydroxybicyclo[3.3.0]-2-octene 602) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-3-phenyl-1-propenyl group 603) (1S,5S,6R,7R)-3-(4-carbamoylbutyl)-6-[(3R,1E)-3-hydroxy-4-phenoxy-1-butenyl]-7-hydroxybicyclo[3.3.0]-2-octene 604) (1S,5S,6R,7R)-3-(4-N,N-dimethylcarbamoylbutyl)-6-[(3R,1E)-3-hydroxy-4-phenoxy-1-butenyl]-7-hydroxybicyclo[3.3.0]-2-octene 605) (1S,5S,6R,7R)-3-(4-N,N-diethylcarbamoylbutyl)-6-[(3R,1E)-3-hydroxy-4-phenoxy-1-butenyl]-7-hydroxybicyclo[3.3.0]-2-octene 606) (1S,5S,6R,7R)-3-[4-N-(2-methoxycarbonylethyl)carbamoylbutyl]-6-[(3R,1E)-3-hydroxy-4-phenoxy-1-butenyl]-7-hydroxybicyclo[3.3.0]-2-octene 607) (1S,5S,6R,7R)-3-[4-N-(4-pyridylmethyl)carbamoylbutyl]-6-[(3R,1E)-3-hydroxy-4-phenoxy-1-butenyl]-7-hydroxybicyclo[3.3.0]-2-octene 608) (1S,5S,6R,7R)-3-(4-N,N-diisopropylcarbamoylbutyl)-6-[(3R,1E)-3-hydroxy-4-phenoxy-1 butenyl]-7-hydroxybicyclo[3.3.0]-2-octene 609) (1S,5S,6R,7R)-3-[4-(1-pyrrolidinyl)carbonylbutyl]-6-[(3R,1E)-3-hydroxy-4-phenoxy-1-butenyl]-7-hydroxybicyclo[3.3.0]-2-octene 610) (1S,5S,6R,7R)-3-(4-piperidinocarbonylbutyl)-6-[(3R, 1E)-3-hydroxy-4-phenoxy-1-butenyl]-7-hydroxybicyclo [3.3.0]-2-octene 611) (1S,5S,6R,7R)-3-(4-morpholinocarbonylbutyl)-6-[(3R, 1E)-3-hydroxy-4-phenoxy-1-butenyl]-7-hydroxybicyclo [3.3.0]-2-octene 612) compounds of compound numbers 10 to 87 of the examples given bove, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-4-phenoxy-1-butenyl group 613) (1S,5S,6R,7R)-3-(4-carbamoylbutyl)-6-[(3R,1E)-3-hydroxy-1-octenyl]-7-hydroxybicyclo[3.3.0]-2-octene 614) (1S,5S,6R,7R)-3-(4-N,N-dimethylcarbamoylbutyl)-6-[(3R,1E)-3-hydroxy-1-octenyl]-7-hydroxybicyclo[3.3.0]-2-octene 615) (1S,5S,6R,7R)-3-(4-N,N-diethylcarbamoylbutyl)-6-[(3R,1E)-3-hydroxy-1-octenyl]-7-hydroxybicyclo[3.3.0]-2-octene 616) (1S,5S,6R,7R)-3-[4-N-(2-ethoxycarbonylethyl)carbamoylbutyl]-6-[(3R,1E)-3-hydroxy-1-octenyl]-7-hydroxybicyclo[3.3.0]-2-octene 617) (1S,5S,6R,7R)-3-[4-N-(4-pyridylmethyl)carbamoylbutyl]-6-[(3R,1E)-3-hydroxy-1-octenyl]-7-hydroxybicyclo[3.3.0]-2-octene 618) (1S,5S,6R,7R)-3-(4-N,N-diisopropylcarbamoylbutyl)-6-[(3R,1E)-3-hydroxy-1-octenyl]-7-hydroxybicyclo[3.3.0]-2-octene 619) (1S,5S,6R,7R)-3-[4-(1-pyrrolidinyl)carbonylbutyl]-6-[(3R,1E)-3-hydroxy-1-octenyl]-7-hydroxybicyclo[3.3.0]-2-octene 620) (1S,5S,6R,7R)-3-(4-piperidinocarbonylbutyl)-6-[(3R,1E)-3-hydroxy-1-octenyl]-7-hydroxybicyclo[3.3.0]-2-octene 621) (1S,5S,6R,7R)-3-(4-morpholinocarbonylbutyl)-6-[(3R,1E)-3-hydroxy-1-octenyl]-7-hydroxybicyclo[3.3.0]-2-octene 622) compounds of compound numbers 10 to 87 of the examples given above, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-1-octenyl group 623) (1S,5S,6R,7S)-3-(4-N,N-dimethylcarbamoylbutyl)-6-[(3S,1E)-3-hydroxy-1-octenyl]-7-hydroxybicyclo[3.3.0]-2-octene 624) (1S,5S,6R,7S)-3-(4-N,N-dimethylcarbamoylbutyl)-6-[(3R,1E)-3-hydroxy-1-octenyl]-7-hydroxybicyclo[3.3.0]-2-octene 625) (1R,5R,6S,7S)-3-(4-N,N-dimethylcarbamoylbutyl)-6-[(3R,1E)-3-hydroxy-1-octenyl]-7-hydroxybicyclo[3.3.0]-2-octene 626) (1R,5R,6S,7S)-3-(4-N,N-dimethylcarbamoylbutyl)-6-[(3S,1E)-3-hydroxy-1-octenyl]-7-hydroxybicyclo[3.3.0]-2-octene 627) (1R,5R,6S,7R)-3-(4-N,N-dimethylcarbamoylbutyl)-6-[(3R,1E)-3-hydroxy-1-octenyl]-7-hydroxybicyclo[3.3.0]-2-octene 628) (1R,5R,6S,7R)-3-(4-N,N-dimethylcarbamoylbutyl)-6-[(3S, 1E)-3-hydroxy-1-octenyl]-7-hydroxybicyclo[3.3.0]-2-octene 629) (1S,5S,6R,7R)-3-(4-N,N-dimethylcarbamoylbutyl)-6-[(1E)-3-hydroxy-1-propenyl]-7-hydroxybicyclo[3.3.0]-2-octene 630) (1S,5S,6R,7R)-3-(4-N,N-dimethylcarbamoylbutyl)-6-[(3S,1E)-3-hydroxy-1-butenyl]-7-hydroxybicyclo[3.3.0]-2-octene 631) (1S,5S,6R,7R)-3-(4-N,N-dimethylcarbamoylbutyl)-6-[(3R,1E)-3-hydroxy-1-butenyl]-7-hydroxybicyclo[3.3.0]-2-octene 632) (1S,5S,6R,7R)-3-(4-N,N-dimethylcarbamoylbutyl)-6-[(3S,1E)-3-hydroxy-1-pentenyl]-7-hydroxybicyclo[3.3.0]-2-octene 633) (1S,5S,6R,7R)-3-(4-N,N-dimethylcarbamoylbutyl)-6-[(3R,1E)-3-hydroxy-1-pentenyl]-7-hydroxybicyclo[3.3.0]-2-octene 634) (1S,5S,6R,7R)-3-(4-N,N-dimethylcarbamoylbutyl)-6-[(3S,1E)-3-hydroxy-1-hexenyl]-7-hydroxybicyclo[3.3.0]-2-octene 635) (1S,5S,6R,7R)-3-(4-N,N-dimethylcarbamoylbutyl)-6-[(3R,1E)-3-hydroxy-1-hexenyl]-7-hydroxybicyclo[3.3.0]-2-octene 636) (1S,5S,6R,7R)-3-(4-N,N-dimethylcarbamoylbutyl)-6-[(3S,1E)-3-hydroxy-1-heptenyl]-7-hydroxybicyclo[3.3.0]-2-octene 637) (1S,5S,6R,7R)-3-(4-N,N-dimethylcarbamoylbutyl)-6-[(3R,1E)-3-hydroxy-1-heptenyl]-7-hydroxybicyclo[3.3.0]-2-octene 638) (1S,5S,6R,7R)-3-(4-N,N-dimethylcarbamoylbutyl)-6-[(3S,1E)-3-hydroxy-1-nonenyl]-7-hydroxybicyclo[3.3.0]-2-octene 639) (1S,5S,6R,7R)-3-(4-N,N-dimethylcarbamoylbutyl)-6-[(3R,1E)-3-hydroxy-1-nonenyl]-7-hydroxybicyclo[3.3.0]-2-octene 640) (1S,5S,6R,7R)-3-(4-N,N-dimethylcarbamoylbutyl)-6-[(3S,1E)-3-hydroxy-1-decenyl]-7-hydroxybicyclo[3.3.0]-2-octene 641) (1S,5S,6R,7R)-3-(4-N,N-dimethylcarbamoylbutyl)-6-[(3R; 1E)-3-hydroxy-1-decenyl]-7-hydroxybicyclo[3.3.0]-2-octene 642) (1S,5S,6R,7R)-3-(4-N,N-dimethylcarbamoylbutyl)-6-[(3S,4R,1E)-3-hydroxy-4-methyl-1-octenyl]-7-hydroxybicyclo[3.3.0]-2-octene 643) (1S,5S,6R,7R)-3-(4-N,N-dimethylcarbamoylbutyl)-6-[(3S,4R,1E)-3-hydroxy-4-methyl-1-octenyl]-7-hydroxybicyclo[3.3.0]-2-octene 644) (1S,5S,6R,7R)-3-(4-N,N-dimethylcarbamoylbutyl)-6-[(3S,4S,1E)-3-hydroxy-4-methyl-1-octenyl]-7-hydroxybicyclo[3.3.0]-2-octene 645) (1S,5S,6R,7R)-3-(4-N,N-dimethylcarbamoylbutyl)-6-[(3R,4S,1E)-3-hydroxy-4-methyl-1-octenyl]-7-hydroxybicyclo[3.3.0]-2-octene 646) (1S,5S,6R,7R)-3-(4-N,N-dimethylcarbamoylbutyl)-6-[(3R,1E)-3-hydroxy-3-cyclopentyl-1-propenyl]-7-hydroxybicyclo[3.3.0]-2-octene 647) (1S,5S,6R,7R)-3-(4-N,N-dimethylcarbamoylbutyl)-6-[(3S,1E)-3-hydroxy-3-(3-ethylcyclopentyl)-1-propenyl]-7-hydroxybicyclo[3.3.0]-2-octene 648) (1S,5S,6R,7R)-3-(4-N,N-dimethylcarbamoylbutyl)-6-[(3R,1E)-3-hydroxy-3(3-ethylcyclopentyl)-1-propenyl]-7-hydroxybicyclo[3.3.0]-2-octene 649) (1S,5S,6R,7R)-3-(4-N,N-dimethylcarbamoylbutyl)-6-[(3R,1E)-3-hydroxy-3-cyclohexyl-1-propenyl]-7-hydroxybicyclo[3.3.0]-2-octene 650) (1S,5S,6R,7R)-3-(4-N,N-dimethylcarbamoylbutyl)-6-[(3R,1E)-3-hydroxy-4-cyclopentyl-1-butenyl]-7-hydroxybicyclo[3.3.0]-2-octene 651) (1S,5S,6R,7R)-3-(4-N,N-dimethylcarbamoylbutyl)-6-[(3S,1E)-3-hydroxy-4-cyclohexyl-1-butenyl]-7-hydroxybicyclo [3.3.0]-2-octene 652) (1S,5S,6R,7R)-3-(4-N,N-dimethylcarbamoylbutyl)-6-[(3R,1E)-3-hydroxy-4-cyclohexyl-1-butenyl]-7-hydroxybicyclo[3.3.0]-2-octene 653) (1S,5S,6R,7R)-3-(4-N,N-dimethylcarbamoylbutyl)-6-[(3S,1E)-3-hydroxy-3-phenyl-1-propenyl]-7-hydroxybicyclo[3.3.0]-2-octene 654) (1S,5S,6R,7R)-3-(4-N,N-dimethylcarbamoylbutyl)-6-[(3S,1E)-3-hydroxy-4-phenyl-1-butenyl]-7-hydroxybicyclo[3.3.0]-2-octene 655) (1S,5S,6R,7R)-3-(4-N,N-dimethylcarbamoylbutyl)-6-[(3R,1E)-3-hydroxy-4-phenyl-1-butenyl]-7-hydroxybicyclo[3.3.0]-2-octene 656) (1S,5S,6R,7R)-3-(4-N,N-dimethylcarbamoylbutyl)-6-[(3S,1E)-3-hydroxy-5-phenyl-1-pentenyl]-7-hydroxybicyclo[3.3.0]-2-octene 657) (1S,5S,6R,7R)-3-(4-N,N-dimethylcarbamoylbutyl)-6-[(3R,1E)-3-hydroxy-5-phenyl-1-pentenyl]-7-hydroxybicyclo[3.3.0]-2-octene
658) (1S,5S,6R,7R)-3-(4-N,N-dimethylcarbamoylbutyl)-6-[(3S,1E)-3-hydroxy-3-(o-tolyl)-1-propenyl]-7-hydroxybicyclo[3.3.0]-2-octene
659) (1S,5S,6R,7R)-3-(4-N,N-dimethylcarbamoylbutyl)-6-[(3R,1E)-3-hydroxy-3-(o-tolyl)-1-propenyl]-7-hydroxybicyclo[3.3.0]-2-octene
660) (1S,5S,6R,7R)-3-(4-N,N-dimethylcarbamoylbutyl)-6-[(3S, 1E)-3-hydroxy-3-(m-tolyl)-1-propenyl]-7-hydroxybicyclo[3.3.0]-2-octene
661) (1S,5S,6R,7R)-3-(4-N,N-dimethylcarbamoylbutyl)-6-[(3R,1E)-3-hydroxy-3-(m-tolyl)-1-propenyl]-7-hydroxybicyclo[3.3.0]-2-octene
662) (1S,5S,6R,7R)-3-(4-N,N-dimethylcarbamoylbutyl)-6-[(3S,1E)-3-hydroxy-3-(p-tolyl)-1-propenyl]-7-hydroxybicyclo[3.3.0]-2-octene
663) (1S,5S,6R,7R)-3-(4-N,N-dimethylcarbamoylbutyl)-6-[(3R,1E)-3-hydroxy-3-(p-tolyl)-1-propenyl]-7-hydroxybicyclo[3.3.0]-2-octene
664) (1S,5S,6R,7R)-3-(4-N,N-dimethylcarbamoylbutyl)-6-[(3S,1E)-3-hydroxy-4-(o-tolyl)-1-butenyl]-7-hydroxybicyclo[3.3.0]-2-octene
665) (1S,5S,6R,7R)-3-(4-N,N-dimethylcarbamoylbutyl)-6-[(3R,1E)-3-hydroxy-4-(o-tolyl)-1-butenyl]-7-hydroxybicyclo[3.3.0]-2-octene
666) (1S,5S,6R,7R)-3-(4-N,N-dimethylcarbamoylbutyl)-6-[(3S,1E)-3-hydroxy-4-(p-tolyl)-1-butenyl]-7-hydroxybicyclo [3.3.0]-2-octene
667) (1S,5S,6R,7R)-3-(4-N,N-dimethylcarbamoylbutyl)-6-[(3R,1E)-3-hydroxy-4-(p-tolyl)-1-butenyl]-7-hydroxybicyclo[3.3.0]-2-octene
668) (1S,5S,6R,7R)-3-(4-N,N-dimethylcarbamoylbutyl)-6-[(3S,1E)-3-hydroxy-5-(o-tolyl)-1-pentenyl]-7-hydroxybicyclo[3.3.0]-2-octene
669) (1S,5S,6R,7R)-3-(4-N,N-dimethylcarbamoylbutyl)-6-[(3R,1E)-3-hydroxy-5-(o-tolyl)-1-pentenyl]-7-hydroxybicyclo[3.3.0]-2-octene
670) (1S,5S,6R,7R)-3-(4-N,N-dimethylcarbamoylbutyl)-6-[(3S, 1E)-3-hydroxy-5-(m-tolyl)-1-pentenyl]-7-hydroxybicyclo[3.3.0]-2-octene
671) (1S,5S,6R,7R)-3-(4-N,N-dimethylcarbamoylbutyl)-6-[(3R,1E)-3-hydroxy-5-(m-tolyl)-1-pentenyl]-7-hydroxybicyclo[3.3.0]-2-octene
672) (1S,5S,6R,7R)-3-(4-N,N-dimethylcarbamoylbutyl)-6-[(3S,1E)-3-hydroxy-5-(p-tolyl)-1-pentenyl]-7-hydroxybicyclo[3.3.0]-2-octene
673) (1S,5S,6R,7R)-3-(4-N,N-dimethylcarbamoylbutyl)-6-[(3R,1E)-3-hydroxy-5-(p-tolyl)-1-pentenyl]-7-hydroxybicyclo[3.3.0]-2-octene
674) (1S,5S,6R,7R)-3-(4-N,N-dimethylcarbamoylbutyl)-6-[(3S,1E)-3-hydroxy-4-(4-methoxyphenyl)-1-butenyl]-7-hydroxybicyclo[3.3.0]-2-octene
675) (1S,5S,6R,7R)-3-(4-N,N-dimethylcarbamoylbutyl)-6-[(3R,1E)-3-hydroxy-4-(4-methoxyphenyl)-1-butenyl]-7-hydroxybicyclo[3.3.0]-2-octene
676) (1S,5S,6R,7R)-3-(4-N,N-dimethylcarbamoylbutyl)-6-[(3S,1E)-3-hydroxy-4-(4-N,N-dimethylaminophenyl)-1-butenyl]-7-hydroxybicyclo[3.3.0]-2-octene
677) (1S,5S,6R,7R)-3-(4-N,N-dimethylcarbamoylbutyl)-6-[(3R,1E)-3-hydroxy-4-(4-N,N-dimethylaminophenyl)-1-butenyl]-7-hydroxybicyclo[3.3.0]-2-octene
678) (1S,5S,6R,7R)-3-(4-N,N-dimethylcarbamoylbutyl)-6-[(3S,1E)-3-hydroxy-4-(3-chlorophenyl)-1-butenyl]-7-hydroxybicyclo[3.3.0]-2-octene
679) (1S,5S,6R,7R)-3-(4-N,N-dimethylcarbamoylbutyl)-6-[(3R,1E)-3-hydroxy-4-(3-chlorophenyl)-1-butenyl]-7-hydroxybicyclo[3.3.0]-2-octene
680) (1S,5S,6R,7R)-3-(4-N,N-dimethylcarbamoylbutyl)-6-[(3S,1E)-3 hydroxy-4-1(4-chlorophenyl)-1-butenyl]-7-hydroxybicyclo[3.3.0]-2-octene
681) (1S,5S,6R,7R)-3-(4-N,N-dimethylcarbamoylbutyl)-6-[(3R,1E)-3-hydroxy-4-(4-chlorophenyl)-1-butenyl]-7-hydroxybicyclo[3.3.0]-2-octene
682) (1S,5S,6R,7R)-3-(4-N,N-dimethylcarbamoylbutyl)-6-[(3S,1E)-3-hydroxy-3-methyl-1-octenyl]-7-hydroxybicyclo[3.3.0]-2-octene
683) (1S,5S,6R,7R)-3-(4-N,N-dimethylcarbamoylbutyl)-6-[(3R,1E)-3-hydroxy-3-methyl-1-octenyl]-7-hydroxybicyclo[3.3.0]-2-octene
684) (1S,5S,6R,7R)-3-(4-N,N-dimethylcarbamoylbutyl)-6-[(3S,1E)-3-hydroxy-3-methyl-3-phenyl-1-propenyl]-7-hydroxybicyclo[3.3.0]-2-octene
685) (1S,5S,6R,7R)-3-(4-N,N-dimethylcarbamoylbutyl)-6-[(3R,1E)-3-hydroxy-3-methyl-3-phenyl-1-propenyl]-7-hydroxybicyclo[3.3.0]-2-octene
686) (1S,5S,6R,7R)-3-(4-N,N-dimethylcarbamoylbutyl)-6-[(3S,1E)-3-hydroxy-3-methyl-4-phenyl-1-butenyl]-7-hydroxybicyclo[3.3.0]-2-octene
687) (1S,5S,6R,7R)-3-(4-N,N-dimethylcarbamoylbutyl)-6-[(3R,1E)-3-hydroxy-3-methyl-4-phenyl-1-butenyl]-7-hydroxybicyclo[3.3.0]-2-octene
688) (1S,5S,6R,7R)-3-(4-N,N-dimethylcarbamoylbutyl)-6-[(3S,1E)-3-hydroxy-3-methyl-5-phenyl-1-pentenyl]-7-hydroxybicyclo[3.3.0]-2-octene
689) (1S,5S,6R,7R)-3-(4-N,N-dimethylcarbamoylbutyl)-6-[(3R,1E)-3-hydroxy-3-methyl-5-phenyl-1-pentenyl]-7-hydroxybicyclo[3.3.0]-2-octene
690) (1S,5S,6R,7R)-3-(4-N,N-dimethylcarbamoylbutyl)-6-[(3S,1E)-3-hydroxy-3-methyl-3(m-tolyl)-1-propenyl]-7-hydroxybicyclo[3.3.0]-2-octene
691) (1S,5S,6R,7R)-3-(4-N,N-dimethylcarbamoylbutyl)-6-[(3R,1E)-3-hydroxy-3-methyl-3(m-tolyl)-1-propenyl]-7-hydroxybicyclo[3.3.0]-2-octene
692) (1S,5S,6R,7R)-3-(4-N,N-dimethylcarbamoylbutyl)-6-[(3S,1E)-3-hydroxy-3-methyl-4-(m-tolyl)-1-butenyl]-7-hydroxybicyclo [3.3.0]-2-octene
693) (1S,5S,6R,7R)-3-(4-N,N-dimethylcarbamoylbutyl)-6-[(3R,1E)-3-hydroxy-3-methyl-4-(m-tolyl)-1-butenyl]-7-hydroxybicyclo[3.3.0]-2-octene
694) (1S,5S,6R,7R)-3-(4-N,N-dimethylcarbamoylbutyl)-6-[(3S,1E)-3-hydroxy-3-methyl-5-(m-tolyl)-1-pentenyl]-7-hydroxybicyclo[3.3.0]-2-octene
695) (1S,5S,6R,7R)-3-(4-N,N-dimethylcarbamoylbutyl)-6-[(3R,1E)-3-hydroxy-3-methyl-5-(m-tolyl)-1-pentenyl]-7-hydroxybicyclo[3.3.0]-2-octene
696) (1S,5S,6R,7R)-3-(4-N,N-dimethylcarbamoylbutyl)-6-[(3S,1E)-3-hydroxy-4,4-dimethyl-1-octenyl]-7-hydroxybicyclo[3.3.0]-2-octene
697) (1S,5S,6R,7R)-3-(4-N,N-dimethylcarbamoylbutyl)-6-[(3R,1 E)-3-hydroxy-4,4-dimethyl-1-octenyl]-7-hydroxybicyclo[3.3.0]-2-octene
698) (1S,5S,6R,7R)-3-(4-N,N-dimethylcarbamoylbutyl)-6-[(3S,1E,5Z)-3-hydroxy-1,5-octadienyl]-7-hydroxybicyclo[3.3.0]-2-octene
699) (1S,5S,6R,7R)-3-(4-N,N-dimethylcarbamoylbutyl)-6-[(3R,1E,5Z)-3-hydroxy-1,5-octadienyl]-7-hydroxybicyclo[3.3.0]-2-octene
700) (1S,5S,6R,7R)-3-(4-N,N-dimethylcarbamoylbutyl)-6-[(3S,1E)-3-hydroxy-6-octyn-1-enyl]-7-hydroxybicyclo[3.3.0]-2-octene 701) (1S,5S,6R,7R)-3-(4-N,N-dimethylcarbamoylbutyl)-6-[(3R,1E)-3-hydroxy-6-octyn-1-enyl]-7-hydroxybicyclo[3.3.0]-2-octene
702) (1S,5S,6R,7R)-3-(4-N,N-dimethylcarbamoylbutyl)-6-[(3R,4S,1E)-3-hydroxy-4-methyl--6-octyn-1-enyl]-7-hydroxybicyclo[3.3.0]-2-octene
703) (1S,5S,6R,7R)-3-(4-N,N-dimethylcarbamoylbutyl)-6-[(3S,4R,1E)-3-hydroxy-4-methyl--6-octyn-1-enyl]-7-hydroxybicyclo[3.3.0]-2-octene
704) (1S,5S,6R,7R)-3-(4-N,N-dimethylcarbamoylbutyl)-6-[(3R,1E)-3-hydroxy-4,4-dimethyl-6-octyn-1-enyl]-7-hydroxybicyclo[3.3.0]-2-octene
705) (1S,5S,6R,7R)-3-(4-N,N-dimethylcarbamoylbutyl)-6-[(3S,1E)-3-hydroxy-4,4-dimethyl-6-octyn-1-enyl]-7-hydroxybicyclo[3.3.0]-2-octene
706) (1S,5S,6R,7R)-3-(4-N,N-dimethylcarbamoylbutyl)-6-[(3R,4S,1E)-3-hydroxy-4-methyl--6-nonyn-1-enyl]-7-hydroxybicyclo[3.3.0]-2-octene
707) (1S,5S,6R,7R)-3-(4-N,N-dimethylcarbamoylbutyl)-6-[(3S,4R,1E)-3-hydroxy-4-methyl-6-nonyn-1-enyl]-7-hydroxybicyclo[3.3.0]-2-octene
708) (1S,5S,6R,7R)-3-(4-N,N-dimethylcarbamoylbutyl)-6-[(3S,4S,1E)-3-hydroxy-4-methyl-6-nonyn-1-enyl]-7-hydroxybicyclo[3.3.0]-2-octene
709) (1S,5S,6R,7R)-3-(4-N,N-dimethylcarbamoylbutyl)-6-[(3S,4R,1E)-3-hydroxy-4-methyl-6-nonyn-1-enyl]-7-hydroxybicyclo[3.3.0]-2-octene
710) (1S,5S,6R,7R)-3-(4-N,N-dimethylcarbamoylbutyl)-6-[(3S,1E)-3-hydroxy-4-phenoxy-1-butenyl]-7-hydroxybicyclo[3.3.0]-2-octene
711) (1S,5S,6S,7R)-3-(4-N,N-dimethylcarbamoylbutyl)-6-[(3S)-3-hydroxy-1-octynyl]-7-hydroxybicyclo [3.3.0]-2-octene
712) (1S,5S,6S,7R)-3-(4-N,N-dimethylcarbamoylbutyl)-6-[(3R)-3-hydroxy-1-octynyl]-7-hydroxybicyclo[3.3.0]-2-octene
713) (1S,5S,6R,7R)-3-(4-N,N-dimethylcarbamoylbutyl)-6-[(3S, 1Z)-3-hydroxy-1-octenyl]-7-hydroxybicyclo[3.3.0]-2-octene
714) (1S,5S,6R,7R)-3-(4-N,N-dimethylcarbamoylbutyl)-6-[(3R,1Z)-3-hydroxy-1-octenyl]-7-hydroxybicyclo[3.3.0]-2-octene
715) (1S,5S,6R,7R)-3-(4-N,N-dimethylcarbamoylbutyl)-6-[(3S)-3-hydroxyoctyl]-7-hydroxybicyclo[3.3.0]-2-octene
716) (1S,5S,6R,7R)-3-(4-N,N-dimethylcarbamoylbutyl)-6-[(3R)-3-hydroxyoctyl]-7-hydroxybicyclo[3.3.0]-2-octene
717) (1S,5S,6R,7R)-3-(4-N,N-dimethylcarbamoylbutyl)-6-[(3S)-3-hydroxy-3-methyloctyl]-7-hydroxybicyclo[3.3.0]-2-octene
718) (1S,5S,6R,7R)-3-(4-N,N-dimethylcarbamoylbutyl)-6-[(3R)-3-hydroxy-3-methyloctyl]-7-hydroxybicyclo[3.3.0]-2-octene
719) (1S,5 S,6R,7R)-3-(4-N,N-dimethylcarbamoylbutyl)-6-[(3S)-3-hydroxy-4,4-dimethyloctyl]7-hydroxybicyclo[3.3.0]-2-octene
720) (1S,5S,6R,7R)-3-(4-N,N-dimethylcarbamoylbutyl)-6-[(3R)-3-hydroxy-4,4-dimethyloctyl]-7-hydroxybicyclo[3.3.0]-2-octene
721) (1S,5S,6R,7R)-3-(4-N,N-dimethylcarbamoylbutyl)-6-[(3S)-3-hydroxy-3-phenylpropyl]-7-hydroxybicyclo[3.3.0]-2-octene
722) (1S,5S,6R,7R)-3-(4-N,N-dimethylcarbamoylbutyl)-6-[(3R)-3-hydroxy-3-phenylpropyl]-7-hydroxybicyclo[3.3.0]-2-octene
723) (1S,5S,6R,7R)-3-(4-N,N-dimethylcarbamoylbutyl)-6-[(3S)-3-hydroxy-4-phenylbutyl]-7-hydroxybicyclo[3.3.0]-2-octene
724) (1S,5S,6R,7R)-3-(4-N,N-dimethylcarbamoylbutyl)-6-[(3R)-3-hydroxy-4-phenylbutyl]-7-hydroxybicyclo[3.3.0]-2-octene
725) (1S,5S,6R,7R)-3-(4-N,N-dimethylcarbamoylbutyl)-6-[(3S)-3-hydroxy-4-(m-tolyl)butyl]-7-hydroxybicyclo[3.3.0]-2-octene
726) (1S,5S,6R,7R)-3-(4-N,N-dimethylcarbamoylbutyl)-6-[(3R)-3-hydroxy-4-(m-tolyl)butyl]-7-hydroxybicyclo[3.3.0]-2-octene
727) (1S,5S,6R,7R)-3-(4-N,N-dimethylcarbamoylbutyl)-6-[(3S)-3-hydroxy-3-cyclopentylpropyl]-7-hydroxybicyclo[3.3.0]-2-octene
728) (1S,5S,6R,7R)-3-(4-N,N-dimethylcarbamoylbutyl)-6-[(3R)-3-hydroxy-3-cyclopentylpropyl]-7-hydroxybicyclo[3.3.0]-2-octene
729) (1S,5S,6R,7R)-3-(4-N,N-dimethylcarbamoylbutyl)-6-[(4S, 1E)-4-hydroxy-4-ethyl-1-octenyl]-7-hydroxybicyclo[3.3.0]-2-octene
730) (1S,5S,6R,7R)-3-(4-N,N-dimethylcarbamoylbutyl)-6-[(4R,1E)-4-hydroxy-4-ethyl-1-octenyl]-7-hydroxybicyclo[3.3.0]-2-octene
731) (1S,5S,6R,7R)-3-(4-N,N-dimethylcarbamoylbutyl)-6-[(1E)-4-hydroxy-4-butyl-1-octenyl]-7-hydroxybicyclo[3.3.0]-2-octene
732) (1S,5S,6R,7R)-3-(4-N,N-dimethylcarbamoylbutyl)-6-[(4S, 1E)-4-hydroxy-4-butyl-1,5-hexadienyl]-7-hydroxybicyclo[3.3.0]-2-octene
733) (1S,5S,6R,7R)-3-(4-N,N-dimethylcarbamoylbutyl)-6-[(4R, 1E)-4-hydroxy-4-butyl-1,5-hexadienyl]-7-hydroxybicyclo[3.3.0]-2-octene
734) (1S,5S,6R,7R)-3-(4-N,N-dimethylcarbamoylbutyl)-6-[(4S,1E)-4-hydroxy-4-cyclopentyl-1-pentenyl]-7-hydroxybicyclo[3.3.0]-2-octene
735) (1S,5S,6R,7R)-3-(4-N,N-dimethylcarbamoylbutyl)-6-[(4R, 1E)-4-hydroxy-4-cyclopentyl-1-pentenyl]-7-hydroxybicyclo[3.3.0]-2-octene
736) (1S,5S,6R,7R)-3-(4-N,N-dimethylcarbamoylbutyl)-6-[(4S,1E)-4-hydroxy-4-cyclohexyl-1-pentenyl]-7-hydroxybicyclo[3.3.0]-2-octene
737) (1S,5S,6R,7R)-3-(4-N,N-dimethylcarbamoylbutyl)-6-[(4R,1E)-4-hydroxy-4-cyclohexyl-1-pentenyl]-7-hydroxybicyclo[3.3.0]-2-octene
738) (1S,5S,6R,7R)-3-(4-N,N-dimethylcarbamoylbutyl)-6-[(4S,1E)-4-hydroxy-4-phenyl-1-pentenyl]-7-hydroxybicyclo[3.3.0]-2-octene
739) (1S,5S,6R,7R)-3-(4-N,N-dimethylcarbamoylbutyl)-6-[(4R,1E)-4-hydroxy-4-phenyl-1-pentenyl]-7-hydroxybicyclo[3.3.0]-2-octene
740) (1S,5S,6R,7R)-3-(4-N,N-dimethylcarbamoylbutyl)-6-[(1E)-3-(1-hydroxycyclopentyl)-1-propenyl]-7-hydroxybicyclo [3.3.0]-2-octene
741) (1S,5S 6R,7R)-3-(4-N,N-dimethylcarbamoylbutyl)-6-[(1E)-3-(1-hydroxycyclohexyl)-1-propenyl]-7-hydroxybicyclo[3.3.0]-2-octene
742) (1S,5S,6R,7R)-3-(4-N,N-dimethylcarbamoylbutyl)-6-[(4S,1E)-4-hydroxy-1-octenyl]-7-hydroxybicyclo[3.3.0]-2-octene
743) (1S,5S,6R,7R)-3-(4-N,N-dimethylcarbamoylbutyl)-6-[(4R,1E)-4-hydroxy-1-octenyl]-7-hydroxybicyclo[3.3.0]-2-octene
744) (1S,5S,6R,7R)-3-(4-N,N-dimethylcarbamoylbutyl)-6-[(1E)-1-octenyl]-7 hydroxybicyclo[3.3.0]-2-octene
745) (1S,5S,6R,7R)-3-(4-N,N-dimethylcarbamoylbutyl)-6-[(1E,3E)-1,3-octadienyl]-7-hydroxybicyclo[3.3.0]-2-octene 746) (1S,5S,6R,7R)-3-(4-N,N-dimethylcarbamoylbutyl)-6-[(1E,5S)-5-methyl-1-nonenyl]-7-hydroxybicyclo[3.3.0]-2-octene 747) (1S,5S,6R,7R)-3-(4-N,N-dimethylcarbamoylbutyl)-6-[(1E,5R)-5-methyl-1-nonenyl]-7-hydroxybicyclo[3.3.0]-2-octene 748) (1S,5S,6R,7R)-3-(4-N,N-dimethylcarbamoylbutyl)-6-[(1E,3E,5S)-5-methyl-1,3-nonadienyl]-7-hydroxybicyclo[3.3.0]-2-octene 749) (1S,5S,6R,7R)-3-(4-N,N-dimethylcarbamoylbutyl)-6-[(1E,3E,5R)-5-methyl-1,3-nonadienyl]-7-hydroxybicyclo[3.3.0]-2-octene 750) (1S,5S,6R,7R)-3-(4-N,N-dimethylcarbamoylbutyl)-6-[(1E,4R)-5-methyl-1,3-octenyl]-7-hydroxybicyclo[3.3.0]-2-octene 751) (1S,5S,6R,7R)-3-(4-N,N-dimethylcarbamoylbutyl)-6-[(1E,4S)-4-methyl-1-octenyl]-7-hydroxybicyclo[3.3.0]-2-octene 752) (1S,5S,6R,7R)-3-(4-N,N-dimethylcarbamoylbutyl)-6-[(1E,3E)-4-methyl-1,3-octadienyl]-7-hydroxybicyclo[3.3.0]-2-octene 753) (1S,5S,6R,7R)-3-(4-N,N-dimethylcarbamoylbutyl)-6-[(1E,5R)-4-ethyl-1-octenyl]-7-hydroxybicyclo[3.3.0]-2-octene 754) (1S,5S,6R,7R)-3-(4-N,N-dimethylcarbamoylbutyl)-6-[(1E,4S)-4-ethyl-1-octenyl]-7-hydroxybicyclo[3.3.0]-2-octene 755) (1S,5S,6R,7R)-3-(4-N,N-dimethylcarbamoylbutyl)-6-[(1E,3E)-4-ethyl-1,3-octadienyl j-7-hydroxybicyclo[3.3.0]-2-octene 756) (1S,5S,6R,7R)-3-(4-N,N-dimethylcarbamoylbutyl)-6-[(1E)-4-butyl-1,3-octadienyl]-7-hydroxybicyclo[3.3.0]-2-octene 757) (1S,5S,6R,7R)-3-(4-N,N-dimethylcarbamoylbutyl)-6-[(1E,5Z)-1,5-octadienyl]-7-hydroxybicyclo[3.3.0]-2-octene 758) (1S,5S,6R,7R)-3-(4-N,N-dimethylcarbamoylbutyl)-6-[(1E,3E,5Z)-1,3,5-octatrienyl]-7-hydroxybicyclo[3.3.0]-2-octene 759) (1S,5S,6R,7R)-3-(4-N,N-dimethylcarbamoylbutyl)-6-[(1E)-3-cyclopentyliden-1-propenyl]-7-hydroxybicyclo[3.3.0]-2-octene 760) (1S,5S,6R,7R)-3-(4-N,N-dimethylcarbamoylbutyl)-6-[(1E)-3-cyclohexyliden-1-propenyl]-7-hydroxybicyclo[3.3.0]-2-octene 761) (1S,5S,6R,7R)-3-(4-N,N-dimethylcarbamoylbutyl)-6-[(1E)-2-phenylvinyl]-7-hydroxybicyclo[3.3.0]-2-octene 762) (1S,5S,6R,7R)-3-(4-N,N-dimethylcarbamoylbutyl)-6-[(1E)-2-(o-tolyl)vinyl]-7-hydroxybicyclo[3.3.0]-2-octene 763) (1S,5S,6R,7R)-3-(4-N,N-dimethylcarbamoylbutyl)-6-[(1E)-2-(m-tolyl)vinyl]-7-hydroxybicyclo[3.3.0]-2-octene 764) (1S,5S,6R,7R)-3-(4-N,N-dimethylcarbamoylbutyl)-6-[(1E)-2-(p-tolyl)vinyl]-7-hydroxybicyclo[3.3.0]-2-octene 765) (1S,5S,6R,7R)-3-(4-N,N-dimethylcarbamoylbutyl)-6-[(1E)-3-phenyl-1-propenyl]-7-hydroxybicyclo[3.3.0]-2-octene 766) (1S,5S,6R,7R)-3-(4-N,N-dimethylcarbamoylbutyl)-6-[(1E)-4-phenyl-1-butenyl]-7-hydroxybicyclo[3.3.0]-2-octene 767) (1S,5S,6R,7R)-3-(4-N,N-dimethylcarbamoylbutyl)-6-[(1E,3E) 4-phenyl-1,3-butadienyl]-7-hydroxybicyclo[3.3.0]-2-octene 768) (1S,5S,6R,7R)-3-(4-N,N-dimethylcarbamoylbutyl)-6-[(1E,3t)-4-phenyl-3-methyl-1,3-butadienyl]-7-hydroxybicyclo[3.3.0]-2-octene 769) (1S,5S,6R,7R)-3-(4-N,N-dimethylcarbamoylbutyl)-6-[(1E)-4-(o-tolyl)-1-butenyl]-7-hydroxybicyclo[3.3.0]-2-octene 770) (1S,5S,6R,7R)-3-(4-N,N-dimethylcarbamoylbutyl)-6-[(1E)-4-(m-tolyl)-1-butenyl]-7-hydroxybicyclo[3.3.0]-2-octene 771) (1S,5S,6R,7R)-3-(4-N,N-dimethylcarbamoylbutyl)-6-[(1E)-4-(p-tolyl)-1-butenyl]-7-hydroxybicyclo[3.3.0]-2-octene 772) (1S,5S,6R,7R)-3-(4-N,N-dimethylcarbamoylbutyl)-6-[(1E,3E)-4-(m-tolyl)-1,3-butadienyl]-7-hydroxybicyclo[3.3.0]-2-octene 773) (1S,5S,6R,7R)-3-(4-N,N-dimethylcarbamoylbutyl)-6-[(1E)-5-(m-tolyl)-1-pentenyl]-7-hydroxybicyclo[3.3.0]-2-octene 774) (1S,5S,6R,7R)-3-(4-N,N-dimethylcarbamoylbutyl)-6-[(31E,3E)-5-(m-tolyl)-3-pentadienyl]-7-hydroxybicyclo[3.3.0]-2-octene 775) (1S,5S,6R,7R)-3-(4-N,N-dimethylcarbamoylbutyl)-6-[(1E)-4,4-bisphenylsufonyl-4-(m-tolyl)-1-butenyl]-7-hydroxybicyclo[3.3.0]-octene 776) (1S,5S,6R,7R)-3-(4-N,N-dimethylcarbamoylbutyl)-6-[(1E,3E)-5-(m-tolyl)-1,3-hexadienyl]-7-hydroxybicyclo[3.3.0]-2-octene 777) (1S,5S,6R,7R)-3-(4-N,N-dimethylcarbamoylbutyl)-6-(4-phenoxybutyl)-7-hydroxybicyclo[3.3.0]-2-octene 778) (1S,5S,6R,7R)-3-(4-N,N-dimethylcarbamoylbutyl)-6-[(1E)-3-oxo-1-propenyl]-7-hydroxybicyclo[3.3.0]-2-octene 779) (1S,5S,6R,7R)-3-(4-N,N-dimethylcarbamoylbutyl)-6-[(1E)-3-oxo-S-butenyl]-7-hydroxybicyclo[3.3.0]-2-octene 780) (1S,5S,6R,7R)-3-(4-N,N-dimethylcarbamoylbutyl)-6-[(1E)-3-oxo-1-pentenyl]-7-hydroxybicyclo[3.3.0]-2-octene 781) (1S,5S,6R,7R)-3-(4-N,N-dimethylcarbamoylbutyl)-6-[(1E)-3-oxo-1-hexenyl]-7-hydroxybicyclo[3.3.0]-2-octene 782) (S,5S,6R,7R)-3-(4-N,N-dimethylcarbamoylbutyl)-6-[(1E)-3-oxo-1-heptenyl]-7-hydroxybicyclo[3.3.0]-2-octene 783) (1S,5S,6R,7R)-3-(4-N,N-dimethylcarbamoylbutyl)-6-[(1E)-3-oxo-1-octenyl]-7-hydroxybicyclo[3.3.0]-2-octene 784) (1S,5S,6R,7R)-3-(4-N,N-dimethylcarbamoylbutyl)-6-[(1E)-3-oxo-1-nonenyl]-7-hydroxybicyclo[3.3.0]-2-octene 785) (1S,5S,6R,7R)-3-(4-N,N-dimethylcarbamoylbutyl)-6-[(1E)-3-oxo-4-decenyl]-7-hydroxybicyclo[3.3.0]-2-octene 786) (1S,5S,6R,7R)-3-(4-N,N-dimethylcarbamoylbutyl)-6-[(4S,1E)-3-oxo-4-methyl-1-octenyl]-7-hydroxybicyclo[3.3.0]-2-octene 787) (1S,5S,6R,7R)-3-(4-N,N-dimethylcarbamoylbutyl)-6-[(4R,1E)-3-oxo-4-methyl-1-octenyl]-7-hydroxybicyclo[3.3.0]-2-octene 788) (1S,5S,6R,7R)-3-(4-N,N-dimethylcarbamoylbutyl)-6-[(1E)-3-oxo-4,4-dimethyl-1-octenyl]-7-hydroxybicyclo[3.3.0]-2-octene 789) (1S,5S,6R,7R)-3-(4-N,N-dimethylcarbamoylbutyl)-6-[(5S,1E)-3-oxo-5-methyl-1-nonenyl]-7-hydroxybicyclo[3.3.0]-2-octene 790) (1S,5S,6R,7R)-3-(4-N,N-dimethylcarbamoylbutyl)-6-[(5R,1E)-3-oxo-5-methyl-1-nonenyl]-7-hydroxybicyclo[3.3.0]-2-octene 791) (1S,5S,6R,7R)-3-(4-N,N-dimethylcarbamoylbutyl)-6-[(1E)-3-oxo-3-cyclopentyl-1-propenyl]-7-hydroxybicyclo[3.3.0]-2-octene
792) (1S,5S,6R,7R)-3-(4-N,N-dimethylcarbamoylbutyl)-6-[(1 E)-3-oxo-3-cyclohexyl-1 propenyl]-7-hydroxybicyclo[3.3.0]-2-octene
793) (1S,5 S,6R,7R)-3-(4-N,N-dimethylcarbamoylbutyl)-6-[(1E)-3-oxo-4-cyclopentyl-1-butenyl]-7-hydroxybicyclo[3.3.0]-2-octene
794) (1S,5S,6R,7R)-3-(4-N,N-dimethylcarbamoylbutyl)-6-[(1E)-3-oxo-4-cyclohexyl-1-butenyl]-7-hydroxybicyclo[3.3.0]-2-octene
795) (1S,5S,6R,7R)-3-(4-N,N-dimethylcarbamoylbutyl)-6-[(1E)-3-oxo-3-phenyl-propenyl]7-hydroxybicyclo[3.3.0]-2-octene
796) (1S,5S,6R,7R)-3-(4-N,N-dimethylcarbamoylbutyl)-6-[(1E)-3-oxo-4-phenyl-1-butenyl]-7-hydroxybicyclo[3.3.0]-2-octene
797) (1S,5S,6R,7R)-3-(4-N,N-dimethylcarbamoylbutyl)-6-[(1E)-3-oxo-5-phenyl-1-pentenyl]-7-hydroxybicyclo[3.3.0]-2-octene
798) (1S,5S,6R,7R)-3-(4-N,N-dimethylcarbamoylbutyl)-6-[(1E)-3-oxo-3-(o-tolyl)-1-propenyl]-7-hydroxybicyclo[3.3.0]-2-octene
799) (1S,5 S,6R,7R)-3-(4-N,N-dimethylcarbamoylbutyl)-6-[(1E)-3-oxo-3-(m-tolyl)-1-propenyl]-7-hydroxybicyclo[3.3.0]-2-octene
800) (1S,5S,6R,7R)-3-(4-N,N-dimethylcarbamoylbutyl)-6-[(1E)-3-oxo-3-(p-tolyl)-1-propenyl]-7-hydroxybicyclo[3.3.0]-2-octene
801) (1S,58,6R,7R)-3-(4-N,N-dimethylcarbamoylbutyl)-6-[(1E)-3-oxo-4-(o-tolyl)-1-butenyl]-7-hydroxybicyclo[3.3.0]-2-octene
802) (1S,5S,6R,7R)-3-(4-N,N-dimethylcarbamoylbutyl)-6-[(1E)-3-oxo-4-(m-tolyl)-1-butenyl]-7-hydroxybicyclo[3.3.0]-2-octene
803) (1S,5S,6R,7R)-3-(4-N,N-dimethylcarbamoylbutyl)-6-[(1E)-3-oxo-4-(p-tolyl)-1-butenyl]-7-hydroxybicyclo[3.3.0]-2-octene
804) (1S,5S,6R,7R)-3-(4-N,N-dimethylcarbamoylbutyl)-6-[(1E)-3-oxo-5-(o-tolyl)-1-pentenyl]7-hydroxybicyclo[3.3.0]-2-octene
805) (1S,5S,6R,7R)-3-(4-N,N-dimethylcarbamoylbutyl)-6-[(1E)-3-oxo-5-(m-tolyl)-1-pentenyl]-7-hydroxybicyclo[3.3.0]-2-octene
806) (1S,5S,6R,7R)-3-(4-N,N-dimethylcarbamoylbutyl)-6-[(1E)-3-oxo-5-(p-tolyl)-1-pentenyl]-7-hydroxybicyclo[3.3.0]-2-octene
807) (1S,5S,6R,7R)-3-(4-N,N-dimethylcarbamoylbutyl)-6-hydroxymethyl-7-hydroxybicyclo[3.3.0]-2-octene
808) (1S,5S,6S,7R)-3-(4-N,N-dimethylcarbamoylbutyl)-6-[(1R)-hydroxyethyl]-7-hydroxybicyclo[3.3.0]-2-octene
809) (1S,5S,6S,7R)-3-(4-N,N-dimethylcarbamoylbutyl)-6-[(1S)-1-hydroxyethyl]-7-hydroxybicyclo[3.3.0]-2-octene
810) (1S,5S,6S,7R)-3-(4-N,N-dimethylcarbamoylbutyl)-6-[(1R)-1-hydroxypentyl]-7-hydroxybicyclo[3.3.0]-2-octene
811) (1S,5S 6S,7R)-3-(4-N,N-dimethylcarbamoylbutyl)-6-[(1S)-1-hydroxypentyl]-7-hydroxybicyclo[3.3.0]-2-octene
812) (1S,5S,6R,7R)-3-(4-N,N-dimethylcarbamoylbutyl)-6-[(1R)-1-hydroxy-1-methylbutyl]-7-hydroxybicyclo[3.3.0]-2-octene
813) (1S,5S,6R,7R)-3-(4-N,N-dimethylcarbamoylbutyl)-6-[(1S)-1-hydroxy-1-methylbutyl]-7-hydroxybicyclo[3.3.0]-2-octene
814) (1 S,5S,6R,7R)-3-(4-N,N-dimethylcarbamoylbutyl)-6-[(1R,2E)—hydroxy-2-nonenyl]-7-hydroxybicyclo[3.3.0]-2-octene
815) (1S,5S,6R,7R)-3-(4-N,N-dimethylcarbamoylbutyl)-6-[(1S,2E)-1-hydroxy-2-nonenyl]-7-hydroxybicyclo[3.3.0]-2-octene
816) (1S,5S,6R,7R)-3-(4-N,N-dimethylcarbamoylbutyl)-6-[(1R,3S,2E)-1,3-dihydroxy-2-nonenyl]-7-hydroxybicyclo[3.3.0]-2-octene
817) (1S,5S,6R,7R)-3-(4-N,N-dimethylcarbamoylbutyl)-6-[(1S,3S,2E)-1,3-dihydroxy-2-nonenyl]-7-hydroxybicyclo[3.3.0]-2-octene
818) (1S,5S,6R,7R)-3-(4-N,N-dimethylcarbamoylbutyl)-6-[(1R,3S,2E)-1,3-dihydroxy-4-cyclopentyl-2-butenyl]-7-hydroxybicyclo[3.3.0]-2-octene
819) (1S,5S,6R,7R)-3-(4-N,N-dimethylcarbamoylbutyl)-6-[(1S,3S,2E)-1,3-dihydroxy-4-cyclopentyl-2-butenyl]-7-hydroxybicyclo[3.3.0]-2-octene
820) (1S,5S,6R,7R)-3-(4-N,N-dimethylcarbamoylbutyl)-6-[(1R,3S,2E)-1,3-dihydroxy-5-phenyl-2-pentenyl]-7-hydroxybicyclo[3.3.0]-2-octene
821) (1S,5S,6R,7R)-3-(4-N,N-dimethylcarbamoylbutyl)-6-[(1S,3S,2E)-1,3-dihydroxy-5-phenyl-2-pentenyl]-7-hydroxybicyclo[3.3.0]-2-octene
822) (1S,5S,6R,7R)-3-(4-N,N-dimethylcarbamoylbutyl)-6-[(1S)-1-hydroxy-2-pentynyl]-7-hydroxybicyclo[3.3.0]-2-octene
823) (1S,5S,6R,7R)-3-(4-N,N-dimethylcarbamoylbutyl)-6-[(1R)-1-hydroxy-2-pentynyl]-7-hydroxybicyclo[3.3.0]-2-octene
824) (1S,5S,6S,7R)-3-(4-N,N-dimethylcarbamoylbutyl)-6-[(1R)-1-hydroxy-5-phenoxypentyl]-7-hydroxybicyclo[3.3.0]-2-octene
825) (1S,5S,6S,7R)-3-(4-N,N-dimethylcarbamoylbutyl)-6-[(1S)-1-hydroxy-5-phenoxypentyl]-7-hydroxybicyclo[3.3.0]-2-octene
826) (1S,5S,6R,7R)-3-(4-N,N-dimethylcarbamoylbutyl)-6-[(R)-hydroxyphenylmethyl]-7-hydroxybicyclo[3.3.0]-2-octene
827) (1S,5S,6R,7R)-3-(4-N,N-dimethylcarbamoylbutyl)-6-[(S)-hydroxyphenylmethyl]-7-hydroxybicyclo[3.3.0]-2-octene
828) (1S,5S,6R,7R)-3-(4-N,N-dimethylcarbamoylbutyl)-6-[(R)-hydroxy(o-tolyl)methyl]-7-hydroxybicyclo[3.3.0]-2-octene
829) (1S,5S,6R,7R)-3-(4-N,N-dimethylcarbamoylbutyl)-6-[(S)-hydroxy(o-tolyl)methyl]-7-hydroxybicyclo[3.3.0]-2-octene
830) (1S,5S,6R,7R)-3-(4-N,N-dimethylcarbamoylbutyl)-6-[(R)-hydroxy(m-tolyl)methyl]-7-hydroxybicyclo[3.3.0]-2-octene
831) (1S,5S,6R,7R)-5-(4-N,N-dimethylcarbamoylbutyl)-6-[(S)-hydroxy(m-tolyl)methyl]-7-hydroxybicyclo[3.3.0]-2-octene
832) (1S,5S,6R,7R)-3-(4-N,N-dimethylcarbamoylbutyl)-6-[(R)-hydroxy(p-tolyl)methyl]-7-hydroxybicyclo[3.3.0]-2-octene
833) (1S,5S,6R,7R)-3-(4-N,N-dimethylcarbamoylbutyl)-6-[(S)-hydroxy(p-tolyl)methyl]-7-hydroxybicyclo[3.3.0]-2-octene
834) (1S,5S,6R,7R)-3-(4-N,N-dimethylcarbamoylbutyl)-6-[(R)-hydroxy(4-methoxyphenyl) methyl]-7-hydroxybicyclo[3.3.0]-2-octene
835) (1S,5S,6R,7R)-3-(4-N,N-dimethylcarbamoylbutyl)-6-[(S)-hydroxy(4-methoxyphenyl) methyl]-7-hydroxybicyclo[3.3.0]-2-octene 836) (1S,5S,6R,7R)-3-(4-N,N-dimethylcarbamoylbutyl)-6-[(R)-hydroxy(4-N,N-dimethylaminophenyl)methyl]-7-hydroxybicyclo[3.3.0]-2-octene 837) (1S,5S,6R,7R)-3-(4-N,N-dimethylcarbamoylbutyl)-6-[(S)-hydroxy(4-N,N-dimethylaminophenyl)methyl]-7-hydroxybicyclo[3.3.0]-2-octene 838) (1S,5S,6R,7R)-3-(4-N,N-dimethylcarbamoylbutyl)-6-[(R)-hydroxy(3-chlorophenyl) methyl]-7-hydroxybicyclo[3.3.0]-2-octene 839) (1S,5S,6R,7R)-3-(4-N,N-dimethylcarbamoylbutyl)-6-[(S)-hydroxy(3-chlorophenyl) methyl]-7-hydroxybicyclo[3.3.0]-2-octene 840) (1S,5S,6R,7R)-3-(4-N,N-dimethylcarbamoylbutyl)-6-formyl-7-hydroxybicyclo[3.3.0]-2-octene 841) (1S,3S,6R,7R)-3-(4-N,N-dimethylcarbamoylbutyl)-6-acetyl-7-hydroxybicyclo[3.3.0]-2-octene 842) (1 S,5S,6R,7R)-3-(4-N,N-dimethylcarbamoylbutyl)-6-benzoyl-7-hydroxybicyclo[3.3.0]-2-octene 843) (1S,5S,6R,7R)-3-(4-N,N-dimethylcarbamoylbutyl)-6-(o-tolyl)-7-hydroxybicyclo[3.3.0]-2-octene 844) (1S,5S,6R,7R)-3-(4-N,N-dimethylcarbamoylbutyl)-6-(m-tolyl)-7-hydroxybicyclo[3.3.0]-2-octene 845) (1S,5S,6R,7R)-3-(4-N,N-dimethylcarbamoylbutyl)-6-(p-tolyl)-7-hydroxybicyclo[3.3.0]-2-octene 846) (1S,5S,6R,7R)-3-(4-N,N-dimethylcarbamoylbutyl)-6-(4-methoxyphenylcarbonyl)-7-hydroxybicyclo[3.3.0]-2-octene 847) (1S,5S,6R,7R)-3-(4-N,N-dimethylcarbamoylbutyl)-6-(4-N,N-dimethylaminophenyl carbonyl)-7-hydroxybicyclo[3.3.0]-2-octene 848) (1S,5S,6R,7R)-3-(4-N,N-dimethyl carbamoylbutyl)-6-(3-chlorophenylcarbonyl)-7-hydroxybicyclo[3.3.0]-2-octene 849) (1S,5S,6R,7R)-3-(4-N,N-dimethylcarbamoylbutyl)-6-[(2E)-2-phenylvinylcarbonyl]-7-hydroxybicyclo[3.3.0]-2-octene 850) (1S,5S,6R,7R)-3-(4-N,N-dimethylcarbamoylbutyl)-6-[(2E)-2-(4-methoxyphenyl)vinyl carbonyl]-7-hydroxybicyclo[3.3.0]-2-octene 851) (1S,5S,6R,7R)-3-(4-N,N-dimethylcarbamoylbutyl)-6-[(2E)-2-(4-N,N-dimethylamino phenyl)vinylcarbonyl]-7-hydroxybicyclo[3.3.0]-2-octene 852) (1S,5S,6R,7R)-3-(4-N,N-dimethylcarbamoylbutyl)-6-[(2E)-2-(3-chlorophenyl)vinyl carbonyl]-7-hydroxybicyclo[3.3.0]-2-octene 853) (1S,5S,6R,7R)-3-(4-N,N-dimethylcarbamoylbutyl)-6-[(2E)-2-(2-thienyl)vinylcarbonyl]-7-hydroxybicyclo[3.3.0]-2-octene 854) (1S,5S,6R,7R)-3-(4-N,N-dimethylcarbamoylbutyl)-6-[(2E)-2-(4-pyridyl)vinylcarbonyl]-7-hydroxybicyclo[3.3.0]-2-octene 855) compounds of compound numbers 623 to 854 of the examples given above, wherein the 4-N,N-dimethylcarbamoylbutyl group, which is a substitution group at position 3 of the bicyclo[3.3.0]-2-octene cycle, has been replaced by either of the 4-carbamoylbutyl group, the 4-N,N-diethylcarbamoylbutyl group, the 4-N-(2-methoxycarbonylethyl)carbamoylbutyl group, the 4-N-(4-pyridylmethyl)carbamoylbutyl group, the 4-N,N-diisopropylcarbamoylbutyl group, the 4-(1-pyrrolidinyl)carbonylbutyl group, the 4-piperidinocarbonylbutyl group or the 4-morpholinocarbonylbutyl group 856) (1S,2R,3R,5S)-7-[(E)-4-carbamoylbutylidene]-2-[(3S,1E)-3-hydroxy-1-octenyl]-3-hydroxybicyclo[3.3.0]octane 857) (1S,2R,3R,5S)-7-[(E)-4-N-methylcarbamoylbutylidene]-2-[(3S,1E)-3-hydroxy-1-octenyl]-3-hydroxybicyclo[3.3.0]octane 858) (1S,2R,3R,5S)-7-[(E)-4-N-ethylcarbamoylbutylidene]-2-[(3S,1E)-3-hydroxy-1-octenyl]-3-hydroxybicyclo[3.3.0]octane 859) (1S,2R,3R,5S)-7-[(E)-4-N-propylcarbamoylbutylidene]-2-[(3S,1E)-3-hydroxy-1-octenyl]-3-hydroxybicyclo[3.3.0]octane 860) (1S,2R,3R,5S)-7-[(E)-4-N-isopropylcarbamoylbutylidene]-2-[(3S,1E)-3-hydroxy-1-octenyl]-3-hydroxybicyclo[3.3.0]octane 861) (1S,2R,3R,5S)-7-[(E)-4-N-butylcarbamoylbutylidene]-2-[(3S,1E)-3-hydroxy-1-octenyl]-3-hydroxybicyclo[3.3.0]octane 862) (1S,2R,3R,5S)-7-[(E)-4-N-t-butylcarbamoylbutylidene]-2-[(3S,1E)-3-hydroxy-1-octenyl]-3-hydroxybicyclo[3.3.0]octane 863) (1S,2R,3R,5S)-7-[(E)-4-N-phenylcarbamoylbutylidene]-2-[(3S,1E)-3-hydroxy-1-octenyl]-3-hydroxybicyclo[3.3.0]octane 864) (1S,2R,3R,5S)-7-[(E)-4-N-benzylcarbamoylbutylidene]-2-[(3S,1E)-3-hydroxy-1-octenyl]-3-hydroxybicyclo[3.3.0]octane 865) (1S,2R,3R,5S)-7-[(E)-4-N-(4-pyridylmethyl)carbamoylbutylidene]-2-[(3S,1E)-3-hydroxy-1-octenyl]-3-hydroxybicyclo[3.3.0]octane 866) (1S,2R,3R,5S)-7-[(E)-4-(1-pyrrolidinyl)carbonylbutylidene]-2-[(3S,1E)-3-hydroxy-1-octenyl]-3-hydroxybicyclo[3.3.0]octane 867) (1S,2R,3R,5S)-7-[(E)-4-piperidinocarbonylbutylidene]-2-[(3S,1E)-3-hydroxy-1-octenyl]3-hydroxybicyclo[3.3.0]octane 868) (1S,2R,3R,5S)-7-[(E)-4-morpholinocarbonylbutylidene]-2-[(3S,1E)-3-hydroxy-1-octenyl]-3-hydroxybicyclo[3.3.0]octane 869) (1S,2R,3R,5S)-7-[(E)-4-(4-N-methyl-1-piperazinyl)carbonylbutylidene]-2-[(3S,1E)-3-hydroxy-1-octenyl]-3-hydroxybicyclo[3.3.0]octane 870) (1S,2R,3R,5S)-7-[(E)-4-N-(2-pyridyl)carbamoylbutylidene]-2-[(3S,1E)-3-hydroxy-1-octenyl]-3-hydroxybicyclo[3.3.0]octane 871) (1S,2R,3R,5S)-7-[(E)-4-N,N-dimethylcarbamoylbutylidene]-2-[(3S, 1E)-3-hydroxy-1-octenyl]-3-hydroxybicyclo[3.3.0]octane 872) (1S,2R,3R,5S)-7-[(E)-4-N,N-diethylcarbamoylbutylidene]-2-[(3S,1E)-3-hydroxy-1-octenyl]-3-hydroxybicyclo[3.3.0]octane 873) (1S,2R,3R,5S)-7-[(E)-4-N,N-dipropylcarbamoylbutylidene]-2-[(3S,1E)-3-hydroxy-1-octenyl]-3-hydroxybicyclo [3.3.0]octane 874) (1S,2R,3R,5S)-7-[(E)-4-N,N-diisopropylcarbamoylbutylidene]-2-[(3S,1E)-3-hydroxy-1-octenyl]-3-hydroxybicyclo[3.3.0]octane 875) (1S,2R,3R,5S)-7-[(E)-4-N,N-dibutylcarbamoylbutylidene]-2-[(3S,1E)-3-hydroxy-1-octenyl]-3-hydroxybicyclo[3.3.0]octane 876) (1S,2R,3R,5S)-7-[(E)-4-N-t-butyl-N-methylcarbamoylbutylidene]-2-[(3S,1E)-3-hydroxy-1-octenyl]-3-hydroxybicyclo[3.3.0]octane 877) (1S,2R,3R,5S)-7-[(E)-4-N-(2-hydroxyethyl)carbamoylbutylidene]-2-[(3S,1E)-3-hydroxy-1-octenyl]-3-hydroxybicyclo[3.3.0]octane 878) (1S,2R,3R,5S)-7-[(E)-4-N-(3-hydroxypropyl)carbamoylbutylidene]-2-[(3S,1E)-3-hydroxy-1-octenyl]-3-hydroxybicyclo[3.3.0]octane 879) (1S,2R,3R,5S)-7-[(E)-3-carbamoylpropylidene]-2-[(3S,1E)-3-hydroxy-1-octenyl]-3-hydroxybicyclo[3.3.0]octane
880) (1S,2R,3R,5S)-7-[(E)-3-N,N-dimethylcarbamoylpropylidene]-2-[(3S,1E)-3-hydroxy-1-octenyl]-3-hydroxybicyclo[3.3.0]octane
881) (1S,2R,3R,5S)-7-[(E)-5-carbamoylpentylidene]-2-[(3S,1E)-3-hydroxy-1-octenyl]-3-hydroxybicyclo[3.3.0]octane
882) (1S,2R,3R,5S)-7-[(E)-5-N,N-dimethylcarbamoylpentylidene]-2-[(3S,1E)-3-hydroxy-1-octenyl]-3-hydroxybicyclo[3.3.0]octane
883) (1S,2R,3R,5S)-7-[(E)-2-(N,N-dimethylcarbamoylmethyl)oxyethylidene]-2-[(3S,1E)-3-hydroxy-1-octenyl]-3-hydroxybicyclo[3.3.0]octane
884) (1S,2R,3R,5S)-7-[(E)-2-(N,N-diisopropylcarbamoylmethyl)oxyethylidene]-2-[(3S,1E)-3-hydroxy-1-octenyl]-3-hydroxybicyclo[3.3.0]octane
885) (1S,2R,3R,5S)-7-[(E)-2-(N-t-butyl-N-methylcarbamoylmethyl)oxyethylidene]-2-[(3S,1E)-3-hydroxy-1-octenyl]-3-hydroxybicyclo[3.3.0]octane
886) (1S,2R,3R,5S)-7-[(E)-2-[(1-pyrrolidinyl)carbonylmethyl]oxyethylidene]-2-[(3S,1E)-3-hydroxy-1-octenyl]-3-hydroxybicyclo[3.3.0]octane
887) (1S,2R,3R,5S)-7-[(E)-2-(piperidinocarbonylmethyl)oxyethylidene]-2-[(3S,1E)-3-hydroxy-1-octenyl]-3-hydroxybicyclo[3.3.0]octane
888) (1S,2R,3R,5S)-7-[(E)-2-(morpholinocarbonylmethyl)oxyethylidene]-2-[(3S,1E)-3-hydroxy-1-octenyl]-3-hydroxybicyclo[3.3.0]octane
889) (1S,2R,3R,5S)-7-[(E)-2-(N,N-dimethylcarbamoylmethyl)thioethylidene]-2-[(3S,1E)-3-hydroxy-1-octenyl]-3-hydroxybicyclo[3.3.0]octane
890) (1S,2R,3R,5S)-7-[(E)-2-N—(N,N-dimethylcarbamoylmethyl)aminoethylidene]-2-[(3S,1E)3-hydroxy-1-octenyl]-3-hydroxybicyclo[3.3.0]octane
891) (1S,2R,3R,5S)-7-[(E)-N,N-dimethylcarbamoylmethoxymethylene]-2-[(3S,1E)-3-hydroxy-1-octenyl]-3-hydroxybicyclo[3.3.0]octane
892) (1S,2R,3R,5S)-7-[(E)-N,N-dimethylcarbamoylmethylthiomethylene]-2-[(3S,1E)-3-hydroxy-1-octenyl]-3-hydroxybicyclo[3.3.0]octane
893) (1S,2R,3R,5S)-7-[(E)-N—(N,N-dimethylcarbamoylmethyl)aminomethylene]-2-[(3S,1E)-3-hydroxy-1-octenyl]-3-hydroxybicyclo[3.3.0]octane
894) (1S,2R,3R,5S)-7-[(E)-4-carbamoylbutylidene]-2-[(3S,1E)-3-hydroxy-3-cyclopentyl-1-propenyl]-3-hydroxybicyclo[3.3.0]octane
895) (1S,2R,3R,5S)-7-[(E)-4-N-methylcarbamoylbutylidene]-2-[(3S,1E)-3-hydroxy-3-cyclopentyl-1-propenyl]-3-hydroxybicyclo[3.3.0]octane
896) (1S,2R,3R,5S)-7-[(E)-4-N-ethylcarbamoylbutylidene]-2-[(3S,1E)-3-hydroxy-3-cyclopentyl-1-propenyl]-3-hydroxybicyclo[3.3.0]octane
897) (1S,2R,3R,5S)-7-[(E)-4-N-propylcarbamoylbutylidene]-2-[(3S,1E)-3-hydroxy-3-cyclopentyl-1-propenyl]-3-hydroxybicyclo[3.3.0]octane
898) (1S,2R,3R,5S)-7-[(E)-4-N-isopropylcarbamoylbutylidene]-2-[(3S,1E)-3-hydroxy-3-cyclopentyl-1-propenyl]-3-hydroxybicyclo[3.3.0]octane
899) (1S,2R,3R,5S)-7-[(E)-4-N-butylcarbamoylbutylidene]-2-[(3S,1E)-3-hydroxy-3-cyclopentyl-1-propenyl]-3-hydroxybicyclo[3.3.0]octane
900) (1S,2R,3R,5S)-7-[(E)-4-N-t-butylcarbamoylbutylidene]-2-[(3S,1E)-3-hydroxy-3-cyclopentyl-1-propenyl]-0.3-hydroxybicyclo[3.3.0]octane
901) (1S,2R,3R,5S)-7-[(E)-4-N-phenylcarbamoylbutylidene]-2-[(3S,1E)-3-hydroxy-3-cyclopentyl-1-propenyl]-3-hydroxybicyclo[3.3.0]octane
902) (1S,2R,3R,5S)-7-[(E)-4-N-benzylcarbamoylbutylidene]-2-[(3S,1E)-3-hydroxy-3-cyclopentyl-1-propenyl]-3-hydroxybicyclo[3.3.0]octane
903) (1S,2R,3R,5S)-7-[(E)-4-N-(4-pyridylmethyl)carbamoylbutylidene]-2-[(3S,1E)-3-hydroxy-3-cyclopentyl-1-propenyl]-3-hydroxybicyclo[3.3.0]octane
904) (1S,2R,3R,5S)-7-[(E)-4-(1-pyrrolidinyl)carbonylbutylidene]-2-[(3S,1E)-3-hydroxy-3-cyclopentyl-1-propenyl]-3-hydroxybicyclo[3.3.0]octane
905) (1S,2R,3R,5S)-7-[(E)-4-piperidinocarbonylbutylidene]-2-[(3S,1E)-3-hydroxy-3-cyclopentyl-1-propenyl]-3-hydroxybicyclo[3.3.0]octane
906) (1S,2R,3R,5S)-7-[(E)-4-morpholinocarbonylbutylidene]-2-[(3S,1E)-3-hydroxy-3-cyclopentyl-1-propenyl]-3-hydroxybicyclo[3.3.6]octane
907) (1S,2R,3R,5S)-7-[(E)-4-(4-N-methyl-1-piperazinyl)carbonylbutylidene]-2-[(3S,1E)-3-hydroxy-3-cyclopentyl-1-propenyl]-3-hydroxybicyclo[3.3.0]octane
908) (1S,2R,3R,5S)-7-[(E)-4-N-(2-pyridyl)carbamoylbutylidene]-2-[(3S,1E)-3-hydroxy-3-cyclopentyl-1-propenyl]-3-hydroxybicyclo[3.3.0]octane
909) (1S,2R,3R,5S)-7-[(E)-4-N,N-dimethylcarbamoylbutylidene]-2-[(3S,1E)-3-hydroxy-3-cyclopentyl-1-propenyl]-3-hydroxybicyclo[3.3.0]octane
910) (1S,2R,3R,5S)-7-[(E)-4-N,N-diethylcarbamoylbutylidene]-2-[(3S,1E)-3-hydroxy-3-cyclopentyl-1-propenyl]-3-hydroxybicyclo[3.3.0]octane
911) (1S,2R,3R,5S)-7-[(E)-4-N,N-dipropylcarbamoylbutylidene]-2-[(3S,1E)-3-hydroxy-3-cyclopentyl-1-propenyl]-3-hydroxybicyclo[3.3.0]octane
912) (1S,2R,3R,5S)-7-[(E)-4-N,N-diisopropylcarbamoylbutylidene]-2-[(3S,1E)-3-hydroxy-3-cyclopentyl-1-propenyl]-3-hydroxybicyclo[3.3.0]octane
913) (1S,2R,3R,5S)-7-[(E)-4-N,N-dibutylcarbamoylbutylidene]-2-[(3S,1E)-3-hydroxy-3-cyclopentyl-1-propenyl]-3-hydroxybicyclo[3.3.0]octane
914) (1S,2R,3R,5S)-7-[(E)-4-N-t-butyl-N-methylcarbamoylbutylidene]-2-[(3S,1E)-3-hydroxy-3-cyclopentyl-1-propenyl]-3-hydroxybicyclo[3.3.0]octane
915) (1S,2R,3R,5S)-7-[(E)-4-N-(2-hydroxyethyl)carbamoylbutylidene]-2-[(3S,1E)-3-hydroxy-3-cyclopentyl-1-propenyl]-3-hydroxybicyclo[3.3.0]octane
916) (1S,2R,3R,5S)-7-[(E)-4-N-(3-hydroxypropyl)carbamoylbutylidene]-2-[(3S,1E)-3-hydroxy-3-cyclopentyl-1-propenyl]-3-hydroxybicyclo[3.3.0]octane
917) (1S,2R,3R,5S)-7-[(E)-3-carbamoylpropylidene]-2-[(3S,1E)-3-hydroxy-3-cyclopentyl-1-propenyl]-3-hydroxybicyclo[3.3.0]octane
918) (1S,2R,3R,5S)-7-[(E)-3-N,N-dimethylcarbamoylpropylidene]-2-[(3S,1E)-3-hydroxy-3-cyclopentyl-1-propenyl]-3-hydroxybicyclo[3.3.0]octane
919) (1S,2R,3R,5S)-7-[(E)-5-carbamoylpentylidene]-2-[(3S,1E)-3-hydroxy-3-cyclopentyl-1-propenyl]-3-hydroxybicyclo[3.3.0]octane
920) (1S,2R,3R,5S)-7-[(E)-5-N,N-dimethylcarbamoylpentylidene]-2-[(3S,1E)-3-hydroxy-3-cyclopentyl-1-propenyl]-3-hydroxybicyclo[3.3.0]octane
921) (1S,2R,3R,5S)-7-[(E)-2-(N,N-dimethylcarbamoylmethyl)oxyethylidene]-2-[(3S,1E)-3-hydroxy-3-cyclopentyl-1-propenyl]-3-hydroxybicyclo[3.3.0]octane
922) (1S,2R,3R,5S)-7-[(E)-2-(N,N-diisopropylcarbamoylmethyl)-oxyethylidene]-2-[(3S,1E)-3-hydroxy-3-cyclopentyl-1-propenyl]-3-hydroxybicyclo[3.3.0] octane 923) (1S,2R,3R,5S)-7-[(E)-2-(N-t-butyl-N-methylcarbamoylmethyl)oxyethylidene]-2-[(3S,1E)3-hydroxy-3-cyclopentyl-1-propenyl]-3-hydroxybicyclo[3.3.0]octane
924) (1S,2R,3R,5S)-7-[(E)-2-[(1-pyrrolidinyl)carbonylmethyl]oxyethylidene]-2-[(3S,1E)-3-hydroxy-3-cyclopentyl-1-propenyl]-3-hydroxybicyclo[3.3.0] octane
925) (1S,2R,3R,5S)-7-[(E)-2-(piperidinocarbonylmethyl)oxyethylidene]-2-[(3S,1E)-3-hydroxy-3-cyclopentyl-1-propenyl]-3-hydroxybicyclo[3.3.0]octane
926) (1S,2R,3R,5S)-7-[(E)-2-(morpholinocarbonylmethyl)oxyethylidene]-2-[(3S,1E)-3-hydroxy-3-cyclopentyl-1-propenyl]-3-hydroxybicyclo(3.3.0]octane
927) (1S,2R,3R,5S)-7-[(E)-2-(N,N-dimethylcarbamoylmethyl)thioethylidene]-2-[(3S,1E)-3-hydroxy-3-cyclopentyl-1-propenyl]-3-hydroxybicyclo[3.3.0]octane
928) (1S,2R,3R,5S)-7-[(E)-2-N—(N,N-dimethylcarbamoylmethyl)aminoethylidene]-2-[(3S,1E)-3-hydroxy-3-cyclopentyl-1-propenyl]-3-hydroxybicyclo[3.3.0]octane
929) (1S,2R,3R,5S)-7-[(E)-N,N-dimethylcarbamoylmethoxymethylene]-2-[(3S,1E)-3-hydroxy-3-cyclopentyl-1-propenyl]-3-hydroxybicyclo[3.3.0]octane
930) (1S,2R,3R,5S)-7-[(E)-N,N-dimethylcarbamoylmethylthiomethylene]-2-[(3S,1E)-3-hydroxy-3-cyclopentyl-1-propenyl]-3-hydroxybicyclo[3.3.0]octane
931) (1S,2R 3R,5S)-7-[(E)-N—(N,N-dimethylcarbamoylmethyl)aminomethylene]-2-[(3S,1E)-3-hydroxy-3-cyclopentyl-1-propenyl]-3-hydroxybicyclo[3.3.0]octane
932) (1S,2R,3R,5S)-7-[(E)-4-carbamoylbutylidene]-2-[(3S,4S, 1E)-3-hydroxy-4-methyl-6-octyn-1-enyl]-3-hydroxybicyclo[3.3.0]octane
933) (1S,2R,3R,5S)-7-[(E)-4-N-methylcarbamoylbutylidene]-2-[(3S,4S,1E)-3-hydroxy-4-methyl-6-octyn-1-enyl]-3-hydroxybicyclo[3.3.0]octane
934) (1S,2R,3R,5S)-7-[(E)-4-N-ethylcarbamoylbutylidene]-2-[(3S,4S,1E)-3-hydroxy-4-methyl-6-octyn-1-enyl]-3-hydroxybicyclo[3.3.0]octane
935) (1S,2R,3R,5S)-7-[(E)-4-N-propylcarbamoylbutylidene]-2-[(3S,4S, 1E)-3-hydroxy-4-methyl-6-octyn-1-enyl]-3-hydroxybicyclo[3.3.0]octane
936) (1S,2R,3R,5S)-7-[(E)-4-N-isopropylcarbamoylbutylidene]-2-[(3S,4S,1E)-3-hydroxy-4-methyl-6-octyn-1-enyl]-3-hydroxybicyclo[3.3.0] octane
937) (1S,2R,3R,5S)-7-[(E)-4-N-butylcarbamoylbutylidene]-2-[(3S,4S, 1E)-3-hydroxy-4-methyl-6-octyn-1-enyl]-3-hydroxybicyclo[3.3.0]octane
938) (1S,2R,3R,5S)-7-[(E)-4-N-t-butylcarbamoylbutylidene]-2-[(3S,4S,1E)-3-hydroxy-4-methyl-6-octyn-1-enyl]-3-hydroxybicyclo[3.3.0]octane
939) (1S,2R,3R,5S)-7-[(E)-4-N-phenylcarbamoylbutylidene]-2-[(3S,4S, 1E)-3-hydroxy-4-methyl-6-octyn-1-enyl]-3-hydroxybicyclo[3.3.0]octane
940) (1S,2R,3R,5S)-7-[(E)-4-N-benzylcarbamoylbutylidene]-2-[(3S,4S,1E)-3-hydroxy-4-methyl-6-octyn-1-enyl]-3-hydroxybicyclo[3.3.0]octane
941) (1 S,2R,3R,5S)-7-[(E)-4-N-(4-pyridylmethyl)carbamoylbutylidene]-2-[(3S,4S,1E)-3-hydroxy-4-methyl-6-octyn-1-enyl]-3-hydroxybicyclo[3.3.0]octane
942) (1S,2R,3R,5S)-7-[(E)-4-(1-pyrrolidinyl)carbonylbutylidene]-2-[(3S,4S,1E)-3-hydroxy-4-methyl-6-octyn-1-enyl]-3-hydroxybicyclo[3.3.0]octane
943) (1S,2R,3R,5S)-7-[(E)-4-piperidinocarbonylbutylidene]-2-[(3S,4S,1E)-3-hydroxy-4-methyl-6-octyn-1-enyl]-3-hydroxybicyclo[3.3.0]octane
944) (1S,2R,3R,5S)-7-[(E)-4-morpholinocarbonylbutylidene]-2-[(3S,4S,1E)-3-hydroxy-4-methyl-6-octyn-1-enyl]-3-hydroxybicyclo[3.3.0]octane
945) (1S,2R,3R,5S)-7-[(E)-4-(4-N-methyl-1-piperazinyl)carbonylbutylidene]-2-[(3S,4S,1E)-3-hydroxy-4-methyl-6-octyn-1-enyl]-3-hydroxybicyclo [3.3.0]octane
946) (1S,2R,3R,5S)-7-[(E)-4-N-(2-pyridyl)carbamoylbutylidene]-2-[(3S,4S,1E)-3-hydroxy-4-methyl-6-octyn-1-enyl]-3-hydroxybicyclo[3.3.0]octane
947) (1S,2R,3R,5S)-7-[(E)-4-N,N-dimethylcarbamoylbutylidene]-2-[(3S,4S,1E)-3-hydroxy-4-methyl-6-octyn-1-enyl]-3-hydroxybicyclo[3.3.0]octane
948) (1S,2R,3R,5S)-7-[(E)-4-N,N-diethylcarbamoylbutylidene]-2-[(3S,4S,1E)-3-hydroxy-4-methyl-6-octyn-1-enyl]-3-hydroxybicyclo[3.3.0]octane
949) (1S,2R,3R,5S)-7-[(E)-4-N,N-dipropylcarbamoylbutylidene]-2-[(3S,4S,1E)-3-hydroxy-4-methyl-6-octyn-1-enyl]-3-hydroxybicyclo[3.3.0]octane
950) (1S,2R,3R,5S)-7-[(E)-4-N,N-diisopropylcarbamoylbutylidene]-2-[(3S,4S,1E)-3-hydroxy-4-methyl-6-octyn-1-enyl]-3-hydroxybicyclo[3.3.0]octane
951) (1S,2R,3R,5S)-7-[(E)-4-N,N-dibutylcarbamoylbutylidene]-2-[(3S,4S,1E)-3-hydroxy-4-methyl-6-octyn-1-enyl]-3-hydroxybicyclo[3.3.0]octane
952) (1S,2R,3R,5S)-7-[(E)-4-N-t-butyl-N-methylcarbamoylbutylidene]-2-[(3S,4S,1E)-3-hydroxy-4-methyl-6-octyn-1-enyl]-3-hydroxybicyclo[3.3.0]octane
953) (1S,2R,3R,5S)-7-[(E)-4-N-(2-hydroxyethyl)carbamoylbutylidene]-2-[(3S,4S,1E)-3-hydroxy-4-methyl-6-octyn-1-enyl]-3-hydroxybicyclo[3.3.0]octane
954) (1S,2R,3R,5S)-7-[(E)-4-N-(3-hydroxypropyl)carbamoylbutylidene]-2-[(3S,4S,1E)-3-hydroxy-4-methyl-6-octyn-1-enyl]-3-hydroxybicyclo[3.3.0]octane
955) (1S,2R,3R,5S)-7-[(E)-3-carbamoylpropylidene]-2-[(3S,4S,1E)-3-hydroxy-4-methyl-6-octyn-1-enyl]-3-hydroxybicyclo[3.3.0] octane
956) (1S,2,R,3R,5S)-7-[(E)-3-N,N-dimethylcarbamoylpropylidene]-2-[(3S,4S,1E)-3-hydroxy-4-methyl-6-octyn-1-enyl]-3-hydroxybicyclo[3.3.0]octane
957) (1S,2R,3R,5S)-7-[(E)-5-carbamoylpentylidene]-2-[(3S,4S,1E)-3-hydroxy-4-methyl-6-octyn-1-enyl]-3-hydroxybicyclo[3.3.0]octane
958) (1S,2R,3R,5S)-7-[(E)-5-N,N-dimethylcarbamoylpentylidene]-2-[(3S,4S,1E)-3-hydroxy-4-methyl-6-octyn-1-enyl]-3-hydroxybicyclo[3.3.0]octane
959) (1S,2R,3R,5S)-7-[(E)-2-(N,N-dimethylcarbamoylmethyl)oxyethylidene]-2-[(3S,4S,1E)-3-hydroxy-4-methyl-6-octyn-1-enyl]-3-hydroxybicyclo[3.3.0]octane
960) (1S,2R,3R,5S)-7-[(E)-2-(N,N-diisopropylcarbamoylmethyl)oxyethylidene]-2-[(3S,4S,1E)3-hydroxy-4-methyl-6-octyn-1-enyl]-3-hydroxybicyclo[3.3.0]octane
961) (1S,2R,3R,5S)-7-[(E)-2-(N-t-butyl-N-methylcarbamoylmethyl)oxyethylidene]-2-[(3S,4S,1E)-3-hydroxy-4-methyl-6-octyn-1-enyl]-3-hydroxybicyclo[3.3.0]octane
962) (1S,2R,3R,5S)-7-[(E)-2-[(1-pyrrolidinyl)carbonylmethyl]oxyethylidene]-2-[(3S,4S,1E)-3-hydroxy-4-methyl-6-octyn-1-enyl]-3-hydroxybicyclo[3.3.0]octane
963) (1S,2R,3R,5S)-7-[(E)-2-(piperidinocarbonylmethyl)oxyethylidene]-2-[(3S,4S,1E)-3-hydroxy-4-methyl-6-octyn-1-enyl]-3-hydroxybicyclo[3.3.0]octane
964) (1S,2R,3R,5S)-7-[(E)-2-(morpholinocarbonylmethyl)oxyethylidene]-2-[(3S,4S,1E)-3-hydroxy-4-methyl-6-octyn-1-enyl]-3-hydroxybicyclo[3.3.0]octane
965) (1S,2R,3R,5S)-7-[(E)-2-(N,N-dimethylcarbamoylmethyl)thioethylidene]-2-[(3S,4S,1E)-3-hydroxy-4-methyl-6-octyn-1-enyl]-3-hydroxybicyclo[3.3.0]octane
966) (1S,2R,3R,5S)-7-[(E)-2-N-(N,N-dimethylcarbamoylmethyl)aminoethylidene]-2-[(3S,4S,1E)-3-hydroxy-4-methyl-6-octyn-1-enyl]-3-hydroxybicyclo[3.3.0]octane 967) (1S,2R,3R,5S)-7-[(E)-N,N-dimethylcarbamoyl-methoxymethylene]-2-[(3S,4S,1E)-3-hydroxy-4-methyl-6-octyn-1-enyl]-3-hydroxybicyclo[3.3.0]octane
968) (1S,2R,3R,5S)-7-[(E)-N,N-dimethylcarbamoylmethylthiomethylene]-2-[(3S,4S,1E)-3-hydroxy-4-methyl-6-octyn-1-enyl]-3-hydroxybicyclo[3.3.0]octane
969) (1S,2R,3R,5S)-7-[(E)-N—(N,N-dimethylcarbamoylmethyl)aminomethylene]-2-[(3S,4S, 1E)-3-hydroxy-4-methyl-6-octyn-1-enyl]-3-hydroxybicyclo[3.3.0]octane
970) (1S,2R,3R,5S)-7-[(E)-4-carbamoylbutylidene]-2-[(3S,4R,1E)-3-hydroxy-4-methyl-6-octyn-1-enyl]-3-hydroxybicyclo[3.3.0]octane
971) (1S,2R,3R,5S)-7-[(E)-4-N-methylcarbamoylbutylidene]-2-[(3S,4R,1E)-3-hydroxy-4-methyl-6-octyn-1-enyl]-3-hydroxybicyclo[3.3.0]octane
972) (1S,2R,3R,5S)-7-[(E)-4-N-ethylcarbamoylbutylidene]-2-[(3S,4R, 1E)-3-hydroxy-4-methyl-6-octyn-1-enyl]-3-hydroxybicyclo[3.3.0]octane
973) (1S,2R,3R,5S)-7-[(E)-4-N-propylcarbamoylbutylidene]-2-[(3S,4R,1E)-3-hydroxy-4-methyl-6-octyn-1-enyl]-3-hydroxybicyclo[3.3.0] octane
974) (1S,2R,3R,5S)-7-[(E)-4-N-isopropylcarbamoylbutylidene]-2-[(3S,4R,1E)-3-hydroxy-4-methyl-6-octyn-1-enyl]-3-hydroxybicyclo[3.3.0]octane
975) (1S,2R,3R,5S)-7-[(E)-4-N-butylcarbamoylbutylidene]-2-[(3S,4R,1E)-3-hydroxy-4-methyl-6-octyn-1-enyl]-3-hydroxybicyclo[3.3.0]octane
976) (1S,2R,3R,5S)-7-[(E)-4-N-t-butylcarbamoylbutylidene]-2-[(3S,4R,1E)-3-hydroxy-4-methyl-6-octyn-1-enyl]-3-hydroxybicyclo [3.3.0]octane
977) (1S,2R,3R,5S)-7-[(E)-4-N-phenylcarbamoylbutylidene]-2-[(3S,4R,1E)-3-hydroxy-4-methyl-6-octyn-1-enyl]-3-hydroxybicyclo[3.3.0]octane
978) (1S,2R,3R,5S)-7-[(E)-4-N-benzylcarbamoylbutylidene]-2-[(3S,4R,1E)-3-hydroxy-4-methyl-6-octyn-1-enyl]-3-hydroxybicyclo[3.3.0]octane
979) (1S,2R,3R,5S)-7-[(E)-4-N-(4-pyridylmethyl)carbamoylbutylidene]-2-[(3S,4R,1E)-3-hydroxy-4-methyl-6-octyn-1-enyl]-3-hydroxybicyclo[3.3.0]octane
980) (1S,2R,3R,5S)-7-[(E)-4-(1-pyrrolidinyl)carbonylbutylidene]-2-[(3S,4R,1E)-3-hydroxy-4-methyl-6-octyn-1-enyl]-3-hydroxybicyclo[3.3.0]octane
981) (1S,2R,3R,5S)-7-[(E)-4-piperidinocarbonylbutylidene]-2-[(3S,4R,1E)-3-hydroxy-4-methyl-6-octyn-1-enyl]-3-hydroxybicyclo[3.3.0]octane
982) (1S,2R,3R,5S)-7-[(E)-4-morpholinocarbonylbutylidene]-2-[(3S,4R,1E)-3-hydroxy-4-methyl-6-octyn-1-enyl]-3-hydroxybicyclo[3.3.0]octane
983) (1S,2R,3R,5S)-7-[(E)-4-(4-N-methyl-1-piperazinyl)carbonylbutylidene]-2-[(3S,4R,1E)-3-hydroxy-4-methyl-6-octyn-1-enyl]-3-hydroxybicyclo[3.3.0]octane
984) (1S,2R,3R,5S)-7-[(E)-4-N-(2-pyridyl)carbamoylbutylidene]-2-[(3S,4R,1E)-3-hydroxy-4-methyl-6-octyn-1-enyl]-3-hydroxybicyclo[3.3.0]octane
985) (1S,2R,3R,5S)-7-[(E)-4-N,N-dimethylcarbamoylbutylidene]-2-[(3S,4R,1E)-3-hydroxy-4-methyl-6-octyn-1-enyl]-3-hydroxybicyclo[3.3.0]octane
986) (1S,2R,3R,5S)-7-[(E)-4-N,N-diethylcarbamoylbutylidene]-2-[(3S,4R,1E)-3-hydroxy-4-methyl-6-octyn-1-enyl]-3-hydroxybicyclo[3.3.0]octane
987) (1S,2R,3R,5S)-7-[(E)-4-N,N-dipropylcarbamoylbutylidene]-2-[(3S,4R,1E)-3-hydroxy-4-methyl-6-octyn-1-enyl]-3-hydroxybicyclo[3.3.0]octane
988) (1S,2R,3R,5S)-7-[(E)-4-N,N-diisopropylcarbamoylbutylidene]-2-[(3S,4R,1E)-3-hydroxy-4-methyl-6-octyn-1-enyl]-3-hydroxybicyclo[3.3.0]octane
989) (1S,2R,3R,5S)-7-[(E)-4-N,N-dibutylcarbamoylbutylidene]-2-[(3S,4R,1E)-3-hydroxy-4-methyl-6-octyn-1-enyl]-3-hydroxybicyclo[3.3.0]octane
990) (1S,2R,3R,5S)-7-[(E)-4-N-t-butyl-N-methylcarbamoylbutylidene]-2-[(3S,4R,1E)-3-hydroxy-4-methyl-6-octyn-1-enyl]-3-hydroxybicyclo[3.3.0]octane
991) (1S,2R,3R,5S)-7-[(E)-4-N-(2-hydroxyethyl)carbamoylbutylidene]-2-[(3S,4R,1E)-3-hydroxy-4-methyl-6-octyn-1-enyl]-3-hydroxybicyclo[3.3.0]octane
992) (1S,2R,3R,5S)-7-[(E)-4-N-(3-hydroxypropyl)carbamoylbutyldene]-2-[(3S,4R,1E)-3-hydroxy-4-methyl-6-octyn-1-enyl]-3-hydroxybicyclo[3.3.0]octane
993) (1S,2R,3R,5S)-7-[(E)-3-carbamoylpropylidene]-2-[(3S,4R,1E)-3-hydroxy-4-methyl-6-octyn-1-enyl]-3-hydroxybicyclo[3.3.0]octane
994) (1S,2R,3R,5S)-7-[(E)-3-N,N-dimethylcarbamoylpropylidene]-2-[(3S,4R,1E)-3-hydroxy-4-methyl-6-octyn-1-enyl]-3-hydroxybicyclo[3.3.0]octane
995) (1S,2R,3R,5S)-7-[(E)-5-carbamoylpentylidene]-2-[(3S,4R,1E)-3-hydroxy-4-methyl-6-octyn-1-enyl]-3-hydroxybicyclo[3.3.0]octane
996) (1S,2R,3R,5S)-7-[(E)-5-N,N-dimethylcarbamoylpentylidene]-2-[(3S,4R,1E)-3-hydroxy-4-methyl-6-octyn-1-enyl]-3-hydroxybicyclo[3.3.0]octane
997) (1S,2R,3R,5S)-7-[(E)-2-(N,N-dimethylcarbamoylmethyl)oxyethylidene]-2-[(3S,4R,1E)-3-hydroxy-4-methyl-6-octyn-1-enyl]-3-hydroxybicyclo[3.3.0]octane
998) (1S,2R,3R,5S)-7-[(E)-2-(N,N-diisopropylcarbamoylmethyl)oxyethylidene]-2[(3S,4R,1E)-3-hydroxy-4-methyl-6-octyn-1-enyl]-3-hydroxybicyclo[3.3.0]octane
999) (1S,2R,3R,5S)-7-[(E)-2-(N-t-butyl-N-methylcarbamoylmethyl)oxyethylidene]-2[(3S,4R,1E)-3-hydroxy-4-methyl-6-octyn-5-enyl]-3-hydroxybicyclo[3.3.0]octane
1000) (1S,2R,3R,5S)-7-[(E)-2-[(1-pyrrolidinyl)carbonylmethyl]oxyethylidene]-2-[(3S,4R,1E)-3-hydroxy-4-methyl-6-octyn-1-enyl]-3-hydroxybicyclo[3.3.0]octane
1001) (1S,2R,3R,5S)-7-[(E)-2-(piperidinocarbonylmethyl)oxyethylidene]-2-[(3S,4R,1E)-3-hydroxy-4-methyl-6-octyn-1-enyl]-3-hydroxybicyclo[3.3.0]octane
1002) (1S,2R,3R,5S)-7-[(E)-2-(morpholinocarbonylmethyl)oxyethylidene]-2-[(3S,4R,1E)-3-hydroxy-4-methyl-6-octyn-1-enyl]-3-hydroxybicyclo[3.3.0]octane
1003) (1S,2R,3R,5S)-7-[(E)-2-(N,N-dimethylcarbamoylmethyl)thioethylidene]-2-[(3S,4R,1E)-3-hydroxy-4-methyl-6-octyn-1-enyl]-3-hydroxybicyclo[3.3.0]octane
1004) (1S,2R,3R,5S)-7-[(E)-2-N—(N,N-dimethylcarbamoylmethyl)aminoethylidene]-2[(3S,4R, 1E)-3-hydroxy-4-methyl-6-octyn-1-enyl]-3-hydroxybicyclo[3.3.0]octane
1005) (1S,2R,3R,5S)-7-[(E)-N,N-dimethylcarbamoyl-methoxymethylene]-2-[(3S,4R,1E)-3-hydroxy-4-methyl-6-octyn-1-enyl]-3-hydroxybicyclo[3.3.0]octane
1006) (1S,2R,3R,5S)-7-[(E)-N,N-dimethylcarbamoylmethylthiomethylene]-2-[(3S,4R,1E)-3-hydroxy-4-methyl-6-octyn-1-enyl]-3-hydroxybicyclo[3.3.0]octane
1007) (1S,2R,3R,5S)-7-[(E)-N—(N,N-dimethylcarbamoylmethyl)aminomethylene]-2-[(3S,4R,1E)-3-hydroxy-4-methyl-6-octyn-1-enyl]-3-hydroxybicyclo[3.3.0]octane
1008) compounds of compound numbers 856 to 893 of the examples given above, wherein the (3S,1E)-3-hydroxy-1-octenyl group which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenyl group, or, the (3R,1E)-3-hydroxy-4-phenoxy-1-butenyl group or the 2-(1-hydroxycyclohexyl)ethynyl group 1009) (1R,2R,3aS,8bS)-2,3,3a,8b-tetrahydro-2-hydroxy-1-[(3S,1E)-3-hydroxy-1-octenyl]-5-(3-carbamoylpropyl)-1H-cyclopenta[b]benzofuran 1010) (1R,2R,3aS,8bS)-2,3,3a, 8b-tetrahydro-2-hydroxy-1-[(3S,1E)-3-hydroxy-1-octenyl]-5(3-N-methylcarbamoyl-propyl)-1H-cyclopenta [b] benzofuran 1011) (1R,2R,3aS,8bS)-2,3,3a,8b-tetrahydro-2-hydroxy-1-[(3S,1E)-3-hydroxy-1-octenyl]-5-(3-N-ethylcarbamoyl-propyl)-1H-cyclopenta [b]benzofuran 1012) (1R,2R,3aS,8bS)-2,3,3a,8b-tetrahydro-2-hydroxy-1-[(3S,1E)-3-hydroxy-1-octenyl]-5-(3-N-propylcarbamoyl-propyl)-1H-cyclopenta[b]benzofuran 1013) (1R,2R,3aS,8bS)-2,3,3a,8b-tetrahydro-2-hydroxy-1-[(3S,1E)-3-hydroxy-1-octenyl]-5-(3-N-isopropylcarbam-oylpropyl)-1H-cyclopenta[b]benzofuran 1014) (1R,2R,3aS,8bS)-2,3,3a,8b-tetrahydro-2-hydroxy-1-[(3S,1E)-3-hydroxy-1-octenyl]-5-(3-N-butylcarbamoyl-propyl)-1H-cyclopenta[b]benzofuran 1015) (1R,2R,3aS,8bS)-2,3,3a,8b-tetrahydro-2-hydroxy-1-[(3S,1E)-3-hydroxy-1-octenyl]-5-(3-N-t-butylcarbamoyl-propyl)-1H-cyclopenta[b]benzofuran 1016) (1R,2R,3aS,8bS)-2,3,3a,8b-tetrahydro-2-hydroxy-1-[(3S, 1E)-3-hydroxy-1-octenyl]-5-(3-N-phenylcarbam-oylpropyl)-1H-cyclopenta[b]benzofuran 1017) (1R,2R,3aS,8bS)-2,3,3a,8b-tetrahydro-2-hydroxy-1-[(3S,1E)-3-hydroxy-1-octenyl]-5-(3-N-benzylcarbamoyl-propyl)-1H-cyclopenta[b]benzofuran 1018) (1R,2R,3aS,8bS)-2,3,3a,8b-tetrahydro-2-hydroxy-1-[(3S,1E)-3-hydroxy-1-octenyl]-5-[3-N-(4-pyridylmethyl)carbamoylpropyl]-1H-cyclopenta[b] benzofuran 1019) (1R,2R,3aS,8bS)-2,3,3a,8b-tetrahydro-2-hydroxy-1-[(3S,1E)-3-hydroxy-1-octenyl]-5-[3-(1-pyrrolidinyl)car-bonylpropyl]-1H-cyclopenta[b]benzofuran 1020) (1R,2R,3aS,8bS)-2,3,3a,8b-tetrahydro-2-hydroxy-1-[(3S,1E)-3-hydroxy-1-octenyl]-5(3-piperidinocarbonyl-propyl)-1H-cyclopenta[b]benzofuran 1021) (1R,2R,3aS,8bS)-2,3,3a,8b-tetrahydro-2-hydroxy-1-[(3S,1E)-3-hydroxy-1-octenyl]-5(3-morpholinocarbonyl-propyl)-1H-cyclopenta[b]benzofuran 1022) (1R,2R,3aS,8bS)-2,3,3a,8b-tetrahydro-2-hydroxy-1-[(3S,1E)-3-hydroxy-1-octenyl]-5-[3-(4-N-methyl-1-pip-erazinyl)carbonylpropyl]-1H-cyclopenta[b]benzofuran 1023) (1R,2R,3aS,8bS)-2,3,3a,8b-tetrahydro-2-hydroxy-1-[(3S,1E)-3-hydroxy-1-octenyl]-5-[3-N-(2-pyridyl)car-bamoylpropyl]-1H-cyclopenta[b]benzofuran 1024) (1R,2R,3aS,8bS)-2,3,3a,8b-tetrahydro-2-hydroxy-1-[(3S,1E)-3-hydroxy-1-octenyl]-5(3-N,N-dimethylcar-bamoylpropyl)-1H-cyclopenta[b]benzofuran 1025) (1R,2R,3aS,8bS)-2,3,3a,8b-tetrahydro-2-hydroxy-1-[(3S,1E)-3-hydroxy-1-octenyl]-5(3-N,N-diethylcarbam-oylpropyl)-1H-cyclopenta[b]benzofuran 1026) (1R,2R,3aS,8bS)-2,3,3a,8b-tetrahydro-2-hydroxy-1-[(3S,1E)-3-hydroxy-1-octenyl]-5(3-N,N-dipropylcar-bamoylpropyl)-1H-cyclopenta[b]benzofuran 1027) (1R,2R,3aS,8bS)-2,3,3a,8b-tetrahydro-2-hydroxy-1-[(3S,1E)-3-hydroxy-1-octenyl]-5(3-N,N-diisopropylcar-bamoylpropyl)-1H-cyclopenta [b]benzofuran 1028) (1R,2R,3aS,8bS)-2,3,3a,8b-tetrahydro-2-hydroxy-1-[(3S,1E)-3-hydroxy-1-octenyl]-5(3-N,N-dibutylcarbam-oylpropyl)-1H-cyclopenta[b]benzofuran 1029) (1R,2R,3aS,8bS)-2,3,3a,8b-tetrahydro-2-hydroxy-1-[(3S,1E)-3-hydroxy-1-octenyl]-5(3-N-t-butyl-N-methyl-carbamoylpropyl)-1H-cyclopenta[b]benzofuran 1030) (1R,2R,3aS,8bS)-2,3,3a,8b-tetrahydro-2-hydroxy-1-[(3S,1E)-3-hydroxy-1-octenyl]-5-[3-N-(2-hydroxyethyl)carbamoylpropyl]-1H-cyclopenta[b]benzofuran 1031) (1R,2R,3aS,8bS)-2,3,3a,8b-tetrahydro-2-hydroxy-1-[(3S,1E)-3-hydroxy-1-octenyl]-5-[3-N-(3-hydroxypro-pyl)carbamoylpropyl]-1H-cyclopenta[b]benzofuran 1032) (1R,2R,3aS,8bS)-2,3,3a,8b-tetrahydro-2-hydroxy-1-[(3S,1E)-3-hydroxy-1-octenyl]-5(2-carbamoylethyl)-1H-cyclopenta[b]benzofuran 1033) (1R,2R,3aS,8bS)-2,3,3a,8b-tetrahydro-2-hydroxy-1-[(3S,1E)-3-hydroxy-1-octenyl]-5(2-N,N-dimethylcar-bamoylethyl)-1H-cyclopenta[b]benzofuran 1034) (1R,2R,3aS,8bS)-2,3,3a,8b-tetrahydro-2-hydroxy-1-[(3S,1E)-3-hydroxy-1-octenyl]-5(4-carbamoylbutyl)-1H-cyclopenta[b]benzofuran 1035) (1R,2R,3aS,8bS)-2,3,3a,8b-tetrahydro-2-hydroxy-1-[(3S,1E)-3-hydroxy-1-octenyl]-5(4-N,N-dimethylcar-bamoylbutyl)-1H-cyclopenta [b]benzofuran 1036) (1R,2R,3aS,8bS)-2,3,3a,8b-tetrahydro-2-hydroxy-1-[(3S,1E)-3-hydroxy-1-octenyl]-5(2-N,N-dimethylcar-bamoylethyloxy)-1H-cyclopenta[b]benzofuran 1037) (1R,2R,3aS,8bS)-2,3,3a,8b-tetrahydro-2-hydroxy-1-[(3S,4R,1E)-3-hydroxy-4-methyl-1-octen-6-ynyl]-5-(3-carbamoylpropyl)-1H-cyclopenta[b]benzofuran 1038) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-methylcarbamoylpropyl)-1H-cyclopenta[b]benzofuran 1039) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-ethylcarbamoylpropyl)-1H-cyclopenta[b]benzofuran 1040) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-propylcarbamoylpropyl)-1H-cyclopenta[b]benzofuran 1041) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-isopropylcarbamoylpropyl)-1H-cyclopenta[b]benzofuran 1042) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-butylcarbamoylpropyl)-1H-cyclopenta[b]benzofuran 1043) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-t-butylcarbamoylpropyl)-1H-cyclopenta[b]benzofuran 1044) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-phenylcarbamoylpropyl)-1H-cyclopenta[b]benzofuran 1045) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-benzylcarbamoylpropyl)-1H-cyclopenta[b]benzofuran 1046) (1R,2R,3aS,8bS)-2,3,3a,8b-tetrahydro-2-hydroxy-1-[(3S,4R,1E)-3-hydroxy-4-methyl-1-octen-6-ynyl]-5-[3-N-(4-pyridylmethyl)carbamoylpropyl]-1H-cyclopenta[b]benzofuran 1047) (1R,2R,3aS,8bS)-2,3,3a,8b-tetrahydro-2-hydroxy-1-[(3S,4R,1E)-3-hydroxy-4-methyl-1-octen-6-ynyl]-5-[3-(1-pyrrolidinyl)carbonylpropyl]-1H-cyclopenta[b]benzofuran 1048) (1R,2R,3aS,8bS)-2,3,3a,8b-tetrahydro-2-hydroxy-1-[(3S,4R,1E)-3-hydroxy-4-methyl-1-octen-6-ynyl]-5-(3-piperidinocarbonylpropyl)-1H-cyclopenta[b]benzofuran 1049) (1R,2R,3aS,8bS)-2,3,3a,8b-tetrahydro-2-hydroxy-1-[(3S,4R, 1E)-3-hydroxy-4-methyl-1-octen-6-ynyl]-5-(3-morpholinocarbonylpropyl)-1H-cyclopenta[b]benzofuran 1050) (1R,2R,3aS,8bS)-2,3,3a,8b-tetrahydro-2-hydroxy-1-[(3S,4R,1E)-3-hydroxy-4-methyl-1-octen-6-ynyl]-5-[3-(4-N-methyl-1-piperazinyl)carbonylpropyl]-1H-cyclopenta[b]benzofuran 1051) (1R,2R,3aS,8bS)-2,3,3a,8b-tetrahydro-2-hydroxy-1-[(3S,4R,1E)-3-hydroxy-4-methyl-1-octen-6-ynyl]-5-[3-N-(2-pyridyl)carbamoylpropyl]-1H-cyclopenta[b]benzofuran 1052) (1R,2R,3aS,8bS)-2,3,3a,8b-tetrahydro-2-hydroxy-1-[(3S,4R,1E)-3-hydroxy-4-methyl-1-octen-6-ynyl]-5-(3-N,N-dimethylcarbamoylpropyl)-1H-cyclopenta[b] benzofuran 1053) (1R,2R,3aS,8bS)-2,3,3a,8b-tetrahydro-2-hydroxy-1-[(3S,4R,1E)-3-hydroxy-4-methyl-1-octen-6-ynyl]-5-(3-N,N-diethylcarbamoylpropyl)-1H-cyclopenta[b]benzofuran 1054) (1R,2R,3aS,8bS)-2,3,3a,8b-tetrahydro-2-hydroxy-1-[(3S,4R,1E)-3-hydroxy-4-methyl-1-octen-6-ynyl]-5-(3-N,N-dipropylcarbamoylpropyl)-1H-cyclopenta[b]benzofuran 1055) (1R,2R,3aS,8bS)-2,3,3a,8b-tetrahydro-2-hydroxy-1-[(3S,4R,1E)-3-hydroxy-4-methyl-1-octen-6-ynyl]-5-(3-N,N-diisopropylcarbamoylpropyl)-1H-cyclopenta[b]benzofuran 1056) (1R,2R,3aS,8bS)-2,3,3a,8b-tetrahydro-2-hydroxy-1-[(3S,4R, 1E)-3-hydroxy-4-methyl-1-octen-6-ynyl]-5-(3-N,N-dibutylcarbamoylpropyl)-1H-cyclopenta[b] benzofuran 1057) (1R,2R,3aS,8bS)-2,3,3a,8b-tetrahydro-2-hydroxy-1-[(3S,4R,1E)-3-hydroxy-4-methyl-1-octen-6-ynyl]-5-(3-N-t-butyl-N-methylcarbamoylpropyl)-1H-cyclopenta[b]benzofuran 1058) (1R,2R,3aS,8bS)-2,3,3a,8b-tetrahydro-2-hydroxy-1-[(3S,4R, 1E)-3-hydroxy-4-methyl-1-octen-6-ynyl]-5-[3-N-(2-hydroxyethyl)carbamoylpropyl]-1H-cyclopenta[b]benzofuran 1059) (1R,2R,3aS,8bS)-2,3,3a,8b-tetrahydro-2-hydroxy-1-[(3S,4R,1E)-3-hydroxy-4-methyl-1-octen-6-ynyl]-5-[3-N-(3-hydroxypropyl)carbamoylpropyl]-1H-cyclopenta[b]benzofuran 1060) (1R,2R,3aS,8bS)-2,3,3a,8b-tetrahydro-2-hydroxy-1-[(3S,4R,1E)-3-hydroxy-4-methyl-1-octen-6-ynyl]-5-(2-carbamoylethyl)-1H-cyclopenta [b]benzofuran 1061) (1R,2R,3aS,8bS)-2,3,3a,8b-tetrahydro-2-hydroxy-1-[(3S,4R,1E)-3-hydroxy-4-methyl-1-octen-6-ynyl]-5-(2-N,N-dimethylcarbamoylethyl)-1H-cyclopenta[b] benzofuran 1062) (1R,2R,3aS,8bS)-2,3,3a,8b-tetrahydro-2-hydroxy-1-[(3S,4R,1E)-3-hydroxy-4-methyl-1-octen-6-ynyl]-5-(4-carbamoylbutyl)-1H-cyclopenta[b]benzofuran 1063) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-dimethylcarbamoylbutyl)-1H-cyclopenta[b]benzofuran 1064) (1R,2R,3aS,8bS)-2,3,3a,8b-tetrahydro-2-hydroxy-1-[(3S,4R,1E)-3-hydroxy-4-methyl-1-octen-6-ynyl]-5-(2-N,N-dimethylearbamoylethyloxy)-1H-cyclopenta[b]benzofuran 1065) (1R,2R,3aS,8bS)-2,3,3a,8b-tetrahydro-2-hydroxy-1-[(3S,4S,1E)-3-hydroxy-4-methyl-1-octen-6-ynyl]-5-(3-carbamoylpropyl)-1H-cyclopenta (b]benzofuran 1066) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-methylcarbamoylpropyl)-1H-cyclopenta[b]benzofuran 1067) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-ethylcarbamoylpropyl)-1H-cyclopenta[b]benzofuran 1068) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-propylcarbamoylpropyl)-1H-cyclopenta[b]benzofuran 1069) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-isopropylcarbamoylpropyl)-1H-cyclopenta [b] benzofuran 1070) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-butylcarbamoylpropyl)-1H-cyclopenta[b]benzofuran 1071) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-t-butylcarbamoylpropyl)-1H-cyclopenta[b]benzofuran 1072) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-phenylcarbamoylpropyl)-1H-cyclopenta[b]benzofuran 1073) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-benzylcarbamoylpropyl)-1H-cyclopenta[b]benzofuran 1074) (1R,2R,3aS,8bS)-2,3,3a,8b-tetrahydro-2-hydroxy-1-[(3S,4S,1E)-3-hydroxy-4-methyl-1-octen-6-ynyl]-5-[3-N-(4-pyridylmethyl)carbamoylpropyl]-1H-cyclopenta[b]benzofuran 1075) (1R,2R,3aS,8bS)-2,3,3a,8b-tetrahydro-2-hydroxy-1-[(3S,4S,1E)-3-hydroxy-4-methyl-1-octen-6-ynyl]-5-[3-(1-pyrrolidinyl)carbonylpropyl]-1H-cyclopenta[b]benzofuran 1076) (1R,2R,3aS,8bS)-2,3,3a,8b-tetrahydro-2-hydroxy-1-[(3S,4S,1E)-3-hydroxy-4-methyl-1-octen-6-ynyl]-5-(3-piperidinocarbonylpropyl)-1H-cyclopenta[b]benzofuran 1077) (1R,2R,3aS,8bS)-2,3,3a,8b-tetrahydro-2-hydroxy-1-[(3S,4S,1E)-3-hydroxy-4-methyl-1-octen-6-ynyl]-5-(3-morpholinocarbonylpropyl)-1H-cyclopenta[b]benzofuran 1078) (1R,2R,3aS,8bS)-2,3,3a,8b-tetrahydro-2-hydroxy-1-[(3S,4S,1E)-3-hydroxy-4-methyl-1-octen-6-ynyl]-5-[3-(4-N-methyl-1-piperazinyl)carbonylpropyl]-1H-cyclopenta[b]benzofuran 1079) (1R,2R,3aS,8bS)-2,3,3a,8b-tetrahydro-2-hydroxy-1-[(3S,4S,1E)-3-hydroxy-4-methyl-1-octen-6-ynyl]-5-[3-N-(2-pyridyl)carbamoylpropyl]-1H-cyclopenta[b]benzofuran 1080) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-dimethylcarbamoylpropyl)-1H-cyclopenta[b]benzofuran 1081) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-diethylcarbamoylpropyl)-1H-cyclopenta[b]benzofuran 1082) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-dipropylcarbamoylpropyl)-1H-cyclopenta[b]benzofuran 1083) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-diisopropylcarbamoylpropyl)-1H-cyclopenta[b]benzofuran 1084) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-dibutylcarbamoylpropyl)-1H-cyclopenta [b] benzofuran 1085) (1R,2R,3aS,8bS)-2,3,3a,8b-tetrahydro-2-hydroxy-1-[(3S,4S,1E)-3-hydroxy-4-methyl-1-octen-6-ynyl]-5-(3-N-t-butyl-N-methylcarbamoylpropyl)-1H-cyclopenta[b]benzofuran 1086) (1R,2R,3aS,8bS)-2,3,3a,8b-tetrahydro-2-hydroxy-1-[(3S,4S,1E)-3-hydroxy-4-methyl-1-octen-6-ynyl]-5-[3-N-(2-hydroxyethyl)carbamoylpropyl]-01H-cyclopenta[b]benzofuran 1087) (1R,2R,3aS,8bS)-2,3,3a,8b-tetrahydro-2-hydroxy-1-[(3S,4S,1E)-3-hydroxy-4-methyl-1-octen-6-ynyl]-5-[3-N-(3-hydroxypropyl)carbamoylpropyl]-1H-cyclopenta[b]benzofuran 1088) (1R,2R,3aS,8bS)-2,3,3a,8b-tetrahydro-2-hydroxy-1-[(3S,4S,1E)-3-hydroxy-4-methyl-1-octen-6-ynyl]-5-(2-carbamoylethyl)-1H-cyclopenta[b]benzofuran 1089) (1R,2R,3aS,8bS)-2,3,3a,8b-tetrahydro-2-hydroxy-1-[(3S,4S,1E)-3-hydroxy-4-methyl-1-octen-6-ynyl]-5-(2-N,N-dimethylcarbamoylethyl)-1H-cyclopenta[b]benzofuran 1090) (1R,2R,3aS,8bS)-2,3,3a,8b-tetrahydro-2-hydroxy-1-[(3S,4S,1E)-3-hydroxy-4-methyl-1-octen-6-ynyl]-5-(4-carbamoylbutyl)-1H-cyclopenta[b]benzofuran 1091) (1R,2R,3aS,8bS)-2,3,3a,8b-tetrahydro-2-hydroxy-1-[(3S,4S,1E)-3-hydroxy-4-methyl-1-octen-6-ynyl]-5-(4-N,N-dimethylcarbamoylbutyl)-1H-cyclopenta[b]benzofuran 1092) (1R,2R,3aS,8bS)-2,3,3a,8b-tetrahydro-2-hydroxy-1-[(3S,4S,1E)-3-hydroxy-4-methyl-1-octen-6-ynyl]-5-(2-N,N-dimethylcarbamoylethyloxy)-1H-cyclopenta[b]benzofuran 1093) compounds of compound numbers 1009 to 1036 of the examples given above, wherein the (3S,1E)-3-hydroxy-1-octenyl group, which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,1E)-3-hydroxy-3-cyclopentyl-1-propenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenyl group or the (3R,1E)-3-hydroxy-4-phenoxy-1-butenyl group 1094) (1S,2R,3R,5S)-7-[(Z)-4-N,N-dimethylcarbamoylbutylidene]-2-[(3S,1E)-3-hydroxy-1-octenyl]-3-hydroxybicyclo[3.3.0]octane 1095) (1R,5S,7R,8R)-3-(4-N,N-dimethylcarbamoylbutyl)-8-[(3S,1E)-3-hydroxy-1-octenyl]-7-hydroxybicyclo[3.3.0]-2-octene 1096) (1S,2R,3R,5S,7R)-7-(4-N,N-dimethylcarbamoylbutyl)-2-[(3S,1E)-3-hydroxy-1-octenyl]-3-hydroxybicyclo[3.3.0]octane 1097) (1S,2R,3R,5S,7R)-7-[2-(N,N-dimethylaminocarbamoylmethoxy)ethyl]-2-[(3R,5S,1E)-3-hydroxy-5-methyl-1-nonenyl]-3-hydroxybicyclo[3.3.0]octane 1098) (1S,3S,5R,6R,7R)-3-(4-N,N-dimethylcarbamoylbutyl)-6-[(3S,1E)-3-hydroxy-1-octenyl]-7-hydroxy-2-oxabicyclo[3.3.0]octane 1099) (1S,5S,6R,7R)-3-(4-N,N-dimethylcarbamoylbutyl)-6-[(3S,1E)-3-hydroxy-1-octenyl]-7-hydroxy-2-oxabicyclo[3.3.0]-3-octen 1100) (1S,5R,6R,7R)-3-[(Z)-4-N,N-dimethylcarbamoylbutylidene]-6-[(3S,1E)-3-hydroxy-1-octenyl]-7-hydroxy-4-oxo-2-oxabicyclo[3.3.0]octane 1101) (1S,3S,5R,6R,7R)-3-(4-N,N-dimethylcarbamoylbutyl)-6-[(3S,1E)-3-hydroxy-1-octenyl]-7-hydroxy-2-thiabicyclo[3.3.0]octane 1102) (1S,5S,6R,7R)-3-(4-N,N-dimethylcarbamoylbutyl)-6-[(3S,1E)-3-hydroxy-1-octenyl]-7-hydroxy-2-azabicyclo[3.3.0]-2-octene 1103) (1S,3S,5R,6R,7R)-3-(4-N,N-dimethylcarbamoylbutyl)-6-[(3S,1E)-3-hydroxy-1-octenyl]-7-hydroxy-2-azabicyclo[3.3.0]octane 1104) compounds of compound numbers 1094 to 1103 of the examples given above, wherein the (3S,1E)-3-hydroxy-1-octenyl group, which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,4S,1E)-3-hydroxy-4-methyl-6-octyn-1-enyl group, the (3S,4R,1E)-3-hydroxy-4-methyl-6-octyn-1-enyl group, the (3S,1E)-3-hydroxy-3-cyclopentyl-1-propenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenyl group or the (3R,1E)-3-hydroxy-4-phenoxy-1-butenyl group 1105) (1S,5S,6R,7R)-3-(5-aminopentyl)-6-[(3S,1E)-3-hydroxy-octenyl]-7-hydroxy bicyclo[3.3.0]-2-octene 1106) (1S,5S,6R,7R)-3-(5-N,N-dimethylaminopentyl)-6-[(3S,1E)-3-hydroxy-1-octenyl]-7-hydroxybicyclo[3.3.0]-2-octene 1107) (1S,5S,6R,7R)-3-(5-N,N-diethylaminopentyl)-6-[(3S,1E)-3-hydroxy-1-octenyl]-7-hydroxybicyclo[3.3.0]-2-octene 1108) (1S,5S,6R,7R)-3-[5-N-(2-methoxycarbonylethyl)aminopentyl]-6-[(3S,1E)-3-hydroxy-1-octenyl]-7-hydroxybicyclo[3.3.0]-2-octene 1109) (1S,5S,6R,7R)-3-[5-N-(4-pyridylmethyl)aminopentyl]-6-[(3S,1E)-3-hydroxy-1-octenyl]-7-hydroxybicyclo[3.3.0]-2-octene 1110) (1S,5S,6R,7R)-3-[5-N,N-diisopropylaminopentyl]-6-[(3S,1E)-3-hydroxy-1-octenyl]-7-hydroxybicyclo[3.3.0]-2-octene 1111) (1S,5S,6R,7R)-3-[5-(1-pyrrolidinyl)pentyl]-6-[(3S,1E)-3-hydroxy-1-octenyl]-7-hydroxybicyclo[3.3.0]-2-octene 1112) (1S,5S,6R,7R)-3-(5-piperidinopentyl)-6-[(3S,1E)-3-hydroxy-1-octenyl]-7-hydroxybicyclo[3.3.0]-2-octene 1113) (1S,5S,6R,7R)-3-(5-morpholinopentyl)-6-[(3S,1E)-3-hydroxy-1-octenyl]-7-hydroxybicyclo[3.3.0]-2-octene 1114) (1S,5S,6R,7R)-3-(5-N-methylaminopentyl)-6-[(3S,1E)-3-hydroxy-1-octenyl]-7-hydroxybicyclo[3.3.0]-2-octene 1115) (1S,5S,6R,7R)-3-(5-N-ethylaminopentyl)-6-[(3S,1E)-3-hydroxy-1-octenyl]-7-hydroxybicyclo[3.3.0]-2-octene 1116) (1S,5S,6R,7R)-3-(5-N-propylaminopentyl-6-[(3S,1E)-3-hydroxy-1-octenyl]-7-hydroxybicyclo[3.3.0]-2-octene 1117) (1S,5S,6R,7R)-3-(5-N-isopropylaminopentyl)-6-[(3S,1E)-3-hydroxy-1-octenyl]-7-hydroxybicyclo[3.3.0]-2-octene 1118) (1S,5S,6R,7R)-3-(5-N-t-butylaminopentyl)-6-[(3S,1E)-3-hydroxy-1-octenyl]-7-hydroxybicyclo[3.3.0]-2-octene 1119) (1S,5S,6R,7R)-3-(5-N-t-butylaminopentyl)-6-[(3S,1E)-3-hydroxy-1-octenyl]-7-hydroxybicyclo[3.3.0]-2-octene 1120) (1S,5S,6R,7R)-3-(5-N-phenylaminopentyl)-6-[(3S,1E)-3-hydroxy-1-octenyl]-7-hydroxybicyclo[3.3.0]-2-octene 1121) (1S,5S,6R,7R)-3-(5-N-benzylaminopentyl)-6-[(3S,1E)-3-hydroxy-1-octenyl]-7-hydroxybicyclo[3.3.0]-2-octene 1122) (1S,5S,6R,7R)-3-[5-(4-N-methyl-1-piperazinyl)pentyl]-6-[(3S,1E)-3-hydroxy-1-octenyl]-7-hydroxybicyclo[3.3.0]-2-octene 1123) (1S,5S,6R,7R)-3-[5-N-(2-pyridyl)aminopentyl]-6-[(3S,1E)-3-hydroxy-1-octenyl]-7-hydroxybicyclo[3.3.0]-2-octene 1124) (1S,5S,6R,7R)-3-(5-N,N-dipropylaminopentyl)-6-[(3S,1E)-3-hydroxy-1-octenyl]-7-hydroxybicyclo[3.3.0]-2-octene 1125) (1S,5S,6R,7R)-3-(5-N,N-dibutylaminopentyl)-6-[(3S,1E)-3-hydroxy-1-octenyl]-7-hydroxybicyclo[3.3.0]-2-octene 1126) (1S,5S,6R,7R)-3-(5-N-t-butyl-N-methylaminopentyl)-6-[(3S,1E)-3-hydroxy-1-octenyl]-7-hydroxybicyclo[3.3.0]-2-octene 1127) (1S,5S,6R,7R)-3-[5-N-(2-hydroxyethyl)aminopentyl]-6-[(3S,1E)-3-hydroxy-1-octenyl]7-hydroxybicyclo[3.3.0]-2-octene 1128) (1S,5S,6R,7R)-3-[5-N-(3-hydroxypropyl)aminopentyl]-6-[(3S,1E)-3-hydroxy-1-octenyl]-7-hydroxybicyclo[3.3.0]-2-octene 1129) (1S,5S,6R,7R)-3-(4-aminobutyl)-6-[(3S,1E)-3-hydroxy-1-octenyl]-7-hydroxy bicyclo[3.3.0]-2-octene 1130) (1S,5S,6R,7R)-3-(4-N,N-dimethylaminobutyl)-6-[(3S,1E)-3-hydroxy-1-octenyl]-7-hydroxybicyclo[3.3.0]-2-octene 1131) (1S,5S,6R,7R)-3-(4-N,N-diisopropylaminobutyl)-6-[(3S,1E)-3-hydroxy-1-octenyl]-7-hydroxybicyclo[3.3.0]-2-octene 1132) (1S,5S,6R,7R)-3-(4-N-t-butyl-N-methylaminobutyl)-6-[(3S,1E)-3-hydroxy-1-octenyl]-7-hydroxybicyclo[3.3.0]-2-octene 1133) (1S,5S,6R,7R)-3-[4-(1-pyrrolidinyl)butyl]-6-[(3S,1E)-3-hydroxy-1-octenyl]-7-hydroxy bicyclo[3.3.0]-2-octene 1134) (1S,5S,6R,7R)-3-(4-piperidinobutyl)-6-[(3S,1E)-3-hydroxy-1-octenyl]-7-hydroxy bicyclo[3.3.0]-2-octene 1135) (1S,5S,6R,7R)-3-(4-morpholinobutyl)-6-[(3S,1E)-3-hydroxy-1-octenyl]-7-hydroxy bicyclo[3.3.0]-2-octene 1136) (1S,5S,6R,7R)-3-(6-aminohexyl)-6-[(3S,1E)-3-hydroxy-1-octenyl]-7-hydroxy bicyclo[3.3.0]-2-octene 1137) (1S,5S,6R,7R)-3-(6-N,N-dimethylaminohexyl)-6-[(3S,1E)-3-hydroxy-1-octenyl]-7-hydroxybicyclo[3.3.0]-2-octene 1138) (1S,5S,6R,7R)-3-(6-N,N-diisopropylaminohexyl)-6-[(3S,1E)-3-hydroxy-1-octenyl]-7-hydroxybicyclo[3.3.0]-2-octene 1139) (1S,5S,6R,7R)-3-(6-N-t-butyl-N-methylaminohexyl)-6-[(3S,1E)-3-hydroxy-1-octenyl]-7-hydroxybicyclo[3.3.0]-2-octene 1140) (1S,5S,6R,7R)-3-[6-(1-pyrrolidinyl)hexyl]-6-[(3S,1E)-3-hydroxy-1-octenyl]-7-hydroxy bicyclo[3.3.0]-2-octene 1141) (1S,5S,6R,7R)-3-(6-piperidinohexyl)-6-[(3S,1E)-3-hydroxy-1-octenyl]-7-hydroxy bicyclo[3.3.0]-2-octene 1142) (1S,5S,6R,7R)-3-(6-morpholinohexyl)-6-[(3S,1E)-3-hydroxy-1-octenyl]-7-hydroxy bicyclo[3.3.0]-2-octene 1143) (1S,5S,6R,7R)-3-[(1Z)-4-N,N-dimethylamino-1-butenyl]-6-[(3S,1E)-3-hydroxy-1-octenyl]-7-hydroxybicyclo[3.3.0]-2-octene 1144) (1S,5S,6R,7R)-3-[(1Z)-5-N,N-dimethylamino-1-pentenyl]-6-[(3S,1E)-3-hydroxy-1-octenyl]-7-hydroxybicyclo[3.3.0]-2-octene 1145) (1S,5S,6R,7R)-3-[(1E)-5-N,N-dimethylamino-1-pentenyl]-6-[(3S,1E)-3-hydroxy-1-octenyl]-7-hydroxybicyclo[3.3.0]-2-octene 1146) (1S,5S,6R,7R)-3-[(1Z)-6-N,N-dimethylamino-1-hexenyl]-6-[(3S,1E)-3-hydroxy-1-octenyl]-7-hydroxybicyclo[3.3.0]-2-octene 1147) (1S,5S,6R,7R)-3-[N-(2-N,N-dimethylaminoethyl)aminomethyl]-6-[(3S,1E)-3-hydroxy-1-octenyl]-7-hydroxybicyclo[3.3.0]-2-octene 1148) (1S,5S,6R,7R)-3-[N-(3-N,N-dimethylaminopropyl)aminomethyl]-6-[(3S,1E)-3-hydroxy-1-octenyl]-7-hydroxybicyclo[3.3.0]-2-octene 1149) (1S,5S,6R,7R)-3-[N-(3-N,N-diisopropylaminopropyl)aminomethyl]-6-[(3S,1E)-3-hydroxy-1-octenyl]-7-hydroxybicyclo[3.3.0]-2-octene 1150) (1S,5S,6R,7R)-3-[N-(3-N-t-butyl-N-methylaminopropyl)aminomethyl]-6-[(3S,1E)-3-hydroxy-1-octenyl]-7-hydroxybicyclo[3.3.0]-2-octene 1151) (1S,5S,6R,7R)-3-[N-[3-(1-pyrrolidinyl)propyl]aminomethyl]-6-[(3S,1E)-3-hydroxy-1-octenyl]-7-hydroxybicyclo[3.3.0]-2-octene 1152) (1S,5S,6R,7R)-3-[N-(3-piperidinopropyl)aminomethyl]-6-[(3S,1E)-3-hydroxy-1-octenyl]-7-hydroxybicyclo[3.3.0]-2-octene 1153) (1S,5S,6R,7R)-3-[N-(3-morpholinopropyl)aminomethyl]-6-[(3S,1E)-3-hydroxy-1-octenyl]-7-hydroxybicyclo[3.3.0]-2-octene 1154) (1S,5S,6R,7R)-3-[N-(4-N,N-dimethylaminobutyl)aminomethyl]-6-[(3S,1E)-3-hydroxy 1-octenyl]-7-hydroxybicyclo[3.3.0]-2-octene 1155) (1S,5S,6R,7R)-3-[N-(3-N,N-dimethylaminopropyl)-N-methylaminomethyl]-6-[(3S,1E)-3-hydroxy-1-octenyl]-7-hydroxybicyclo[3.3.0]-2-octene 1156) (1S,5S,6R,7R)-3-[2-N-(2-N,N-dimethylaminoethyl)aminoethyl]-6-[(3S,1E)-3-hydroxy-1-octenyl]-7-hydroxybicyclo[3.3.0]-2-octene 1157) (1S,5S,6R,7R)-3-[2-N-(2-N,N-diisopropylaminoethyl)aminoethyl]-6-[(3S,1E)-3-hydroxy-1-octenyl]-7-hydroxybicyclo[3.3.0]-2-octene 1158) (1S,5S,6R,7R)-3-[2-N-(2-N-t-butyl-N-methylaminoethyl)aminoethyl]-6-[(3S,1E)-3-hydroxy-1-octenyl]-7-hydroxybicyclo[3.3.0]-2-octene 1159) (1S,5S,6R,7R)-3-[2-N-[2-(1-pyrrolidinyl)ethyl]aminoethyl]-6-[(3S,1E)-3-hydroxy-1-octenyl]-7-hydroxybicyclo[3.3.0]-2-octene 1160) (1S,5S,6R,7R)-3-[2-N-(2-piperidinoethyl)aminoethyl]-6-[(3S,1E)-3-hydroxy-1-octenyl]-7-hydroxybicyclo[3.3.0]-2-octene 1161) (1S,5S,6R,7R)-3-[2-N-(2-morpholinoethyl)aminoethyl]-6-[(3S,1E)-3-hydroxy-1-octenyl]-7-hydroxybicyclo[3.3.0]-2-octene 1162) (1S,5S,6R,7R)-3-[2-N-(3-N,N-dimethylaminopropyl)aminoethyl]-6-[(3S,1E)-3-hydroxy-1-octenyl]-7-hydroxybicyclo[3.3.0]-2-octene 1163) (1S,5S,6R,7R)-3-[(3-N,N-dimethylaminopropyl)oxymethyl]-6-[(3S,1E)-3-hydroxy-1-octenyl]-7-hydroxybicyclo[3.3.0]-2-octene 1164) (1S,5S,6R,7R)-3-[(3-N,N-diisopropylaminopropyl)oxymethyl]-6-[(3S,1E)-3-hydroxy-1-octenyl]-7-hydroxybicyclo[3.3.0]-2-octene 1165) (1S,5S,6R,7R)-3-[(3-N-t-butyl-N-methylaminopropyl)oxymethyl]-6-[(3S,1E)-3-hydroxy-1-octenyl]-7-hydroxybicyclo[3.3.0]-2-octene 1166) (1S,5S,6R,7R)-3-[[3-(1-pyrrolidinyl)propyl]oxymethyl]-6-[(3S,1E)-3-hydroxy-1-octenyl]-7-hydroxybicyclo[3.3.0]-2-octene 1167) (1S,5S,6R,7R)-3-[(3-piperidinopropyl)oxymethyl]-6-[(3S,1E)-3-hydroxy-1-octenyl]-7-hydroxybicyclo[3.3.0]-2-octene 1168) (1S,5S,6R,7R)-3-[(3-morpholinopropyl)oxymethyl]-6-[(3S,1E)-3-hydroxy-1-octenyl]-7-hydroxybicyclo[3.3.0]-2-octene 1169) (1S,5S,6R,7R)-3-[2-(2-N,N-dimethylaminoethyl)oxyethyl]-6-[(3S,1E)-3-hydroxy-1-octenyl]-7-hydroxybicyclo([3.3.0]-2-octene 1170) (1S,5S,6R,7R)-3-[2-(2-N,N-diisopropylaminoethyl)oxyethyl]-6-[(3S,1E)-3-hydroxy-1-octenyl]-76-hydroxybicyclo[3.3.0]-2-octene 1171) (1S,5S,6R,7R)-3-[2-(2-N-t-butyl-N-methylaminoethyl)oxyethyl]-6-[(3S, E)-3-hydroxy-1-octenyl]-7-hydroxybicyclo[3.3.0]-2-octene 1172) (1S,5S,6R,7R)-3-[2-[2-(1-pyrrolidinyl)ethyl]oxyethyl]-6-[(3S,1E)-3-hydroxy-1-octenyl]-7-hydroxybicyclo[3.3.0]-2-octene 1173) (1S,5S,6R,7R)-3-[2-(2-piperidinoethyl)oxyethyl]-6-[(3S,1E)-3-hydroxy-1-octenyl]-7-hydroxybicyclo[3.3.0]-2-octene 1174) (1S,5S,6R,7R)-3-[2-(2-morpholinoethyl)oxyethyl]-6-[(3S,1E)-3-hydroxy-1-octenyl]-7-hydroxybicyclo[3.3.0]-2-octene 1175) (1S,5S,6R,7R)-3-[(3-N,N-dimethylaminopropyl)thiomethyl]-6-[(3S,1E)-3-hydroxy-1-octenyl]-7-hydroxybicyclo[3.3.0]-2-octene 1176) (1S,5S,6R,7R)-3-[(3-N,N-diisopropylaminopropyl)thiomethyl]-6-[(3S,1E)-3-hydroxy-1-octenyl]-7-hydroxybicyclo[3.3.0]-2-octene 1177) (1S,5S,6R,7R)-3-[(3-N-t-butyl-N-methylaminopropyl)thiomethyl]-6-[(3S, 1E)-3-hydroxy-octenyl]-7-hydroxybicyclo[3.3.0]-2-octene 1178) (1S,5S,6R,7R)-3-[[3-(1-pyrrolidinyl)propyl]thiomethyl]-6-[(3S,1E)-3-hydroxy-1-octenyl]-7-hydroxybicyclo[3.3.0]-2-octene 1179) (1S,5S,6R,7R)-3-[(3-piperidinopropyl)thiomethyl]-6-[(3S,1E)-3-hydroxy-1-octenyl]-7-hydroxybicyclo [3.3.0]-2-octene 1180) (1S,5S,6R,7R)-3-[(3-morpholinopropyl)thiomethyl]-6-[(3S, 1E)-3-hydroxy-1-octenyl]-7-hydroxybicyclo[3.3.0]-2-octene 1181) (1S,5S,6R,7R)-3-[2-(2-N,N-dimethylaminoethyl)thioethyl]-6-[(3S,1E)-3-hydroxy-1-octenyl]-7-hydroxybicyclo[3.3.0]-2-octene 1182) (1S,5S,6R,7R)-3-[2-(2-N,N-diisopropylaminoethyl)thioethyl]-6-[(3S,1E)-3-hydroxy-1-octenyl]-7-hydroxybicyclo[3.3.0]-2-octene 1183) (1S,5S,6R,7R)-3-[2-(2-N-t-butyl-N-methylaminoethyl)thioethyl]-6-[(3S,1E)-3-hydroxy-1-octenyl]-7-hydroxybicyclo[3.3.0]-2-octene 1184) (1S,5S,6R,7R)-3-[2-[2-(1-pyrrolidinyl)ethyl]thioethyl]-6-[(3S,1E)-3-hydroxy-1-octenyl]-7-hydroxybicyclo[3.3.0]-2-octene 1185) (1S,5S,6R,7R)-3-[2-(2-piperidinoethyl)thioethyl]-6-[(3S, 1E)-3-hydroxy-1-octenyl]-7-hydroxybicyclo[3.3.0]-2-octene 1186) (1S,5S,6R,7R)-3-[2-(2-morpholinoethyl)thioethyl]-6-[(3S,1E)-3-hydroxy-1-octenyl]-7-hydroxybicyclo[3.3.0]-2-octene 1187) (1S,5S,6R,7R)-3-[(3-N,N-dimethylaminophenyl)methyl]-6-[(3S,1E)-3-hydroxy-1-octenyl]-7-hydroxybicyclo[3.3.0]-2-octene 1188) (1S,5S,6R,7R)-3-[[2-(aminomethyl)phenyl]methyl]-6-[(3S,1E)-3-hydroxy-1-octenyl]-7-hydroxybicyclo[3.3.0]-2-octene 1189) (1S,5S,6R,7R)-3-[[4-(aminomethyl)phenyl]methyl]-6-[(3S,1E)-3-hydroxy-1-octenyl]-7-hydroxybicyclo[3.3.0]-2-octene 1190) (1S,5S,6R,7R)-3-[2-[3-(aminomethyl)phenyl]ethyl]-6-[(3S,1E)-3-hydroxy-1-octenyl]-7-hydroxybicyclo[3.3.0]-2-octene 1191) (1S,5S,6R,7R)-3-[2-[3-(piperidinomethyl)phenyl]ethyl]-6-[(3S,1E)-3-hydroxy-1-octenyl]-7-hydroxybicyclo[3.3.0]-2-octene 1192) (1S,5S,6R,7R)-3-[2-(4-piperidyl)ethyl]-6-[(3S,1E)-3-hydroxy-1-octenyl]-7-hydroxy bicyclo[3.3.0]-2-octene 1193) (1S,5S,6R,7R)-3-[2-(4-pyridyl)ethyl]-6-[(3S,1E)-3-hydroxy-1-octenyl]-7-hydroxy bicyclo[3.3.0]-2-octene 1194) (1S,5S,6R,7R)-3-[4-(2-pyridyl)butyl]-6-[(3S,1E)-3-hydroxy-1-octenyl]-7-hydroxy bicyclo[3.3.0]-2-octene 1195) (1S,5S,6R,7R)-3-(5-aminopentyl)-6-[(3S,5S,1E)-3-hydroxy-5-methyl-1-nonenyl]-7-hydroxybicyclo[3.3.0]-2-octene 1196) (1S,5S,6R,7R)-3-(5-N,N-dimethylaminopentyl)-6-[(3S,5S,1E)-3-hydroxy-5-methyl-1-nonenyl]-7-hydroxybicyclo[3.3.0]-2-octene 1197) (1S,5S,6R,7R)-3-(5-N,N-diethylaminopentyl)-6-[(3S,5S,1E)-3-hydroxy-5-methyl-1-nonenyl]-7-hydroxybicyclo[3.3.0]-octene 1198) (1S,5S,6R,7R)-3-[5-N-(2-methoxycarbonylethyl)aminopentyl]-6-[(3S,5S,1 E)-3-hydroxy-5-methyl-1-nonenyl]-7-hydroxybicyclo[3.3.0]-2-octene 1199) (1S,5S,6R,7R)-3-[5-N-(4-pyridylmethyl)aminopentyl]-6-[(3S,5S,1E)-3-hydroxy-5-methyl-1-nonenyl]-7-hydroxybicyclo[3.3.0]-2-octene 1200) (1S,5S,6R,7R)-3-[5-N,N-diisopropylaminopentyl]-6-[(3S,5S,1E)-3-hydroxy-5-methyl-1-nonenyl]-7-hydroxybicyclo[3.3.0]-2-octene 1201) (1S,5S,6R,7R)-3-[5-(1-pyrrolidinyl)pentyl]-6-[(3S,5S,1E)-3-hydroxy-5-methyl-1-nonenyl]-7-hydroxybicyclo[3.3.0]-2-octene 1202) (1S,5S,6R,7R)-3-(5-piperidinopentyl)-6-[(3S,5S,1E)-3-hydroxy-5-methyl-1-nonenyl]-7-hydroxybicyclo [3.3.0]-2-octene 1203) (1S,5S,6R,7R)-3-(5-morpholinopentyl)-6-[(3S,5S,1E)-3-hydroxy-5-methyl-1-nonenyl]7-hydroxybicyclo[3.3.0]-2-octene 1204) (1S,5S,6R,7R)-3-(5-N-methylaminopentyl)-6-[(3S,5S,1E)-3-hydroxy-5-methyl-1-nonenyl]-7-hydroxybicyclo[3.3.0]-2-octene 1205) (1S,5S,6R,7R)-3-(5-N-ethylaminopentyl)-6-[(3S,5S,1E)-3-hydroxy-5-methyl-1-nonenyl]7-hydroxybicyclo[3.3.0]-2-octene 1206) (1S,5S,6R,7R)-3-(5-N-propylaminopentyl)-6-[(3S,5S,1E)-3-hydroxy-5-methyl-1-nonenyl]-7-hydroxybicyclo[3.3.0]-2-octene 1207) (1S,5S,6R,7R)-3-(5-N-isopropylaminopentyl)-6-[(3S,5S,1E)-3-hydroxy-5-methyl-1-nonenyl]-7-hydroxybicyclo[3.3.0]-octene 1208) (1S,5S,6R,7R)-3-(5-N-butylaminopentyl)-6-[(3S,5S,1E)-3-hydroxy-5-methyl-1-nonenyl]-7-hydroxybicyclo[3.3.0]-2-octene 1209) (1S,5S,6R,7R)-3-(5-N-t-butylaminopentyl)-6-[(3S,5S,1E)-3-hydroxy-5-methyl-1-nonenyl]-7-hydroxybicyclo[3.3.0]-2-octene 1210) (1S,5S,6R,7R)-3-(5-N-phenylaminopentyl)-6-[(3S,5S,1E)-3-hydroxy-5-methyl-1-nonenyl]-7-hydroxybicyclo[3.3.0]-2-octene 1211) (1S,5S,6R,7R)-3-(5-N-benzylaminopentyl)-6-[(3S,5S,1E)-3-hydroxy-5-methyl-1-nonenyl]-7-hydroxybicyclo[3.3.0]-2-octene 1212) (1S,5S,6R,7R)-3-[5-(4-N-methyl-1-piperazinyl)pentyl]-6-[(3S,5S,1E)-3-hydroxy-5-methyl-1-nonenyl]-7-hydroxybicyclo[3.3.0]-2-octene 1213) (1S,5S,6R,7R)-3-[5-N-(2-pyridyl)aminopentyl]-6-[(3S,5S,1E)-3-hydroxy-5-methyl-1-nonenyl]-7-hydroxybicyclo[3.3.0]-2-octene 1214) (1S,5S,6R,7R)-3-(5-N,N-dipropylaminopentyl)-6-[(3S,5S,1E)-3-hydroxy-5-methyl-1-nonenyl]-7-hydroxybicyclo[3.3.0]-2-octene 1215) (1S,5S,6R,7R)-3-(5-N,N-dibutylaminopentyl)-6-[(3S,5S,1E)-3-hydroxy-5-methyl-1-nonenyl]-7-hydroxybicyclo[3.3.0]-2-octene 1216) (1S,5S,6R,7R)-3-(5-N-t-butyl-N-methylaminopentyl)-6-[(3S,5S,1E)-3-hydroxy-5-methyl-1-nonenyl]-7-hydroxybicyclo[3.3.0]-2-octene 1217) (1S,5S,6R,7R)-3-[5-N-(2-hydroxyethyl)aminopentyl]-6-[(3S,5S,1E)-3-hydroxy-5-methyl-1-nonenyl]-7-hydroxybicyclo[3.3.0]-2-octene 1218) (1S,5S,6R,7R)-3-[5-N-(3-hydroxypropyl)aminopentyl]-6-[(3S,5S,1E)-3-hydroxy-5-methyl-1-nonenyl]-7-hydroxybicyclo[3.3.0]-2-octene 1219) (1S,5S,6R,7R)-3-(4-aminobutyl)-6-[(3S,5S,1E)-3-hydroxy-5-methyl-1-nonenyl]-7-hydroxybicyclo[3.3.0]-2-octene 1220) (1S,5S,6R,7R)-3-(4-N,N-dimethylaminobutyl)-6-[(3S,5S,1E)-3-hydroxy-5-methyl-1-nonenyl]-7-hydroxybicyclo[3.3.0]-2-octene 1221) (1S,5S,6R,7R)-3-(4-N,N-diisopropylaminobutyl)-6-[(3S,5S,1E)-3-hydroxy-5-methyl-1-nonenyl]-7-hydroxybicyclo[3.3.0]-2-octene 1222) (1S,5S,6R,7R)-3-(4-N-t-butyl-N-methylaminobutyl)-6-[(3S,5S,1E)-3-hydroxy-5-methyl-1-nonenyl]-7-hydroxybicyclo[3.3.0]-2-octene 1223) (1S,5S,6R,7R)-3-[4-(1-pyrrolidinyl)butyl]-6-[(3S,5S,1E)-3-hydroxy-5-methyl-1-nonenyl]-7-hydroxybicyclo[3.3.0]-2-octene 1224) (1S,5S,6R,7R)-3-(4-piperidinobutyl)-6-[(3S,5S,1E)-3-hydroxy-5-methyl-1-nonenyl]-7-hydroxybicyclo[3.3.0]-2-octene 1225) (1S,5S,6R,7R)-3-(4-morpholinobutyl)-6-[(3S,5S,1E)-3-hydroxy-5-methyl-1-nonenyl]-7-hydroxybicyclo[3.3.0]-2-octene 1226) (1S,5S,6R,7R)-3-(6-aminohexyl)-6-[(3S,5S,1E)-3-hydroxy-5-methyl-1-nonenyl]-7-hydroxybicyclo[3.3.0]-2-octene 1227) (1S,5S,6R,7R)-3-(6-N,N-dimethylaminohexyl-6-[(3S,5S,1E)-3-hydroxy-5-methyl-1-nonenyl]-7-hydroxybicyclo[3.3.0]-2-octene 1228) (1S,5S,6R,7R)-3-(6-N,N-diisopropylaminohexyl)-6-[(3S,5S,1E)-3-hydroxy-5-methyl-1-nonenyl]-7-hydroxybicyclo[3.3.0]-2-octene 1229) (1S,5S,6R,7R)-3-(6-N-t-butyl-N-methylaminohexyl)-6-[(3S,5S,1E)-3-hydroxy-5-methyl-1-nonenyl]-7-hydroxybicyclo[3.3.0]-2-octene 1230) (1S,5S,6R,7R)-3-[6-(1-pyrrolidinyl]hexyl]-6-[(3S,5S,1E)-3-hydroxy-5-methyl-1-nonenyl]-7-hydroxybicyclo[3.3.0]-2-octene 1231) (1S,5S,6R,7R)-37(6-piperidinohexyl)-6-[(3S,5S,1E)-3-hydroxy-5-methyl-1-nonenyl]-7-hydroxybicyclo[3.3.0]-2-octene 1232) (1S,5S,6R,7R)-3-(6-morpholinohexyl)-6-[(3S,5S,1E)-3-hydroxy-5-methyl-1-nonenyl]-7-hydroxybicyclo[3.3.0]-2-octene 1233) (1S,5S,6R,7R)-3-[(1Z)-4-N,N-dimethylamino-1-butenyl]-6-[(3S,5S,1E)-3-hydroxy-5-methyl-1-nonenyl]-7-hydroxybicyclo[3.3.0]-2-octene 1234) (1S,5S,6R,7R)-3-[(1Z)-5-N,N-dimethylamino-1-pentenyl]-6-[(3S,5S,1E)-3-hydroxy-5-methyl-1-nonenyl]-7-hydroxybicyclo[3.3.0]-2-octene 1235) (1S,5S,6R,7R)-3-[(1E)-5-N,N-dimethylamino-1-pentenyl]-6-[(3S,5S,1E)-3-hydroxy-5-methyl-1-nonenyl]-7-hydroxybicyclo[3.3.0]-2-octene 1236) (1S,5S,6R,7R)-3-[(1Z)-6-N,N-dimethylamino-1-hexenyl]-6-[(3S,5S,1E)-3-hydroxy-5-methyl-1-nonenyl]-7-hydroxybicyclo[3.3.0]-2-octene 1237) (1S,5S,6R,7R)-3-[N-(2-N,N-dimethylaminoethyl)aminomethyl]-6-[(3S,5S,1E)-3-hydroxy-5-methyl-1-nonenyl]-7-hydroxybicyclo[3.3.0]-2-octene 1238) (1S,5S,6R,7R)-3-[N-(3-N,N-dimethylaminopropyl)aminomethyl]-6-[(3S,5S,1E)-3-hydroxy-5-methyl-1-nonenyl]-7-hydroxybicyclo[3.3.0]-2-octene 1239) (1S,5S,6R,7R)-3-[N-(3-N,N-diisopropylaminopropyl)aminomethyl]-6-[(3S,5S,1E)-3-hydroxy-5-methyl-1-nonenyl]-7-hydroxybicyclo[3.3.0]-2-octene 1240) (1S,5S,6R,7R)-3-[N-(3 N-t-butyl-N-methytaminopropyl)aminomethyl]-6-[(3S,5S,1E)-3-hydroxy-5-methyl-1-nonenyl]-7-hydroxybicyclo[3.3.0]-2-octene 1241) (1S,5S,6R,7R)-3-[N-[3-(1-pyrrolidinyl)propyl]aminomethyl]-6-[(3S,5S,1E)-3-hydroxy-5-methyl-1-nonenyl]-7-hydroxybicyclo[3.3.0]-2-octene 1242) (1S,5S,6R,7R)-3-[N-(3-piperidinopropyl)aminomethyl]-6-[(3S,5S,1E)-3-hydroxy-5-methyl-1-nonenyl]-7-hydroxybicyclo[3.3.0]-2-octene 1243) (1S,5S,6R,7R)-3-[N-(3-morpholinopropyl)aminomethyl]-6-[(3S,5S,1E)-3-hydroxy-5-methyl-1-nonenyl]-7-hydroxybicyclo[3.3.0]-2-octene 1244) (1S,5S,6R,7R)-3-[N-(4-N,N-dimethylaminobutyl)aminomethyl]-6-[(3S,5S,1E)-3-hydroxy-5-methyl-1-nonenyl]-7-hydroxybicyclo[3.3.0]-2-octene 1245) (1S,5S,6R,7R)-3-[N-(3-N,N-dimethylaminopropyl)-N-methylaminomethyl]-6-[(3S,5S,1E)-3-hydroxy-5-methyl-1-nonenyl]-7-hydroxybicyclo[3.3.0]-2-octene 1246) (1S,5S,6R,7R)-3-[2-N-(2-N,N-dimethylaminoethyl)aminoethyl]-6-[(3S,5S,1E)-3-hydroxy-5-methyl-1-nonenyl]-7-hydroxybicyclo[3.3.0]-2-octene 1247) (1S,5S,6R,7R)-3-[2-N-(2-N,N-diisopropylaminoethyl)aminoethyl]-6-[(3S,5S,1E)-3-hydroxy-5-methyl-1-nonenyl]-7-hydroxybicyclo[3.3.0]-2-octene 1248) (1S,5S,6R,7R)-3-[2-N-(2-N-t-butyl-N-methylaminoethyl)aminoethyl]-6-[(3S,5S,1E)-3-hydroxy-5-methyl-1-nonenyl]-7-hydroxybicyclo[3.3.0]-2-octene 1249) (1S,5S,6R,7R)-3-[2-N-[2-(1-pyrrolidinyl)ethyl]aminoethyl]-6-[(3S,5S,1E)-3-hydroxy-5-methyl-1-nonenyl]-7-hydroxybicyclo[3.3.0]-2-octene 1250) (1S,5S,6R,7R)-3-[2-N-(2-piperidinoethyl)aminoethyl]-6-[(3S,5S,1E)-3-hydroxy-5-methyl-1-nonenyl]-7-hydroxybicyclo[3.3.0]-2-octene 1251) (1S,5S,6R,7R)-3-[2-N-(2-morpholinoethyl)aminoethyl]-6-[(3S,5S,1E)-3-hydroxy-5-methyl-1-nonenyl]-7-hydroxybicyclo[3.3.0]-2-octene 1252) (1S,5S,6R,7R)-3-[2-N-(3-N,N-dimethylaminopropyl)aminoethyl]-6-[(3S,5S,1E)-3-hydroxy-5-methyl-1-nonenyl]-7-hydroxybicyclo[3.3.0]-2-octene 1253) (1S,5S,6R,7R)-3-[(3-N,N-dimethylaminopropyl)oxymethyl]-6-[(3S,5S,1E)-3-hydroxy-5-methyl-1-nonenyl]-7-hydroxybicyclo[3.3.0]-2-octene 1254) (1S,5S,6R,7R)-3-[(3-N,N-diisopropylaminopropyl)oxymethyl]-6-[(3S,5S,1E)-3-hydroxy-5-methyl-1-nonenyl]-7-hydroxybicyclo[3.3.0]-2-octene 1255) (1S,5S,6R,7R)-3-[(3-N-t-butyl-N-methylaminopropyl)oxymethyl]-6-[(3S,5S,1E)-3-hydroxy-5-methyl-1-nonenyl]-7-hydroxybicyclo[3.3.0]-2-octene 1256) (1S,5S,6R,7R)-3-[[3-(1-pyrrolidinyl)propyl]oxymethyl]-6-[(3S,5S,1E)-3-hydroxy-5-methyl-1-nonenyl]-7-hydroxybicyclo[3.3.0]-2-octene 1257) (1S,5S,6R,7R)-3-[(3-piperidinopropyl)oxymethyl]-6-[(3S,5S,1E)-3-hydroxy-5-methyl-1-nonenyl]-7-hydroxybicyclo[3.3.0]-2-octene 1258) (1S,5S,6R,7R)-3-[(3-morpholinopropyl)oxymethyl]-6-[(3S,5S,1E)-3-hydroxy-5-methyl]-nonenyl]-7-hydroxybicyclo[3.3.0]-2-octene 1259) (1S,5S,6R,7R)-3-[2-(2-N,N-dimethylaminoethyl)oxyethyl]-6-[3S, 5S,1E)-3-hydroxy-5-methyl-1-nonenyl]-7-hydroxybicyclo[3.3.0]-2-octene 1260) (1S,5S,6R,7R)-3-[2-(2-N,N-diisopropylaminoethyl)oxyethyl]-6-[(3S,5S,1E)-3-hydroxy-5-methyl-1-nonenyl]-7-hydroxybicyclo[3.3.0]-2-octene 1261) (1S,5S,6R,7R)-3-[2-(2-N-t-butyl-N-methylaminoethyl)oxyethyl]-6-[(3S,5S,1E)-3-hydroxy-5-methyl-1-nonenyl]-7-hydroxybicyclo[3.3.0]-2-octene 1262) (1S,5S,6R,7R)-3-[2-[2-(1-pyrrolidinyl)ethyl]oxyethyl]-6-[(3S,5S,1E)-3-hydroxy-5-methyl-1-nonenyl]-7-hydroxybicyclo[3.3.0]-2-octene 1263) (1S,5S,6R,7R)-3-[2-(2-piperidinoethyl)oxyethyl]-6-[(3S,5S,1E)-3-hydroxy-5-methyl-1-nonenyl]-7-hydroxybicyclo[3.3.0]-2-octene 1264) (1S,5S,6R,7R)-3-[2-(2-morpholinoethyl)oxyethyl]-6-[(3S,5S,1E)-3-hydroxy-5-methyl-1-nonenyl]-7-hydroxybicyclo[3.3.0]-2-octene 1265) (1S,5S,6R,7R)-3-[(3-N,N-dimethylaminopropyl)thiomethyl]-6-[(3S,5S,1E)-3-hydroxy-5-methyl-1-nonenyl]-7-hydroxybicyclo[3.3.0]-2-octene 1266) (1S,5S,6R,7R)-3-[(3-N,N-diisopropylaminopropyl)thiomethyl]-6-[(3S,5S,1E)-3-hydroxy-5-methyl-1-nonenyl]-7-hydroxybicyclo[3.3.0]-2-octene 1267) (1S,5S,6R,7R)-3-[(3-N-t-butyl-N-methylaminopropyl)thiomethyl]-6-[(3S,5S,1E)-3-hydroxy-5-methyl-1-nonenyl]-7-hydroxybicyclo[3.3.0]-2-octene 1268) (1S,5S,6R,7R)-3-[[3-(1-pyrrolidinyl)propyl]thiomethyl]-6-[(3S,5S,1E)-3-hydroxy-5-methyl-1-nonenyl]-7-hydroxybicyclo[3.3.0]-2-octene 1269) (1S,5S,6R,7R)-3-[(3-piperidinopropyl)thiomethyl]-6-[(3S,5S,1E)-3-hydroxy-5-methyl-1-nonenyl]-7-hydroxybicyclo[3.3.0]-2-octene 1270) (1S,5S,6R,7R)-3-[(3-morpholinopropyl)thiomethyl]-6-[(3S,5S,1E)-3-hydroxy-5-methyl-1-nonenyl]-7-hydroxybicyclo[3.3.0]-2-octene 1271) (1S,5S,6R,7R)-3-[2-(2-N,N-dimethylaminoethyl)thioethyl]-6-[(3S,5S,1E)-3-hydroxy-5-methyl-1-nonenyl]-7-hydroxybicyclo[3.3.0]-2-octene 1272) (1S,5S,6R,7R)-3-[2-(2-N,N-diisopropylaminoethyl)thioethyl]-6-[(3S,5S, 1E)-3-hydroxy-5-methyl-1-nonenyl]-7-hydroxybicyclo[3.3.0]-2-octene 1273) (1S,5S,6R,7R)-3-[2-(2-N-t-butyl-N-methylaminoethyl)thioethyl]-6-[(3S,5S,1E)-3-hydroxy-5-methyl-1-nonenyl]-7-hydroxybicyclo[3.3.0]-2-octene 1274) (1S,5S,6R,7R)-3-[2-[2-(1-pyrrolidinyl)ethyl]thioethyl]-6-[(3S,5S,1E)-3-hydroxy-5-methyl-1-nonenyl]-7-hydroxybicyclo[3.3.0]-2-octene 1275) (1S,5S,6R,7R)-3-[2-(2-piperidinoethyl)thioethyl]-6-[(3S,5S,1E)-3-hydroxy-5-methyl-1-nonenyl]-7-hydroxybicyclo[3.3.0]-2-octene 1276) (1S,5S,6R,7R)-3-[2-(2-morpholinoethyl)thioethyl]-6-[(3S,5S,1E)-3-hydroxy-5-methyl-1-nonenyl]-7-hydroxybicyclo[3.3.0]-2-octene 1277) (1S,5S,6R,7R)-3-[(3-N,N-dimethylaminophenyl)methyl]-6-[(3S,5S,1E)-3-hydroxy-5-methyl-1-nonenyl]-7-hydroxybicyclo[3.3.0]-2-octene 1278) (1S,5S,6R,7R)-3-[[2-(aminomethyl)phenyl]methyl]-6-[(3S,5S,1E)-3-hydroxy-5-methyl-1-nonenyl]-7-hydroxybicyclo[3.3.0]-2-octene 1279) (1S,5S,6R,7R)-3-[[4-(aminomethyl)phenyl]methyl]-6-[(3S,5S,1E)-3-hydroxy-5-methyl-1-nonenyl]-7-hydroxybicyclo[3.3.0]-2-octene 1280) (1S,5S,6R,7R)-3-[2-[3-(aminomethyl)phenyl]ethyl]-6-[(3S,5S,1E)-3-hydroxy-5-methyl-1-nonenyl]-7-hydroxybicyclo[3.3.0]-2-octene 1281) (1S,5S,6R,7R)-3-[2-[3-(piperidinomethyl)phenyl]ethyl]-6-[(3S,5S,1E)-3-hydroxy-5-methyl-1-nonenyl]-7-hydroxybicyclo[3.3.0]-2-octene 1282) (1S,5S,6R,7R)-3-[2-(4-piperidyl)ethyl]-6-[(3S,5S,1E)-3-hydroxy-5-methyl-1-nonenyl]7-hydroxybicyclo[3.3.0]-2-octene 1283) (1S,5S,6R,7R)-3-[2-(4-pyridyl)ethyl]-6-[(3S,5S,1E)-3-hydroxy-5-methyl-1-nonenyl]-7-hydroxybicyclo[3.3.0]-2-octene 1284) (1S,5S,6R,7R)-3-[4-(2-pyridyl)butyl]-6-[(3S,5S,1E)-3-hydroxy-5-methyl-1-nonenyl]-7-hydroxybicyclo[3.3.0]-2-octene 1285) (1S,5S,6R,7R)-3-(5-aminopentyl)-6-[(4S,1E)-4-hydroxy-4-methyl-1-octenyl]-7-hydroxy bicyclo[3.3.0]-2-octene 1286) (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene 1287) (1S,5S,6R,7R)-3-(5-N,N-diethylaminopentyl)-6-[(4S,1E)-4-hydroxy-4-methyl-1-octenyl]-7-hydroxybicyclo[3.3.0]-2-octene 1288) (1S,5S,6R,7R)-3-[5-N-(2-methoxycarbonylethyl)aminopentyl]-6-[(4S,1E)-4-hydroxy-4-methyl-1-octenyl]-7-hydroxybicyclo[3.3.0]-2-octene 1289) (1S,5S,6R,7R)-3-[5-N-(4-pyridylmethyl)aminopentyl]-6-[(4S,1E)-4-hydroxy-4-methyl-1-octenyl]-7-hydroxybicyclo[3.3.0]-2-octene 1290) (1S,5S,6R,7R)-3-[5-N,N-diisopropylaminopentyl]-6-[(4S,1E)-4-hydroxy-4-methyl-1-octenyl]-7-hydroxybicyclo[3.3.0]-2-octene 1291) (1S,5S,6R,7R)-3-[5-(1-pyrrolidinyl)pentyl]-6-[(4S,1E)-4-hydroxy-4-methyl-1-octenyl-7-hydroxybicyclo[3.3.0]-2-octene 1292) (1S,5S,6R,7R)-3-(5-piperidinopentyl)-6-[(4S,1E)-4-hydroxy-4-methyl-1-octenyl]-7-hydroxybicyclo[3.3.0]-2-octene 1293) (1S, 5S,6R,7R)-3-(5-morpholinopentyl)-6-[(4S,1E)-4-hydroxy-4-methyl-1-octenyl]-7-hydroxybicyclo[3.3.0]-2-octene 1294) (1S,5S,6R,7R)-3-(5-N-methylaminopentyl)-6-[(4S,1E)-4-hydroxy-4-methyl-1-octenyl]-7-hydroxybicyclo [3.3.0]-2-octene 1295) (1S,5S,6R,7R)-3-(5-N-ethylaminopentyl)-6-[(4S,1E)-4-hydroxy-4-methyl-1-octenyl]-7-hydroxybicyclo [3.3.0]-2-octene 1296) (1S,5S,6R,7R)-3-(5-N-propylaminopentyl)-6-[(4S,1E)-4-hydroxy-4-methyl-1-octenyl]-7-hydroxybicyclo [3.3.0]-2-octene 1297) (1S,5S,6R,7R)-3-(5-N-isopropylaminopentyl)-6-[(4S,1E)-4-hydroxy-4-methyl-1-octenyl]-7-hydroxybicyclo[3.3.0]-2-octene 1298) (1S,5S,6R,7R)-3-(5-N-butylaminopentyl)-6-[(4S,1E)-4-hydroxy-4-methyl-1-octenyl]-7-hydroxybicyclo [3.3.0]-2-octene 1299) (1S,5S,6R,7R)-3-(5-N-t-butylaminopentyl)-6-[(4S,1E)-4-hydroxy-4-methyl-1-octenyl]-7-hydroxybicyclo[3.3.0]-2-octene 1300) (1S,5S,6R,7R)-3-(5-N-phenylaminopentyl)-6-[(4S,1E)-4-hydroxy-4-methyl-1-octenyl]-7-hydroxybicyclo[3.3.0]-2-octene 1301) (1S,5S,6R,7R)-3-(5-N-benzylaminopentyl)-6-[(4S,1E)-4-hydroxy-4-methyl-1-octenyl]-7-hydroxybicyclo[3.3.0]-2-octene 1302) (1S,5S,6R,7R)-3-[5-(4-N-methyl-1-piperazinyl)pentyl]-6-[(4S,1E)-4-hydroxy-4-methyl-1-octenyl]-7-hydroxybicyclo[3.3.0]-2-octene 1303) (1S,5S,6R,7R)-3-[5-N-(2-pyridyl)aminopentyl]-6-[(4S,1E)-4-hydroxy-4-methyl-1-octenyl]-7-hydroxybicyclo[3.3.0]-2-octene 1304) (1S,5S,6R,7R)-3-(5-N,N-dipropylaminopentyl)-6-[(4S,1E)-4-hydroxy-4-methyl-1-octenyl]-7-hydroxybicyclo[3.3.0]-2-octene 1305) (1S,5S,6R,7R)-3-(5-N,N-dibutylaminopentyl)-6-[(4S,1E)-4-hydroxy-4-methyl-1-octenyl]-7-hydroxybicyclo[3.3.0]-2-octene 1306) (1S,5S,6R,7R)-3-(5-N-t-butyl-N-methylaminopentyl)-6-[(4S,1E)-4-hydroxy-4-methyl-1-octenyl]-7-hydroxybicyclo[3.3.0]-2-octene 1307) (1S,5S,6R,7R)-3-[5-N-(2-hydroxyethyl)aminopentyl]-6-[(4S,1E)-4-hydroxy-4-methyl-1-octenyl]-7-hydroxybicyclo[3.3.0]-2-octene 1308) (1S,5S,6R,7R)-3-[5-N-(3-hydroxypropyl)aminopentyl]-6-[(4S,1E)-4-hydroxy-4-methyl-1-octenyl]-7-hydroxybicyclo[3.3.0]-2-octene 1309) (1S,5S,6R,7R)-3-(4-aminobutyl)-6-[(4S,1E)-4-hydroxy-4-methyl-1-octenyl]-7-hydroxybicyclo[3.3.0]-2-octene 1310) (1S,5S,6R,7R)-3-(4-N,N-dimethylaminobutyl)-6-[(4S,1E)-4-hydroxy-4-methyl-1-octenyl]-7-hydroxybicyclo[3.3.0]-2-octene 1311) (1S,5S,6R,7R)-3-(4-N,N-diisopropylaminobutyl)-6-[(4S,1E)-4-hydroxy-4-methyl-1-octenyl]-7-hydroxybicyclo[3.3.0]-2-octene 1312) (1S,5S,6R,7R)-3-(4-N-t-butyl-N-methylaminobutyl)-6-[(4S,1E)-4-hydroxy-4-methyl-1-octenyl]-7-hydroxybicyclo[3.3.0]-2-octene 1313) (1S,5S,6R,7R)-3-[4-(1-pyrrolidinyl)butyl]-6-[(4S,1E)-4-hydroxy-4-methyl-1-octenyl]-7-hydroxybicyclo[3.3.0]-2-octene 1314) (1S,5S,6R,7R)-3-(4-piperidinobutyl)-6-[(4S,1E)-4-hydroxy-4-methyl-1-octenyl]-7-hydroxybicyclo[3.3.0]-2-octene 1315) (1S,5S,6R,7R)-3-(4-morpholinobutyl)-6-[(4S,1E)-4-hydroxy-4-methyl-1-octenyl]-7-hydroxybicyclo[3.3.0]-2-octene 1316) (1S,5S,6R,7R)-3-(6-aminohexyl)-6-[(4S,1E)-4-hydroxy-4-methyl-1-octenyl]-7-hydroxy bicyclo[3.3.0]-2-octene 1317) (1S,5S,6R,7R)-3-(6-N,N-dimethylaminohexyl)-6-[(4S,1E)-4-hydroxy-4-methyl-1-octenyl]-7-hydroxybicyclo[3.3.0]-2-octene 1318) (1S,5S,6R,7R)-3-(6-N,N-diisopropylaminohexyl)-6-[(4S,1E)-4-hydroxy-4-methyl-1-octenyl]-7-hydroxybicyclo[3.3.0]-2-octene 1319) (1S,5S,6R,7R)-3-(6-N-t-butyl-N-methylaminohexyl)-6-[(4S,1E)-4-hydroxy-4-methyl-1-octenyl]-7-hydroxybicyclo[3.3.0]-2-octene 1320) (1S,5S,6R,7R)-3-[6-(1-pyrrolidinyl)hexyl]-6-[(4S,1E)-4-hydroxy-4-methyl-1-octenyl]-7-hydroxybicyclo[3.3.0]-2-octene 1321) (1S,5S,6R,7R)-3-(6-piperidinohexyl)-6-[(4S,1E)-4-hydroxy-4-methyl-1-octenyl]-7-hydroxybicyclo[3.3.0]-2-octene 1322) (1S,5S,6R,7R)-3-(6-morpholinohexyl)-6-[(4S,1E)-4-hydroxy-4-methyl-1-octenyl]-7-hydroxybicyclo[3.3.0]-2-octene 1323) (1S,5S,6R,7R)-3-[(1Z)-4-N,N-dimethylamino-1-butenyl]-6-[(4S,1E)-4-hydroxy-4-methyl-1-octenyl]-7-hydroxybicyclo[3.3.0]-2-octene 1324) (1S,5S,6R,7R)-3-[(1Z)-5-N,N-dimethylamino-1-pentenyl]-6-[(4S,1E)-4-hydroxy-4-methyl-1-octenyl]-7-hydroxybicyclo[3.3.0]-2-octene 1325) (1S,5S,6R,7R)-3-[(1E)-5-N,N-dimethylamino-1-pentenyl]-6-[(4S,1E)-4-hydroxy-4-methyl-1-octenyl]-7-hydroxybicyclo[3.3.0]-2-octene 1326) (1S,5S,6R,7R)-3-[(1 Z)-6-N,N-dimethylamino-1-hexenyl]-6-[(4S,1E)-4-hydroxy-4-methyl-1-octenyl]-7-hydroxybicyclo[3.3.0]-2-octene 1327) (1S,5S,6R,7R)-3-[N-(2-N,N-dimethylaminoethyl)aminomethyl]-6-[(4S,1E)-4-hydroxy-4-methyl-1-octenyl]-7-hydroxybicyclo[3.3.0]-2-octene 1328) (1S,5S,6R,7R)-3-[N-(3-N,N-dimethylaminopropyl)aminomethyl]-6-[(4S,1E)-4-hydroxy-4-methyl-1-octenyl]-7-hydroxybicyclo[3.3.0]-2-octene 1329) (1S,5S,6R,7R)-3-[N-(3-N,N-diisopropylaminopropyl)aminomethyl]-6-[(4S,1E)-4-hydroxy-4-methyl-1-octenyl]-7-hydroxybicyclo[3.3.0]-2-octene 1330) (1S,5S,6R,7R)-3-[N-(3-N-t-butyl-N-methylaminopropyl)aminomethyl]-6-[(4S,1E)-4-hydroxy-4-methyl-1-octenyl]-7-hydroxybicyclo[3.3.0]-2-octene 1331) (1S,5S,6R,7R)-3-[N-[3-(1-pyrrolidinyl)propyl]aminomethyl]-6-[(4S,1E)-4-hydroxy-4-methyl-1-octenyl]-7-hydroxybicyclo[3.3.0]-2-octene 1332) (1S,5S,6R,7R)-3-[N-(3-piperidinopropyl)aminomethyl]-6-[(4S,1E)-4-hydroxy-4-methyl-1-octenyl]-7-hydroxybicyclo[3.3.0]-2-octene 1333) (1S,5S,6R,7R)-3-[N-(3-morpholinopropyl)aminomethyl]-6-[(4S,1E)-4-hydroxy-4-methyl-1-octenyl]-7-hydroxybicyclo[3.3.0]-2-octene 1334) (1S,5S,6R,7R)-3-[N-(4-N,N-dimethylaminobutyl)aminomethyl]-6-[(4S,1E)-4-hydroxy-4-methyl-1-octenyl]-7-hydroxybicyclo[3.3.0]-2-octene 1335) (1S,5S,6R,7R)-3-[N-(3-N,N-dimethylaminopropyl)-N-methylaminomethyl]-6-[(4S,1E)₄-hydroxy-4-methyl-1-octenyl]-7-hydroxybicyclo[3.3.0]-2-octene 1336) (1S,5S,6R,7R)-3-[2-N-(2-N,N-dimethylaminoethyl)aminoethyl]-6-[(4S,1E)-4-hydroxy-4-methyl-1-octenyl]-7-hydroxybicyclo[3.3.0]-2-octene 1337) (1S,5S,6R,7R)-3-[2-N-(2-N,N-diisopropylaminoethyl)aminoethyl]-6-[(4S,1E)-4-hydroxy-4-methyl-1-octenyl]-7-hydroxybicyclo[3.3.0]-2-octene 1338) (1S,5S,6R,7R)-3-[2-N-(2-N-t-butyl-N-methylaminoethyl)aminoethyl]-6-[(4S,1E)-4-hydroxy-4-methyl-1-octenyl]-7-hydroxybicyclo[3.3.0]-2-octene 1339) (1S,5S,6R,7R)-3-[2-N-[2-(1-pyrrolidinyl)ethyl]aminoethyl]-6-[(4S,1E)-4-hydroxy-4-methyl-1-octenyl]-7-hydroxybicyclo[3.3.0]-2-octene 1340) (1S,5S,6R,7R)-3-[2-N-(2-piperidinoethyl)aminoethyl]-6-[(4S,1E)-4-hydroxy-4-methyl-1-octenyl]-7-hydroxybicyclo[3.3.0]-2-octene 1341) (1S,5S,6R,7R)-3-[2-N-(2-morpholinoethyl)aminoethyl]-6-[(4S,1E)-4-hydroxy-4-methyl-1-octenyl]-7-hydroxybicyclo[3.3.0]-2-octene 1342) (1S,5S,6R,7R)-3-[2-N-(3-N,N-dimethylaminopropyl)aminoethyl]-6-[(4S,1E)-4-hydroxy-4-methyl-1-octenyl]-7-hydroxybicyclo[3.3.0]-2-octene 1343) (1S,5S,6R,7R)-3-[(3-N,N-dimethylaminopropyl)oxymethyl]-6-[(4S,1E)-4-hydroxy-4-methyl-1-octenyl]-7-hydroxybicyclo[3.3.0]-2-octene 1344) (1S,5S,6R,7R)-3-[(3-N,N-diisopropylaminopropyl)oxymethyl]-6-[(4S,1E)-4-hydroxy-4-methyl-1-octenyl]-7-hydroxybicyclo[3.3.0]-2-octene 1345) (1S,5S,6R,7R)-3-[(3-N-t-butyl-N-methylaminopropyl)oxymethyl]-6-[(4S,1E)-4-hydroxy-4-methyl-1-octenyl]-7-hydroxybicyclo[3.3.0]-2-octene 1346) (1S,5S,6R,7R)-3-[[3-(1-pyrrolidinyl)propyl]oxymethyl]-6-[(4S,1E)-4-hydroxy-4-methyl-1-octenyl]-7-hydroxybicyclo[3.3.0]-2-octene 1347) (1S,5S,6R,7R)-3-[(3-piperidinopropyl)oxymethyl]-6-[(4S,1E)-4-hydroxy-4-methyl-1-octenyl]-7-hydroxybicyclo[3.3.0]-2-octene 1348) (1S,5S,6R,7R)-3-[(3-morpholinopropyl)oxymethyl]-6-[(4S,1E)-4-hydroxy-4-methyl-1-octenyl]-7-hydroxybicyclo[3.3.0]-2-octene 1349) (1S,5S,6R,7R)-3-[2-(2-N,N-dimethylaminoethyl)oxyethyl]-6-[(4S,1E)-4-hydroxy-4-methyl-1-octenyl]-7-hydroxybicyclo[3.3.0]-2-octene 1350) (1S,5S,6R,7R)-3-[2-(2-N,N-diisopropylaminoethyl)oxyethyl]-6-[(4S,1E)-4-hydroxy-4-methyl-1-octenyl]-7-hydroxybicyclo[3.3.0]-2-octene 1351) (1S,5S,6R,7R)-3-[2-(2-N-t-butyl-N-methylaminoethyl)oxyethyl]-6-[(4S,1E)-4-hydroxy-4-methyl-1-octenyl]-7-hydroxybicyclo[3.3.0]-2-octene 1352) (1S,5S,6R,7R)-3-[2-[2-(1-pyrrolidinyl)ethyl]oxyethyl]-6-[(4S,1E)-4-hydroxy-4-methyl-1-octenyl]-7-hydroxybicyclo[3.3.0]-2-octene 1353) (1S,5S,6R,7R)-3-[2-(2-piperidinoethyl)oxyethyl]-6-[(4S,1E)-4-hydroxy-4-methyl-1-octenyl]-7-hydroxybicyclo[3.3.0]-2-octene 1354) (1S,5S,6R,7R)-3-[2-(2-morpholinoethyl)oxyethyl]-6-[(4S,1E)-4-hydroxy-4-methyl-1-octenyl]-7-hydroxybicyclo[3.3.0]-2-octene 1355) (1S,5S,6R,7R)-3-[(3-N,N-dimethylaminopropyl)thiomethyl]-6-[(4S,1E)-4-hydroxy-4-methyl-1-octenyl]-7-hydroxybicyclo[3.3.0]-2-octene 1356) (1S,5S,6R,7R)-3-[(3-N,N-diisopropylaminopropyl)thiomethyl]-6-[(4S,1E)-4-hydroxy-4-methyl-1-octenyl]-7-hydroxybicyclo[3.3.0]-2-octene 1357) (1S,5S,6R,7R)-3-[(3-N-t-butyl-N-methylaminopropyl)thiomethyl]-6-[(4S,1E)-4-hydroxy-4-methyl-1-octenyl]-7-hydroxybicyclo[3.3.0]-2-octene 1358) (1S,5S,6R,7R)-3-[[3-(1-pyrrolidinyl)propyl]thiomethyl]-6-[(4S,1E)-4-hydroxy-4-methyl-1-octenyl]-7-hydroxybicyclo[3.3.0]-2-octene 1359) (1S,5S,6R,7R)-3-[(3-piperidinopropyl)thiomethyl]-6-[(4S,1E)-4-hydroxy-4-methyl-1-octenyl]-7-hydroxybicyclo[3.3.0]-2-octene 1360) (1S,5S,6R,7R)-3-[(3-morpholinopropyl)thiomethyl]-6-[(4S,1E)-4-hydroxy-4-methyl-1-octenyl]-7-hydroxybicyclo[3.3.0]-2-octene 1361) (1S,5S,6R,7R)-3-[2-(2-N,N-dimethylaminoethyl)thioethyl]-6-[(4S,1E)-4-hydroxy-4-methyl-1-octenyl]-7-hydroxybicyclo[3.3.0]-2-octene 1362) (1S,5S,6R,7R)-3-[2-(2-N,N-diisopropylaminoethyl)thioethyl]-6-[(4S,1E)-4-hydroxy-4-methyl-1-octenyl]-7-hydroxybicyclo[3.3.0]-2-octene 1363) (1S,5S,6R,7R)-3-[2-(2-N-t-butyl-N-methylaminoethyl)thioethyl]-6-[(4S, 1E)-4-hydroxy-4-methyl-1-octenyl]-7-hydroxybicyclo[3.3.0]-2-octene 1364) (1S,5S,6R,7R)-3-[2-[2-(1-pyrrolidinyl)ethyl]thioethyl]-6-[(4S,1E)-4-hydroxy-4-methyl-1-octenyl]-7-hydroxybicyclo[3.3.0]-2-octene 1365) (1S,5S,6R,7R)-3-[2-(2-piperidinoethyl)thioethyl]-6-[(4S, 1E)-4-hydroxy-4-methyl-1-octenyl]-7-hydroxybicyclo[3.3.0]-2-octene 1366) (1S,5S,6R,7R)-3-[2-(2-morpholinoethyl)thioethyl]-6-[(4S, 1E)-4-hydroxy-4-methyl-1-octenyl]-7-hydroxybicyclo[3.3.0]-2-octene 1367) (1S,5S,6R,7R)-3-[(3-N,N-dimethylaminophenyl)methyl]-6-[(4S,1E)-4-hydroxy-4-methyl-1-octenyl]-7-hydroxybicyclo[3.3.0]-2-octene 1368) (1-S,5S,6R,7R)-3-[[2-(aminomethyl)phenyl]methyl]-6-[(4S,1E)-4-hydroxy-4-methyl-1-octenyl]-7-hydroxybicyclo[3.3.0]-2-octene 1369) (1S,5S,6R,7R)-3-[[4-(aminomethyl)phenyl]methyl]-6-[(4S,1E)-4-hydroxy-4-methyl-1-octenyl]-7-hydroxybicyclo[3.3.0]-2-octene 1370) (1S,5S,6R,7R)-3-[2-[3-(aminomethyl)phenyl]ethyl]-6-[(4S,1E)-4-hydroxy-4-methyl-1-octenyl]-7-hydroxybicyclo[3.3.0]-2-octene 1371) (1S,5S,6R,7R)-3-[2-[3-(piperidinomethyl)phenyl]ethyl]-6-[(4S,1E)-4-hydroxy-4-methyl-1-octenyl]-7-hydroxybicyclo[3.3.0]-2-octene 1372) (1S,5S,6R,7R)-3-[2-(4-piperidyl)ethyl]-6-[(4S,1E)-4-hydroxy-4-methyl-1-octenyl]-7-hydroxybicyclo[3.3.0]-2-octene 1373) (1S,5S,6R,7R)-3-[2-(4-pyridyl)ethyl]-6-[(4S,1E)-4-hydroxy-4-methyl-1-octenyl]-7-hydroxybicyclo[3.3.0]-2-octene 1374) (1S,5S,6R,7R)-3-[4-(2-pyridyl)butyl]-6-[(4S,1E)-4-hydroxy-4-methyl-1-octenyl]-7-hydroxybicyclo[3.3.0]-2-octene 1375) (1S,5S,6R,7R)-3-(5-aminopentyl)-6-[(3S,1E)-3-hydroxy-4-(m-tolyl)-1-butenyl]-7-hydroxybicyclo[3.3.0]-2-octene 1376) (1S,5S,6R,7R)-3-(5-N,N-dimethylaminopentyl)-6-[(3S,1E)-3-hydroxy-4-(m-tolyl)-1-butenyl]-7-hydroxybicyclo[3.3.0]-2-octene 1377) (1S,5S,6R,7R)-3-(5-N,N-diethylaminopentyl)-6-[(3S, 1E)-3-hydroxy-4-(m-tolyl)-1-butenyl]-7-hydroxybicyclo[3.3.0]-2-octene 1378) (1S,5S,6R,7R)-3-[5-N-(2-methoxycarbonylethyl)aminopentyl]-6-[(3S,1E)-3-hydroxy-4-(m-tolyl)-1-butenyl]-7-hydroxybicyclo[3.3.0]-2-octene 1379) (1S,5S,6R,7R)-3-[5-N-(4-pyridylmethyl)aminopentyl]-6-[(3S,1E)-3-hydroxy-4-(m-tolyl)-1-butenyl]-7-hydroxybicyclo[3.3.0]-2-octene 1380) (1S,5S,6R,7R)-3-[5-N,N-diisopropylaminopentyl]-6-[(3S,1E)-3-hydroxy-4-(m-tolyl)-1-butenyl]-7-hydroxybicyclo[3.3.0]-2-octene 1381) (1S,5S,6R,7R)-3-[5-(1-pyrrolidinyl)pentyl]-6-[(3S, 1E)-3-hydroxy-4-(m-tolyl)-1-butenyl]-7-hydroxybicyclo[3.3.0]-2-octene 1382) (1S,5S,6R,7R)-3-(5-piperidinopentyl)-6-[(3S,1E)-3-hydroxy-4-(M-tolyl)-1-butenyl]-7-hydroxybicyclo[3.3.0]-2-octene 1383) (1S,5S,6R,7R)-3-(5-morpholinopentyl)-6-[(3S,1E)-3-hydroxy-4-(m-tolyl)-1-butenyl]-7-hydroxybicyclo[3.3.0]-2-octene 1384) (1S,5S,6R,7R)-3-(5-N-methylaminopentyl)-6-[(3S, 1E)-3-hydroxy-4-(m-tolyl)-1-butenyl]-7-hydroxybicyclo[3.3.0]-2-octene 1385) (1S,5S,6R,7R)-3-(5-N-ethylaminopentyl)-6-[(3S, 1E)-3-hydroxy-4-(m-tolyl)-1-butenyl]-7-hydroxybicyclo[3.3.0]-2-octene 1386) (1S,5S,6R,7R)-3-(5-N-propylaminopentyl)-6-[(3S, 1E)-3-hydroxy-4-(m-tolyl)-1-butenyl]-7-hydroxybicyclo[3.3.0]-2-octene 1387) (1S,5S,6R,7R)-3-(5-N-isopropylaminopentyl)-6-[(3S,1 E)-3-hydroxy-4-(m-tolyl)-1-butenyl]-7-hydroxybicyclo[3.3.0]-2-octene 1388) (1S,5S,6R,7R)-3-(5-N-butylaminopentyl)-6-[(3S,1E)-3-hydroxy-4-(m-tolyl)-1-butenyl]-7-hydroxybicyclo[3.3.0]-2-octene 1389) (1S,5S,6R,7R)-3-(5-N-t-butylaminopentyl)-6-[(3S,1E)-3-hydroxy-4-(m-tolyl)-1-butenyl]-7-hydroxybicyclo[3.3.0]-2-octene 1390) (1S,5S,6R,7R)-3-(5-N-phenylaminopentyl)-6-[(3S,1E)-3-hydroxy-4-(m-tolyl)-1-butenyl]-7-hydroxybicyclo[3.3.0]-2-octene 1391) (1S,5S,6R,7R)-3-(5-N-benzylaminopentyl)-6-[(3S,1E)-3-hydroxy-4-(m-tolyl)-1-butenyl]-7-hydroxybicyclo[3.3.0]-2-octene 1392) (1S,5S,6R,7R)-3-[5-(4-N-methyl-1-piperazinyl)pentyl]-6-[(3S,1E)-3-hydroxy-4-(m-tolyl)-1-butenyl]-7-hydroxybicyclo[3.3.0]-2-octene 1393) (1S,5S,6R,7R)-3-[5-N-(2-pyridyl)aminopentyl]-6-[(3S,1E)-3-hydroxy-4-(m-tolyl)-1-butenyl]-7-hydroxybicyclo[3.3.0]-2-octene 1394) (1S,5S,6R,7R)-3-(5-N,N-dipropylaminopentyl)-6-[(3S, 1E)-3-hydroxy-4-(m-tolyl)-1-butenyl]-7-hydroxybicyclo[3.3.0]-2-octene 1395) (1S,5S,6R,7R)-3-(5-N,N-dibutylaminopentyl)-6-[(3S,1E)-3-hydroxy-4-(m-tolyl)-1-butenyl]-7-hydroxybicyclo[3.3.0]-2-octene 1396) (1S,5S,6R,7R)-3-(5-N-t-butyl-N-methylaminopentyl)-6-[(3S,1E)-3-hydroxy-4-m-tolyl)-1-butenyl]-7-hydroxybicyclo[3.3.0]-2-octene 1397) (1S,5S,6R,7R)-3-[5-N-(2-hydroxyethyl)aminopentyl]-6-[(3S,1E)-3-hydroxy-4-(m-tolyl)-1-butenyl]-7-hydroxybicyclo[3.3.0]-2-octene 1398) (1S,5S,6R,7R)-3-[5-N-(3-hydroxypropyl)aminopentyl]-6-[(3S,1E)-3-hydroxy-4-(m-tolyl)-1-butenyl]-7-hydroxybicyclo[3.3.0]-2-octene 1399) (1S,5S,6R,7R)-3-(4-aminobutyl)-6-[(3S,1E)-3-hydroxy-4-(m-tolyl)-1-butenyl]-7-hydroxy bicyclo[3.3.0]-2-octene 1400) (1S,5S,6R,7R)-3-(4-N,N-dimethylaminobutyl)-6-[(3S,1E)-3-hydroxy-4-(m-tolyl)-1-butenyl]-7-hydroxybicyclo[3.3.0]-2-octene 1401) (1S,5S,6R,7R)-3-(4-N,N-diisopropylaminobutyl)-6-[(3S,1E)-3-hydroxy-4-(m-tolyl)-1 butenyl]-7-hydroxybicyclo[3.3.0]-2-octene 1402) (1S,5S,6R,7R)-3-(4-N-t-butyl-N-methylaminobutyl)-6-[(3S,1E)-3-hydroxy-4-(m-tolyl)-1-butenyl]-7-hydroxybicyclo[3.3.0]-2-octene 1403) (1S,5S,6R,7R)-3-[4-(1-pyrrolidinyl)butyl]-6-[(3S,1E)-3-hydroxy-4-(m-tolyl)-1-butenyl]-7-hydroxybicyclo[3.3.0]-2-octene 1404) (1S,5S,6R,7R)-3-(4-piperidinobutyl)-6-[(3S,1E)-3-hydroxy-4-(m-tolyl)-1-butenyl]-7-hydroxybicyclo[3.3.0]-2-octene 1405) (1S,5S,6R,7R)-3-(4-morpholinobutyl)-6-[(3S,1E)-3-hydroxy-4-(m-tolyl)-1-butenyl]-7-hydroxybicyclo[3.3.0]-2-octene 1406) (1S,5S,6R,7R)-3-(6-aminohexyl)-6-[(3S,1E)-3-hydroxy-4-(m-tolyl)-1-butenyl]-7-hydroxybicyclo[3.3.0]-2-octene 1407) (1S,5S,6R,7R)-3-(6-N,N-dimethylaminohexyl)-6-[(3S,1E)-3-hydroxy-4-(m-tolyl)-1-butenyl]-7-hydroxybicyclo[3.3.0]-2-octene 1408) (1S,5S,6R,7R)-3-(6-N,N-diisopropylaminohexyl)-6-[(3S,1E)-3-hydroxy-4-(m-tolyl)-1-butenyl]-7-hydroxybicyclo[3.3.0]-2-octene 1409) (1S,5S,6R,7R)-3-(6-N-t-butyl-N-methylaminohexyl)-6-[(3S,1 E)-3-hydroxy-4-(m-tolyl)-1-butenyl]-7-hydroxybicyclo[3.3.0]-2-octene 1410) (1S,5S,6R,7R)-3-[6-(1-pyrrolidinyl)hexyl]-6-[(3S,1E)-3-hydroxy-4-(m-tolyl)-1-butenyl]-7-hydroxybicyclo[3.3.0]-2-octene 1411) (1S,5S,6R,7R)-3-(6-piperidinohexyl)-6-[(3S,1E)-3-hydroxy-4-(m-tolyl)-1-butenyl]-7-hydroxybicyclo[3.3.0]-2-octene 1412) (1S,5S,6R,7R)-3-(6-morpholinohexyl)-6-[(3S,1E)-3-hydroxy-4-(m-tolyl)-1-butenyl]-7-hydroxybicyclo[3.3.0]-2-octene 1413) (1S,5S,6R,7R)-3-[(1Z)-4-N,N-dimethylamino-1-butenyl]-6-[(3S,1E)-3-hydroxy-4-(m-tolyl)-1-butenyl]-7-hydroxybicyclo[3.3.0]-2-octene 1414) (1S,5S,6R,7R)-3-[(1Z)-5-N,N-dimethylamino-1-pentenyl]-6-[(3S,1E)-3-hydroxy-4-(m-tolyl)-1-butenyl]-7-hydroxybicyclo[3.3.0]-2-octene 1415) (1S,5S,6R,7R)-3-[(1E)-5-N,N-dimethylamino-1-pentenyl]-6-[(3S,1E)-3-hydroxy-4-(m-tolyl)-1-butenyl]-7-hydroxybicyclo[3.3.0]-2-octene 1416) (1S,5S,6R,7R)-3-[(1Z)-6-N,N-dimethylamino-1-hexenyl]-6-[(3S,1E)-3-hydroxy-4-(m-tolyl)-1-butenyl]-7-hydroxybicyclo[3.3.0]-2-octene 1417) (1S,5S,6R,7R)-3-[N-(2-N,N-dimethylaminoethyl)aminomethyl]-6-[(3S,1E)-3-hydroxy-4-(m-tolyl)-1-butenyl]-7-hydroxybicyclo[3.3.0]-2-octene 1418) (1S,5S,6R,7R)-3-[N-(3-N,N-dimethylaminopropyl)aminomethyl]-6-[(3S,1E)-3-hydroxy-4-(m-tolyl)-1-butenyl]-7-hydroxybicyclo[3.3.0]-2-octene 1419) (1S,5S,6R,7R)-3-[N-(3-N,N-diisopropylaminopropyl)aminomethyl]-6-[(3S,1E)-3-hydroxy-4-(m-tolyl)-1-butenyl]-7-hydroxybicyclo[3.3.0]-2-octene 1420) (1S,5S,6R,7R)-3-[N-(3-N-t-butyl-N-methylaminopropyl)aminomethyl]-6-[(3S,1E)-3-hydroxy-4-(m-tolyl)-1-butenyl]-7-hydroxybicyclo[3.3.0]-2-octene 1421) (1S,5S,6R,7R)-3-[N-[3-(1-pyrrolidinyl)propyl]aminomethyl]-6-[(3S,1E)-3-hydroxy-4-(m-tolyl)-1-butenyl]-7-hydroxybicyclo[3.3.0]-2-octene 1422) (1S,5S,6R,7R)-3-[N-(3-piperidinopropyl)aminomethyl]-6-[(3S,1E)-3-hydroxy-4-(m-tolyl)-1-butenyl]-7-hydroxybicyclo[3.3.0]-2-octene 1423) (1S,5S,6R,7R)-3-[N-(3-morpholinopropyl)aminomethyl]-6-[(3S,1E)-3-hydroxy-4-(m-tolyl)-1-butenyl]-7-hydroxybicyclo[3.3.0]-2-octene 1424) (1S,5S,6R,7R)-3-[N-(4-N,N-dimethylaminobutyl)aminomethyl]-6-[(3S,1E)-3-hydroxy-4-(m-tolyl)-1-butenyl]-7-hydroxybicyclo[3.3.0]-2-octene 1425) (1S,5S,6R,7R)-3-[N-(3-N,N-dimethylaminopropyl)-N-methylaminomethyl]-6-[(3S,1E)-3-hydroxy-4-(m-tolyl)-1-butenyl]-7-hydroxybicyclo[3.3.0]-2-octene 1426) (1S,5S,6R,7R)-3-[2-N-(2-N,N-dimethylaminoethyl)aminoethyl]-6-[(3S,1E)-3-hydroxy-4-(m-tolyl)-1-butenyl]-7-hydroxybicyclo[3.3.0]-2-octene 1427) (1S,5S,6R,7R)-3-[2-N-(2-N,N-diisopropylaminoethyl)aminoethyl]-6-[(3S,7E)-3-hydroxy-4-(m-tolyl)-1-butenyl]-7-hydroxybicyclo[3.3.0]-2-octene 1428) (1S,5S,6R,7R)-3-[2-N-(2-N-t-butyl-N-methylaminoethyl)aminoethyl]-6-[(3S,1E)-3-hydroxy-4-(m-tolyl)-1-butenyl]-7-hydroxybicyclo[3.3.0]-2-octene 1429) (1S,5S,6R,7R)-3-[2-N-[2-(1-pyrrolidinyl)ethyl]aminoethyl]-6-[(3S,1E)-3-hydroxy-4-(m-tolyl)-1-butenyl]-7-hydroxybicyclo[3.3.0]-2-octene 1430) (1S,5S,6R,7R)-3-[2-N-(2-piperidinoethyl)aminoethyl]-6-[(3S,1E)-3-hydroxy-4-(m-tolyl)-1-butenyl]-7-hydroxybicyclo[3.3.0]-2-octene 1431) (1S,5S,6R,7R)-3-[2-N-(2-morpholinoethyl)aminoethyl]-6-[(3S,1E)-3-hydroxy-4-(m-tolyl)-1-butenyl]-7-hydroxybicyclo[3.3.0]-2-octene 1432) (1S,5S,6R,7R)-3-[2-N-(3-N,N-dimethylaminopropyl)aminoethyl]-6-[(3S,1E)-3-hydroxy-4-(m-tolyl)-1-butenyl]-7-hydroxybicyclo[3.3.0]-2-octene 1433) (1S,5S,6R,7R)-3-[(3-N,N-dimethylaminopropyl)oxymethyl]-6-[(3S,1E)-3-hydroxy-4-(m-tolyl)-1-butenyl]-7-hydroxybicyclo[3.3.0]-2-octene 1434) (1S,5S,6R,7R)-3-[(3-N,N-diisopropylaminopropyl)oxymethyl]-6-[(3S,1E)-3-hydroxy-4-(m-tolyl)-1-butenyl]-7-hydroxybicyclo[3.3.0]-2-octene 1435) (1S,5S,6R,7R)-3-[(3-N-t-butyl-N-methylaminopropyl)oxymethyl]-6-[(3S,1E)-3-hydroxy-4-(m-tolyl)-1-butenyl]-7-hydroxybicyclo[3.3.0]-2-octene 1436) (1S,5S,6R,7R)-3-[[3-(1-pyrrolidinyl)propyl]oxymethyl]-6-[(3S,1E)-3-hydroxy-4-(m-tolyl)-1-butenyl]-7-hydroxybicyclo[3.3.0]-2-octene 1437) (1S,5S,6R,7R)-3-[(3-piperidinopropyl)oxymethyl]-6-[(3S,1E)-3-hydroxy-4-(m-tolyl)-1-butenyl]-7-hydroxybicyclo[3.3.0]-2-octene 1438) (1S,5S,6R,7R)-3-[(3-morpholinopropyl)oxymethyl]-6-[(3S,1E)-3-hydroxy-4-(m-tolyl)-1-butenyl]-7-hydroxybicyclo[3.3.0]-2-octene 1439) (1S,5S,6R,7R)-3-[2-(2-N,N-dimethylaminoethyl)oxyethyl]-6-[(3S,1E)-3-hydroxy-4-(m-tolyl)-1-butenyl]-7-hydroxybicyclo[3.3.0]-2-octene 1440) (1S,5S,6R,7R)-3-[2-(2-N,N-diisopropylaminoethyl)oxyethyl]-6-[(3S,1E)-3-hydroxy-4-(m-tolyl)-1-butenyl]-7-hydroxybicyclo[3.3.0]-2-octene 1441) (1S,5S,6R,7R)-3-[2-(2-N-t-butyl-N-methylaminoethyl)oxyethyl]-6-[(3S,1E)-3-hydroxy-4-(m-tolyl)-1-butenyl]-7-hydroxybicyclo[3.3.0]-2-octene 1442) (1S,5S,6R,7R)-3-[2-[2-(1-pyrrolidinyl)ethyl]oxyethyl]-6-[(3S,1E)-3-hydroxy-4-(m-tolyl)-1-butenyl]-7-hydroxybicyclo[3.3.0]-2-octene 1443) (1S,5S,6R,7R)-3-[2-(2-piperidinoethyl)oxyethyl]-6-[(3S,1E)-3-hydroxy-4-(m-tolyl)-1-butenyl]-7-hydroxybicyclo[3.3.0]-2-octene 1444) (1S,5S,6R,7R)-3-[2-(2-morpholinoethyl)oxyethyl]-6-[(3S,1E)-3-hydroxy-4-(m-tolyl)-1-butenyl]-7-hydroxybicyclo[3.3.0]-2-octene 1445) (1S,5S,6R,7R)-3-[(3-N,N-dimethylaminopropyl)thiomethyl]-6-[(3S,1E)-3-hydroxy-4-(m-tolyl)-1-butenyl]-7-hydroxybicyclo[3.3.0]-2-octene 1446) (1S,5S,6R,7R)-3-[(3-N,N-diisopropylaminopropyl)thiomethyl]-6-[(3S,1E)-3-hydroxy-4-(m-tolyl)-1-butenyl]-7-hydroxybicyclo[3.3.0]-2-octene 1447) (1S,5S,6R,7R)-3-[(3-N-t-butyl-N-methylaminopropyl)thiomethyl]-6-[(3S,1E)-3-hydroxy-4-(m-tolyl)-1-butenyl]-7-hydroxybicyclo[3.3.0]-2-octene 1448) (1S,5S,6R,7R)-3-[[3-(1-pyrrolidinyl)propyl]thiomethyl]-6-[(3S,1E)-3-hydroxy-4-(m-tolyl)-1-butenyl]-7-hydroxybicyclo[3.3.0]-2-octene 1449) (1S,5S,6R,7R)-3-[(3-piperidinopropyl)thiomethyl]-6-[(3S,1E)-3-hydroxy-4-(m-tolyl)-1-butenyl]-7-hydroxybicyclo[3.3.0]-2-octene 1450) (1S,5S,6R,7R)-3-[(3-morpholinopropyl)thiomethyl]-6-[(3S,1E)-3-hydroxy-4-(m-tolyl)-1-butenyl]-7-hydroxybicyclo[3.3.0]-2-octene 1451) (1S,5S,6R,7R)-3-[2-(2-N,N-dimethylaminoethyl)thioethyl]-6-[(3S,1E)-3-hydroxy-4-(m-tolyl)-1-butenyl]-7-hydroxybicyclo[3.3.0]-2-octene 1452) (1S,5S,6R,7R)-3-[2-(2-N,N-diisopropylaminoethyl)thioethyl]-6-[(3S,1E)-3-hydroxy-4-(m-tolyl)-1-butenyl]-7-hydroxybicyclo[3.3.0]-2-octene 1453) (1S,5S,6R,7R)-3-[2-(2-N-t-butyl-N-methylaminoethyl)thioethyl]-6-[(3S,1E)-3-hydroxy-4-(m-tolyl)-1-butenyl]-7-hydroxybicyclo[3.3.0]-2-octene 1454) (1S,5S,6R,7R)-3-[2-[2-(1-pyrrolidinyl)ethyl] thioethyl]-6-[(3S,1E)-3-hydroxy-4-(m-tolyl)-1-butenyl]-7-hydroxybicyclo[3.3.0]-2-octene 1455) (1S,5S,6R,7R)-3-[2-(2-piperidinoethyl)thioethyl]-6-[(3S,1E)-3-hydroxy-4-(m-tolyl)-1 butenyl]-7-hydroxybicyclo[3.3.0]-2-octene 1456) (1S,5S,6R,7R)-3-[2-(2-morpholinoethyl)thioethyl]-6-[(3S,1E)-3-hydroxy-4-(m-tolyl)-1-butenyl]-7-hydroxybicyclo[3.3.0]-2-octene 1457) (1S,5S,6R,7R)-3-[(3-N,N-dimethylaminophenyl)methyl]-6-[(3S,1E)-3-hydroxy-4-(m-tolyl)-1-butenyl]-7-hydroxybicyclo[3.3.0]-2-octene 1458) (1S,5S,6R,7R)-3-[[2-(aminomethyl)phenyl]methyl]-6-[(3S,1E)-3-hydroxy-4-(m-tolyl)-1-butenyl]-7-hydroxybicyclo[3.3.0]-2-octene 1459) (1S,5S,6R,7R)-3-[[4-(aminomethyl)phenyl]methyl]-6-[(3S,1E)-3-hydroxy-4-(m-tolyl)-1-butenyl]-7-hydroxybicyclo[3.3.0]-2-octene 1460) (1S,5S,6R,7R)-3-[2-[3-(aminomethyl)phenyl]ethyl]-6-[(3S,1E)-3-hydroxy-4-(m-tolyl)-1-butenyl]-7-hydroxybicyclo[3.3.0]-2-octene 1461) (1S,5S,6R,7R)-3-[2-[3-(piperidinomethyl)phenyl]ethyl]-6-[(3S,1E)-3-hydroxy-4-(m-tolyl)-1-butenyl]-7-hydroxybicyclo[3.3.0]-2-octene 1462) (1S,5S,6R,7R)-3-[2-(4-piperidyl)ethyl]-6-[(3S,1E)-3-hydroxy-4-(m-tolyl)-1-butenyl]-7-hydroxybicyclo[3.3.0]-2-octene 1463) (1S,5S,6R,7R)-3-[2-(4-pyridyl)ethyl]-6-[(3S,1E)-3-hydroxy-4-(m-tolyl)-1-butenyl]-7-hydroxybicyclo[3.3.0]-2-octene 1464) (1S,5S,6R,7R)-3-[4-(2-pyridyl)butyl]-6-[(3S,1E)-3-hydroxy-4-(m-tolyl)-1-butenyl]-7-hydroxybicyclo[3.3.0]-2-octene 1465) (1S,5S,6R,7R)-3-(5-aminopentyl)-6-[(3R,1E)-3-hydroxy-4-(m-tolyl)-1-butenyl]-7-hydroxybicyclo[3.3.0]-2-octene 1466) (1S,5S,6R,7R)-3-(5-N,N-dimethylaminopentyl)-6-[(3R,1E)-3-hydroxy-4-(m-tolyl)-1-butenyl]-7-hydroxybicyclo[3.3.0]-2-octene 1467) (1S,5S,6R,7R)-3-(5-N,N-diethylaminopentyl)-6-[(3R,1E)-3-hydroxy-4-(m-tolyl)-1-butenyl]-7-hydroxybicyclo[3.3.0]-2-octene 1468) (1S,5S,6R,7R)-3-[5-N-(2-methoxycarbonylethyl)aminopentyl]-6-[(3R,1E)-3-hydroxy-4-(m-tolyl)-1-butenyl]-7-hydroxybicyclo[3.3.0]-2-octene 1469) (1S,5S,6R,7R)-3-[5-N-(4-pyridylmethyl)aminopentyl]-6-[(3R,1E)-3-hydroxy-4-(m-tolyl)-1-butenyl]-7-hydroxybicyclo[3.3.0]-2-octene 1470) (1S,5S,6R,7R)-3-[5-N,N-diisopropylaminopentyl]-6-[(3R,1E)-3-hydroxy-4-(m-tolyl)-1-butenyl]-7-hydroxybicyclo[3.3.0]-2-octene 1471) (1S,5S,6R,7R)-3-[5-(1-pyrrolidinyl)pentyl]-6-[(3R,1E)-3-hydroxy-4-(m-tolyl)-1-butenyl]-7-hydroxybicyclo[3.3.0]-2-octene 1472) (1S,5S,6R,7R)-3-(5-piperidinopentyl)-6-[(3R,1E)-3-hydroxy-4-(m-tolyl)-1-butenyl]-7-hydroxybicyclo[3.3.0]-2-octene 1473) (1S,5S,6R,1R)-3-(5-morpholinopentyl)-6-[(3R,1E)-3-hydroxy-4-(m-tolyl)-1-butenyl]-7-hydroxybicyclo[3.3.0]-2-octene 1474) (1S,5S,6R,7R)-3-(5-N-methylaminopentyl)-6-[(3R,1E)-3-hydroxy-4-(m-tolyl)-1 butenyl]-7-hydroxybicyclo[3.3.0]-2-octene 1475) (1S,5S,6R,7R)-3-(5-N-ethylaminopentyl)-6-[(3R,1E)-3-hydroxy-4-(m-tolyl)-1-butenyl]-7-hydroxybicyclo[3.3.0]-2-octene 1476) (1S,5S,6R,7R)-3-(5-N-propylaminopentyl)-6-[(3R,1E)-3-hydroxy-4-(m-tolyl)-1-butenyl]-7-hydroxybicyclo[3.3.0]-2-octene 1477) (1S,5S,6R,7R)-3-(5-N-isopropylaminopentyl)-6-[(3R,1E)-3-hydroxy-4-(m-tolyl)-1-butenyl]-hydroxybicyclo[3.3.0]-2-octene 1478) (1S,5S,6R,7R)-3-(5-N-butylaminopentyl)-6-[(3R,1E)-3-hydroxy-4-(m-tolyl)-1-butenyl]-7-hydroxybicyclo[3.3.0]-2-octene 1479) (1S,5S,6R,7R)-3-(5-N-t-butylaminopentyl)-6-[(3R,1E)-3-hydroxy-4-(m-tolyl)-1-butenyl]-7-hydroxybicyclo[3.3.0]-2-octene 1480) (1S,5S,6R,7R)-3-(5-N-phenylaminopentyl)-6-[(3R,1E)-3-hydroxy-4-(m-tolyl)-1-butenyl]-7-hydroxybicyclo[3.3.0]-2-octene 1481) (1S,5S,6R,7R)-3-(5-N-benzylaminopentyl)-6-[(3R,1E)-3-hydroxy-4-(m-tolyl)-1-butenyl]-7-hydroxybicyclo[3.3.0]-2-octene 1482) (1S,5S,6R,7R)-3-[5-(4-N-methyl-1-piperazinyl)pentyl]-6-[(3R, 1E)-3-hydroxy-4-(m-tolyl)-1-butenyl]-7-hydroxybicyclo[3.3.0]-2-octene 1483) (1S,5S,6R,7R)-3-[5-N-(2-pyridyl)aminopentyl]-6-[(3R,1E)-3-hydroxy-4-(m-tolyl)-1-butenyl]-7-hydroxybicyclo[3.3.0]-2-octene 1484) (1S,5S,6R,7R)-3-(5-N,N-dipropylaminopentyl)-6-[(3R,1E)-3-hydroxy-4-(m-tolyl)-1-butenyl]-7-hydroxybicyclo[3.3.0]-2-octene 1485) (1S,5S,6R,7R)-3-(5-N,N-dibutylaminopentyl)-6-[(3R,1E)-3-hydroxy-4-(m-tolyl)-1-butenyl]-7-hydroxybicyclo[3.3.0]-2-octene 1486) (1S,5S,6R,7R)-3-(5-N-t-butyl-N-methylaminopentyl)-6-[(3R,1E)-3-hydroxy-4-(m-tolyl)-1-butenyl]-7-hydroxybicyclo[3.3.0]-2-octene.

1487) (1S,5S,6R,7R)-3-[5-N-(2-hydroxyethyl)aminopentyl]-6-[(3R,1E)-3-hydroxy-4-(m-tolyl)-1-butenyl]-7-hydroxybicyclo[3.3.0]-2-octene 1488) (1S,5S,6R,7R)-3-[5-N-(3-hydroxypropyl)aminopentyl]-6-[(3R,1E)-3-hydroxy-4-(m-tolyl)-1-butenyl]-7-hydroxybicyclo[3.3.0]-2-octene 1489) (1S,5S,6R,7R)-3-(4-aminobutyl)-6-[(3R,1E)-3-hydroxy-4-(m-tolyl)-1-butenyl]-7-hydroxybicyclo[3.3.0]-2-octene 1490) (1S,5S,6R,7R)-3-(4-N,N-dimethylaminobutyl)-6-[(3R,1E)-3-hydroxy-4-(m-tolyl)-1 butenyl]-7-hydroxybicyclo[3.3.0]-2-octene 1491) (1S,5S,6R,7R)-3-(4-N,N-diisopropylaminobutyl)-6-[(3R,1E)-3-hydroxy-4-(m-tolyl)-1-butenyl]-7-hydroxybicyclo[3.3.0]-2-octene 1492) (1S,5S,6R,7R)-3-(4-N-t-butyl-N-methylaminobutyl)-6-[(3R,1E)-3-hydroxy-4-(m-tolyl)-1-butenyl]-7-hydroxybicyclo[3.3.0]-2-octene 1493) (1S,5S,6R,7R)-3-[4-(1-pyrrolidinyl)butyl]-6-[(3R,1E)-3-hydroxy-4-(m-tolyl)-1-butenyl]-7-hydroxybicyclo[3.3.0]-2-octene 1494) (1S,5S,6R,7R)-3-(4-piperidinobutyl)-6-[(3R,1E)-3-hydroxy-4-(m-tolyl)-1-butenyl]-7-hydroxybicyclo[3.3.0]-2-octene 1495) (1S,5S,6R,7R)-3-(4-morpholinobutyl)-6-[(3R,1E)-3-hydroxy-4-(m-tolyl)-1-butenyl]-7-hydroxybicyclo[3.3.0]-2-octene 1496) (1S,5S,6R,7R)-3-(6-aminohexyl)-6-[(3R,1E)-3-hydroxy-4-(m-tolyl)-1-butenyl]-7-hydroxybicyclo[3.3.0]-2-octene 1497) (1S,5S,6R,7R)-3-(6-N,N-dimethylaminohexyl)-6-[(3R,1E)-3-hydroxy-4-(m-tolyl)-1-butenyl]-7-hydroxybicyclo[3.3.0]-2-octene 1498) (1S,5S,6R,7R)-3-(6-N,N-diisopropylaminohexyl)-6-[(3R,1E)-3-hydroxy-4-(m-tolyl)-1-butenyl]-7-hydroxybicyclo[3.3.0]-2-octene 1499) (1S,5S,6R,7R)-3-(6-N-t-butyl-N-methylaminohexyl)-6-[(3R, 1E)-3-hydroxy-4-(m-tolyl)-1-butenyl]-7-hydroxybicyclo[3.3.0]-2-octene 1500) (1S,5S,6R,7R)-3-[6-(1-pyrrolidinyl)hexyl]-6-[(3R, 1E)-3-hydroxy-4-(m-tolyl)-1-butenyl]-7-hydroxybicyclo[3.3.0]-2-octene 1501) (1S,5S,6R,7R)-3-(6-piperidinohexyl)-6-[(3R,1E)-3-hydroxy-4-(m-tolyl)-1-butenyl]-7-hydroxybicyclo[3.3.0]-2-octene 1502) (1S,5S,6R,7R)-3-(6-morpholinohexyl)-6-[(3R,1E)-3-hydroxy-4-(m-tolyl)-1-butenyl]-7-hydroxybicyclo[3.3.0]-2-octene 1503) (1S,5S,6R,7R)-3-[(1Z)-4-N,N-dimethylamino-1-butenyl]-6-[(3R, 1E)-3-hydroxy-4-(m-tolyl)-1-butenyl]-7-hydroxybicyclo[3.3.0]-2-octene 1504) (1S,5S,6R,7R)-3-[(1Z)-5-N,N-dimethylamino-1-pentenyl]-6-[(3R,1E)-3-hydroxy-4-(m-tolyl)-1-butenyl]-7-hydroxybicyclo[3.3.0]-2-octene 1505) (1S,5S,6R,7R)-3-[(1E)-5-N,N-dimethylamino-1-pentenyl]-6-[(3R,1E)-3-hydroxy-4-(m-tolyl)-1-butenyl]-7-hydroxybicyclo[3.3.0]-2-octene 1506) (1S,5S,6R,7R)-3-[(1Z)-6-N,N-dimethylamino-1-hexenyl]-6-[(3R,1E)-3-hydroxy-4-(m-tolyl)-1-butenyl]-7-hydroxybicyclo[3.3.0]-2-octene 1507) (1S,5S,6R,7R)-3-[N-(2-N,N-dimethylaminoethyl)aminomethyl]-6-[(3R,1E)-3-hydroxy-4-(m-tolyl)-1-butenyl]-7-hydroxybicyclo[3.3.0]-2-octene 1508) (1S,5S,6R,7R)-3-[N-(3-N,N-dimethylaminopropyl)aminomethyl]-6-[(3R,1E)-3-hydroxy-4-(m-tolyl)-1-butenyl]-7-hydroxybicyclo[3.3.0]-2-octene 1509) (1S,5S,6R,7R)-3-[N-(3-N,N-diisopropylaminopropyl)aminomethyl]-6-[(3R,1E)-3-hydroxy-4-(m-tolyl)-1-butenyl]-7-hydroxybicyclo[3.3.0]-2-octene 1510) (1S,5S,6R,7R)-3-[N-(3-N-t-butyl-N-methylaminopropyl)aminomethyl]-6-[(3R,1E)-3-hydroxy-4-(m-tolyl)-1-butenyl]-7-hydroxybicyclo[3.3.0]-2-octene 1511) (1S,5S,6R,7R)-3-[N-[3-(1-pyrrolidinyl)propyl]aminomethyl]-6-[(3R,1E)-3-hydroxy-4-(m-tolyl)-1-butenyl]-7-hydroxybicyclo[3.3.0]-2-octene 1512) (1S,5S,6R,7R)-3-[N-(3-piperidinopropyl)aminomethyl]-6-[(3R,1E)-3-hydroxy-4-(m-tolyl)-1-butenyl]-7-hydroxybicyclo[3.3.0]-2-octene 1513) (1S,5S,6R,7R)-3-[N-(3-morpholinopropyl)aminomethyl]-6-[(3R,1E)-3-hydroxy-4-(m-tolyl)-1-butenyl]-7-hydroxybicyclo[3.3.0]-2-octene 1514) (1S,5S,6R,7R)-3-[N-(4-N,N-dimethylaminobutyl)aminomethyl]-6-[(3R,1E)-3-hydroxy-4-(m-tolyl)-1-butenyl]-7-hydroxybicyclo[3.3.0]-2-octene 1515) (1S,5S,6R,7R)-3-[N-(3-N,N-dimethylaminopropyl)-N-methylaminomethyl]-6-[(3R,1E)-3-hydroxy-4-(m-tolyl)-1-butenyl]-7-hydroxybicyclo[3.3.0]-2-octene 1516) (1S,5S,6R,7R)-3-[2-N-(2-N,N-dimethylaminoethyl)aminoethyl]-6-[(3R,1E)-3-hydroxy-4-(m-tolyl)-1-butenyl]-7-hydroxybicyclo[3.3.0]-2-octene 1517) (1S,5S,6R,7R)-3-[2-N-(2-N,N-diisopropylaminoethyl)aminoethyl]-6-[(3R,1E)-3-hydroxy-4-(m-tolyl)-1-butenyl]-7-hydroxybicyclo[3.3.0]-2-octene 1518) (1S,5S,6R,7R)-3-[2-N-(2-N-t-butyl-N-methylaminoethyl)aminoethyl]-6-[(3R,1E)-3-hydroxy-4-(m-tolyl)-1-butenyl]-7-hydroxybicyclo[3.3.0]-2-octene 1519) (1S,5S,6R,7R)-3-[2-N-[2-(1-pyrrolidinyl)ethyl]aminoethyl]-6-[(3R,1E)-3-hydroxy-4-(m-tolyl)-1-butenyl]-7-hydroxybicyclo[3.3.0]-2-octene 1520) (1S,5S,6R,7R)-3-[2-N-(2-piperidinoethyl)aminoethyl]-6-[(3R,1E)-3-hydroxy-4-(m-tolyl)-1-butenyl]-7-hydroxybicyclo[3.3.0]-2-octene 1521) (1S,5S,6R,7R)-3-[2-N-(2-morpholinoethyl)aminoethyl]-6-[(3R,1E)-3-hydroxy-4(m-tolyl)-1-butenyl]-7-hydroxybicyclo[3.3.0]-2-octene 1522) (1S,5S,6R,7R)-3-[2-N-(3-N,N-dimethylaminopropyl)aminoethyl]-6-[(3R,1E)-3-hydroxy-4-(m-tolyl)-1-butenyl]-7-hydroxybicyclo[3.3.0]-2-octene 1523) (1S,5S,6R,7R)-3-[(3-N,N-dimethylaminopropyl)oxymethyl]-6-[(3R,1E)-3-hydroxy-4-(m-tolyl)-1-butenyl]-7-hydroxybicyclo[3.3.0]-2-octene 1524) (1S,5S,6R,7R)-3-[(3-N,N-diisopropylaminopropyl)oxymethyl]-6-[(3R,1E)-3-hydroxy-4-(m-tolyl)-1-butenyl]-7-hydroxybicyclo[3.3.0]-2-octene 1525) (1S,5S,6R,7R)-3-[(3-N-t-butyl-N-methylaminopropyl)oxymethyl]-6-[(3R,1E)-3-hydroxy-4-(m-tolyl)-1-butenyl]-7-hydroxybicyclo[3.3.0]-2-octene 1526) (1S,5S,6R,7R)-3-[[3-(1-pyrrolidinyl)propyl]oxymethyl]-6-[(3R,1E)-3-hydroxy-4-(m-tolyl)-1-butenyl]-7-hydroxybicyclo[3.3.0]-2-octene 1527) (1S,5S,6R,7R)-3-[(3-piperidinopropyl)oxymethyl]-6-[(3R,1E)-3-hydroxy-4-(m-tolyl)-1-butenyl]-7-hydroxybicyclo[3.3.0]-2-octene 1528) (1S,5S,6R,7R)-3-[(3-morpholinopropyl)oxymethyl]-6-[(3R,1E)-3-hydroxy-4-(m-tolyl)-1-butenyl]-7-hydroxybicyclo[3.3.0]-2-octene 1529) (1S,5S,6R,7R)-3-[2-(2-N,N-dimethylaminoethyl)oxyethyl]-6-[(3R,1E)-3-hydroxy-4-(m-tolyl)-1-butenyl]-7-hydroxybicyclo[3.3.0]-2-octene 1530) (1S,5S,6R,7R)-3-[2-(2-N,N-diisopropylaminoethyl)oxyethyl]-6-[(3R,1E)-3-hydroxy-4-(m-tolyl)-1-butenyl]-7-hydroxybicyclo[3.3.0]-2-octene 1531) (1S,5S,6R,7R)-3-[2-(2-N—t-butyl-N-methylaminoethyl)oxyethyl]-6-[(3R,1E)-3-hydroxy-4-(m-tolyl)-1-butenyl]-7-hydroxybicyclo[3.3.0]-2-octene 1532) (1S,5S,6R,7R)-3-[2-[2-(1-pyrrolidinyl)ethyl]oxyethyl]-6-[(3R,1E)-3-hydroxy-4-(m-tolyl)-1-butenyl]-7-hydroxybicyclo[3.3.0]-2-octene 1533) (1S,5S,6R,7R)-3-[2-(2-piperidinoethyl)oxyethyl]-6-[(3R,1E)-3-hydroxy-4-(m-tolyl)-1-butenyl]-7-hydroxybicyclo[3.3.0]-2-octene 1534) (1S,5S,6R,7R)-3-[2-(2-morpholinoethyl)oxyethyl]-6-[(3R,1E)-3-hydroxy-4-(m-tolyl)-1-butenyl]-7-hydroxybicyclo[3.3.0]-2-octene 1535) (1S,5S,6R,7R)-3-[(3-N,N-dimethylaminopropyl)thiomethyl]-6-[(3R,1E)-3-hydroxy-4-(m-tolyl)-1-butenyl]-7-hydroxybicyclo[3.3.0]-2-octene 1536) (1S,5S,6R,7R)-3-[(3-N,N-diisopropylaminopropyl)thiomethyl]-6-[(3R,1E)-3-hydroxy-4-(m-tolyl)-1-butenyl]-7-hydroxybicyclo[3.3.0]-2-octene 1537) (1S,5S,6R,7R)-3-[(3-N—t-butyl-N-methylaminopropyl)thiomethyl]-6-[(3R,1E)-3-hydroxy-4-(m-tolyl)-1-butenyl]-7-hydroxybicyclo[3.3.0]-2-octene 1538) (1S,5S,6R,7R)-3-[[3-(1-pyrrolidinyl)propyl]thiomethyl]-6-[(3R,1E)-3-hydroxy-4-(m-tolyl)-1-butenyl]-7-hydroxybicyclo[3.3.0]-2-octene 1539) (1S,5S,6R,7R)-3-[(3-piperidinopropyl)thiomethyl]-6-[(3R,1E)-3-hydroxy-4-(m-tolyl)-1-butenyl]-7-hydroxybicyclo[3.3.0]-2-octene 1540) (1S,5S,6R,7R)-3-[(3-morpholinopropyl)thiomethyl]-6-[(3R,1E)-3-hydroxy-4-(m-tolyl)-1 butenyl]-7-hydroxybicyclo[3.3.0]-2-octene 1541) (1S,5S,6R,7R)-3-[2-(2-N,N-dimethylaminoethyl)thioethyl]-6-[(3R,1E)-3-hydroxy-4-(m-tolyl)-1-butenyl]-7-hydroxybicyclo[3.3.0]-2-octene 1542) (1S,5S,6R,7R)-3-[2-(2-N,N-diisopropylaminoethyl)thioethyl]-6-[(3R, 1E)-3-hydroxy-4-(m-tolyl)-1-butenyl]-7-hydroxybicyclo[3.3.0]-2-octene 1543) (1S,5S,6R,7R)-3-[2-(2-N—t-butyl-N-methylaminoethyl)thioethyl]-6-[(3R,1E)-3-hydroxy-4-(m-tolyl)-1-butenyl]-7-hydroxybicyclo[3.3.0]-2-octene 1544) (1S,5S,6R,7R)-3-[2-[2-(1-pyrrolidinyl)ethyl]thioethyl]-6-[(3R,1E)-3-hydroxy-4-(m-tolyl)-1-butenyl]-7-hydroxybicyclo[3.3.0]-2-octene 1545) (1S,5S,6R,7R)-3-[2-(2-piperidinoethyl)thioethyl]-6-[(3R,1E)-3-hydroxy-4-(m-tolyl)-1-butenyl]-7-hydroxybicyclo[3.3.0]-2-octene 1546) (1S,5S,6R,7R)-3-[2-(2-morpholinoethyl)thioethyl]-6-[(3R,1E)-3-hydroxy-4-(m-tolyl)-1-butenyl]-7-hydroxybicyclo[3.3.0]-2-octene 1547) (1S,5S,6R,7R)-3-[(3-N,N-dimethylaminophenyl)methyl]-6-[(3R,1E)-3-hydroxy-4-(m-tolyl)-1-butenyl]-7-hydroxybicyclo[3.3.0]-2-octene 1548) (1S,5S,6R,7R)-3-[[2-(aminomethyl)phenyl]methyl]-6-[(3R,1E)-3-hydroxy-4-(m-tolyl)-1-butenyl]-7-hydroxybicyclo[3.3.0]-2-octene 1549) (1S,5S,6R,7R)-3-[[4-(aminomethyl)phenyl]methyl]-6-[(3R,1E)-3-hydroxy-4-(m-tolyl)-1-butenyl]-7-hydroxybicyclo[3.3.0]-2-octene 1550) (1S,5S,6R,7R)-3-[2-[3-(aminomethyl)phenyl]ethyl]-6-[(3R,1E)-3-hydroxy-4-(m-tolyl)-1-butenyl]-7-hydroxybicyclo[3.3.0]-2-octene 1551) (1S,5S,6R,7R)-3-[2-[3-(piperidinomethyl)phenyl]ethyl]-6-[(3R, 1E)-3-hydroxy-4-(m-tolyl)-1-butenyl]-7-hydroxybicyclo[3.3.0]-2-octene 1552) (1S,5S,6R,7R)-3-[2-(4-piperidyl)ethyl]-6-[(3R,1E)-3-hydroxy-4-(m-tolyl)-1-butenyl]-7-hydroxybicyclo[3.3.0]-2-octene 1553) (1S,5S,6R,7R)-3-[2-(4-pyridyl)ethyl]-6-[(3R,1E)-3-hydroxy-4-(m-tolyl)-1-butenyl]-7-hydroxybicyclo[3.3.0]-2-octene 1554) (1S,5S,6R,7R)-3-[4-(2-pyridyl)butyl]-6-[(3R,1E)-3-hydroxy-4-(m-tolyl)-1-butenyl]-7-hydroxybicyclo[3.3.0]-2-octene 1555) (1S,5S,6R,7R)-3-(5-aminopentyl)-6-[(E)-4-(m-tolyl)-1-butenyl]-7-hydroxybicyclo[3.3.0]2-octene 1556) (1S,5S 5S,6R,7R)-3-(5-N,N-dimethylaminopentyl)-6-[(E)-4-(m-tolyl)-1-butenyl]-7-hydroxy bicyclo[3.3.0]-2-octene 1557) (1S,5S,6R,7R)-3-(5-N,N-diethylaminopentyl)-6-[(E)-4-(m-tolyl)-1-buten yl]-7-hydroxy bicyclo[3.3.0]-2-octene 1558) (1S,5S,6R,7R)-3-[5-N-(2-methoxycarbonylethyl)aminopentyl]-6-[(E)-4-(m-tolyl)-1-butenyl]-7-hydroxybicyclo[3.3.0]-2-octene 1559) (1S,5S,6R,7R)-3-[5-N-(4-pyridylmethyl)aminopentyl]-6-[(E)-4-(m-tolyl)-1-butenyl]-7-hydroxybicyclo[3.3.0]-2-octene 1560) (1S,5S,6R,7R)-3-[5-N,N-diisopropylaminopentyl]-6-[(E)-4-(m-tolyl)-1-butenyl]-7-hydroxybicyclo[3.3.0]-2-octene 1561) (1S,5S,6R,7R)-3-[5-(1-pyrrolidinyl)pentyl]-6-[(E)-4-(m-tolyl)-1-butenyl]-7-hydroxy bicyclo[3.3.0]-2-octene 1562) (1S,5S,6R,7R)-3-(5-piperidinopentyl)-6-[(E)-4-(m-tolyl)-1-butenyl]-7-hydroxy bicyclo[3.3.0]-2-octene 1563) (1S,5S,6R,7R)-3-(5-morpholinopentyl)-6-[(E)-4-(m-tolyl)-1-butenyl]-7-hydroxy bicyclo[3.3.0]-2-octene.

1564) (1S,5S,6R,7R)-3-(5-N-methylaminopentyl)-6-[(E)-4-(m-tolyl)-1-butenyl]-7-hydroxy bicyclo[3.3.0]-2-octene 1565) (1S,5S,6R,7R)-3-(5-N-ethylaminopentyl)-6-[(E)-4-(m-tolyl)-1-butenyl]-7-hydroxy bicyclo[3.3.0]-2-octene 1566) (1S,5S,6R,7R)-3-(5-N-propylaminopentyl)-6-[(E)-4-(m-tolyl)-1-butenyl]-7-hydroxy bicyclo[3.3.0]-2-octene 1567) (1S,5S,6R,7R)-3-(5-N-isopropylaminopentyl)-6-[(E)-4-(m-tolyl)-1-butenyl]-7-hydroxy bicyclo[3.3.0]-2-octene 1568) (1S,5S,6R,7R)-3-(5-N-butylaminopentyl)-6-[(E)-4-(m-tolyl)-1-butenyl]-7-hydroxy bicyclo[3.3.0]-2-octene 1569) (1S,5S,6R,7R)-3-(5-N—t-butylaminopentyl)-6-[(E)-4-(m-tolyl)-1-butenyl]-7-hydroxy bicyclo[3.3.0]-2-octene 1570) (1S,5S,6R,7R)-3-(5-N-phenylaminopentyl)-6-[(E)-4-(m-tolyl)-1-butenyl]-7-hydroxy bicyclo[3.3.0]-2-octene 1571) (1S,5S,6R,7R)-3-(5-N-benzylaminopentyl)-6-[(E)-4-(m-tolyl)-1-butenyl]-7-hydroxy bicyclo[3.3.0]-2-octene 1572) (1S,5S,6R,7R)-3-[5-(4-N-methyl-1-piperazinyl)pentyl]-6-[(E)-4-(m-tolyl)-1-butenyl]-7-hydroxybicyclo[3.3.0]-2-octene 1573) (1S,5S,6R,7R)-3-[5-N-(2-pyridyl)aminopentyl]-6-[(E)-4-(m-tolyl)-1-butenyl]-7-hydroxy bicyclo[3.3.0]-2-octene 1574) (1S,5S,6R,7R)-3-(5-N,N-dipropylaminopentyl)-6-[(E)-4-(m-olyl)-1-butenyl]-7-hydroxy bicyclo[3.3.0]-2-octene 1575) (1S,5S,6R,7R)-3-(5-N,N-dibutylaminopentyl)-6-[(E)-4-(m-tolyl)-1-butenyl]-7-hydroxy bicyclo[3.3.0]-2-octene 1576) (1S,5S,6R,7R)-3-(5-N—t-butyl-N-methylaminopentyl)-6-[(E)-4-(m-tolyl)-1-butenyl]-7-hydroxybicyclo[3.3.0]-2-octene 1577) (1S,5S,6R,7R)-3-[5-N-(2-hydroxyethyl)aminopentyl]-6-[(E)-4-(m-tolyl)-1-butenyl]-7-hydroxybicyclo[3.3.0]-2-octene 1578) (1 S,5S,6R,7R)-3-[5-N-(3-hydroxypropyl)aminopentyl-6-[(E)-4-(m-tolyl)—butenyl]-7-hydroxybicyclo[3.3.0]-2-octene 1579) (1S,5S,6R,7R)-3-(4-aminobutyl)-6-[(E)-4-(m-tolyl)-1-butenyl]-7-hydroxybicyclo[3.3.0]2-octene 1580) (1S,5S,6R,7R)-3-(4-N,N-dimethylaminobutyl)-6-[(E)-4-(m-tolyl)-S-butenyl]-7-hydroxy bicyclo[3.3.0]-2-octene 1581) (1S,5S,6R,7R)-3-(4-N,N-diisopropylaminobutyl)-6-[(E)-4-(m-tolyl)-1-butenyl]-7-hydroxybicyclo[3.3.0]-2-octene 1582) (1S,5S,6R,7R)-3-(4-N—t-butyl-N-methylaminobutyl)-6-[(E)-4-(m-tolyl)-1-butenyl]-7-hydroxybicyclo[3.3.0]-2-octene 1583) (1S,5S,6R,7R)-3-[4-(1-pyrrolidinyl)butyl]-6-[(E)-4-(m-tolyl)-1-butenyl]-7-hydroxy bicyclo[3.3.0]-2-octene 1584) (1S,5S,6R,7R)-3-(4-piperidinobutyl)-6-[(E)-4-(m-tolyl)-1-butenyl]-7-hydroxy bicyclo[3.3.0]-2-octene 1585) (1S,5S,6R,7R)-3-(4-morpholinobutyl)-6-[(E)-4-(m-tolyl)-1-butenyl]-7-hydroxy bicyclo[3.3.0]-2-octene 1586) (1S,5S,6R,7R)-3-(6-aminohexyl)-6-[(E)-4-(m-tolyl)-1-butenyl]-7-hydroxybicyclo[3.3.0]-2-octene 1587) (1S,5S,6R,7R)-3-(6-N,N-dimethylaminohexyl)-6-[(E)-4-(m-tolyl)-1-butenyl]-7-hydroxy bicyclo[3.3.0]-2-octene 1588) (1S,5S,6R,7R)-3-(6-N,N-diisopropylaminohexyl)-6-[(E)-4-(m-tolyl)-8-butenyl]-7-hydroxybicyclo[3.3.0]-2-octene 1589) (1S,5S,6R,7R)-3-(6-N—t-butyl-N-methylaminohexyl)-6-[(E)-4-(m-tolyl)-1-butenyl]-7-hydroxybicyclo[3.3.0]-2-octene 1590) (1S,5S,6R,7R)-3-[6-(1-pyrrolidinyl)hexyl]-6-[(E)-4-(m-tolyl)-1-butenyl]-7-hydroxy bicyclo[3.3.0]-2-octene 1591) (1S,5S,6R,7R)-3-(6-piperidinohexyl)-6-[(E)-4-S(m-tolyl)—butenyl]-7-hydroxy bicyclo[3.3.0]-2-octene 1592) (1S,5S,6R,7R)-3-(6-morpholinohexyl)-6-[(E)-4-(m-tolyl)-1-butenyl]-7-hydroxy bicyclo[3.3.0]-2-octene 1593) (1S,5S,6R,7R)-3-[(1Z)-4-N,N-dimethylamino-1-butenyl]-6-[(E)-4-(m-tolyl)-1-butenyl]-7-hydroxybicyclo[3.3.0]-2-octene 1594) (1S,5S,6R,7R)-3-[(1Z)-5-N,N-dimethylamino-1-pentenyl]-6-[(E)-4-(m-tolyl)-1-butenyl]-7-hydroxybicyclo[3.3.0]-2-octene 1595) (1S,5S,6R,7R)-3-[(1E)-5-N,N-dimethylamino-1-pentenyl]-6-[(E)-4-(m-tolyl)-1-butenyl]-7-hydroxybicyclo[3.3.0]-2-octene 1596) (1S,5S,6R,7R)-3-[(1Z)-6-N,N-dimethylamino-1-hexenyl]-6-[(E)-4-(m-tolyl)-1-butenyl]-7-hydroxybicyclo[3.3.0]-2-octene 1597) (1S,5S,6R,7R)-3-[N-(2-N,N-dimethylaminoethyl)aminomethyl]-6-[(E)-4-(m-tolyl)-1 butenyl]-7-hydroxybicyclo[3.3.0]-2-octene 1598) (1S,5S,6R,7R)-3-[N-(3-N,N-dimethylaminopropyl)aminomethyl]-6-[(E)-4-(m-tolyl)-1-butenyl]-7-hydroxybicyclo[3.3.0]-2-octene 1599) (1S,5S,6R,7R)-3-[N-(3-N,N-diisopropylaminopropyl)aminomethyl]-6-[(E)-4-(m-tolyl)-1-butenyl]-7-hydroxybicyclo[3.3.0]-2-octene 1600) (1S,5S,6R,7R)-3-[N-(3-N—t-butyl-N-methylaminopropyl)aminomethyl]-6-[(E)-4-(m-tolyl)-1-butenyl]-7-hydroxybicyclo[3.3.0]-2-octene 1601) (1S,5S,6R,7R)-3-[N-[3-(1-pyrrolidinyl)propyl]aminomethyl]-6-[(E)-4-(m-tolyl)-1-butenyl]-7-hydroxybicyclo[3.3.0]-2-octene 1602) (1S,5S,6R,7R)-3-[N-(3-piperidinopropyl)aminomethyl]-6-[(E)-4-(m-tolyl)-1-butenyl]-7-hydroxybicyclo[3.3.0]-2-octene 1603) (1S,5S,6R,7R)-3-[N-(3-morpholinopropyl)aminomethyl]-6-[(E)-4-(m-tolyl)-1-butenyl]-7-hydroxybicyclo[3.3.0]-2-octene 1604) (1S,5S,6R,7R)-3-[N-(4-N,N-dimethylaminobutyl)aminomethyl]-6-[(E)-4-(m-tolyl)-1-butenyl]-7-hydroxybicyclo[3.3.0]-2-octene 1605) (1S,5S,6R,7R)-3-[N-(3-N,N-dimethylaminopropyl)-N-methylaminomethyl]-6-[(E)-4-(m-tolyl)-1-butenyl]-7-hydroxybicyclo[3.3.0]-2-octene 1606) (1S,5S,6R,7R)-3-[2-N-(2-N,N-dimethylaminoethyl)aminoethyl]-6-[(E)-4-(m-tolyl)-1-butenyl]-7-hydroxybicyclo[3.3.0]-2-octene 1607) (1S,5S,6R,7R)-3-[2-N-(2-N,N-diisopropylaminoethyl)aminoethyl]-6-[(E)-4-(m-tolyl)-1 butenyl]-7-hydroxybicyclo[3.3.0]-2-octene 1608) (1S,5S,6R,7R)-3-[2-N-(2-N—t-butyl-N-methylaminoethyl)aminoethyl]-6-[(E)-4-(m-tolyl)-1-butenyl]-7-hydroxybicyclo[3.3.0]-2-octene 1609) (1S,5S,6R,7R)-3-[2-N-[2-(1-pyrrolidinyl)ethyl]aminoethyl]-6-[(E)-4-(m-tolyl)-1-butenyl]-7-hydroxybicyclo[3.3.0]-2-octene 1610) (1S,5S,6R,7R)-3-[2-N-(2-piperidinoethyl)aminoethyl]-6-[(E)-4-(m-tolyl)-1-butenyl]-7-hydroxybicyclo[3.3.0]-2-octene 1611) (1S,5S,6R,7R)-3-[2-N-(2-morpholinoethyl)aminoethyl]-6-[(E)-4-(m-tolyl)-1-butenyl]-7-hydroxybicyclo[3.3.0]-2-octene 1612) (1S,5S,6R,7R)-3-[2-N-(3-N,N-dimethylaminopropyl)aminoethyl]-6-[(E)-4-(m-tolyl)-1-butenyl]-7-hydroxybicyclo[3.3.0]-2-octene 1613) (1S,5S,6R,7R)-3-[(3-N,N-dimethylaminopropyl)oxymethyl]-6-[(E)-4-(m-tolyl)-butenyl]-7-hydroxybicyclo[3.3.0]-2-octene 1614) (1S,5S,6R,7R)-3-[(3-N,N-diisopropylaminopropyl)oxymethyl]-6-[(E)-4-(m-tolyl)-1-butenyl]-7-hydroxybicyclo[3.3.0]-2-octene 1615) (1S,5S,6R,7R)-3-[(3-N—t-butyl-N-methylaminopropyl)oxymethyl]-6-[(E)-4-(m-tolyl)-1-butenyl]-7-hydroxybicyclo[3.3.0]-2-octene 1616) (1S,5S,6R,7R)-3-[[3-(1-pyrrolidinyl)propyl]oxymethyl]-6-[(E)-4-(m-tolyl)-1-butenyl]-7-hydroxybicyclo[3.3.0]-2-octene 1617) (1S,5S,6R,7R)-3-[(3-piperidinopropyl)oxymethyl]-6-[(E)-4-(m-tolyl)-1-butenyl]-7-hydroxybicyclo[3.3.0]-2-octene 1618) (1S,5S,6R,7R)-3-[(3-morpholinopropyl)oxymethyl]-6-[(E)-4-(m-tolyl)-1-butenyl]-7-hydroxybicyclo[3.3.0]-2-octene 1619) (1S,5S,6R,7R)-3-[2-(2-N,N-dimethylaminoethyl)oxyethyl]-6-[(E)-4-(m-tolyl)-1-butenyl]-7-hydroxybicyclo[3.3.0]-2-octene 1620) (1S,5S,6R,7R)-3-[2-(2-N,N-diisopropylaminoethyl)oxyethyl]-6-[(E)-4-(m-tolyl)-1-butenyl]-7-hydroxybicyclo[3.3.0]-2-octene 1621) (1S,5S,6R,7R)-3-[2-(2-N—t-butyl-N-methylaminoethyl)oxyethyl]-6-[(E)-4-(m-tolyl)-1-butenyl]-7-hydroxybicyclo[3.3.0]-2-octene 1622) (1S,5S,6R,7R)-3-[2-[2-(1-pyrrolidinyl)ethyl]oxyethyl]-6-[(E)-4-(m-tolyl)-1-butenyl]-7-hydroxybicyclo[3.3.0]-2-octene 1623) (1S,5S,6R,7R)-3-[2-(2-piperidinoethyl)oxyethyl]-6-[(E)-4-(m-tolyl)-1-butenyl]-7-hydroxybicyclo[3.3.0]-2-octene 1624) (1S,5S,6R,7R)-3-[2-(2-morpholinoethyl)oxyethyl]-6-[(E)-4-(m-tolyl)-1-butenyl]-7-hydroxybicyclo[3.3.0]-2-octene 1625) (1S,5S,6R,7R)-3-[(3-N,N-dimethylaminopropyl)thiomethyl]-6-[(E)-4-(m-tolyl)-1-butenyl]-7-hydroxybicyclo[3.3.0]-2-octene 1626) (1S,5S,6R,7R)-3-[(3-N,N-diisopropylaminopropyl)thiomethyl]-6-[(E)-4-(m-tolyl)-1-butenyl]-7-hydroxybicyclo[3.3.0]-2-octene 1627) (1S,5S,6R,7R)-3-[(3-N—t-butyl-N-methylaminopropyl)thiomethyl]-6-[(E)-4-(m-tolyl)-1-butenyl]-7-hydroxybicyclo[3.3.0]-2-octene 1628) (1S,5S,6R,7R)-3-[[3-(1-pyrrolidinyl)propyl]thiomethyl]-6-[(E)-4-(m-tolyl)-1-butenyl]-7-hydroxybicyclo[3.3.0]-2-octene 1629) (1S,5S,6R,7R)-3-[(3-piperidinopropyl)thiomethyl]-6-[(E)-4-(m-tolyl)-1-butenyl]-7-hydroxybicyclo[3.3.0]-2-octene 1630) (1S,5S,6R,7R)-3-[(3-morpholinopropyl)thiomethyl]-6-[(E)-4-(m-tolyl)-1-butenyl]-7-hydroxybicyclo[3.3.0]-2-octene 1631) (1S,5S,6R,7R)-3-[2-(2-N,N-dimethylaminoethyl)thioethyl]-6-[(E)-4-(m-tolyl)-1-butenyl]-7-hydroxybicyclo[3.3.0]-2-octene 1632) (1S,5S,6R,7R)-3-[2-(2-N,N-diisopropylaminoethyl)thioethyl]-6-[(E)-4-(m-tolyl)-1-butenyl]-7-hydroxybicyclo[3.3.0]-2-octene 1633) (1S,5S,6R,7R)-3-[2-(2-N—t-butyl-N-methylaminoethyl)thioethyl]-6-[(E)-4-(m-tolyl)-1-butenyl]-7-hydroxybicyclo[3.3.0]-2-octene 1634) (1S,5S,6R,7R)-3-[2-[2-(1-pyrrolidinyl)ethyl]thioethyl]-6-[(E)-4-(m-tolyl)-1-butenyl]-7-hydroxybicyclo[3.3.0]-2-octene 1635) (1S,5S,6R,7R)-3-[2-(2-piperidinoethyl)thioethyl]-6-[(E)-4-(m-tolyl)-1-butenyl]-7-hydroxybicyclo[3.3.0]-2-octene 1636) (1S,5S,6R,7R)-3-[2-(Z-morpholinoethyl)thioethyl]-6-[(E)-4-(m-tolyl)-1-butenyl]-7-hydroxybicyclo[3.3.0]-2-octene 1637) (1S,5S,6R,7R)-3-[(3-N,N-dimethylaminophenyl)methyl]-6-[(E)-4-(m-tolyl)-1-butenyl]-7-hydroxybicyclo[3.3.0]-2-octene 1638) (1S,5S,6R,7R)-3-[[2-(aminomethyl)phenyl]methyl]-6-[(E)-4-(m-tolyl)-1-butenyl]-7-hydroxybicyclo[3.3.0]-2-octene 1639) (1S,5S,6R,7R)-3-[[4-(aminomethyl)phenyl]methyl]-6-[(E)-4-(m-tolyl)-1-butenyl]-7-hydroxybicyclo[3.3.0]-2-octene 1640) (1S,5S,6R,7R)-3-[2-[3-(aminomethyl)phenyl]ethyl]-6-[(E)-4-(m-tolyl)-1-butenyl]-7-hydroxybicyclo[3.3.0]-2-octene 1641) (1S,5S,6R,7R)-3-[2-[3-(piperidinomethyl)phenyl]ethyl]-6-[(E)-4-(m-tolyl)-1-butenyl]-7-hydroxybicyclo[3.3.0]-2-octene 1642) (1S,5S,6R,7R)-3-[2-(4-piperidyl)ethyl]-6-[(E)-4-(m-tolyl)-1-butenyl]-7-hydroxy bicyclo[3.3.0]-2-octene 1643) (1S,5S,6R,7R)-3-[2-(4-pyridyl)ethyl]-6-[(E)-4-(m-tolyl)-1-butenyl]-7-hydroxy bicyclo [3.3.0]-2-octene 1644) (1S,5S,6R,7R)-3-[4-(2-pyridyl)butyl]-6-[(E)-4-(m-tolyl)-1-butenyl]-7-hydroxy bicyclo[3.3.0]-2-octene 1645) (1S,5S,6R,7R)-3-(5-aminopentyl)-6-[(3S,5R,1E)-3-hydroxy-5-methyl-1-nonenyl]-7-hydroxybicyclo[3.3.0]-2-octene 1646) (1S,5S,6R,7R)-3-(5-N,N-dimethylaminopentyl)-6-[(3S,5R,1E)-3-hydroxy-5-methyl-1-nonenyl]-7-hydroxybicyclo[3.3.0]-2-octene 1647) (1S,5S,6R,7R)-3-(5-N,N-diethylaminopentyl)-6-[(3S,5R,1E)-3-hydroxy-5-methyl-1-nonenyl]-7-hydroxybicyclo[3.3.0]-2-octene 1648) (1S,5S,6R,7R)-3-[5-N-(3-hydroxypropyl)aminopentyl]-6-[(3S,5R,1E)-3-hydroxy-5-methyl-1-nonenyl]-7-hydroxybicyclo[3.3.0]-2-octene 1649) (1S,5S,6R,7R)-3-[5-N-(4-pyridylmethyl)aminopentyl]-6-[(3S,5R,1E)-3-hydroxy-5-methyl-1-nonenyl]-7-hydroxybicyclo[3.3.0]-2-octene 1650) (1S,5S,6R,7R)-3-[5-N,N-diisopropylaminopentyl]-6-[(3S,5R,1E)-3-hydroxy-5-methyl-1-nonenyl]-7-hydroxybicyclo[3.3.0]-2-octene 1651) (1S,5S,6R,7R)-3-[5-(1-pyrrolidinyl)pentyl]-6-[(3S,5R,1E)-3-hydroxy-5-methyl-1-nonenyl]-7-hydroxybicyclo[3.3.0]-2-octene 1652) (1S,5S,6R,7R)-3-(5-piperidinopentyl)-6-[(3S,5R,1E)-3-hydroxy-5-methyl-1-nonenyl]-7-hydroxybicyclo[3.3.0]-2-octene 1653) (1S,5S,6R,7R)-3-(5-morpholinopentyl)-6-[(3S,5R,1E)-3-hydroxy-5-methyl-1-nonenyl]7-hydroxybicyclo[3.3.0]-2-octene 1654) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,5R,1E)-3-hydroxy-5-methyl-1-nonenyl group 1655) (1S,5S,6R,7R)-3-(5-aminopentyl)-6-[(4R,1E)-4-hydroxy-4-methyl-1-octenyl]-7-hydroxy bicyclo[3.3.0]-2-octene 1656) (1S,5S,6R,7R)-3-(5-N,N-dimethylaminopentyl)-6-[(4R,1E)-4-hydroxy-4-methyl-1-octenyl]-7-hydroxybicyclo[3.3.0]-2-octene 1657) (1S,5S,6R,7R)-3-(5-N,N-diethylaminopentyl)-6-[(4R,1E)-4-hydroxy-4-methyl-1-octenyl]-7-hydroxybicyclo[3.3.0]-2-octene 1658) (1S,5S,6R,7R)-3-[5-N-(3-hydroxypropyl)aminopentyl]-6-[(4R,1E)-4-hydroxy-4-methyl]-octenyl]-7-hydroxybicyclo[3.3.0]-2-octene 1659) (1S,5S,6R,7R)-3-[5-N-(4-pyridylmethyl)aminopentyl]-6-[(4R, 1E)-4-hydroxy-4-methyl-1-octenyl]-7-hydroxybicyclo[3.3.0]-2-octene 1660) (1S,5S,6R,7R)-3-[5-N,N-diisopropylaminopentyl]-6-[(4R,1E)-4-hydroxy-4-methyl-1-octenyl]-7-hydroxybicyclo[3.3.0]-2-octene 1661) (1S,5S,6R,7R)-3-[5-(1-pyrrolidinyl)pentyl]-6-[(4R,1E)-4-hydroxy 4-methyl-1-octenyl]-7-hydroxybicyclo[3.3.0]-2-octene 1662) (1S,5S,6R,7R)-3-(5-piperidinopentyl)-6-[(4R,1E)-4-hydroxy-4-methyl-1-octenyl]-7-hydroxybicyclo[3.3.0]-2-octene 1663) (1S,5S,6R,7R)-3-(5-morpholinopentyl)-6-[(4R,1E)-4-hydroxy-4-methyl-1-octenyl]-7-hydroxybicyclo[3.3.0]-2-octene 1664) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (4R,1E)-4-hydroxy-4-methyl-1-octenyl group 1665) (1S,5S,6R,7R)-3-(5-aminopentyl)-6-[(3S,4S,1E)-3-hydroxy-4-methyl-6-octyn-1-enyl]-7-hydroxybicyclo[3.3.0]-2-octene 1666) (1S,5S,6R,7R)-3-(5-N,N-dimethylaminopentyl)-6-[(3S,4S,1E)-3-hydroxy-4-methyl-6-octyn-1-enyl]-7-hydroxybicyclo[3.3.0]-2-octene 1667) (1S,5S,6R,7R)-3-(5-N,N-diethylaminopentyl)-6-[(3S,4S,1E)-3-hydroxy-4-methyl-6-octyn-1-enyl]-7-hydroxybicyclo[3.3.0]-2-octene 1668) (1S,5S,6R,7R)-3-[S—N-(3-hydroxypropyl)aminopentyl]-6-[(3S,4S,1E)-3-hydroxy-4-methyl-6-octyn-1'-enyl]-7-hydroxybicyclo[3.3.0]-2-octene 1669) (1S,5S,6R,7R)-3-[5-N-(4-pyridylmethyl)aminopentyl]-6-[(3S,4S,1E)-3-hydroxy-4-methyl-6-octyn-1'-enyl]-7-hydroxybicyclo[3.3.0]-2-octene 1670) (1S,5S,6R,7R)-3-[5-N,N-diisopropylaminopentyl]-6-[(3S,4S,1E)-3-hydroxy-4-methyl-6-octyn-1-enyl]-7-hydroxybicyclo[3.3.0]-2-octene 1671) (S,5S,6R,7R)-3-[5-(1-pyrrolidinyl)pentyl]-6-[(3S,4S,1E)-3-hydroxy-4-methyl-6-octyn-1-enyl]-7-hydroxybicyclo[3.3.0]-2-octene 1672) (1S,5S,6R,7R)-3-(5-piperidinopentyl)-6-[(3S,4S,1E)-3-hydroxy-4-methyl-6-octyn-1-enyl]-7-hydroxybicyclo[3.3.0]-2-octene 1673) (1S,5S,6R,7R)-3-(5-morpholinopentyl)-6-[(3S,4S,1E)-3-hydroxy-4-methyl-6-octyn-enyl]-7-hydroxybicyclo[3.3.0]-2-octene 1674) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,4S,1E)-3-hydroxy-4-methyl-6-octyn-1-enyl group 1675) (1S,5S,6R,7R)-3-(5-aminopentyl)-6-[(3S,4R,1E)-3-hydroxy-4-methyl-6-octyn-1-enyl]7-hydroxybicyclo[3.3.0]-2-octene 1676) (1S,5S,6R,7R)-3-(5-N,N-dimethylaminopentyl)-6-[(3S,4R,1E)-3-hydroxy-4-methyl-6-octyn-1-enyl]-7-hydroxybicyclo[3.3.0]-2-octene 1677) (1S,5S,6R,7R)-3-(5-N,N-diethylaminopentyl)-6-[(3S, 4R, E)-3-hydroxy-4-methyl-6-octyn-1-enyl]-7-hydroxybicyclo[3.3.0]-2-octene 1678) (1S,5S,6R,7R)-3-[5-N-(3-hydroxypropyl)aminopentyl]-6-[(3S,4R,1E)-3-hydroxy-4-methyl-6-octyn-1-enyl]-7-hydroxybicyclo[3.3.0]-2-octene 1679) (1S,5S,6R,7R)-3-[5-N-(4-pyridylmethyl)aminopentyl]-6-[(3S,4R,1E)-3-hydroxy-4-methyl-6-octyn-1-enyl]-7-hydroxybicyclo[3.3.0]-2-octene 1680) (1S,5S,6R,7R)-3-[5-N,N-diisopropylaminopentyl]-6-[(3S,4R,1E)-3-hydroxy-4-methyl-6-octyn-1-enyl]-7-hydroxybicyclo[3.3.0]-2-octene 1681) (1S,5S,6R,7R)-3-[5-(1-pyrrolidinyl)pentyl]-6-[(3S,4R,1E)-3-hydroxy-4-methyl-6-octyn-1-enyl]-7-hydroxybicyclo[3.3.0]-2-octene 1682) (1S,5S,6R,7R)-3-(5-piperidinopentyl)-6-[(3S,4R,1E)-3-hydroxy-4-methyl-6-octyn-1-enyl]-7-hydroxybicyclo[3.3.0]-2-octene 1683) (1S,5S,6R,7R)-3-(5-morpholinopentyl)-6-[(3S,4R,1E)-3-hydroxy-4-methyl-6-octyn-1-enyl]-7-hydroxybicyclo[3.3.0]-2-octene 1684) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,4R,1E)-3-hydroxy-4-methyl-6-octyn-1-enyl group 1685) (1S,5S,6R,7R)-3-(5-aminopentyl)-6-[(3S,1E)-3-hydroxy-3-cyclopentyl-1-propenyl]-7-hydroxybicyclo[3.3.0]-2-octene 1686) (1S,5S,6R,7R)-3-(5-N,N-dimethylaminopentyl)-6-[(3S,1E)-3-hydroxy-3-cyclopentyl-1-propenyl]-7-hydroxybicyclo[3.3.0]-2-octene 1687) (1S,5S,6R,7R)-3-(5-N,N-diethylaminopentyl)-6-[(3S,1E)-3-hydroxy-3-cyclopentyl-1-propenyl]-7-hydroxybicyclo[3.3.0]-2-octene 1688) (1S,5S,6R,7R)-3-[5-N-(3-hydroxypropyl)aminopentyl]-6-[(3S,1E)-3-hydroxy-3-cyclopentyl-1-propenyl]-7-hydroxybicyclo[3.3.0]-2-octene 1689) (1S,5S,6R,7R)-3-[5-N-(4-pyridylmethyl)aminopentyl]-6-[(3S,1E)-3-hydroxy-3-cyclopentyl-1-propenyl]-7-hydroxybicyclo[3.3.0]-2-octene 1690) (1S,5S,6R,7R)-3-[5-N,N-diisopropylaminopentyl]-6-[(3S,1E)-3-hydroxy-3-cyclopentyl]-propenyl]-7-hydroxybicyclo[3.3.0]-2-octene 1691) (1S,5S,6R,7R)-3-[5-(1-pyrrolidinyl)pentyl]-6-[(3S,1E)-3-hydroxy-3-cyclopentyl-1-propenyl]-7-hydroxybicyclo[3.3.0]-2-octene 1692) (1S,5S,6R,7R)-3-(5-piperidinopentyl)-6-[(3S,1E)-3-hydroxy-3-cyclopentyl-1-propenyl]-7-hydroxybicylo[3.3.0]-2-octene 1693) (1S,5S,6R,7R)-3-(5-morpholinopentyl)-6-[(3S,1E)-3-hydroxy-3-cyclopentyl-1-propenyl]-7-hydroxybicyclo[3.3.0]-2-octene 1694) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-3-cyclopentyl-1-propenyl group 1695) (1S,5S,6R,7R)-3-(5-aminopentyl)-6-[(3S,1E)-3-hydroxy-3-cyclohexyl-1-propenyl]-7-hydroxybicyclo[3.3.0]-2-octene 1696) (1S,5S,6R,7R)-3-(5-N,N-dimethylaminopentyl)-6-[(3S,1E)-3-hydroxy-3-cyclohexyl-1-propenyl]-7-hydroxybicyclo[3.3.0]-2-octene 1697) (1S,5S,6R,7R)-3-(5-N,N-diethylaminopentyl)-6-[(3S,1E)-3-hydroxy-3-cyclohexyl-1-propenyl]-7-hydroxybicyclo[3.3.0]-2-octene 1698) (1S,5S,6R,7R)-3-[5-N-(3-hydroxypropyl)aminopentyl]-6-[(3S,1E)-3-hydroxy-3-cyclohexyl-1-propenyl]-7-hydroxybicyclo[3.3.0]-2-octene
1699) (1S,5S,6R,7R)-3-[5-N-(4-pyridylmethyl)aminopentyl]-6-[(3S,1E)-3-hydroxy-3-cyclohexyl-1-propenyl]-7-hydroxybicyclo[3.3.0]-2-octene
1700) (1S,5S,6R,7R)-3-[5-N,N-diisopropylaminopentyl]-6-[(3S,1E)-3-hydroxy-3-cyclohexyl-1-propenyl]-7-hydroxybicyclo[3.3.0]-2-octene
1701) (1S,5S,6R,7R)-3-[5-(1-pyrrolidinyl)pentyl]-6-[(3S,1E)-3-hydroxy-3-cyclohexyl-1-propenyl]-7-hydroxybicyclo[3.3.0]-2-octene
1702) (1S,5S,6R,7R)-3-(5-piperidinopentyl)-6-[(3S,1E)-3-hydroxy-3-cyclohexyl-1-propenyl]-7-hydroxybicyclo[3.3.0]-2-octene
1703) (1S,5S,6R,7R)-3-(5-morpholinopentyl)-6-[(3S,1E)-3-hydroxy-3-cyclohexyl-1-propenyl]-7-hydroxybicyclo[3.3.0]-2-octene
1704) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-3-cyclohexyl-1-propenyl group
1705) (1S,5S,6R,7R)-3-(5-aminopentyl)-6-[(3S,1E)-3-hydroxy-4-cyclopentyl-1-butenyl]-7-hydroxybicyclo[3.3.0]-2-octene
1706) (1S,5S,6R,7R)-3-(5-N,N-dimethylaminopentyl)-6-[(3S,1E)-3-hydroxy-4-cyclopentyl-1-butenyl]-7-hydroxybicyclo[3.3.0]-2-octene
1707) (1S,5S,6R,7R)-3-(5-N,N-diethylaminopentyl)-6-[(3S,1E)-3-hydroxy-4-cyclopentyl-1 butenyl]-7-hydroxybicyclo[3.3.0]-2-octene
1708) (1S,5S,6R,7R)-3-[5-N-(3-hydroxypropyl)aminopentyl]-6-[(3S,1E)-3-hydroxy-4-cyclopentyl-1-butenyl]-7-hydroxybicyclo[3.3.0]-2-octene
1709) (1S,5S,6R,7R)-3-[5-N-(4-pyridylmethyl)aminopentyl]-6-[(3S,1E)-3-hydroxy-4-cyclopentyl-1-butenyl]-7-hydroxybicyclo[3.3.0]-2-octene
1710) (1S,5S,6R,7R)-3-[5-N,N-diisopropylaminopentyl]-6-[(3S,1E)-3-hydroxy-4-cyclopentyl-1-butenyl]-7-hydroxybicyclo [3.3.0]-2-octene
1711) (1S,5S,6R,7R)-3-[5-(1-pyrrolidinyl)pentyl]-6-[(3S,1E)-3-hydroxy-4-cyclopentyl-1-butenyl]-7-hydroxybicyclo [3.3.0]-2-octene
1712) (1S,5S,6R,7R)-3-(5-piperidinopentyl)-6-[(3S,1E)-3-hydroxy-4-cyclopentyl-1-butenyl]-7-hydroxybicyclo[3.3.0]-2-octene
1713) (1S,5S,6R,7R)-3-(5-morpholinopentyl)-6-[(3S,1E)-3-hydroxy-4-cyclopentyl-1-butenyl]-7-hydroxybicyclo[3.3.0]-2-octene
1714) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3S,1E)-3-hydroxy-4-cyclopentyl-1-butenyl group
1715) (1S,5S,6R,7R)-3-(5-aminopentyl)-6-[(3R,1E)-3-hydroxy-3-phenyl-1-propenyl]-7-hydroxybicyclo[3.3.0]-2-octene
1716) (1S,5S,6R,7R)-3-(5-N,N-dimethylaminopentyl)-6-[(3R,1E)-3-hydroxy-3-phenyl-1-propenyl]-7-hydroxybicyclo[3.3.0]-2-octene
1717) (1S,5S,6R,7R)-3-(5-N,N-diethylaminopentyl)-6-[(3R,1E)-3-hydroxy-3-phenyl-1-propenyl]-7-hydroxybicyclo[3.3.0]-2-octene
1718) (1S,5S,6R,7R)-3-[5-N-(3-hydroxypropyl)aminopentyl]-6-[(3R,1E)-3-hydroxy-3-phenyl-1-propenyl]-7-hydroxybicyclo[3.3.0]-2-octene
1719) (1S,5S,6R,7R)-3-[5-N-(4-pyridylmethyl)aminopentyl]-6-[(3R,1E)-3-hydroxy-3-phenyl-1-propenyl]-7-hydroxybicyclo[3.3.0]-2-octene
1720) (1S,5S,6R,7R)-3-[5-N,N-diisopropylaminopentyl]-6-[(3R,1E)-3-hydroxy-3-phenyl-1-propenyl]-7-hydroxybicyclo[3.3.0]-2-octene
1721) (1S,5S,6R,7R)-3-[5-(1-pyrrolidinyl)pentyl]-6-[(3R,1E)-3-hydroxy-3-phenyl-1-propenyl]-7-hydroxybicyclo[3.3.0]-2-octene
1722) (1S,5S,6R,7R)-3-(5-piperidinopentyl)-6-[(3R,1E)-3-hydroxy-3-phenyl-1-propenyl]-7-hydroxybicyclo[3.3.0]-2-octene
1723) (1S,5S,6R,7R)-3-(5-morpholinopentyl)-6-[(3R,1E)-3-hydroxy-3-phenyl-1-propenyl]-7-hydroxybicyclo[3.3.0]-2-octene
1724) compounds of compound numbers-1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-3-phenyl-1-propenyl group
1725) (1S,5S,6R,7R)-3-(5-aminopentyl)-6-[(3R,1E)-3-hydroxy-4-phenoxy-1-butenyl]-7-hydroxybicyclo[3.3.0]-2-octene
1726) (1S,5S,6R,7R)-3-(5-N,N-dimethylaminopentyl)-6-[(3R,1E)-3-hydroxy-4-phenoxy-1-butenyl]-7-hydroxybicyclo[3.3.0]-2-octene
1727) (1S,5S,6R,7R)-3-(5-N,N-diethylaminopentyl)-6-[(3R,1E)-3-hydroxy-4-phenoxy-1-butenyl]-7-hydroxybicyclo[3.3.0]-2-octene
1728) (1S,5S,6R,7R)-3-[5-N-(3-hydroxypropyl)aminopentyl]-6-[(3R,1E)-3-hydroxy-4-phenoxy-1-butenyl]-7-hydroxybicyclo[3.3.0]-2-octene
1729) (1S,5S,6R,7R)-3-[5-N-(4-pyridylmethyl)aminopentyl]-6-[(3R,1E)-3-hydroxy-4-phenoxy-1-butenyl]-7-hydroxybicyclo[3.3.0]-2-octene
1730) (1S,5S,6R,7R)-3-[5-N,N-diisopropylaminopentyl]-6-[(3R,1E)-3-hydroxy-4-phenoxy-1-butenyl]-7-hydroxybicyclo[3.3.0]-2-octene
1731) (1S,5S,6R,7R)-3-[5-(1-pyrrolidinyl)pentyl]-6-[(3R,1E)-3-hydroxy-4-phenoxy-1-butenyl]-7-hydroxybicyclo[3.3.0]-2-octene
1732) (1S,5S,6R,7R)-3-(5-piperidinopentyl)-6-[(3R,1E)-3-hydroxy-4-phenoxy-1-butenyl]-7-hydroxybicyclo[3.3.0]-2-octene
1733) (1S,5S,6R,7R)-3-(5-morpholinopentyl)-6-[(3R,1E)-3-hydroxy-4-phenoxy-1-butenyl]-7-hydroxybicyclo[3.3.0]-2-octene
1734) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-4-phenoxy-1-butenyl group
1735) (1S,5S,6R,7R)-3-(5-aminopentyl)-6-[(3R,1E)-3-hydroxy-1-octenyl]-7-hydroxy bicyclo[3.3.0]-2-octene
1736) (1S,5S,6R,7R)-3-(5-N,N-dimethylaminopentyl)-6-[(3R,1E)-3-hydroxy-1-octenyl]-7-hydroxybicyclo[3.3.0]-2-octene
1737) (1S,5S,6R,7R)-3-(5-N,N-diethylaminopentyl)-6-[(3R,1E)-3-hydroxy-1-octenyl]-7-hydroxybicyclo[3.3.0]-2-octene 1738) (1S,5S,6R,7R)-3-[5-N-(3-hydroxypropyl)aminopentyl]-6-[(3R,1E)-3-hydroxy-1-octenyl]-7-hydroxybicyclo[3.3.0]-2-octene
1739) (1S,5S,6R,7R)-3-[5-N-(4-pyridylmethyl)aminopentyl]-6-[(3R,1E)-3-hydroxy-1-octenyl]-7-hydroxybicyclo[3.3.0]-2-octene
1740) (1S,5S,6R,7R)-3-[5-N,N-diisopropylaminopentyl]-6-[(3R,1E)-3-hydroxy-1-octenyl]-7-hydroxybicyclo[3.3.0]-2-octene
1741) (1S,5S,6R,7R)-3-[5-(1-pyrrolidinyl)pentyl]-6-[(3R,1E)-3-hydroxy-1-octenyl]-7-hydroxy bicyclo[3.3.0]-2-octene
1742) (1S,5S,6R,7R)-3-(5-piperidinopentyl)-6-[(3R,1E)-3-hydroxy-1-octenyl]-7-hydroxy bicyclo[3.3.0]-2-octene
1743) (1S,5S,6R,7R)-3-(5-morpholinopentyl)-6-[(3R,1E)-3-hydroxy-1-octenyl]-7-hydroxy bicyclo[3.3.0]-2-octene
1744) compounds of compound numbers 1114 to 1194 of the examples given above, wherein the (3S,1E)-3-hydroxy-1-octenyl group, which is a substitution group at position 6 in the structure of the bicyclo[3.3.0]-2-octene cycle, has been replaced by the (3R,1E)-3-hydroxy-1-octenyl group
1745) (1S,5S,6R,7S)-3-(5-N,N-dimethylaminopentyl)-6-[(3S,1E)-3-hydroxy-1-octenyl]-7-hydroxybicyclo[3.3.0]-2-octene
1746) (1S,5S,6R,7S)-3-(5-N,N-dimethylaminopentyl)-6-[(3R,1E)-3-hydroxy-1-octenyl]-7-hydroxybicyclo[3.3.0]-2-octene
1747) (1R,5R,6S,7S)-3-(5-N,N-dimethylaminopentyl)-6-[(3R,1E)-3-hydroxy-1-octenyl]-7-hydroxybicyclo[3.3.0]-2-octene
1748) (1R,5R,6S,7S)-3-(5-N,N-dimethylaminopentyl)-6-[(3S,1E)-3-hydroxy-1-octenyl]-7-hydroxybicyclo[3.3.0]-2-octene
1749) (1R,5R,6S,7R)-3-(5-N,N-dimethylaminopentyl)-6-[(3R,1E)-3-hydroxy-1-octenyl]-7-hydroxybicyclo[3.3.0]-2-octene
1750) (1R,5R,6S,7R)-3-(5-N,N-dimethylaminopentyl)-6-[(3S,1E)-3-hydroxy-1-octenyl]-7-hydroxybicyclo[3.3.0]-2-octene
1751) (1S,5S,6R,7R)-3-(5-N,N-dimethylaminopentyl)-6-[(1E)-3-hydroxy-1-propenyl]-7-hydroxybicyclo[3.3.0]-2-octene
1752) (1S,5S,6R,7R)-3-(5-N,N-dimethylaminopentyl)-6-[(3S,1E)-3-hydroxy-1-butenyl]-7-hydroxybicyclo[3.3.0]-2-octene
1753) (1S,5S,6R,7R)-3-(5-N,N-dimethylaminopentyl)-6-[(3R,1E)-3-hydroxy-1-butenyl]-7-hydroxybicyclo[3.3.0]-2-octene
1754) (1S,5S,6R,7R)-3-(5-N,N-dimethylaminopentyl)-6-[(3S,1E)-3-hydroxy-1-pentenyl]-7-hydroxybicyclo[3.3.0]-2-octene
1755) (1S,5S,6R,7R)-3-(5-N,N-dimethylaminopentyl)-6-[(3R,1E)-3-hydroxy-1-pentenyl]-7-hydroxybicyclo[3.3.0]-2-octene
1756) (1S,5S,6R,7R)-3-(5-N,N-dimethylaminopentyl)-6-[(3S,1E)-3-hydroxy-1-hexenyl]-7-hydroxybicyclo[3.3.0]-2-octene
1757) (1S,5S,6R,7R)-3-(5-N,N-dimethylaminopentyl)-6-[(3R,1E)-3-hydroxy-1-hexenyl]-7-hydroxybicyclo[3.3.0]-2-octene
1758) (1S,5S,6R,7R)-3-(5-N,N-dimethylaminopentyl)-6-[(3S,1E)-3-hydroxy-1-heptenyl]-7-hydroxybicyclo[3.3.0]-2-octene
1759) (1S,5S,6R,7R)-3-(5-N,N-dimethylaminopentyl)-6-[(3R,1E)-3-hydroxy-1-heptenyl]-7-hydroxybicyclo[3.3.0]-2-octene
1760) (1S,5S,6R,7R)-3-(5-N,N-dimethylaminopentyl)-6-[(3S,1E)-3-hydroxy-1-nonenyl]-7-hydroxybicyclo[3.3.0]-2-octene
1761) (1S,5S,6R,7R)-3-(5-N,N-dimethylaminopentyl)-6-[(3R,1E)-3-hydroxy-1-nonenyl]-7-hydroxybicyclo[3.3.0]-2-octene
1762) (1S,5S,6R,7R)-3-(5-N,N-dimethylaminopentyl)-6-[(3S,1E)-3-hydroxy-1-decenyl]-7-hydroxybicyclo[3.3.0]-2-octene
1763) (1S,5S,6R,7R)-3-(5-N,N-dimethylaminopentyl)-6-[(3R,1E)-3-hydroxy-1-decenyl]-7-hydroxybicyclo[3.3.0]-2-octene
1764) (1S,5S,6R,7R)-3-(5-N,N-dimethylaminopentyl)-6-[(3S,4R,1E)-3-hydroxy-4-methyl-1-octenyl]-7-hydroxybicyclo[3.3.0]-2-octene
1765) (1S,5S,6R,7R)-3-(5-N,N-dimethylaminopentyl)-6-[(3S,4R,1E)-3-hydroxy-4-methyl-1-octenyl]-7-hydroxybicyclo[3.3.0]-2-octene
1766) (1S,5S,6R,7R)-3-(5-N,N-dimethylaminopentyl)-6-[(3S,4S,1E)-3-hydroxy-4-methyl-1-octenyl]-7-hydroxybicyclo[3.3.0]-2-octene
1767) (1S,5S,6R,7R)-3-(5-N,N-dimethylaminopentyl)-6-[(3R,4S,1E)-3-hydroxy-4-methyl-1-octenyl]-7-hydroxybicyclo[3.3.0]-2-octene
1768) (1S,5S,6R,7R)-3-(5-N,N-dimethylaminopentyl)-6-[(3R,1E)-3-hydroxy-3-cyclopentyl-1-propenyl]-7-hydroxybicyclo[3.3.0]-2-octene
1769) (1S,5S,6R,7R)-3-(5-N,N-dimethylaminopentyl)-6-[(3S,1E)-3-hydroxy-3-(3-ethylcyclopentyl)-1-propenyl]-7-hydroxybicyclo[3.3.0]-2-octene
1770) (1S,5S,6R,7R)-3-(5-N,N-dimethylaminopentyl)-6-[(3R,1E)-3-hydroxy-3-(3-ethylcyclopentyl)-1-propenyl]-7-hydroxybicyclo[3.3.0]-2-octene
1771) (1S,5S,6R,7R)-3-(5-N,N-dimethylaminopentyl)-6-[(3R,1E)-3-hydroxy-3-cyclohexyl-1-propenyl]-7-hydroxybicyclo[3.3.0]-2-octene
1772) (1S,5S,6R,7R)-3-(5-N,N-dimethylaminopentyl)-6-[(3R,1E)-3-hydroxy-4-cyclopentyl-1 butenyl]-7-hydroxybicyclo[3.3.0]-2-octene
1773) (1S,5S,6R,7R)-3-(5-N,N-dimethylaminopentyl)-6-[(3S, 1E)-3-hydroxy-4-cyclohexyl-1-butenyl]-7-hydroxybicyclo[3.3.0]-2-octene
1774) (1S,5S,6R,7R)-3-(5-N,N-dimethylaminopentyl)-6-[(3R, 1E)-3-hydroxy-4-cyclohexyl-1-butenyl]-7-hydroxybicyclo[3.3.0]-2-octene
1775) (1S,5S,6R,7R)-3-(5-N,N-dimethylaminopentyl)-6-[(3S,1E)-3-hydroxy-3-phenyl-1-propenyl]-7-hydroxybicyclo[3.3.0]-2-octene
1776) (1S,5S,6R,7R)-3-(5-N,N-dimethylaminopentyl)-6-[(3S, 1E)-3-hydroxy-4-phenyl-1-butenyl]-7-hydroxybicyclo[3.3.0]-2-octene
1777) (1S,5S,6R,7R)-3-(5-N,N-dimethylaminopentyl)-6-[(3R,1E)-3-hydroxy-4-phenyl-1-butenyl]-7-hydroxybicyclo[3.3.0]-2-octene
1778) (1S,5S,6R,7R)-3-(5-N,N-dimethylaminopentyl)-6-[(3S,1E)-3-hydroxy-5-phenyl-1-pentenyl]-7-hydroxybicyclo[3.3.0]-2-octene
1779) (1S,5S,6R,7R)-3-(5-N,N-dimethylaminopentyl)-6-[(3R,1E)-3-hydroxy-5-phenyl-1-pentenyl]-7-hydroxybicyclo[3.3.0]-2-octene
1780) (1S,5S,6R,7R)-3-(5-N,N-dimethylaminopentyl)-6-[(3S,1E)-3-hydroxy-3-(o-tolyl)-1-propenyl]-7-hydroxybicyclo[3.3.0]-2-octene
1781) (1S,5S,6R,7R)-3-(5-N,N-dimethylaminopentyl)-6-[(3R,1E)-3-hydroxy-3-(o-tolyl)-1-propenyl]-7-hydroxybicyclo[3.3.0]-2-octene 1782) (1S,5S,6R,7R)-3-(5-N,N-dimethylaminopentyl)-6-[(3S,1E)-3-hydroxy-3-(m-tolyl)-1-propenyl]-7-hydroxybicyclo[3.3.0]-2-octene 1783) (1S,5S,6R,7R)-3-(5-N,N-dimethylaminopentyl)-6-[(3R,1E)-3-hydroxy-3-(m-tolyl)-1-propenyl]-7-hydroxybicyclo[3.3.0]-2-octene 1784) (1S,5S,6R,7R)-3-(5-N,N-dimethylaminopentyl)-6-[(3S,1E)-3-hydroxy-3-(p-tolyl)-1-propenyl]-7-hydroxybicyclo[3.3.0]-2-octene 1785) (1S,5S,6R,7R)-3-(5-N,N-dimethylaminopentyl)-6-[(3R,1E)-3-hydroxy-3-(p-tolyl)-1-propenyl]-7-hydroxybicyclo[3.3.0]-2-octene 1786) (1S,5S,6R,7R)-3-(5-N,N-dimethylaminopentyl)-6-[(3S, 1E)-3-hydroxy-4-(o-tolyl)-1-butenyl]-7-hydroxybicyclo[3.3.0]-2-octene 1787) (1S,5S,6R,7R)-3-(5-N,N-dimethylaminopentyl)-6-[(3R,1E)-3-hydroxy-4-(o-tolyl)-1-butenyl]-7-hydroxybicyclo[3.3.0]-2-octene 1788) (1S,5S,6R,7R)-3-(5-N,N-dimethylaminopentyl)-6-[(3S,1E)-3-hydroxy-4-(p-tolyl)-1-butenyl]-7-hydroxybicyclo[3.3.0]-2-octene 1789) (1S,5S,6R,7R)-3-(5-N,N-dimethylaminopentyl)-6-[(3R,1E)-3-hydroxy-4-(p-tolyl)-1 butenyl]-7-hydroxybicyclo[3.3.0]-2-octene 1790) (1S,5S,6R,7R)-3-(5-N,N-dimethylaminopenty)-6-[(3S,1E)-3-hydroxy-5-(o-tolyl)-1-pentenyl]-7-hydroxybicyclo[3.3.0]-2-octene 1791) (1S,5S,6R,7R)-3-(5-N,N-dimethylaminopentyl-6-[(3R,1E)-3-hydroxy-5-(o-tolyl)-1-pentenyl]-7-hydroxybicyclo[3.3.0]-2-octene 1792) (1S,5S,6R,7R)-3-(5-N,N-dimethylaminopentyl)-6-[(3S,1E)-3-hydroxy-5-(m-tolyl)-1-pentenyl]-7-hydroxybicyclo[3.3.0]-2-octene 1793) (1S,5S,6R,7R)-3-(5-N,N-dimethylaminopentyl)-6-[(3R,1E)-3-hydroxy-5-(m-tolyl)-1-pentenyl]-7-hydroxybicyclo[3.3.0]-2-octene 1794) (1S,5S,6R,7R)-3-(5-N,N-dimethylaminopentyl)-6-[(3S,1E)-3-hydroxy-5-(p-tolyl)-1-pentenyl]-7-hydroxybicyclo[3.3.0]-2-octene 1795) (1S,5S,6R,7R)-3-(5-N,N-dimethylaminopentyl)-6-[(3R,1E)-3-hydroxy-5-(β-tolyl)-1-pentenyl]-7-hydroxybicyclo[3.3.0]-2-octene 1796) (1S,5S,6R,7R)-3-(5-N,N-dimethylaminopentyl)-6-[(3S,1E)-3-hydroxy-4-(4-methoxyphenyl)-1-butenyl]-7-hydroxybicyclo[3.3.0]-2-octene 1797) (1S,5S,6R,7R)-3-(5-N,N-dimethylaminopentyl)-6-[(3R,1E)-3-hydroxy-4-(4-methoxyphenyl)-1-butenyl]-7-hydroxybicyclo[3.3.0]-2-octene 1798) (1S,5S,6R,7R)-3-(5-N,N-dimethylaminopentyl)-6-[(3S,1E)-3-hydroxy-4-(4-methoxyphenyl)-1-butenyl]-7-hydroxybicyclo[3.3.0]-2-octene 1799) (1S,5S,6R,7R)-3-(5-N,N-dimethylaminopentyl)-6-[(3R,1E)-3-hydroxy-4-(4-N,N-dimethylaminophenyl)-1-butenyl]-7-hydroxybicyclo[3.3.0]-2-octene 1800) (1S,5S,6R,7R)-3-(5-N,N-dimethylaminopentyl)-6-[(3S,1E)-3-hydroxy-4-(3-chlorophenyl)-1-butenyl]-7-hydroxybicyclo[3.3.0]-2-octene 1801) (1S,5S,6R,7R)-3-(5-N,N-dimethylaminopentyl)-6-[(3R,1E)-3-hydroxy-4-(3-chlorophenyl)-1-butenyl]-7-hydroxybicyclo[3.3.0]-2-octene 1802) (1S,5S,6R,7R)-3-(5-N,N-dimethylaminopentyl)-6-[(3S,1E)-3-hydroxy-4-(4-chlorophenyl)-1-butenyl]-7-hydroxybicyclo[3.3.0]-2-octene 1803) (1S,5S,6R,7R)-3-(5-N,N-dimethylaminopentyl)-6-[(3R,1E)-3-hydroxy-4-(4-chlorophenyl)-1-butenyl]-7-hydroxybicyclo[3.3.0]-2-octene 1804) (1S,5S,6R,7R)-3-(5-N,N-dimethylaminopentyl)-6-[(3S,1E)-3-hydroxy-3-methyl-1-octenyl]-7-hydroxybicyclo[3.3.0]-2-octene 1805) (1S,5S,6R,7R)-3-(5-N,N-dimethylaminopentyl)-6-[(3R,1E)-3-hydroxy-3-methyl-1-octenyl]-7-hydroxybicyclo[3.3.0]-2-octene 1806) (1S,5S,6R,7R)-3-(5-N,N-dimethylaminopentyl)-6-[(3S,1E)-3-hydroxy-3-methyl-3-phenyl-1-propenyl]-7-hydroxybicyclo[3.3.0]-2-octene 1807) (1S,5S,6R,7R)-3-(5-N,N-dimethylaminopentyl)-6-[(3R,1E)-3-hydroxy-3-methyl-3-phenyl-1-propenyl]-7-hydroxybicyclo[3.3.0]-2-octene 1808) (1S,5S,6R,7R)-3-(5-N,N-dimethylaminopentyl)-6-[(3S,1E)-3-hydroxy-3-methyl-4-phenyl-1-butenyl]-7-hydroxybicyclo[3.3.0]-2-octene 1809) (1S,5S,6R,7R)-3-(5-N,N-dimethylaminopentyl)-6-[(3R,1E)-3-hydroxy-3-methyl-4-phenyl-1-butenyl]-7-hydroxybicyclo[3.3.0]-2-octene 1810) (1S,5S,6R,7R)-3-(5-N,N-dimethylaminopentyl)-6-[(3S,1E)-3-hydroxy-3-methyl-5-phenyl-1-pentenyl]-7-hydroxybicyclo[3.3.0]-2-octene 1811) (1S,5S,6R,7R)-3-(5-N,N-dimethylaminopentyl)-6-[(3R,1E)-3-hydroxy-3-methyl-5-phenyl-1-pentenyl]-7-hydroxybicyclo[3.3.0]-2-octene 1812) (1S,5S,6R,7R)-3-(5-N,N-dimethylaminopentyl)-6-[(3S,1E)-3-hydroxy-3-methyl-3(m-tolyl)-1-propenyl]-7-hydroxybicyclo[3.3.0]-2-octene 1813) (1S,5S,6R,7R)-3-(5-N,N-dimethylaminopentyl)-6-[(3R,1E)-3-hydroxy-3-methyl-3(m-tolyl)-1-propenyl]-7-hydroxybicyclo[3.3.0]-2-octene 1814) (1S,5S,6R,7R)-3-(5-N,N-dimethylaminopentyl)-6-[(3S,1E)-3-hydroxy-3-methyl-4-(m-tolyl)-1-butenyl]-7-hydroxybicyclo[3.3.0]-2-octene 1815) (1S,5S,6R,7R)-3-(5-N,N-dimethylaminopentyl)-6-[(3R,1E)-3-hydroxy-3-methyl-4-(m-tolyl)-1-butenyl]-7-hydroxybicyclo[3.3.0]-2-octene 1816) (1S,5S,6R,7R)-3-(5-N,N-dimethylaminopentyl)-6-[(3S,1E)-3-hydroxy-3-methyl-5(m-tolyl)-1-pentenyl]-7-hydroxybicyclo[3.3.0]-2-octene 1817) (1S,5S,6R,7R)-3-(5-N,N-dimethylaminopentyl)-6-[(3R,1E)-3-hydroxy-3-methyl-5(m-tolyl)-1-pentenyl]-7-hydroxybicyclo[3.3.0]-2-octene 1818) (1S,5S,6R,7R)-3-(5-N,N-dimethylaminopentyl)-6-[(3S,1E)-3-hydroxy-4,4-dimethyl-loctenyl]-7-hydroxybicyclo [3.3.0]-2-octene 1819) (1S,5S,6R,7R)-3-(5-N,N-dimethylaminopentyl)-6-[(3R,1E)-3-hydroxy-4,4-dimethyl-loctenyl]-7-hydroxybicyclo[3.3.0]-2-octene 1820) (1S,5S,6R,7R)-3-(5-N,N-dimethylaminopentyl)-6-[(3S,1E,5Z)-3-hydroxy-1,5-octadienyl]-7-hydroxybicyclo[3.3.0]-2-octene 1821) (1S,5S,6R,7R)-3-(5-N,N-dimethylaminopentyl)-6-[(3R,1E,5Z)-3-hydroxy-1,5-octadienyl]-7-hydroxybicyclo[3.3.0]-2-octene 1822) (1S,5S,6R,7R)-3-(5-N,N-dimethylaminopentyl)-6-[(3S,1E)-3-hydroxy-6-octyn-1-enyl]7-hydroxybicyclo[3.3.0]-2-octene 1823) (1S,5S,6R,7R)-3-(5-N,N-dimethylaminopentyl)-6-[(3R,1E)-3-hydroxy-6-octyn-1-enyl]-7-hydroxybicyclo[3.3.0]-2-octene 1824) (1S,5S,6R,7R)-3-(5-N,N-dimethylaminopentyl)-6-[(3R,4S,1E)-3-hydroxy-4-methyl-6-octyn-1-enyl]-7-hydroxybicyclo[3.3.0]-2-octene 1825) (1S,5S,6R,7R)-3-(5-N,N-dimethylaminopentyl)-6-[(3S,4R,1E)-3-hydroxy-4-methyl-6-octyn-1-enyl]-7-hydroxybicyclo[3.3.0]-2-octene 1826) (1S,5S,6R,7R)-3-(5-N,N-dimethylaminopentyl)-6-[(3R, E)-3-hydroxy-4,4-dimethyl-6-octyn-1-enyl]-7-hydroxybicyclo[3.3.0]-2-octene 1827) (1S,5S,6R,7R)-3-(5-N,N-dimethylaminopentyl)-6-[(3S,1E)-3-hydroxy-4,4-dimethyl-6-octyn-1-enyl]-7-hydroxybicyclo[3.3.0]-2-octene 1828) (1S,5S,6R,7R)-3-(5-N,N-dimethylaminopentyl)-6-[(3R,4S,1E)-3-hydroxy-4-methyl-6-nonyn-1-enyl]-7-hydroxybicyclo[3.3.0]-2-octene 1829) (1S,5S,6R,7R)-3-(5-N,N-dimethylaminopentyl)-6-[(3S,4R,1E)-3-hydroxy-4-methyl-6-nonyn-1-enyl]-7-hydroxybicyclo [3.3.0]-2-octene 1830) (1S,5S,6R,7R)-3-(5-N,N-dimethylaminopentyl)-6-[(3S,4S, E)-3-hydroxy-4-methyl-6-nonyn-1-enyl]-7-hydroxybicyclo[3.3.0]-2-octene 1831) (1S,5S,6R,7R)-3-(5-N,N-dimethylaminopentyl)-6-[(3S,4R, E)-3-hydroxy-4-methyl-6-nonyn-1-enyl]-7-hydroxybicyclo[3.3.0]-2-octene 1832) (1S,5S,6R,7R)-3-(5-N,N-dimethylaminopentyl)-6-[(3S,1E)-3-hydroxy-4-phenoxy-1-butenyl]-7-hydroxybicyclo[3.3.0]-2-octene 1833) (1S,5S,6S,7R)-3-(5-N,N-dimethylaminopentyl)-6-[(3S)-3-hydroxy-1-octynyl]-7-hydroxybicyclo[3.3.0]-2-octene 1834) (1S,5S,6S,7R)-3-(5-N,N-dimethylaminopentyl)-6-[(3R)-3-hydroxy-1-octynyl]-7-hydroxybicyclo[3.3.0]-2-octene 1835) (1S,5S,6R,7R)-3-(5-N,N-dimethylaminopentyl)-6-[(3S, 1Z)-3-hydroxy-1-octenyl]-7-hydroxybicyclo[3.3.0]-2-octene 1836) (1S,5S,6R,7R)-3-(5-N,N-dimethylaminopentyl)-6-[(3R,1Z)-3-hydroxy-1-octenyl]-7-hydroxybicyclo[3.3.0]-2-octene 1837) (1S,5S,6R,7R)-3-(5-N,N-dimethylaminopentyl)-6-[(3S)-3-hydroxyoctyl]-7-hydroxy bicyclo[3.3.0]-2-octene 1838) (1S,5S,6R,7R)-3-(5-N,N-dimethylaminopentyl)-6-[(3R)-3-hydroxyoctyl]-7-hydroxy bicyclo[3.3.0]-2-octene 1839) (1S,5S,6R,7R)-3-(5-N,N-dimethylaminopentyl)-6-[(3S)-3-hydroxy-3-methyloctyl]-7-hydroxybicyclo[3.3.0]-2-octene 1840) (1S,5S,6R,7R)-3-(5-N,N-dimethylaminopentyl)-6-[(3R)-3-hydroxy-3-methyloctyl]-7-hydroxybicyclo[3.3.0]-2-octene 1841) (1S,5S,6R,7R)-3-(5-N,N-dimethylaminopentyl)-6-[(3S)-3-hydroxy-4,4-dimethyloctyl]-7-hydroxybicyclo[3.3.0]-2-octene 1842) (1S,5S,6R,7R)-3-(5-N,N-dimethylaminopentyl)-6-[(3R)-3-hydroxy-4,4-dimethyloctyl]-7-hydroxybicyclo[3.3.0]-2-octene 1843) (1S,5S,6R,7R)-3-(5-N,N-dimethylaminopentyl)-6-[(3S)-3-hydroxy-3-phenylpropyl]-7-hydroxybicyclo[3.3.0]-2-octene 1844) (1S,5S,6R,7R)-3-(5-N,N-dimethylaminopentyl)-6-[(3R)-3-hydroxy-3-phenylpropyl]-7-hydroxybicyclo[3.3.0]-2-octene 1845) (1S,5S,6R,7R)-3-(5-N,N-dimethylaminopentyl)-6-[(3S)-3-hydroxy-4-phenylbutyl]-7-hydroxybicyclo[3.3.0]-2-octene 1846) (1S,5S,6R,7R)-3-(5-N,N-dimethylaminopentyl)-6-[(3R)-3-hydroxy-4-phenylbutyl]-7-hydroxybicyclo[3.3.0]-2-octene 1847) (1S,5S,6R,7R)-3-(5-N,N-dimethylaminopentyl)-6-[(3S)-3-hydroxy-4-(m-tolyl)butyl]-7-hydroxybicyclo[3.3.0]-2-octene 1848) (1S,5S,6R,7R)-3-(5-N,N-dimethylaminopentyl)-6-[(3R)-3-hydroxy-4-(m-tolyl)butyl]-7-hydroxybicyclo[3.3.0]-2-octene 1849) (1S,5S,6R,7R)-3-(5-N,N-dimethylaminopentyl)-6-[(3S)-3-hydroxy-3-cyclopentylpropyl]7-hydroxybicyclo[3.3.0]-2-octene 1850) (1S,5S,6%,7R)-3-(5-N,N-dimethylaminopentyl)-6-[(3R)-3-hydroxy-3-cyclopentylpropyl]-7-hydroxybicyclo[3.3.0]-2-octene 1851) (1S,5S,6R,7R)-3-(5-N,N-dimethylaminopentyl)-6-[(4S,1E)-4-hydroxy-4-ethyl-1-octenyl]-7-hydroxybicyclo[3.3.0]-2-octene 1852) (1S,5S,6R,7R)-3-(5-N,N-dimethylaminopentyl)-6-[(4R,1E)-4-hydroxy-4-ethyl-1-octenyl]-7-hydroxybicyclo[3.3.0]-2-octene 1853) (1S,5S,6R,7R)-3-(5-N,N-dimethylaminopentyl)-6-[(1E)-4-hydroxy-4-butyl-1-octenyl]-7-hydroxybicyclo[3.3.0]-2-octene 1854) (1S,5S,6R,7R)-3-(5-N,N-dimethylaminopentyl)-6-[(4S,1E)-4-hydroxy-4-butyl-1,5-hexadienyl]-7-hydroxybicyclo [3.3.0]-2-octene 1855) (1S,5S,6R,7R)-3-(5-N,N-dimethylaminopentyl)-6-[(4R,1E)-4-hydroxy-4-butyl-1,5-hexadienyl]-7-hydroxybicyclo [3.3.0]-2-octene 1856) (1S,5S,6R,7R)-3-(5-N,N-dimethylaminopentyl)-6-[(4S,1E)-4-hydroxy-4-cyclopentyl-1-pentenyl]-7-hydroxybicyclo[3.3.0]-2-octene 1857) (1S,5S,6R,7R)-3-(5-N,N-dimethylaminopentyl)-6-[(4R,1E)-4-hydroxy-4-cyclopentyl-1-pentenyl]-7-hydroxybicyclo[3.3.0]-2-octene 1858) (1S,5S,6R,7R)-3-(S—N,N-dimethylaminopentyl)-6-[(4S,1E)-4-hydroxy-4-cyclohexyl-1-pentenyl]-7-hydroxybicyclo[3.3.0]-2-octene 1859) (1S,5S,6R,7R)-3-(5-N,N-dimethylaminopentyl)-6-[(4R,1E)-4-hydroxy-4-cyclohexyl-1-pentenyl]-7-hydroxybicyclo[3.3.0]-2-octene 1860) (1S,5S,6R,7R)-3-(5-N,N-dimethylaminopentyl)-6-[(4S,1E)-4-hydroxy-4-phenyl-1-pentenyl]-7-hydroxybicyclo[3.3.0]-2-octene 1861) (1S,5S,6R,7R)-3-(5-N,N-dimethylaminopentyl)-6-[(4R,1E)-4-hydroxy-4-phenyl-1-pentenyl]-7-hydroxybicyclo[3.3.0]-2-octene 1862) (1S,5S,6R,7R)-3-(5-N,N-dimethylaminopentyl)-6-[(1E)-3-(1-hydroxycyclopentyl)-1-propenyl]-7-hydroxybicyclo[3.3.0]-2-octene 1863) (1S,5S,6R,7R)-3-(5-N,N-dimethylaminopentyl)-6-[(1E)-3-(1-hydroxycyclohexyl)-1-propenyl]-7-hydroxybicyclo[3.3.0]-2-octene 1864) (1S,5S,6R,7R)-3-(5-N,N-dimethylaminopentyl)-6-[(4S,1E)-4-hydroxy-1-octenyl]-7-hydroxybicyclo[3.3.0]-2-octene 1865) (1S,5S,6R,7R)-3-(5-N,N-dimethylaminopentyl)-6-[(4R,1E)-4-hydroxy-1-octenyl]-7-hydroxybicyclo[3.3.0]-2-octene 1866) (1S,5S,6R,7R)-3-(5-N,N-dimethylaminopentyl)-6-[(1E)-1-octenyl]-7-hydroxy bicyclo[3.3.0]-2-octene 1867) (1S,5S,6R,7R)-3-(5-N,N-dimethylaminopentyl)-6-[(1E,3E)-1,3-octadienyl]-7-hydroxy bicyclo[3.3.0]-2-octene 1868) (1S,5S,6R,7R)-3-(5-N,N-dimethylaminopentyl)-6-[(1E,8S)-5-methyl-1-nonenyl]-7-hydroxybicyclo[3.3.0]-2-octene 1869) (1S,5S,6R,7R)-3-(5-N,N-dimethylaminopentyl)-6-[(1E,9R)-5-methyl-1-nonenyl]-7-hydroxybicyclo[3.3.0]-2-octene 1870) (1S,5S,6R,7R)-3-(5-N,N-dimethylaminopentyl)-6-[(1E,3E,5S)-5-methyl-1,3-nonadienyl]-7-hydroxybicyclo[3.3.0]-2-octene 1871) (1S,5S,6R,7R)-3-(5-N,N-dimethylaminopentyl)-6-[(1E,3E,5R)-5-methyl-1,3-nonadienyl]-7-hydroxybicyclo[3.3.0]-2-octene 1872) (1S,5S,6R,7R)-3-(5-N,N-dimethylaminopentyl)-6-[(1E,4R)-4-methyl-1-octenyl]-7-hydroxybicyclo[3.3.0]-2-octene 1873) (1S,5S,6R,7R)-3-(5-N,N-dimethylaminopentyl)-6-[(1E,4S)-4-methyl-1-octenyl]-7-hydroxybicyclo[3.3.0]-2-octene 1874) (1S,5S,6R,7R)-3-(5-N,N-dimethylaminopentyl)-6-[(1E,3E)-4-methyl-1,3-octadienyl]-7-hydroxybicyclo[3.3.0]-2-octene 1875) (1S,5S,6R,7R)-3-(5-N,N-dimethylaminopentyl)-6-[(1E,4R)-4-ethyl-1-octenyl]-7-hydroxybicyclo[3.3.0]-2-octene 1876) (1S,5S,6R,7R)-3-(5-N,N-dimethylaminopentyl)-6-[(1E,4S)-4-ethyl-1-octenyl]-7-hydroxybicyclo[3.3.0]-2-octene 1877) (1S,5S,6R,7R)-3-(5-N,N-dimethylaminopentyl)-6-[(1E,3E)-4-ethyl-1,3-octadienyl]-7-hydroxybicyclo[3.3.0]-2-octene 1878) (1S,5S,6R,7R)-3-(5-N,N-dimethylaminopentyl)-6-[(1E)-4-butyl-1,3-octadienyl]-7-hydroxybicyclo[3.3.0]-2-octene 1879) (1S,5S,6R,7R)-3-(5-N,N-dimethylaminopentyl)-6-[(1E,5Z)-1,5-octadienyl]-7-hydroxybicyclo[3.3.0]-2-octene 1880) (1S,5S,6R,7R)-3-(5-N,N-dimethylaminopentyl)-6-[(1E,3E,5Z)-1,3,5-octatrienyl]-7-hydroxybicyclo[3.3.0]-2-octene 1881) (1S,5S,6R,7R)-3-(5-N,N-dimethylaminopentyl)-6-[(1E)-3-cyclopentyliden-1-propenyl]-7-hydroxybicyclo[3.3.0]-2-octene 1882) (1S,5S,6R,7R)-3-(5-N,N-dimethylaminopentyl)-6-[(1E)-3-cyclohexyliden-1-propenyl]-7-hydroxybicyclo[3.3.0]-2-octene 1883) (1S,5S,6R,7R)-3-(5-N,N-dimethylaminopentyl)-6-[(1E)-2-phenylvinyl]-7-hydroxy bicyclo[3.3.0]-2-octene 1884) (1S,5S,6R,7R)-3-(5-N,N-dimethylaminopentyl)-6-[(1E)-2-(o-tolyl)vinyl]-7-hydroxy bicyclo[3.3.0]-2-octene 1885) (1S,5S,6R,7R)-3-(5-N,N-dimethylaminopentyl)-6-[(1E)-2-(m-tolyl)vinyl]-7-hydroxy bicyclo[3.3.0]-2-octene 1886) (1S,5S,6R,7R)-3-(5-N,N-dimethylaminopentyl)-6-[(1E)-2-(p-tolyl)vinyl]-7-hydroxy bicyclo[3.3.0]-2-octene 1887) (1S,5S,6R,7R)-3-(5-N,N-dimethylaminopentyl)-6-[(1E)-3-phenyl-1-propenyl]-7-hydroxy bicyclo[3.3.0]-2-octene 1888) (1S,5S,6R,7R)-3-(5-N,N-dimethylaminopentyl)-6-[(1E)-4-phenyl-1-butenyl]-7-hydroxy bicyclo[3.3.0]-2-octene.

1889) (1S,5S,6R,7R)-3-(5-N,N-dimethylaminopentyl)-6-[(1E,3E)-4-phenyl-1,3-butadienyl]-7-hydroxybicyclo[3.3.0]-2-octene 1890) (1S,5S,6R,7R)-3-(5-N,N-dimethylaminopentyl)-6-[(1E,3E)-4-phenyl-3-methyl-1,3-butadienyl]-7-hydroxybicyclo[3.3.0]-2-octene 1891) (1S,5S,6R,7%)-3-(5-N,N-dimethylaminopentyl)-6-[(1E)-4-(o-tolyl)-1-butenyl]-7-hydroxy bicyclo[3.3.0]-2-octene 1892) (1S,5S,6R,7R)-3-(5-N,N-dimethylaminopentyl)-6-[(1E)-4-(m-tolyl)-1-butenyl]-7-hydroxybicyclo [3.3.0]-2-octene 1893) (1S,5S,6R,7R)-3-(5-N,N-dimethylaminopentyl)-6-[(1E)-4-(p-tolyl)-1-butenyl]-7-hydroxy bicyclo[3.3.0]-2-octene 1894) (1S,5S,6R,7R)-3-(5-N,N-dimethylaminopentyl)-6-[(1E,3E)-4-(m-tolyl)-1,3-butadienyl]-7-hydroxybicyclo[3.3.0]-2-octene 1895) (1S,5S,6R,7R)-3-(5-N,N-dimethylaminopentyl)-6-[(1E)-5-(m-tolyl)-1-pentenyl]-7-hydroxybicyclo[3.3.0]-2-octene 1896) (1S,5S,6R,7R)-3-(5-N,N-dimethylaminopentyl)-6-[(1E,3E)-5-(m-tolyl)-1,3-pentadienyl]-7-hydroxybicyclo[3.3.0]-2-octene 1897) (1S,5S,6R,7R)-3-(5-N,N-dimethylaminopentyl)-6-[(1E)-4,4-bisphenylsulfonyl-4-(m-tolyl)-1-butenyl]-7-hydroxybicyclo[3.3.0]-2-octene 1898) (1S,5S,6R,7R)-3-(5-N,N-dimethylaminopentyl)-6-[(1E,3E)-5-(m-tolyl)-1,3-hexadienyl]-7-hydroxybicyclo[3.3.0]-2-octene 1899) (1S,5S,6R,7R)-3-(5-N,N-dimethylaminopentyl)-6-(4-phenoxybutyl)-7-hydroxy bicyclo[3.3.0]-2-octene 1900) (1S,5S,6R,7R)-3-(5-N,N-dimethylaminopentyl)-6-[(1E)-3-oxo-1-propenyl]-7-hydroxy bicyclo[3.3.0]-2-octene 1901) (1S,5S,6R,7R)-3-(5-N,N-dimethylaminopentyl)-6-[(1E)-3-oxo-1-butenyl]-7-hydroxy bicyclo[3.3.0]-2-octene 1902) (1S,5S,6R,7R)-3-(5-N,N-dimethylaminopentyl)-6-[(1E)-3-oxo-1-pentenyl]-7-hydroxy bicyclo[3.3.0]-2-octene 1903) (1S,5S,6R,7R)-3-(5-N,N-dimethylaminopentyl)-6-[(1E)-3-oxo-1-hexenyl]-7-hydroxy bicyclo[3.3.0]-2-octene 1904) (1S,5S,6R,7R)-3-(5-N,N-dimethylaminopentyl)-6-[(1E)-3-oxo-1-heptenyl]-7-hydroxy bicyclo[3.3.0]-2-octene 1905) (1S,5S,6R,7R)-3-(5-N,N-dimethylaminopentyl)-6-[(1E)-3-oxo-1-octenyl]-7-hydroxy bicyclo[3.3.0]-2-octene 1906) (1S,5S,6R,7R)-3-(5-N,N-dimethylaminopentyl)-6-[(1E)-3-oxo-1-nonenyl]-7-hydroxy bicyclo[3.3.0]-2-octene 1907) (1S,5S,6R,7R)-3-(5-N,N-dimethylaminopentyl)-6-[(1E)-3-oxo-1-decenyl]-7-hydroxy bicyclo[3.3.0]-2-octene 1908) (1S,5S,6R,7R)-3-(5-N,N-dimethylaminopentyl)-6-[(4S,1E)-3-oxo-4-methyl-1-octenyl]-7-hydroxybicyclo[3.3.0]-2-octene 1909) (1S,5S,6R,7R)-3-(5-N,N-dimethylaminopentyl)-6-[(4R,1E)-3-oxo-4-methyl-1-octenyl]-7-hydroxybicyclo[3.3.0]-2-octene 1910) (1S,5S,6R,7R)-3-(5-N,N-dimethylaminopentyl)-6-[(1E)-3-oxo-4,4-dimethyl-1-octenyl]-7-hydroxybicyclo[3.3.0]-2-octene 1911) (1S,5S,6R,7R)-3-(5-N,N-dimethylaminopentyl)-6-[(5S,1E)-3-oxo-5-methyl-1-nonenyl]-7-hydroxybicyclo[3.3.0]-2-octene 1912) (1S,5S,6R,7R)-3-(5-N,N-dimethylaminopentyl)-6-[(5R,1E)-3-oxo-5-methyl-1-nonenyl]-7-hydroxybicyclo[3.3.0]-2-octene 1913) (1S,5S,6R,7R)-3-(5-N,N-dimethylaminopentyl)-6-[(1E)-3-oxo-3-cyclopentyl-1-propenyl]-7-hydroxybicyclo[3.3.0]-2-octene 1914) (1S,5S,6R,7R)-3-(5-N,N-dimethylaminopentyl)-6-[(1E)-3-oxo-3-cyclohexyl-1-propenyl]-7-hydroxybicyclo[3.3.0]-2-octene
1915) (1S,5S,6R,7R)-3-(5-N,N-dimethylaminopentyl)-6-[(1E)-3-oxo-4-cyclopentyl-1-butenyl]-7-hydroxybicyclo[3.3.0]-2-octene
1916) (1S,5S,6R,7R)-3-(5-N,N-dimethylaminopentyl)-6-[(1E)-3-oxo-4-cyclohexyl-1-butenyl]-7-hydroxybicyclo[3.3.0]-2-octene
1917) (1S,5S,6R,7R)-3-(5-N,N-dimethylaminopentyl)-6-[(1E)-3-oxo-3-phenyl-S-propenyl]-7-hydroxybicyclo[3.3.0]-2-octene
1918) (1S,5S,6R,7R)-3-(5-N,N-dimethylaminopentyl)-6-[(1E)-3-oxo-4-phenyl-1-butenyl]-7-hydroxybicyclo[3.3.0]-2-octene
1919) (1S,5S,6R,7R)-3-(5-N,N-dimethylaminopentyl)-6-[(1E)-3-oxo-5-phenyl-1-pentenyl]-7-hydroxybicyclo[3.3.0]-2-octene
1920) (1S,5S,6R,7R)-3-(5-N,N-dimethylaminopentyl)-6-[(1E)-3-oxo-3-(o-tolyl)-1-propenyl]-7-hydroxybicyclo[3.3.0]-2-octene
1921) (1S,5S,6R,7R)-3-(5-N,N-dimethylaminopentyl)-6-[(1E)-3-oxo-3-(m-tolyl)-1-propenyl]-7-hydroxybicyclo[3.3.0]-2-octene
1922) (1S,5S,6R,7R)-3-(5-N,N-dimethylaminopentyl)-6-[(1E)-3-oxo-3-(p-tolyl)-1-propenyl]-7-hydroxybicyclo[3.3.0]-2-octene
1923) (1S,5S,6R,7R)-3-(5-N,N-dimethylaminopentyl)-6-[(1E)-3-oxo-4-(o-tolyl)-1-butenyl]-7-hydroxybicyclo[3.3.0]-2-octene
1924) (1S,5S,6R,7R)-3-(5-N,N-dimethylaminopentyl)-6-[(1E)-3-oxo-4-(m-tolyl)-1-butenyl]-7-hydroxybicyclo[3.3.0]-2-octene
1925) (1S,5S,6R,7R)-3-(5-N,N-dimethylaminopentyl)-6-[(1E)-3-oxo-4-(p-tolyl)-1-butenyl]-7-hydroxybicyclo[3.3.0]-2-octene
1926) (1S,5S,6R,7R)-3-(5-N,N-dimethylaminopentyl)-6-[(1E)-3-oxo-5-(o-tolyl)-1-pentenyl]-7-hydroxybicyclo[3.3.0]-2-octene
1927) (1S,5S,6R,7R)-3-(5-N,N-dimethylaminopentyl)-6-[(1E)-3-oxo-5-(m-tolyl)-1-pentenyl]-7-hydroxybicyclo[3.3.0]-2-octene
1928) (1S,5S,6R,7R)-3-(5-N,N-dimethylaminopentyl)-6-[(1E)-3-oxo-5-(p-tolyl)-1-pentenyl]-7-hydroxybicyclo[3.3.0]-2-octene
1929) (1S,5S,6R,7R)-3-(5-N,N-dimethylaminopentyl)-6-hydroxymethyl-7-hydroxy bicyclo[3.3.0]-2-octene
1930) (1S,5S,6S,7R)-3-(5-N,N-dimethylaminopentyl)-6-[(1R)-1-hydroxyethyl]-7-hydroxy bicyclo[3.3.0]-2-octene
1931) (1S,5S,6S,7R)-3-(5-N,N-dimethylaminopentyl)-6-[(1S)-1-hydroxyethyl]-7-hydroxy bicyclo[3.3.0]-2-octene
1932) (1S,5S,6S,7R)-3-(5-N,N-dimethylaminopentyl)-6-[(1R)-1-hydroxypentyl]-7-hydroxy bicyclo[3.3.0]-2-octene
1933) (1S,5S,6S,7R)-3-(5-N,N-dimethylaminopentyl)-6-[(1S)-1-hydroxypentyl]-7-hydroxy bicyclo[3.3.0]-2-octene
1934) (1S,5S,6R,7R)-3-(5-N,N-dimethylaminopentyl)-6-[(1R)-1-hydroxy-1-methylbutyl]-7-hydroxybicyclo[3.3.0]-2-octene
1935) (1S,5S,6R,7R)-3-(5-N,N-dimethylaminopentyl)-6-[(1S)-1-hydroxy-1-methylbutyl]-7-hydroxybicyclo[3.3.0]-2-octene
1936) (1S,5S,6R,7R)-3-(5-N,N-dimethylaminopentyl)-6-[(1R,2E)-1-hydroxy-2-nonenyl]-7-hydroxybicyclo[3.3.0]-2-octene
1937) (1S,5S,6R,7R)-3-(5-N,N-dimethylaminopentyl)-6-[(1S,2E)-1-hydroxy-2-nonenyl]-7-hydroxybicyclo[3.3.0]-2-octene
1938) (1S,5S,6R,7R)-3-(5-N,N-dimethylaminopentyl)-6-[(1R,3S,2E)-1,3-dihydroxy-2-nonenyl]-7-hydroxybicyclo[3.3.0]-2-octene
1939) (1S,5S,6R,7R)-3-(5-N,N-dimethylaminopentyl)-6-[(1S,3S,2E)-1,3-dihydroxy-2-nonenyl]-7-hydroxybicyclo[3.3.0]-2-octene
1940) (1S,5S,6R,7R)-3-(5-N,N-dimethylaminopentyl)-6-[(1R,3S,2E)-1,3-dihydroxy-4-cyclopentyl-2-butenyl]-7-hydroxybicyclo[3.3.0]-2-octene
1941) (1S,5S,6R,7R)-3-(5-N,N-dimethylaminopentyl)-6-[(1S,3S,2E)-1,3-dihydroxy-4-cyclopentyl-2-butenyl]-7-hydroxybicyclo[3.3.0]-2-octene
1942) (1S,5S,6R,7R)-3-(5-N,N-dimethylaminopentyl)-6-[(1R,3S,2E)-1,3-dihydroxy-5-phenyl-2-pentenyl]-7-hydroxybicyclo[3.3.0]-2-octene
1943) (1S,5S,6R,7R)-3-(5-N,N-dimethylaminopentyl)-6-[(1S,3S,2E)-1,3-dihydroxy-5-phenyl-2-pentenyl]-7-hydroxybicyclo[3.3.0]-2-octene
1944) (1S,5S,6R,7R)-3-(5-N,N-dimethylaminopentyl)-6-[(1S)-1-hydroxy-2-pentynyl]-7-hydroxybicyclo[3.3.0]-2-octene
1945) (1S,5S,6R,7R)-3-(5-N,N-dimethylaminopentyl)-6-[(1R)-1-hydroxy-2-pentynyl]-7-hydroxybicyclo[3.3.0]-2-octene
1946) (1S,5S,6S,7R)-3-(5-N,N-dimethylaminopentyl)-6-[(1R)-1-hydroxy-5-phenoxypentyl]-7-hydroxybicyclo[3.3.0]-2-octene
1947) (1S,5S,6S,7R)-3-(5-N,N-dimethylaminopentyl)-6-[(1S)-1-hydroxy-5-phenoxypentyl]-7-hydroxybicyclo[3.3.0]-2-octene
1948) (1S,5S,6R,7R)-3-(5-N,N-dimethylaminopentyl)-6-[(R)-hydroxyphenylmethyl]-7-hydroxybicyclo[3.3.0]-2-octene
1949) (1S,5S,6R,7R)-3-(5-N,N-dimethylaminopentyl)-6-[(S)-hydroxyphenylmethyl]-7-hydroxybicyclo[3.3.0]-2-octene
1950) (1S,5S,6R,7R)-3-(5-N,N-dimethylaminopentyl)-6-[(R)-hydroxy(o-tolyl)methyl]-7-hydroxybicyclo[3.3.0]-2-octene
1951) (1S,5S,6R,7R)-3-(5-N,N-dimethylaminopentyl)-6-[(S)-hydroxy(o-tolyl)methyl]-7-hydroxybicyclo[3.3.0]-2-octene
1952) (1S,5S,6R,7R)-3-(5-N,N-dimethylaminopentyl)-6-[(R)-hydroxy(m-tolyl)methyl]-7-hydroxybicyclo[3.3.0]-2-octene
1953) (1S,5S,6R,7R)-3-(5-N,N-dimethylaminopentyl)-6-[(S)-hydroxy(m-tolyl)methyl]-7-hydroxybicyclo[3.3.0]-2-octene
1954) (1S,5S,6R,7R)-3-(5-N,N-dimethylaminopentyl)-6-[(R)-hydroxy(p-tolyl)methyl]-7-hydroxybicyclo[3.3.0]-2-octene
1955) (1S,5S,6R,7R)-3-(5-N,N-dimethylaminopentyl)-6-[(S)-hydroxy(p-tolyl)methyl]-7-hydroxybicyclo[3.3.0]-2-octene
1956) (1S,5S,6R,7R)-3-(5-N,N-dimethylaminopentyl)-6-[(R)-hydroxy(4-methoxyphenyl) methyl]-7-hydroxybicyclo[3.3.0]-2-octene
1957) (1S,5S,6R,7R)-3-(5-N,N-dimethylaminopentyl)-6-[(S)-hydroxy(4-methoxyphenyl) methyl]-7-hydroxybicyclo[3.3.0]-2-octene
1958) (1S,5S,6R,7R)-3-(5-N,N-dimethylaminopentyl)-6-[(R)-hydroxy(4-N,N-dimethylamino phenyl)methyl]-7-hydroxybicyclo[3.3.0]-2-octene 1959) (1S,5S,6R,7R)-3-(5-N,N-dimethylaminopentyl)-6-[(S)-hydroxy(4-N,N-dimethylamino phenyl)methyl]-7-hydroxybicyclo[3.3.0]-2-octene 1960) (1S,5S,6R,7R)-3-(5-N,N-dimethylaminopentyl)-6-[(R)-hydroxy(3-chlorophenyl)methyl]-7-hydroxybicyclo[3.3.0]-2-octene 1961) (1S,5S,6R,7R)-3-(5-N,N-dimethylaminopentyl)-6-[(S)-hydroxy(3-chlorophenyl)methyl]-7-hydroxybicyclo[3.3.0]-2-octene 1962) (1S,5S,6R,7R)-3-(5-N,N-dimethylaminopentyl)-6-formyl-7-hydroxybicyclo[3.3.0]-2-octene 1963) (1S,5S,6R,7R)-3-(5-N,N-dimethylaminopentyl)-6-acetyl-7-hydroxybicyclo[3.3.0]-2-octene 1964) (1S,5S,6R,7R)-3-(5-N,N-dimethylaminopenty)-6-benzoyl-7-hydroxybicyclo[3.3.0]-2-octene 1965) (1S,5S,6R,7R)-3-(5-N,N-dimethylaminopentyl)-6-(o-tolyl)-7-hydroxybicyclo[3.3.0]-2-octene 1966) (1S,5S,6R,7R)-3-(5-N,N-dimethylaminopentyl)-6-(m-tolyl)-7-hydroxybicyclo[3.3.0]-2-octene 1967) (1S,5S,6R,7R)-3-(5-N,N-dimethylaminopentyl)-6-(p-tolyl)-7-hydroxybicyclo[3.3.0]-2-octene 1968) (1S,5S,6R,7R)-3-(5-N,N-dimethylaminophenyl)-6-(4-methoxyphenylcarbonyl)-7-hydroxy bicyclo [3.3.0]-2-octene 1969) (1S,5S,6R,7R)-3-(5-N,N-dimethylaminopentyl)-6-(4-N,N-dimethylaminophenyl carbonyl)-7-hydroxybicyclo[3.3.0]-2-octene 1970) (1S,5S,6R,7R)-3-(5-N,N-dimethylaminopentyl)-6-(3-chlorophenylcarbonyl)-7-hydroxy bicyclo[3.3.0]-2-octene 1971) (1S,5S,6R,7R)-3-(5-N,N-dimethylaminopentyl)-6-[(2E)-2-phenylvinylcarbonyl]-7-hydroxybicyclo[3.3.0]-2-octene 1972) (1S,5S,6R,7R)-3-(5-N,N-dimethylaminopentyl)-6-[(2E)-2-(4-methoxyphenyl)vinyl carbonyl]-7-hydroxybicyclo[3.3.0]-2-octene 1973) (1S,5S,6R,7R)-3-(5-N,N-dimethylaminopentyl)-6-[(2E)-2-(4-N,N-dimethylaminophenyl) vinylcarbonyl]-7-hydroxybicyclo[3.3.0]-2-octene 1974) (1,5S,6R,7R)-3-(5-N,N-dimethylaminopentyl)-6-[(2E)-2-(3-chlorophenyl)vinyl carbonyl]-7-hydroxybicyclo[3.3.0]-2-octene 1975) (1S,5S,6R,7R)-3-(5-N,N-dimethylaminopentyl)-6-[(2E)-2(2-thienyl)vinylcarbonyl]-7-hydroxybicyclo[3.3.0]-2-octene 1976) (1S,5S,6R,7R)-3-(5-N,N-dimethylaminopentyl)-6-[(2E)-2-(4-pyridyl)vinylcarbonyl]-7-hydroxybicyclo[3.3.0]-2-octene 1977) compounds of compound numbers 1655 to 1976 of the examples given above, wherein the 5-N,N-dimethylaminopentyl group, which is a substitution group at position 3 in the structure of the bicyclo[3.3.0]-2-octene cycle, has been replaced by either of the 5-aminopentyl group, the 5-N,N-diethylaminopentyl group, the 5-N-(3-hydroxypropyl)aminopentyl group, the 5-N-(4-pyridylmethyl)aminopentyl group, the 5-N,N-diisopropylaminopentyl group, the 5-(1-pyrrolidinyl)pentyl group or the 5-piperidinopentyl group, the 5-morpholinopentyl group 1978) (1S,2R,3R,5S)-7-[(E)-5-aminopentylidene]-2-[(3S,1E)-3-hydroxy-1-octenyl]-3-hydroxy bicyclo[3.3.0]octane 1979) (1S,2R,3R,5S)-7-[(E)-5-N-methylaminopentylidene]-2-[(3S,1E)-3-hydroxy-1-octenyl]-3-hydroxybicyclo[3.3.0]octane 1980) (1S,2R,3R,5S)-7-[(E)-5-N-ethylaminopentylidene]-2-[(3S,1E)-3-hydroxy-1-octenyl]-3-hydroxybicyclo[3.3.0] octane 1981) (1S,2R,3R,5S)-7-[(E)-5-N-propylaminopentylidene]-2-[(3S, 1E)-3-hydroxy-1-octenyl]-3-hydroxybicyclo[3.3.0]

1982) (1S,2R,3R,5S)-7-[(E)-5-N-isopropylaminopentylidene]-2-[(3S,1E)-3-hydroxy-1-octenyl]-3-hydroxybicyclo[3.3.0]octane 1983) (1S,2R,3R,5S)-7-[(E)-5-N-butylaminopentylidene]-2-[(3S,1E)-3-hydroxy-1-octenyl]-3-hydroxybicyclo[3.3.0]octane 1984) (1S,2R,3R,5S)-7-[(E)-5-N-t-butylaminopentylidene]-2-[(3S,1E)-3-hydroxy-1-octenyl]-3-hydroxybicyclo[3.3.0]octane 1985) (1S,2R,3R,5S)-7-[(E)-5-N-phenylaminopentylidene]-2-[(3S,1E)-3-hydroxy-1-octenyl]-3-hydroxybicyclo[3.3.0]octane 1986) (1S,2R,3R,5S)-7-[(E)-5-N-benzylaminopentylidene]-2-[(3S,1E)-3-hydroxy-1-octenyl]-3-hydroxybicyclo[3.3.0]octane 1987) (1S,2R,3R,5S)-7-[(E)-5-N-(4-pyridylmethyl)aminopentylidene]-2-[(3S,1E)-3-hydroxy-1-octenyl]-3-hydroxybicyclo[3.3.0]octane 1988) (1S,2R,3R,5S)-7-[(E)-5-(1-pyrrolidinyl)pentylidene]-2-[(3S,1E)-3-hydroxy-1-octenyl]-3-hydroxybicyclo[3.3.0]octane 1989) (1S,2R,3R,5S)-7-[(E)-5-piperidinopentylidene]-2-[(3S,1E)-3-hydroxy-1-octenyl]-3-hydroxybicyclo[3.3.0] octane 1990) (1S,2R,3R,5S)-7-[(E)-5-morpholinopentylidene]-2-[(3S,1E)-3-hydroxy-1-octenyl]-3-hydroxybicyclo[3.3.0] octane 1991) (1S,2R,3R,5S)-7-[(E)-5-(4-N-methyl-1-piperazinyl) pentylidene]-2-[(3S,1E)-3-hydroxy-1-octenyl]-3-hydroxybicyclo[3.3.0]octane 1992) (1S,2R,3R,5S)-7-[(E)-5-N-(2-pyridyl)aminopentylidene]-2-[(3S,1E)-3-hydroxy-1-octenyl]-3-hydroxybicyclo[3.3.0]octane 1993) (1S,2R,3R,5S)-7-[(E)-5-N,N-dimethylaminopentylidene]-2-[(3S,1E)-3-hydroxy-loctenyl]-3-hydroxybicyclo[3.3.0]octane 1994) (1S,2R,3R,5S)-7-[(E)-5-N,N-diethylaminopentylidene]-2-[(3S,1E)-3-hydroxy-1-octenyl]-3-hydroxybicyclo[3.3.0]octane 1995) (1S,2R,3R,5S)-7-[(E)-5-N,N-dipropylaminopentylidene]-2-[(3S,1E)-3-hydroxy-loctenyl]-3-hydroxybicyclo[3.3.0]octane 1996) (1S,2R,3R,5S)-7-[(E)-5-N,N-diisopropylaminopentylidene]-2-[(3S,1E)-3-hydroxy-1-octenyl]-3-hydroxybicyclo[3.3.0]octane 1997) (1S,2R,3R,5S)-7-[(E)-5-N,N-dibutylaminopentylidene]-2-[(3S,1E)-3-hydroxy-1-octenyl]-3-hydroxybicyclo[3.3.0]octane 1998) (1S,2R,3R,5S)-7-[(E)-5-N-t-butyl-N-methylaminopentylidene]-2-[(3S,1E)-3-hydroxy-1-octenyl]-3-hydroxybicyclo[3.3.0]octane 1999) (1S,2R,3R,5S)-7-[(E)-5-N-(2-hydroxyethyl)aminopentylidene]-2-[(3S,1E)-3-hydroxy-1-octenyl]-3-hydroxybicyclo[3.3.0]octane 2000) (1S,2R,3R,5S)-7-[(E)-5-N-(3-hydroxypropyl)aminopentylidene]-2-[(3S,1E)-3-hydroxy-1-octenyl]-3-hydroxybicyclo[3.3.0]octane 2001) (1S,2R,3R,5S)-7-[(E)-4-aminobutylidene]-2-[(3S,1 E)-3-hydroxy-1-octenyl]-3-hydroxy bicyclo[3.3.0]octane 2002) (1S,2R,3R,5S)-7-[(E)-4-N,N-dimethylaminobutylidene]-2-[(3S,1E)-3-hydroxy-1-octenyl]-3-hydroxybicyclo[3.3.0]octane 2003) (1S,2R,3R,5S)-7-[(E)-6-aminohexylidene]-2-[(3S,1E)-3-hydroxy-1-octenyl]-3-hydroxy bicyclo[3.3.0]octane 2004) (1S,2R,3R,5S)-7-[(E)-6-N,N-dimethylaminohexylidene]-2-[(3S,1E)-3-hydroxy-1-octenyl]-3-hydroxybicyclo[3.3.0]octane 2005) (1S,2R,3R,5S)-7-[(E)-2-(2-N,N-diisopropylaminoethyl)oxyethylidene]-2-[(3S,1E)-3-hydroxy-1-octenyl]-3-hydroxybicyclo[3.3.0]octane 2006) (1S,2R,3R,5S)-7-[(E)-2-(2-N-t-butyl-N-methylaminoethyl)oxyethylidene]-2-[(3S,1E)-3-hydroxy-1-octenyl]-3-hydroxybicyclo[3.3.0]octane 2007) (1S,2R,3R,5S)-7-[(E)-2-[2-(1-pyrrolidinyl)ethyl]oxyethylidene]-2-[(3S,1E)-3-hydroxy-1-octenyl]-3-hydroxybicyclo[3.3.0]octane 2008) (1S,2R,3R,5S)-7-[(E)-2-(2-piperidinoethyl)oxyethylidene]-2-[(3S,1E)-3-hydroxy-1-octenyl]-3-hydroxybicyclo[3.3.0]octane 2009) (1S,2R,3R,5S)-7-[(E)-2-(2-morpholinoethyl)oxyethylidene]-2-[(3S,1E)-3-hydroxy-1-octenyl]-3-hydroxybicyclo[3.3.0] octane 2010) (1S,2R,3R,5S)-7-[(E)-2-(2-N,N-dimethylaminoethyl)thioethylidene]-2-[(3S,1E)-3-hydroxy-1-octenyl]-3-hydroxybicyclo[3.3.0]octane 2011) (1S,2R,3R,5S)-7-[(E)-2-N-(2-N,N-dimethylaminoethyl)aminoethylidene]-2-[(3S,1E)-3-hydroxy-1-octenyl]-3-hydroxybicyclo[3.3.0]octane 2012) (1S,2R,3R,5S)-7-[(E)-(2-N,N-dimethylaminoethyl)oxymethylene]-2-[(3S,1E)-3-hydroxy-1-octenyl]-3-hydroxybicyclo[3.3.0]octane 2013) (1S,2R,3R,5S)-7-[(E)-(2-N,N-dimethylaminoethyl)thiomethylene]-2-[(3S,1E)-3-hydroxy-1-octenyl]-3-hydroxybicyclo[3.3.0]octane 2014) (1S,2R,3R,5S)-7-[(E)-N-(2-N,N-dimethylaminoethyl)aminomethylene]E-2-[(3S,1E)-3-hydroxy-1-octenyl]-3-hydroxybicyclo[3.3.0]octane 2015) (1S,2R,3R,5S)-7-[(E)-5-aminopentylidene]-2-[(3S,1E)-3-hydroxy-3-cyclopentyl-1-propenyl]-3-hydroxybicyclo[3.3.0]octane 2016) (1S,2R,3R,5S)-7-[(E)-5-N-methylaminopentylidene]-2-[(3S,1E)-3-hydroxy-3-cyclopentyl-1-propenyl]-3-hydroxybicyclo[3.3.0]octane 2017) (1S,2R,3R,5S)-7-[(E)-5-N-ethylaminopentylidene]-2-[(3S,1E)-3-hydroxy-3-cyclopentyl-propenyl]-3-hydroxybicyclo[3.3.0]octane 2018) (1S,2R,3R,5S)-7-[(E)-5-N-propylaminopentylidene]-2-[(3S,1E)-3-hydroxy-3-cyclopentyl-1-propenyl]-3-hydroxybicyclo[3.3.0]octane 2019) (1S,2R,3R,5S)-7-[(E)-5-N-isopropylaminopentylidene]-2-[(3S,1E)-3-hydroxy-3-cyclopentyl-1-propenyl]-3-hydroxybicyclo [3.3.0]octane 2020) (1S,2R,3R,5S)-7-[(E)-5-N-butylaminopentylidene]-2-[(3S, E)-3-hydroxy-3-cyclopentyl-1-propenyl]-3-hydroxybicyclo[3.3.0]octane 2021) (1S,2R,3R,5S)-7-[(E)-5-N-t-butylaminopentylidene]-2-[(3S,1E)-3-hydroxy-3-cyclopentyl-1-propenyl]-3-hydroxybicyclo[3.3.0]octane 2022) (1S,2R,3R,5S)-7-[(E)-5-N-phenylaminopentylidene]-2-[(3S,1E)-3-hydroxy-3-cyclopentyl-1-propenyl]-3-hydroxybicyclo[3.3.0]octane 2023) (1S,2R,3R,5S)-7-[(E)-5-N-benzylaminopentylidene]-2-[(3S,1E)-3-hydroxy-3-cyclopentyl-1-propenyl]-3-hydroxybicyclo[3.3.0]octane 2024) (1S,2R,3R,5S)-7-[(E)-5-N-(4-pyridylmethyl)aminopentylidene]-2-[(3S,1E)-3-hydroxy-3-cyclopentyl-1-propenyl]-3-hydroxybicyclo[3.3.0]octane 2025) (1S,2R,3R,5S)-7-[(E)-5-(1-pyrrolidinyl)pentylidene]-2-[(3S,1E)-3-hydroxy-3-cyclopentyl-1-propenyl]-3-hydroxybicyclo[3.3.0]octane 2026) (1S,2R,3R,5S)-7-[(E)-5-piperidinopentylidene]-2-[(3S,1E)-3-hydroxy-3-cyclopentyl-1-propenyl]-3-hydroxybicyclo[3.3.0]octane 2027) (1S,2R,3R,5S)-7-[(E)-5-morpholinopentylidene]-2-[(3S,1E)-3-hydroxy-3-cyclopentyl-1-propenyl]-3-hydroxybicyclo[3.3.0]octane 2028) (1S,2R,3R,5S)-7-[(E)-5-(4-N-methyl-1-piperazinyl)pentylidene]-2-[(3S,1E)-3-hydroxy-3-cyclopentyl-1-propenyl]-3-hydroxybicyclo[3.3.0]octane 2029) (1S,2R,3R,5S)-7-[(E)-5-N-(2-pyridyl)aminopentylidene]-2-[(3S,1E)-3-hydroxy-3-cyclopentyl-1-propenyl]-3-hydroxybicyclo[3.3.0] octane 2030) (1S,2R,3R,5S)-7-[(E)-5-N,N-dimethylaminopentylidene]-2-[(3S,1E)-3-hydroxy-3-cyclopentyl-1-propenyl]-3-hydroxybicyclo[3.3.0]octane 2031) (1S,2R,3R,5S)-7-[(E)-5-N,N-diethylaminopentylidene]-2-[(3S,1E)-3-hydroxy-3-cyclopentyl-1-propenyl]-3-hydroxybicyclo[3.3.0]octane 2032) (1S,2R,3R,5S)-7-[(E)-5-N,N-dipropylaminopentylidene]-2-[(3S,1E)-3-hydroxy-3-cyclopentyl-1-propenyl]-3-hydroxybicyclo[3.3.0]octane 2033) (1S,2R,3R,5S)-7-[(E)-5-N,N-diisopropylaminopentylidene]-2-[(3S,1E)-3-hydroxy-3-cyclopentyl-1-propenyl]-3-hydroxybicyclo[3.3.0]octane 2034) (1S,2R,3R,5S)-7-[(E)-5-N,N-dibutylaminopentylidene]-2-[(3S,1E)-3-hydroxy-3-cyclopentyl-1-propenyl]-3-hydroxybicyclo[3.3.0]octane 2035) (1S,2R,3R,5S)-7-[(E)-5-N-t-butyl-N-methylaminopentylidene]-2-[(3S,1E)-3-hydroxy-3- cyclopentyl-1-propenyl]-3-hydroxybicyclo[3.3.0]octane 2036) (1S,2R,3R,5S)-7-[(E)-5-N-(2-hydroxyethyl)aminopentylidene]-2-[(3S,1E)-3-hydroxy-3-cyclopentyl-1-propenyl]-3-hydroxybicyclo[3.3.0]octane 2037) (1S,2R,3R,5S)-7-[(E)-5-N-(3-hydroxypropyl)aminopentylidene]-2-[(3S,1E)-3-hydroxy-3-cyclopentyl-1-propenyl]-3-hydroxybicyclo[3.3.0]octane 2038) (1S,2R,3R,5S)-7-[(E)-4-aminobutylidene]-2-[(3S,1E)-3-hydroxy-3-cyclopentyl-1-propenyl]-3-hydroxybicyclo [3.3.0]octane 2039) (1S,2R,3R,5S)-7-[(E)-4-N,N-dimethylaminobutylidene]-2-[(3S,1E)-3-hydroxy-3-cyclopentyl-1-propenyl]-3-hydroxybicyclo[3.3.0]octane 2040) (1S,2R,3R,5S)-7-[(E)-6-aminohexylidene]-2-[(3S,1E)-3-hydroxy-3-cyclopentyl-1 propenyl]-3-hydroxybicyclo [3.3.0]octane 2041) (1S,2R,3R,5S)-7-[(E)-6-N,N-dimethylaminohexylidene]-2-[(3S,1E)-3-hydroxy-3-cyclopentyl-1-propenyl]-3-hydroxybicyclo[3.3.0]octane 2042) (1S,2R,3R,5S)-7-[(E)-2-(2-N,N-dimethylaminoethyl)oxyethylidene]-2-[(3S,1E)-3-hydroxy-3-cyclopentyl-1-propenyl]-3-hydroxybicyclo[3.3.0]octane 2043) (1,2R,3R,5S)-7-[(E)-2-(2-N,N-diisopropylaminoethyl)oxyethylidene]-2-[(3S,1E)-3-hydroxy-3-cyclopentyl-1-propenyl]-3-hydroxybicyclo[3.3.0]octane 2044) (1S,2R,3R,5S)-7-[(E)-2-(2-N-t-butyl-N-methylaminoethyl)oxyethylidene]-2-[(3S,1E)-3-hydroxy-3-cyclopentyl-1-propenyl]-3-hydroxybicyclo[3.3.0]octane 2045) (1S,2R,3R,5S)-7-[(E)-2-[2-(1-pyrrolidinyl)ethyl]oxyethylidene]-2-[(3S,1E)-3-hydroxy-3-cyclopentyl-1-propenyl]-3-hydroxybicyclo[3.3.0]octane 2046) (1S,2R,3R,5S)-7-[(E)-2-(2-piperidinoethyl)oxyethylidene]-2-[(3S,1E)-3-hydroxy-3-cyclopentyl-1-propenyl]-3-hydroxybicyclo[3.3.0]octane 2047) (1S,2R¹³R,5S)-7-[(E)-2-(2-morpholinoethyl)oxyethylidene]-2-[(3S,1E)-3-hydroxy-3-cyclopentyl-1-propenyl]-3-hydroxybicyclo[3.3.0]octane 2048) (1S,2R,3R,5S)-7-[(E)-2-(2-N,N-dimethylaminoethyl)thioethylidene]-2-[(3S,1E)-3-hydroxy-3-cyclopentyl-1-propenyl]-3-hydroxybicyclo[3.3.0]octane 2049) (1S,2R,3R,5S)-7-[(E)-2-N-(2-N,N-dimethylaminoethyl)aminoethylidene]-2-[(3S,1E)-3-hydroxy-3-cyclopentyl-1-propenyl]-3-hydroxybicyclo[3.3.0]octane 2050) (S,2R,3R,5S)-7-[(E)-(2-N,N-dimethylaminoethyl)oxymethylene]-2-[(3S,1E)-3-hydroxy-3-cyclopentyl-1-propenyl]-3-hydroxybicyclo[3.3.0]octane 2051) (1S,2R¹³R,5S)-7-[(E)-(2-N,N-dimethylaminoethyl)thiomethylene]-2-[(3S, 1E)-3-hydroxy-3-cyclopentyl-1-propenyl]-3-hydroxybicyclo[3.3.0]octane 2052) (1S,2R,3R,5S)-7-[(E)-N-(2-N,N-dimethylaminoethyl)aminomethylene]-2-[(3S,1E)-3-hydroxy-3-cyclopentyl-1-propenyl]-3-hydroxybicyclo[3.3.0]octane 2053) (1S,2R,3R,5S)-7-[(E)-5-aminopentylidene]-2-[(3S,4S,1E)-3-hydroxy-4-methyl-6-octyn-1-enyl]-3-hydroxybicyclo[3.3.0] octane 2054) (1S,2R,3R,5S)-7-[(E)-5-N-methylaminopentylidene]-2-[(3S,4S,1E)-3-hydroxy-4-methyl-6-octyn-1-enyl]-3-hydroxybicyclo[3.3.0]octane 2055) (1S,2R,3R,5S)-7-[(E)-5-N-ethylaminopentylidene]-2-[(3S,4S, E)-3-hydroxy-4-methyl-6-octyn-1-enyl]-3-hydroxybicyclo [3.3.0] octane 2056) (1S,2R,3R,5S)-7-[(E)-5-N-propylaminopentylidene]-2-[(3S,4S,1E)-3-hydroxy-4-methyl-6-octyn-1-enyl]-3-hydroxybicyclo[3.3.0]octane 2057) (1S,2R¹³R,5S)-7-[(E)-5-N-isopropylaminopentylidene]-2-[(3S,4S,1E)-3-hydroxy-4-methyl-6-octyn-1-enyl]-3-hydroxybicyclo[3.3.0]octane 2058) (1S,2R¹³R,5S)-7-[(E)-5-N-butylaminopentylidene]-2-[(3S,4S,1E)-3-hydroxy-4-methyl 6-octyn-1-enyl]-3-hydroxybicyclo[3.3.0]-octane 2059) (1S,2R,3R,5S)-7-[(E)-5-N-t-butylaminopentylidene]-2-[(3S,4S,1E)-3-hydroxy-4-methyl-6-octyn-1-enyl]-3-hydroxybicyclo[3.3.0]octane 2060) (1S,2R,3R,5S)-7-[(E)-5-N-phenylaminopentylidene]-2-[(3S,4S,1E)-3-hydroxy-4-methyl-6-octyn-1-enyl]-3-hydroxybicyclo[3.3.0]octane 2061) (1S,2R,3R,5S)-7-[(E)-5-N-benzylaminopentylidene]-2-[(3S,4S,1E)-3-hydroxy-4-methyl-6-octyn-1-enyl]-3-hydroxybicyclo[3.3.0]octane 2062) (1S,2R,3R,5S)-7-[(E)-5-N-(4-pyridylmethyl)aminopentylidene]-2-[(3S,4S,0E)-3-hydroxy-4-methyl-6-octyn-1-enyl]-3-hydroxybicyclo[3.3.0]octane 2063) (1S,2R,3R,5S)-7-[(E)-5-(1-pyrrolidinyl)pentylidene]-2-[(3S,4S,1E)-3-hydroxy-4-methyl-6-octyn-1-enyl]-3-hydroxybicyclo[3.3.0]octane 2064) (1S,2R,3R,5S)-7-[(E)-5-piperidinopentylidene]-2-[(3S,4S,1E)-3-hydroxy-4-methyl-6-octyn-1-enyl]-3-hydroxybicyclo[3.3.0]octane 2065) (1S,2R,3R,5S)-7-[(E)-5-morpholinopentylidene]-2-[(3S,4S,1E)-3-hydroxy-4-methyl-6-octyn-1-enyl]-3-hydroxybicyclo[3.3.0]octane 2066) (1S,2R,3R,5S)-7-[(E)-5-(4-N-methyl-1-piperazinyl)pentylidene]-2-[(3S,4S,1E)-3-hydroxy-4-methyl-6-octyn-1-enyl]-3-hydroxybicyclo[3.3.0]octane 2067) (1S,2R,3R,5S)-7-[(E)-5-N-(2-pyridyl)aminopentylidene]-2-[(3S,4S,1E)-3-hydroxy-4-methyl-6-octyn-1-enyl]-3-hydroxybicyclo[3.3.0]octane 2068) (1S,2R,3R,5S)-7-[(E)-5-N,N-dimethylaminopentylidene]-2-[(3S,4S,1E)-3-hydroxy-4-methyl-6-octyn-1-enyl]-3-hydroxybicyclo[3.3.0]octane 2069) (1S,2R,3R,5S)-7-[(E)-5-N,N-diethylaminopentylidene]-2-[(3S,4S,1E)-3-hydroxy-4-methyl-6-octyn-1-enyl]-3-hydroxybicyclo[3.3.0]octane 2070) (1S,2R,3R,5S)-7-[(E)-5-N,N-dipropylaminopentylidene]-2-[(3S,4S,1E)-3-hydroxy-4-methyl-6-octyn-1-enyl]-3-hydroxybicyclo[3.3.0]octane 2071) (1S,2R,3R,5S)-7-[(E)-5-N,N-diisopropylaminopentylidene]-2-[(3S,4S,1E)-3-hydroxy-4-methyl-6-octyn-1-enyl]-3-hydroxybicyclo[3.3.0]octane 2072) (1S,2R,3R,5S)-7-[(E)-5-N,N-dibutylaminopentylidene]-2-[(3S,4S,1E)-3-hydroxy-4-methyl-6-octyn-1-enyl]-3-hydroxybicyclo[3.3.0]octane 2073) (1S,2R,3R,5S)-7-[(E)-5-N-t-butyl-N-methylaminopentylidene]-2-[(3S,4S,1E)-3-hydroxy-4-methyl-6-octyn-1-enyl]-3-hydroxybicyclo[3.3.0]octane 2074) (1S,2R,3R,5S)-7-[(E)-5-N-(2-hydroxyethyl)aminopentylidene]-2-[(3S,4S,1E)-3-hydroxy-4-methyl-6-octyn-1-enyl]-3-hydroxybicyclo[3.3.0]octane 2075) (1S,2R,3R,5S)-7-[(E)-5-N-(3-hydroxypropyl)aminopentylidene]-2-[(3S,4S,1E)-3-hydroxy-4-methyl-6-octyn-1-enyl]-3-hydroxybicyclo[3.3.0]octane 2076) (1S,2R,3R,5S)-7-[(E)-4-aminobutylidene]-2-[(3S,4S,1E)-3-hydroxy-4-methyl-6-octyn 1-enyl]-3-hydroxybicyclo[3.3.0]octane 2077) (1S,2R,3R,5S)-7-[(E)-4-N,N-dimethylaminobutylidene]-2-[(3S,4S,1E)-3-hydroxy-4-methyl-6-octyn-1-enyl]-3-hydroxybicyclo[3.3.0]octane 2078) (1S,2R,3R,5S)-7-[(E)-6-aminohexylidene]-2-[(3S,4S,1E)-3-hydroxy-4-methyl-6-octyn-1-enyl]-3-hydroxybicyclo[3.3.0]octane 2079) (1S,2R,3R,5S)-7-[(E)-6-N,N-dimethylaminohexylidene]-2-[(3S,4S,1E)-3-hydroxy-4-methyl-6-octyn-1-enyl]-3-hydroxybicyclo[3.3.0]octane 2080) (1S,2R,3R,5S)-7-[(E)-2-(2-N,N-dimethylaminoethyl)oxyethylidene]-2-[(3S,4S,1E)-3-hydroxy-4-methyl-6-octyn-1-enyl]-3-hydroxybicyclo[3.3.0]octane 2081) (1S,2R,3R,5S)-7-[(E)-2-(2-N,N-diisopropylaminoethyl)oxyethylidene]-2-[(3S,4S,1E)-3-hydroxy-4-methyl-6-octyn-1-enyl]-3-hydroxybicyclo[3.3.0]octane 2082) (1S,2R,3R,5S)-7-[(E)-2-(2-N-t-butyl-N-methylaminoethyl)oxyethylidene]-2-[(3S,4S,1E)-3-hydroxy-4-methyl-6-octyn-1-enyl]-3-hydroxybicyclo[3.3.0]octane 2083) (1S,2R,3R,5S)-7-[(E)-2-[2-(1-pyrrolidinyl)ethyl]oxyethylidene]-2-[(3S,4S,1E)-3-hydroxy-4-methyl-6-octyn-1-enyl]-3-hydroxybicyclo[3.3.0]octane 2084) (1S,2R,3R,5S)-7-[(E)-2-(2-piperidinoethyl)oxyethylidene]-2-[(3S,4S,1E)-3-hydroxy-4-methyl-6-octyn-1-enyl]-3-hydroxybicyclo[3.3.0]octane 2085) (1S,2R,3R,5S)-7-[(E)-2-(2-morpholinoethyl)oxyethylidene]-2-[(3S,4S,1E)-3-hydroxy-4-methyl-6-octyn-1-enyl]-3-hydroxybicyclo[3.3.0]octane 2086) (1S,2R,3R,5S)-7-[(E)-2-(2-N,N-dimethylaminoethyl)thioethylidene]-2-[(3S,4S,1E)-3-hydroxy-4-methyl-6-octyn-1-enyl]-3-hydroxybicyclo[3.3.0]octane 2087) (1S,2R,3R,5S)-7-[(E)-2-N-(2-N,N-dimethylaminoethyl)aminoethylidene]-2-[(3S,4S,1E)-3-hydroxy-4-methyl-6-octyn-1-enyl]-3-hydroxybicyclo[3.3.0]octane 2088) (1S,2R,3R,5S)-7-[(E)-(2-N,N-dimethylaminoethyl)oxymethylene]-2-[(3S,4S,1E)-3-hydroxy-4-methyl-6-octyn-1-enyl]-3-hydroxybicyclo[3.3.0]octane 2089) (1S,2R,3R,5S)-7-[(E)-(2-N,N-dimethylaminoethyl)thiomethylene]-2-[(3S,4S,1E)-3-hydroxy-4-methyl-6-octyn-1-enyl]-3-hydroxybicyclo[3.3.0]octane 2090) (1S,2R,3R,5S)-7-[(E)-N-(2-N,N-dimethylaminoethyl)aminomethylene]-2-[(3S,4S,1E)-3-hydroxy-4-methyl-6-octyn-1-enyl]-3-hydroxybicyclo[3.3.0]octane 2091) (1S,2R,3R,5S)-7-[(E)-5-aminopentylidene]-2-[(3S,4R,1E)-3-hydroxy-4-methyl-6-octyn-1-enyl]-3-hydroxybicyclo[3.3.0]octane 2092) (1S,2R,3R,5S)-7-[(E)-5-N-methylaminopentylidene]-2-[(3S,4R,1E)-3-hydroxy-4-methyl-6-octyn-1-enyl]-3-hydroxybicyclo[3.3.0]octane 2093) (1S,2R,3R,5S)-7-[(E)-5-N-ethylaminopentylidene]-2-[(3S,4R,1E)-3-hydroxy-4-methyl-6-octyn-1-enyl]-3-hydroxybicyclo[3.3.0]octane 2094) (1S,2R,3R,5S)-7-[(E)-5-N-propylaminopentylidene]-2-[(3S,4R,1E)-3-hydroxy-4-methyl-6-octyn-1-enyl]-3-hydroxybicyclo[3.3.0]octane 2095) (1S,2R,3R,5S)-7-[(E)-5-N-isopropylaminopentylidene]-2-[(3S,4R,1E)-3-hydroxy-4-methyl-6-octyn-1-enyl]-3-hydroxybicyclo[3.3.0]octane 2096) (1S,2R,3R,5S)-7-[(E)-5-N-butylaminopentylidene]-2-[(3S,4R,1E)-3-hydroxy-4-methyl-6-octyn-1-enyl]-3-hydroxybicyclo[3.3.0]octane 2097) (1S,2R,3R,5S)-7-[(E)-5-N-t-butylaminopentylidene]-2-[(3S,4R,1E)-3-hydroxy-4-methyl-6-octyn-1-enyl]-3-hydroxybicyclo[3.3.0]octane 2098) (1S,2R,3R,5S)-7-[(E)-5-N-phenylaminopentylidene]-2-[(3S,4R,1E)-3-hydroxy-4-methyl-6-octyn-1-enyl]-3-hydroxybicyclo[3.3.0]octane 2099) (1S,2R,3R,5S)-7-[(E)-5-N-benzylaminopentylidene]-2-[(3S,4R,1E)-3-hydroxy-4-methyl-6-octyn-1-enyl]-3-hydroxybicyclo[3.3.0]octane 2100) (1S,2R,3R,5S)-7-[(E)-5-N-(4-pyridylmethyl)aminopentylidene]-2-[(3S,4R,1E)-3-hydroxy-4-methyl-6-octyn-1-enyl]-3-hydroxybicyclo[3.3.0]octane 2101) (1S,2R,3R,5S)-7-[(E)-5-(1-pyrrolidinyl)pentylidene]-2-[(3S,4R,1E)-3-hydroxy-4-methyl-6-octyn-1-enyl]-3-hydroxybicyclo[3.3.0]octane 2102) (1S,2R,3R,5S)-7-[(E)-5-piperidinopentylidene]-2-[(3S,4R,1E)-3-hydroxy-4-methyl-6-octyn-1-enyl]-3-hydroxybicyclo[3.3.0]octane 2103) (1S,2R,3R,5S)-7-[(E)-5-morpholinopentylidene]-2-[(3S,4R,1E)-3-hydroxy-4-methyl-6-octyn-1-enyl]-3-hydroxybicyclo[3.3.0]octane 2104) (1S,2R,3R,5S)-7-[(E)-5-(4-N-methyl-1-piperazinyl)pentylidene]-2-[(3S,4R,1E)-3-hydroxy-4-methyl-6-octyn-1-enyl]-3-hydroxybicyclo[3.3.0]octane.

2105) (1S,2R,3R,5S)-7-[(E)-5-N-(2-pyridyl)aminopentylidene]-2-[(3S,4R,1E)-3-hydroxy-4-methyl-6-octyn-1-enyl]-3-hydroxybicyclo[3.3.0]octane 2106) (1S,2R,3R,5S)-7-[(E)-5-N,N-dimethylaminopentylidene]-2-[(3S,4R,1E)-3-hydroxy-4-methyl-6-octyn-1-enyl]-3-hydroxybicyclo[3.3.0]octane 2107) (1S,2R,3R,5S)-7-[(E)-5-N,N-diethylaminopentylidene]-2-[(3S,4R,1E)-3-hydroxy-4-methyl-6-octyn-1-enyl]-3-hydroxybicyclo[3.3.0]octane 2108) (1S,2R,3R,5S)-7-[(E)-5-N,N-dipropylaminopentylidene]-2-[(3S,4R,1E)-3-hydroxy-4-methyl-6-octyn-1-enyl]-3-hydroxybicyclo[3.3.0]octane 2109) (1S,2R,3R,5S)-7-[(E)-5-N,N-diisopropylaminopentylidene]-2-[(3S,4R,1E)-3-hydroxy-4-methyl-6-octyn-1-enyl]-3-hydroxybicyclo[3.3.0]octane 2110) (1S,2R,3R,5S)-7-[(E)-5-N,N-dibutylaminopentylidene]-2-[(3S,4R,1E)-3-hydroxy-4-methyl-6-octyn-1-enyl]-3-hydroxybicyclo[3.3.0]octane 2111) (1S,2R,3R,5S)-7-[(E)-5-N-t-butyl-N-methylaminopentylidene]-2-[(3S,4R,1E)-3-hydroxy-4-methyl-6-octyn-1-enyl]-3-hydroxybicyclo[3.3.0]octane 2112) (1S,2R,3R,5S)-7-[(E)-5-N-(2-hydroxyethyl)aminopentylidene]-2-[(3S,4R,1E)-3-hydroxy-4-methyl-6-octyn-1-enyl]-3-hydroxybicyclo[3.3.0]octane 2113) (1S,2R,3R,5S)-7-[(E)-5-N-(3-hydroxypropyl)aminopentylidene]-2-[(3S,4R,1E)-3-hydroxy-4-methyl-6-octyn-1-enyl]-3-hydroxybicyclo[3.3.0]octane 2114) (1S,2R,3R,5S)-7-[(E)-4-aminobutylidene]-2-[(3S,4R,1E)-3-hydroxy-4-methyl-6-octyn-1-enyl]-3-hydroxybicyclo[3.3.0]octane 2115) (1S,2R,3R,5S)-7-[(E)-4-N,N-dimethylaminobutylidene]-2-[(3S,4R,1E)-3-hydroxy-4-methyl-6-octyn-1-enyl]-3-hydroxybicyclo[3.3.0]octane 2116) (1S,2R,3R,5S)-7-[(E)-6-aminohexylidene]-2-[(3S,4R,1E)-3-hydroxy-4-methyl-6-octyn-1-enyl]-3-hydroxybicyclo[3.3.0]octane 2117) (1S,2R,3R,5S)-7-[(E)-6-N,N-dimethylaminohexylidene]-2-[(3S,4R,1E)-3-hydroxy-4-methyl-6-octyn-1-enyl]-3-hydroxybicyclo[3.3.0]octane 2118) (1S,2R,3R,5S)-7-[(E)-2-(2-N,N-dimethylaminoethyl)oxyethylidene]-2-[(3S,4R,1E)-3-hydroxy-4-methyl-6-octyn-1-enyl]-3-hydroxybicyclo[3.3.0]octane 2119) (1S,2R,3R,5S)-7-[(E)-2-(2-N,N-diisopropylaminoethyl)oxyethylidene]-2-[(3S,4R,1E)-3-hydroxy-4-methyl-6-octyn-1-enyl]-3-hydroxybicyclo[3.3.0]octane 2120) (1S,2R,3R,5S)-7-[(E)-2-(2-N-t-butyl-N-methylaminoethyl)oxyethylidene]-2-[(3S,4R,1E)-3-hydroxy-4-methyl-6-octyn-1-enyl]-3-hydroxybicyclo[3.3.0]octane 2121) (1 S,2R,3R,5S)-7-[(E)-2-[2-(1-pyrrolidinyl)ethyl]oxyethylidene]-2-[(3S,4R,1E)-3-hydroxy-4-methyl-6-octyn-1-enyl]-3-hydroxybicyclo[3.3.0]octane 2122) (1S,2R,3R,5S)-7-[(E)-2-(2-piperidinoethyl)oxyethylidene]-2-[(3S,4R,1E)-3-hydroxy-4-methyl-6-octyn-1-enyl]-3-hydroxybicyclo[3.3.0]octane 2123) (1S,2R,3R,5S)-7-[(E)-2-(2-morpholinoethyl)oxyethylidene]-2-[(3S,4R,1E)-3-hydroxy-4-methyl-6-octyn-1-enyl]-3-hydroxybicyclo[3.3.0]octane 2124) (1S,2R,3R,5S)-7-[(E)-2-(2-N,N-dimethylaminoethyl)thioethylidene]-2-[(3S,4R,1E)-3-hydroxy-4-methyl-6-octyn-1-enyl]-3-hydroxybicyclo[3.3.0]octane 2125) (1S,2R,3R,5S)-7-[(E)-2-N-(2-N,N-dimethylaminoethyl)aminoethylidene]-2-[(3S,4R,1E)-3-hydroxy-4-methyl-6-octyn-1-enyl]-3-hydroxybicyclo[3.3.0]octane 2126) (1S,2R,3R,5S)-7-[(E)-(2-N,N-dimethylaminoethyl)oxymethylene]-2-[(3S,4R,1E)-3-hydroxy-4-methyl-6-octyn-1-enyl]-3-hydroxybicyclo[3.3.0]octane 2127) (1S,2R,3R,5S)-7-[(E)-(2-N,N-dimethylaminoethyl)thiomethylene]-2-[(3S,4R,1E)-3-hydroxy-4-methyl-6-octyn-1-enyl]-3-hydroxybicyclo[3.3.0]octane 2128) (1S,2R,3R,5S)-7-[(E)-N-(2-N,N-dimethylaminoethyl)aminomethylene]-2-[(3S,4R,1E)3-hydroxy-4-methyl-6-octyn-1-enyl]-3-hydroxybicyclo[3.3.0]octane 2129) compounds of compound numbers 1978 to 2014 of the examples given above, wherein the (3S,1E)-3-hydroxy-1-octenyl group, which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenyl group or the (3R,1E)-3-hydroxy-4-phenoxy-1-butenyl group, the 2-(1-hydroxycyclohexyl)ethynyl group 2130) (1R,2R,3aS,8bS)-2,3,3a,8b-tetrahydro-2-hydroxy-1-[(3S,1E)-3-hydroxy-1-octenyl]-5-(4-aminobutyl)-1H-cyclopenta [b]benzofuran 2131) (1R,2R,3aS,8bS)-2,3,3a,8b-tetrahydro-2-hydroxy-1-[(3S,1E)-3-hydroxy-1-octenyl]-5-(4-N-methylaminobutyl)-1H-cyclopenta[b]benzofuran
2132) (1R,2R,3aS,8bS)-2,3,3a,8b-tetrahydro-2-hydroxy-1-[(3S,1E)-3-hydroxy-1-octenyl]-5-(4-N-ethylaminobutyl)-1H-cyclopenta[b]benzofuran
2133) (1R,2R,3aS,8bS)-2,3,3a,8b-tetrahydro-2-hydroxy-1-[(3S,1E)-3-hydroxy-1-octenyl]-5-(4-N-propylaminobutyl)-1H-cyclopenta[b]benzofuran
2134) (1R,2R,3aS,8bS)-2,3,3a,8b-tetrahydro-2-hydroxy-1-[(3S,1E)-3-hydroxy-1-octenyl]-5-(4-N-isopropylaminobutyl)-1H-cyclopenta[b]benzofuran
2135) (1R,2R,3aS,8bS)-2,3,3a,8b-tetrahydro-2-hydroxy-1-[(3S,1E)-3-hydroxy-1-octenyl]-5-(4-N-butylaminobutyl)-1H-cyclopenta[b]benzofuran
2136) (1R,2R,3aS,8bS)-2,3,3a,8b-tetrahydro-2-hydroxy-1-[(3S,1E)-3-hydroxy-1-octenyl]-5-(4-N-t-butylaminobutyl)-1H-cyclopenta[b]benzofuran
2137) (1R,2R,3aS,8bS)-2,3,3a,8b-tetrahydro-2-hydroxy-1-[(3S,1E)-3-hydroxy-1-octenyl]-5-(4-N-phenylaminobutyl)-1H-cyclopenta[b]benzofuran
2138) (1R,2R,3aS,8bS)-2,3,3a,8b-tetrahydro-2-hydroxy-1-[(3S,1E)-3-hydroxy-1-octenyl]-5-(4-N-benzylaminobutyl)-1H-cyclopenta[b]benzofuran
2139) (1R,2R,3aS,8bS)-2,3,3a,8b-tetrahydro-2-hydroxy-1-[(3S,1E)-3-hydroxy-1-octenyl]-5-[4-N-(4-pyridylmethyl)aminobutyl]-1H-cyclopenta[b]benzofuran
2140) (1R,2R,3aS,8bS)-2,3,3a,8b-tetrahydro-2-hydroxy-1-[(3S,1E)-3-hydroxy-1-octenyl]-5[4-(1-pyrrolidinyl)butyl]-1H-cyclopenta[b]benzofuran
2141) (1R,2R,3aS,8bS)-2,3,3a,8b-tetrahydro-2-hydroxy-1-[(3S,1E)-3-hydroxy-1-octenyl]-5-(4-piperidinobutyl)-1H-cyclopenta[b]benzofuran
2142) (1R,2R,3aS,8bS)-2,3,3a,8b-tetrahydro-2-hydroxy-1-[(3S,1E)-3-hydroxy-1-octenyl]-5-(4-morpholinobutyl)-1H-cyclopenta[b]benzofuran
2143) (1R,2R,3aS,8bS)-2,3,3a,8b-tetrahydro-2-hydroxy-1-[(3S,1E)-3-hydroxy-1-octenyl]-5[4-(4-N-methyl-1-piperazinyl)butyl]-1H-cyclopenta[b]benzofuran
2144) (1R,2R,3aS,8bS)-2,3,3a,8b-tetrahydro-2-hydroxy-1-[(3S,1E)-3-hydroxy-1-octenyl]-5-[4-N-(2-pyridyl)aminobutyl]-1H-cyclopenta[b]benzofuran
2145) (1R,2R,3aS,8bS)-2,3,3a,8b-tetrahydro-2-hydroxy-1-[(3S,1E)-3-hydroxy-1-octenyl]-5-(4-N,N-dimethylaminobutyl)-1H-cyclopenta[b]benzofuran
2146) (1R,2R,3aS,8bS)-2,3,3a,8b-tetrahydro-2-hydroxy-1-[(3S,1E)-3-hydroxy-1-octenyl]-5-(4-N,N-diethylaminobutyl)-1H-cyclopenta[b]benzofuran
2147) (1R,2R,3aS,8bS)-2,3,3a,8b-tetrahydro-2-hydroxy-1-[(3S,1E)-3-hydroxy-1-octenyl]-5-(4-N,N-dipropylaminobutyl)-1H-cyclopenta[b]benzofuran
2148) (1R,2R,3aS,8bS)-2,3,3a,8b-tetrahydro-2-hydroxy-1-[(3S,1E)-3-hydroxy-1-octenyl]-5-(4-N,N-diisopropylaminobutyl)-1H-cyclopenta[b]benzofuran
2149) (1R,2R,3aS,8bS)-2,3,3a,8b-tetrahydro-2-hydroxy-1-[(3S,1E)-3-hydroxy-1-octenyl]-5-(4-N,N-dibutylaminobutyl)-1H-cyclopenta[b]benzofuran
2150) (1R,2R,3aS,8bS)-2,3,3a,8b-tetrahydro-2-hydroxy-1-[(3S,1E)-3-hydroxy-1-octenyl]-5-(4-N-t-butyl-N-methylaminobutyl)-1H-cyclopenta[b]benzofuran
2151) (1R,2R,3aS,8bS)-2,3,3a,8b-tetrahydro-2-hydroxy-1-[(3S,1E)-3-hydroxy-1-octenyl]-5-[4-N-(2-hydroxyethyl)aminobutyl]-1H-cyclopenta[b]benzofuran
2152) (1R,2R,3aS,8bS)-2,3,3a,8b-tetrahydro-2-hydroxy-1-[(3S,1E)-3-hydroxy-1-octenyl]-5-[4-N-(3-hydroxypropyl)aminobutyl]-1H-cyclopenta[b]benzofuran
2153) (1R,2R,3aS,8bS)-2,3,3a,8b-tetrahydro-2-hydroxy-1-[(3S,1E)-3-hydroxy-1-octenyl]-5(3-aminopropyl)-1H-cyclopenta[b]benzofuran
2154) (1R,2R,3aS,8bS)-2,3,3a,8b-tetrahydro-2-hydroxy-1-[(3S,1E)-3-hydroxy-1-octenyl]-5(3-N,N-dimethylaminopropyl)-1H-cyclopenta[b]benzofuran
2155) (1R,2R,3aS,8bS)-2,3,3a,8b-tetrahydro-2-hydroxy-1-[(3S,1E)-3-hydroxy-1-octenyl]-5(5-aminopentyl)-1H-cyclopenta[b]benzofuran
2156) (1R,2R,3aS,8bS)-2,3,3a,8b-tetrahydro-2-hydroxy-1-[(3S,1E)-3-hydroxy-1-octenyl]-5(5-N,N-dimethylaminopentyl)-1H-cyclopenta[b]benzofuran
2157) (1R,2R,3aS,8bS)-2,3,3a,8b-tetrahydro-2-hydroxy-1-[(3S,1E)-3-hydroxy-1-octenyl]-5(3-N,N-dimethylaminopropyloxy)-1H-cyclopenta[b]benzofuran
2158) (1R,2R,3aS,8bS)-2,3,3a,8b-tetrahydro-2-hydroxy-1-[(3S,4R,1E)-3-hydroxy-4-methyl-1-octen-6-ynyl]-5-(4-aminobutyl)-1H-cyclopenta[b]benzofuran
2159) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-methylaminobutyl)-1H-cyclopenta[b]benzofuran
2160) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-ethylaminobutyl)-1H-cyclopenta[b]benzofuran
2161) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-propylaminobutyl)-1H-cyclopenta [b]benzofuran
2162) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-isopropylaminobutyl)-1H-cyclopenta[b]benzofuran
2163) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-butylaminobutyl)-1H-cyclopenta[b]benzofuran
2164) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-t-butylaminobutyl)-1H-cyclopenta[b]benzofuran
2165) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-phenylaminobutyl)-1H-cyclopenta [b]benzofuran
2166) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-benzylaminobutyl)-1H-cyclopenta[b] benzofuran
2167) (1R,2R,3aS,8bS)-2,3,3a,8b-tetrahydro-2-hydroxy-1-[(3S,4R,1E)-3-hydroxy-4-methyl-1-octen-6-ynyl]-5-[4-N-(4-pyridylmethyl)aminobutyl]-1H-cyclopenta[b]benzofuran
2168) (1R,2R,3aS,8bS)-2,3,3a,8b-tetrahydro-2-hydroxy-1-[(3S,4R,1E)-3-hydroxy-4-methyl-1-octen-6-ynyl]-5-[4-(1-pyrrolidinyl)butyl]-1H-cyclopenta[b]benzofuran
2169) (1R,2R,3aS,8bS)-2,3,3a,8b-tetrahydro-2-hydroxy-1-[(3S,4R,1E)-3-hydroxy-4-methyl-1-octen-6-ynyl]-5-(4-piperidinobutyl)-1H-cyclopenta[b]benzofuran
2170) (1R,2R,3aS,8bS)-2,3,3a,8b-tetrahydro-2-hydroxy-1-[(3S,4R,1E)-3-hydroxy-4-methyl-1-octen-6-ynyl]-5-(4-morpholinobutyl)-1H-cyclopenta[b]benzofuran.
2171) (1R,2R,3aS,8bS)-2,3,3a,8b-tetrahydro-2-hydroxy-1-[(3S,4R,1E)-3-hydroxy-4-methyl-1-octen-6-ynyl]-5-[4-(4-N-methyl-1-piperazinyl)butyl]-1H-cyclopenta[b]benzofuran
2172) (1R,2R,3aS,8bS)-2,3,3a,8b-tetrahydro-2-hydroxy-1-[(3S,4R,1E)-3-hydroxy-4-methyl-1-octen-6-ynyl]-5-[4-N-(2-pyridyl)aminobutyl]-1H-cyclopenta[b]benzofuran
2173) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-dimethylaminobutyl)-1H-cyclopenta[b]benzofuran 2174) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-diethylaminobutyl)-1H-cyclopenta[b]benzofuran 2175) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-dipropylaminobutyl)-1H-cyclopenta[b]benzofuran 2176) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-diisopropylaminobutyl)-1H-cyclopenta [b]benzofuran 2177) (1R,2R,3aS,8bS)-2,3,3a,8b-tetrahydro-2-hydroxy-1-[(3S,4R,1E)-3-hydroxy-4-methyl-1-octen-6-ynyl]-5-(4-N,N-dibutylaminobutyl)-1H-cyclopenta[b]benzofuran 2178) (1R,2R,3aS,8bS)-2,3,3a,8b-tetrahydro-2-hydroxy-1-[(3S,4R,1E)-3-hydroxy-4-methyl-1-octen-6-ynyl]-5-(4-N-t-butyl-N-methylaminobutyl)-1H-cyclopenta[b]benzofuran 2179) (1R,2R,3aS,8bS)-2,3,3a,8b-tetrahydro-2-hydroxy-1-[(3S,4R,1E)-3-hydroxy-4-methyl-1-octen-6-ynyl]-5-[4-N-(2-hydroxyethyl)aminobutyl]-1H-cyclopenta[b]benzofuran 2180) (1R,2R,3aS,8bS)-2,3,3a,8b-tetrahydro-2-hydroxy-1-[(3S,4R,1E)-3-hydroxy-4-methyl-1-octen-6-ynyl]-5-[4-N-(3-hydroxypropyl)aminobutyl]-1H-cyclopenta[b]benzofuran 2181) (1R,2R,3aS,8bS)-2,3,3a,8b-tetrahydro-2-hydroxy-1-[(3S,4R,1E)-3-hydroxy-4-methyl-1-octen-6-ynyl]-5-(3-aminopropyl)-1H-cyclopenta[b]benzofuran 2182) (1R,2R,3aS,8bS)-2,3,3a,8b-tetrahydro-2-hydroxy-1-[(3S,4R,1E)-3-hydroxy-4-methyl-1-octen-6-ynyl]-5-(3-N,N-dimethylaminopropyl)-1H-cyclopenta [b]benzofuran 2183) (1R,2R,3aS,8bS)-2,3,3a,8b-tetrahydro-2-hydroxy-1-[(3S,4R,1E)-3-hydroxy-4-methyl-1-octen-6-ynyl]-5-(5-aminopentyl)-1H-cyclopenta[b]benzofuran 2184) (1R,2R,3aS,8bS)-2,3,3a,8b-tetrahydro-2-hydroxy-1-[(3S,4R,1E)-3-hydroxy-4-methyl-1-octen-6-ynyl]-5-(5-N,N-dimethylaminopentyl)-1H-cyclopenta[b]benzofuran 2185) (1R,2R,3aS,8bS)-2,3,3a,8b-tetrahydro-2-hydroxy-1-[(3S,4R,1E)-3-hydroxy-4-methyl-1* octen-6-ynyl]-5-(3-N,N-dimethylaminopropyloxy)-1H-cyclopenta[b]benzofuran 2186) (1R,2R,3aS,8bS)-2,3,3a,8b-tetrahydro-2-hydroxy-1-[(3S,4S, 1E)-3-hydroxy-4-methyl-1-octen-6-ynyl]-5-(4-aminobutyl)-1H-cyclopenta[b]benzofuran 2187) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-methylaminobutyl)-1H-cyclopenta[b]benzofuran 2188) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-ethylaminobutyl)-1H-cyclopenta[b]benzofuran 2189) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-propylaminobutyl)-1H-cyclopenta[b]benzofuran 2190) (1R,2R,3aS,8bS)-2,3,3a,8b-tetrahydro-2-hydroxy-1-[(3S,4S, 1E)-3-hydroxy-4-methyl-1-octen-6-ynyl]-5-(4-N-isopropylaminobutyl)-1H-cyclopenta[b]benzofuran 2191) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-butylaminobutyl)-1H-cyclopenta[b]benzofuran 2192) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-t-butylaminobutyl)-1H-cyclopenta[b]benzofuran 2193) (1R,2R,3aS,8bS)-2,3,3a,8b-tetrahydro-2-hydroxy-1-[(3S,4S,1E)-3-hydroxy-4-methyl-1-octen-6-ynyl]-5-(4-N-phenylaminobutyl)-1H-cyclopenta[b]benzofuran 2194) (1R,2R,3aS,8bS)-2,3,3a,8b-tetrahydro-2-hydroxy-1-[(3S,4S, 1E)-3-hydroxy-4-methyl-1-octen-6-ynyl]-5-(4-N-benzylaminobutyl)-1H-cyclopenta[b]benzofuran 2195) (1R,2R,3aS,8bS)-2,3,3a,8b-tetrahydro-2-hydroxy-1-[(3S,4S,1E)-3-hydroxy-4-methyl-1-octen-6-ynyl]-5-[4-N-(4-pyridylmethyl)aminobutyl]-1H-cyclopenta[b]benzofuran 2196) (1R,2R,3aS,8bS)-2,3,3a,8b-tetrahydro-2-hydroxy-1-[(3S,4S,1E)-3-hydroxy-4-methyl-1-octen-6-ynyl]-5-[4-(1-pyrrolidinyl)butyl]-1H-cyclopenta[b]benzofuran 2197) (1R,2R,3aS,8bS)-2,3,3a,8b-tetrahydro-2-hydroxy-1-[(3S,4S,1E)-3-hydroxy-4-methyl-1-octen-6-ynyl]-5-(4-piperidinobutyl)-1H-cyclopenta[b]benzofuran 2198) (1R,2R,3aS,8bS)-2,3,3a,8b-tetrahydro-2-hydroxy-1-[(3S,4S,1E)-3-hydroxy-4-methyl-1-octen-6-ynyl]-5-(4-morpholinobutyl)-1H-cyclopenta[b]benzofuran 2199) (1R,2R,3aS,8bS)-2,3,3a,8b-tetrahydro-2-hydroxy-1-[(3S,4S,1E)-3-hydroxy-4-methyl-1-octen-6-ynyl]-5-[4-(4-N-methyl-1-piperazinyl)butyl]-1H-cyclopenta[b]benzofuran 2200) (1R,2R,3aS,8bS)-2,3,3a,8b-tetrahydro-2-hydroxy-1-[(3S,4S,1E)-3-hydroxy-4-methyl-1-octen-6-ynyl]-5-[4-N-(2-pyridyl)aminobutyl]-1H-cyclopenta [b]benzofuran 2201) (1R,2R,3aS,8bS)-2,3,3a,8b-tetrahydro-2-hydroxy-1-[(3S,4S,1E)-3-hydroxy-4-methyl-1-octen-6-ynyl]-5-(4-N,N-dimethylaminobutyl)-1H-cyclopenta[b]benzofuran 2202) (1R,2R,3aS,8bS)-2,3,3a,8b-tetrahydro-2-hydroxy-1-[(3S,4S,1E)-3-hydroxy-4-methyl-1-octen-6-ynyl]-5-(4-N,N-diethylaminobutyl)-1H-cyclopenta[b]benzofuran 2203) (1R,2R,3aS,8bS)-2,3,3a,8b-tetrahydro-2-hydroxy-1-[(3S,4S,1E)-3-hydroxy-4-methyl-1-octen-6-ynyl]-5-(4-N,N-dipropylaminobutyl)-1H-cyclopenta [b]benzofuran 2204) (1R,2R,3aS,8bS)-2,3,3a,8b-tetrahydro-2-hydroxy-1-[(3S,4S,1E)-3-hydroxy-4-methyl-1 N octen-6-ynyl]-5-(4-N,N-diisopropylaminobutyl)-1H-cyclopenta[b]benzofuran 2205) (1R,2R,3aS,8bS)-2,3,3a,8b-tetrahydro-2-hydroxy-1-[(3S,4S,1E)-3-hydroxy-4-methyl-1 octen-6-ynyl]-5-(4-N,N-dibutylaminobutyl)-1H-cyclopenta[b]benzofuran 2206) (1R,2R,3aS,8bS)-2,3,3a,8b-tetrahydro-2-hydroxy-1'-[(3S,4S,1E)-3-hydroxy-4-methyl-1-octen-6-ynyl]-5-(4-N-t-butyl-N-methylaminobutyl)-1H-cyclopenta[b]benzofuran 2207) (1R,2R,3aS,8bS)-2,3,3a,8b-tetrahydro-2-hydroxy-1-[(3S,4S,1E)-3-hydroxy-4-methyl-1-octen-6-ynyl]-5-[4-N-(2-hydroxyethyl)aminobutyl]-1H-cyclopenta[b]benzofuran 2208) (1R,2R,3aS,8bS)-2,3,3a,8b-tetrahydro-2-hydroxy-1-[(3S,4S,1E)-3-hydroxy-4-methyl-1-octen-6-ynyl]-5-[4-N-(3-hydroxypropyl)aminobutyl]-1H-cyclopenta[b]benzofuran 2209) (1R,2R,3aS,8bS)-2,3,3a,8b-tetrahydro-2-hydroxy-1-[(3S,4S,1E)-3-hydroxy-4-methyl-1-octen-6-ynyl]-5-(3-aminopropyl)-1H-cyclopenta[b]benzofuran 2210) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-dimethylaminopropyl)-1H-cyclopenta[b]benzofuran 2211) (1R,2R,3aS,8bS)-2,3,3a,8b-tetrahydro-2-hydroxy-1-[(3S,4S,1E)-3-hydroxy-4-methyl-1-octen-6-ynyl]-5-(5-aminopentyl)-11H-cyclopenta[b]benzofuran 2212) (1R,2R,3aS,8bS)-2,3,3a,8b-tetrahydro-2-hydroxy-1-[(3S,4S,1E)-3-hydroxy-4-methyl-1-octen-6-ynyl]-5-(5-N,N-dimethylaminopentyl)-1H-cyclopenta[b]benzofuran 2213) (1R,2R,3aS,8bS)-2,3,3a,8b-tetrahydro-2-hydroxy-1-[(3S,4S,1E)-3-hydroxy-4-methyl-1-octen-6-ynyl]-5-(3-N,N-dimethylaminopropyloxy)-1H-cyclopenta[b]benzofuran 2214) compounds of compound numbers 2130 to 1256 of the examples given above, wherein the (3S,1E)-3-hydroxy-1-octenyl group, which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,1E)-3-hydroxy-3-cyclopentyl-1-propenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenyl group or the (3R,1E)-3-hydroxy-4-phenoxy-1-butenyl 2215) (1S,2R,3R,5S)-7-[(Z)-5-N,N-dimethylaminopentylidene]-2-[(3S,1E)-3-hydroxy-1-octenyl]-3-hydroxybicyclo[3.3.0]octane 2216) (1R,5S,7R,8R)-3-(5-N,N-dimethylaminopentyl)-8-[(3S,1E)-3-hydroxy-1-octenyl]-7-hydroxybicyclo[3.3.0]-2-octene 2217) (1S,2R,3R,5S,7R)-7-(5-N,N-dimethylaminopentyl)-2-[(3S, 1E)-3-hydroxy-1-octenyl]-3-hydroxybicyclo[3.3.0]octane 2218) (1 S,2R,3R,5S,7R)-7-[2-(2-N,N-dimethylaminoethoxy)ethyl]-2-[(3R,5 S,1E)-3-hydroxy-5-methyl-1-nonenyl]-3-hydroxybicyclo[3.3.0]octane 2219) (1S,3S,5R,6R,7R)-3-(5-N,N-dimethylaminopentyl)-6-[(3S,1E)-3-hydroxy-1-octenyl]-7-hydroxy-2-oxabicyclo[3.3.0]octane 2220) (1S,5S,6R,7R)-3-(5-N,N-dimethylaminopentyl)-6-[(3S,1E)-3-hydroxy-1-octenyl]-7-hydroxy-2-oxabicyclo[3.3.0]-3-octen 2221) (1S,5R,6R,7R)-3-[(Z)-5-N,N-dimethylaminopentylidene]-6-[(3S,1E)-3-hydroxy-1-octenyl]-7-hydroxy-4-oxo-2-oxabicyclo[3.3.0]octane 2222) (1S,3S,5R,6R,7R)-3-(5-N,N-dimethylaminopentyl)-6-[(3S,1E)-3-hydroxy-1-octenyl]-7-hydroxy-2-thiabicyclo[3.3.0]octane 2223) (1S,5S,6R,7R)-3-(5-N,N-dimethylaminopentyl)-6-[(3S,1E)-3-hydroxy-1-octenyl]-7-hydroxy-2-azabicyclo[3.3.0]-2-octene 2224) (1S,3S,5R,6R,7R)-3-(5-N,N-dimethylaminopentyl)-6-[(3S,1E)-3-hydroxy-1-octenyl]-7-hydroxy-2-azabicyclo[3.3.0]octane 2225) compunds of compound numbers 2215 to 1224 of the examples given above, wherein the (3S,1E)-3-hydroxy-1-octenyl group, which is a substitution group bonded to the carbon at position 12 of the prostacyclin carbon identification number, has been replaced by either of the (3S,5S,1E)-3-hydroxy-5-methyl-1-nonenyl group, the (3S,5R,1E)-3-hydroxy-5-methyl-1-nonenyl group, the (4S,1E)-4-hydroxy-4-methyl-1-octenyl group, the (4R,1E)-4-hydroxy-4-methyl-1-octenyl group, the (3S,1E)-3-hydroxy-4-(m-tolyl)-1-butenyl group, the (3R,1E)-3-hydroxy-4-(m-tolyl)-1-butenyl group, the (E)-4-(m-tolyl)-1-butenyl group, the (3S,4S,1E)-3-hydroxy-4-methyl-6-octyn-1-enyl group, the (3S,4R,1E)-3-hydroxy-4-methyl-6-octyn-1-enyl group, the (3S,1E)-3-hydroxy-3-cyclopentyl-1-propenyl group, the (3S,1E)-3-hydroxy-3-cyclohexyl-1-propenyl group, the (3S,1E)-3-hydroxy-4-cyclopentyl-1-butenyl group, the (3R,1E)-3-hydroxy-3-phenyl-1-propenylgroup or the (3R,1E)-3-hydroxy-4-phenoxy-1-butenyl group 2226) compunds of compound numbers 1 to 174, 262 to 435, 523 to 532, 543 to 728, 855 to 1104, 1105 to 1284, 1375 to 1554, 1645 to 1654, 1665 to 1850 and 1977 to 2225 of the examples given above, wherein the hydroxyl groups/group, which are/is bonded to the carbon at position 11 and/or at position 15 of the prostacyclin carbon identification number, has/have been substituted for either of the acetoxy group, t-butyldimethylsilyloxy group, trimethylsilyloxy group or the tetrahydropyran-2-yloxy group 2227) compunds of compound numbers 175 to 261, 533 to 542, 729 to 743, 855, 1008, 1093, 1104, 1285 to 1374, 1655 to 1664, 1851 to 1865, 1977, 2129, 2214 and 2225 of the examples given above, wherein the hydroxyl groups/group, which are/is bonded to the carbon at position 11 and/or at position 16 of the prostacyclin carbon identification number, has/have been substituted for either of the acetoxy group, the t-butyldimethylsilyloxy group, the trimethylsilyloxy group or the tetrahydropyran-2-yloxy group 2228) compunds of compound numbers 436 to 522, 744 to 855, 1008, 1093, 1104, 1555 to 1644, 1866 to 1977, 2129, 2214 and 2225 of the examples given above, wherein the hydroxyl group, which is bonded to the carbon at position 11 of the prostacyclin carbon identification number, has been substituted for either of the acetoxy group, the t-butyldimethylsilyloxy group, the trimethylsilyloxy group or the tetrahydropyran-2-yloxy group 2229) (1S,2R,3R,5S)-7-[(E)-2-(2-N,N-dimethylaminoethyl)oxyethylidene]-2-[(3S,1E)-3-hydroxy-1-octenyl]-3-hydroxybicyclo[3.3.0]octane.

The nitrogen-containing compound represented by the above Formula (1) has an activity for the remedy of neural damage. Therefore, the nitrogen-containing compound of the present invention can be used as an agent for the treatment of disorders due to neural damage, or and agent for the treatment of lesion of nerves due to external injuries.

Among the nitrogen-containing compound represented by the above Formula (1) of the present invention, those having an amido group at the extremity of the α-chain of prostacyclin analog structure, in other words, those whose $A^4$ in the above Formula (1) is a carbonyl group are derived from functional groups such as a carboxyl group, an alkoxycarbonyl group or a cyano group, by the method described in pages 137 through 173 of the "Fourth Edition of the Experimental Chemistry Course" by the Chemical Society of Japan, Volume 220 (Maruzen Co., Ltd.). In other words, the target amide can be obtained by inserting a functional group such as a carboxyl group, an alkoxycarbonyl group or a cyano group at the site corresponding to the α-chain of the synthetic intermediate having the prostacyclin analog structure indicated by G in the above Formula (1), and by adding the appropriate chemical modification. For example, as indicated in Scheme 1 below,

Scheme 1

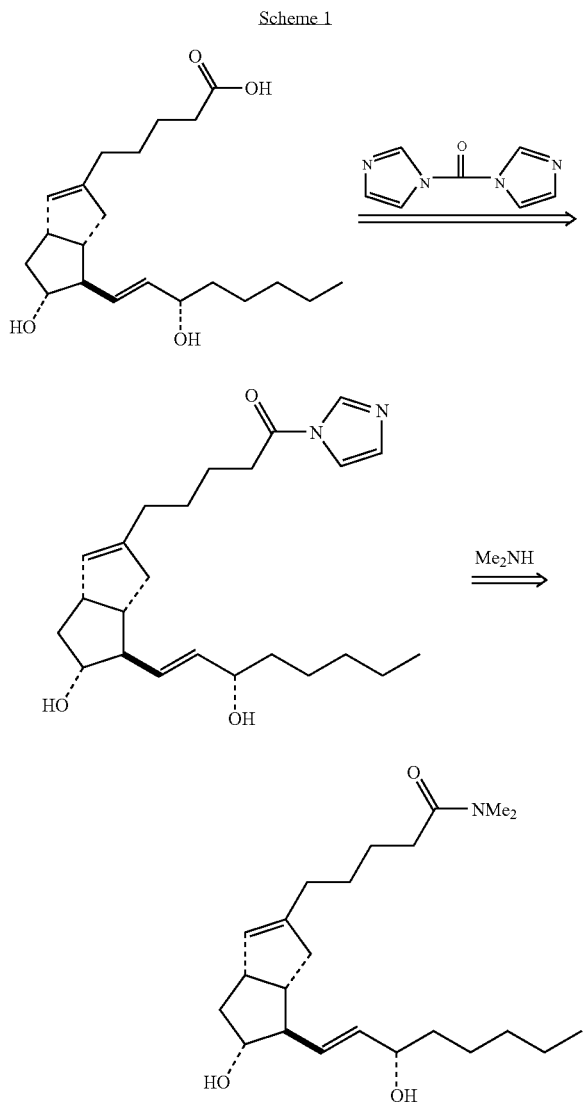

Scheme 2

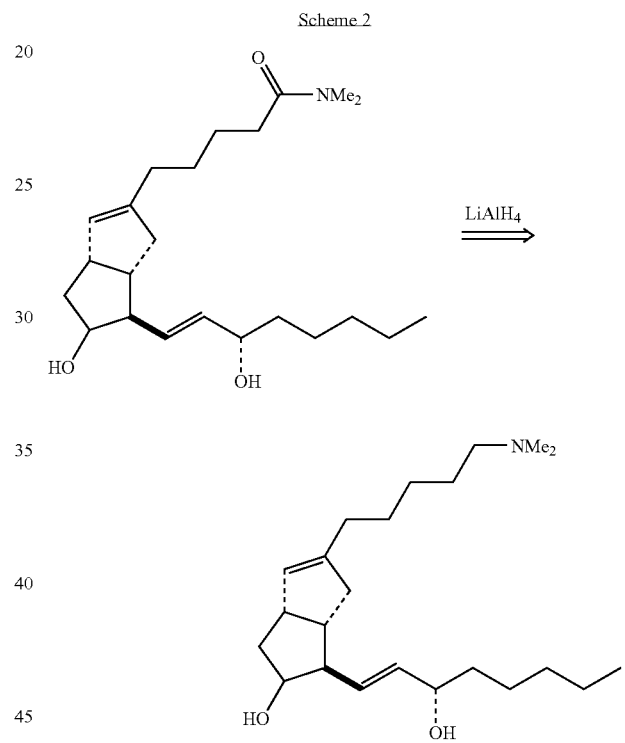

by converting the carboxyl group at position 1 of an isocarbacyclin into an imidazolylcarbonyl group using 1,1'-carbonyldiimidazole, then reacting with an amine to convert into an amide group, the target amide can be obtained. Usually, the reaction uses polar aprotic solvents such as dimethylformamide, N-methylpyrrolidone, hexamethyl phosphoric triamide, dimethyl sulfoxide. However, dimethylformamide and N-methylpyrrolidone are used preferably. The reaction is performed at a temperature range of 0 to 100° C. with a timeframe of 10 minutes to 24 hours. However, it is performed preferably at a temperature range of 10 to 60° C. with a timeframe of 15 minutes to 18 hours.

Among the nitrogen-containing compound represented by the above Formula (1) of the present invention, those having an amino group at the extremity of the α-chain of prostacyclin analog structure, in other words, those whose $A^4$ in the above Formula (1) represents a single bond, or an aliphatic hydrocarbon group having 1 to 3 carbon atoms, are derived from functional groups such as an amide group, an imino group, a halogen group, a carbonyl group, a cyano group or an azide group by the method described in pages 279 through 317 of the "Fourth Edition of the Experimental Chemistry Course" by the Chemical Society of Japan, Volume 20 (Maruzen Co., Ltd.). In other words, the target amines can be obtained by inserting a functional group such as an amide group, an imino group, a halogen group, a carbonyl group, a cyano group or an azide group at the site corresponding to the α-chain of the synthetic intermediate having the prostacyclin analog structure indicated by G in the above Formula (1), and by adding an adequate chemical modification. For example, as indicated in Scheme 2 below, from an amide obtained using a method, for example, indicated in Scheme 1, the target amine can be obtained with reducing agents such as lithium aluminium hydride or borane. Usually, the reaction uses ether solvents such as tetrahydrofurane, dioxane, dimethoxyethane, and preferably uses tetrehydrofurane. The reaction is performed at a temperature range of 0 to 100° C. and with a timeframe of 10 minutes to 24 hours. However, it is performed preferably at a temperature range of 10 to 60° C. with a timeframe of 15 minutes to 18 hours.

In addition, modifications at sites on the cyclic structure and at sites on the ω-chain of the nitrogen-containing compound represented by the above Formula (1) of the present invention can be achieved following routes indicated for example in Scheme 3, Scheme 4 and Scheme 5, but are not limited to the these.

Scheme 3
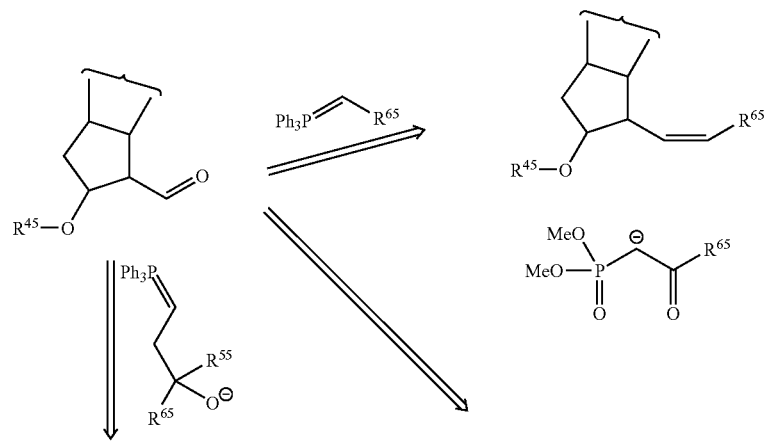
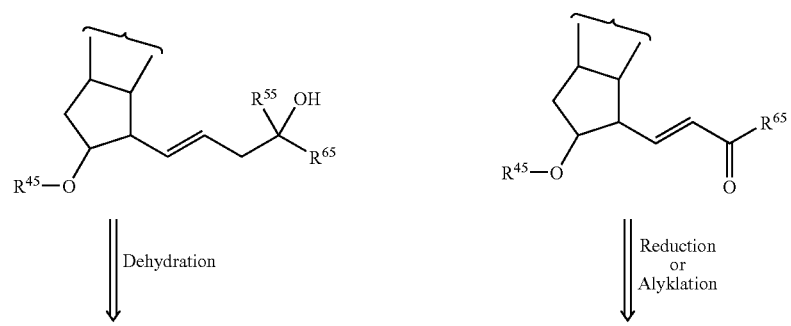
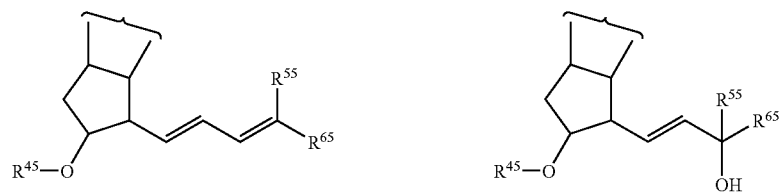
Scheme 4
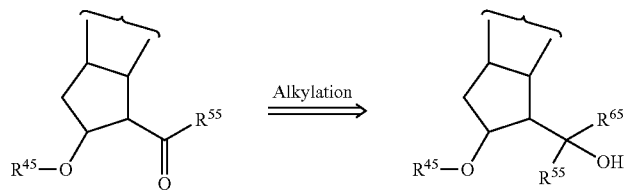

-continued
Scheme 5

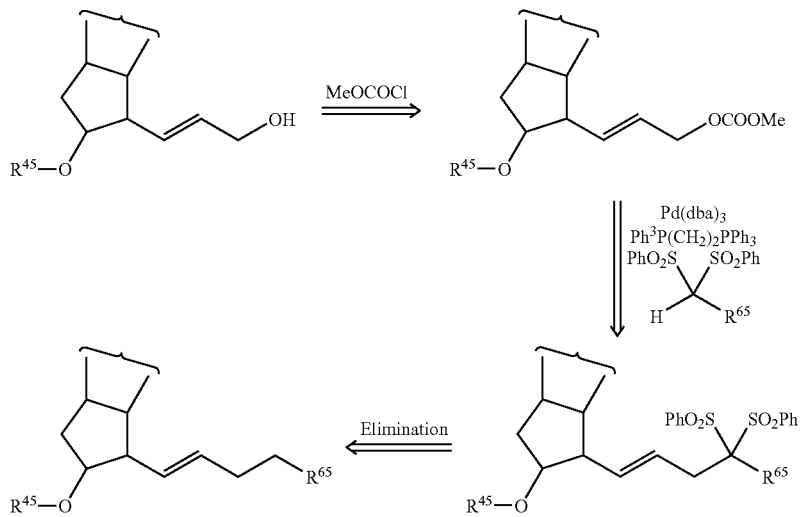

[In the above, $R^{45}$, $R^{55}$, $R^{65}$ in Scheme 3, Scheme 4 and Scheme 5 are functional groups chosen among those exemplified by $R^4$, $R^5$, $R^6$, respectively.]

The nitrogen-containing compound of the present invention is produced by combining the modifications of the sites on the α-chain, the sites on the cyclic structure and the site on the ω-chain.

Since the nitrogen-containing compound of the present invention has an activity for the remedy of nerve damage, it can be used as an agent for the treatment of disorders caused by nerve damage, or for the treatment of lesions of the nerves due to external injuries. There are no particular limitations on the scope of application of such an agent for treating neural damage or lesion of nerves due to external injuries. The drug agent of the present invention is particularly useful for mammals, and can be suitably used for livestock, laboratory animals, pets and humans, among others.

The agent for the treatment of disorders caused by nerve damage, or for the treatment of lesions of the nerves due to external injuries of the present invention, can be used for the treatment of animal or human disorders or lesions. There are no particular limitations on the scope of disorders, which must be caused by a neural damage. The following can be cited as concrete examples, 1) Neuro-degenerative disorders such as Alzheimer's disease, Pick's disease, Lewy body disease, Parkinson's disease, Huntington's chorea, spinocerebellar degeneration and amyotrophic lateral sclerosis,
2) demyelinating disorders such as acute disseminated encephalomyelitis and multiple sclerosis,
3) metabolic disorders such as brain lipidosis and Wilson's Disease,
4) infectious disorders such as meningitis and Creutzfeld-Jacob disease,
5) peripheral neural damage such as polyneuritis and Guillain-Barre Syndrome,
6) cerebrovascular disorders such as cerebral infarction and transient ischemia,
7) nervous disorders (neuropathies) associated with diabetes and renal diseases and
8) brain tumors.

However, it is preferably used in disorders cited from 1) through 5).

No particular restriction exists on the method of administration. However, oral administration, percutaneous administration, nasal administration, intravenous injection, intraperitoneal administration, rectal administration or intracerebroventricular administration are preferred.

For the clinical application of the nitrogen-containing compound or the salts thereof of the present invention, or clathrate compounds, it is desirable to produce a pharmaceutical preparation formed by the nitrogen-containing compound and a pharmaceutically accepted solid or liquid carrier, and to further add diluents, in other words additives such as excipients and stabilizers, as necessary. The amine injectable preparation of the present invention to be used for therapeutic administration must be sterile. Sterilization can be easily achieved by filtration through a sterilization filter membrane such as a membrane filter having a pore diameter of 0.2 μm.

In such pharmaceutical composition, the proportion of the above-mentioned active ingredient with respect to the constituents of the carrier can be modulated, for example, between 0.000001 and 90% W/W. Therapeutic effective dose depends on the method of administration, age, and the disorder considered, however, 0.01% g to 1000 mg/day/individual is possible, and 0.01 μg to 10 mg/day/individual is preferred. For each administration route, it is desirable to determine the efficacy of absorption into the body for each compound, separately.

Concerning the formulation and the administration form, oral administration is possible by making formulations such as granules, subtle granules, powders, pills, tablets, capsules or liquids, or, parenteral administration is possible by making agents for local applications such as suppositories, aerosols, or ointments and skin patches. As injectable agents, intravenous administration, intra-arterial administration, intramuscular administration, subcutaneous administration are possible. In addition, prior to use, powders for injectable solution can be prepared. In addition, nasal administration, intraperitoneal administration, rectal administration or intracerebroventricular administration are possible.

Organic or inorganic, solid or liquid carriers or diluents can also be used to prepare the nitrogen-containing compound of the current invention to serve as a pharmaceutical preparation suited for oral, enteral or parenteral administration.

Binding agents such as acacia, corn starch, or gelatin, excipients such as microcrystalline cellulose, disintegrants such as cornstarch and alginic acid, lubricants such as magnesium stearate, and sweeteners such as saccharose and lactose can be cited as representative carriers or diluents entering in the composition of tablets and capsules. If the formulation is a capsule, in addition to the above substances, liquid carriers such as lipid oils may be included. Various sorts of other substances may be used as coating agents or agents for improving the physical state of the dose units. Sterile compositions for injection, may be formulated according to a pharmaceutical method of the art. For example, it is desirable to dissolve or suspend the active compound in an excipient such as water or natural vegetal oil or synthetic lipid excipient such as ethyl oleate. It is also possible to include buffers such as citrate, acetate, phosphate, and antioxydants such as ascorbate, according to accepted pharmaceutical methods.

The tablet form can be obtained by the usual method, for example it can be made by using excipients such as lactose, starch or crystalline cellulose; binding agents such as carboxymethyl cellulose, methyl cellulose or polyvinyl pyrrolidone; disintegrants such as sodium alginate, sodium bicarbonate and sodium lauryl sulfate.

Likewise, pills, powders, granules can be made by the usual method using the above-mentioned excipients. Liquid agents and suspensions can be made by the usual method using, for example, glycerin esters such as tricaprilyn or triacetin, or alcohols such as ethanol. Capsules can be obtained by filling capsules, for instance, made of gelatin with granules, powders, or liquids.

As a formulation for oral administration, the nitrogen-containing compound of the present invention, can be converted into a cyclodextrin clathrate compound. The clathrate can be prepared by adding a solution made by dissolving cyclodextrin in water and/or an organic solvent capable of mixing easily with water, to a solution made by dissolving the nitrogen-containing compound in an organic solvent capable of mixing easily with water. The mixture is heated, then vacuum concentrated under refrigeration, filtered or decanted to separate the product and isolate the target cyclodextrin clathrate compound. The proportion of organic solvent and water varies with the solubility of the starting material and of the product. It is desirable that the temperature when preparing cyclodextrin clathrate compound does not exceed 70° C. α-cyclodextrin, β-cyclodextrin, γ-cyclodextrin or any combination of the above, can be used for the preparation of cyclodextrin clathrate compound. The stability of the nitrogen-containing compound can be increased by a conversion into a cyclodextrin clathrate compound.

As formulation for subcutaneous, intramuscular and intravenous administration, injectable agents exist in the form of aqueous and non-aqueous solutions. For example, physiological saline can be used for aqueous solutions. For non-aqueous solution, for example, propyleneglycol, polyethylene glycol, olive oil, ethyl oleate can be used, and anticeptic agents and stabilizers can be added to the above, as needed. Injectable agents are sterilized by suitably performing treatments such as filtration through bacterial retention filters or mixing with bactericides.

As formulations for percutaneous administration, ointments and creams can be cited as examples. Ointments can be made by the usual method with fats such as castor oil and olive oil, and emulsifiers such as diethyleneglycol, sorbitan monofatty acid ester; creams can be made using vaseline with grease oil and emulsifiers such as diethyleneglycol, sorbitan monofatty acid ester.

For rectal administration, a usual suppository such as a gelatin soft capsule may be used.

Preparations for parenteral administration can be administered as emulsions. In other words, water is added to a homogenous solution made of vegetal oils such as soybean oil, phospholipids such as lecithins and the nitrogen-containing compound of the present invention, and homogenized by homogenizers such as, for example, pressure injection homogenizer or ultrasonic homogenizer, to give lipid emulsion which can also be used as an injectable agent.

EMBODIMENTS

In the following, the present invention will be explained more concretely by giving examples and reference examples. However, the present invention is not limited to these examples and reference examples.

REFERENCE EXAMPLE 1

Preparation of (1S,5S,6R,7R)-3-(4-carbamoylbutyl)-6-[(4S,1E)-4-hydroxy-4-methyl-1-octenyl]-7-hydroxybicyclo[3.3.0]-2-octene

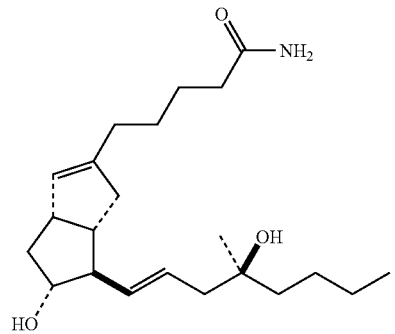

73 mg of (1S,5S,6R,7R)-3-(4-carboxybutyl)-6-[(4S,1E)-4-hydroxy-4-methyl-1-octenyl]-7-hydroxybicyclo[3.3.0]-2-octene was taken and dissolved in 2 mL of dimethylformamide. After addition of 49 mg of 1,1'-carbonyldiimidazole, it was stirred at 50° C. for 1 hour. It was then cooled to ambient temperature, 5 mL of 25% ammonium hydroxide in water was added, and stirred for 1 hour. An aqueous solution saturated with potassium hydrogen sulfate was added and extracted with ethyl acetate. The organic layer was washed with an aqueous solution saturated with sodium bicarbonate, then with a saturated saline solution, and dried with anhydrous sodium sulfate. After filtration and concentration, it was subjected to a silicagel column chromatography, to obtain 29 mg of the compound presented in the title (40% yield).

1H-NMR (270 MHz, CDCl$_3$): δ 0.91 (brt, 3H, J=7.1 Hz), 1.17 (s, 3H), 1.2–1.7 (m, 15H), 1.8–2.5 (m, 11H), 2.9–3.1 (m, 1H), 3.7–3.9 (m, 1H), 5.30 (brs, 1H), 5.3–5.5 (m, 1H), 5.5–5.7 (m, 1H).

REFERENCE EXAMPLE 2

The compound shown in Table 1 was obtained with a method identical to Reference example 1.

TABLE 1

| Ref. Ex. No. | starting material | product | Yield % | NMR data δ |
|---|---|---|---|---|
| 2 | (1S,5S,6R,7R)-3-(4-carboxybutyl)-6-[(3S,1E)-3-hydroxy-1-octenyl]-7-hydroxybicyclo[3.3.0]-2-octene | (1S,5S,6R,7R)-3-(4-carbamoylbutyl)-6-[(3S,1E)-3-hydroxy-1-octenyl]-7-hydroxybicyclo[3.3.0]-2-octene | 36 | 0.7–1.0(m, 3H), 1.0–2.5 (m, 24H), 2.9–3.1(m, 1H), 3.7–3.9(m, 1H), 4.0–4.2(m, 1H), 5.29(brs, 1H), 5.3–5.6(m, 2H), 6.0–6.1(m, 1H), 6.6–6.9(m, 1H) |

REFERENCE EXAMPLE 3

Preparation of (1S,5S,6R,7R)-3-(4-carbamoylbutyl)-6-[(3S,5S,1 E)-3-hydroxy-5-methyl-1-nonenyl]-7-hydrodroxybicyclo[3.3.0]-2-octene

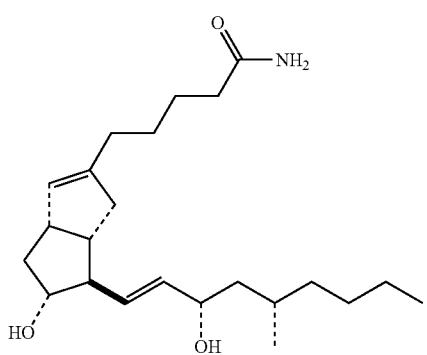

59 mg of (1S,5S,6R,7R)-3-(4-methoxycarbonylbutyl)-6-[(3S,5S,1E)-3-hydroxy-5-methyl-1-nonenyl]-7-hydroxybicyclo[3.3.0]-2-octene was taken and dissolved in 3 mL acetonitrile, under stirring, 10 mL of 25% ammonium hydroxide in water was added and stirred for 6 days. After concentration, it was subjected to a silicagel column chromatography, to obtain 34 mg of the compound presented in the title(60% yield).

1H-NMR (270 MHz, CDCl$_3$):δ0.88 (d, 3H, J=6.5 Hz), 0.7–1.0 (m, 3H), 1.0–2.5 (m, 25H), 2.9–3.1 (m, 1H), 3.7–3.9 (q, 1H, J=8.9 Hz), 4.0–4.2 (m, 1H), 5.29 (brs, 1H), 5.3–5.6 (m, 2H), 6.0–6.1 (m, 1H), 6.6–6.9 (m, 1H).

REFERENCE EXAMPLE 4

Preparation of (1S,5S,6R,7R)-3-(4-N,N-dimethylcarbamoylbutyl)-6-[(4S,1E)-4-hydroxy-4-methyl-1-octenyl]-7-hydroxybicyclo[3.3.0]-2-octene

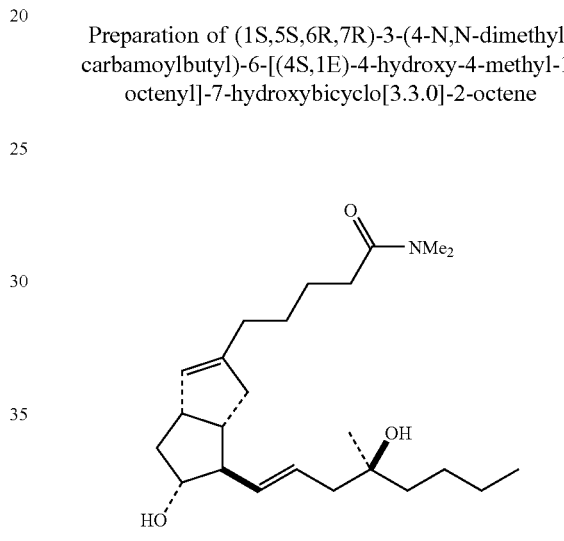

36 mg of (1S,5S,6R,7R)-3-(4-carboxybutyl)-6-[(4S,1E)-4-hydroxy-4-methyl-1-octenyl]-7-hydroxybicyclo[3.3.0]-2-octene was taken and dissolved in 1.5 mL of dimethylformamide. After addition of 32 mg of 1,1'-carbonyldiimidazole, it was stirred at 50° C. for 1 hour. It was then cooled to ambient temperature, 25 mg of imidazole and 33 mg of methylamine hydrochloride were added, and stirred at 50° C. for 1.5 hours. An aqueous solution saturated with ammonium chloride was added and extracted with ethyl acetate. The organic layer was washed with a saturated saline solution, and dried with anhydrous sodium sulfate. After filtration and concentration, it was subjected to a silicagel column chromatography, to obtain 22 mg of the compound presented in the title (57% yield).

1H-NMR (270 MHz, CDCl$_3$): δ 0.91 (brt, 3H, J=6.8 Hz), 1.16 (s, 3H), 1.2–1.7 (m, 15H), 1.8–2.5 (m, 9H), 2.9–3.1 (m, 1H), 2.94 (s, 3H), 3.00 (s, 3H), 3.7–3.9 (m, 1H), 5.30 (brs, 1H), 5.3–5.5 (m, 1H), 5.5–5.7 (m, 1H).

REFERENCE EXAMPLES 5–8

The compounds shown in Table 2 were obtained with a method identical to Reference example 4.

TABLE 2

| Ref. Ex. No. | starting material | product | Yield % | NMR data δ |
|---|---|---|---|---|
| 5 | (1S,5S,6R,7R)-3-(4-carboxybutyl)-6-[(3S,1E)-3-hydroxy-4-(m-tolyl)-1-butenyl]-7-hydroxybicyclo[3.3.0]-2-octene | (1S,5S,6R,7R)-3-(4-N,N-dimethylcarbamoylbutyl)-6-[(3S,1E)-3-hydroxy-4-(m-tolyl)-1-butenyl]-7-hydroxybicyclo[3.3.0]-2-octene | 35 | 1.2–1.8(m, 6H), 2.33(s, 3H), 1.9–2.5(m, 12H), 2.7–3.1(m, 1H), 2.94(s, 3H), 3.01(s, 3H), 3.5–3.7 (m, 1H), 4.2–4.5(m, 1H), 5.27 (brs, 1H), 5.45–5.65 (m, 2H), 6.9–7.1(m, 3H), 7.1–7.2(m, 1H) |
| 6 | (1S,5S,6R,7R)-3-(4-carboxybutyl)-6-[(3R,1E)-3-hydroxy-4-(m-tolyl)-1-butenyl]-7-hydroxybicyclo[3.3.0]-2-octene | (1S,5S,6R,7R)-3-(4-N,N-dimethylcarbamoylbutyl)-6-[(3R,1E)-3-hydroxy-4-(m-tolyl)-1-butenyl]-7-hydroxybicyclo[3 3.0]-2-octene | 78 | 1.2–1.75(m, 6H), 2.33(s, 3H), 1.75–2.5(m, 12H), 2.94(s, 3H), 3.00(s, 3H), 2.9–3.1(m, 1H), 3.5–3.7 (m, 1H), 4.34, (q, 1H, J=6.2Hz), 5.27(brs, 1H), 5.3–5.5(m, 1H), 5.5–5.7 (m, 1H), 6.9–7.1(m, 3H), 7.1–7.2(m, 1H) |
| 7 | (1S,5S,6R,7R)-3-(4-carboxybutyl)-6-[(E)-4-(m-tolyl)-1-butenyl]-7-hydroxybicyclo-[3.3.0]-2-octene | (1S,5S,6R,7R)-3-(4-N,N-dimethylcarbamoyl-butyl)-6-[(E)-4-(m-tolyl)-1-butenyl]-7-hydroxybicyclo[3.3.0]-2-octene | 60 | 1.2–2.1(m, 12H), 2.33(s, 3H), 2.1–2.5(m, 5H), 2.5–2.8(m, 2H), 2.94(s, 3H), 3.00(s, 3H), 2.9–3.1 (m, 1H), 3.5–3.7(m, 1H), 5.2–5.3(m, 2H), 5.4–5.6 (m, 1H), 6.9–7.1(m, 3H), 7.1–7.2(m, 1H) |
| 8 | (1S,5S,6R,7R)-3-(4-carboxybutyl)-6-[4-(m-tolyl)-1,3-butadienyl]-7-hydroxybicyclo[3.3.0]-2-octene | (1S,5S,6R,7R)-3-(4-N,N-dimethylcarbamoyl-butyl)-6-[4-(m-tolyl)-1,3-butadienyl]-7-hydroxybicyclo[3.3.0]-2-octene | 35 | 1.2–1.9(m, 7H), 1.95–2.2 (m, 4H), 2.32(s, 3H), 2.2–2.5(m, 4H), 2.95(s, 3H), 3.01(s, 3H), 2.9–3.1 (m, 1H), 3.7–3.9(m, 1H), 5.31(brs, 1H), 5.65–5.8 (m, 1H), 6.15–6.55(m, 2H), 6.65–6.8(m, 1H), 6.95–7.1(m, 1H), 7.1–7.3 (m, 3H) |

REFERENCE EXAMPLE 9

Preparation of (1S,5S,6R,7R)-3-[4-N-(2-ethoxycarbonylethyl)carbamoylbutyl]-6-[(4S,1E)-4-hydroxy-4-methyl-1-octenyl]-7-hydroxybicyclo[3.3.0]-2-octene

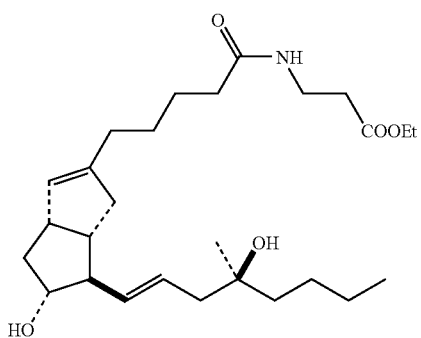

36 mg of (1S,5S,6R,7R)-3-(4-carboxybutyl)-6-[(4S,1E)-4-hydroxy-4-methyl-1-octenyl]-7-hydroxybicyclo[3.3.0]-2-octene was taken and dissolved in 1 mL of dimethylformamide. After addition of 24 mg of 1,1'-carbonyldiimidazole, it was stirred for 20 hours. 14 mg of imidazole and 31 mg of ethyl 3-aminopropionate were added and stirred for 8 hours. An aqueous solution saturated with ammonium chloride was added and extracted with ethyl acetate. The organic layer was washed with a saturated saline solution, and dried with anhydrous sodium sulfate. After filtration and concentration, it was subjected to silicagel column chromatography, to obtain 36 mg of the compound presented in the title (79% yield).

1H-NMR (270 MHz, CDCl$_3$):δ0.91 (brt, 3H, J=6.1 Hz), 1.16 (s, 3H), 1.27 (t, 3H, J=7.2 Hz), 1.2–1.7 (m, 13H), 2.53 (t, 2H, J=5.9 Hz), 1.8–2.6 (m, 11H), 2.9–3.1 (m, 1H), 3.51 (q, 2H, J=5.8 Hz), 3.77 (q, 1H, J=7.0 Hz), 4.15 (q, 2H, J=7.1 Hz), 5.28 (brs, 1H), 5.3–5.5 (m, 1H), 5.5–5.7 (m, 1H), 6.0–6.2 (m, 1H).

REFERENCE EXAMPLE 10

Preparation of (1S,5S,6R,7R)-3-(4-piperidinocarbonylbutyl)-6-[(3S,5S,1E)-3-hydroxy-5-methyl-1-nonenyl]-7-hydroxybicyclo[3.3.0]-2-octene

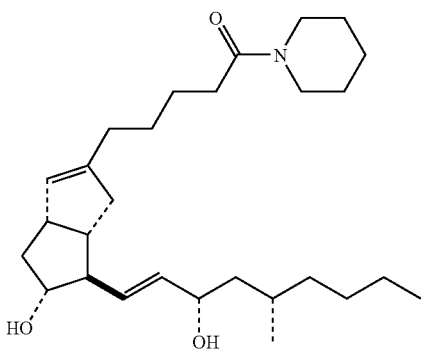

3 ml of toluene and 1 mL of 15% trimethylaluminium-hexane solution were added to a nitrogen exchanged flask. 148 µL of piperidine was added and stirred at ambient temperature for 3 hours. 59 mg of (1S,5S,6R,7R)-3-(4-methoxycarbonylbutyl)-6-[(3S,5S,1E)-3-hydroxy-5-methyl-1-nonenyl]-7-hydroxybicyclo[3.3.0]-2-octene was dissolved and added in 4 mL of toluene, and stirred at 60° C. for 18 hours. An aqueous solution saturated with potassium hydrogen sulfate was added, extracted with ethyl acetate. The organic layer was washed with an aqueous solution saturated with sodium bicarbonate, and dried with anhydrous sodium sulfate. After filtration and concentration, it was subjected to a silicagel column chromatography, to obtain 62 mg of the compound presented in the title (93% yield).

1H-NMR (270 MHz, CDCl$_3$):δ0.8–0.95 (m, 3H), 0.90 (d, 3H, J=6.2 Hz), 1.1–1.7 (m, 22H), 1.8–2.5 (m, 9H), 2.9–3.1 (m, 1H), 3.3–3.5 (m, 2H), 3.5–3.6 (m, 2H), 3.77 (q, 1H, J=6.8 Hz), 4.1–4.25 (m, 1H), 5.29 (brs, 1H), 5.45–5.6 (m, 2H).

REFERENCE EXAMPLES 11–13

The compounds shown in Table 3 were obtained with a method identical to Reference example 10.

TABLE 3

| Ref. Ex. No. | starting material carboxylic acid derivatives | amine | product | Yield % | NMR data δ |
|---|---|---|---|---|---|
| 11 | (1S,5S,6R,7R)-3-(4-methoxycarbonylbutyl)-6-[(3S,5S,1E)-3-hydroxy-5-methyl-1-nonenyl]-7-hydroxybicyclo-[3.3.0]-2-octene | diethylamine | (1S,5S,6R,7R)-3-(4-N,N-diethylcarbamoylbutyl)-6-[(3S,5S,1E)-3-hydroxy-5-methyl-1-nonenyl]-7-hydroxybicyclo[3.3.0]-2-octene | 42 | 0.7–1.0(m, 6H), 1.11(t, 3H, J=7.0Hz), 1.17(t, 3H, J=7.2Hz), 1.0–1.8(m, 13H), 1.8–2.1(m, 4H), 2.1–2.5(m, 5H), 2.9–3.1 (m, 1H), 3.30(q, 2H, J=7.2Hz), 3.37(q, 2H, J=7.1Hz), 3.7–3.8(m, 1H), 4.1–4.2(m, 1H), 5.29 (brs, 1H), 5.4–5.6(m, 2H) |
| 12 | (1S,5S,6R,7R)-3-(4-methoxycarbonylbutyl)-6-[(3S,5S,1E)-3-hydroxy-5-methyl-1-nonenyl]-7-hydroxybicyclo-[3.3.0]-2-octene | morpholine | (1S,5S,6R,7R)-3-(4-morpholinocarbonylbutyl)-6-[(3S,5S,1E)-3-hydroxy-5-methyl-1-nonenyl]-7-hydroxybicyclo[3.3.0]-2-octene | 92 | 0.7–1.0(m, 6H), 1.0–2.1 (m, 21H), 2.1–2.5(m, 4H), 2.9–3.1(m, 1H), 3.4–3.5(m, 2H), 3.5–3.7 (m, 6H), 3.7–3.8(m, 1H), 4.1–4.2(m, 1H), 5.29(brs, 1H), 5.4–5.6(m, 2H) |
| 13 | (1S,5S,6R,7R)-3-(4-methoxycarbonylbutyl)-6-[(3S,5S,1E)-3-hydroxy-5-methyl-1-nonenyl]-7-hydroxybicyclo-[3.3.0]-2-octene | 4-aminomethylpyridine | (1S,5S,6R,7R)-3-[4-N-(4-pyridylmethyl) carbamoylbutyl]-6-[(3S,5S,1E)-3-hydroxy-5-methyl-1-nonenyl]-7-hydroxybicyclo-[3.3.0]-2-octene | 71 | 0.7–1.0(m, 6H), 1.0–2.5 (m, 25H), 2.9–3.1(m, 1H), 3.7–3.85(m, 1H), 4.1–4.2(m, 1H)4.45(d, 2H, J=6.2Hz), 5.27(brs, 1H), 5.4–5.6(m, 2H), 6.0–6.2(m, 1H), 7.20(d, 2H, J=5.9Hz), 8.53(d, 2H, J=5.9Hz) |

REFERENCE EXAMPLE 14

Preparation of (1S,5S,6R,7R)-3-(4-N,N-diisopropyl-carbamoylbutyl)-6-[(E)-4-(m-tolyl)-1-butenyl]-7-(tetrahydropyran-2-yloxy)-bicyclo[3.3.0]-2-octene

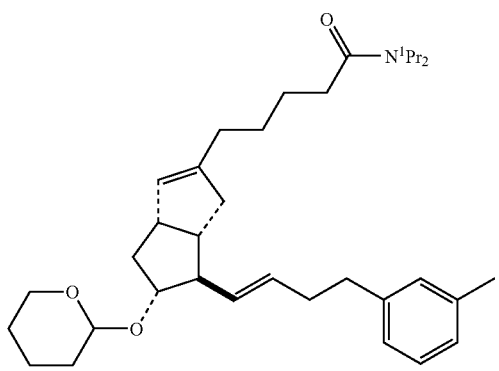

40 mg of (1S,5S,6R,7R)-3-(4-carboxybutyl)-6-[(E)-4-(m-tolyl)-1-butenyl]-7-(tetrahydropyran-2-yloxy)-bicyclo[3.3.0]-2-octene was dissolved in 4 mL of dimethylformamide, and 27 mg of 1-hydroxybenzotriazole monohydrate was added. While stirring on ice, 71 μL of diisopropylamine was added and stirred at 0° C. for 20 minutes. 38 mg of 1-(3-dimethylaminopropyl)-3-ethylcarbodiimide monohydrochloride was added, and stirred for 13 hours. An aqueous solution of ammonium chloride was added and extracted with ethyl acetate. The organic layer was washed with a saline solution, and dried with anhydrous sodium sulfate. After filtration and concentration, it was subjected to a silicagel column chromatography, to obtain 29 mg of the compound presented in the title (56% yield).

1H-NMR (270 MHz, CDCl$_3$):δ 1.22 (d, 6H, J=5.0 Hz), 1.37 (d, 6H, J=5.0 Hz), 1.1–1.8 (m, 13H), 2.34 (s, 3H), 1.8–2.7 (m, 11H), 2.9–3.1 (m, 1H), 3.5–4.0 (m, 5H), 4.1–4.3 (m, 1H), 5.15–5.3 (m, 2H), 5.45–5.9 (m, 2H), 6.9–7.05 (m, 3H), 7.1–7.25 (m, 1H).

REFERENCE EXAMPLE 15

Preparation of (1S,2R,3R,5S)-7-[(E)-4-N,N-dimethylcarbamoylbutylidene]-2-[(3S,1E)-3-hydroxy-4-methyl-6-octyne-1-enyl]-3-hydroxybicyclo[3.3.0]octane.

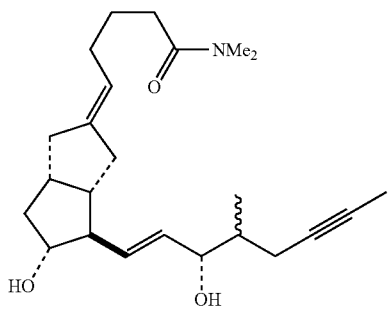

59 mg of (1S,2R,3R,5S)-7-[(E)-4-carboxybutylidene]-2-[(3S,1E)-3-hydroxy-4-methyl-6-octyne-1-enyl]-3-hydroxybicyclo[3.3.0]octane was taken and was dissolved in 2 mL of dimethylformamide. 25 mg of 1,1'-carbonyldiimidazole was added and, stirred at ambient temperature for 5 hours. 20 mg of imidazole and 23 mg of dimethylamine hydrochloride were added, and stirred at ambient temperature for 18 hours. An aqueous solution saturated with ammonium chloride was added and extracted with ethyl acetate. The organic layer was washed with a saturated saline solution, and dried with anhydrous sodium sulfate. After filtration and concentration, it was subjected to a silicagel column chromatography, to obtain 17 mg of the compound presented in the title (26% yield).

1H-NMR (270 MHz, CDCl$_3$):δ0.96 and 1.00 (d, 3H, J=6.9 Hz), 1.1–1.3 (m, 1H), 1.5–2.5 (m, 22H), 2.94 (s, 3H), 3.0 (s, 3H), 3.65–3.8 (m, 1H), 3.9–4.05 and 4.1–4.2 (m, 1H), 5.2–5.3 (m, 1H), 5.45–5.65 (m, 2H).

REFERENCE EXAMPLE 16

Preparation of (1R,2R,3aS,8bS)-2,3,3a,8b-tetrahydro-2-hydroxy-1-[(3S,1E)-3-hydroxy-4-methyl-1-octene-6-ynyl]-5-(3-N,N-dimethylcarbamoylpropyl)-1H-cyclopenta[b] benzofuran

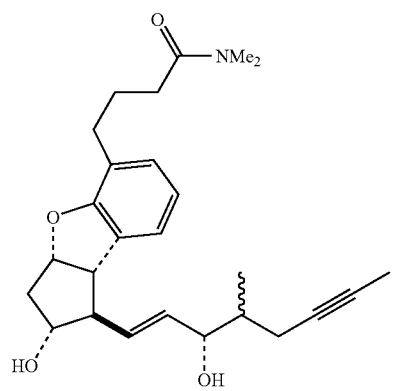

20 mg of (1R,2R,3aS,8bS)-2,3,3a,8b-tetrahydro-2-hydroxy-1-[(3S,1E)-3-hydroxy-4-methyl-1-octene-6-ynyl]-5-(3-carboxypropyl)-1H-cyclopenta[b] benzofuran was taken and dissolved in 2 mL of dimethylformamide. 16 mg of 1,1'-carbonyldiimidazole was added and stirred at 50° C. for 1 hour. 13 mg of imidazole and 16 mg of dimethylamine hydrochloride was added, and stirred at 50° C. for 1 hour. An aqueous solution saturated with ammonium chloride was added and extracted with ethyl acetate. The organic layer was washed with a saturated saline solution, and dried with anhydrous sodium sulfate. After filtration and concentration, it was subjected to a silicagel column chromatography, to obtain 5 mg of the compound presented in the title (23% yield).

1H-NMR (270 MHz, CDCl$_3$): δ 0.9–1.1 (m, 3H), 1.2–1.7 (m, 5H), 1.79 (brs, 3H), 1.9–2.8 (m, 9H), 2.96 (s, 3H), 3.0 (s, 3H), 3.49 (t, 1H, J=8.5 Hz), 3.9–4.3 (m, 2H), 5.0–5.2 (m, 1H), 5.5–5.8 (m, 2H), 6.7–6.85 (m, 1H), 6.9–7.05 (m, 2H).

EXAMPLE 1

Preparation of (1S,5S,6R,7R)-3-(5-aminopentyl)-6-[(3S,5S,1E)-3-hydroxy-5-methyl-1-nonenyl]-7-hydroxybicyclo[3.3.0]-2-octene

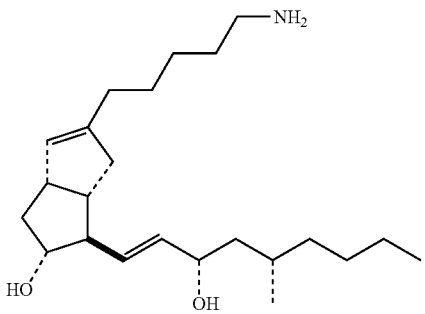

29 mg of (1S,5S,6R,7R)-3-(4-carbamoylbutyl)-6-[(3S,5S,1E)-3-hydroxy-5-methyl-1-nonenyl]-7-hydroxybicyclo[3.3.0]-2-octene obtained in Reference example 3 was taken and dissolved in 4 mL of tetrahydrofurane. 20 mg of lithium aluminium hydride was added, and stirred for 4 hours. 100 μL of an aqueous solution saturated with sodium sulfate was added, then 500 mg of anhydrous sodium sulfate was added, and stirred for 18 hours. A filtration was performed over celite, and after washing the residue with ethyl acetate, the filtrate was concentrated and subjected to a silicagel column chromatography, to obtain 8 mg of the compound presented in the title (29% yield).

1H-NMR (270 MHz, CDCl$_3$): δ 0.7–1.0 (m, 6H), 1.0–1.6 (m, 16H), 1.8–2.1 (m, 4H), 2.2–2.5 (m, 3H), 2.72 (t, 2H, J=7.0 Hz), 2.7–3.1 (m, 5H), 3.76 (q, 1H, J=8.6 Hz), 4.0–4.15 (m, 1H), 5.27 (brs, 1H), 5.4–5.6 (m, 2H).

EXAMPLE 2

The compound shown in Table 4 was obtained with a method identical to Example 1.

EXAMPLE 3

Preparation of (1S,5S,6R,7R)-3-(5-N-acetylaminopentyl)-6-[(3S,5S,1E)-3-hydroxy-5-methyl-1-nonenyl]-7-hydroxybicyclo[3.3.0]-2-octene

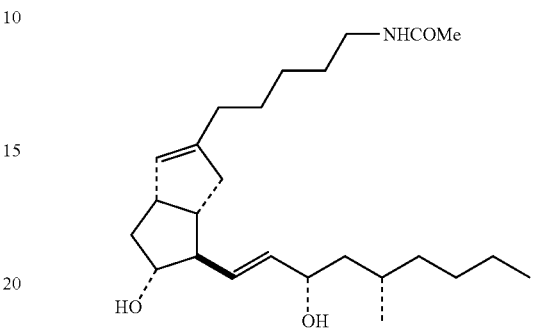

20 μL of acetic acid was dissolved in 2 mL of dimethylformamide. After adding 60 mg of 1,1'-carbonyldiimidazole, it was stirred at 50° C. for 1 hour. It was cooled to ambient temperature, and 18 mg of (1S,5S,6R,7R)-3-(5-aminopentyl)-6-[(3S,5S,1E)-3-hydroxy-5-methyl-1-nonenyl]-7-hydroxybicyclo[3.3.0]-2-octene was added, and stirred for 18 hours. An aqueous solution saturated with potassium hydrogen sulfate was added and extracted with ethyl acetate. The organic layer was washed with an aqueous solution saturated with sodium bicarbonate, then with a saturated saline solution, and dried with anhydrous sodium sulfate. After filtration and concentration, it was subjected to silicagel column chromatography, to obtain 3.5 mg of the compound presented in the title (22% yield).

1H-NMR (270 MHz, CDCl$_3$): δ 0.7–1.0 (m, 6H), 1.0–1.6 (m, 16H), 1.96 (s, 3H), 1.8–2.1 (m, 4H), 2.2–2.5 (m, 3H), 2.7–3.1 (m, 3H), 3.1–3.4 (m, 2H), 3.76 (q, 1H, J=8.6 Hz), 4.0–4.15 (m, 1H), 5.27 (brs, 1H), 5.4–5.6 (m, 2H), 6.6–6.8 (m, 1H).

TABLE 4

| Example No. | starting material | product | Yield % | NMR data δ |
|---|---|---|---|---|
| 2 | (1S,5S,6R,7R)-3-(4-carbamoylbutyl)-6-[(3S,1E)-3-hydroxy-1-octenyl]-7-hydroxybicyclo[3.3.0]-2-octene | (1S,5S,6R,7R)-3-(5-aminopentyl)-6-[(3S,1E)-3-hydroxy-1-octenyl]-7-hydroxybicyclo[3.3.0]-2-octene | 17 | 0.7–1.0(m, 3H), 1.0–1.6 (m, 15H), 1.8–2.1(m, 4H), 2.2–2.5(m, 3H), 2.73 (t, 2H, J=7.0Hz), 2.7–3.1 (m, 5H), 3.6–3.85(m, 1H), 4.0–4.15(m, 1H), 5.26(brs, 1H), 5.4–5.6(m, 2H) |

EXAMPLE 4

The compound shown in Table 5 was obtained with a method identical to Example 3.

TABLE 5

| | starting material | | | | NMR data |
|---|---|---|---|---|---|
| Example No. | amine | acid | product | Yield % | δ |
| 4 | (1S,5S,6R,7R)-3-(5-aminopentyl)-6-[(3S,5S,1E)-3-hydroxy-5-methyl-1-nonenyl]-7-hydroxybicyclo-[3.3.0]-2-octene | benzoic acid | (1S,5S,6R,7R)-3-(5-N-benzoylamino-pentyl)-6-[(3S,5S,1E)-3-hydroxy-5-methyl-1-nonenyl]-7-hydroxy-bicyclo[3.3.0]-2-octene | 37 | 0.7–1.0(m, 6H), 1.0–1.6 (m, 16H), 1.8–2.1(m, 4H), 2.2–2.5(m, 3H), 2.7–3.1(m, 3H), 3.3–3.5 (m, 2H), 3.77(q, 1H, J=8.5Hz), 4.0–4.15(m, 1H), 5.27(brs, 1H), 5.4–5.6(m, 2H), 7.0–7.2 (m, 1H), 7.2–7.5(m, 3H), 7.7–7.85(m, 2H) |

EXAMPLE 5

Preparation of (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene

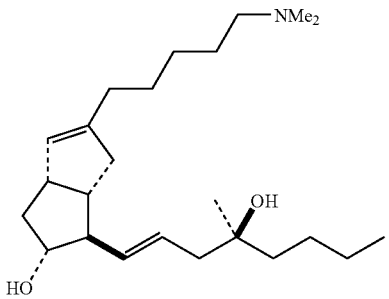

36 mg of (1S,5S,6R,7R)-3-(4-carboxybutyl)-6-[(4S,1E)-4-hydroxy-4-methyl-1-octenyl]-7-hydroxybicyclo[3.3.0]-2-octene was taken and was dissolved in 1.5 mL of dimethylformamide. After addition of 32 mg of 1,1'-carbonyldiimidazole, it was stirred at 50° C. for 1 hour. It was then cooled to ambient temperature, 27 mg of imidazole was added, and 33 mg of dimethylamine hydrochloride was further added. After stirring at 50° C. for 1.5 hours, an aqueous solution saturated with ammonium chloride was added and extraction was performed with ethyl acetate. The organic layer was washed with a saturated saline solution, and dried with anhydrous sodium sulfate. After filtration and concentration, 1.5 mL of tetrahydrofurane was added. While stirring on ice, 38 mg of lithium aluminium hydride was added and stirring continued at 0° C. for 15 minutes, then at 50° C. for 1.5 hours. While stirring at ambient temperature, 200 μL of an aqueous solution saturated with sodium sulfate was added, then 800 mg of anhydrous sodium sulfate and 4 mL of ethyl acetate were added, and stirred for 1 hour. A filtration was performed over celite, and after washing the residue with ethyl acetate, the filtrate was concentrated and subjected to silicagel column chromatography, to obtain 19 mg of the compound presented in the title (51% yield).

1H-NMR (270 MHz, CDCl$_3$):δ0.91 (brt, 3H, J=6.9 Hz), 1.16 (s, 3H), 1.2–1.6 (m, 15H), 1.8–2.5 (m, 11H), 2.24 (s, 6H), 2.9–3.1 (m, 1H), 3.7–3.9 (m, 1H), 5.27 (brs, 1H), 5.3–5.5 (m, 1H), 5.5–5.7 (m, 1H).

EXAMPLES 6–16

The compounds shown in Table 6 were obtained with a method identical to Example 5.

TABLE 6

| Example No. | starting material | product | Yield % | NMR data δ |
|---|---|---|---|---|
| 6 | (1S,5S,6R,7R)-3-(4-carboxybutyl)-6-[(3S,1E)-3-hydroxy-1-octenyl]-7-hydroxy-bicyclo[3.3.0]-2-octene | (1S,5S,6R,7R)-3-(5-N,N-dimethylamino-pentyl)-6-[(3S,1E)-3-hydroxy-1-octenyl]-7-hydroxybicyclo[3.3.0]-2-octene | 46 | 0.92(brt, 3H, J=6.8Hz), 1.2–1.6(m, 15H), 1.8–2.5 (m, 11H), 2.23(s, 6H), 2.9–3.1(m, 1H), 3.7–3.9 (m, 1H), 4.1–4.2(m, 1H), 5.27(brs, 1H), 5.4–5.6(m, 2H) |
| 7 | (1S,5S,6R,7R)-3-(4-carboxybutyl)-6-[(3S,5S,1E)-3-hydroxy-5-methyl-1-nonenyl]-7-hydroxybicyclo-[3.3.0]-2-octene | (1S,5S,6R,7R)-3-(5-N,N-dimethylamino-pentyl)-6-[(3S,5S,1E)-3-hydroxy-5-methyl-1-nonenyl]-7-hydroxybicyclo[3.3.0]-2-octene | 47 | 0.7–1.0(m, 6H), 1.1–1.7 (m, 15H), 1.75–2.2(m, 7H), 2.23(s, 6H), 2.1–2.5 (m, 5H), 2.9–3.1(m, 1H), 3.7–3.8(m, 1H), 4.1–4.2 (m, 1H), 5.27(brs, 1H), 5.4–5.6(m, 2H) |

TABLE 6-continued

| Example No. | starting material | product | Yield % | NMR data δ |
|---|---|---|---|---|
| 8 | (1S,5S,6R,7R)-3-(4-carboxybutyl)-6-[(3S,5R,1E)-3-hydroxy-5-methyl-1-nonenyl]-7-hydroxybicyclo[3.3.0]-2-octene | (1S,5S,6R,7R)-3-(5-N,N-dimethylamino-pentyl)-6-[(3S,5R,1E)-3-hydroxy-5-methyl-1-nonenyl]-7-hydroxy bicyclo[3.3.0]-2-octene | 38 | 0.7–1.0(m, 6H), 1.1–1.6 (m, 15H), 1.75–2.2(m, 7H), 2.23(s, 6H), 2.2–2.5 (m, 5H), 2.9–3.1(m, 1H), 3.7–3.8(m, 1H), 4.1–4.2 (m, 1H), 5.26(brs, 1H), 5.4–5.6(m, 2H) |
| 9 | (1S,5S,6R,7R)-3-(4-carboxybutyl)-6-[(4R,1E)-4-hydroxy-4-methyl-1-octenyl]-7-hydroxybicyclo-[3.3.0]-2-octene | (1S,5S,6R,7R)-3-(5-N,N-dimethylamino-pentyl)-6-[(4R,1E)-4-hydroxy-4-methyl-1-octenyl]-7-hydroxy bicyclo[3.3.0]-2-octene | 17 | 0.92(brt, 3H, J=7.0Hz), 1.16(s, 3H), 1.2–1.6(m, 15H), 1.8–2.5(m, 11H), 2.24(s, 6H), 2.9–3.1(m, 1H), 3.7–3.9(m, 1H), 5.26 (brs, 1H), 5.3–5.5(m, 1H), 5.5–5.7(m, 1H) |
| 10 | (1S,5S,6R,7R)-3-(4-carboxybutyl)-6-[(3S,1E)-3-hydroxy-4-methyl-6-octyne-1-enyl]-7-hydroxy-bicyclo[3.3.0]-2-octene | (1S,5S,6R,7R)-3-(5-N,N-dimethylamino-pentyl)-6-[(3S,1E)-3-hydroxy-4-methyl-6-octyne-1-enyl]-7-hydroxybicyclo-[3.3.0]-2-octene | 34 | 0.95 and 1.00(d, 3H, J=2.3Hz), 1.1–1.7(m, 10H), 1.8–2.5(m, 14H), 2.24(s, 6H), 2.9–3.1(m, 1H), 3.7–3.9(m, 1H), 4.1–4.2(m, 1H), 5.26(brs, 1H), 5.4–5.6(m, 2H) |
| 11 | (1S,5S,6R,7R)-3-(4-carboxybutyl)-6-[(3S,1E)-3-hydroxy-3-cyclopentyl-1-propenyl]-7-hydroxy bicyclo[3.3.0]-2-octene | (1S,5S,6R,7R)-3-(5-N,N-dimethylamino-pentyl)-6-[(3S,1E)-3-hydroxy-3-cyclopentyl-1-propenyl]-7-hydroxy-bicyclo[3.3.0]-2-octene | 50 | 1.1–1.6(m, 16H), 1.8–2.5 (m, 11H), 2.24(s, 6H), 2.9–3.1(m, 1H), 3.7–3.9 (m, 1H), 4.1–4.2(m, 1H), 5.25(brs, 1H), 5.35–5.7 (m, 2H) |
| 12 | (1S,5S,6R,7R)-3-(4-carboxybutyl)-6-[(3S,1E)-3-hydroxy-3-cyclohexyl-1-propenyl]-7-hydroxybicyclo-[3.3.0]-2-octene | (1S,5S,6R,7R)-3-(5-N,N-dimethylamino pentyl)-6-[(3S,1E)-3-hydroxy-3-cyclohexyl-1-propenyl]-7-hydroxy-bicyclo[3.3.0]-2-octene | 39 | 1.1–1.6(m, 18H), 1.8–2.5 (m, 11H), 2.24(s, 6H), 2.9–3.1(m, 1H), 3.7–3.9 (m, 1H), 4.1–4.2(m, 1H), 5.24(brs, 1H), 5.3–5.7(m, 2H) |
| 13 | (1S,5S,6R,7R)-3-(4-carboxybutyl)-6-[(3S,1E)-3-hydroxy-4-cyclopentyl-1-butenyl]-7-hydroxybicyclo-[3.3.0]-2-octene | (1S,5S,6R,7R)-3-(5-N,N-dimethylamino pentyl)-6-[(3S,1E)-3-hydroxy-4-cyclopentyl-1-butenyl]-7-hydroxy-bicyclo[3.3.0]-2-octene | 43 | 1.1–1.75(m, 18H), 1.8–2.6 (m, 11H), 2.24(s, 6H), 2.9–3.1(m, 1H), 3.7–3.9 (m, 1H), 4.1–4.2(m, 1H), 5.25(brs, 1H), 5.4–5.6(m, 2H) |
| 14 | (1S,5S,6R,7R)-3-(4-carboxybutyl)-6-[(3R,1E)-3-hydroxy-1-octenyl]-7-hydroxy-bicyclo[3.3.0]-2-octene | (1S,5S,6R,7R)-3-(5-N,N-dimethylamino-pentyl)-6-[(3R,1E)-3-hydroxy-1-octenyl]-7-hydroxybicyclo-[3.3.0]-2-octene | 44 | 0.93(brt, 3H, J=6.9Hz), 1.2–1.7(m, 15H), 1.8–2.5 (m, 11H), 2.24(s, 6H), 2.9–3.1(m, 1H), 3.7–3.9 (m, 1H), 4.1–4.2(m, 1H), 5.28 (brs, 1H), 5.4–5.6(m, 2H) |
| 15 | (1S,5S,6R,7R)-3-(2-carboxymethyloxy-ethyl)-6-[(3S,1E)-3-hydroxy-1-octenyl]-7-hydroxybicyclo-[3.3.0]-2-octene | (1S,5S,6R,7R)-3-[2-(2-N,N-dimethylamino-ethyl)oxyethyl]-6-[(3S,1E)-3-hydroxy-1-octenyl]-7-hydroxy bicyclo[3.3.0]-2-octene | 21 | 0.94(brt, 3H, J=6.9Hz), 1.2–1.6(m, 9H), 1.8–2.5 (m, 11H), 2.24(s, 6H), 2.8–3.1(m, 1H), 3.4–4.2 (m, 6H), 5.28(brs, 1H), 5.4–5.7(m, 2H) |
| 16 | (1S,5S,6R,7R)-3-(2-carboxymethylthio-ethyl)-6-[(3S,1E)-3-hydroxy-1-octenyl]-7-hydroxybicyclo-[3.3.0]-2-octene | (1S,5S,6R,7R)-3-[2-(2-N,N-dimethylamino-ethyl)thioethyl]-6-[(3S,1E)-3-hydroxy-1-octenyl]-7-hydroxy bicyclo[3.3.0]-2-octene | 15 | 0.91(brt, 3H, J=6.8Hz), 1.2–1.6(m, 9H), 1.8–2.5 (m, 11H), 2.23(s, 6H), 2.9–3.4(m, 5H), 3.7–3.9 (m, 1H), 4.1–4.2(m, 1H), 5.26(brs, 1H), 5.4–5.6(m, 2H) |

EXAMPLE 17

Preparation of (1S,5S,6R,7R)-3-(5-N,N-dimethylaminopentyl)-6-[(3R,1E)-3-hydroxy-4-(m-tolyl)-1-butenyl]-7-hydroxybicyclo[3.3.0]-2-octene

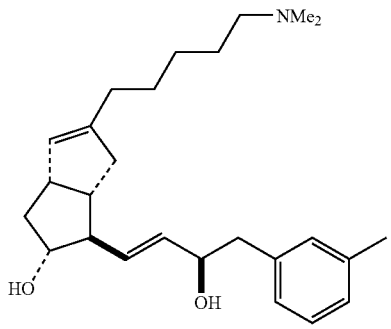

39 mg of (1S,5S,6R,7R)-3-(4-N,N-dimethylcarbamoylbutyl)-6-[(3R,1E)-3-hydroxy-4-(m-tolyl)-1-butenyl]-7-hydroxybicyclo[3.3.0]-2-octene obtained in Reference example 6 was taken, 4 mL of tetrahydrofuran was added, then 36 mg of lithium aluminium hydride was added, and stirred at ambient temperature for 5 hours. While stirring at ambient temperature, 100 μL of an aqueous solution saturated with sodium sulfate was added, then 300 mg of anhydrous sodium sulfate was added, and stirred for 1.5 hours. A filtration was performed over celite, and after washing the residue with ethyl acetate, the filtrate was concentrated and subjected to a silicagel column chromatography, to obtain 26 mg of the compound presented in the title (70% yield).

1H-NMR (270 MHz, CDCl$_3$): δ 1.2–1.6 (m, 7H), 1.7–2.1 (m, 7H), 2.22 (s, 6H), 2.33 (s, 3H), 2.2–2.5 (m, 4H), 2.7–2.9 (m, 2H), 2.9–3.1 (m, 1H)3.55–3.7 (m, 1H), 4.34 (q, 1H, J=6.5 Hz), 5.26 (brs, 1H), 5.45 (dd, 1H, J=15.8, 8.2 Hz), 5.59 (dd, 1H, J=15.5, 6.6 Hz), 6.9–7.1 (m, 3H), 7.1–7.25 (m, 1H).

EXAMPLES 18–26

The compounds shown in Table 7 were obtained with a method identical to Example 17.

TABLE 7

| Example No. | starting material | product | Yield % | NMR data δ |
|---|---|---|---|---|
| 18 | (1S,5S,6R,7R)-3-[4-N-(2-ethoxycarbonylethyl)-carbamoylbutyl]-6-[(4S,1E)-4-hydroxy-4-methyl-1-octenyl]-7-hydroxybicyclo[3.3.0]-2-octene | (1S,5S,6R,7R)-3-[5-N-(3-hydroxypropyl)-aminopentyl]-6-[(4S,1E)-4-hydroxy-4-methyl-1-octenyl]-7-hydroxybicyclo-[3.3.0]-2-octene | 68 | 0.91(brt, 3H, J=6.6Hz), 1.16(s, 3H), 1.1–2.5(m, 29H), 2.9–3.1(m, 1H), 3.41(q, 2H, J=6.1Hz), 3.63(t, 2H, J=5.4Hz), 4.7–4.9(m, 1H), 5.29(brs, 1H), 5.41(dd, 1H, J=15.4, 8.4Hz), 5.5–5.7(m, 1H), 5.9–6.0(m, 1H) |
| 19 | (1S,5S,6R,7R)-3-(4-N,N-diethylcarbamoyl-butyl)-6-[(3S,5S,1E)-3-hydroxy-5-methyl-1-nonenyl]-7-hydroxy-bicyclo[3.3.0]-2-octene | (1S,5S,6R,7R)-3-(5-N,N-diethylamino-pentyl)-6-[(3S,5S,1E)-3-hydroxy-5-methyl-1-nonenyl]-7-hydroxy-bicyclo[3.3.0]-2-octene | 43 | 0.7–1.0(m, 6H), 1.04(t, 6H, J=7.2Hz), 1.1–1.6(m, 15H), 1.75–2.2(m, 7H), 2.2–2.5(m, 5H), 2.56(q, 4H, J=6.4Hz), 2.9–3.1(m, 1H), 3.7–3.8(m, 1H), 4.1–4.2(m, 1H), 5.27(brs, 1H), 5.4–5.6(m, 2H) |
| 20 | (1S,5S,6R,7R)-3-(4-morpholinocarbonyl-butyl)-6-[(3S,5S,1E)-3-hydroxy-5-methyl-1-nonenyl]-7-hydroxy-bicyclo[3.3.0]-2-octene | (1S,5S,6R,7R)-3-(5-morpholinopentyl)-6-[(3S,5S,1E)-3-hydroxy-5-methyl-1-nonenyl]-7-hydroxybicyclo-[3.3.0]-2-octene | 50 | 0.7–1.0(m, 6H), 1.0–1.6 (m, 15H), 1.75–2.1(m, 5H), 2.1–2.65(m, 10H), 2.9–3.1(m, 1H), 3.6–3.8 (m, 6H), 4.0–4.2(m, 1H), 5.26(brs, 1H), 5.4–5.6(m, 2H) |
| 21 | (1S,5S,6R,7R)-3-(4-piperidinocarbonylbutyl)-6-[(3S,5S,1E)-3-hydroxy-5-methyl-1-nonenyl]-7-hydroxybicyclo[3.3.0]-2-octene | (1S,5S,6R,7R)-3-(5-piperidinopentyl)-6-[(3S,5S,1E)-3-hydroxy-5-methyl-1-nonenyl]-7-hydroxybicyclo-[3.3.0]-2-octene | 81 | 0.7–1.0(m, 6H), 1.0–1.7 (m, 21H), 1.7–2.1(m, 9H), 2.2–2.5(m, 7H), 2.9–3.1(m, 1H), 3.7–3.85 (m, 1H), 4.1–4.25(m, 1H), 5.27(brs, 1H), 5.45–5.6(m, 2H) |
| 22 | (1S,5S,6R,7R)-3-[4-N-(4-pyridylmethyl)-carbamoylbutyl]-6-[(3S,5S,1E)-3-hydroxy-5-methyl-1-nonenyl]-7-hydroxybicyclo-[3.3.0]-2-octene | (1S,5S,6R,7R)-3-[5-N-(4-pyridylmethyl)amino-pentyl]-6-[(3S,5S,1E)-3-hydroxy-5-methyl-1-nonenyl]-7-hydroxy-bicyclo[3.3.0]-2-octene | 89 | 0.8–0.95(m, 6H), 1.0–2.1 (m, 18H), 2.04(t, 2H, J=8.5Hz), 2.27(t, 2H, J=7.4Hz), 2.2–2.5(m, 5H), 2.9–3.1(m, 1H), 3.7–3.85(m, 1H), 4.1–4.2 (m, 1H), 4.46 (d, 2H, J=5.9Hz), 5.27(brs, 1H), 5.45–5.6(m, 2H), 5.9–6.0 (m, 1H), 7.20(d, 2H, J=5.9Hz), 8.54(d, 2H, J=5.9Hz) |

TABLE 7-continued

| Example No. | starting material | product | Yield % | NMR data δ |
|---|---|---|---|---|
| 23 | (1S,5S,6R,7R)-3-(4-N,N-dimethyl-carbamoylbutyl)-6-[(3S,1E)-3-hydroxy-4-(m-tolyl)-1-butenyl]-7-hydroxybicyclo-[3.3.0]-2-octene | (1S,5S,6R,7R)-3-(5-N,N-dimethylamino-pentyl)-6-[(3S,1E)-3-hydroxy-4-(m-tolyl)-1-butenyl]-7-hydroxy bicyclo[3.3.0]-2-octene | 43 | 1.2–1.55(m, 7H), 1.8–2.1 (m, 7H), 2.23(s, 6H), 2.33(s, 3H), 2.1–2.5(m, 4H), 2.7–2.9(m, 2H), 2.9–3.1(m, 1H), 3.6–3.8 (m, 1H), 4.32(q, 1H, J=6.5Hz), 5.26(brs, 1H), 5.49(dd, 1H, J=15.3, 8.5Hz), 5.60(dd, 1H, J=15.4, 6.2Hz), 6.9–7.1 (m, 3H), 7.1–7.25(m, 1H) |
| 24 | (1S,5S,6R,7R)-3-(4-N,N-dimethyl-carbamoylbutyl)-6-[(3R,1E)-3-hydroxy-4-(m-tolyl)-1-butenyl]-7-hydroxybicyclo-[3.3.0]-2-octene | (1S,5S,6R,7R)-3-(5-N,N-dimethylamino-pentyl)-6-[(3R,1E)-3-hydroxy-4-(m-tolyl)-1-butenyl]-7-hydroxy-bicyclo[3.3.0]-2-octene | 70 | 1.2–1.55(m, 7H), 1.6–2.1 (m, 7H), 2.22(s, 6H), 2.33(s, 3H), 2.1–2.5(m, 4H), 2.75–2.9(m, 2H), 2.9–3.1(m, 1H), 3.5–3.7 (m, 1H), 4.33(q, 1H, J=6.5Hz), 5.26(brs, 1H), 5.45(dd, 1H, J=15.8, 8.2Hz), 5.59(dd, 1H, J=15.5, 6.6Hz), 6.9–7.1 (m, 3H), 7.1–7.2(m, 1H) |
| 25 | (1S,5S,6R,7R)-3-(4-N,N-dimethyl-carbamoylbutyl)-6-[(E)-4-(m-tolyl)-1-butenyl]-7-hydroxy-bicyclo[3.3.0]-2-octene | (1S,5S,6R,7R)-3-(5-N,N-dimethylamino-pentyl)-6-[(E)-4-(m-tolyl)-1-butenyl]-7-hydroxybicyclo-[3.3.0]-2-octene | 81 | 1.2–2.1(m, 13H), 2.22(s, 6H), 2.33(s, 3H), 2.15–2.5(m, 6H), 2.5–2.7 (m, 2H), 2.9–3.05(m, 1H), 3.5–3.7(m, 1H), 5.2–5.3(m, 2H), 5.45–5.6 (m, 1H), 6.9–7.1(m, 3H), 7.1–7.2(m, 1H) |
| 26 | (1S,5S,6R,7R)-3-(4-N,N-dimethyl-carbamoylbutyl)-6-[(1E,3E)-6-(m-tolyl)-1,3-hexadienyl]-7-hydroxybicyclo-[3.3.0]-2-octene | (1S,5S,6R,7R)-3-(5-N,N-dimethylamino-pentyl)-6-[(1E,3E)-6-(m-tolyl)-1,3-hexa-dienyl]-7-hydroxy-bicyclo[3.3.0]-2-octene | 7 | 1.2–1.7(m, 7H), 2.33(s, 9H), 1.7–2.7(m, 14H), 2.9–3.1(m, 1H), 3.5–3.7 (m, 1H), 5.30(brs, 1H), 5.35–5.55(m, 1H), 5.55–5.75(m, 1H), 5.9–6.2 (m, 2H), 6.8–7.05(m, 3H), 7.05–7.2(m, 1H) |

EXAMPLE 27

Preparation of (1S,5S,6R,7R)-3-[5-(1-pyrrolidinyl) pentyl]-6-[(E)-4-(m-tolyl)-1-butenyl]-7-hydroxybicyclo[3.3.0]-2-octene

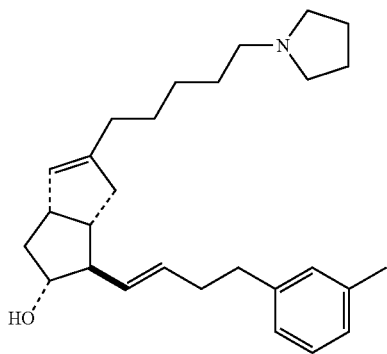

24 mg of (1S,5S,6R,7R)-3-(4-carboxybutyl)-6-[(E)-4-(m-tolyl)-1-butenyl]-7-hydroxybicyclo[3.3.0]-2-octene was taken and dissolved in 2 mL of dimethylformamide. 25 mg of 1,1'-carbonyldiimidazole was added and stirred at 50° C. for 1.5 hours. It was then cooled to ambient temperature and 100 mg pyrrolidine was added. After stirring at 50° C. for 2 hours, an aqueous solution saturated with ammonium chloride was added and extracted with ethyl acetate. The organic layer was washed with a saturated saline solution, and dried with anhydrous sodium sulfate. After filtration and concentration, 3 mL of tetrahydrofurane was added. While stirring on ice, 112 mg of lithium aluminium hydride was added, and stirring continued at 50° C. for 3 hours. While stirring at ambient temperature, 200 μL of an aqueous solution saturated with sodium sulfate was added, then 1 g of anhydrous sodium sulfate was added- and stirred for 16 hours. A filtration was performed over celite, and after washing the residue with ethyl acetate, the filtrate was concentrated and subjected to silicagel column chromatography, to obtain 18 mg of the compound presented in the title (65% yield).

1H-NMR (270 MHz, CDCl$_3$): δ1.2–1.6 (m, 7H), 1.7–2.1 (m, 10H), 2.33 (s, 3H), 2.15–2.7 (m, 12H), 2.8–3.1 (m, 1H), 3.5–3.7 (m, 1H), 5.15–5.3 (m, 2H), 5.45–5.65 (m, 1H), 6.9–7.1 (m, 3H), 7.1–7.2 (m, 1H).

EXAMPLES 28–33

The compounds shown in Table 8 were obtained with a method identical to Example 27.

29 mg of (1S,5S,6R,7R)-3-(4-N,N-diisopropylcarbamoylbutyl)-6-[(E)-4-(m-tolyl)-1-butenyl]-7-(tetrahydropyran-2-yloxy)-bicyclo[3.3.0]-2-octene obtained in Reference

TABLE 8

| Example No. | starting material | | | | NMR data |
|---|---|---|---|---|---|
| | carboxylic acid | amine | product | Yield % | δ |
| 28 | (1S,5S,6R,7R)-3-(4-carboxybutyl)-6-[(3S,1E)-3-hydroxy-1-octenyl]-7-hydroxybicyclo-[3.3.0]-2-octene | methylamine | (1S,5S,6R,7R)-3-(5-N-methylamino-pentyl)-6-[(3S,1E)-3-hydroxy-1-octenyl]-7-hydroxybicyclo-[3.3.0]-2-octene | 33 | 0.94(brt, 3H, J=6.9Hz), 1.2–1.6(m, 16H), 1.8–2.6 (m, 11H), 2.42(s, 3H), 2.9–3.1(m, 1H), 3.7–3.9 (m, 1H), 4.1–4.2(m, 1H), 5.28(brs, 1H), 5.4–5.6(m, 2H) |
| 29 | (1S,5S,6R,7R)-3-(4-carboxybutyl)-6-[(3S,1E)-3-hydroxy-1-octenyl]-7-hydroxybicyclo-[3.3.0]-2-octene | cyclohexylamine | (1S,5S,6R,7R)-3-(5-N-cyclohexyl-aminopentyl)-6-[(3S,1E)-3-hydroxy-1-octenyl]-7-hydroxy-bicyclo[3.3.0]-2-octene | 14 | 0.93(brt, 3H, J=6.9Hz), 0.9–2.5(m, 37H), 2.9–3.1 (m, 1H), 3.7–3.9(m, 1H), 4.1–4.2(m, 1H), 5.26(brs, 1H),5.4–5.6(m, 2H) |
| 30 | (1S,5S,6R,7R)-3-(4-carboxybutyl)-6-[(3S,1E)-3-hydroxy-1-octenyl]-7-hydroxybicyclo-[3.3.0]-2-octene | benzylamine | (1S,5S,6R,7R)-3-(5-N-benzylamino-pentyl)-6-[(3S,1E)-3-hydroxy-1-octenyl]-7-hydroxybicyclo-[3.3.0]-2-octene | 33 | 0.92(brt, 3H, J=6.7Hz), 1.1–1.7(m, 16H), 1.8–2.7 (m, 11H), 2.9–3.1(m, 1H), 3.77(s, 2H), 3.7–3.9 (m, 1H), 4.1–4.2(m, 1H), 5.27(brs, 1H), 5.4–5.6(m, 2H), 7.1–7.3(m, 5H) |
| 31 | (1S,5S,6R,7R)-3-(4-carboxybutyl)-6-[(3S,1E)-3-hydroxy-1-octenyl]-7-hydroxybicyclo-[3.3.0]-2-octene | N-methylpiperazine | (1S,5S,6R,7R)-3-[5-(4-N-methyl-1-piperazinyl)pentyl]-6-[(3S,1E)-3-hydroxy-1-octenyl]-7-hydroxy-bicyclo[3.3.0]-2-octene | 23 | 0.92(brt, 3H, J=6.8Hz), 1.2–1.6(m, 15H), 1.8–2.9 (m, 19H), 2.29(s, 3H), 2.9–3.1(m, 1H), 3.7–3.9 (m, 1H), 4.1–4.2(m, 1H), 5.28(brs, 1H), 5.4–5.6(m, 2H) |
| 32 | (1S,5S,6R,7R)-3-(4-carboxybutyl)-6-[(4R,1E)-4-hydroxy-4-methyl-1-octenyl]-7-hydroxybicyclo-3.3.0]-2-octene | Butylamine | (1S,5S,6R,7R)-3-(5-N-butylamino-pentyl)-6-[(4R,1E)-4-hydroxy-4-methyl-1-octenyl]-7-hydroxy-bicyclo[3.3.0]-2-octene | 41 | 0.7–1.0(m, 6H), 1.17(s, 3H), 1.2–1.6(m, 19H), 1.8–2.7(m, 14H), 2.9–3.1 (m, 1H), 3.7–3.9(m, 1H), 5.27(brs, 1H), 5.3–5.5(m, 1H), 5.5–5.7(m, 1H) |
| 33 | (1S,5S,6R,7R)-3-(4-carboxybutyl)-6-[(E)-4-(m-tolyl)-1-butenyl]-7-hydroxy-bicyclo[3.3.0]-2-octene | morpholine | (1S,5S,6R,7R)-3-(5-morpholinopentyl)-6-[(E)-4-(m-tolyl)-1-butenyl]-7-hydroxy-bicyclo[3.3.0]-2-octene | 87 | 1.2–1.6(m, 6H), 1.6–2.1 (m, 11H), 2.33(s, 3H), 2.1–2.5(m, 6H), 2.5–2.75 (m, 2H), 2.8–3.1(m, 1H), 3.5–3.75(m, 5H)5.2–5.3 (m, 2H)5.4–5.6(m, 1H), 6.9–7.05(m, 3H), 7.1–7.2(m, 1H) |

EXAMPLE 34

Preparation of (1S,5S,6R,7R)-3-(5-N,N-diisopropylaminopentyl)-6-[(E)-4-(m-tolyl)-1-butenyl]-7-hydroxybicyclo[3.3.0]-2-octene

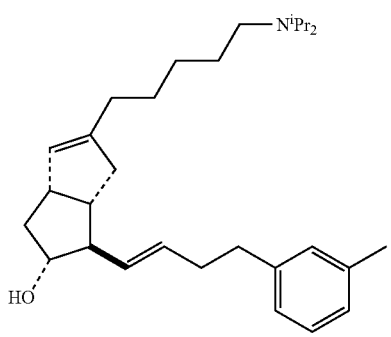

example 14 was dissolved in 5 mL of tetrahydrofuran and 118 mg of lithium aluminium hydride was added. After stirring at 50° C. for 2 hours, 150 μL of an aqueous solution saturated with sodium sulfate was added, then anhydrous sodium sulfate was further added, and stirred for 18 hours. After filtration and concentration, the obtained oily matter was dissolved in 5 mL of methanol, and 20 mg of p-toluene sulfonic acid monohydrate was added. After stirring for 1.5 hours, an aqueous solution of potassium carbonate was added. After concentration extraction was performed with ethyl acetate, and the organic layer was washed with a saturated saline solution. It was then dried with anhydrous sodium sulfate, filtered, concentrated, and subjected to a silicagel column chromatography, to obtain 3 mg of the compound presented in the title (12% yield).

1H-NMR (270 MHz, CDCl$_3$): δ 1.03 (d, 12H, J=6.2 Hz), 1.2–2.1 (m, 14H), 2.2–2.5 (m, 5H), 2.33 (s, 3H), 2.55–2.75 (m, 2H), 2.8–3.2 (m, 3H), 3.6–3.7 (m, 1H), 5.2–5.3 (m, 2H), 5.4–5.7 (m, 1H), 6.9–7.1 (m, 3H), 7.1–7.25 (m, 1H).

EXAMPLE 35

Preparation of (1S,2R,3R,5S)-7-[(E)-5-N,N-dimethylaminopentylidene]-2-[(3S, 1E)-3-hydroxy-4-methyl-6-octyne-1-enyl]-3-hydroxybicyclo[3.3.0]octane

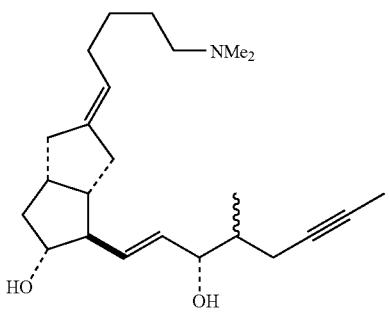

14 mg of (1S,2R,3R,5S)-7-[(E)-4-N,N-dimethylcarbamoylbutylidene]-2-[(3S,1E)-3-hydroxy-4-methyl-6-octyne-1-enyl]-3-hydroxybicyclo[3.3.0]octane obtained in Reference example 15 was taken and 4 mL of tetrahydrofuran was added. In addition, while stirring on ice, 15 mg of lithium aluminium hydride was added and stirred at ambient temperature for 4 hours. While stirring at ambient temperature, 100 μL of an aqueous solution saturated with sodium sulfate was added, 300 mg anhydrous sodium sulfate was added, and stirred for 16 hours. A filtration was performed over celite, and after washing the residue with ethyl acetate, the filtrate was concentrated and subjected to a silicagel column chromatography, to obtain 9 mg of the compound presented in the title (65% yield).

1H-NMR (270 MHz, CDCl$_3$): δ 0.96 and 1.01 (d, 3H, J=6.8 Hz), 1.1–1.6 (m, 7H), 1.79 (t, 3H, J=2.4 Hz), 2.24 (s, 6H), 1.7–2.5 (m, 15H), 3.7–3.9 (m, 1H), 3.9–4.2 (m, 1H), 5.2–5.3 (m, 1H), 5.4–5.6 (m, 2H).

EXAMPLE 36

Preparation of (1S,2R,3R,5S)-7-[(E)-5-N,N-dimethylaminopentylidene]-2-[(3S,1E)-3-hydroxy-1-octenyl]-3-hydroxybicyclo[3.3.0]octane

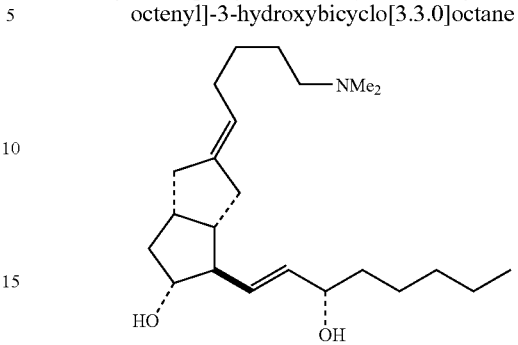

28 mg of (1S,2R,3R,5S)-7-[(E)-4-carboxybutylidene]-2-[(3,1E)-3-hydroxy-1-octenyl]-3-hydroxybicyclo[3.3.0]octane was taken and was dissolved in 1.5 mL of dimethylformamide. 35 mg of 1,1'-carbonyldiimidazole was added and stirred at 50° C. for 1 hour. It was then cooled to ambient temperature, 27 mg of imidazole was added, and 33m of dimethylamine hydrochloride was also added. After stirring at 50° C. for 1.5 hours, an aqueous solution saturated with ammonium chloride was added and extraction was performed with ethyl acetate. The organic layer was washed with a saturated saline solution, and dried with anhydrous sodium sulfate. After filtration and concentration, 1.5 mL of tetrahydrofurane was added. While stirring on ice, 38 mg of lithium aluminium hydride was added and stirring continued at 0° C. for 15 minutes, then at 50° C. for 1.5 hours. While stirring at ambient temperature, 200 μL of an aqueous solution saturated with sodium sulfate was added, then 800 mg of anhydrous sodium sulfate and 4 mL of ethyl acetate were added, and stirred for 1 hour. A filtration was performed over celite, and after washing the residue with ethyl acetate, the filtrate was concentrated and subjected to a silicagel column chromatography, to obtain 11 mg of the compound presented in the title (41% yield).

1H-NMR (270 MHz, CDCl$_3$): δ 0.93 (brt, 3H, J=6.8 Hz), 1.1–1.6 (m, 12H), 2.24 (s, 6H), 1.7–2.5 (m, 15H), 3.7–3.9 (m, 1H), 3.9–4.2 (m, 1H), 5.2–5.3 (m, 1H), 5.4–5.6 (m, 2H).

EXAMPLE 37

The compound shown in Table 9 was obtained with a method identical to Example 36.

TABLE 9

| Example No. | starting material | product | Yield % | NMR data δ |
|---|---|---|---|---|
| 37 | (1S,2R,3R,5S)-7-[(E)-4-carboxybutylidene]-2-[(3S,1E)-3-hydroxy-3-cyclopentyl-1-propenyl]-3-hydroxybicyclo[3.3.0]octane | (1S,2R,3R,5S)-7-[(E)-5-N,N-dimethylaminopentylidene]-2-[(3S,1E)-3-hydroxy-3-cyclopentyl-1-propenyl]-3-hydroxybicyclo[3.3.0]octane | 37 | 1.0–1.7(m, 13H), 2.23(s, 6H), 1.7–2.5(m, 15H), 3.7–3.9(m, 1H), 3.9–4.2 (m, 1H), 5.2–5.3(m, 1H), 5.4–5.6(m, 2H) |

EXAMPLE 38

Preparation of (1S,2R,3R,5S)-7-[(E)-5-morpholino-pentylidene]-2-[(3S,1E)-3-hydroxy-4-methyl-6-oc-tyne-1-enyl]-3-hydroxybicyclo[3.3.0]octane

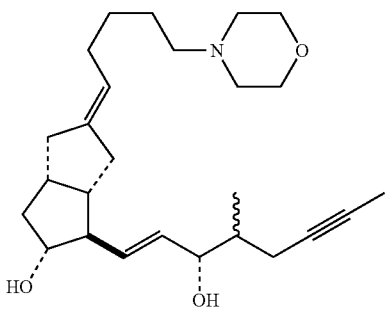

20 mg of (1S,2R,3R,5S)-7-[(E)-4-carboxybutylidene]-2-[(3S,1E)-3-hydroxy-4-methyl-6-octyne-1-enyl]-3-hydroxy-bicyclo[3.3.0]octane was taken and dissolved in 2 mL of dimethylformamide. After addition of 20 mg of 1,1'-carbo-nyldiimidazole, it was stirred at 50° C. for 1.5 hours. It was then cooled to ambient temperature, and 100 mg of morpholine was added. After stirring at 50° C. for 2 hours, an aqueous solution saturated with ammonium chloride was added and extraction was performed with ethyl acetate. The organic layer was washed with a saturated saline solution, and dried with anhydrous sodium sulfate. After filtration and concentration, 3 mL of tetrahydrofurane was added. While stirring, 100 mg of lithium aluminium hydride was added, and stirring continued at 50° C. for 3 hours. While stirring at ambient temperature, 200 μL of an aqueous solution saturated with sodium sulfate was added, then 1 g of anhydrous sodium sulfate was added, and stirred for 16 hours. A filtration was performed over celite, and after washing the residue with ethyl acetate, the filtrate was concentrated and subjected to a silicagel column chromatography, to obtain 7 mg of the compound presented in the title (40% yield).

1H-NMR (270 MHz, CDCl$_3$):δ 0.96 and 1.01 (d, 3H, J=6.8 Hz), 1.1–1.6 (m, 7H), 1.79 (t, 3H, J=2.4 Hz), 1.7–2.7 (m, 19H), 3.6–3.9 (m, 5H), 3.9–4.2 (m, 1H), 5.2–5.3 (m, 1H), 5.4–5.6 (m, 2H).

EXAMPLES 39–40

The compounds shown in Table 10 were obtained with a method identical to Example 38.

TABLE 10

| | starting material | | | NMR data | |
|---|---|---|---|---|---|
| Example No. | carboxylic acid | amine | product | Yield % | δ |
| 39 | (1S,2R,3R,5S)-7-[(E)-4-carboxy-butylidene]-2-[(3S,1E)-3-hydroxy-4-methyl-6-octyne-1-enyl]-3-hydroxy-bicyclo[3.3.0]octane | diethylamine | (1S,2R,3R,5S)-7-[(E)-5-N,N-diethyl-aminopentylidene]-2-[(3S,1E)-3-hydroxy-4-methyl-6-octyne-1-enyl]-3-hydroxy-bicyclo[3.3.0]octane | 35 | 0.96 and 1.01(d, 3H, J=6.8Hz), 1.05(t, 6H, J=7.1Hz), 1.1–1.6(m, 7H), 1.79(t, 3H, J=2.4Hz), 1.7–2.5(m, 15H), 2.55(q, 4H, J=6.5Hz), 3.7–3.9(m, 1H), 3.9–4.2(m, 1H), 5.2–5.3(m, 1H), 5.4–5.6(m, 2H) |
| 40 | (1S,2R,3R,5S)-7-[(E)-4-carboxybutyli-dene]-2-[(3S,1E)-3-hy-droxy-4-methyl-6-octyne-1-enyl]-3-hydroxy-bicyclo[3.3.0]octane | pyrrolidine | (1S,2R,3R,5S)-7-[(E)-5-(1-pyrrolidinyl)-pentylidene]-2-[(3S,1E)-3-hydroxy-4-methyl-6-octyne-1-enyl]-3-hydroxy-bicyclo[3.3.0]octane | 42 | 0.96 and 1.01(d, 3H, J=6.7Hz), 1.1–1.7(m, 11H), 1.7–2.7(m, 22H), 3.7–3.9(m, 1H), 3.9–4.2 (m, 1H), 5.2–5.3(m, 1H), 5.4–5.6(m, 2H) |

REFERENCE EXAMPLE 17

Preparation of (1R,2R,3aS,8bS)-2,3,3a,8b-tetrahydro-2-hydroxy-1-[(3S,1E)-3-hydroxy-4-methyl-1'-octene-6-ynyl]-5-(4-N,N-dimethylaminobutyl)-1H-cyclopenta[b]benzofuran

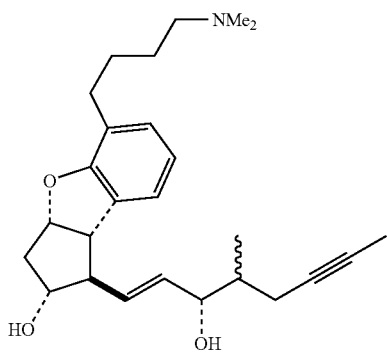

10 mg of (1R,2R,3aS,8bS)-2,3,3a,8b-tetrahydro-2-hydroxy-1-[(3S,1E)-37-hydroxy-4-methyl-1-octene-6-ynyl]-5-(3-carboxypropyl)-1H-cyclopenta[b]benzofuran was taken and was dissolved in 2 mL of dimethylformamide. After addition of 8.1 mg of 1,1'-carbonyldiimidazole, it was stirred at 50° C. for 1 hour. It was then cooled to ambient temperature, 6.8 mg of imidazole was added, 8.2 mg dimethylamine hydrochloride was further added. After stirring at 50° C. for 1 hour, an aqueous solution saturated with ammonium chloride was added and extraction was performed with ethyl acetate. The organic layer was washed with a saturated saline solution, and dried with anhydrous sodium sulfate. After filtration and concentration, 2 mL of tetrahydrofurane was added. While stirring on ice, 9.5 mg of lithium aluminium hydride was added, and stirring continued at 0° C. for 15 minutes, and at 50° C. for 1 hour. While stirring at ambient temperature, 100 µL of an aqueous solution saturated with sodium sulfate was added, 400 mg of anhydrous sodium sulfate was added, and stirred for 1 hour. A filtration was performed over celite, and after washing the residue with ethyl acetate, the filtrate was concentrated and subjected to a silicagel column chromatography, to obtain 7.5 mg of the compound presented in the title (73% yield).

1H-NMR (270 MHz, CDCl$_3$): δ 0.9–1.1 (m, 3H), 1.2–1.7 (m, 7H), 1.79 (brs, 3H), 1.9–2.7 (m, 9H), 2.24 (s, 6H), 3.49 (t, 1H, J=8.5 Hz), 3.9–4.3 (m, 2H), 5.0–5.2 (m, 1H), 5.5–5.8 (m, 2H), 6.7–6.85 (m, 1H), 6.9–7.05 (m, 2H).

EXAMPLE 41

Preparation of (1R,2R,3aS,8bS)-2,3,3a,8b-tetrahydro-2-hydroxy-1-[(3S,1E)-3-hydroxy-4-methyl-1-octene-6-ynyl]-5-(4-morpholinobutyl)-1H-cyclopenta[b]benzofuran

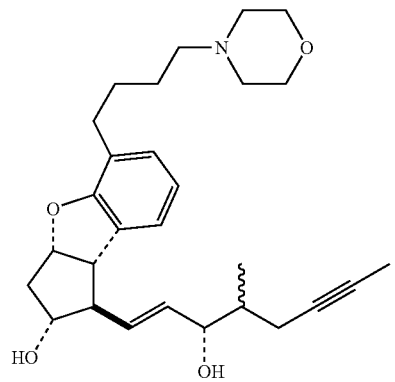

10 mg of (1R,2R,3aS,8bS)-2,3,3a,8b-tetrahydro-2-hydroxy-1-[(3S,1E)-3-hydroxy-4-methyl-1-octene-6-ynyl]-5-(3-carboxypropyl)-1H-cyclopenta[b]benzofuran was taken and was dissolved in 2 mL of dimethylformamide. After addition of 8.1 mg of 1,1'-carbonyldiimidazole, it was stirred at 50° C. for 1 hour. It was cooled to ambient temperature, and 50 mg morpholine was added. After stirring at 50° C. for 1 hour, an aqueous solution saturated with ammonium chloride was added and extracted with ethyl acetate. The organic layer was washed with a saturated saline solution, and dried with anhydrous sodium sulfate. After filtration and concentration, 2 mL of tetrahydrofurane was added. While stirring on ice, 9.5 mg of lithium aluminium hydride was added and stirring continued at 0° C. for 15 minutes, then at 50° C. for 1 hour. While stirring at ambient temperature, 100 µL of an aqueous solution saturated with sodium sulfate was added, then 400 mg of anhydrous sodium sulfate was added, and stirred for 1 hour. A filtration was performed over celite, and after washing the residue with ethyl acetate, the filtrate was concentrated and subjected to a silicagel column chromatography, to obtain 5.3 mg of the compound presented in the title (48% yield).

1H-NMR (270 MHz, CDCl$_3$): δ 0.9–1.1 (m, 3H), 1.2–1.7 (m, 7H), 1.78 (brs, 3H), 1.9–2.7 (m, 13H), 3.3–3.6 (m, 1H), 3.6–4.3 (m, 6H), 5.0–5.2 (m, 1H), 5.5–5.8 (m, 2H), 6.7–6.85 (m, 1H), 6.9–7.05 (m, 2H).

EXAMPLES 42–43

The compounds shown in Table 11 were obtained with a method identical to Example 41.

TABLE 11

| Example No. | starting material | product | Yield % | NMR data δ |
|---|---|---|---|---|
| 42 | (1R,2R,3aS,8bS)-2,3,3a,8b-tetrahydro-2-hydroxy-1-[(3S,1E)-3-hydroxy-4-methyl-1-octene-6-ynyl]-5-(3-carboxypropyl)-1H-cyclopenta[b]benzofuran | (1R,2R,3aS,8bS)-2,3,3a,8b-tetrahydro-2-hydroxy-1-[(3S,1E)-3-hydroxy-4-methyl-1-octene-6-ynyl]-5-(4-piperidinobutyl)-1H-cyclopenta[b]benzofuran | 54 | 0.9–1.1(m, 3H), 1.2–1.7 (m, 13H), 1.79(brs, 3H), 1.8–2.7(m, 13H), 3.3–3.6 (m, 1Hz), 3.9–4.3(m, 2H), 5.0–5.2(m, 1H), 5.5–5.8 (m, 2H), 6.7–6.85(m, 1H), 6.9–7.05(m, 2H) |

TABLE 11-continued

| Example No. | starting material | product | Yield % | NMR data δ |
|---|---|---|---|---|
| 43 | (1R,2R,3aS,8bS)-2,3,3a,8b-tetrahydro-2-hydroxy-1-[(3S,1E)-3-hydroxy-4-methyl-1-octene-6-ynyl]-5-(3-carboxypropyl)-1H-cyclopenta[b]benzofuran | (1R,2R,3aS,8bS)-2,3,3a,8b-tetrahydro-2-hydroxy-1-[(3S,1E)-3-hydroxy-4-methyl-1-octene-6-ynyl]-5-[4-(1-pyrrolidinyl)butyl]-1H-cyclopenta[b]benzofuran | 43 | 0.9–1.1(m, 3H), 1.2–1.7 (m, 13H), 1.80(brs, 3H), 1.8–2.7(m, 11H), 3.3–3.6 (m, 1Hz), 3.9–4.3(m, 2H), 5.0–5.2(m, 1H), 5.5–5.8 (m, 2H), 6.7–6.85(m, 1H), 6.9–7.05(m, 2H) |

REFERENCE EXAMPLE 18

Method for Measuring The Ability of Learning and Memory in a Rat by the Step-Through Passive Avoidance Test A step-through passive avoidance instrument made of two chambers separated by a guillotine door was used as the experimental apparatus. One chamber is an illuminated chamber made of transparent acrylic boards (floor: 15 cm×25 cm, height: 15 cm), the other chamber is a dark chamber made of black acryl boards (same dimensions). In addition, the floor of the dark chamber was equipped with a grid made of 4 mm diameter stainless steel pieces separated by 15 mm spacing. The grid was connected to an apparatus for delivering electric shocks (shock generator scrambler).

First, the guillotine door was opened for one minute to let a rat freely explore the interior of the apparatus. Then, for acquisition trials, the door was closed and the rat was put into the illuminated chamber. 30 seconds later, the door was opened and immediately after the four legs of the rat were put inside the dark chamber, the door was closed and an electric shock was delivered. The strength of the electric shock was 0.5 mA for 5 seconds. The training was repeated until the rat remained in the illuminated chamber for more than 120 seconds when the rat was placed in the illuminated chamber immediately after the electric shock and the door was opened in a similar way. 24 hours after the acquisition trials, the rat was put into the illuminating chamber for retention trials, 30 seconds after, the guillotine door was opened, and the time taken for the four legs of the rat to enter the dark chamber was measured (step-through latency). The maximum observation time during retention trials was set to 300 seconds.

REFERENCE EXAMPLE 19

Method for Measuring the Ability of Learning and Memory in a Rat by the Y-Maze Test (Spontaneous Alternation Behavior Test)

A Y-shaped maze made by connecting three arms having a length of 35 cm each, a wall height of 25 cm and a floor width of 10 cm at an angle of 120° with respect to each other. The apparatus was settled on the laboratory floor.

A rat was placed at the extremity of one of the arms, was allowed to freely explore the maze for 8 minutes, and a record was taken of the order in which the arms were explored by the rat. By calling (A) the "Total arm entries", and among them, by calling (B) the "Number of spontaneous alternations" which is the number of cases where 3 different arms were selected in sequence, the "Percentage of spontaneous alternations" was calculated with: $(B/(A-2))\times 100$.

REFERENCE EXAMPLE 20

Preparation of a Model for Alzheimer's Disease by the Continuous Intracerebroventricular Administration of β-Amyloid Proteins 7 week old Wistar male rats (weight 220 to 250 g) were used (N=5 to 10).

β-amyloid protein (1–42) was dissolved in 35% acetonitrile-0.1% trifluoroacetic acid in water, injected in a mini-osmotic pump, which had been set to deliver 300 pmol/day (volume: 230 μL, flow: 0.5 μL/hour), and connected to a dental syringe needle through a polyethylene tube. Animals in control group were connected to a pump to which β-amyloid protein (40–1) orvehicleonly was injected. After anesthetizing the rats with pentobarbital (50 mg/Kg, i.p.), an incision was performed in each of their scalps, and following the brainatlas, holes were drilled in the cranium. The syringe needle was inserted so that the tip of the needle was inside the lateral ventricle (A=−0.3 mm, L=1.2 mm, H=4.5 mm), and fixed with dental cement. The osmotic pump was then implanted under the dorsal skin.

Taking the day when the mini-osmotic pump was implanted as day 0, on day 5, a Y-maze test was performed following the method indicated in Reference example 2, on day 13 and day 14, a passive avoidance test was performed following the method indicated in Reference example 1, and a decrease in the ability of learning and memory was observed in the group which was administered β-amyloid protein (1–42) in comparison to the group which was administered β-amyloid protein (40–1) or the group which was administered vehicle only.

REFERENCE EXAMPLE 21

Method for Evaluating the Promotion Activity on the Neurite Outgrowth (1)

Mouse neuroblastoma Neuro2A cells (obtained from DAINIPPON PHARMACEUTICAL CO., LTD.) were suspended with a density of $2.5\times 10^4$ cells/mL in DMEM containing 10% FCS and 2 mM of Gln, and were plated on commercially available 24-well tissue culture plates with a quantity of 400 μL/well. After an overnight culture under the conditions where the temperature was 37° C., and the carbon dioxide content of the air was 5%, the media was exchanged to an identical media containing the test compound, and the culture was further continued for 24 hours. Then microscope photographs were taken with a 20× lens. Using the photographs, by counting the total number of cells in the field of view and the number of cells with extended neurite, the proportion of cells with extended neurite is calculated.

REFERENCE EXAMPLE 22

Method for Evaluating the Promotion Activity on the Neurite Outgrowth (2)

The cells used and the performed culture method were identical to those in Reference example (1). After being cultured in a media containing the test compound for 24 hours, microscope photographs were taken with a 20× lens. Transparent sheets were used to cover the latter photographs, in order to copy neural projections with a uniform thickness. The copied sheets were imported into a personal computer as image data, using a scanner. Using image processing software, the area covered by the neurites were calculated, and, since the thickness used to mark the neurite was uniform, the analysis was performed considering that the area was proportional to the length, and allowing to compute the length of neurite per cell.

REFERENCE EXAMPLE 23

Method for Measuring the Activity of Decreasing Blood Pressure

A catheter for monitoring the blood pressure was inserted and placed in the femoral artery, and a catheter for the administration of drug solution was inserted and placed in the femoral vein of male Wistar rats (10–11 weeks old, Charles River) under ether anesthesia. The animals were placed in a Ballman cage, and awakened. After the blood pressure stabilized, a solvent containing ethanol and Tween80 adjusted to the same amount as those in each administered solution was injected by bolus administration. After monitoring blood pressure and heart rate for 60 minutes to verify the absence of effects, the test compound was administered and the blood pressure and the heart rate were further monitored for 60 minutes. The doses of the solvent and the test compound were all 1 mL/Kg. The measurements of the blood pressure and the heart rate were performed immediately before administration (0 minutes), at 3, 5, 10, 15, 30 and 60 minutes after administration. For each animal, the blood pressure value measured at each time point was normalized by defining the blood pressure at 0 minute as 100.

The test compound was used once it had been dissolved with ethanol and diluted in physiological saline containing Tween80, with, the quantity of test compound, the concentration of ethanol and Tween80 in the administration solution for each group as indicated in Table 12 below.

TABLE 12

| Dose (mg/kg) | Concentration of Ethanol (%) | Concentration of Tween80 (%) |
|---|---|---|
| 0.1 | 1 | 0.198 |
| 1 | 10 | 0.18 |

REFERENCE EXAMPLE 24

Measurement of the Permeability of the Compound Through the Blood Brain Barrier

Bovine cerebral capillary endothelial cells were cultured on a 100 mm diameter plate (coated with collagen I) to obtain confluency. The cells were cultured for 15 minutes in an incorporation media (141 mM NaCl, 4 mM KCl, 2 mM $CaCl_2$, 1 mM $H_2SO_4$, 10 mM HEPES, 10 mM D-glucose) containing the test compound (1 μM), to incorporate the test compound into the cells. Then, the test compound incorporated into the cells was extracted with ethanol extraction, and quantified by HPLC. The rate of incorporation was calculated with the equation below.

amount of test compound in the ethanol-extracted fraction/amount of test compound in the incorporation solution×100(%)

EXAMPLE 44

Measurement of the Ameliorating Effect on Learning and Memory Deficit (1)

Test compound: (1S,5S,6R,7R)-3-(4-carbamoylbutyl)-6-[(4S,1E)-4-hydroxy-4-methyl-1-octenyl]-7-hydroxybicyclo[3.3.0]-2-octene.

The ameliorating effect on learning and memory deficit was evaluated with the evaluation methods of Reference examples 18 and 20. The test compound was dissolved in the β-amyloid protein solution, and injected at the same time as the β-amyloid protein, using an osmotic pump. The results are shown in Table 13 below.

TABLE 1

| | Time taken to move into the dark chamber during retention trials mean value ± standard error (unit: seconds) |
|---|---|
| β-amyloid protein(40-1) 300 pmol/day group | 207.3 ± 51.5 (n = 6) |
| β-amyloid protein(1-42) 300 pmol/day group | 140.2 ± 53.8 (n = 5) |
| β-amyloid protein(1-42) 300 pmol/day and test compound 12 fmol/day group | 217.8 ± 44.9 (n = 6) |

The time taken to move into the dark chamber was extended for the test compound group when compared to the β-amyloid protein(1–42) only group. In other words, in the present experiment, the test compound displayed an activity to ameliorate the learning and memory deficit.

EXAMPLE 45

Measurement of the Ameliorating Effect on Learning and Memory Deficit (2)

Test compound: (1S,5S,6R,7R)-3-(4-N,N-dimethylcarbamoylbutyl)-6-[(4S,1E)-4-hydroxy-4-methyl-1-octenyl]-7-hydroxybicyclo[3.3.0]-2-octene The ameliorating effect on learning and memory deficit was evaluated with the evaluation methods of Reference examples 18 and 20. The test compound was dissolved in the β-amyloid protein solution, and injected at the same time as the β-amyloid protein, using an osmotic pump. The results are shown in Table 14 below.

TABLE 14

| | Time taken to move into the dark chamber during retention trials mean value ± standard error (unit: seconds) |
|---|---|
| β-amyloid protein(40-1) 300 pmol/day group | 263.3 ± 36.7 (n = 3) |
| β-amyloid protein(1-42) 300 pmol/day group | 132.8 ± 58.1 (n = 5) |

TABLE 14-continued

|  | Time taken to move into the dark chamber during retention trials mean value ± standard error (unit: seconds) |
|---|---|
| β-amyloid protein(1–42) 300 pmol/day and test compound 12 fmol/day group | 212.2 ± 58.5 (n = 5) |

The time taken to move into the dark chamber was extended for the test compound group when compared to the β-amyloid protein(1–42) only group. In other words, in the present experiment, the test compound displayed an activity to ameliorate learning and memory deficit.

EXAMPLE 46

Measurement of the Ameliorating Effect on Learning and Memory Deficit (3)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

The ameliorating effect on learning and memory deficit was evaluated with the evaluation methods of Reference examples 18 and 20. The test compound was dissolved in the β-amyloid protein solution, and injected at the same time as the β-amyloid protein, using an osmotic pump. The results are shown in Table 15 below.

TABLE 15

|  | Time taken to move into the dark chamber during retention trials mean value ± standard error (unit: seconds) |
|---|---|
| β-amyloid protein(40-1) 300 pmol/day group | 263.3 ± 36.7 (n = 3) |
| β-amyloid protein(1–42) 300 pmol/day group | 132.8 ± 58.1 (n = 5) |
| β-amyloid protein(1–42) 300 pmol/day and test compound 12 fmol/day group | 242.0 ± 36.3 (n = 4) |

The time taken to move into the dark chamber was extended for the test compound group when compared to the β-amyloid protein(1–42) only group. In other words, in the present experiment, the test compound displayed an activity to amliorate learning and memory deficit.

EXAMPLE 47

Measurement of the Ameliorating Effect on Learning and Memory Deficit (4)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

The ameliorating effect on learning and memory deficit was evaluated with the evaluation methods of Reference examples 18 and 20. The test compound was dissolved in the β-amyloid protein solution, and injected at the same time as the β-amyloid protein, using an osmotic pump. The results are shown in Table 16 below.

TABLE 16

|  | Time taken to move into the dark chamber during retention trials mean value ± standard error (unit: seconds) |  |
|---|---|---|
| Vehicle only group | 286.7 ± 13.3 | (n = 6) |
| β-amyloid protein (1–42) 300 pmol/day group | 191.7 ± 49.0 | (n = 6) |
| β-amyloid protein (1–42) 300 pmol/day and test compound 12 fmol/day group | 300.0 ± 0.0 | (n = 5) |

The time taken to move into the dark chamber was extended for the test compound group when compared to the β-amyloid protein(1–42) only group. In other words, in the present experiment, the test compound displayed an activity to ameliorate learning and memory deficit.

EXAMPLE 48

Measurement of the Ameliorating Effect on Learning and Memory Deficit (5)

Test compound: (1S,5S,6R,7R)-3-(4-carbamoylbutyl)-6-[(4S,1E)-4-hydroxy-4-methyl-1-octenyl]-7-hydroxybicyclo[3.3.0]-2-octene The ameliorating effect on learning and memory deficit was evaluated with the evaluation methods of Reference examples 19 and 20. The test compound was dissolved in the β-amyloid protein solution, and injected at the same time as the β-amyloid protein, using an osmotic pump. The results are shown in Table 17 below.

TABLE 17

|  | Occurrence of spontaneous alternation behavior mean value ± standard error (unit: %) |  |
|---|---|---|
| β-amyloid protein (40-1) 300 pmol/day group | 72.2 ± 2.9 | (n = 6) |
| β-amyloid protein (1–42) 300 pmol/day group | 65.6 ± 3.4 | (n = 6) |
| β-amyloid protein (1–42) 300 pmol/day and test compound 12 fmol/day group | 74.1 ± 2.5 | (n = 6) |

The occurrence of spontaneous alternation behavior increased for the test compound group when compared to the β-amyloid protein(1–42) only group. In other words, in the present experiment, the test compound displayed an activity to ameliorate learning and memory deficit.

EXAMPLE 49

Measurement of the Ameliorating Effect on Learning and Memory Deficit (6)

Test compound: (1S,5S,6R,7R)-3-(4-N,N-dimethylcarbamoylbutyl)-6-[(4S,1E)-4-hydroxy-4-methyl-1-octenyl]-7-hydroxybicyclo[3.3.0]-2-octene The ameliorating effect on learning and memory deficit was evaluated with the evaluation methods of Reference examples 19 and 20. The test compound was dissolved in the β-amyloid protein solution, and injected at the same time as the β-amyloid protein, using an osmotic pump. The results are shown in Table 18 below.

TABLE 18

| | Occurrence of spontaneous alternation behavior mean value ± standard error (unit: %) | |
|---|---|---|
| β-amyloid protein (40-1) 300 pmol/day group | 76.3 ± 4.9 | (n = 6) |
| β-amyloid protein (1-42) 300 pmol/day group | 66.5 ± 4.7 | (n = 6) |
| β-amyloid protein (1-42) 300 pmol/day and test compound 12 fmol/day group | 72.1 ± 3.7 | (n = 6) |

The occurrence of spontaneous alternation behavior increased for the test compound group when compared to the β-amyloid protein(1–42) only group. In other words, in the present experiment, the test compound displayed an activity to ameliorate learning and memory deficit.

EXAMPLE 50

Measurement of the Ameliorating Effect on Learning and Memory Deficit (7)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene The ameliorating effect on learning and memory deficit was evaluated with the evaluation methods of Reference examples 19 and 20. The test compound was dissolved in the β-amyloid protein solution, and injected at the same time as the β-amyloid protein, using an osmotic pump. The results are shown in Table 19 below.

TABLE 19

| | Occurrence of spontaneous alternation behavior mean value ± standard error (unit: %) | |
|---|---|---|
| β-amyloid protein (40-1) 300 pmol/day group | 76.3 ± 4.9 | (n = 6) |
| β-amyloid protein (1-42) 300 pmol/day group | 66.5 ± 4.7 | (n = 6) |
| β-amyloid protein (1-42) 300 pmol/day and test compound 12 fmol/day group | 73.2 ± 5.1 | (n = 6) |

The occurrence of spontaneous alternation behavior increased for the test compound group when compared to the β-amyloid protein(1–42) only group. In other words, in the present experiment, the test compound displayed an activity to ameliorate learning and memory deficit.

EXAMPLE 51

Measurement of the Ameliorating Effect on Learning and Memory Deficit 8)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene The ameliorating effect on learning and memory deficit was evaluated with the evaluation methods of Reference examples 19 and 20. The test compound was dissolved in the β-amyloid protein solution, and injected at the same time as the β-amyloid protein, using an osmotic pump. The results are shown in Table 20 below.

TABLE 20

| | Occurrence of spontaneous alternation behavior mean value ± standard error (unit: %) | |
|---|---|---|
| Vehicle only group | 68.2 ± 2.3 | (n = 6) |
| β-amyloid protein (1-42) 300 pmol/day group | 59.1 ± 3.0 | (n = 6) |
| β-amyloid protein (1-42) 300 pmol/day and test compound 12 fmol/day group | 71.7 ± 4.0 | (n = 6) |

The occurrence of spontaneous alternation behavior increased for the test compound group when compared to the β-amyloid protein(1–42) only group. In other words, in the present experiment, the test compound displayed an activity to ameliorate learning and memory deficit.

EXAMPLE 52

Evaluation of the Promotion Activity on the Neurite Outgrowth (1)

Test compound: (1S,5S,6R,7R)-3-(4-carbamoylbutyl)-6-[(4S,1E)-4-hydroxy-4-methyl-1-octenyl]-7-hydroxybicyclo[3.3.0]-2-octene The promotion activity on the neurite outgrowth was evaluated with the method of Reference example 21.

In addition to the test compound, $PGE_1$, whose promotion activity on the neurite outgrowth is known in other neuroblastoma cell strain (Miki et al., Drugs and treatments, Vol. 21, No.1, p93), was administered to an additional group for comparison. The results are shown in Table 21 below.

TABLE 21

| Compound | Proportion of cells with neurite (%) mean value ± standard error |
|---|---|
| Test compound not added | 8.8 ± 1.3 |
| $PGE_1$ (10 nM) | 26.0 ± 3.0 |
| Test compound (10 nM) | 40.3 ± 3.5 |

This experiment shows that a promotion activity on the neurite outgrowth was detected for the test compound (level of significance: $p<0.01$). In addition, test compound showed a strong promotion activity when compared to $PGE_1$ which is known to have a promotion activity on the neurite outgrowth (level of significance: $p<0.05$).

EXAMPLE 53

Evaluation of the Promotion Activity on the Neurite Outgrowth (2)

Test compound: (1S,5S,6R,7R)-3-(4-N,N-dimethylcarbamoylbutyl)-6-[(4S,1E)-4-hydroxy-4-methyl-1-octenyl]-7-hydroxybicyclo[3.3.0]-2-octene The promotion activity on the neurite outgrowth was evaluated with the method of Reference example 22.

In addition to the test compound, as in Example 52, $PGE_1$ was administered to an additional group for comparison. The results are shown in Table 22 below.

TABLE 22

| Compound | Length of neurite per single cell (pixel/cell) mean value ± standard error |
|---|---|
| Test compound not added | 6.1 ± 0.9 |
| PGE$_1$ (1 nM) | 14.2 ± 1.5 |
| Test compound (1 nM) | 22.6 ± 3.0 |

This experiment shows that a promotion activity on the neurite outgrowth was detected for the test compound level of significance: p<0.01). In addition, test compound showed a strong promotion activity when compared to PGE$_1$ which is known to have a promotion activity on the neurite outgrowth (level of significance: p<0.05).

EXAMPLE 54

Evaluation of the Promotion Activity on the Neurite Outgrowth (3)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

The promotion activity on the neurite outgrowth was evaluated with the method of Reference example 21.

In addition to the test compound, as in Example 52, PGE$_1$ was administered to an additional group for comparison. The results are shown in Table 23 below.

TABLE 23

| Compound | Proportion of cells with neurite (%) mean value ± standard error |
|---|---|
| Test compound not added | 6.1 ± 0.9 |
| PGE$_1$ (10 nM) | 19.5 ± 1.9 |
| Test compound (10 nM) | 38.7 ± 6.6 |

This experiment shows that a promotion activity on the neurite outgrowth was detected for the test compoundlevel of significance: p<0.01). In addition, test compound showed a strong promotion activity when compared to PGE$_1$ which is known to have a promotion activity on the neurite outgrowth (level of significance: p<0.05).

EXAMPLE 55

Evaluation of the Promotion Activity on the Neurite Outgrowth (4)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene The promotion activity on the neurite outgrowth was evaluated with the method of Reference example 22.

In addition to the test compound, as in Example 52, PGE, was administered to an additional group for comparison. The results are shown in Table 24 below.

TABLE 24

| Compound | Length of neurite per single cell (pixel/cell) mean value ± standard error |
|---|---|
| Test compound not added | 1.2 ± 0.13 |
| PGE$_1$ (100 nM) | 5.7 ± 1.03 |
| Test compound (100 nM) | 8.0 ± 1.37 |

This experiment shows that a promotion activity on the neurite outgrowth was detected for the test compound.(level of significance: p<0.01).

EXAMPLE 56

Evaluation of the Promotion Activity on the Neurite Outgrowth (5)

Test compound A: (1R,2R,3aS,8bS)-2,3,3a,8b-tetrahydro-2-hydroxy-1-[(3S,1E)-3-hydroxy-4-methyl-1-octene-6-ynyl]-5-(4-N,N-dimethylaminobutyl)-1H-cyclopenta[b]benzofuran.

Test compound B: (1S,5S,6R,7R)-3-(5-N,N-dimethylaminopentyl)-6-[(E)-4-(m-tolyl)-1-butenyl]-7-hydroxybicyclo[3.3.0]-2-octene.

Test compound C: (1S,2R,3R,5S)-7-[(E)-5-N,N-dimethylaminopentylidene]-2-[(3S, 1E)-3-hydroxy-4-methyl-6-octyne-1-enyl]-3-hydroxybicyclo[3.3.0]octane.

Test compound D: (1S,5S,6R,7R)-3-(5-N,N-dimethylaminopentyl)-6-[(3S,1E)-3-hydroxy-4-(m-tolyl)-1-butenyl]-7-hydroxybicyclo[3.3.0]-2-octene.

Test compound E: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

The promotion activity on the neurite outgrowth was evaluated with the method of Reference example 21.

In parallel to the test compounds, as in Example 52, PGE$_1$ was administered to an additional group for comparison. The results are shown in Table 25 below.

TABLE 25

| Compound | Concentration of test compound (μM) | Promotion activity on the neurite outgrowth (value relative to PGE$_1$) |
|---|---|---|
| Vehicle | — | 0.79 |
| PGE$_1$ | 10 | 1.00 |
| Test compound A | 10 | 1.17 |
| Test compound B | 10 | 1.63 |
| Test compound C | 10 | 1.15 |
| Test compound D | 10 | 1.31 |
| Test compound E | 10 | 1.58 |

EXAMPLE 57

Evaluation of the Promotion Activity on the Neurneurite Outgrowth (6)

Test compound A: (1S,5S,6R,7R)-3-(5-morpholinopentyl)-6-[(E)-4-(m-tolyl)-1-butenyl]-7-hydroxybicyclo[3.3.0]-2-octene.

Test compound B: (1S,5S,6R,7R)-3-[5-N,N-diisopropylaminopentyl]-6-[(E)-4-(m-tolyl)-1-butenyl]-7-hydroxybicyclo[3.3.0]-2-octene.

Test compound C: (1S,5S,6R,7R)-3-[5-(1-pyrrolidinyl)pentyl]-6-[(3R,1E)-3-hydroxy-4-(m-tolyl)-1-butenyl]-7-hydroxybicyclo[3.3.0]-2-octene.

The promotion activity on the neurneurite outgrowth was evaluated using the method of Reference example 21.

In parallel to the test compounds, as in Example 52, $PGE_1$ was administered to an additional group for comparison. The results are shown in Table 26 below.

TABLE 26

| Compound | Concentration of compound (μM) | Promotion activity on the neurite outgrowth (value relative to PGE1) |
|---|---|---|
| Vehicle | — | 0.45 |
| $PGE_1$ | 10 | 1.00 |
| Test compound A | 10 | 1.15 |
| Test compound B | 0.1 | 1.12 |
| Test compound C | 10 | 1.25 |

EXAMPLE 58

Evaluation of the Promotion Activity on the Neurneurite Outgrowth (7)

Test compound A: (1S,5S,6R,7R)-3-(4-N,N-dimethylcarbamoylbutyl)-6-[(4S,1E)-4-hydroxy-4-methyl-1-octenyl]-7-hydroxybicyclo[3.3.0]-2-octene.

Test compound B: (1S,5S,6R,7R)-3-(4-N,N-dimethylcarbamoylbutyl)-6-[(E)-4-(m-tolyl)-1-butenyl]-7-hydroxybicyclo[3.3.0]-2-octene.

The promotion activity on the neurneurite outgrowth was evaluated with the method of Reference example 21.

In parallel to the test compounds, as in Example 52, $PGE_1$ was administered to an additional group for comparison. The results are shown in Table 27 below.

TABLE 27

| Compound | Concentration of compound (μM) | Promotion activity on the neurite outgrowth (value relative to PGE1) |
|---|---|---|
| Vehicle | — | 0.53 |
| $PGE_1$ | 10 | 1.00 |
| Test compound A | 10 | 1.39 |
| Test compound B | 10 | 1.50 |

EXAMPLE 59

Measurement of the Blood Pressure Decreasing Activity (1)

Test compound: (1S,5S,6R,7R)-3-(4-carbamoylbutyl)-6-[(4S,1E)-4-hydroxy-4-methyl-1-octenyl]-7-hydroxybicyclo[3.3.0]-2-octene.

The effect on the blood pressure was evaluated with the method of Reference example 23. The variation in the blood pressure after administration of the test compound was as indicated in Table 28 below.

TABLE 28

| | Dose mg/kg | Blood pressure (values normalized to 100 at 0 minute) (± standard error) | | | | | | |
|---|---|---|---|---|---|---|---|---|
| | | 0 min | 3 min | 5 min | 10 min | 15 min | 30 min | 60 min |
| Solvent only | 0 | 100 | 98.4 (2.0) | 97.5 (0.9) | 102.6 (2.3) | 100.6 (1.1) | 102.2 (4.8) | 98.8 (3.6) |
| Test compound | 0.1 | 100 | 102.2 (1.0) | 101.1 (0.4) | 100.0 (1.9) | 101.5 (1.9) | 97.3 (1.9) | 101.1 (2.8) |
| Solvent only | 0 | 100 | 101.8 (1.1) | 99.2 (0.5) | 98.5 (1.5) | 100.0 (1.2) | 99.8 (1.7) | 97.0 (1.2) |
| Test compound | 1 | 100 | 93.7 (5.6) | 95.7 (5.7) | 101.0 (4.8) | 100.9 (3.2) | 101.1 (2.0) | 104.8 (3.2) |

In the 1 mg/Kg group, the test compound exerted a decrease in blood pressure immediately after administration. However, it was observed that recovery was fast, only a slight decrease existed after 3 minutes, and after 10 minutes, the blood pressure returned to normal values. No significant variations were observed in the 0.1 mg/Kg group. In other words, it is clear that the test compound is a compound having an extremely small activity on the circulatory system.

EXAMPLE 60

Measurement of the Blood Pressure Decreasing Activity (2)

Test compound: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

The effect on the blood pressure was evaluated with the method of Reference example 23. The variation in the blood pressure after administration of the test compound was as indicated in Table 28 below.

TABLE 29

| | Dose | Blood pressure (values normalized to 100 at 0 minute) (± standard error) | | | | | |
|---|---|---|---|---|---|---|---|
| | mg/kg | 0 min | 3 min | 5 min | 10 min | 15 min | 30 min | 60 min |
| Solvent only | 0 | 100 | 101.1 (0.8) | 99.7 (1.8) | 103.7 (3.0) | 105.2 (3.2) | 101.4 (3.0) | 98.3 (2.7) |
| Test compound | 0.1 | 100 | 100.8 (2.2) | 99.7 (2.9) | 102.1 (1.7) | 101.7 (2.8) | 101.2 (1.3) | 101.5 (3.7) |
| Solvent only | 0 | 100 | 101.7 (1.0) | 98.5 (1.1) | 97.8 (1.0) | 98.7 (1.5) | 98.2 (2.8) | 94.0 (3.5) |
| Test compound | 1 | 100 | 108.1 (1.6) | 105.1 (1.1) | 105.9 (0.8) | 105.9 (1.8) | 105.0 (1.8) | 99.9 (2.5) |

In other words, it is clear that, since no significant variations were observed in the 0.1 mg/Kg dose and the 1 mg/Kg dose, the test compound is a compound having an extremely small activity on the circulatory system.

EXAMPLE 61

Measurement of the Permeability Through the Blood Brain Barrier (1)

Test compound A: (1S,5S,6R,7R)-3-(4-carbamoylbutyl)-6-[(4S,1E)-4-hydroxy-4-methyl-1-octenyl]-7-hydroxybicyclo[3.3.0]-2-octene.

Test compound B: (1S,5S,6R,7R)-3-(4-carboxybutyl)-6-[(4S,1E)-4-hydroxy-4-methyl-1-octenyl]-7-hydroxybicyclo[3.3.0]-2-octene.

Permeability through the blood brain barrier was measured with the method of Reference example 24. As a reference, measurements were also performed for the well-known isocarbacyclin derivative (test compound B), and compared. The results are shown in Table 30 below.

TABLE 30

| Compound | Rate of incorporation into bovine capillary endothelial cells (mean value of two experiments) |
|---|---|
| Test compound A | 5.09% |
| Test compound B | below detection limit |

It is clear from this experiment that the test compound has a high permeability through the blood brain barrier.

EXAMPLE 62

Measurement of the Permeability Through the Blood Brain Barrier (2)

Test compound A: (1S,5S,6R,7R)-3-(5-N,N-dimethylaminopentyl)-6-[(4S,1E)-4-hydroxy-4-methyl-1-octenyl]-7-hydroxybicyclo[3.3.0]-2-octene.

Test compound B: (1S,5S,6R,7R)-3-(4-carboxybutyl)-6-[(4S,1E)-4-hydroxy-4-methyl-1-octenyl]-7-hydroxybicyclo [3.3.0]-2-octene.

Permeability through the blood brain barrier was measured with the method of Reference example 24. As a reference, measurements were also performed for the well-known isocarbacyclin derivative (test compound B), and compared. The results are shown in Table 31 below.

TABLE 31

| Compound | Rate of incorporation into bovine capillary endothelial cells (mean value of two experiments) |
|---|---|
| Test compound A | 15.8% |
| Test compound B | below detection limit |

In other words, it is clear that the test compound A has a high permeability through the blood brain barrier.

USABILITY IN THE INDUSTRY

The nitrogen-containing compound of the present invention represented by the above equation (1) has an activity for the remedy of nerve damage. Therefore, the compound of the present invention can be used as a therapeutic agent for diorders due to nerve damage or nerve lesions due to external injuries.

What is claimed is:

1. A nitrogen-containing compound represented by Formula (2) shown below or a salt thereof:

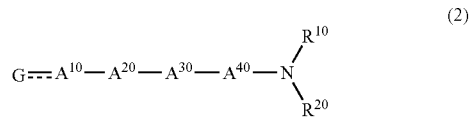

(2)

In Formula (2), the symbol ═══ represents a single bond or a double bond

G represents one functional group chosen from the group consisting of the Formulae (G1), (G2), (G3), (G4) and (G5) shown below:

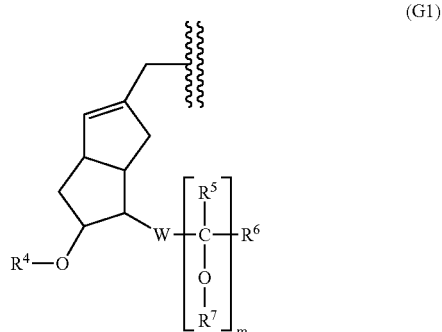

(G1)

-continued (G2)
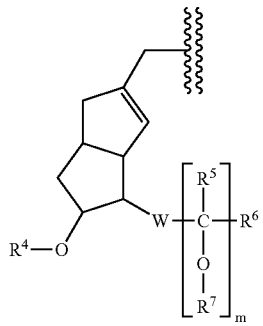

(G3)
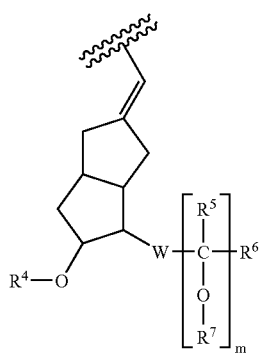

(G4)
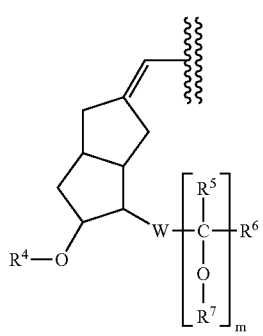

(G5)
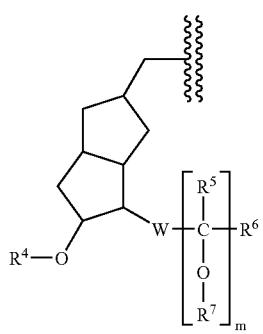

-continued (G10)
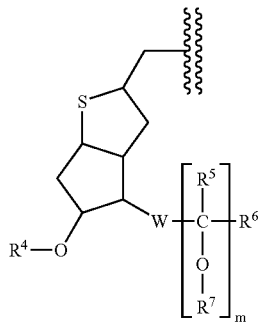

(In Formula (G 1), Formula (G2), Formula (G3), Formula (G4) and Formula (G5), the symbol ξ represents the site of linkage with $A^{10}$;

$R^4$ represents a hydrogen atom, an acyl group having 2 to 10 carbon atoms, a tri(hydrocarbon group having 1 to 7 carbon atoms) silyl group or a functional group forming the acetal bond together with the oxygen atom bonded to $R^4$;

W represents a single bond, —$CH_2$—, —$(CH_2)_2$—, —$(CH_2)_3$—, —CH=CH—, —CH=$CHCH_2$—, —C≡C— of —C≡$CCH_2$—;

m may be either 0 or 1, however, when W is a single bond, m is equal to 1;

$R^5$ and $R^6$ are either identical or different and, either represent one functional group chosen from the following items 1) to 4):

1) a hydrogen atom, 2) a substituted or an unsubstituted aliphatic hydrocarbon group having 1 to 10 carbon atoms, when the substituents are selected from the group consisting of:

fluorine atom,
chlorine atom,
bromine atom,
iodine atom,
hydroxyl group,
alkoxy group having 1 to 4 carbon atoms,
aryloxy group having 6 to 10 carbon atoms,
aralkoxy group having 7 to 9 carbon atoms,
acyloxy group having 2 to 10 carbon atoms,
sulfonyloxy group having 1 to 8 carbon atoms,
oxo group,
carboxyl group,
alkoxycarbonyl group having 2 to 10 carbon atoms,
carbamoyl group having 1 to 15 carbon atoms,
amino group having 0 to 14 carbon atoms,
acylamino group having 1 to 10 carbon atoms,
sulfonylamino group having 1 to 8 carbon atoms,
imino group having 1 to 10 carbon atoms,
cyano group,
nitro group, sulfide group having 1 to 6 carbon atoms,
sulfinyl group having 1 to 6 carbon atoms, and
sulfonyl group having 1 to 6 carbon atoms,
substituted or unsubstituted alicyclic hydrocarbon group having 3 to 8 carbon atoms, wherein the substituents are selected from the group consisting of:
  aliphatic hydrocarbon group having 1 to 6 carbon atoms,
  fluorine atom,
  chlorine atom,
  bromine atom,
  iodine atom,
  hydroxyl group,
  alkoxy group having 1 to 4 carbon atoms,
  aryloxy group having 6 to 10 carbon atoms,
  aralkoxy group having 7 to 9 carbon atoms,
  acyloxy group having 2 to 10 carbon atoms,
  sulfonyloxy group having 1 to 8 carbon atoms,
  oxo group,
  acyl group having 1 to 10 carbon atoms,
  carboxyl group,
  alkoxycarbonyl group having 2 to 10 carbon atoms,
  carbamoyl group having 1 to 15 carbon atoms,
  amino group having 0 to 14 carbon atoms,
  acylamino group having 1 to 10 carbon atoms,
  sulfonylamino group having 1 to 8 carbon atoms,
  imino group having 1 to 10 carbon atoms,
  cyano group,
  nitro group,
  sulfide group having 1 to 6 carbon atoms,
  sulfinyl group having 1 to 6 carbon atoms, and
  sulfonyl group having 1 to 6 carbon atoms, and
substituted or unsubstituted aromatic hydrocarbon group having 6 to 10 carbon atoms, wherein the substituents are selected from the group consisting of:
  alkyl group having 1 to 4 carbon atoms,
  fluorine atom,
  chlorine atom,
  bromine atom,
  iodine atom,
  hydroxyl group,
  alkoxy group having 1 to 4 carbon atoms,
  aryloxy group having 6 to 10 carbon atoms,
  aralkoxy group having 7 to 9 carbon atoms,
  acyloxy group having 2 to 10 carbon atoms,
  sulfonyloxy group having 1 to 8 carbon atoms,
  acyl group having 1 to 10 carbon atoms,
  carboxyl group,
  alkoxycarbonyl group having 2 to 10 carbon atoms,
  carbamoyl group having 1 to 15 carbon atoms,
  amino group having 0 to 14 carbon atoms,
  acylamino group having 1 to 10 carbon atoms,
  sulfonylamino group having 1 to 8 carbon atoms,
  cyano group,
  nitro group,
  sulfide group having 1 to 6 carbon atoms,
  sulfinyl group having 1 to 6 carbon atoms, and
  sulfonyl group having 1 to 6 carbon atoms,
3) a substituted or an unsubstituted alicyclic hydrocarbon group having 3 to 8 carbon atoms wherein the substituents are selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and sulfonyl group having 1 to 6 carbon atoms, 4) a substituted or an unsubstituted aromatic hydrocarbon group having 6 to 10 carbon atoms, wherein the substituents are selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and sulfonyl group having 1 to 6 carbon atoms, or, when $R^5$ and $R^6$ are bonded to each other, they represent a substituted or an unsubstituted alicyclic hydrocarbon chain having 4 to 7 carbon atoms wherein the substituents are selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and, sulfonyl group having 1 to 6 carbon atoms;

$R^7$ represents a hydrogen atom, an acyl group having 2 to 10 carbon atoms, a tri(hydrocarbon group having 1 to 7 carbon atoms) silyl group, an alkoxycarbonyl group having 2 to 5 carbon atoms, a sulfonyl group having 1 to 8 carbon atoms, a functional group forming the acetal bond together with the oxygen atom bound to $R^7$, or, when $R^7$ and $R^5$ are bonded to each other, it represents one portion of the bond forming the carbonyl group together with the carbon atom bonded to $R^5$ and the oxygen atom bonded to $R^7$;

$A^{20}$ represents a single bond, a Formula (A2A) shown below, a Formula (A2B) shown below or a Formula (A2C) shown below:

(A2A)
(A2B)

(in the formula, R³ represents a hydrogen atom, an alkyl group having 1 to 4 carbon atoms, or an acyl group having 1 to 10 carbon atoms)

(A2C)

(in the formula, n represents 0, 1, or 2)
$A^{10}$ represents the items 1) or 2) below:
1) a single bond,
2) a functional group which bridges G and $A^{20}$ through an identical atom or through different atoms, and chosen from: an aliphatic hydrocarbon group having 1 to 3 carbon atoms, an alicyclic hydrocarbon group having 3 to 8 carbon atoms, a heterocyclic group selected from the group consisting of morpholino, pyrrolidinyl, and piperidino, and a phenylene group;
$A^{30}$ represents the items 1) or 2) below:
1) a single bond,
2) a functional group which bridges $A^{20}$ and $A^{40}$ through an identical atom or through different atoms, and chosen from: an aliphatic hydrocarbon group having 1 to 3 carbon atoms, an alicyclic hydrocarbon group having 3 to 8 carbon atoms, a heterocyclic group selected from the group consisting of morpholino, pyrrolidinyl, and piperidino, and a phenylene group;
$A^{40}$ represents any of the items 1) to 3) below:
1) a single bond,
2) an aliphatic hydrocarbon group having 1 to 3 carbon atoms, which bridges the nitrogen atom, bonded to $R^{10}$ and $R^{20}$, and $A^{30}$ through an identical atom or through different atoms;
3) when $A^{40}$ and $R^{10}$ are bonded to each other, a functional group forming a 5 to 8 membered ring together with the nitrogen atom they are bonded to (when $A^{40}$ or $R^{10}$ and the nitrogen atom they are bonded to are bonded through a double bond, $R^{20}$ represents the bond between $A^{40}$ or $R^{10}$ and the nitrogen atom);
however, in the combination of G, $A^{10}$, $A^{20}$, $A^{30}$, and $A^{40}$, when G represents the Formula (G1) and either of $A^{10}$ or $A^{30}$ is a phenylene group, $A^{20}$ may not be a single bond and when $A^{20}$ represents a single bond, then G and the nitrogen atom bonded to $R^{10}$ and $R^{20}$ must be bonded with more than two carbon atoms in between; in addition, when $A^{20}$ represents one of the Formula (A2A), Formula (A2B) or Formula (A2C), $A^{20}$ and the nitrogen atom bonded to $R^{10}$ and $R^{20}$ must be bonded with more than two carbon atoms in between;
$R^{10}$ and $R^{20}$ are either identical or different, and either represents one functional group chosen from the following items 1) to 7):
1) a hydrogen atom (however, when $R^{10}$ and $R^{20}$ both represent a hydrogen atom, only in the case where G is equal to Formula (G1)),
2) a substituted or an unsubstituted alkyl group having 1 to 10 carbon atoms, wherein the substituents are selected from the group consisting of fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, sulfonyl group having 1 to 6 carbon atoms, cycloalkyl group having 3 to 8 carbon atoms, and phenyl group,
3) a substituted or an unsubstituted cycloalkyl group having 3 to 8 carbon atoms, wherein the substituents are selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, an acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and sulfonyl group having 1 to 6 carbon atoms,
4) a substituted or an unsubstituted phenyl group, wherein the substituents are selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, cyano group, nitro group, sulfide group having 1 to 6 carbon atoms, sulfinyl group having 1 to 6 carbon atoms, and sulfonyl group having 1 to 6 carbon atoms,
5) a substituted or an unsubstituted heterocyclic group selected from the group consisting of morpholino, pyrrolidinyl, and piperidino and, alkyl group having 1 to 4 carbon atoms, wherein the substituents are selected from the group consisting of fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and sulfonyl group having 1 to 6 carbon atoms, 6) an acyl group having 1 to 10 carbon atoms, 7) a sulfonyl group having 1 to 8 carbon atoms; however, when either $R^{10}$ or $R^{20}$ represents a sulfonyl group having 1 to 8 carbon atoms, the other may neither be an acyl group having 1 to 10 carbon atoms nor a sulfonyl group having 1 to 8 carbon atoms, or, when $R^{10}$ and $R^{20}$ are bonded together, they represent a functional group forming a cyclic amino group having 4 to 8 carbon atoms together with the nitrogen atom they are bonded to, wherein said cyclic amino group having 4 to 8 carbon atoms may be substituted with one or more substituents selected from the group consisting of alkyl group having 1 to 4 carbon atoms, fluorine atom, chlorine atom, bromine atom, iodine atom, hydroxyl group, alkoxy group having 1 to 4 carbon atoms, aryloxy group having 6 to 10 carbon atoms, aralkoxy group having 7 to 9 carbon atoms, acyloxy group having 2 to 10 carbon atoms, sulfonyloxy group having 1 to 8 carbon atoms, oxo group, acyl group having 1 to 10 carbon atoms, carboxyl group, alkoxycarbonyl group having 2 to 10 carbon atoms, carbamoyl group having 1 to 15 carbon atoms, amino group having 0 to 14 carbon atoms, acylamino group having 1 to 10 carbon atoms, sulfonylamino group having 1 to 8 carbon atoms, imino group having 1 to 10 carbon atoms, cyano group, nitro group, sulfide group having 1 to 6 carbon atoms, sulfinyl group having 1 to 6 carbon atoms, and sulfonyl group having 1 to 6 carbon atoms.

2. A nitrogen-containing compound or a salt thereof of claim 1, wherein G in the above Formula (2) is one functional group chosen from the group consisting of the Formulae (G1E), (G2E), (G3E), (G4E), and (G5E) shown below:

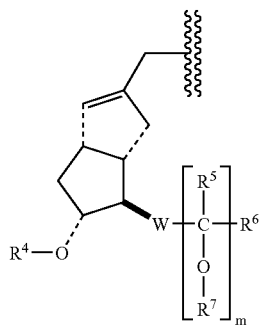
(G1E)

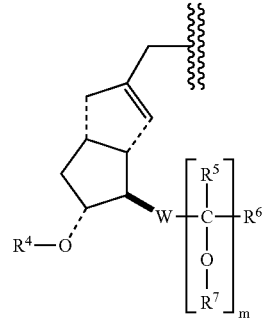
(G2E)

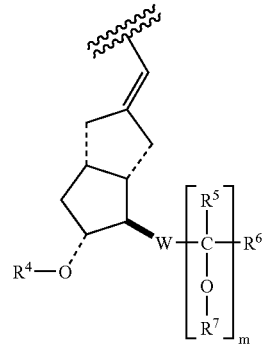
(G3E)

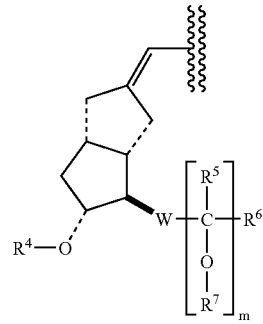
(G4E)

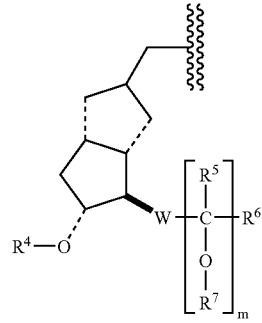
(G5E)

In the above Formula (G1E), Formula (G2E), Formula (G3E), Formula (G4E) and Formula (G5E), the symbol ▬ indicates that the bond is in the β position with respect to the carbon atom forming the cyclic structure it is bonded to, and the symbol ---- indicates that the bonds are in the a position with respect to the carbon atoms forming the cyclic structures they are bonded to.

3. A nitrogen-containing compound or a salt thereof of claim 1, wherein G in the above Formula (2) is a functional group having the Formula (G1).

4. A nitrogen-containing compound or a salt thereof of claim 2, wherein G in the above Formula (2) is a functional group having the Formula (G1E).

5. A nitrogen-containing compound or a salt thereof of claim 2, wherein G in the above Formula (2) is one functional group chosen from the group consisting of the above Formulae (G2E), (G3E), (G4E) and (G5E).

6. A nitrogen-containing compound of a salt thereof of claim 2, wherein G in the above Formula (2) is a functional group having the Formula (G3E).

* * * * *